(12) United States Patent
Collier et al.

(10) Patent No.: US 9,084,734 B2
(45) Date of Patent: Jul. 21, 2015

(54) PEPTIDE PERSONAL CARE COMPOSITIONS AND METHODS FOR THEIR USE

(75) Inventors: Katherine D. Collier, Los Altos, CA (US); Anthony Day, San Francisco, CA (US); Hans de Nobel, Heemstede (NL); David A. Estell, San Francisco, CA (US); Grant C. Ganshaw, Tracy, CA (US); Marc Kolkman, Oegsteest (NL); Raj Lad, San Mateo, CA (US); Jeffrey V. Miller, Menlo Park, CA (US); Christopher J. Murray, Soquel, CA (US); Scott D. Power, San Bruno, CA (US); Brian Schmidt, Half Moon Bay, CA (US); Anita van Kimmenade, San Bruno, CA (US); Gudrun Vogtentanz, Sunnyvale, CA (US)

(73) Assignee: Danisco US Inc., Palo Alto, CA (US)

(*) Notice: Subject to any disclaimer, the term of this patent is extended or adjusted under 35 U.S.C. 154(b) by 2284 days.

(21) Appl. No.: 11/919,717

(22) PCT Filed: Apr. 25, 2006

(86) PCT No.: PCT/US2006/015711
§ 371 (c)(1),
(2), (4) Date: Aug. 25, 2011

(87) PCT Pub. No.: WO2006/121610
PCT Pub. Date: Nov. 16, 2006

(65) Prior Publication Data
US 2012/0014885 A1    Jan. 19, 2012

Related U.S. Application Data

(60) Provisional application No. 60/678,601, filed on May 5, 2005.

(51) Int. Cl.
*A61K 8/02* (2006.01)
*A61K 8/64* (2006.01)
(Continued)

(52) U.S. Cl.
CPC ... *A61K 8/64* (2013.01); *A61K 8/66* (2013.01); *A61Q 1/02* (2013.01); *A61Q 1/04* (2013.01);
(Continued)

(58) Field of Classification Search
None
See application file for complete search history.

(56) References Cited

U.S. PATENT DOCUMENTS 3,755,560 A   8/1973   Yancey et al.
3,929,678 A   12/1975  Laughlin et al.
(Continued)

FOREIGN PATENT DOCUMENTS

EP   0 065 193   5/1982
EP   776 657     11/1996
(Continued)

OTHER PUBLICATIONS

Altschul, et al., J. Mol. Biol. 215:403-410 [1990] "*Basic Local Alignment Search Tool*".
(Continued)

*Primary Examiner* — Carlos Azpuru
(74) *Attorney, Agent, or Firm* — Danisco US Inc.

(57) ABSTRACT

The present invention provides peptides and supported peptides for treating various diseases and conditions. In particularly preferred embodiments, the present invention provides compositions and methods for personal care. In some embodiments the present invention provides compositions for use in skin and/or hair care, as well as cosmetic compositions. IN alternative particularly preferred embodiments, the present invention provides peptides and supported peptides for treating diseases of the skin, such as rosacea. In some particularly preferred embodiments, the supported peptides of the present invention are anti-VEGF peptides. In alternative particularly preferred embodiments, the anti-VEGF peptides are expressed on a scaffold protein. In some most preferred embodiments, the scaffold protein comprises BBI.

31 Claims, 27 Drawing Sheets

```
CK37281 YNLYGWT- (SEQ ID NO:1)
CK37282 -TLWPTFW (SEQ ID NO:2)
CK37283 -NLWPHFW (SEQ ID NO:3)
CK37284 -SLWPAFW (SEQ ID NO:4)
CK37286 -APWNSHI (SEQ ID NO:5)
CK37287 -APWNLHI (SEQ ID NO:6)
CK37289 -TLWPSYW (SEQ ID NO:7)
Consensus LWP  W
```

(51) Int. Cl.
| | |
|---|---|
| A61K 8/66 | (2006.01) |
| A61Q 1/02 | (2006.01) |
| A61Q 1/04 | (2006.01) |
| A61Q 1/10 | (2006.01) |
| A61Q 7/02 | (2006.01) |
| A61Q 9/00 | (2006.01) |
| A61Q 15/00 | (2006.01) |
| A61Q 17/04 | (2006.01) |
| A61Q 19/02 | (2006.01) |
| A61Q 19/04 | (2006.01) |
| A61Q 19/10 | (2006.01) |
| C07K 7/06 | (2006.01) |

(52) U.S. Cl.
CPC .. *A61Q 1/10* (2013.01); *A61Q 7/02* (2013.01); *A61Q 9/00* (2013.01); *A61Q 15/00* (2013.01); *A61Q 17/04* (2013.01); *A61Q 19/02* (2013.01); *A61Q 19/04* (2013.01); *A61Q 19/10* (2013.01); *C07K 7/06* (2013.01)

(56) References Cited

U.S. PATENT DOCUMENTS

| | | |
|---|---|---|
| 4,152,416 A | 5/1979 | Spitzer et al. |
| 4,421,769 A | 12/1983 | Dixon et al. |
| 4,683,195 A | 7/1987 | Mullis et al. |
| 4,683,202 A | 7/1987 | Mullis et al. |
| 4,937,370 A | 6/1990 | Sabatelli |
| 4,965,188 A | 10/1990 | Mullis et al. |
| 4,999,186 A | 3/1991 | Sabatelli et al. |
| 5,011,681 A | 4/1991 | Ciotti et al. |
| 5,073,371 A | 12/1991 | Turner et al. |
| 5,073,372 A | 12/1991 | Turner et al. |
| 5,087,372 A | 2/1992 | Toyomoto et al. |
| 5,411,873 A | 5/1995 | Adams et al. |
| 5,429,950 A | 7/1995 | Power et al. |
| 5,679,543 A | 10/1997 | Lawlis |
| 5,827,508 A | 10/1998 | Tanner et al. |
| 5,935,556 A | 8/1999 | Tanner et al. |
| 5,968,485 A | 10/1999 | Robinson |
| 5,972,316 A | 10/1999 | Robinson |
| 6,063,611 A | 5/2000 | VanSolingen et al. |
| 6,537,968 B1 | 3/2003 | Ledey et al. |

FOREIGN PATENT DOCUMENTS

| | | |
|---|---|---|
| WO | WO96/03964 | 2/1996 |
| WO | WO 98/22085 | 5/1998 |
| WO | WO98/22085 | 5/1998 |
| WO | WO 00/06110 | 2/2000 |
| WO | WO 00/24372 | 4/2000 |
| WO | WO01/74317 | 10/2001 |
| WO | WO01/79479 | 10/2001 |
| WO | WO02/083088 | 10/2002 |
| WO | WO03/072049 | 9/2003 |
| WO | 2005046709 | * 5/2005 |
| WO | WO2005/046709 | 5/2005 |
| WO | WO2005/047302 | 5/2005 |

OTHER PUBLICATIONS

Beucage et al., Tetrahedr. Lett., 22:1859-1869 [1981] "*Deoxynucleoside Phosphoramidites—A New Class of Key Intermediates for Deoxypolnucleotide Synthesis*".
Billings et al., Pro. Natl. Acad. Sci., 89:3120-3124 [1992]).
Birk, Int. J. Pept. Protein Res., 25:113-131 [1985] "*The Bowman-Birk inhibitor*".
Bode and Huber, Eur. J. Biochem., 204:433-451 [1992]). "*Natural protein proteinase inhibitors and their interaction with proteinases*".
Chen et al., J. Biol. Chem., 267:1990-1994 [1992].
Chou et al., Proc. Natl. Acad. Sci. USA 71:1748-1752 [1974]; "*Non-Selective Inhibition of Transformed Cell Browth by a Protease Inhibitor*".
Derian et al., Cell Growth Different., 8:743-749 [1997]).
Devereux et al., Nuc. Acids Res., 12:387 [1984]). "*A Comprehensive set of sequence analysis programs for the VAX*".
Ferrari et al., J. Bact., 170:289-295 [1988] "*Transcription of Bacillus subtilis Subtilisin and Expression of Subtilisin in Sporulation Mutants*".
Hahn et al., Mol. Microbiol., 21:763-775 [1996] "*Regulatory inputs for the synthesis of ComK,the competence transcription factor of Bacillus subtilis*".
Hengen, TIBS 20:285-286 [1995] "*Methods and reagants*".
Henikoff et al., Proc. Natl. Acad Sci. USA 89:10915 [1989].
Henner et al., J. Bact., 170: 296-300 [1988] "*Location of the Targets of the hpr-97, sacU32(hy), and sacQ36(Hy) Mutations in Upstream Regions of the Subtilisin Promoter*".
Higgins and Sharp, Gene 73:237-244 [1988])"*Clustal: a package for performing multiple sequence alignment on a microcomputer*".
Kajino at al., Appl. Env. Microbiol., 66:638-642 [2000] "*A Protein Disulfide Isomerase Gene Fusion Expression System That Increases the Extracellular Productivity of Bacillus brevis*".
Karlin et al., Proc. Natl Acad. Sci USA 90:5873 [1993]; "*Applications and statistics for multiple high-scroinf segments in molecular sequences.*".
Kennedy, Am. J. Clin. Neutr., 68:1406S-1412S [1998] "*The Bowman-Birk inhibitor from soybeans as an anticarcinogenic agent*".
Landon, Meth. Enzymol., 47:145-149 [1977] "*Cleavage at Aspartyl-Prolyl Bonds*".
Laskowski and Kato, Ann. Rev. Biochem., 49:593-626 [1980] "*Protein inhibitors of proteinase*".
Lin et al., Eur. J. Biochem., 212:549-555 [1993] "*The 0.25-nm X-Ray structure of the Bowman birk-Type inhibitor from mung bean in ternary complex with porcine trypsin*".
Livingstone and Barton, Comput. Appl. Biosci.., 9:745-756 [1993] "*Protein sequence alignments: a strategy for the hierarchical analysis of residue conservation*".
Matthes et al., EMBO J., 3:801-805 [1984] "*Simultaneous rapid chemical synthesis of over one hundred oligonucleotides on a microscale*".
Meima et al., J. Biol. Chem., 277:6994-7001, [2002] "*The bdbDC Operon of Bacillus subtilis Encodes Thiol-disulfide Oxidoreductases Required for Competence Development*".
Morinaga et al., Biotechnol., 2:646-649 [1984] "*Improvement of Oligonucleotide-Directed Site-Specific Mutagensis Using Double-Stranded Plasmid DNA*".
Neidhardt et al., J. Bacteriol., 119: 736-747 [1974].
Nelson and Long, Anal. Biochem., 180:147-151 [1989] "*A General Method of Site-Specific Mutagensis Using a Modification of the Thermus Aquatics Polymerase Chain Reaction*".
Odani and Ikenaka, J. Biochem., 71: 839-848 [1972] "*Studies on Soybean Tryspin Inhibitors*".
Paine et al., J. Invest. Dermatol., 116:587-595 [2001] "*An Alternative Approach to Depigmentation by Soybean Extracts via Inhibition of the PAR-2 Pathway*".
Pearson et al., Proc. Natl. Acad. Sci. USA 85:2444-2448 [1988] "*Improved tools for biological sequence comparison*".
Sagarin, Cosmetics, Science and Technology, 2nd Edition, vol. 1, pp. 32-43 [1972] "Emollient Creams and Lotions".
Sahu et al., J. Immunol., 157: 884-891, [1996] "*Inhibition of Human Complement by a C3-Binding Peptide Isolated from a Phage-Displayed Random Peptide Library*".
Sarkar and Sommer, Biotechn., 8:404-407 [1990].
Sayre et al., J. Soc. Cosmet. Chem., 41:103-109 [1990] "*Physical sunscreens*".
Shaw et al., J. Mol. Biol., 320:303-309 [2002] "*Novel Combination of Two Classic Catalyic Schemes*".
Song et al., J. Mol. Biol., 275:347-63 [1998] "*Kunitz-type Soybean Trypsin Inhibitor Revisited Refined Structure of its Complex with Porcine Trypsin Reveals an Insight Into the Interaction Between a Homologous Inhibitor From Erythrina Caffra and Tissue-type Plasminogen Activator*".
Taylor, J. Theor. Biol., 119:205-218 [1986] "*The Classification of Amino Acid Conservation*".
Ullrich & Schlessinger, Cell 61:203-212 [1990].

(56) References Cited

OTHER PUBLICATIONS van Tilbeurgh et al., Meth. Enzymol., 160:45-59 [1988] *"Flurogenic and Chromogenic Glycosidases as Substrates and Ligands of Carbohydrates"*.

Voss et al., Eur. J. Biochem., 242:122-131 [1996] *"Crystal structure of the bifunctional soybean Bowman-Birk inhibitor at 0.28-nm resolution"*.

Werner & Wemmer, Biochem., 31:999-1010 [1992] *"Three-Dimensional Structure of Soybean Trypsin/Chymotrypsin Bowman-Birk Inhibitor in Solution"*.

Yavelow et al., Cancer Res. (Suppl.) 43:2454s-2459s [1983] *"Bowman-Birk Soybean Protease Inhibitor as an Anticarcinogen"*.

Yavelow et al., Proc. Natl. Acad. Sci. USA 82:5395-5399 [1985] *"Nanomolar Concentrations of Bowman-Birk soybean protease inhibitor suppress x-ray induced transformation in vitro"*.

Christmann, A., et al., "The cystine knot of a squash-type protease inhibitor as a structural scaffold for *Escherichia coli* cell surface display of conformationally constrained peptides." *Protein Engineering* 12(9): 797-806, 1999.

Fernandez-Carneado, J., et al., "Surface Grafting onto Template-Assembled Synthetic Protein Scaffolds in Molecular Recognition." *Biopolymers* 55(6): 451-458, 2000.

Murphy, W.L., et al., "Sustained release of vascular endothelial growth factor from mineralized poly(lactide-co-glycolide) scaffolds for tissue engineering." *Biomaterials* 21: 2521-2527, 2000.

Tsunogae, Y., et al., "Crystallization of Bowman-Birk Type Protease Inhibitor (Peanut) and Its Complex with Trypsin." *J. Biochem.* 100: 243-246, 1986.

International Search Report and the Written Opinion of the International Searching Authority for International Application No. PCT/US2006/015711 mailed Dec. 5, 2006.

International Preliminary Report on Patentability for International Application No. PCT/US2006/015711 mailed Nov. 6, 2007.

Siemeister, et al., "The pivotal role of VEGF in tumor angiogenesis: Molecular facts and therapeutic opportunities", Cancer and Metastasis Reviews, 17:241-8.

\* cited by examiner

Leader-AmpC Sequence

```
        SpeI
        ~~~~~
IleProLeuValProPheTyrSerHisSerThrProValSerGluLysGlnLeuAlaGluValValAlaAlaAsnThrIleThrProLeuMetLysAlaGlnSerValPro(SEQ ID NO: 228)
ATTCCACTAGTCGTTCCTTTCTATTCTCACTCCACTCCAGTGTCAGAAAAACAGCTGGCGGAGGTGTCGCGGAATACGATTACCCCGCTGATGAAAGCACAGAGTGTTCCA
TAAGGTGATCAGCAAGGAAAGATAAGAGTGAGGTGAGGTCACAGTCTTTTTGTCGACCGCCTCCACCAGCGCCTTATGCTAATGGGCGACTACTTTCGTGTCTCACAAGGT(SEQ ID NO: 227)
```

Digest with Spe and Dra (Note: Second Dra Site in Vector)

```
        SpeI                                                                                      DraIII
        ~~~~~                                                                                     ~~~~~~
IleProLeuValProPheTyrSerHisSerThrProValSerGluLysGlnLeuAlaGluValValAlaAlaAsnThrIleThrProLeuMetLysAlaGlnSerValPro(SEQ ID NO: 230)
ATTCCA   CTAGTCCTTCCTTTCTATTCTCACTCCACTCCAGTGTCAGAAAAACAGCTGGCGGAGGTGTCGCGGAATACGATTACCCCGCTGATGAAAGCACAGA   GTGTTCCA
TAAGGTGATC   AGCAAGGAAAGATAAGAGTGAGGTGAGGTCACAGTCTTTTTGTCGACCGCCTCCACCAGCGCCTTATGCTAATGGGCGACTACTTTCGTGTCT   CACAAGGT(SEQ ID NO: 229)
```

Replace with Stuffer Fragment

```
IlePro   LeuValSerIleLysSerThrThrAlaCysLeuGlnIleLeuLeuLysThrGlyGlyGlyGlyArgGluTyrAsp <-- out of frame stuffer sequence(SEQ ID NO: 232)
                   bla correct sequence frame -->        AlaGluValValAlaAlaAsnThrIleThrProLeuMetLysAla   GlnSerValPro(SEQ ID NO: 233)
ATTCCA   CTAGTGTTTCGATAAGTCGACAACAGCTGTCTGCGAGATCCGCAGATCCGCAGATCCTGCAGATCCTCAAGACTG
TAAGGTGATC   ACAGAAGCTAGTTCAGCTGTTGTCGACAGACGCTCTAGGACGTCTAGGACGTCTAGGAGTTCTGAC      AGAGTGTTCCA
             SpeI   SalI        PstI    BbsI                                           DraIII         CACAAGGT(SEQ ID NO: 231)
                                                                                       ~~~~~~
                                        BbsI
                                        ~~~~
```

Digest Stuffer Fragment with Bbs

```
IlePro   LeuValSerIleLysSerThrThrAlaCysLeuGlnIleLeuLeuLysThrGly                                                              AlaGluValValAlaAlaAsnThrIleThrProLeuMetLysAlaGlnSerValPro(SEQ ID NO: 235)
                                                                                                                                                                   DraIII
                                                                                                                                                                   ~~~~~~
ATTCCA   CTAGTGTTTCGATAAGTCGACAACAGCTGTCTGCGAGATCCGCAGATCCTGCAGATCCTCAAGACTG                GCGGAGGTGTCGCGGAATACGATTACCCCGCTGATGAAAGCACAGA   GTGTTCCA
TAAGGTGATC   ACAGAAGCTAGTTCAGCTGTTGTCGACAGACGCTCTAGGACGTCTAGGACGTCTAGGAGTTCTGAC               TCCACCAGCGCCTTATGCTAATGGGCGACTACTTTCGTGTCT   CACAAGGT(SEQ ID NO: 234)
             SpeI   SalI        PstI    BbsI
                                        ~~~~
```

Replace with N-term Library (VegF)

```
IlePro   LeuValProPheTyrSerHisSer AlaCysXxxXxxXxxXxxXxxXxxXxxCysGlyGlyGlySer   ThrProValSerGluLysGlnLeu   AlaGluValValAlaAla(SEQ ID NO: 237)
ATTCC   ACTAGTGTTCCTTTCTATTCTCACTCT GCTTGTXXXXXXXXXXXXXXXXXXXXTGTGGGTGGAGGTTCG  ACGCCAGTGTCAGAAAAACAGCTG   GCGGAGGTGTCGCG
TAAGGTGAT   CAGCAAGGAAAGATAAGAGTGAGA  CGAACAXXXXXXXXXXXXXXXXXXXXXACACCCACCTCCAAGC  TGCGGTCACAGTCTTTTTGTCGAC   TCCACCAGCGC(SEQ ID NO: 236)
```

FIG. 5

```
NcoI                              HindIII
M  G  A  N  L  R  L  S  K  L  G  L  L  L  M  K  S  D  H  Q  H  S  N  D
CCATGGGTGC GAACCTGCGT CTGTCTAAGC TTGGCCTGCT TATGAAATCA GACCATCAG C ACAGCAATGA SacI                          BsrGI                                   PstI
D  E  S  S  K  P  C  C  D  Q  C  A  T  K  S  N  P  P  Q  C            R  C
CGATGAGAGC TCTAAACCCT GTTGCGATCA ATGCGCATGT ACAAAATCAA ATCCTCCAC A GTGTCGGTGT EcoRI                   SphI
S  D  M  R  L  N  S  C  H  S  A  C  K  S  C  I  C  A  L  S  Y  P  A  Q
TCCGATATGC GTCTGAATTC CTGTCATAGT GCATGCAAAA GCTGTATCTG CGCCCTGAG T TATCCAGCTC SalI
C  F  C  V  D  I  T  D  F  C  Y  E  P  C  K  P  S  E  D  D     K  E  N
AATGTTTTTG CGTCGACATC ACGGACTTCT GCTATGAGCC ATGTAAACCA AGCGAGGAC G ATAAAGAGAA XhoI
H  H  H  H  H  *                           (SEQ ID NO: 18)
CCATCATCAC CATCACCATT AACTCGAG             (SEQ ID NO: 19)
```

*FIG. 9*

BBI-VEG1: ddesskpccdqcacynlygwtcrcsdmrlnschsackscicalsypaqcfcvditdfcyepckpseddken (SEQ ID NO: 22)

BBI-VEGF2: ddesskpccdqcactksnppqcrcsdmrlnschsackscacynlygwtcfcvditdfcyepckpseddken (SEQ ID NO: 23)

BBI-VEGF12: ddesskpccdqcacynlygwtcrcsdmrlnschsackscacynlygwtcfcvditdfcyepckpseddken (SEQ ID NO: 24)

```
                aprE promoter region
      ~~~~~~~~~~~~~~~~~~~~~~~~~~~~~~~~~~~~~~~~~~~~~~~~~~
      EcoRI
      ~~~~~
1     AATTCTCCAT TTTCTTCTGC TATCAAAATA ACAGACTCGT GATTTTCCAA
                aprE promoter region
      ~~~~~~~~~~~~~~~~~~~~~~~~~~~~~~~~~~~~~~~~~~~~~~~~~~
51    ACGAGCTTTC AAAAAAGCCT CTGCCCCTTG CAAATCGGAT GCCTGTCTAT
                aprE promoter region
      ~~~~~~~~~~~~~~~~~~~~~~~~~~~~~~~~~~~~~~~~~~~~~~~~~~
                                            EagI
                                            ~~~~~~~~
                                            NotI
                                            ~~~~~~~~~~
101   AAAATTCCCG ATATTGGTTA ACAGCGGCG CAATGGCGGC CGCATCTGAT
                aprE promoter region
      ~~~~~~~~~~~~~~~~~~~~~~~~~~~~~~~~~~~~~~~~~~~~~~~~~~
151   GTCTTTGCTT GGCGAATGTT CATCTTATTT CTTCCTCCCT CTCAATAATT
                aprE promoter region
      ~~~~~~~~~~~~~~~~~~~~~~~~~~~~~~~~~~~~~~~~~~~~~~~~~~
201   TTTTCATTCT ATCCCTTTTC TGTAAAGTTT ATTTTTCAGA ATACTTTTAT
                aprE promoter region
      ~~~~~~~~~~~~~~~~~~~~~~~~~~~~~~~~~~~~~~~~~~~~~~~~~~
251   CATCATGCTT TGAAAAAATA TCACGATAAT ATCCATTGTT CTCACGGAAG
                aprE promoter region
      ~~~~~~~~~~~~~~~~~~~~~~~~~~~~~~~~~~~~~~~~~~~~~~~~~~
301   CACACGCAGG TCATTTGAAC GAATTTTTTC GACAGGAATT TGCCGGGACT
                aprE promoter region
      ~~~~~~~~~~~~~~~~~~~~~~~~~~~~~~~~~~~~~~~~~~~~~~~~~~
351   CAGGAGCATT TAACCTAAAA AAGCATGACA TTTCAGCATA ATGAACATTT
                aprE promoter region
      ~~~~~~~~~~~~~~~~~~~~~~~~~~~~~~~~~~~~~~~~~~~~~~~~~~
401   ACTCATGTCT ATTTTCGTTC TTTTCTGTAT GAAAATAGTT ATTTCGAGTC
                aprE promoter region
      ~~~~~~~~~~~~~~~~~~~~~~~~~~~~~~~~~~~~~~~~~~~~~~~~~~
451   TCTACGGAAA TAGCGAGAGA TGATATACCT AAATAGAGAT AAAATCATCT
```

FIG. 14A

```
                              aprE promoter region
                ~~~~~~~~~~~~~~~~~~~~~~~~~~~~~~~~~~~~~~~~~~~~~~~~~~~~~
    501    CAAAAAAATG GGTCTACTAA AATATTATTC CATCTATTAC AATAAATTCA aprE promoter region
                ~~~~~~~~~~~~~~~~~~~~~~~~~~~~~~~~~~~~~~~~~~~~~~~~~~~~~
    551    CAGAATAGTC TTTTAAGTAA GTCTACTCTG AATTTTTTTA AAAGGAGAGG AprE signal peptide
                              ~~~~~~~~~~~~~~~~~~~~~~~~~~~~~~~~~~~~~~
        aprE promoter region
        ~~~~~~~~
                    M   R   S   K   K   L   W   I   S   L   L   F   A   L   T  ·
    601    GTAAAGAGTC AGAAGCAAAA AATTGTGGAT CAGCTTGTTG TTTGCGTTAA AprE signal peptide
                ~~~~~~~~~~~~~~~~~~~~~~~~~~~~~~~~~~~~~~~~~~~~~~~~~~~~~
                                                                BCE103
                                                              ~~~~~~~
             ·  L   I   F     T   M   A   F   S   N   M   S   A   Q   A   D   D
    651    CGTTAATCTT TACGATGGCG TTCAGCAACA TGTCTGCGCA GGCTGATGAT BCE103
                ~~~~~~~~~~~~~~~~~~~~~~~~~~~~~~~~~~~~~~~~~~~~~~~~~~~~~
               Y   S   V   V   E   E   H   G   Q   L   S   I   S   N   G   E   L  ·
    701    TATTCAGTTG TAGAGGAACA TGGGCAACTA AGTATTAGTA ACGGTGAATT BCE103
                ~~~~~~~~~~~~~~~~~~~~~~~~~~~~~~~~~~~~~~~~~~~~~~~~~~~~~
                                                                  NcoI
                                                                ~~~~~
             ·  V   N   E   R   G   E   Q   V   Q   L   K   G   M   S   S   H   G  ·
    751    AGTCAATGAA CGAGGCGAAC AAGTTCAGTT AAAAGGGATG AGTTCCCATG BCE103
                ~~~~~~~~~~~~~~~~~~~~~~~~~~~~~~~~~~~~~~~~~~~~~~~~~~~~~
        NcoI
        ~
             ·  L   Q   W   Y   G   Q   F   V   N   Y   E   S   M   K   W   L
    801    GTTTGCAATG GTACGGTCAA TTTGTAAACT ATGAAAGCAT GAAATGGCTA BCE103
                ~~~~~~~~~~~~~~~~~~~~~~~~~~~~~~~~~~~~~~~~~~~~~~~~~~~~~
               R   D   D   W   G   I   T   V   F   R   A   A   M   Y   T   S   S  ·
    851    AGAGATGATT GGGGAATAAC TGTATTCCGA GCAGCAATGT ATACCTCTTC BCE103
                ~~~~~~~~~~~~~~~~~~~~~~~~~~~~~~~~~~~~~~~~~~~~~~~~~~~~~
             ·  G   G   Y   I   D   D   P   S   V   K   E   K   V   K   E   T   V  ·
    901    AGGAGGATAT ATTGACGATC CATCAGTAAA GGAAAAAGTA AAAGAGACTG BCE103
                ~~~~~~~~~~~~~~~~~~~~~~~~~~~~~~~~~~~~~~~~~~~~~~~~~~~~~
             ·  E   A   A   I   D   L   G   I   Y   V   I   I   D   W   H   I
    951    TTGAGGCTGC GATAGACCTT GGCATATATG TGATCATTGA TTGGCATATC
```

*FIG. 14B*

```
                              BCE103
         ~~~~~~~~~~~~~~~~~~~~~~~~~~~~~~~~~~~~~~~~~~~~~~~~~~~~~~
           L   S   D   N   D   P   N   I   Y   K   E   E   A   K   D   F   F  ·
    1001 CTTTCAGACA ATGACCCGAA TATATATAAA GAAGAAGCGA AGGATTTCTT

BCE103
         ~~~~~~~~~~~~~~~~~~~~~~~~~~~~~~~~~~~~~~~~~~~~~~~~~~~~~~
          ·  D   E   M   S   E   L   Y   G   D   Y   P   N   V   I   Y   E   I  ·
    1051 TGATGAAATG TCAGAGTTGT ATGGAGACTA TCCGAATGTG ATATACGAAA

BCE103
         ~~~~~~~~~~~~~~~~~~~~~~~~~~~~~~~~~~~~~~~~~~~~~~~~~~~~~~
          ·  A   N   E   P   N   G   S   D   V   T   W   D   N   Q   I   K
    1101 TTGCAAATGA ACCGAATGGT AGTGATGTTA CGTGGGACAA TCAAATAAAA

BCE103
         ~~~~~~~~~~~~~~~~~~~~~~~~~~~~~~~~~~~~~~~~~~~~~~~~~~~~~~
           P   Y   A   E   E   V   I   P   V   I   R   D   N   D   P   N   N  ·
    1151 CCGTATGCAG AAGAAGTGAT TCCGGTTATT CGTGACAATG ACCCTAATAA

BCE103
         ~~~~~~~~~~~~~~~~~~~~~~~~~~~~~~~~~~~~~~~~~~~~~~~~~~~~~~
          ·  I   V   I   V   G   T   G   T   W   S   Q   D   V   H   H   A   A  ·
    1201 CATTGTTATT GTAGGTACAG GTACATGGAG TCAGGATGTC CATCATGCAG

BCE103
         ~~~~~~~~~~~~~~~~~~~~~~~~~~~~~~~~~~~~~~~~~~~~~~~~~~~~~~
          ·  D   N   Q   L   A   D   P   N   V   M   Y   A   F   H   F   Y
    1251 CCGATAATCA GCTTGCAGAT CCTAACGTCA TGTATGCATT TCATTTTTAT

BCE103
         ~~~~~~~~~~~~~~~~~~~~~~~~~~~~~~~~~~~~~~~~~~~~~~~~~~~~~~
             A   G   T   H   G   Q   N   L   R   D   Q   V   D   Y   A   L   D  ·
    1301 GCAGGAACAC ATGGACAAAA TTTACGAGAC CAAGTAGATT ATGCATTAGA

BCE103
         ~~~~~~~~~~~~~~~~~~~~~~~~~~~~~~~~~~~~~~~~~~~~~~~~~~~~~~
          ·  Q   G   A   A   I   F   V   S   E   W   G   T   S   A   A   T   G  ·
    1351 TCAAGGAGCA GCGATATTTG TTAGTGAATG GGGGACAAGT GCAGCTACAG

BCE103
         ~~~~~~~~~~~~~~~~~~~~~~~~~~~~~~~~~~~~~~~~~~~~~~~~~~~~~~
          ·  D   G   G   V   F   L   D   E   A   Q   V   W   I   D   F   M
    1401 GTGATGGTGG TGTGTTTTTA GATGAAGCAC AAGTGTGGAT TGACTTTATG

BCE103
         ~~~~~~~~~~~~~~~~~~~~~~~~~~~~~~~~~~~~~~~~~~~~~~~~~~~~~~
             D   E   R   N   L   S   W   A   N   W   S   L   T   H   K   D   E  ·
    1451 GATGAAAGAA ATTTAAGCTG GGCCAACTGG TCTCTAACGC ATAAGGATGA

BCE103
         ~~~~~~~~~~~~~~~~~~~~~~~~~~~~~~~~~~~~~~~~~~~~~~~~~~~~~~
              PstI
             ~~~~~~~~
          ·  S   S   A   A   L   M   P   G   A   N   P   T   G   W   T   E  ·
    1501 GTCATCTGCA GCGTTAATGC CAGGTGCAAA TCCAACTGGT GGTTGGACAG
```

*FIG. 14C*

```
                              BCE103
       ~~~~~~~~~~~~~~~~~~~~~~~~~~~~~~~~~~~~~~~~~~~~~~~~~~~~~~~~~~~
          .  A   E   L   S   P   S   G   T   F   V   R  E  K   I   R   E
     1551 AGGCTGAACT ATCTCCATCT GGTACATTTG TGAGGGAAAA AATAAGAGAA

BCE103
       ~~~~~~~~~~~~~~~
                                                1st CBD Linker
                                        ~~~~~~~~~~~~~~~~~~~~~~~~~~~~~~~
            S   A   S   I   P   P   S   D   P   T   P   P   S   D   P   G   E .
     1601 TCAGCATCTA TTCCGCCAAG CGATCCAACA CCGCCATCTG ATCCAGGAGA BBI
                 ~~~~~~~~~~~~~~~~~~~~~~~~~~~~~~~~~~~~~~~~~~~~~~~~~~~~~~
         fusion site
         ~~~~~~~~
     1st CBD Linker
     ~~~~~~~~~~~~
           BamHI                SacI
           ~~~~~~               ~~~~~~
         . P   D   P   D   D   E   S   K   P   C   C   D   Q   C   A   C .
     1651 ACCGGATCCA GACGATGAGA GCTCTAAACC CTGTTGCGAT CAATGCGCAT BBI
                  ~~~~~~~~~~~~~~~~~~~~~~~~~~~~~~~~~~~~~~~~~~~~~~~~~~~~~~
         . T   K   S   N   P   P   Q   C   R   C   S   D   M   R   L   N
     1701 GTACGAAATC AAATCCTCCA CAGTGTCGGT GTTCCGATAT GCGTCTGAAT BBI
                  ~~~~~~~~~~~~~~~~~~~~~~~~~~~~~~~~~~~~~~~~~~~~~~~~~~~~~~
                SphI
                ~~~~~~
            S   C   H   S   A   C   K   S   C   I   C   A   L   S   Y   P   A .
     1751 AGCTGTCATA GTGCATGCAA AAGCTGTATC TGCGCCCTGA GTTATCCAGC BBI
                  ~~~~~~~~~~~~~~~~~~~~~~~~~~~~~~~~~~~~~~~~~~~~~~~~~~~~~~
                  SalI
                  ~~~~~~
         . Q   C   F   C   V   D   I   T   D   F   C   Y   E   P   C   K   P .
     1801 TCAATGTTTT TGCGTCGACA TCACGGACTT CTGCTATGAG CCATGTAAAC 6xHIS
                                  ~~~~~~~~~~~~~~~~~~~~~~~~~
                 BBI
                ~~~~~~~~~~~~~~~~~~~~~~~~~~
         . S   E   D   D   K   E   N   H   H   H   H   H   H   Stop   (SEQ ID NO:36)
     1851 CAAGCGAGGA CGATAAAGAG AACCATCATC ACCATCACCA TTAAAAGTTA LAT terminator
                  ~~~~~~~~~~~~~~~~~~~~~~~~~~~~~~~~~~~~~~~~~~~~~~~
                                                            HindIII
                                                            ~~~~~~
     1901 ACAGAGGACG GATTTCCTGA AGGAAATCCG TTTTTTTATT TTAAGCTTG     (SEQ ID NO:35)
```

*FIG. 14D*

```
            ~~~~~~
                              12BBIck81
                    ~~~~~~~~~~~~~~~~~~~~~~~~~~~~~~~~~~~~~~~~~~~~~~~~~~~
    BamHI          SacI
    ~~~~~~        ~~~~~~
             D   P   D    D   E   S   S    K   P   C    C   D   Q    C   A   C   Y·
      1    GGATCCAGAC  GATGAGAGCT  CTAAACCCTG  TTGCGATCAA  TGCGCATGTT
           CCTAGGTCTG  CTACTCTCGA  GATTTGGGAC  AACGCTAGTT  ACGCGTACAA

12BBIck81
                    ~~~~~~~~~~~~~~~~~~~~~~~~~~~~~~~~~~~~~~~~~~~~~~~~~~~
                                         PstI                   EcoRI
                                        ~~~~~~                 ~~~~~~
           ·  N   L   Y    G   W   T    C   R   C   S    D   M    R   L   N   S
      51   ATAATTTGTA  TGGGTGGACT  TGTCGCTGCA  GCGATATGCG  TCTGAATTCC
           TATTAAACAT  ACCCACCTGA  ACAGCGACGT  CGCTATACGC  AGACTTAAGG

12BBIck81
                    ~~~~~~~~~~~~~~~~~~~~~~~~~~~~~~~~~~~~~~~~~~~~~~~~~~~
             C   H   S   A    C   K   S    C   A   C    Y   N   L   Y   G   W   T·
     101   TGTCATAGTG  CCTGCAAAAG  CTGCGCATGT  TATAACCTGT  ACGGGTGGAC
           ACAGTATCAC  GGACGTTTTC  GACGCGTACA  ATATTGGACA  TGCCCACCTG

12BBIck81
                    ~~~~~~~~~~~~~~~~~~~~~~~~~~~~~~~~~~~~~~~~~~~~~~~~~~~
                SalI
               ~~~~~~
           · C   F   C    V   D   I   T    D   F   C    Y   E   P    C   K   P   S·
     151   CTGTTTTTGC  GTCGACATCA  CGGACTTCTG  CTATGAGCCA  TGTAAACCAA
           GACAAAAACG  CAGCTGTAGT  GCCTGAAGAC  GATACTCGGT  ACATTTGGTT

12BBIck81
                    ~~~~~~~~~~~~~~~~~~~~~~~~~~~~
           ·  E    D   D    K   E   N    *     (SEQ ID NO:38)
     201   GCGAGGACGA  TAAAGAGAAC  TAA         (SEQ ID NO:37)
           CGCTCCTGCT  ATTTCTCTTG  ATT
```

| FIG. 20A |
| FIG. 20B |
| FIG. 20C |
| FIG. 20D |

```
                                        hiPDI
         ~~~~~~~~~~~~~~~~~~~~~~~~~~~~~~~~~~~~~~~~~~~~~~~~~~
         AprE signal cleavage site
         ~~~~~~~~~~~~~~~~~~~~~~~~~
           BssHII    NheI         BsrGI
           ~~~~~~    ~~~~         ~~~~~
           S  A  Q   A  S  D  V   V  Q  L   K  K  D   T  F  D  D ·
   1     AGCGCGCAGG CTAGCGATGT TGTACAACTG AAAAAAGACA CTTTCGACGA
         TCGCGCGTCC GATCGCTACA ACATGTTGAC TTTTTTCTGT GAAAGCTGCT hiPDI
         ~~~~~~~~~~~~~~~~~~~~~~~~~~~~~~~~~~~~~~~~~~~~~~~~~~
         · F  I  K   T  N  D  L   V  L  A   E  F  F   A  P  W  C ·
  51     CTTCATCAAA ACAAATGACC TTGTTCTTGC TGAATTTTTC GCGCCGTGGT
         GAAGTAGTTT TGTTTACTGG AACAAGAACG ACTTAAAAAG CGCGGCACCA hiPDI
         ~~~~~~~~~~~~~~~~~~~~~~~~~~~~~~~~~~~~~~~~~~~~~~~~~~
         ·  G  H  C   K  A  L   A  P  E  Y   E  E  A   A  T  T
 101     GCGGTCACTG CAAAGCTCTT GCTCCTGAGT ACGAGGAAGC TGCAACTACA
         CGCCAGTGAC GTTTCGAGAA CGAGGACTCA TGCTCCTTCG ACGTTGATGT hiPDI
         ~~~~~~~~~~~~~~~~~~~~~~~~~~~~~~~~~~~~~~~~~~~~~~~~~~
            L  K  E   K  N  I  K   L  A  K   V  D  C   T  E  E  T ·
 151     CTGAAAGAAA AGAACATCAA ACTTGCTAAA GTAGACTGCA CAGAAGAGAC
         GACTTTCTTT TCTTGTAGTT TGAACGATTT CATCTGACGT GTCTTCTCTG hiPDI
         ~~~~~~~~~~~~~~~~~~~~~~~~~~~~~~~~~~~~~~~~~~~~~~~~~~
         · D  L  C   Q  Q  H  G   V  E  G   Y  P  T   L  K  V  F ·
 201     TGATCTTTGC CAACAACATG GTGTTGAGGG CTACCCAACT CTTAAAGTTT
         ACTAGAAACG GTTGTTGTAC CACAACTCCC GATGGGTTGA GAATTTCAAA
```

FIG. 20A

```
                                 hiPDI
         ~~~~~~~~~~~~~~~~~~~~~~~~~~~~~~~~~~~~~~~~~~~~~~~~~~~
           · R  G  L   D  N  V   S  P  Y   K  G  Q   R  K  A  A
     251   TCCGTGGCCT TGACAACGTA TCTCCTTACA AAGGTCAACG TAAAGCTGCT
           AGGCACCGGA ACTGTTGCAT AGAGGAATGT TTCCAGTTGC ATTTCGACGA hiPDI
         ~~~~~~~~~~~~~~~~~~~~~~~~~~~~~~~~~~~~~~~~~~~~~~~~~~~
           A  I  T   S  Y  M   I  K  Q   S  L  P   A  V  S   E  V  ·
     301   GCAATCACTT CATACATGAT CAAACAATCT CTGCCTGCTG TATCTGAAGT
           CGTTAGTGAA GTATGTACTA GTTTGTTAGA GACGGACGAC ATAGACTTCA hiPDI
         ~~~~~~~~~~~~~~~~~~~~~~~~~~~~~~~~~~~~~~~~~~~~~~~~~~~
           · T  K  D   N  L  E   E  F  K   K  A  D   K  A  V  L  V  ·
     351   TACAAAAGAC AACCTTGAAG AATTTAAAAA AGCTGACAAA GCTGTTCTTG
           ATGTTTTCTG TTGGAACTTC TTAAATTTTT TCGACTGTTT CGACAAGAAC hiPDI
         ~~~~~~~~~~~~~~~~~~~~~~~~~~~~~~~~~~~~~~~~~~~~~~~~~~~
           · A  Y  V   D  A  S   D  K  A  S   S  E  V   F  T  Q
     401   TTGCTTATGT AGATGCTTCT GACAAAGCAT CTAGCGAAGT TTTCACTCAA
           AACGAATACA TCTACGAAGA CTGTTTCGTA GATCGCTTCA AAAGTGAGTT hiPDI
         ~~~~~~~~~~~~~~~~~~~~~~~~~~~~~~~~~~~~~~~~~~~~~~~~~~~
           V  A  E  K   L  R  D   N  Y  P   F  G  S   S  D  A  ·
     451   GTTGCTGAAA AACTGCGCGA TAACTACCCA TTCGGCTCTA GCTCTGATGC
           CAACGACTTT TTGACGCGCT ATTGATGGGT AAGCCGAGAT CGAGACTACG hiPDI
         ~~~~~~~~~~~~~~~~~~~~~~~~~~~~~~~~~~~~~~~~~~~~~~~~~~~
           · A  L  A   E  A  E  G   V  K  A   P  A  I   V  L  Y  K ·
     501   TGCACTGGCT GAAGCTGAGG GCGTTAAAGC ACCTGCTATT GTTCTTTACA
           ACGTGACCGA CTTCGACTCC CGCAATTTCG TGGACGATAA CAAGAAATGT hiPDI
         ~~~~~~~~~~~~~~~~~~~~~~~~~~~~~~~~~~~~~~~~~~~~~~~~~~~
           · D  F  D   E  G  K   A  V  F  S   E  K  F   E  V  E
     551   AAGACTTTGA TGAAGGTAAA GCGGTTTTCT CTGAAAAATT CGAAGTAGAG
           TTCTGAAACT ACTTCCATTT CGCCAAAAGA GACTTTTTAA GCTTCATCTC hiPDI
         ~~~~~~~~~~~~~~~~~~~~~~~~~~~~~~~~~~~~~~~~~~~~~~~~~~~
           A  I  E  K   F  A  K   T  G  A   T  P  L   I  G  E  I  ·
     601   GCAATCGAAA AATTCGCTAA AACAGGTGCT ACTCCACTTA TTGGCGAAAT
           CGTTAGCTTT TTAAGCGATT TTGTCCACGA TGAGGTGAAT AACCGCTTTA hiPDI
         ~~~~~~~~~~~~~~~~~~~~~~~~~~~~~~~~~~~~~~~~~~~~~~~~~~~
           · G  P  E   T  Y  S  D   Y  M  S   A  G  I   P  L  A  Y ·
     651   CGGACCTGAA ACTTACTCTG ATTACATGTC AGCTGGCATC CCTCTGGCAT
           GCCTGGACTT TGAATGAGAC TAATGTACAG TCGACCGTAG GGAGACCGTA
```

*FIG. 20B*

```
                                          hiPDI
      ---------------------------------------------------------------
                      SapI
                    ---------
           ·  I   F   A   E   T   A    E   E   R   K    E   L   S    D   K   L
      701  ACATTTTCGC  TGAAACAGCT  GAAGAGCGTA  AAGAACTCAG  CGACAAACTT
           TGTAAAAGCG  ACTTTGTCGA  CTTCTCGCAT  TTCTTGAGTC  GCTGTTTGAA hiPDI
      ---------------------------------------------------------------
            K   P   I   A    E   A   Q    R   G   V    I   N   F    G   T   I   D  ·
      751  AAACCAATCG  CTGAAGCTCA  ACGTGGCGTT  ATTAACTTTG  GTACTATTGA
           TTTGGTTAGC  GACTTCGAGT  TGCACCGCAA  TAATTGAAAC  CATGATAACT hiPDI
      ---------------------------------------------------------------
           ·  A   K   A   F   G   A   H    A   G   N    L   N   L    K   T   D   K  ·
      801  CGCTAAAGCA  TTTGGTGCTC  ACGCTGGAAA  CCTGAATCTG  AAAACTGACA
           GCGATTTCGT  AAACCACGAG  TGCGACCTTT  GGACTTAGAC  TTTTGACTGT hiPDI
      ---------------------------------------------------------------
           ·  F   P   A   F   A   I    Q   E   V    A   K   N   Q    K   F   P
      851  AATTCCCTGC  TTTCGCAATC  CAAGAAGTTG  CTAAAAACCA  AAAATTCCCT
           TTAAGGGACG  AAAGCGTTAG  GTTCTTCAAC  GATTTTTGGT  TTTTAAGGGA hiPDI
      ---------------------------------------------------------------
            F   D   Q   E    K   E   I    T   F   E    A   I   K    A   F   V   D  ·
      901  TTTGATCAAG  AAAAGAAAT  TACTTTTGAA  GCGATCAAAG  CATTCGTTGA
           AAACTAGTTC  TTTTTCTTTA  ATGAAAACTT  CGCTAGTTTC  GTAAGCAACT hiPDI
      ---------------------------------------------------------------
           ·  D   F   V    A   G   K   I    E   P   S    I   K   S    E   P   I   P  ·
      951  CGATTTTGTT  GCTGGTAAAA  TCGAACCAAG  CATCAAATCA  GAACCAATCC
           GCTAAAACAA  CGACCATTTT  AGCTTGGTTC  GTAGTTTAGT  CTTGGTTAGG hiPDI
      ---------------------------------------------------------------
           ·  E   K   Q    E   G   P    V   T   V   V    V   A   K    N   Y   N
     1001  CTGAAAAACA  AGAAGGTCCT  GTTACTGTAG  TTGTAGCTAA  AAACTACAAT
           GACTTTTTGT  TCTTCCAGGA  CAATGACATC  AACATCGATT  TTTGATGTTA hiPDI
      ---------------------------------------------------------------
            E   I   V   L    D   D   T    K   D   V    L   I   E   F    Y   A   P  ·
     1051  GAAATCGTTC  TGGACGATAC  TAAAGATGTA  TTAATTGAAT  TTTACGCTCC
           CTTTAGCAAG  ACCTGCTATG  ATTTCTACAT  AATTAACTTA  AAATGCGAGG hiPDI
      ---------------------------------------------------------------
           ·  W   C   G    H   C   K   A    L   A   P    K   Y   E    E   L   G   A  ·
     1101  TTGGTGCGGT  CACTGCAAAG  CTCTTGCTCC  TAAATACGAA  GAACTTGGTG
           AACCACGCCA  GTGACGTTTC  GAGAACGAGG  ATTTATGCTT  CTTGAACCAC
```

*FIG. 20C*

```
                              hiPDI
       ------------------------------------------------------------
        ·  L   Y   A   K   S   E       F   K   D   R   V   V   I   A   K   V
 1151   CTCTGTATGC  AAAAAGCGAG  TTCAAAGACC  GTGTTGTAAT  TGCTAAAGTT
        GAGACATACG  TTTTTCGCTC  AAGTTTCTGG  CACAACATTA  ACGATTTCAA hiPDI
       ------------------------------------------------------------
         D   A   T   A   N   D   V       P   D   E       I   Q   G   F   P   T   I  ·
 1201   GATGCAACAG  CTAACGATGT  TCCAGATGAA  ATTCAAGGAT  TCCCTACTAT
        CTACGTTGTC  GATTGCTACA  AGGTCTACTT  TAAGTTCCTA  AGGGATGATA hiPDI
       ------------------------------------------------------------
        ·  K   L   Y       P   A   G   A       K   G   Q       P   V   T       Y   S   G   S  ·
 1251   CAAACTATAC  CCAGCTGGTG  CAAAAGGTCA  ACCTGTTACT  TACTCTGGTT
        GTTTGATATG  GGTCGACCAC  GTTTTCCAGT  TGGACAATGA  ATGAGACCAA hiPDI
       ------------------------------------------------------------
        ·  R   T   V       E   D   L       I   K   F   I       A   E   N       G   K   Y
 1301   CACGCACTGT  TGAAGACCTT  ATCAAATTCA  TTGCTGAAAA  CGGTAAATAC
        GTGCGTGACA  ACTTCTGGAA  TAGTTTAAGT  AACGACTTTT  GCCATTTATG hiPDI
       ------------------------------------------------------------
                                                     SpeI
                                                  ~~~~~~~
         K   A   A   I       S   E   D       A   E   E       T   S   S       A   T   E   T  ·
 1351   AAAGCTGCAA  TCTCAGAAGA  TGCTGAAGAG  ACTAGTTCAG  CAACTGAAAC
        TTTCGACGTT  AGAGTCTTCT  ACGACTTCTC  TGATCAAGTC  GTTGACTTTG hiPDI
       ------------------------------------------------------------
        ·  T   T   E       T   A   T   K       S   E   E       A   A   K       E   T   A   T  ·
 1401   AACTACAGAA  ACTGCTACAA  AGTCAGAAGA  AGCTGCAAAA  GAAACTGCAA
        TTGATGTCTT  TGACGATGTT  TCAGTCTTCT  TCGACGTTTT  CTTTGACGTT

Enteropeptidase  cleavage  linker
                                    ---------------------------------------
                hiPDI                                            N-term BBI
       ---------------------------------                         ----------
        ·  E   H   D       E   L   G       S   G   S   G       D   D   D       D   K   D
 1451   CAGAACACGA  CGAACTTGGA  TCTGGTTCCG  GAGATGACGA  TGACAAAGAC
        GTCTTGTGCT  GCTTGAACCT  AGACCAAGGC  CTCTACTGCT  ACTGTTTCTG N-term BBI
        ----------
            SacI
           ~~~~~~~
         D   E   S   S
 1501   GATGAGAGCT  CT       (SEQ ID NO:39)
        CTACTCTCGA  GA       (SEQ ID NO:40)
```

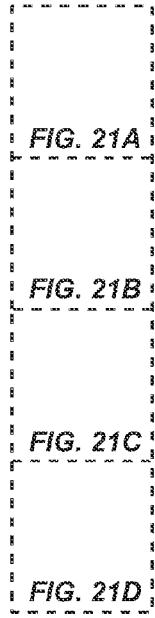

```
               aprE promoter
         ~~~~~~~~~~~~~~~~~~~~~~~~~~~~~~~~~~~~~~~~~~~~~~~~~~~~~~
    EcoRI
    ~~~~~~
 1  GAATTCTCCA TTTTCTTCTG CTATCAAAAT AACAGACTCG TGATTTTCCA
    CTTAAGAGGT AAAAGAAGAC GATAGTTTTA TTGTCTGAGC ACTAAAAGGT aprE promoter
         ~~~~~~~~~~~~~~~~~~~~~~~~~~~~~~~~~~~~~~~~~~~~~~~~~~~~~~
51  AACGAGCTTT CAAAAAAGCC TCTGCCCCTT GCAAATCGGA TGCCTGTCTA
    TTGCTCGAAA GTTTTTTCGG AGACGGGGAA CGTTTAGCCT ACGGACAGAT aprE promoter
         ~~~~~~~~~~~~~~~~~~~~~~~~~~~~~~~~~~~~~~~~~~~~~~~~~~~~~~
                                               NotI
                                            ~~~~~~~~~~
101 TAAAATTCCC GATATTGGTT AAACAGCGGC GCAATGGCGG CCGCATCTGA
    ATTTTAAGGG CTATAACCAA TTTGTCGCCG CGTTACCGCC GGCGTAGACT
```

FIG. 21A

```
                             aprE promoter
               ~~~~~~~~~~~~~~~~~~~~~~~~~~~~~~~~~~~~~~~~~~~~~~~~~~
151     TGTCTTTGCT TGGCGAATGT TCATCTTATT TCTTCCTCCC TCTCAATAAT
        ACAGAAACGA ACCGCTTACA AGTAGAATAA AGAAGGAGGG AGAGTTATTA aprE promoter
               ~~~~~~~~~~~~~~~~~~~~~~~~~~~~~~~~~~~~~~~~~~~~~~~~~~
201     TTTTTCATTC TATCCCTTTT CTGTAAAGTT TATTTTTCAG AATACTTTTA
        AAAAGTAAG ATAGGGAAAA GACATTTCAA ATAAAAGTC TTATGAAAAT aprE promoter
               ~~~~~~~~~~~~~~~~~~~~~~~~~~~~~~~~~~~~~~~~~~~~~~~~~~
251     TCATCATGCT TTGAAAAAAT ATCACGATAA TATCCATTGT TCTCACGGAA
        AGTAGTACGA AACTTTTTTA TAGTGCTATT ATAGGTAACA AGAGTGCCTT aprE promoter
               ~~~~~~~~~~~~~~~~~~~~~~~~~~~~~~~~~~~~~~~~~~~~~~~~~~
301     GCACACGCAG GTCATTTGAA CGAATTTTTT CGACAGGAAT TTGCCGGGAC
        CGTGTGCGTC CAGTAAACTT GCTTAAAAAA GCTGTCCTTA AACGGCCCTG aprE promoter
               ~~~~~~~~~~~~~~~~~~~~~~~~~~~~~~~~~~~~~~~~~~~~~~~~~~
351     TCAGGAGCAT TTAACCTAAA AAAGCATGAC ATTTCAGCAT AATGAACATT
        AGTCCTCGTA AATTGGATTT TTTCGTACTG TAAAGTCGTA TTACTTGTAA aprE promoter
               ~~~~~~~~~~~~~~~~~~~~~~~~~~~~~~~~~~~~~~~~~~~~~~~~~~
401     TACTCATGTC TATTTTCGTT CTTTTCTGTA TGAAAATAGT TATTTCGAGT
        ATGAGTACAG ATAAAAGCAA GAAAAGACAT ACTTTTATCA ATAAAGCTCA aprE promoter
               ~~~~~~~~~~~~~~~~~~~~~~~~~~~~~~~~~~~~~~~~~~~~~~~~~~
451     CTCTACGGAA ATAGCGAGAG ATGATATACC TAAATAGAGA TAAAATCATC
        GAGATGCCTT TATCGCTCTC TACTATATGG ATTTATCTCT ATTTTAGTAG aprE promoter
               ~~~~~~~~~~~~~~~~~~~~~~~~~~~~~~~~~~~~~~~~~~~~~~~~~~
501     TCAAAAAAAT GGGTCTACTA AAATATTATT CCATCTATTA CAATAAATTC
        AGTTTTTTTA CCCAGATGAT TTTATAATAA GGTAGATAAT GTTATTTAAG aprE promoter
               ~~~~~~~~~~~~~~~~~~~~~~~~~~~~~~~~~~~~~~~~~~~~~~~~~~
551     ACAGAATAGT CTTTTAAGTA AGTCTACTCT GAATTTTTTT AAAAGGAGAG
        TGTCTTATCA GAAAATTCAT TCAGATGAGA CTTAAAAAAA TTTTCCTCTC aprE promoter                         Cutinase signal peptide
        ~~~~~~~~~                             ~~~~~~~~~~~~~~~~~~~~~~~
               AprE signal peptide
               ~~~~~~~~~~~~~~~~~~~~~~~~~~
                V   R   S   K   K   L   W   I   S   L   L   F   A   L
601     GGTAAAGAGT GAGAAGCAAA AAATTGTGGA TCAGCTTGTT GTTTGCGTTA
        CCATTTCTCA CTCTTCGTTT TTTAACACCT AGTCGAACAA CAAACGCAAT
```

*FIG. 21B*

```
                                                                Cutinase
                                                                ~~~~~
                Cutinase signal peptide
       ~~~~~~~~~~~~~~~~~~~~~~~~~~~~~~~~~~~~~~~~~~~~~~~~~~~~~~~
         T   L   A   A   S   C   L   S   V   C   A   T   V   A   A   A   P  ·
   651   ACGCTGGCGG CCTCTTGCCT GTCCGTCTGT GCCACTGTCG CGGCGGCTCC
         TGCGACCGCC GGAGAACGGA CAGGCAGACA CGGTGACAGC GCCGCCGAGG Cutinase
       ~~~~~~~~~~~~~~~~~~~~~~~~~~~~~~~~~~~~~~~~~~~~~~~~~~~~~~~
         ·  L   P   D   T   P   G   A   P   F   P   A   V   A   N   F   D   R  ·
   701   CCTGCCGGAT ACACCGGGAG CGCCATTTCC GGCTGTCGCC AATTTCGACC
         GGACGGCCTA TGTGGCCCTC GCGGTAAAGG CCGACAGCGG TTAAAGCTGG Cutinase
       ~~~~~~~~~~~~~~~~~~~~~~~~~~~~~~~~~~~~~~~~~~~~~~~~~~~~~~~
         ·  S   G   P   Y   T   T   S   S   Q   S   E   G   P   S   C   R
   751   GCAGTGGCCC CTACACCACC AGCAGCCAGA GCGAGGGGCC GAGCTGTCGC
         CGTCACCGGG GATGTGGTGG TCGTCGGTCT CGCTCCCCGG CTCGACAGCG Cutinase
       ~~~~~~~~~~~~~~~~~~~~~~~~~~~~~~~~~~~~~~~~~~~~~~~~~~~~~~~
         I   Y   R   P   R   D   L   G   Q   G   G   V   R   H   P   V   I  ·
   801   ATCTATCGGC CCGCGACCT GGGTCAGGGG GGCGTGCGTC ATCCGGTGAT
         TAGATAGCCG GGGCGCTGGA CCCAGTCCCC CCGCACGCAG TAGGCCACTA Cutinase
       ~~~~~~~~~~~~~~~~~~~~~~~~~~~~~~~~~~~~~~~~~~~~~~~~~~~~~~~
         ·  L   W   G   N   G   T   G   A   G   P   S   T   Y   A   G   L   L  ·
   851   TCTCTGGGGC AATGGCACCG GTGCCGGGCC GTCCACCTAT GCCGGCTTGC
         AGAGACCCCG TTACCGTGGC CACGGCCCGG CAGGTGGATA CGGCCGAACG Cutinase
       ~~~~~~~~~~~~~~~~~~~~~~~~~~~~~~~~~~~~~~~~~~~~~~~~~~~~~~~
         ·  S   H   W   A   S   H   G   F   V   V   A   A   A   E   T   S
   901   TATCGCACTG GGCAAGCCAC GGTTTCGTGG TGGCGGCGGC GGAAACCTCC
         ATAGCGTGAC CCGTTCGGTG CCAAAGCACC ACCGCCGCCG CCTTTGGAGG Cutinase
       ~~~~~~~~~~~~~~~~~~~~~~~~~~~~~~~~~~~~~~~~~~~~~~~~~~~~~~~
         N   A   G   T   G   R   E   M   L   A   C   L   D   Y   L   V   R  ·
   951   AATGCCGGTA CCGGGCGGGA AATGCTCGCC TGCCTGGACT ATCTGGTACG
         TTACGGCCAT GGCCCGCCCT TTACGAGCGG ACGGACCTGA TAGACCATGC Cutinase
       ~~~~~~~~~~~~~~~~~~~~~~~~~~~~~~~~~~~~~~~~~~~~~~~~~~~~~~~
         ·  E   N   D   T   P   Y   G   T   Y   S   G   K   L   N   T   G   R  ·
  1001   TGAGAACGAC ACCCCCTACG GCACCTATTC CGGCAAGCTC AATACCGGGC
         ACTCTTGCTG TGGGGGATGC CGTGGATAAG GCCGTTCGAG TTATGGCCCG Cutinase
       ~~~~~~~~~~~~~~~~~~~~~~~~~~~~~~~~~~~~~~~~~~~~~~~~~~~~~~~
         ·  V   G   T   S   G   H   S   Q   G   G   G   G   S   I   M   A
  1051   GAGTCGGCAC TTCTGGGCAT TCCCAGGGTG GTGGCGGCTC GATCATGGCC
         CTCAGCCGTG AAGACCCGTA AGGGTCCCAC CACCGCCGAG CTAGTACCGG
```

*FIG. 21C*

```
                                  Cutinase
        ~~~~~~~~~~~~~~~~~~~~~~~~~~~~~~~~~~~~~~~~~~~~~~~~~~~~~~~~~~~
           G   Q   D   T   R   V   R   T   T   A   P   I   Q   P   Y   T   L  ·
      1101 GGGCAGGATA CGAGGGTGCG TACCACGGCG CCGATCCAGC CCTACACCCT
           CCCGTCCTAT GCTCCCACGC ATGGTGCCGC GGCTAGGTCG GGATGTGGGA Cutinase
        ~~~~~~~~~~~~~~~~~~~~~~~~~~~~~~~~~~~~~~~~~~~~~~~~~~~~~~~~~~~
          ·  G   L   G   H   D   S   A   S   Q   R   R   Q   Q   G   P   M   F  ·
      1151 CGGCCTGGGG CACGACAGCG CCTCGCAGCG GCGGCAGCAG GGGCCGATGT
           GCCGGACCCC GTGCTGTCGC GGAGCGTCGC CGCCGTCGTC CCCGGCTACA Cutinase
        ~~~~~~~~~~~~~~~~~~~~~~~~~~~~~~~~~~~~~~~~~~~~~~~~~~~~~~~~~~~
          ·  L   M   S   G   G   D   T   I   A   F   P   Y   L   N   A
      1201 TCCTGATGTC CGGTGGCGGT GACACCATCG CCTTTCCCTA CCTCAACGCT
           AGGACTACAG GCCACCGCCA CTGTGGTAGC GGAAAGGGAT GGAGTTGCGA Cutinase
        ~~~~~~~~~~~~~~~~~~~~~~~~~~~~~~~~~~~~~~~~~~~~~~~~~~~~~~~~~~~
           Q   P   V   Y   R   R   A   N   V   P   V   F   W   G   E   R   R  ·
      1251 CAGCCGGTCT ACCGGCGTGC CAATGTGCCG GTGTTCTGGG GCGAACGGCG
           GTCGGCCAGA TGGCCGCACG GTTACACGGC CACAAGACCC CGCTTGCCGC
                                  Cutinase
        ~~~~~~~~~~~~~~~~~~~~~~~~~~~~~~~~~~~~~~~~~~~~~~~~~~~~~~~~~~~
          ·  Y   V   S   H   F   E   P   V   G   S   G   G   A   Y   R   G   P  ·
      1301 TTACGTCAGC CACTTCGAGC CGGTCGGTAG CGGTGGGGCC TATCGCGGCC
           AATGCAGTCG GTGAAGCTCG GCCAGCCATC GCCACCCCGG ATAGCGCCGG Cutinase
        ~~~~~~~~~~~~~~~~~~~~~~~~~~~~~~~~~~~~~~~~~~~~~~~~~~~~~~~~~~~
          ·  S   T   A   W   F   R   F   Q   L   M   D   D   Q   D   A   R
      1351 CGAGCACGGC ATGGTTCCGC TTCCAGCTGA TGGATGACCA AGACGCCCGC
           GCTCGTGCCG TACCAAGGCG AAGGTCGACT ACCTACTGGT TCTGCGGGCG Cutinase
        ~~~~~~~~~~~~~~~~~~~~~~~~~~~~~~~~~~~~~~~~~~~~~~~~~~~~~~~~~~~
                                            Alw44I
                                           ~~~~~~~~
           A   T   F   Y   G   A   Q   C   S   L   C   T   S   L   W   S  ·
      1401 GCTACCTTCT ACGGCGCGCA GTGCAGTCTG TGCACTTCTC TGCTTTGGTC
           CGATGGAAGA TGCCGCGCGT CACGTCAGAC ACGTGAAGAG ACGAAACCAG Linker 2
                                   ~~~~~~~~~~~~~~~~~~~~~~~~~~~~~~
           Cutinase
        ~~~~~~~~~~~~~~~~~~~~~~~~~
                                                       BamHI
                                                      ~~~~~~~
          ·  V   E   R   R   G   L   D   N   N   D   P   I   P   D
      1451 TGTTGAACGC AGAGGTCTTG ACAACAATGA TCCTATTCCG GATCC   (SEQ ID NO:41)
           ACAACTTGCG TCTCCAGAAC TGTTGTTACT AGGATAAGGC CTAGG   (SEQ ID NO:42)
```

*FIG. 21D*

SEQUENCE LISTING

<160> NUMBER OF SEQ ID NOS: 253

<210> SEQ ID NO 1
<211> LENGTH: 7
<212> TYPE: PRT
<213> ORGANISM: Artificial Sequence
<220> FEATURE:
<223> OTHER INFORMATION: synthetic VEGF binding phage clone

<400> SEQUENCE: 1

Tyr Asn Leu Tyr Gly Trp Thr
1               5

<210> SEQ ID NO 2
<211> LENGTH: 7
<212> TYPE: PRT
<213> ORGANISM: Artificial Sequence
<220> FEATURE:
<223> OTHER INFORMATION: synthetic VEGF binding phage clone

<400> SEQUENCE: 2

Thr Leu Trp Pro Thr Phe Trp
1               5

<210> SEQ ID NO 3
<211> LENGTH: 7
<212> TYPE: PRT
<213> ORGANISM: Artificial Sequence
<220> FEATURE:
<223> OTHER INFORMATION: synthetic VEGF binding phage clone

<400> SEQUENCE: 3

Asn Leu Trp Pro His Phe Trp
1               5

<210> SEQ ID NO 4
<211> LENGTH: 7
<212> TYPE: PRT
<213> ORGANISM: Artificial Sequence
<220> FEATURE:
<223> OTHER INFORMATION: synthetic VEGF binding phage clone

<400> SEQUENCE: 4

Ser Leu Trp Pro Ala Phe Trp
1               5

<210> SEQ ID NO 5
<211> LENGTH: 7
<212> TYPE: PRT
<213> ORGANISM: Artificial Sequence
<220> FEATURE:
<223> OTHER INFORMATION: synthetic VEGF binding phage clone

<400> SEQUENCE: 5

Ala Pro Trp Asn Ser His Ile
1               5

<210> SEQ ID NO 6
<211> LENGTH: 7
<212> TYPE: PRT
<213> ORGANISM: Artificial Sequence
<220> FEATURE:
<223> OTHER INFORMATION: synthetic VEGF binding phage clone

<400> SEQUENCE: 6

Ala Pro Trp Asn Leu His Ile
1               5

```
<210> SEQ ID NO 7
<211> LENGTH: 7
<212> TYPE: PRT
<213> ORGANISM: Artificial Sequence
<220> FEATURE:
<223> OTHER INFORMATION: synthetic VEGF binding phage clone

<400> SEQUENCE: 7

Thr Leu Trp Pro Ser Tyr Trp
1               5

<210> SEQ ID NO 8
<211> LENGTH: 7
<212> TYPE: PRT
<213> ORGANISM: Artificial Sequence
<220> FEATURE:
<223> OTHER INFORMATION: synthetic VEGF binding phage clone

<400> SEQUENCE: 8

Tyr Asn Leu Tyr Gly Trp Thr
1               5

<210> SEQ ID NO 9
<211> LENGTH: 7
<212> TYPE: PRT
<213> ORGANISM: Artificial Sequence
<220> FEATURE:
<223> OTHER INFORMATION: synthetic VEGF binding phage clone

<400> SEQUENCE: 9

Ala Pro Trp Asn Ser His Ile
1               5

<210> SEQ ID NO 10
<211> LENGTH: 7
<212> TYPE: PRT
<213> ORGANISM: Artificial Sequence
<220> FEATURE:
<223> OTHER INFORMATION: synthetic VEGF binding phage clone

<400> SEQUENCE: 10

Ala Pro Trp Asn Leu His Ile
1               5

<210> SEQ ID NO 11
<211> LENGTH: 7
<212> TYPE: PRT
<213> ORGANISM: Artificial Sequence
<220> FEATURE:
<223> OTHER INFORMATION: synthetic VEGF binding phage clone

<400> SEQUENCE: 11

Thr Leu Trp Pro Ser Tyr Trp
1               5

<210> SEQ ID NO 12
<211> LENGTH: 7
<212> TYPE: PRT
<213> ORGANISM: Artificial Sequence
<220> FEATURE:
<223> OTHER INFORMATION: synthetic VEGF binding phage clone

<400> SEQUENCE: 12

Ser Leu Trp Pro Ala Phe Trp
1               5
```

```
<210> SEQ ID NO 13
<211> LENGTH: 7
<212> TYPE: PRT
<213> ORGANISM: Artificial Sequence
<220> FEATURE:
<223> OTHER INFORMATION: synthetic randomized sequence

<400> SEQUENCE: 13

His Leu Ala Pro Ser Ala Val
1               5

<210> SEQ ID NO 14
<211> LENGTH: 10
<212> TYPE: PRT
<213> ORGANISM: Artificial Sequence
<220> FEATURE:
<223> OTHER INFORMATION: conserved sequence of SEQ ID NO:1-12
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (7)..(8)
<223> OTHER INFORMATION: Xaa can be any naturally occurring amino acid

<400> SEQUENCE: 14

Ala Cys Xaa Leu Trp Pro Xaa Xaa Trp Cys
1               5                   10

<210> SEQ ID NO 15
<211> LENGTH: 8
<212> TYPE: PRT
<213> ORGANISM: Artificial Sequence
<220> FEATURE:
<223> OTHER INFORMATION: conserved binding sequence of SEQ ID NO:1-12
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 15

Xaa Xaa Leu Trp Pro Xaa Trp Cys
1               5

<210> SEQ ID NO 16
<211> LENGTH: 7
<212> TYPE: PRT
<213> ORGANISM: Artificial Sequence
<220> FEATURE:
<223> OTHER INFORMATION: synthetic PS-AV1 peptide

<400> SEQUENCE: 16

Lys Tyr Tyr Leu Tyr Trp Trp
1               5

<210> SEQ ID NO 17
<211> LENGTH: 7
<212> TYPE: PRT
<213> ORGANISM: Artificial Sequence
<220> FEATURE:
<223> OTHER INFORMATION: synthetic PS-AV2 peptide

<400> SEQUENCE: 17

Thr Leu Trp Lys Ser Tyr Trp
```

<210> SEQ ID NO 18
<211> LENGTH: 99
<212> TYPE: PRT
<213> ORGANISM: Artificial Sequence
<220> FEATURE:
<223> OTHER INFORMATION: synthetic BBI sequence

<400> SEQUENCE: 18

```
Met Gly Ala Asn Leu Arg Leu Ser Lys Leu Gly Leu Leu Met Lys Ser
1               5                   10                  15
Asp His Gln His Ser Asn Asp Asp Glu Ser Ser Lys Pro Cys Cys Asp
            20                  25                  30
Gln Cys Ala Cys Thr Lys Ser Asn Pro Pro Gln Cys Arg Cys Ser Asp
        35                  40                  45
Met Arg Leu Asn Ser Cys His Ser Ala Cys Lys Ser Cys Ile Cys Ala
    50                  55                  60
Leu Ser Tyr Pro Ala Gln Cys Phe Cys Val Asp Ile Thr Asp Phe Cys
65                  70                  75                  80
Tyr Glu Pro Cys Lys Pro Ser Glu Asp Asp Lys Glu Asn His His His
                85                  90                  95
His His His
```

<210> SEQ ID NO 19
<211> LENGTH: 308
<212> TYPE: DNA
<213> ORGANISM: Artificial Sequence
<220> FEATURE:
<223> OTHER INFORMATION: synthetic BBI sequence

<400> SEQUENCE: 19

```
ccatgggtgc gaacctgcgt ctgtctaagc ttggcctgct tatgaaatca gaccatcagc    60
acagcaatga cgatgagagc tctaaaccct gttgcgatca atgcgcatgt acaaaatcaa   120
atcctccaca gtgtcggtgt tccgatatgc gtctgaattc ctgtcatagt gcatgcaaaa   180
gctgtatctg cgccctgagt tatccagctc aatgttttg cgtcgacatc acggacttct   240
gctatgagcc atgtaaacca agcgaggacg ataaagaaa ccatcagcac catcaccatt    300
aactcgag                                                            308
```

<210> SEQ ID NO 20
<211> LENGTH: 9
<212> TYPE: PRT
<213> ORGANISM: Artificial Sequence
<220> FEATURE:
<223> OTHER INFORMATION: synthetic BBI trypsin loop

<400> SEQUENCE: 20

```
Cys Thr Lys Ser Asn Pro Pro Gln Cys
1               5
```

<210> SEQ ID NO 21
<211> LENGTH: 9
<212> TYPE: PRT
<213> ORGANISM: Artificial Sequence
<220> FEATURE:
<223> OTHER INFORMATION: synthetic BBI chymotrypsin loop

<400> SEQUENCE: 21

```
Cys Ala Leu Ser Tyr Pro Ala Gln Cys
1               5
```

<210> SEQ ID NO 22
<211> LENGTH: 70
<212> TYPE: PRT
<213> ORGANISM: Artificial Sequence
<220> FEATURE:
<223> OTHER INFORMATION: synthetic fusion peptide

<400> SEQUENCE: 22

Asp Asp Glu Ser Ser Lys Pro Cys Cys Asp Gln Cys Ala Cys Tyr Asn
1               5                   10                  15

Leu Tyr Gly Trp Thr Cys Arg Cys Ser Asp Met Arg Leu Asn Ser Cys
            20                  25                  30

His Ser Ala Cys Lys Ser Cys Ile Cys Ala Leu Ser Tyr Pro Ala Gln
        35                  40                  45

Cys Phe Cys Val Asp Leu Thr Asp Phe Cys Glu Pro Cys Lys Pro Ser
    50                  55                  60

Glu Asp Asp Lys Glu Asn
65                  70

<210> SEQ ID NO 23
<211> LENGTH: 71
<212> TYPE: PRT
<213> ORGANISM: Artificial Sequence
<220> FEATURE:
<223> OTHER INFORMATION: synthetic fusion peptide

<400> SEQUENCE: 23

Asp Asp Glu Ser Ser Lys Pro Cys Cys Asp Gln Cys Ala Cys Thr Lys
1               5                   10                  15

Ser Asn Pro Pro Gln Cys Arg Cys Ser Asp Met Arg Leu Asn Ser Cys
            20                  25                  30

His Ser Ala Cys Lys Ser Cys Ala Cys Tyr Asn Leu Tyr Gly Trp Thr
        35                  40                  45

Cys Phe Cys Val Asp Leu Thr Asp Phe Cys Tyr Glu Pro Cys Lys Pro
    50                  55                  60

Ser Glu Asp Asp Lys Glu Asn
65                  70

<210> SEQ ID NO 24
<211> LENGTH: 71
<212> TYPE: PRT
<213> ORGANISM: Artificial Sequence
<220> FEATURE:
<223> OTHER INFORMATION: synthetic fusion peptide

<400> SEQUENCE: 24

Asp Asp Glu Ser Ser Lys Pro Cys Cys Asp Gln Cys Ala Cys Tyr Asn
1               5                   10                  15

Leu Tyr Gly Trp Thr Cys Arg Cys Ser Asp Met Arg Ile Asn Ser Cys
            20                  25                  30

His Ser Ala Cys Lys Ser Cys Ala Cys Tyr Asn Leu Tyr Gly Trp Thr
        35                  40                  45

Cys Phe Cys Val Asp Leu Thr Asp Phe Cys Tyr Glu Pro Cys Lys Pro
    50                  55                  60

Ser Glu Asp Asp Lys Glu Asn
65                  70

<210> SEQ ID NO 25
<211> LENGTH: 71

```
<212> TYPE: PRT
<213> ORGANISM: Artificial Sequence
<220> FEATURE:
<223> OTHER INFORMATION: synthetic BBI isoform

<400> SEQUENCE: 25

Asp Asp Glu Ser Ser Lys Pro Cys Cys Asp Gln Cys Ala Cys Thr Lys
1               5                   10                  15

Ser Asn Pro Pro Gln Cys Arg Cys Ser Asp Met Arg Leu Asn Ser Cys
            20                  25                  30

His Ser Ala Cys Lys Ser Cys Ile Cys Ala Leu Ser Tyr Pro Ala Gln
        35                  40                  45

Cys Phe Cys Val Asp Ile Thr Asp Phe Cys Tyr Glu Pro Cys Lys Pro
50                  55                  60

Ser Glu Asp Asp Lys Glu Asn
65                  70

<210> SEQ ID NO 26
<211> LENGTH: 98
<212> TYPE: DNA
<213> ORGANISM: Artificial Sequence
<220> FEATURE:
<223> OTHER INFORMATION: synthetic oligonucleotide

<400> SEQUENCE: 26
ctagtgtctt cgatcaagtc gacaacagcc tgtctgcaga tcctgaagac tggcggaggt      60
ggtcgcgaat acgattaccc cgctgatgaa agcacaga                             98

<210> SEQ ID NO 27
<211> LENGTH: 91
<212> TYPE: DNA
<213> ORGANISM: Artificial Sequence
<220> FEATURE:
<223> OTHER INFORMATION: synthetic oligonucleotide

<400> SEQUENCE: 27
gtgctttcat cagcggggta atcgtattcg cgaccacctc cgccagtctt caggatctgc      60
agacaggctg ttgtcgactt gatcgaagac a                                    91

<210> SEQ ID NO 28
<211> LENGTH: 94
<212> TYPE: DNA
<213> ORGANISM: Artificial Sequence
<220> FEATURE:
<223> OTHER INFORMATION: primer

<400> SEQUENCE: 28
actagtcgtt cctttctatt ctcactctgc ttgtaccctg tggccgacct tctggtgcgg      60
tggaggttcg acgccagtgt cagaaaaaca gctg                                 94

<210> SEQ ID NO 29
<211> LENGTH: 27
<212> TYPE: DNA
<213> ORGANISM: Artificial Sequence
<220> FEATURE:
<223> OTHER INFORMATION: primer

<400> SEQUENCE: 29
agcagagtga gaatagaaag gaacgac                                         27

<210> SEQ ID NO 30
<211> LENGTH: 25
```

```
<212> TYPE: DNA
<213> ORGANISM: Artificial Sequence
<220> FEATURE:
<223> OTHER INFORMATION: primer

<400> SEQUENCE: 30
ccgccagctg tttttctgac actgg                                              25

<210> SEQ ID NO 31
<211> LENGTH: 14
<212> TYPE: PRT
<213> ORGANISM: Artificial Sequence
<220> FEATURE:
<223> OTHER INFORMATION: synthetic random library peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(9)
<223> OTHER INFORMATION: Xaa can be any naturally occurring amino acid

<400> SEQUENCE: 31

Xaa Cys Xaa Xaa Xaa Xaa Xaa Xaa Xaa Cys Gly Gly Gly Ser
1               5                   10

<210> SEQ ID NO 32
<211> LENGTH: 6
<212> TYPE: PRT
<213> ORGANISM: Mus musculus

<400> SEQUENCE: 32

Ser Leu Ile Gly Arg Leu
1               5

<210> SEQ ID NO 33
<211> LENGTH: 7
<212> TYPE: PRT
<213> ORGANISM: Artificial Sequence
<220> FEATURE:
<223> OTHER INFORMATION: synthetic peptide

<400> SEQUENCE: 33

Lys Tyr Asp Leu Tyr Trp Trp
1               5

<210> SEQ ID NO 34
<211> LENGTH: 7
<212> TYPE: PRT
<213> ORGANISM: Artificial Sequence
<220> FEATURE:
<223> OTHER INFORMATION: synthetic peptide

<400> SEQUENCE: 34

Asp Tyr Lys Leu Tyr Trp Trp
1               5

<210> SEQ ID NO 35
<211> LENGTH: 1950
<212> TYPE: DNA
<213> ORGANISM: Artificial Sequence
<220> FEATURE:
<223> OTHER INFORMATION: synthetic aprE-BCE103-BBI-histag expression
      cassette

<400> SEQUENCE: 35
aattctccat tttcttctgc tatcaaaata acagactcgt gattttccaa acgagctttc    60
```

```
aaaaaagcct ctgccccttg caaatcggat gcctgtctat aaaattcccg atattggtta      120
aacagcggcg caatggcggc cgcatctgat gtctttgctt ggcgaatgtt catcttattt      180
cttcctccct ctcaataatt ttttcattct atccttttc tgtaaagttt attttcaga       240
atacttttat catcatgctt tgaaaaaata tcacgataat atccattgtt ctcacggaag      300
cacacgcagg tcatttgaac gaattttttc gacaggaatt tgccgggact caggagcatt      360
taacctaaaa aagcatgaca tttcagcata atgaacattt actcatgtct attttcgttc      420
ttttctgtat gaaatagtt atttcgagtc tctacggaaa tagcgagaga tgatatacct      480
aaatagagat aaaatcatct caaaaaatg ggtctactaa atatattc catctattac        540
aataaattca cagaatagtc ttttaagtaa gtctactctg aattttttta aaggagagg      600
gtaaagagtg agaagcaaaa aattgtggat cagcttgttg tttgcgttaa cgttaatctt     660
tacgatggcg ttcagcaaca tgtctgcgca ggctgatgat tattcagttg tagaggaaca     720
tgggcaacta agtattagta acggtgaatt agtcaatgaa cgaggcgaac aagttcagtt     780
aaaagggatg agttcccatg gtttgcaatg gtacggtcaa tttgtaaact atgaaagcat     840
gaaatggcta agagatgatt ggggaataac tgtattccga gcagcaatgt atacctcttc     900
aggaggatat attgacgatc catcagtaaa ggaaaaatga aaagagactg ttgaggctgc     960
gatagacctt ggcatatatg tgatcattga ttggcatatc ctttcagaca atgacccgaa    1020
tatatataaa gaagaagcga aggatttctt tgatgaaatg tcagagttgt atggagacta    1080
tccgaatgtg atatacgaaa ttgcaaatga accgaatggt agtgatgtta cgtgggacaa    1140
tcaaataaaa ccgtatgcag aagaagtgat tccggttatt cgtgacaatg accctaataa    1200
cattgttatt gtaggtacag gtacatggag tcaggatgtc catcatgcag ccgataatca    1260
gcttgcagat cctaacgtca tgtatgcatt tcatttttat gcaggaacac atggacaaaa    1320
tttacgagac caagtagatt atgcattaga tcaaggagca gcgatatttg ttatgtaatg    1380
ggggacaagt gcagctacag gtgatggtgg tgtgttttta gatgaagcac aagtgtggat    1440
tgactttatg gatgaaagaa atttaagctg ggccaactgg tctctaacgc ataaggatga    1500
gtcatctgca gcgttaatgc caggtgcaaa tccaactggt ggttggacag aggctgaact    1560
atctccatct ggtacatttg tgagggaaaa aataagagaa tcagcatcta ttccgccaag    1620
cgatccaaca ccgccatctg atccaggaga accggatcca gacgatgaga gctctaaacc    1680
ctgttgcgat caatgcgcat gtacgaaatc aaatcctcca cagtgtcggt gttccgatat    1740
gcgtctgaat agctgtcata gtgcatgcaa agctgtatc tgcgccctga ttatccagc     1800
tcaatgtttt tgcgtcgaca tcacggactt ctgctatgag ccatgtaaac caagcgagga    1860
cgataaagag aaccatcatc accatcacca ttaaaagtta acagaggacg gatttcctga    1920
aggaaatccg ttttttattt ttaagcttg                                       1950
```

<210> SEQ ID NO 36
<211> LENGTH: 426
<212> TYPE: PRT
<213> ORGANISM: Artificial Sequence
<220> FEATURE:
<223> OTHER INFORMATION: synthetic peptide encoded by SEQ ID NO:35

<400> SEQUENCE: 36

Met Arg Ser Lys Lys Leu Trp Ile Ser Leu Leu Phe Ala Leu Thr Leu
1               5                   10                  15

Ile Phe Thr Met Ala Phe Ser Asn Met Ser Ala Gln Ala Asp Asp Tyr

```
            20                  25                  30
Ser Val Val Glu Glu His Gly Gln Leu Ser Ile Ser Asn Gly Glu Leu
        35                  40                  45

Val Asn Glu Arg Gly Glu Gln Val Gln Leu Lys Gly Met Ser Ser His
50                  55                  60

Gly Leu Gln Trp Tyr Gly Gln Phe Val Asn Tyr Glu Ser Met Lys Trp
65                  70                  75                  80

Leu Arg Asp Asp Trp Gly Ile Thr Val Phe Arg Ala Ala Met Tyr Thr
                85                  90                  95

Ser Ser Gly Gly Tyr Ile Asp Asp Pro Ser Val Lys Glu Lys Lys Glu
            100                 105                 110

Thr Val Glu Ala Ala Ile Asp Leu Gly Ile Tyr Val Ile Ile Asp Trp
        115                 120                 125

His Ile Leu Ser Asp Asn Asp Pro Asn Ile Tyr Lys Glu Glu Ala Lys
    130                 135                 140

Asp Phe Phe Asp Glu Met Ser Glu Leu Tyr Gly Asp Tyr Pro Asn Val
145                 150                 155                 160

Ile Tyr Glu Ile Ala Asn Glu Pro Asn Gly Ser Asp Val Thr Trp Asp
                165                 170                 175

Asn Gln Ile Lys Pro Tyr Ala Glu Glu Val Ile Pro Val Ile Arg Asp
            180                 185                 190

Asn Asp Pro Asn Asn Ile Val Ile Val Gly Thr Gly Thr Trp Ser Gln
        195                 200                 205

Asp Val His His Ala Ala Asp Asn Gln Leu Ala Asp Pro Asn Val Met
    210                 215                 220

Tyr Ala Phe His Phe Tyr Ala Gly Thr His Gly Gln Asn Leu Arg Asp
225                 230                 235                 240

Gln Val Asp Tyr Ala Leu Asp Gln Gly Ala Ala Ile Phe Val Met Trp
                245                 250                 255

Gly Thr Ser Ala Ala Thr Gly Asp Gly Gly Val Phe Leu Asp Glu Ala
            260                 265                 270

Gln Val Trp Ile Asp Phe Met Asp Glu Arg Asn Leu Ser Trp Ala Asn
        275                 280                 285

Trp Ser Leu Thr His Lys Asp Glu Ser Ser Ala Ala Leu Met Pro Gly
    290                 295                 300

Ala Asn Pro Thr Gly Gly Trp Thr Glu Ala Glu Leu Ser Pro Ser Gly
305                 310                 315                 320

Thr Phe Val Arg Glu Lys Ile Arg Glu Ser Ala Ser Ile Pro Pro Ser
                325                 330                 335

Asp Pro Thr Pro Pro Ser Asp Pro Gly Glu Pro Asp Pro Asp Asp Glu
            340                 345                 350

Ser Ser Lys Pro Cys Cys Asp Gln Cys Ala Cys Thr Lys Ser Asn Pro
        355                 360                 365

Pro Gln Cys Arg Cys Ser Asp Met Arg Leu Asn Ser Cys His Ser Ala
    370                 375                 380

Cys Lys Ser Cys Ile Cys Ala Leu Ser Tyr Pro Ala Gln Cys Phe Cys
385                 390                 395                 400

Val Asp Ile Thr Asp Phe Cys Tyr Glu Pro Cys Lys Pro Ser Glu Asp
                405                 410                 415

Asp Lys Glu Asn His His His His His
            420                 425

<210> SEQ ID NO 37
```

<211> LENGTH: 223
<212> TYPE: DNA
<213> ORGANISM: Artificial Sequence
<220> FEATURE:
<223> OTHER INFORMATION: synthetic 12BBIck81

<400> SEQUENCE: 37

```
ggatccagac gatgagagct ctaaaccctg ttgcgatcaa tgcgcatgtt ataatttgta      60
tgggtggact tgtcgctgca gcgatatgcg tctgaattcc tgtcatagtg cctgcaaaag     120
ctgcgcatgt tataacctgt acgggtggac ctgttttgc gtcgacatca cggacttctg      180
ctatgagcca tgtaaaccaa gcgaggacga taaagagaac taa                        223
```

<210> SEQ ID NO 38
<211> LENGTH: 73
<212> TYPE: PRT
<213> ORGANISM: Artificial Sequence
<220> FEATURE:
<223> OTHER INFORMATION: synthetic 12BBIck81

<400> SEQUENCE: 38

Asp Pro Asp Asp Glu Ser Ser Lys Pro Cys Cys Asp Gln Cys Ala Cys
1               5                   10                  15

Tyr Asn Leu Tyr Gly Trp Thr Cys Arg Cys Ser Asp Met Arg Leu Asn
            20                  25                  30

Ser Cys His Ser Ala Cys Lys Ser Cys Ala Cys Tyr Asn Leu Tyr Gly
        35                  40                  45

Trp Thr Cys Phe Cys Val Asp Ile Thr Asp Phe Cys Tyr Glu Pro Cys
    50                  55                  60

Lys Pro Ser Glu Asp Asp Lys Glu Asn
65                  70

<210> SEQ ID NO 39
<211> LENGTH: 503
<212> TYPE: PRT
<213> ORGANISM: Artificial Sequence
<220> FEATURE:
<223> OTHER INFORMATION: synthetic

<400> SEQUENCE: 39

Ser Ala Gln Ala Ser Asp Val Val Gln Leu Lys Lys Asp Thr Phe Asp
1               5                   10                  15

Asp Phe Ile Lys Thr Asn Asp Leu Val Leu Ala Glu Phe Phe Ala Pro
            20                  25                  30

Trp Cys Gly His Cys Lys Ala Leu Ala Pro Glu Tyr Glu Glu Ala Ala
        35                  40                  45

Thr Thr Leu Lys Glu Lys Asn Ile Lys Leu Ala Lys Val Asp Cys Thr
    50                  55                  60

Glu Glu Thr Asp Leu Cys Gln Gln His Val Glu Gly Tyr Pro Thr Leu
65                  70                  75                  80

Lys Val Phe Arg Gly Leu Asp Asn Val Ser Pro Tyr Lys Gly Gln Arg
                85                  90                  95

Lys Ala Ala Ala Ile Thr Ser Tyr Met Ile Lys Gln Ser Leu Pro Ala
            100                 105                 110

Val Ser Glu Val Thr Lys Asp Asn Leu Glu Glu Phe Lys Ala Asp
            115                 120                 125

Lys Ala Val Leu Val Ala Tyr Val Asp Ala Ser Asp Lys Ala Ser Ser
        130                 135                 140

Glu Val Phe Thr Gln Val Ala Glu Lys Leu Arg Asp Asn Tyr Pro Phe

|     |     |     | 145 |     |     |     | 150 |     |     |     | 155 |     |     |     | 160 |
| --- | --- | --- | --- | --- | --- | --- | --- | --- | --- | --- | --- | --- | --- | --- | --- |

Gly Ser Ser Ser Asp Ala Ala Leu Ala Glu Ala Glu Gly Val Lys Ala
                165                      170                      175

Pro Ala Ile Val Leu Tyr Lys Asp Phe Asp Glu Gly Lys Ala Val Phe
            180                      185                      190

Ser Glu Lys Phe Glu Val Glu Ala Ile Glu Lys Phe Ala Lys Thr Gly
        195                      200                      205

Ala Thr Pro Leu Ile Gly Glu Ile Gly Pro Thr Tyr Ser Asp Tyr
    210                      215                      220

Met Ser Ala Gly Ile Pro Leu Ala Tyr Ile Phe Ala Glu Thr Ala Glu
225                      230                      235                      240

Glu Arg Lys Glu Leu Ser Asp Lys Leu Lys Pro Ile Ala Glu Ala Gln
                245                      250                      255

Arg Gly Val Ile Asn Phe Gly Thr Ile Asp Ala Lys Ala Phe Gly Ala
            260                      265                      270

His Ala Gly Asn Leu Asn Leu Lys Thr Asp Lys Phe Pro Ala Phe Ala
        275                      280                      285

Ile Gln Glu Val Ala Lys Asn Gln Lys Phe Pro Phe Asp Gln Glu Lys
    290                      295                      300

Glu Ile Thr Phe Glu Ala Ile Lys Ala Phe Val Asp Asp Phe Val Ala
305                      310                      315                      320

Gly Lys Ile Glu Pro Ser Ile Lys Ser Glu Pro Ile Pro Glu Lys Gln
                325                      330                      335

Glu Gly Pro Val Thr Val Val Ala Lys Asn Tyr Asn Glu Ile Val
            340                      345                      350

Leu Asp Asp Thr Lys Asp Val Leu Ile Glu Phe Tyr Ala Pro Trp Cys
        355                      360                      365

Gly His Cys Lys Ala Leu Ala Pro Lys Tyr Glu Leu Gly Ala Leu
    370                      375                      380

Tyr Ala Lys Ser Glu Phe Lys Asp Arg Val Val Ile Ala Lys Val Asp
385                      390                      395                      400

Ala Thr Ala Asn Asp Val Pro Asp Glu Ile Gln Gly Phe Pro Thr Ile
                405                      410                      415

Lys Leu Tyr Pro Ala Gly Ala Lys Gly Gln Pro Val Thr Tyr Ser Gly
            420                      425                      430

Ser Arg Thr Val Glu Asp Leu Ile Lys Phe Ile Ala Glu Asn Gly Lys
        435                      440                      445

Tyr Lys Ala Ala Ile Ser Glu Asp Ala Glu Thr Ser Ser Ala Thr
    450                      455                      460

Glu Thr Thr Thr Glu Thr Ala Thr Lys Ser Glu Glu Ala Ala Lys Glu
465                      470                      475                      480

Thr Ala Thr Glu His Asp Glu Leu Gly Ser Gly Ser Gly Asp Asp Asp
                485                      490                      495

Asp Lys Asp Asp Glu Ser Ser
            500

<210> SEQ ID NO 40
<211> LENGTH: 1512
<212> TYPE: DNA
<213> ORGANISM: Artificial Sequence
<220> FEATURE:
<223> OTHER INFORMATION: synthetic

<400> SEQUENCE: 40
agcgcgcagg ctagcgatgt tgtacaactg aaaaaagaca ctttcgacga cttcatcaaa     60

```
acaaatgacc ttgttcttgc tgaatttttc gcgccgtggt gcggtcactg caaagctctt    120
gctcctgagt acgaggaagc tgcaactaca ctgaaagaaa agaacatcaa acttgctaaa    180
gtagactgca cagaagagac tgatctttgc aacaacatg gtgttgaggg ctacccaact     240
cttaaagttt tccgtggcct tgacaacgta tctccttaca aaggtcaacg taaagctgct    300
gcaatcactt catacatgat caaacaatct ctgcctgctg tatctgaagt tacaaaagac    360
aaccttgaag aatttaaaaa agctgacaaa gctgttcttg ttgcttatgt agatgcttct    420
gacaaagcat ctagcgaagt tttcactcaa gttgctgaaa actgcgcga taactaccca    480 ttcggctcta gctctgatgc tgcactggct gaagctgagg gcgttaaagc acctgctatt    540
gttctttaca aagactttga tgaaggtaaa gcggttttct ctgaaaaatt cgaagtagag    600
gcaatcgaaa aattcgctaa aacaggtgct actccactta ttggcgaaat cggacctgaa    660
acttactctg attacatgtc agctggcatc cctctggcat acattttcgc tgaaacagct    720
gaagagcgta agaactcag cgacaaactt aaaccaatcg ctgaagctca acgtggcgtt     780
attaactttg gtactattga cgctaaagca tttggtgctc acgctggaaa cctgaatctg    840
aaaactgaca aattccctgc tttcgcaatc caagaagttg ctaaaaacca aaaattccct    900
tttgatcaag aaaaagaaat tacttttgaa gcgatcaaag cattcgttga cgattttgtt    960
gctggtaaaa tcgaaccaag catcaaatca gaaccaatcc ctgaaaaaca agaaggtcct   1020
gttactgtag ttgtagctaa aaactacaat gaaatcgttc tggacgatac taaagatgta   1080
ttaattgaat tttacgctcc ttggtgcggt cactgcaaag ctcttgctcc taaatacgaa   1140
gaacttggtg ctctgtatgc aaaaagcgag ttcaaagacc gtgttgtaat tgctaaagtt   1200
gatgcaacag ctaacgatgt tccagatgaa attcaaggat ccctactat caaactatac     1260 ccagctggtg caaaaggtca acctgttact tactctggtt cacgcactgt tgaagacctt   1320
atcaaattca ttgctgaaaa cggtaaatac aaagctgcaa tctcagaaga tgctgaagag   1380
actagttcag caactgaaac aactacagaa actgctacaa agtcagaaga agctgcaaaa   1440
gaaactgcaa cagaacacga cgaacttgga tctggttccg gagatgacga tgacaaagac   1500
gatgagagct ct                                                       1512
```

<210> SEQ ID NO 41
<211> LENGTH: 295
<212> TYPE: PRT
<213> ORGANISM: Artificial Sequence
<220> FEATURE:
<223> OTHER INFORMATION: synthetic aprE cutinase expression cassette

<400> SEQUENCE: 41

```
Val Arg Ser Lys Lys Leu Trp Ile Ser Leu Leu Phe Ala Leu Thr Leu
1               5                   10                  15

Ala Ala Ser Cys Leu Ser Val Cys Ala Thr Val Ala Ala Pro Leu
            20                  25                  30

Pro Asp Thr Pro Gly Ala Pro Phe Pro Ala Val Ala Asn Phe Asp Arg
        35                  40                  45

Ser Gly Pro Tyr Thr Thr Ser Ser Gln Ser Glu Gly Pro Ser Cys Arg
    50                  55                  60

Ile Tyr Arg Pro Arg Asp Leu Gly Gln Gly Gly Val Arg His Pro Val
65                  70                  75                  80

Ile Leu Trp Gly Asn Gly Thr Gly Ala Gly Pro Ser Thr Tyr Ala Gly
                85                  90                  95
```

Leu Leu Ser His Trp Ala Ser His Gly Phe Val Ala Ala Ala Glu
            100                 105                 110

Thr Ser Asn Ala Gly Thr Gly Arg Glu Met Leu Ala Cys Leu Asp Tyr
        115                 120                 125

Leu Val Arg Glu Asn Asp Thr Pro Tyr Gly Thr Tyr Ser Gly Lys Leu
    130                 135                 140

Asn Thr Gly Arg Val Gly Thr Ser Gly His Ser Gln Gly Gly Gly
145                 150                 155                 160

Ser Ile Met Ala Gly Gln Asp Thr Arg Val Arg Thr Thr Ala Pro Ile
                165                 170                 175

Gln Pro Tyr Thr Leu Gly Leu Gly His Asp Ser Ala Ser Gln Arg Arg
            180                 185                 190

Gln Gln Gly Pro Met Phe Leu Met Ser Gly Gly Asp Thr Ile Ala
        195                 200                 205

Phe Pro Tyr Leu Asn Ala Gln Pro Val Tyr Arg Arg Ala Asn Val Pro
    210                 215                 220

Val Phe Trp Gly Glu Arg Arg Tyr Val Ser His Phe Glu Pro Val Gly
225                 230                 235                 240

Ser Gly Gly Ala Tyr Arg Gly Pro Ser Thr Ala Trp Phe Arg Phe Gln
                245                 250                 255

Leu Met Asp Asp Gln Asp Ala Arg Ala Thr Phe Tyr Gly Ala Gln Cys
            260                 265                 270

Ser Leu Cys Thr Ser Leu Leu Trp Ser Val Glu Arg Arg Gly Leu Asp
        275                 280                 285

Asn Asn Asp Pro Ile Pro Asp
    290                 295

<210> SEQ ID NO 42
<211> LENGTH: 1495
<212> TYPE: DNA
<213> ORGANISM: Artificial Sequence
<220> FEATURE:
<223> OTHER INFORMATION: synthetic aprEcutinase expression cassette

<400> SEQUENCE: 42
gaattctcca ttttcttctg ctatcaaaat aacagactcg tgattttcca acgagctttc     60
caaaaaagcc tctgcccctt gcaaatcgga tgcctgtcta taaaattccc gatattggtt    120
aaacagcggc gcaatggcgg ccgcatctga tgtctttgct ggcgaatgt tcatcttatt    180 tcttcctccc tctcaataat ttttcattc tatcccttt ctgtaaagtt tattttcag    240 aatactttta tcatcatgct ttgaaaaaat atcacgataa tatccattgt tctcacggaa    300
gcacacgcag gtcatttgaa cgaattttt cgacaggaat tgccgggac tcaggagcat    360 ttaacctaaa aaagcatgac atttcagcat aatgaacatt tactcatgtc tattttcgtt    420 ctttctgta tgaaaatagt tatttcgagt ctctacggaa atagcgagag atgatatacc    480
taaatagaga taaaatcatc tcaaaaaaat gggtctacta aaatattatt ccatctatta    540
caataaattc acagaatagt cttttaagta agtctactct gaatttttt aaaaggagag    600 ggtaaagagt gagaagcaaa aaattgtgga tcagcttgtt gtttgcgtaa acgctggcgg    660
cctcttgcct gtccgtctgt gccactgtcg cggcggctcc cctgccggat acaccgggag    720
cgccatttcc ggctgtcgcc aatttcgacc gcagtggccc ctacaccacc agcagccaga    780
gcgaggggcc gagctgtcgc atctatcggc ccgcgacct gggtcagggg ggcgtgcgtc    840
atccggtgat tctctggggc aatggcaccg gtgccgggcc gtccacctat gccggcttgc    900

```
tatcgcactg ggcaagccac ggtttcgtgg tggcggcggc ggaaacctcc aatgccggta      960
ccgggcggga aatgctcgcc tgcctggact atctggtacg tgagaacgac accccctacg     1020
gcacctattc cggcaagctc aataccgggc gagtcggcac ttctgggcat tcccagggtg     1080
gtggcggctc gatcatggcc gggcaggata cgagggtgcg taccacggcg ccgatccagc     1140
cctacaccct cggcctgggg cacgacagcg cctcgcagcg gcggcagcag gggccgatgt     1200
tcctgatgtc cggtggcggt gacaccatcg cctttcccta cctcaacgct cagccggtct     1260
accggcgtgc caatgtgccg gtgttctggg gcgaacggcg ttacgtcagc cacttcgagc     1320
cggtcggtag cggtggggcc tatcgcggcc cgagcacggc atggttccgc ttccagctga     1380
tggatgacca agacgcccgc gctaccttct acggcgcgca gtgcagtctg tgcacttctc     1440
tgctttggtc tgttgaacgc agaggtcttg acaacaatga tcctattccg gatcc         1495
```

<210> SEQ ID NO 43
<211> LENGTH: 10
<212> TYPE: PRT
<213> ORGANISM: Artificial Sequence
<220> FEATURE:
<223> OTHER INFORMATION: synthetic CK37281

<400> SEQUENCE: 43

Ala Cys Tyr Asn Leu Tyr Gly Trp Thr Cys
1               5                   10

<210> SEQ ID NO 44
<211> LENGTH: 288
<212> TYPE: DNA
<213> ORGANISM: Artificial Sequence
<220> FEATURE:
<223> OTHER INFORMATION: synthetic proBBI with C-terminal hexahistidine

<400> SEQUENCE: 44

```
aacctgcgtc tgtctaagct tggcctgctt atgaaatcag accatcagca cagcaatgac       60
gatgagagct ctaaaccctg ttgcgatcaa tgcgcatgta cgaaatcaaa tcctccacag      120
tgtcggtgtt ccgatatgcg tctgaatagc tgtcatagtg catgcaaaag ctgtatctgc      180
gccctgagtt atccagctca atgttttttgc gtcgacatca cggacttctg ctatgagcca      240
tgtaaaccaa gcgaggacga taaagagaac catcatcacc atcaccat                   288
```

<210> SEQ ID NO 45
<211> LENGTH: 96
<212> TYPE: PRT
<213> ORGANISM: Artificial Sequence
<220> FEATURE:
<223> OTHER INFORMATION: synthetic peptide encoded by SEQ ID NO:44

<400> SEQUENCE: 45

Asn Leu Arg Leu Ser Lys Leu Gly Leu Leu Met Lys Ser Asp His Gln
1               5                   10                  15

His Ser Asn Asp Asp Glu Ser Ser Lys Pro Cys Cys Asp Gln Cys Ala
            20                  25                  30

Cys Thr Lys Ser Asn Pro Pro Gln Cys Arg Cys Ser Asp Met Arg Leu
        35                  40                  45

Asn Ser Cys His Ser Ala Cys Lys Ser Cys Ile Cys Ala Leu Ser Tyr
    50                  55                  60

Pro Ala Gln Cys Phe Cys Val Asp Ile Thr Asp Phe Cys Tyr Glu Pro
65                  70                  75                  80

Cys Lys Pro Ser Glu Asp Asp Lys Glu Asn His His His His His His

<210> SEQ ID NO 46
<211> LENGTH: 213
<212> TYPE: DNA
<213> ORGANISM: Artificial Sequence
<220> FEATURE:
<223> OTHER INFORMATION: synthetic gene encoding BBI

<400> SEQUENCE: 46

```
gacgatgaga gctctaaacc ctgttgcgat caatgcgcat gtacgaaatc aaatcctcca      60
cagtgtcggt gttccgatat gcgtctgaat agctgtcata gtgcatgcaa aagctgtatc     120
tgcgccctga gttatccagc tcaatgtttt tgcgtcgaca tcacggactt ctgctatgag     180
ccatgtaaac caagcgagga cgataaagag aac                                  213
```

<210> SEQ ID NO 47
<211> LENGTH: 71
<212> TYPE: PRT
<213> ORGANISM: Artificial Sequence
<220> FEATURE:
<223> OTHER INFORMATION: synthetic BBI encoded by SEQ ID NO:46

<400> SEQUENCE: 47

Asp Asp Glu Ser Ser Lys Pro Cys Cys Asp Gln Cys Ala Cys Thr Lys
1               5                   10                  15

Ser Asn Pro Pro Gln Cys Arg Cys Ser Asp Met Arg Leu Asn Ser Cys
            20                  25                  30

His Ser Ala Cys Lys Ser Cys Ile Cys Ala Leu Ser Tyr Pro Ala Gln
        35                  40                  45

Cys Phe Cys Val Asp Ile Thr Asp Phe Cys Tyr Glu Pro Cys Lys Pro
    50                  55                  60

Ser Glu Asp Asp Lys Glu Asn
65                  70

<210> SEQ ID NO 48
<211> LENGTH: 34
<212> TYPE: DNA
<213> ORGANISM: Artificial Sequence
<220> FEATURE:
<223> OTHER INFORMATION: primer

<400> SEQUENCE: 48

```
cagcacggat ccagacgatg agagctctaa accc                                  34
```

<210> SEQ ID NO 49
<211> LENGTH: 84
<212> TYPE: DNA
<213> ORGANISM: Artificial Sequence
<220> FEATURE:
<223> OTHER INFORMATION: primer

<400> SEQUENCE: 49

```
ctgcagaagc ttaaaaataa aaaacggat tccttcagg aaatccgtcc tctgttaact       60
tttagttctc tttatcgtcc tcgc                                             84
```

<210> SEQ ID NO 50
<211> LENGTH: 88
<212> TYPE: DNA
<213> ORGANISM: Artificial Sequence
<220> FEATURE:
<223> OTHER INFORMATION: primer

```
<400> SEQUENCE: 50
ctgcagaagc ttaaaaataa aaaaacggat ttccttcagg aaatccgtcc tctgttaact    60
tttaatggtg atggtgatga tggttctc                                      88

<210> SEQ ID NO 51
<211> LENGTH: 31
<212> TYPE: DNA
<213> ORGANISM: Artificial Sequence
<220> FEATURE:
<223> OTHER INFORMATION: primer

<400> SEQUENCE: 51
gatatgcgtc tgaattcctg tcatagtgca t                                  31

<210> SEQ ID NO 52
<211> LENGTH: 31
<212> TYPE: DNA
<213> ORGANISM: Artificial Sequence
<220> FEATURE:
<223> OTHER INFORMATION: primer

<400> SEQUENCE: 52
atgcactatg acaggaattc agacgcatat c                                  31

<210> SEQ ID NO 53
<211> LENGTH: 74
<212> TYPE: DNA
<213> ORGANISM: Artificial Sequence
<220> FEATURE:
<223> OTHER INFORMATION: synthetic oligonucleotide

<400> SEQUENCE: 53
ctaaaccctg ttgcgatcaa tgcgcatgtt ataatttgta tgggtggact tgtcgctgca    60
gcgatatgcg tctg                                                     74

<210> SEQ ID NO 54
<211> LENGTH: 82
<212> TYPE: DNA
<213> ORGANISM: Artificial Sequence
<220> FEATURE:
<223> OTHER INFORMATION: synthetic oligonucleotide

<400> SEQUENCE: 54
aattcagacg catatcgctg cagcgacaag tccacccata caaattataa catgcgcatt    60
gatcgcaaca gggtttagag ct                                            82

<210> SEQ ID NO 55
<211> LENGTH: 67
<212> TYPE: DNA
<213> ORGANISM: Artificial Sequence
<220> FEATURE:
<223> OTHER INFORMATION: synthetic oligonucleotide

<400> SEQUENCE: 55
aattcctgtc atagtgcctg caaaagctgc gcatgttata acctgtacgg gtggacctgt    60
ttttgcg                                                             67

<210> SEQ ID NO 56
<211> LENGTH: 67
<212> TYPE: DNA
<213> ORGANISM: Artificial Sequence
<220> FEATURE:
<223> OTHER INFORMATION: synthetic oligonucleotide
```

<400> SEQUENCE: 56
tcgacgcaaa aacaggtcca cccgtacagg ttataacatg cgcagctttt gcaggcacta    60
tgacagg                                                             67

<210> SEQ ID NO 57
<211> LENGTH: 80
<212> TYPE: DNA
<213> ORGANISM: Artificial Sequence
<220> FEATURE:
<223> OTHER INFORMATION: synthetic oligonucleotide

<400> SEQUENCE: 57
ctaaaccctg ttgcgatcaa tgcgcatgtg ttgttcagga ctggggtcac caccgttgtc    60
gctgcagcga tatgcgtctg                                               80

<210> SEQ ID NO 58
<211> LENGTH: 88
<212> TYPE: DNA
<213> ORGANISM: Artificial Sequence
<220> FEATURE:
<223> OTHER INFORMATION: synthetic oligonucleotide

<400> SEQUENCE: 58
aattcagacg catatcgctg cagcgacaac ggtggtgacc ccagtcctga acaacacatg    60
cgcattgatc gcaacagggt ttagagct                                      88

<210> SEQ ID NO 59
<211> LENGTH: 53
<212> TYPE: DNA
<213> ORGANISM: Artificial Sequence
<220> FEATURE:
<223> OTHER INFORMATION: synthetic oligonucleotide

<400> SEQUENCE: 59
caaaagctgt atctgcgttg ttcaggactg gggtcaccac cgttgttttt gcg           53

<210> SEQ ID NO 60
<211> LENGTH: 61
<212> TYPE: DNA
<213> ORGANISM: Artificial Sequence
<220> FEATURE:
<223> OTHER INFORMATION: synthetic oligonucleotide

<400> SEQUENCE: 60
tcgacgcaaa aacaacggtg gtgacccccag tcctgaacaa cgcagataca gcttttgcat   60
g                                                                   61

<210> SEQ ID NO 61
<211> LENGTH: 74
<212> TYPE: DNA
<213> ORGANISM: Artificial Sequence
<220> FEATURE:
<223> OTHER INFORMATION: synthetic oligonucleotide

<400> SEQUENCE: 61
ctaaaccctg ttgcgatcaa tgcagctgtg gtcgtaaaat cccgatccag tgtcgctgca    60
gcgatatgcg tctg                                                     74

<210> SEQ ID NO 62
<211> LENGTH: 82
<212> TYPE: DNA

```
<213> ORGANISM: Artificial Sequence
<220> FEATURE:
<223> OTHER INFORMATION: synthetic oligonucleotide

<400> SEQUENCE: 62
aattcagacg catatcgctg cagcgacact ggatcgggat tttacgacca cagctgcatt    60
gatcgcaaca gggtttagag ct                                             82

<210> SEQ ID NO 63
<211> LENGTH: 74
<212> TYPE: DNA
<213> ORGANISM: Artificial Sequence
<220> FEATURE:
<223> OTHER INFORMATION: synthetic oligonucleotide

<400> SEQUENCE: 63
ctaaaccctg ttgcgatcaa tgcggttgtg ctcgttctaa cctggacgaa tgtcgctgca    60
gcgatatgcg tctg                                                      74

<210> SEQ ID NO 64
<211> LENGTH: 82
<212> TYPE: DNA
<213> ORGANISM: Artificial Sequence
<220> FEATURE:
<223> OTHER INFORMATION: synthetic oligonucleotide

<400> SEQUENCE: 64
aattcagacg catatcgctg cagcgacatt cgtccaggtt agaacgagca caccgcatt    60 gatcgcaaca gggtttagag ct                                             82

<210> SEQ ID NO 65
<211> LENGTH: 74
<212> TYPE: DNA
<213> ORGANISM: Artificial Sequence
<220> FEATURE:
<223> OTHER INFORMATION: synthetic oligonucleotide

<400> SEQUENCE: 65
ctaaaccctg ttgcgatcaa tgcggttgtc agcgtgctct gccgatcctg tgtcgctgca    60
gcgatatgcg tctg                                                      74

<210> SEQ ID NO 66
<211> LENGTH: 82
<212> TYPE: DNA
<213> ORGANISM: Artificial Sequence
<220> FEATURE:
<223> OTHER INFORMATION: synthetic oligonucleotide

<400> SEQUENCE: 66
aattcagacg catatcgctg cagcgacaca ggatcggcag agcacgctga caaccgcatt    60
gatcgcaaca gggtttagag ct                                             82

<210> SEQ ID NO 67
<211> LENGTH: 74
<212> TYPE: DNA
<213> ORGANISM: Artificial Sequence
<220> FEATURE:
<223> OTHER INFORMATION: synthetic oligonucleotide

<400> SEQUENCE: 67
ctaaaccctg ttgcgatcaa tgccagtgtg gtcgtctgca catgaaaacc tgtcgctgca    60
gcgatatgcg tctg                                                      74
```

<210> SEQ ID NO 68
<211> LENGTH: 82
<212> TYPE: DNA
<213> ORGANISM: Artificial Sequence
<220> FEATURE:
<223> OTHER INFORMATION: synthetic oligonucleotide

<400> SEQUENCE: 68
aattcagacg catatcgctg cagcgacagg ttttcatgtg cagacgacca cactggcatt    60
gatcgcaaca gggtttagag ct                                             82

<210> SEQ ID NO 69
<211> LENGTH: 67
<212> TYPE: DNA
<213> ORGANISM: Artificial Sequence
<220> FEATURE:
<223> OTHER INFORMATION: synthetic oligonucleotide

<400> SEQUENCE: 69
aattcctgtc atagtgcctg caaaagctgt atctgcgccc gtagtttgcc agctcaatgt    60
ttttgcg                                                              67

<210> SEQ ID NO 70
<211> LENGTH: 67
<212> TYPE: DNA
<213> ORGANISM: Artificial Sequence
<220> FEATURE:
<223> OTHER INFORMATION: synthetic oligonucleotide

<400> SEQUENCE: 70
tcgacgcaaa acattgagc tggcaaacta cgggcgcaga tacagctttt gcaggcacta     60
tgacagg                                                              67

<210> SEQ ID NO 71
<211> LENGTH: 74
<212> TYPE: DNA
<213> ORGANISM: Artificial Sequence
<220> FEATURE:
<223> OTHER INFORMATION: synthetic oligonucleotide

<400> SEQUENCE: 71
ctaaaccctg ttgcgatcaa tgcaactgta cgtactcaac ccctccacag tgtcgctgca    60
gcgatatgcg tctg                                                      74

<210> SEQ ID NO 72
<211> LENGTH: 82
<212> TYPE: DNA
<213> ORGANISM: Artificial Sequence
<220> FEATURE:
<223> OTHER INFORMATION: synthetic oligonucleotide

<400> SEQUENCE: 72
aattcagacg catatcgctg cagcgacact gtggaggggt tgagtacgta cagttgcatt    60
gatcgcaaca gggtttagag ct                                             82

<210> SEQ ID NO 73
<211> LENGTH: 51
<212> TYPE: DNA
<213> ORGANISM: Artificial Sequence
<220> FEATURE:
<223> OTHER INFORMATION: synthetic oligonucleotide primer

```
<400> SEQUENCE: 73
ctgtatctgc aaacgctcaa aatctcgtgg ctgttttttgc gtcgacatca c            51

<210> SEQ ID NO 74
<211> LENGTH: 51
<212> TYPE: DNA
<213> ORGANISM: Artificial Sequence
<220> FEATURE:
<223> OTHER INFORMATION: synthetic oligonucleotide primer

<400> SEQUENCE: 74
cgcaaaaaca gccacgagat tttgagcgtt tgcagataca gcttttgcat g             51

<210> SEQ ID NO 75
<211> LENGTH: 51
<212> TYPE: DNA
<213> ORGANISM: Artificial Sequence
<220> FEATURE:
<223> OTHER INFORMATION: synthetic oligonucleotide primer

<400> SEQUENCE: 75
ctgtatctgc tggtataatc aaatgacaac atgttttttgc gtcgacatca c            51

<210> SEQ ID NO 76
<211> LENGTH: 51
<212> TYPE: DNA
<213> ORGANISM: Artificial Sequence
<220> FEATURE:
<223> OTHER INFORMATION: synthetic oligonucleotide primer

<400> SEQUENCE: 76
cgcaaaaaca tgttgtcatt tgattatacc agcagataca gcttttgcat g             51

<210> SEQ ID NO 77
<211> LENGTH: 51
<212> TYPE: DNA
<213> ORGANISM: Artificial Sequence
<220> FEATURE:
<223> OTHER INFORMATION: synthetic oligonucleotide primer

<400> SEQUENCE: 77
ctgtatctgc catcaacttg gcccgaattc atgttttttgc gtcgacatca c            51

<210> SEQ ID NO 78
<211> LENGTH: 51
<212> TYPE: DNA
<213> ORGANISM: Artificial Sequence
<220> FEATURE:
<223> OTHER INFORMATION: synthetic oligonucleotide primer

<400> SEQUENCE: 78
cgcaaaaaca tgaattcggg ccaagttgat ggcagataca gcttttgcat g             51

<210> SEQ ID NO 79
<211> LENGTH: 51
<212> TYPE: DNA
<213> ORGANISM: Artificial Sequence
<220> FEATURE:
<223> OTHER INFORMATION: synthetic oligonucleotide primer

<400> SEQUENCE: 79
ctgtatctgc catccgtggg caccgtattc ttgttttttgc gtcgacatca c            51

<210> SEQ ID NO 80
<211> LENGTH: 51
```

```
<212> TYPE: DNA
<213> ORGANISM: Artificial Sequence
<220> FEATURE:
<223> OTHER INFORMATION: synthetic oligonucleotide primer

<400> SEQUENCE: 80
cgcaaaaaca agaatacggt gcccacggat ggcagataca gcttttgcat g            51

<210> SEQ ID NO 81
<211> LENGTH: 51
<212> TYPE: DNA
<213> ORGANISM: Artificial Sequence
<220> FEATURE:
<223> OTHER INFORMATION: synthetic oligonucleotide primer

<400> SEQUENCE: 81
ctgtatctgc aatcttcatt atcttcaaca gtgttttttgc gtcgacatca c           51

<210> SEQ ID NO 82
<211> LENGTH: 51
<212> TYPE: DNA
<213> ORGANISM: Artificial Sequence
<220> FEATURE:
<223> OTHER INFORMATION: synthetic oligonucleotide primer

<400> SEQUENCE: 82
cgcaaaaaca ctgttgaaga taatgaagat tgcagataca gcttttgcat g            51

<210> SEQ ID NO 83
<211> LENGTH: 51
<212> TYPE: DNA
<213> ORGANISM: Artificial Sequence
<220> FEATURE:
<223> OTHER INFORMATION: synthetic oligonucleotide primer

<400> SEQUENCE: 83
ctgtatctgc acaccgtctc tttatcgccc gtgttttttgc gtcgacatca c           51

<210> SEQ ID NO 84
<211> LENGTH: 51
<212> TYPE: DNA
<213> ORGANISM: Artificial Sequence
<220> FEATURE:
<223> OTHER INFORMATION: synthetic oligonucleotide primer

<400> SEQUENCE: 84
cgcaaaaaca cgggcgataa agagacggtg tgcagataca gcttttgcat g            51

<210> SEQ ID NO 85
<211> LENGTH: 51
<212> TYPE: DNA
<213> ORGANISM: Artificial Sequence
<220> FEATURE:
<223> OTHER INFORMATION: synthetic oligonucleotide primer

<400> SEQUENCE: 85
ctgtatctgc cttacagatc aatctaaacc gtgttttttgc gtcgacatca c           51

<210> SEQ ID NO 86
<211> LENGTH: 51
<212> TYPE: DNA
<213> ORGANISM: Artificial Sequence
<220> FEATURE:
<223> OTHER INFORMATION: synthetic oligonucleotide primer

<400> SEQUENCE: 86
```
cgcaaaaaca cggtttagat tgatctgtaa ggcagataca gcttttgcat g        51

<210> SEQ ID NO 87
<211> LENGTH: 51
<212> TYPE: DNA
<213> ORGANISM: Artificial Sequence
<220> FEATURE:
<223> OTHER INFORMATION: synthetic oligonucleotide primer

<400> SEQUENCE: 87
ctgtatctgc gttacaacat caatgggcat gtgttttgc gtcgacatca c         51

<210> SEQ ID NO 88
<211> LENGTH: 51
<212> TYPE: DNA
<213> ORGANISM: Artificial Sequence
<220> FEATURE:
<223> OTHER INFORMATION: synthetic oligonucleotide primer

<400> SEQUENCE: 88
cgcaaaaaca catgcccatt gatgttgtaa cgcagataca gcttttgcat g        51

<210> SEQ ID NO 89
<211> LENGTH: 51
<212> TYPE: DNA
<213> ORGANISM: Artificial Sequence
<220> FEATURE:
<223> OTHER INFORMATION: synthetic oligonucleotide primer

<400> SEQUENCE: 89
ctgtatctgc cgcgcatcac cgtatgattg gtgttttgc gtcgacatca c         51

<210> SEQ ID NO 90
<211> LENGTH: 51
<212> TYPE: DNA
<213> ORGANISM: Artificial Sequence
<220> FEATURE:
<223> OTHER INFORMATION: synthetic oligonucleotide primer

<400> SEQUENCE: 90
cgcaaaaaca ccaatcatac ggtgatgcgc ggcagataca gcttttgcat g        51

<210> SEQ ID NO 91
<211> LENGTH: 51
<212> TYPE: DNA
<213> ORGANISM: Artificial Sequence
<220> FEATURE:
<223> OTHER INFORMATION: synthetic oligonucleotide primer

<400> SEQUENCE: 91
ctgtatctgc tcaacacaaa aaattccgca atgttttgc gtcgacatca c         51

<210> SEQ ID NO 92
<211> LENGTH: 51
<212> TYPE: DNA
<213> ORGANISM: Artificial Sequence
<220> FEATURE:
<223> OTHER INFORMATION: synthetic oligonucleotide primer

<400> SEQUENCE: 92
cgcaaaaaca ttgcggaatt ttttgtgttg agcagataca gcttttgcat g        51

<210> SEQ ID NO 93
<211> LENGTH: 51
<212> TYPE: DNA
<213> ORGANISM: Artificial Sequence

```
<220> FEATURE:
<223> OTHER INFORMATION: synthetic oligonucleotide primer

<400> SEQUENCE: 93
ctgtatctgc acacaatttc gctctgcaac atgttttgc gtcgacatca c            51

<210> SEQ ID NO 94
<211> LENGTH: 51
<212> TYPE: DNA
<213> ORGANISM: Artificial Sequence
<220> FEATURE:
<223> OTHER INFORMATION: synthetic oligonucleotide primer

<400> SEQUENCE: 94
cgcaaaaaca tgttgcagag cgaaattgtg tgcagataca gcttttgcat g            51

<210> SEQ ID NO 95
<211> LENGTH: 51
<212> TYPE: DNA
<213> ORGANISM: Artificial Sequence
<220> FEATURE:
<223> OTHER INFORMATION: synthetic oligonucleotide primer

<400> SEQUENCE: 95
ctgtatctgc ccggatcatg ttccgcatct tgttttgc gtcgacatca c              51

<210> SEQ ID NO 96
<211> LENGTH: 51
<212> TYPE: DNA
<213> ORGANISM: Artificial Sequence
<220> FEATURE:
<223> OTHER INFORMATION: synthetic oligonucleotide primer

<400> SEQUENCE: 96
cgcaaaaaca aagatgcgga acatgatccg ggcagataca gcttttgcat g            51

<210> SEQ ID NO 97
<211> LENGTH: 51
<212> TYPE: DNA
<213> ORGANISM: Artificial Sequence
<220> FEATURE:
<223> OTHER INFORMATION: synthetic oligonucleotide primer

<400> SEQUENCE: 97
ctgtatctgc tcaggctttc cgctttctac atgttttgc gtcgacatca c             51

<210> SEQ ID NO 98
<211> LENGTH: 51
<212> TYPE: DNA
<213> ORGANISM: Artificial Sequence
<220> FEATURE:
<223> OTHER INFORMATION: synthetic oligonucleotide primer

<400> SEQUENCE: 98
cgcaaaaaca tgtagaaagc ggaaagcctg agcagataca gcttttgcat g            51

<210> SEQ ID NO 99
<211> LENGTH: 56
<212> TYPE: DNA
<213> ORGANISM: Artificial Sequence
<220> FEATURE:
<223> OTHER INFORMATION: synthetic oligonucleotide primer

<400> SEQUENCE: 99
tcaatgcgca tgtgaagaga tctggactat gctttgccgg tgttccgata tgcgtc        56
```

```
<210> SEQ ID NO 100
<211> LENGTH: 57
<212> TYPE: DNA
<213> ORGANISM: Artificial Sequence
<220> FEATURE:
<223> OTHER INFORMATION: synthetic oligonucleotide primer

<400> SEQUENCE: 100
cggaacaccg gcaaagcata gtccagatct cttcacatgc gcattgatcg caacagg        57

<210> SEQ ID NO 101
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 101
caaaagctgt gcttgtgaag agatctggac tatgctttgc ttttgcgtcg acatcacgg      59

<210> SEQ ID NO 102
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 102
acgcaaaagc aaagcatagt ccagatctct tcacaagcac agcttttgca tgcactatg     59

<210> SEQ ID NO 103
<211> LENGTH: 56
<212> TYPE: DNA
<213> ORGANISM: Artificial Sequence
<220> FEATURE:
<223> OTHER INFORMATION: synthetic oligonucleotide primer

<400> SEQUENCE: 103
tcaatgcgca tgttgggccc ttactgtcaa acatgccgg tgttccgata tgcgtc          56

<210> SEQ ID NO 104
<211> LENGTH: 57
<212> TYPE: DNA
<213> ORGANISM: Artificial Sequence
<220> FEATURE:
<223> OTHER INFORMATION: synthetic oligonucleotide primer

<400> SEQUENCE: 104
cggaacaccg gcatgttttg acagtaaggg cccaacatgc gcattgatcg caacagg        57

<210> SEQ ID NO 105
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 105
caaaagctgt gcttgttggg cccttactgt caaaacatgc ttttgcgtcg acatcacgg      59

<210> SEQ ID NO 106
<211> LENGTH: 59
<212> TYPE: DNA
<213> ORGANISM: Artificial Sequence
<220> FEATURE:
<223> OTHER INFORMATION: synthetic oligonucleotide primer
```

<400> SEQUENCE: 106
acgcaaaagc atgttttgac agtaagggcc caacaagcac agcttttgca tgcactatg    59

<210> SEQ ID NO 107
<211> LENGTH: 56
<212> TYPE: DNA
<213> ORGANISM: Artificial Sequence
<220> FEATURE:
<223> OTHER INFORMATION: synthetic oligonucleotide primer

<400> SEQUENCE: 107
tcaatgcgca tgtcttacag tactgtggac tacatgccgg tgttccgata tgcgtc    56

<210> SEQ ID NO 108
<211> LENGTH: 57
<212> TYPE: DNA
<213> ORGANISM: Artificial Sequence
<220> FEATURE:
<223> OTHER INFORMATION: synthetic oligonucleotide primer

<400> SEQUENCE: 108
cggaacaccg gcatgtagtc cacagtactg taagacatgc gcattgatcg caacagg    57

<210> SEQ ID NO 109
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 109
caaaagctgt gcttgtctta cagtactgtg gactacatgc ttttgcgtcg acatcacgg    59

<210> SEQ ID NO 110
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 110
acgcaaaagc atgtagtcca cagtactgta agacaagcac agcttttgca tgcactatg    59

<210> SEQ ID NO 111
<211> LENGTH: 56
<212> TYPE: DNA
<213> ORGANISM: Artificial Sequence
<220> FEATURE:
<223> OTHER INFORMATION: synthetic oligonucleotide primer

<400> SEQUENCE: 111
tcaatgcgca tgtactcttt ggaacagatc tccttgccgg tgttccgata tgcgtc    56

<210> SEQ ID NO 112
<211> LENGTH: 57
<212> TYPE: DNA
<213> ORGANISM: Artificial Sequence
<220> FEATURE:
<223> OTHER INFORMATION: synthetic oligonucleotide primer

<400> SEQUENCE: 112
cggaacaccg gcaaggagat ctgttccaaa gagtacatgc gcattgatcg caacagg    57

<210> SEQ ID NO 113

```
<210> SEQ ID NO 113
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 113
caaaagctgt gcttgtactc tttggaatcg atctccttgc ttttgcgtcg acatcacgg      59

<210> SEQ ID NO 114
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 114
acgcaaaagc aaggagatcg attccaaaga gtacaagcac agcttttgca tgcactatg      59

<210> SEQ ID NO 115
<211> LENGTH: 56
<212> TYPE: DNA
<213> ORGANISM: Artificial Sequence
<220> FEATURE:
<223> OTHER INFORMATION: synthetic oligonucleotide primer

<400> SEQUENCE: 115
tcaatgcgca tgtacaaaca tcgattctac tccttgccgg tgttccgata tgcgtc         56

<210> SEQ ID NO 116
<211> LENGTH: 57
<212> TYPE: DNA
<213> ORGANISM: Artificial Sequence
<220> FEATURE:
<223> OTHER INFORMATION: synthetic oligonucleotide primer

<400> SEQUENCE: 116
cggaacaccg gcaaggagta gaatcgatgt ttgtacatgc gcattgatcg caacagg        57

<210> SEQ ID NO 117
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 117
caaaagctgt gcttgcacaa acatcgattc tactccttgt ttttgcgtcg acatcacgg      59

<210> SEQ ID NO 118
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 118
acgcaaaaac aaggagtaga atcgatgttt gtgcaagcac agcttttgca tgcactatg      59

<210> SEQ ID NO 119
<211> LENGTH: 56
<212> TYPE: DNA
<213> ORGANISM: Artificial Sequence
<220> FEATURE:
<223> OTHER INFORMATION: synthetic oligonucleotide primer

<400> SEQUENCE: 119
```
tcaatgcgca tgtacaaaaa tcgatcgtac tccttgccgg tgttccgata tgcgtc    56

<210> SEQ ID NO 120
<211> LENGTH: 57
<212> TYPE: DNA
<213> ORGANISM: Artificial Sequence
<220> FEATURE:
<223> OTHER INFORMATION: synthetic oligonucleotide primer

<400> SEQUENCE: 120
cggaacaccg gcaaggagta cgatcgattt ttgtacatgc gcattgatcg caacagg    57

<210> SEQ ID NO 121
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 121
caaaagctgt gcttgcacaa aaatcgatcg tactccttgt ttttgcgtcg acatcacgg    59

<210> SEQ ID NO 122
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 122
acgcaaaaac aaggagtacg atcgattttt gtgcaagcac agcttttgca tgcactatg    59

<210> SEQ ID NO 123
<211> LENGTH: 56
<212> TYPE: DNA
<213> ORGANISM: Artificial Sequence
<220> FEATURE:
<223> OTHER INFORMATION: synthetic oligonucleotide primer

<400> SEQUENCE: 123
tcaatgcgca tgtcacctgc agacaactga acatgccgg tgttccgata tgcgtc    56

<210> SEQ ID NO 124
<211> LENGTH: 57
<212> TYPE: DNA
<213> ORGANISM: Artificial Sequence
<220> FEATURE:
<223> OTHER INFORMATION: synthetic oligonucleotide primer

<400> SEQUENCE: 124
cggaacaccg gcatgtttca gttgtctgca ggtgacatgc gcattgatcg caacagg    57

<210> SEQ ID NO 125
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 125
caaaagctgt gcttgccacc tgcagacaac tgaaacatgt ttttgcgtcg acatcacgg    59

<210> SEQ ID NO 126
<211> LENGTH: 59
<212> TYPE: DNA

```
<213> ORGANISM: Artificial Sequence
<220> FEATURE:
<223> OTHER INFORMATION: synthetic oligonucleotide primer

<400> SEQUENCE: 126
acgcaaaaac atgtttcagt tgtctgcagg tggcaagcac agcttttgca tgcactatg      59

<210> SEQ ID NO 127
<211> LENGTH: 56
<212> TYPE: DNA
<213> ORGANISM: Artificial Sequence
<220> FEATURE:
<223> OTHER INFORMATION: synthetic oligonucleotide primer

<400> SEQUENCE: 127
tcaatgcgca tgtggctact tcatcccatc gatttgccgg tgttccgata tgcgtc         56

<210> SEQ ID NO 128
<211> LENGTH: 57
<212> TYPE: DNA
<213> ORGANISM: Artificial Sequence
<220> FEATURE:
<223> OTHER INFORMATION: synthetic oligonucleotide primer

<400> SEQUENCE: 128
cggaacaccg gcaaatcgat gggatgaagt agccacatgc gcattgatcg caacagg        57

<210> SEQ ID NO 129
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 129
caaaagctgt gcttgcggct acttcatccc atcgatttgt ttttgcgtcg acatcacgg      59

<210> SEQ ID NO 130
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 130
acgcaaaaac aaatcgatgg gatgaagtag ccgcaagcac agcttttgca tgcactatg      59

<210> SEQ ID NO 131
<211> LENGTH: 56
<212> TYPE: DNA
<213> ORGANISM: Artificial Sequence
<220> FEATURE:
<223> OTHER INFORMATION: synthetic oligonucleotide primer

<400> SEQUENCE: 131
tcaatgcgca tgtttacgta tccttgctaa caaatgccgg tgttccgata tgcgtc         56

<210> SEQ ID NO 132
<211> LENGTH: 57
<212> TYPE: DNA
<213> ORGANISM: Artificial Sequence
<220> FEATURE:
<223> OTHER INFORMATION: synthetic oligonucleotide primer

<400> SEQUENCE: 132
cggaacaccg gcatttgtta gcaaggatac gtaaacatgc gcattgatcg caacagg        57
```

<210> SEQ ID NO 133
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 133
caaaagctgt gcttgcttac gtatccttgc taacaaatgt ttttgcgtcg acatcacgg    59

<210> SEQ ID NO 134
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 134
acgcaaaaac atttgttagc aaggatacgt aagcaagcac agcttttgca tgcactatg    59

<210> SEQ ID NO 135
<211> LENGTH: 60
<212> TYPE: DNA
<213> ORGANISM: Artificial Sequence
<220> FEATURE:
<223> OTHER INFORMATION: synthetic oligonucleotide primer

<400> SEQUENCE: 135
gcgatcaatg cgcctgcaga actcaaccat atcctttatg tcggtgttcc gatatgcgtc    60

<210> SEQ ID NO 136
<211> LENGTH: 60
<212> TYPE: DNA
<213> ORGANISM: Artificial Sequence
<220> FEATURE:
<223> OTHER INFORMATION: synthetic oligonucleotide primer

<400> SEQUENCE: 136
ggaacaccga cataaaggat atggttgagt tctgcaggcg cattgatcgc aacagggttt    60

<210> SEQ ID NO 137
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 137
caaaagctgt gcctgcagaa cacaacctta cccactttgt ttttgcgtcg acatcacgg    59

<210> SEQ ID NO 138
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 138
acgcaaaaac aaagtgggta aggttgtgtt ctgcaggcac agcttttgca tgcactatg    59

<210> SEQ ID NO 139
<211> LENGTH: 59
<212> TYPE: DNA
<213> ORGANISM: Artificial Sequence
<220> FEATURE:

<223> OTHER INFORMATION: synthetic oligonucleotide primer

<400> SEQUENCE: 139
caaaagctgt gcctgcctgt taacacctac tcttaactgt ttttgcgtcg acatcacgg    59

<210> SEQ ID NO 140
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 140
acgcaaaaac agttaagagt aggtgttaac aggcaggcac agcttttgca tgcactatg    59

<210> SEQ ID NO 141
<211> LENGTH: 57
<212> TYPE: DNA
<213> ORGANISM: Artificial Sequence
<220> FEATURE:
<223> OTHER INFORMATION: synthetic oligonucleotide primer

<400> SEQUENCE: 141
tcaatgcgca tgcgctcttc caactcattc taactgtcgg tgttccgata tgcgtct    57

<210> SEQ ID NO 142
<211> LENGTH: 57
<212> TYPE: DNA
<213> ORGANISM: Artificial Sequence
<220> FEATURE:
<223> OTHER INFORMATION: synthetic oligonucleotide primer

<400> SEQUENCE: 142
cggaacaccg acagttagaa tgagttggaa gagcgcatgc gcattgatcg caacagg    57

<210> SEQ ID NO 143
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 143
caaaagctgt gcctgcgcgc ttcctacaca ctctaactgt ttttgcgtcg acatcacgg    59

<210> SEQ ID NO 144
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 144
acgcaaaaac agttagagtg tgtaggaagc gcgcaggcac agcttttgca tgcactatg    59

<210> SEQ ID NO 145
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 145
caaaagctgt gcctgccctt taggcctttg cccaccttgt ttttgcgtcg acatcacgg    59

```
<210> SEQ ID NO 146
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 146
acgcaaaaac aaggtgggca aaggcctaaa gggcaggcac agcttttgca tgcactatg      59

<210> SEQ ID NO 147
<211> LENGTH: 56
<212> TYPE: DNA
<213> ORGANISM: Artificial Sequence
<220> FEATURE:
<223> OTHER INFORMATION: synthetic oligonucleotide primer

<400> SEQUENCE: 147
aagctgtatc tgctggaaca tcgattctac accttgtttt tgcgtcgaca tcacgg         56

<210> SEQ ID NO 148
<211> LENGTH: 56
<212> TYPE: DNA
<213> ORGANISM: Artificial Sequence
<220> FEATURE:
<223> OTHER INFORMATION: synthetic oligonucleotide primer

<400> SEQUENCE: 148
acgcaaaaac aaggtgtaga atcgatgttc cagcagatac agcttttgca tgcact         56

<210> SEQ ID NO 149
<211> LENGTH: 60
<212> TYPE: DNA
<213> ORGANISM: Artificial Sequence
<220> FEATURE:
<223> OTHER INFORMATION: synthetic oligonucleotide primer

<400> SEQUENCE: 149
gcgatcaatg catctgtact tggattgaca gtactccttg tcggtgttcc gatatgcgtc     60

<210> SEQ ID NO 150
<211> LENGTH: 60
<212> TYPE: DNA
<213> ORGANISM: Artificial Sequence
<220> FEATURE:
<223> OTHER INFORMATION: synthetic oligonucleotide primer

<400> SEQUENCE: 150
ggaacaccga caaggagtac tgtcaatcca agtacagatg cattgatcgc aacagggttt     60

<210> SEQ ID NO 151
<211> LENGTH: 56
<212> TYPE: DNA
<213> ORGANISM: Artificial Sequence
<220> FEATURE:
<223> OTHER INFORMATION: synthetic oligonucleotide primer

<400> SEQUENCE: 151
aagctgtatc tgcacatgga tcgatagtac tccttgtttt tgcgtcgaca tcacgg         56

<210> SEQ ID NO 152
<211> LENGTH: 56
<212> TYPE: DNA
<213> ORGANISM: Artificial Sequence
<220> FEATURE:
<223> OTHER INFORMATION: synthetic oligonucleotide primer
```

<400> SEQUENCE: 152
acgcaaaaac aaggtgtaga atcgatccat gtgcagatac agcttttgca tgcact    56

<210> SEQ ID NO 153
<211> LENGTH: 56
<212> TYPE: DNA
<213> ORGANISM: Artificial Sequence
<220> FEATURE:
<223> OTHER INFORMATION: synthetic oligonucleotide primer

<400> SEQUENCE: 153
aagctgtatc tgtacatgga tcgattggac accttgtttt tgcgtcgaca tcacgg    56

<210> SEQ ID NO 154
<211> LENGTH: 56
<212> TYPE: DNA
<213> ORGANISM: Artificial Sequence
<220> FEATURE:
<223> OTHER INFORMATION: synthetic oligonucleotide primer

<400> SEQUENCE: 154
acgcaaaaac aaggtgtcca atcgatccat gtacagatac agcttttgca tgcact    56

<210> SEQ ID NO 155
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 155
caaaagctgc gcatgtgtta ctacagattg gatcgaatgt ttttgcgtcg acatcacgg    59

<210> SEQ ID NO 156
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 156
acgcaaaaac attcgatcca atctgtagta acacatgcgc agcttttgca tgcactatg    59

<210> SEQ ID NO 157
<211> LENGTH: 61
<212> TYPE: DNA
<213> ORGANISM: Artificial Sequence
<220> FEATURE:
<223> OTHER INFORMATION: synthetic oligonucleotide primer

<400> SEQUENCE: 157
caaaagctgt gcctgcccaa cactttggac tcatatgtgt ttttgcgtcg acatcacgga    60
c                                                                   61

<210> SEQ ID NO 158
<211> LENGTH: 61
<212> TYPE: DNA
<213> ORGANISM: Artificial Sequence
<220> FEATURE:
<223> OTHER INFORMATION: synthetic oligonucleotide primer

<400> SEQUENCE: 158
acgcaaaaac acatatgagt ccaaagtgtt gggcaggcac agcttttgca tgcactatga    60
c                                                                   61

<210> SEQ ID NO 159
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 159
caaaagctgc gcatgttact actctcaatt ccaccaatgt ttttgcgtcg acatcacgg    59

<210> SEQ ID NO 160
<211> LENGTH: 59
<212> TYPE: DNA
<213> ORGANISM: Artificial Sequence
<220> FEATURE:
<223> OTHER INFORMATION: synthetic oligonucleotide primer

<400> SEQUENCE: 160
acgcaaaaac attggtggaa ttgagagtag taacatgcgc agcttttgca tgcactatg    59

<210> SEQ ID NO 161
<211> LENGTH: 69
<212> TYPE: DNA
<213> ORGANISM: Artificial Sequence
<220> FEATURE:
<223> OTHER INFORMATION: synthetic oligonucleotide primer

<400> SEQUENCE: 161
caaaagctgt ctttgtccgg aaaacgataa cgtttctcct tgtaattgcg tcgacatcac    60
ggacttctg                                                            69

<210> SEQ ID NO 162
<211> LENGTH: 69
<212> TYPE: DNA
<213> ORGANISM: Artificial Sequence
<220> FEATURE:
<223> OTHER INFORMATION: synthetic oligonucleotide primer

<400> SEQUENCE: 162
tgtcgacgca attacaagga gaaacgttat cgttttccgg acaaagacag cttttgcatg    60
cactatgac                                                            69

<210> SEQ ID NO 163
<211> LENGTH: 47
<212> TYPE: DNA
<213> ORGANISM: Artificial Sequence
<220> FEATURE:
<223> OTHER INFORMATION: synthetic oligonucleotide primer

<400> SEQUENCE: 163
caaaagctgt gcttgtaaac acaacgtacg tcttttatgt ttttgcg               47

<210> SEQ ID NO 164
<211> LENGTH: 55
<212> TYPE: DNA
<213> ORGANISM: Artificial Sequence
<220> FEATURE:
<223> OTHER INFORMATION: synthetic oligonucleotide primer

<400> SEQUENCE: 164
tcgacgcaaa aacataaaag acgtacgttg tgtttacaag cacagctttt gcatg        55

<210> SEQ ID NO 165

```
<211> LENGTH: 47
<212> TYPE: DNA
<213> ORGANISM: Artificial Sequence
<220> FEATURE:
<223> OTHER INFORMATION: synthetic oligonucleotide primer

<400> SEQUENCE: 165
caaatcttgc gcgtgcacac tttggaaatc ttactggtgt ttttgcg        47

<210> SEQ ID NO 166
<211> LENGTH: 55
<212> TYPE: DNA
<213> ORGANISM: Artificial Sequence
<220> FEATURE:
<223> OTHER INFORMATION: synthetic oligonucleotide primer

<400> SEQUENCE: 166
tcgacgcaaa aacaccagta agatttccaa agtgtgcacg cgcaagattt gcatg        55

<210> SEQ ID NO 167
<211> LENGTH: 47
<212> TYPE: DNA
<213> ORGANISM: Artificial Sequence
<220> FEATURE:
<223> OTHER INFORMATION: synthetic oligonucleotide primer

<400> SEQUENCE: 167
caaatcttgc gcatgtaaat attacctta ctggtggtgt ttttgcg        47

<210> SEQ ID NO 168
<211> LENGTH: 55
<212> TYPE: DNA
<213> ORGANISM: Artificial Sequence
<220> FEATURE:
<223> OTHER INFORMATION: synthetic oligonucleotide primer

<400> SEQUENCE: 168
tcgacgcaaa aacaccacca gtaaaggtaa tatttacatg cgcaagattt gcatg        55

<210> SEQ ID NO 169
<211> LENGTH: 47
<212> TYPE: DNA
<213> ORGANISM: Artificial Sequence
<220> FEATURE:
<223> OTHER INFORMATION: synthetic oligonucleotide primer

<400> SEQUENCE: 169
caaatcttgc atctgtaaat atgatcttta ctggtggtgt ttttgcg        47

<210> SEQ ID NO 170
<211> LENGTH: 55
<212> TYPE: DNA
<213> ORGANISM: Artificial Sequence
<220> FEATURE:
<223> OTHER INFORMATION: synthetic oligonucleotide primer

<400> SEQUENCE: 170
tcgacgcaaa aacaccacca gtaaagatca tatttacaga tgcaagattt gcatg        55

<210> SEQ ID NO 171
<211> LENGTH: 47
<212> TYPE: DNA
<213> ORGANISM: Artificial Sequence
<220> FEATURE:
<223> OTHER INFORMATION: synthetic oligonucleotide primer

<400> SEQUENCE: 171
```

```
caaatcttgc atctgtgatt ataaacttta ctggtggtgt ttttgcg                    47
```

<210> SEQ ID NO 172
<211> LENGTH: 55
<212> TYPE: DNA
<213> ORGANISM: Artificial Sequence
<220> FEATURE:
<223> OTHER INFORMATION: synthetic oligonucleotide primer

<400> SEQUENCE: 172

```
tcgacgcaaa aacaccacca gtaaagttta atcacaga tgcaagattt gcatg           55
```

<210> SEQ ID NO 173
<211> LENGTH: 37
<212> TYPE: DNA
<213> ORGANISM: Artificial Sequence
<220> FEATURE:
<223> OTHER INFORMATION: synthetic oligonucleotide primer

<400> SEQUENCE: 173

```
gatccaggtg gagctgcttt agttgacgat gagagct                              37
```

<210> SEQ ID NO 174
<211> LENGTH: 29
<212> TYPE: DNA
<213> ORGANISM: Artificial Sequence
<220> FEATURE:
<223> OTHER INFORMATION: synthetic oligonucleotide primer

<400> SEQUENCE: 174

```
ctcatcgtca actaaagcag ctccacctg                                       29
```

<210> SEQ ID NO 175
<211> LENGTH: 70
<212> TYPE: DNA
<213> ORGANISM: Artificial Sequence
<220> FEATURE:
<223> OTHER INFORMATION: synthetic oligonucleotide primer

<400> SEQUENCE: 175

```
gatccaggtg aacctgaccc aactcctcca tctgatcctg gagaataccc agcttgggac    60
gatgagagct                                                            70
```

<210> SEQ ID NO 176
<211> LENGTH: 62
<212> TYPE: DNA
<213> ORGANISM: Artificial Sequence
<220> FEATURE:
<223> OTHER INFORMATION: synthetic oligonucleotide primer

<400> SEQUENCE: 176

```
ctcatcgtcc caagctgggt attctccagg atcagatgga ggagttgggt caggttcacc    60
tg                                                                    62
```

<210> SEQ ID NO 177
<211> LENGTH: 79
<212> TYPE: DNA
<213> ORGANISM: Artificial Sequence
<220> FEATURE:
<223> OTHER INFORMATION: synthetic oligonucleotide primer

<400> SEQUENCE: 177

```
gatccggcga acctgcgtct gtctaagctt ggcctgctta tgaaatcaga ccatcagcac    60
```
agcaatgacg atgagagct 79

<210> SEQ ID NO 178
<211> LENGTH: 71
<212> TYPE: DNA
<213> ORGANISM: Artificial Sequence
<220> FEATURE:
<223> OTHER INFORMATION: synthetic oligonucleotide primer

<400> SEQUENCE: 178
ctcatcgtca ttgctgtgct gatggtctga tttcataagc aggccaagct tagacagacg    60
caggttcgcc g    71

<210> SEQ ID NO 179
<211> LENGTH: 43
<212> TYPE: DNA
<213> ORGANISM: Artificial Sequence
<220> FEATURE:
<223> OTHER INFORMATION: synthetic oligonucleotide primer

<400> SEQUENCE: 179
gatccaaaat cagaccatca gcacagcaat gacgatgaga gct    43

<210> SEQ ID NO 180
<211> LENGTH: 35
<212> TYPE: DNA
<213> ORGANISM: Artificial Sequence
<220> FEATURE:
<223> OTHER INFORMATION: synthetic oligonucleotide primer

<400> SEQUENCE: 180
ctcatcgtca ttgctgtgct gatggtctga ttttg    35

<210> SEQ ID NO 181
<211> LENGTH: 205
<212> TYPE: DNA
<213> ORGANISM: Artificial Sequence
<220> FEATURE:
<223> OTHER INFORMATION: synthetic oligonucleotide

<400> SEQUENCE: 181
gatccaggag aaccggaccc aacgccccca agtgatccag gagagtatcc agcatgggat    60
tcaaatcaaa tttacacaaa tgaaattgtg tatcataacg gtcagttatg gcaagcgaaa    120
tggtggacac aaaatcaaga gccaggtgac ccatacggtc cgtgggaacc actcaaatct    180
gacccagatt cagacgatga gagct    205

<210> SEQ ID NO 182
<211> LENGTH: 197
<212> TYPE: DNA
<213> ORGANISM: Artificial Sequence
<220> FEATURE:
<223> OTHER INFORMATION: synthetic oligonucleotide

<400> SEQUENCE: 182
ctcatcgtct gaatctgggt cagatttgag tggttcccac ggaccgtatg ggtcacctgg    60
ctcttgattt tgtgtccacc atttcgcttg ccataactga ccgttatgat acacaatttc    120
atttgtgtaa atttgatttg aatcccatgc tggatactct cctggatcac ttgggggcgt    180
tgggtccggt tctcctg    197

<210> SEQ ID NO 183
<211> LENGTH: 6

```
<212> TYPE: PRT
<213> ORGANISM: Artificial Sequence
<220> FEATURE:
<223> OTHER INFORMATION: synthetic linker

<400> SEQUENCE: 183

Trp Gly Asp Pro His Tyr
1               5

<210> SEQ ID NO 184
<211> LENGTH: 6
<212> TYPE: PRT
<213> ORGANISM: Artificial Sequence
<220> FEATURE:
<223> OTHER INFORMATION: synthetic linker

<400> SEQUENCE: 184

Asp Asn Asn Asp Pro Ile
1               5

<210> SEQ ID NO 185
<211> LENGTH: 6
<212> TYPE: PRT
<213> ORGANISM: Artificial Sequence
<220> FEATURE:
<223> OTHER INFORMATION: synthetic linker

<400> SEQUENCE: 185

Val Val Ala Asp Pro Asn
1               5

<210> SEQ ID NO 186
<211> LENGTH: 37
<212> TYPE: DNA
<213> ORGANISM: Artificial Sequence
<220> FEATURE:
<223> OTHER INFORMATION: synthetic oligonucleotide primer

<400> SEQUENCE: 186
tggcgttcag caacatgagc gcgcaggctg atgatta                            37

<210> SEQ ID NO 187
<211> LENGTH: 37
<212> TYPE: DNA
<213> ORGANISM: Artificial Sequence
<220> FEATURE:
<223> OTHER INFORMATION: synthetic oligonucleotide primer

<400> SEQUENCE: 187
taatcatcag cctgcgcgct catgttgctg aacgcca                            37

<210> SEQ ID NO 188
<211> LENGTH: 128
<212> TYPE: DNA
<213> ORGANISM: Artificial Sequence
<220> FEATURE:
<223> OTHER INFORMATION: synthetic oligonucleotide

<400> SEQUENCE: 188
gacatcacgg acttctgcta tgagccatgt aaaccaagcg aggacgataa agagaactaa   60
aagcttaact cgaggttaac agaggacgga tttcctgaag gaaatccgtt tttttatttt  120
taattaag                                                          128

<210> SEQ ID NO 189
<211> LENGTH: 130
```

```
<212> TYPE: DNA
<213> ORGANISM: Artificial Sequence
<220> FEATURE:
<223> OTHER INFORMATION: synthetic oligonucleotide

<400> SEQUENCE: 189
agctcttaat taaaaataaa aaaacggatt tccttcagga aatccgtcct ctgttaacct    60
cgagttaagc ttttagttct ctttatcgtc ctcgcttggt ttacatggct catagcagaa   120
gtccgtgatg                                                         130

<210> SEQ ID NO 190
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 190
cagcaacatg agcgcgcagg ctg                                           23

<210> SEQ ID NO 191
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 191
atcgtctgga tccggatagt gggggtctcc ccaagatgct gattctctta ttttttccc    59

<210> SEQ ID NO 192
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 192
atcgtctgga tccggtatgg gatcattgtt gtcagatgct gattctctta ttttttccc    59

<210> SEQ ID NO 193
<211> LENGTH: 59
<212> TYPE: DNA
<213> ORGANISM: Artificial Sequence
<220> FEATURE:
<223> OTHER INFORMATION: synthetic oligonucleotide

<400> SEQUENCE: 193
atcgtctgga tccgggttgg gatctgcaac tacagatgct gattctctta ttttttccc    59

<210> SEQ ID NO 194
<211> LENGTH: 25
<212> TYPE: DNA
<213> ORGANISM: Artificial Sequence
<220> FEATURE:
<223> OTHER INFORMATION: primer

<400> SEQUENCE: 194
gcataaggat gagtcatctg cagcg                                         25

<210> SEQ ID NO 195
<211> LENGTH: 57
<212> TYPE: DNA
<213> ORGANISM: Artificial Sequence
<220> FEATURE:
```

<223> OTHER INFORMATION: primer

<400> SEQUENCE: 195
atcgtctgga tccggatagt gggggtctcc ccacggttct cctggatcag atggcgg     57

<210> SEQ ID NO 196
<211> LENGTH: 57
<212> TYPE: DNA
<213> ORGANISM: Artificial Sequence
<220> FEATURE:
<223> OTHER INFORMATION: primer

<400> SEQUENCE: 196
atcgtctgga tccggtatgg gatcattgtt gtccggttct cctggatcag atggcgg     57

<210> SEQ ID NO 197
<211> LENGTH: 57
<212> TYPE: DNA
<213> ORGANISM: Artificial Sequence
<220> FEATURE:
<223> OTHER INFORMATION: primer

<400> SEQUENCE: 197
atcgtctgga tccgggttgg gatctgcaac taccggttct cctggatcag atggcgg     57

<210> SEQ ID NO 198
<211> LENGTH: 9
<212> TYPE: PRT
<213> ORGANISM: Artificial Sequence
<220> FEATURE:
<223> OTHER INFORMATION: synthetic linker

<400> SEQUENCE: 198

Trp Gly Asp Pro His Tyr Pro Asp Pro
1               5

<210> SEQ ID NO 199
<211> LENGTH: 9
<212> TYPE: PRT
<213> ORGANISM: Artificial Sequence
<220> FEATURE:
<223> OTHER INFORMATION: synthetic linker

<400> SEQUENCE: 199

Asp Asn Asn Asp Pro Ile Pro Asp Pro
1               5

<210> SEQ ID NO 200
<211> LENGTH: 9
<212> TYPE: PRT
<213> ORGANISM: Artificial Sequence
<220> FEATURE:
<223> OTHER INFORMATION: synthetic linker

<400> SEQUENCE: 200

Val Val Ala Asp Pro Asn Pro Asp Pro
1               5

<210> SEQ ID NO 201
<211> LENGTH: 24
<212> TYPE: PRT
<213> ORGANISM: Artificial Sequence
<220> FEATURE:
<223> OTHER INFORMATION: synthetic linker

<400> SEQUENCE: 201

Ile Pro Pro Ser Asp Pro Thr Pro Pro Ser Asp Pro Gly Glu Pro Trp
1               5                   10                  15

Gly Asp Pro His Tyr Pro Asp Pro
            20

<210> SEQ ID NO 202
<211> LENGTH: 24
<212> TYPE: PRT
<213> ORGANISM: Artificial Sequence
<220> FEATURE:
<223> OTHER INFORMATION: synthetic linker

<400> SEQUENCE: 202

Ile Pro Pro Ser Asp Pro Thr Pro Pro Ser Asp Pro Gly Glu Pro Asp
1               5                   10                  15

Asn Asn Asp Pro Ile Pro Asp Pro
            20

<210> SEQ ID NO 203
<211> LENGTH: 24
<212> TYPE: PRT
<213> ORGANISM: Artificial Sequence
<220> FEATURE:
<223> OTHER INFORMATION: synthetic linker

<400> SEQUENCE: 203

Ile Pro Pro Ser Asp Pro Thr Pro Pro Ser Asp Pro Gly Glu Pro Val
1               5                   10                  15

Val Ala Asp Pro Asn Pro Asp Pro
            20

<210> SEQ ID NO 204
<211> LENGTH: 40
<212> TYPE: DNA
<213> ORGANISM: Artificial Sequence
<220> FEATURE:
<223> OTHER INFORMATION: synthetic oligonucleotide

<400> SEQUENCE: 204
gatccaggtg gagacgacga tgacaaagac gatgagagct                               40

<210> SEQ ID NO 205
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 205
ctcatcgtct ttgtcatcgt cgtctccacc tg                                       32

<210> SEQ ID NO 206
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 206
gatccaggtg ctgctcatta cgacgatgag agct                                     34

<210> SEQ ID NO 207
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 207
ctcatcgtcg taatgagcag cacctg                                        26

<210> SEQ ID NO 208
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 208
gatccacgtg ctaaaagaga cgatgagagc t                                  31

<210> SEQ ID NO 209
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 209
ctcatcgtct cttttagcac gtg                                           23

<210> SEQ ID NO 210
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 210
gatccaggcg ctgcacacta caacgacgat gagagct                            37

<210> SEQ ID NO 211
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 211
ctcatcgtcg ttgtagtgtg cagcgcctg                                     29

<210> SEQ ID NO 212
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 212
gatccattcc ttgaagacga tgagagct                                      28

<210> SEQ ID NO 213
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 213
ctcatcgtct tcaaggaatg                                               20

<210> SEQ ID NO 214
<211> LENGTH: 29
<212> TYPE: DNA
<213> ORGANISM: Artificial Sequence
<220> FEATURE:
<223> OTHER INFORMATION: synthetic oligonucleotide primer

<400> SEQUENCE: 214
cccataccgg agccagacga tgagagctc                                29

<210> SEQ ID NO 215
<211> LENGTH: 32
<212> TYPE: DNA
<213> ORGANISM: Artificial Sequence
<220> FEATURE:
<223> OTHER INFORMATION: synthetic oligonucleotide primer

<400> SEQUENCE: 215
catcgtctgg ctccggtatg ggatcattgt tg                            32

<210> SEQ ID NO 216
<211> LENGTH: 21
<212> TYPE: PRT
<213> ORGANISM: Artificial Sequence
<220> FEATURE:
<223> OTHER INFORMATION: synthetic linker

<400> SEQUENCE: 216

Asp Asn Asn Asp Pro Ile Pro Glu Pro Asp Asp Glu Ser Phe Asn Met
1               5                   10                  15

Pro Ile Pro Glu Pro
            20

<210> SEQ ID NO 217
<211> LENGTH: 58
<212> TYPE: DNA
<213> ORGANISM: Artificial Sequence
<220> FEATURE:
<223> OTHER INFORMATION: synthetic oligonucleotide

<400> SEQUENCE: 217
gatccaggcg ctgcacacta caaatcagac catcagcaca gcaatgacga tgagagct    58

<210> SEQ ID NO 218
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 218
ctcatcgtca ttgctgtgct gatggtctga tttgtagtgt gcagcgcctg             50

<210> SEQ ID NO 219
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 219
gatccaggcg ctgcacacta cgtagaattt caagacgatg agagct                 46

<210> SEQ ID NO 220
<211> LENGTH: 38

```
<212> TYPE: DNA
<213> ORGANISM: Artificial Sequence
<220> FEATURE:
<223> OTHER INFORMATION: synthetic oligonucleotide

<400> SEQUENCE: 220
ctcatcgtct tgaaattcta cgtagtgtgc agcgcctg                          38

<210> SEQ ID NO 221
<211> LENGTH: 18
<212> TYPE: PRT
<213> ORGANISM: Artificial Sequence
<220> FEATURE:
<223> OTHER INFORMATION: synthetic cleavage site

<400> SEQUENCE: 221

Asp Asn Asn Asp Pro Ile Pro Asp Pro Gly Ala Ala His Tyr Val Glu
1               5                   10                  15

Phe Gln

<210> SEQ ID NO 222
<211> LENGTH: 87
<212> TYPE: PRT
<213> ORGANISM: Artificial Sequence
<220> FEATURE:
<223> OTHER INFORMATION: synthetic fusion protein

<400> SEQUENCE: 222

Lys Ile Arg Glu Ser Ala Ser Asp Asn Asn Asp Pro Ile Pro Asp Pro
1               5                   10                  15

Asp Asp Glu Ser Ser Lys Pro Cys Cys Asp Gln Cys Ala Cys Thr Lys
                20                  25                  30

Ser Asn Pro Pro Gln Cys Arg Cys Ser Asp Met Arg Leu Asn Ser Cys
            35                  40                  45

His Ser Ala Cys Lys Ser Cys Ala Cys Tyr Asn Leu Tyr Gly Trp Thr
        50                  55                  60

Cys Phe Cys Val Asp Ile Thr Asp Phe Cys Tyr Glu Pro Cys Lys Pro
65                  70                  75                  80

Ser Glu Asp Asp Lys Glu Asn
                85

<210> SEQ ID NO 223
<211> LENGTH: 46
<212> TYPE: DNA
<213> ORGANISM: Artificial Sequence
<220> FEATURE:
<223> OTHER INFORMATION: primer

<400> SEQUENCE: 223
aacatgagcg cgcaggctga tgacgcggca attcaacaaa cgttag               46

<210> SEQ ID NO 224
<211> LENGTH: 77
<212> TYPE: DNA
<213> ORGANISM: Artificial Sequence
<220> FEATURE:
<223> OTHER INFORMATION: primer

<400> SEQUENCE: 224
tcgtctggat ccggtatggg atcattgttg tcaccagaac cactagttga tcctttaccg   60
ctggtcattt tttggtg                                                 77
```

```
<210> SEQ ID NO 225
<211> LENGTH: 60
<212> TYPE: DNA
<213> ORGANISM: Artificial Sequence
<220> FEATURE:
<223> OTHER INFORMATION: synthetic oligonucleotide

<400> SEQUENCE: 225
tgcacttctc tgctttggtc tgttgaacgc agaggtcttg acaacaatga tcctattccg      60

<210> SEQ ID NO 226
<211> LENGTH: 60
<212> TYPE: DNA
<213> ORGANISM: Artificial Sequence
<220> FEATURE:
<223> OTHER INFORMATION: synthetic oligonucleotide

<400> SEQUENCE: 226
gatccggaat aggatcattg ttgtcaagac ctctgcgttc aacagaccaa agcagagaag      60

<210> SEQ ID NO 227
<211> LENGTH: 111
<212> TYPE: DNA
<213> ORGANISM: Artificial Sequence
<220> FEATURE:
<223> OTHER INFORMATION: synthetic Bbs1 cloning site

<400> SEQUENCE: 227
taaggtgatg agcaaggaaa gataagagtg agatgcggtc acagtctttt tgtcgaccgc      60
ctccaccagc gcttatgcta atggggcgac tactttcgtg tctcacaagg t             111

<210> SEQ ID NO 228
<211> LENGTH: 37
<212> TYPE: PRT
<213> ORGANISM: Artificial Sequence
<220> FEATURE:
<223> OTHER INFORMATION: synthetic Bbs1 cloning site

<400> SEQUENCE: 228

Ile Pro Leu Val Val Pro Phe Tyr Ser His Ser Thr Pro Val Ser Gln
1               5                   10                  15

Lys Gln Leu Ala Gln Val Val Ala Asn Thr Ile Thr Pro Leu Met Lys
            20                  25                  30

Ala Gln Ser Val Pro
        35

<210> SEQ ID NO 229
<211> LENGTH: 112
<212> TYPE: DNA
<213> ORGANISM: Artificial Sequence
<220> FEATURE:
<223> OTHER INFORMATION: synthetic Bbs1 cloning site

<400> SEQUENCE: 229
taaggtgatc agcaaggaaa gataagagtg agatgcggtc acagtctttt tgtcgaccgg      60
ctccaccagc cgcttatgct aatggggcga ctactttcgt gtctcacaag gt            112

<210> SEQ ID NO 230
<211> LENGTH: 37
<212> TYPE: PRT
<213> ORGANISM: Artificial Sequence
<220> FEATURE:
<223> OTHER INFORMATION: synthetic Bbs1 cloning site

<400> SEQUENCE: 230
```

Ile Pro Leu Val Val Pro Phe Tyr Ser His Ser Thr Pro Val Ser Glu
1               5                   10                  15

Lys Gln Leu Ala Glu Val Val Ala Asn Thr Ile Thr Pro Leu Met Lys
            20                  25                  30

Ala Gln Ser Val Pro
        35

<210> SEQ ID NO 231
<211> LENGTH: 112
<212> TYPE: DNA
<213> ORGANISM: Artificial Sequence
<220> FEATURE:
<223> OTHER INFORMATION: synthetic Bbs1 cloning site

<400> SEQUENCE: 231
taaggtgatc acagaatcta gttcagctgt tgtcggacag acgtctagga cttctgaccg    60
cctccaccag cgcttatgct aatggggcga ctactttcgt gtctcacaag gt          112

<210> SEQ ID NO 232
<211> LENGTH: 27
<212> TYPE: PRT
<213> ORGANISM: Artificial Sequence
<220> FEATURE:
<223> OTHER INFORMATION: synthetic Bbs1 cloning site

<400> SEQUENCE: 232

Ile Pro Leu Val Ser Ser Ile Lys Ser Thr Thr Ala Cys Leu Gln Ile
1               5                   10                  15

Leu Lys Thr Gly Gly Gly Gly Arg Glu Tyr Asp
            20                  25

<210> SEQ ID NO 233
<211> LENGTH: 18
<212> TYPE: PRT
<213> ORGANISM: Artificial Sequence
<220> FEATURE:
<223> OTHER INFORMATION: synthetic Bbs1 cloning site

<400> SEQUENCE: 233

Ala Glu Val Val Ala Asn Thr Ile Thr Pro Leu Met Lys Ala Gln Ser
1               5                   10                  15

Val Pro

<210> SEQ ID NO 234
<211> LENGTH: 112
<212> TYPE: DNA
<213> ORGANISM: Artificial Sequence
<220> FEATURE:
<223> OTHER INFORMATION: synthetic Bbs1 cloning site

<400> SEQUENCE: 234
taaggtgatc acagaagcta gttcagctgt tgtcggacag acgtctagga cttctgaccg    60
cctccaccag cgcttatgct aatggggcga ctactttcgt gtctcacaag gt          112

<210> SEQ ID NO 235
<211> LENGTH: 20
<212> TYPE: PRT
<213> ORGANISM: Artificial Sequence
<220> FEATURE:
<223> OTHER INFORMATION: synthetic Bbs1 cloning site

<400> SEQUENCE: 235

```
Ile Pro Ala Glu Val Val Ala Asn Thr Ile Thr Pro Leu Met Lys Ala
1               5                   10                  15

Gln Ser Val Pro
            20
```

<210> SEQ ID NO 236
<211> LENGTH: 114
<212> TYPE: DNA
<213> ORGANISM: Artificial Sequence
<220> FEATURE:
<223> OTHER INFORMATION: synthetic Bbs1 cloning site
<220> FEATURE:
<221> NAME/KEY: misc_feature
<222> LOCATION: (40)..(60)
<223> OTHER INFORMATION: n is a, c, g, or t

<400> SEQUENCE: 236

```
taaggtgatc agcaaggaaa gataagagtg agacgaacan nnnnnnnnnn nnnnnnnnnn    60
acgccacctc caagctgcgg tcacagtctt tttgtcgacc gcctccacca gcgc         114
```

<210> SEQ ID NO 237
<211> LENGTH: 38
<212> TYPE: PRT
<213> ORGANISM: Artificial Sequence
<220> FEATURE:
<223> OTHER INFORMATION: synthetic Bbs1 cloning site
<220> FEATURE:
<221> NAME/KEY: misc_feature
<222> LOCATION: (14)..(20)
<223> OTHER INFORMATION: Xaa can be any naturally occurring amino acid

<400> SEQUENCE: 237

```
Ile Pro Leu Val Val Pro Phe Tyr Ser His Ser Ala Cys Xaa Xaa Xaa
1               5                   10                  15

Xaa Xaa Xaa Xaa Cys Gly Gly Gly Ser Thr Pro Val Ser Glu Lys Gln
            20                  25                  30

Leu Ala Glu Val Val Ala
        35
```

<210> SEQ ID NO 238
<211> LENGTH: 13
<212> TYPE: PRT
<213> ORGANISM: Artificial Sequence
<220> FEATURE:
<223> OTHER INFORMATION: synthetic peptide

<400> SEQUENCE: 238

```
Ala Cys Tyr Asn Leu Tyr Gly Trp Thr Cys Gly Gly Gly
1               5                   10
```

<210> SEQ ID NO 239
<211> LENGTH: 7
<212> TYPE: PRT
<213> ORGANISM: Artificial Sequence
<220> FEATURE:
<223> OTHER INFORMATION: synthetic peptide

<400> SEQUENCE: 239

```
Lys Tyr Tyr Leu Tyr Trp Trp
1               5
```

<210> SEQ ID NO 240
<211> LENGTH: 7
<212> TYPE: PRT
<213> ORGANISM: Artificial Sequence
<220> FEATURE:

<223> OTHER INFORMATION: synthetic peptide

<400> SEQUENCE: 240

Trp Tyr Thr Leu Tyr Lys Trp
1               5

<210> SEQ ID NO 241
<211> LENGTH: 5
<212> TYPE: PRT
<213> ORGANISM: Artificial Sequence
<220> FEATURE:
<223> OTHER INFORMATION: synthetic peptide

<400> SEQUENCE: 241

Tyr Leu Tyr Trp Trp
1               5

<210> SEQ ID NO 242
<211> LENGTH: 7
<212> TYPE: PRT
<213> ORGANISM: Artificial Sequence
<220> FEATURE:
<223> OTHER INFORMATION: synthetic peptide

<400> SEQUENCE: 242

Arg Tyr Ser Leu Tyr Tyr Trp
1               5

<210> SEQ ID NO 243
<211> LENGTH: 7
<212> TYPE: PRT
<213> ORGANISM: Artificial Sequence
<220> FEATURE:
<223> OTHER INFORMATION: synthetic peptide

<400> SEQUENCE: 243

Tyr Tyr Leu Tyr Tyr Trp Lys
1               5

<210> SEQ ID NO 244
<211> LENGTH: 7
<212> TYPE: PRT
<213> ORGANISM: Artificial Sequence
<220> FEATURE:
<223> OTHER INFORMATION: synthetic peptide

<400> SEQUENCE: 244

Asn Tyr Gln Leu Tyr Gly Trp
1               5

<210> SEQ ID NO 245
<211> LENGTH: 7
<212> TYPE: PRT
<213> ORGANISM: Artificial Sequence
<220> FEATURE:
<223> OTHER INFORMATION: synthetic peptide

<400> SEQUENCE: 245

Thr Leu Trp Lys Ser Tyr Trp
1               5

<210> SEQ ID NO 246
<211> LENGTH: 7
<212> TYPE: PRT
<213> ORGANISM: Artificial Sequence
<220> FEATURE:
<223> OTHER INFORMATION: synthetic peptide

<400> SEQUENCE: 246

Thr Lys Trp Pro Ser Tyr Trp
1               5

<210> SEQ ID NO 247
<211> LENGTH: 7
<212> TYPE: PRT
<213> ORGANISM: Artificial Sequence
<220> FEATURE:
<223> OTHER INFORMATION: synthetic peptide

<400> SEQUENCE: 247

Pro Leu Trp Pro Ser Tyr Trp
1               5

<210> SEQ ID NO 248
<211> LENGTH: 7
<212> TYPE: PRT
<213> ORGANISM: Artificial Sequence
<220> FEATURE:
<223> OTHER INFORMATION: synthetic peptide

<400> SEQUENCE: 248

Arg Leu Trp Pro Ser Tyr Trp
1               5

<210> SEQ ID NO 249
<211> LENGTH: 7
<212> TYPE: PRT
<213> ORGANISM: Artificial Sequence
<220> FEATURE:
<223> OTHER INFORMATION: synthetic peptide

<400> SEQUENCE: 249

Thr Leu Trp Pro Lys Tyr Trp
1               5

<210> SEQ ID NO 250
<211> LENGTH: 7
<212> TYPE: PRT
<213> ORGANISM: Artificial Sequence
<220> FEATURE:
<223> OTHER INFORMATION: synthetic peptide

<400> SEQUENCE: 250

Arg Tyr Asp Leu Tyr Trp Trp
1               5

<210> SEQ ID NO 251
<211> LENGTH: 7
<212> TYPE: PRT
<213> ORGANISM: Artificial Sequence
<220> FEATURE:
<223> OTHER INFORMATION: synthetic peptide

<400> SEQUENCE: 251

Asp Tyr Arg Leu Tyr Trp Trp
1               5

<210> SEQ ID NO 252
<211> LENGTH: 7
<212> TYPE: PRT
<213> ORGANISM: Artificial Sequence
<220> FEATURE:
<223> OTHER INFORMATION: synthetic peptide

```
<400> SEQUENCE: 252

Glu Tyr Lys Leu Tyr Trp Trp
1               5

<210> SEQ ID NO 253
<211> LENGTH: 7
<212> TYPE: PRT
<213> ORGANISM: Artificial Sequence
<220> FEATURE:
<223> OTHER INFORMATION: synthetic peptide

<400> SEQUENCE: 253

Arg Tyr Pro Leu Tyr Trp Trp
1               5
```

PEPTIDE PERSONAL CARE COMPOSITIONS AND METHODS FOR THEIR USE

CROSS-REFERENCE TO RELATED APPLICATIONS

The present application claims priority to International Application No. PCT/US06/015711, filed Apr. 25, 2006 and U.S. Provisional Patent Application Ser. No. 60/678,601 filed May 5, 2005, the contents of which are fully incorporated herein by reference.

SEQUENCE LISTING

The sequence listing submitted via EFS, in compliance with 37 C.F.R. §1.52(e), is incorporated herein by reference. The sequence listing text file submitted via EFS contains the file "GC874-US-SEQ-LIST.txt" created on Aug. 24, 2011, which is 78,808 bytes in size.

FIELD OF THE INVENTION

The present invention provides peptides and supported peptides for treating various diseases and conditions. In particularly preferred embodiments, the present invention provides compositions and methods for personal care. In some embodiments, the present invention provides compositions for use in skin and/or hair care, as well as cosmetic compositions. In alternative particularly preferred embodiments, the present invention provides peptides and supported peptides for treating diseases of the skin, such as rosacea. In some particularly preferred embodiments, the supported peptides of the present invention are anti-VEGF peptides. In alternative particularly preferred embodiments, the anti-VEGF peptides are expressed on a scaffold protein. In some most preferred embodiments, the scaffold protein comprises BBI.

BACKGROUND OF THE INVENTION

Angiogenesis is the development of a blood supply to a given area of tissue. Angiogenesis is part of normal embryonic development and revascularization of wound beds, as well as due to the stimulation of vessel growth by inflammatory or malignant cells. Angiogenesis is also the process through which tumors or inflammatory conditions derive a blood supply through the generation of microvessels.

Angiogenesis is regulated in normal and malignant cancer tissues by the balance of angiogenic stimuli and angiogenic inhibitors that are produced in the target tissue and at distant sites (See, Fidler et al., [1998]; and McNamara et al., [1998]). Vascular endothelial growth factor-A (VEGF, also known as vascular permeability factor, "VPF") is a primary stimulant of angiogenesis. VEGF is a multifunctional cytokine that is induced by hypoxia and oncogenic mutations and can be produced by a wide variety of tissues (See, Kerbel et al., [1998]; and Mazure et al., [1996]).

The recognition of VEGF as a primary stimulus of angiogenesis in pathological conditions has led to various attempts to block VEGF activity. Inhibitory anti-VEGF receptor antibodies, soluble receptor constructs, antisense strategies, RNA aptamers against VEGF and low molecular weight VEGF receptor tyrosine kinase (RTK) inhibitors have all been proposed for use in interfering with VEGF signaling (See, Siemeister et al., [1998]). In fact, monoclonal antibodies against VEGF have been shown to inhibit human tumor xenograft growth and ascites formation in mice (See, Kim et al., [1993]; Asano et al., [1998]; Mesiano et al., [1998]; Luo et al., [1998a] and [1998b]; and Borgstrom et al., [1996] and [1998]).

RTKs comprise a large family of transmembrane receptors for polypeptide growth factors with diverse biological activities. The intrinsic function of RTKs is activated upon ligand binding, which results in phosphorylation of the receptor and multiple cellular substrates, and subsequently in a variety of cellular responses. (See, Ullrich & Schlessinger, Cell 61:203-212 [1990]).

Angiogenesis, involving VEGF and RTKs is not only involved in cancer development, as many other diseases or conditions affecting different physiological systems are angiogenesis-dependent, such as arthritis and atherosclerotic plaques (bone and ligaments), diabetic retinopathy, neovascular glaucoma, macular degeneration, ocular herpes, trachoma and corneal graft neovascularization (eye), psoriasis, scleroderma, rosacea, hemangioma and hypertrophic scarring (skin), vascular adhesions and angiofibroma (blood system).

VEGF is an angiogenesis factor of major importance for skin vascularization (Detmar [2000]). VEGF expression is upregulated in the hyperplastic epidermis of psoriasis (Detmar and Yeo et al. [1995]), in healing wounds and in other skin diseases characterized by enhanced angiogenesis (Detmar [2000], supra). Targeted overexpression of VEGF in the epidermis of transgenic mice was reported to result in enhanced skin vascularization with equal numbers of tortuous and leaky blood vessels (See e.g., Brown et al. [1998]). Also, chronic synthesis of VEGF in mouse skin leads to the first histologically equivalent murine model of human psoriasis (Xia et al. [2003]) that is reversible by binding agents specific for VEGF.

Proteases are involved in a wide variety of biological processes. Disruption of the balance between proteases and protease inhibitors is often associated with pathologic tissue destruction. Indeed, various studies have focused on the role of proteases in tissue injury, and it is thought that the balance between proteases and protease inhibitors is a major determinant in maintaining tissue integrity. Serine proteases from inflammatory cells, including neutrophils, are implicated in various inflammatory disorders, such as pulmonary emphysema, arthritis, atopic dermatitis and psoriasis.

Proteases also appear to function in the spread of certain cancers. Normal cells exist in contact with a complex protein network, called the extracellular matrix (ECM). The ECM is a barrier to cell movement and cancer cells must devise ways to break their attachments, degrade, and move through the ECM in order to metastasize. Proteases are enzymes that degrade other proteins and have long been thought to aid in freeing the tumor cells from their original location by chewing up the ECM. Recent studies have suggested that they may promote cell shape changes and motility through the activation of a protein in the tumor cell membrane called Protease-Activated Receptor-2 (PAR2). This leads to a cascade of intracellular reactions that activates the motility apparatus of the cell. Thus, it is hypothesized that one of the first steps in tumor metastasis is a reorganization of the cell shape, such that it forms a distinct protrusion at one edge facing the direction of migration. The cell then migrates through a blood vessel wall and travels to distal locations, eventually reattaching and forming a metastatic tumor. For example, human prostatic epithelial cells constitutively secrete prostate-specific antigen (PSA), a kallikrein-like serine protease, which is a normal component of the seminal plasma. The protease acts to degrade the extracellular matrix and facilitate invasion of cancerous cells.

Synthetic and natural protease inhibitors have been shown to inhibit tumor promotion in vivo and in vitro. Previous investigations have indicated that certain protease inhibitors belonging to a family of structurally-related proteins classified as serine protease inhibitors or SERPINS, are known to inhibit several proteases including trypsin, cathepsin G, thrombin, and tissue kallikrein, as well as neutrophil elastase. The SERPINS are extremely effective at preventing/suppressing carcinogen-induced transformation in vitro and carcinogenesis in animal model systems. Systemic delivery of purified protease inhibitors apparently reduces joint inflammation and cartilage and bone destruction as well.

Topical administration of protease inhibitors finds use in such conditions as atopic dermatitis, a common form of inflammation of the skin, which may be localized to a few patches or involve large portions of the body. The depigmenting activity of protease inhibitors and their capability to prevent ultraviolet-induced pigmentation have been demonstrated both in vitro and in vivo (See e.g., Paine et al., J. Invest. Dermatol., 116:587-595 [2001]). Protease inhibitors have also been reported to facilitate wound healing. For example, secretory leukocyte protease inhibitor was demonstrated to reverse the tissue destruction and speed the wound healing process when topically applied. In addition, serine protease inhibitors can also help to reduce pain in lupus erythematosus patients (See e.g., U.S. Pat. No. 6,537,968).

The Bowman-Birk protease inhibitor (BBI) is a designation of a family of stable, low molecular weight trypsin and chymotrypsin enzyme inhibitors found in soybeans and various other seeds, mainly leguminous seeds and vegetable materials. BBI comprises a family of disulfide bonded proteins with a molecular weight of about 8 kD (See e.g., Chou et al., Proc. Natl. Acad. Sci. USA 71:1748-1752 [1974]; Yavelow et al., Proc. Natl. Acad. Sci. USA 82:5395-5399 [1985]; and Yavelow et al., Cancer Res. (Suppl.) 43:2454 s-2459 s [1983]). BBI has a pseudo-symmetrical structure of two tricyclic domains each containing an independent native binding loop, the native loops containing binding sites for both trypsin and chymotrypsin (See, Liener, in Summerfield and Bunting (eds), *Advances in Legume Science*, Royal Bot. Gardens, Kew, England). These binding sites each have a canonical loop structure, which is a motif found in a variety of serine proteinase inhibitors (Bode and Huber, Eur. J. Biochem., 204:433-451 [1992]). Commonly, as in one of the soybean inhibitors, one of the native loops inhibits trypsin and the other inhibits chymotrypsin (See, Chen et al., J. Biol. Chem., 267:1990-1994 [1992]; Werner & Wemmer, Biochem., 31:999-1010 [1992]; Lin et al., Eur. J. Biochem., 212:549-555 [1993]; and Voss et al., Eur. J. Biochem., 242:122-131 [1996]) though in other organisms (e.g., *Arabidopsis*), both loops are specific for trypsin.

STI inhibits the proteolytic activity of trypsin by the formation of a stable stoichiometric complex (See e.g., Liu, Chemistry and Nutritional Value of Soybean Components, In: *Soybeans, Chemistry, Technology and Utilization*, pp. 32-35, Aspen Publishers, Inc., Gaithersburg, Md., [1999]). STI consists of 181 amino acid residues with two disulfide bridges and is roughly spherically shaped (See e.g., Song et al., J. Mol. Biol., 275:347-63 [1998]). The trypsin inhibitory loop lies within the first disulfide bridge. The Kunitz-type soybean trypsin inhibitor (STI) has played a key role in the early study of proteinases, having been used as the main substrate in the biochemical and kinetic work that led to the definition of the standard mechanism of action of proteinase inhibitors.

Eglin C is a small monomeric protein that belongs to the potato chymotrypsin inhibitor family of serine protease inhibitors. The proteins that belong to this family are usually small (60-90 amino acid residues in length) and contain no disulfide bonds. Eglin C, however, is highly resistant to denaturation by acidification or heat regardless of the lack of disulfide bonds to help stabilize its tertiary structure. The protein occurs naturally in the leech *Hirudo medicinalis*.

As noted above, protease inhibitors interfere with the action of proteases. Naturally occurring protease inhibitors can be found in a variety of foods such as cereal grains (oats, barley, and maize), Brussels sprouts, onion, beetroot, wheat, finger millet, and peanuts. One source of interest is the soybean. The average level of protease inhibitors present in soybeans is around 1.4 percent and 0.6 percent for Kunitz and Bowman-Birk respectively, two of the most important protease inhibitors. Notably, these low levels make it impractical to isolate the natural protease inhibitor for clinical and other applications. Indeed, despite much research in the personal care arena, there remains a need in the art for personal care compositions that have desired characteristics without undesirable chemical modification of the proteins. There also remains a need in the art for a method of delivering a protein into a personal care composition so as to effectively deliver the protein in a useable form.

SUMMARY OF THE INVENTION

The present invention provides peptides and supported peptides for treating various diseases and conditions. In particularly preferred embodiments, the present invention provides compositions and methods for personal care. In some embodiments, the present invention provides compositions for use in skin and/or hair care, as well as cosmetic compositions. In alternative particularly preferred embodiments, the present invention provides peptides and supported peptides for treating diseases of the skin, such as rosacea. In some particularly preferred embodiments, the supported peptides of the present invention are anti-VEGF peptides. In alternative particularly preferred embodiments, the anti-VEGF peptides are expressed on a scaffold protein. In some most preferred embodiments, the scaffold protein comprises BBI.

In some preferred embodiments, the present invention provides cosmetic and/or pharmaceutical compounds suitable for improving the appearance of skin. The present invention further provides peptides that block binding of a protein. In some preferred embodiments, the protein is VEGF. In some particularly preferred embodiments, the peptide is expressed in a protease-resistant scaffold. In some especially preferred embodiments, the scaffold is a protease inhibitor (e.g., BBI, STI, or Eglin chymotrypsin inhibitor). In some most preferred embodiments, the protease inhibitor is BBI.

In some embodiments, the present invention provides personal care compositions comprising a scaffold, wherein the scaffold comprises at least one protease inhibitor and at least one peptide selected from the group consisting of SEQ ID NOS:1-17. In alternative embodiments, any of the additional peptide sequences provided herein find use in the present invention. In further embodiments, additional sequences find use in the present invention, including but not limited to SEQ ID NOS:20-25, 31, 32-34, 43, and 238. In yet further embodiments, the at least one peptide sequence is selected from the group consisting of YNLYGWT (SEQ ID NO:1), KYYLYWW (SEQ ID NO:239), WYTLYKW (SEQ ID NO:240), TYRLYWW (SEQ ID NO:241), RYSLYYW (SEQ ID NO:242), YYLYYWK (SEQ ID NO:243), NYQLYGW (SEQ ID NO:244), TLWKSYW (SEQ ID NO:245), TKWPSYW (SEQ ID NO:246), PLWPSYW (SEQ ID NO:247), RLWPSYW (SEQ ID NO:248), TLWPKYW (SEQ ID NO:249), KYDLYWW (SEQ ID NO:33), RYDLYWW (SEQ ID NO:250), DYRLYWW (SEQ ID NO:251), DYK-LYWW (SEQ ID NO:34), EYKLYWW (SEQ ID NO:252), and RYPLYWW (SEQ ID NO:253). In some particularly preferred embodiments, the peptide sequence comprises the motif set forth in SEQ ID NO:31. In yet further embodiments, the scaffold comprises an amino acid sequence selected from the group consisting of SEQ ID NOS:22-25.

In yet additional embodiments, the protease inhibitor is selected from the group consisting of Bowman-Birk inhibitor, soybean trypsin inhibitor, and Elgin chymotrypsin inhibitor. In some particularly preferred embodiments, the Bowman-Birk inhibitor is a modified Bowman-Birk inhibitor. In further embodiments, the scaffold comprises from about 0.001 weight percent to about 5 weight percent of the personal care composition, while in alternative embodiments, the scaffold comprises from about 0.01 weight percent to about 2.0 weight percent of the personal care composition, and in yet additional embodiments, the scaffold comprises from about 0.01 weight percent to about 1 weight percent of the personal care composition.

The present invention also provides personal care compositions comprising skin care compositions. In some preferred embodiments, the skin care compositions are selected from the group consisting of skin creams, lotions, sprays, emulsions, colloidal suspensions, foams, aerosols, liquids, gels, sera, and solids. In additional embodiments, the skin care compositions are moisturizing body washes, body washes, antimicrobial cleansers, skin protective creams, body lotions, facial creams, moisturizing creams, facial cleansing emulsions, facial gels, facial sera, surfactant-based facial cleansers, facial exfoliating gels, anti-acne treatments, facial toners, exfoliating creams, facial masks, after shave balms, pre-shave balms, tanning compositions, skin lightening compositions, skin redness reduction compositions, sunscreens, depilatories, hair growth inhibitors, and radioprotectives. In additional embodiments, the skin care compositions comprise topically applied over-the-counter compositions, anti-fungal treatments, anti-acne treatments, skin protectants, sunscreens, deodorants, and antiperspirants.

In some preferred embodiments, the skin care compositions are capable of lightening the skin tone, while in alternative embodiments the skin care compositions are capable of reducing redness in skin tone. In yet further embodiments, the skin care compositions are capable of preventing skin tone darkening, while in additional embodiments, the skin care compositions are capable of preventing skin color development. In some preferred embodiments, the skin care compositions are radioprotective. In alternative embodiments, the skin care compositions comprise at least one radioprotectives. In some particularly preferred embodiments, the radioprotectives are selected from the group consisting of sunscreens. In some most preferred embodiments, the sunscreens are selected from non-water-resistant sunscreens, very water-resistant sunscreens, and water-in-silicone sunscreens.

The present invention also provides personal care compositions that are capable of preventing hair growth. In some embodiments, the hair is selected from the group consisting of facial hair, leg hair, arm hair, and torso hair.

The present invention also provides personal care compositions that are hair care compositions. In some embodiments, the hair care composition is selected from the group consisting of shampoos, conditioners, hair styling compositions, hair colorants, permanent wave formulations, creams, gels, mousses, sprays, emulsions, colloidal suspensions, liquids, foams, and solids. In further embodiments, the hair care compositions comprise at least one radioprotectant. In some preferred embodiments, the radioprotectant is a sunscreen selected from non-water-resistant sunscreens, very water-resistant sunscreens, and water-in-silicone sunscreens. In some embodiments, the hair care composition is radioprotective.

The present invention further provides personal care compositions that are oral care compositions. In some preferred embodiments, the oral care compositions are selected from the group consisting of toothpastes, tooth gels, mouth rinses, mouthwashes, anti-caries compositions, tooth whitening compositions, chewing gums, denture adhesives, and breath fresheners.

The present invention also provides personal care compositions that are cosmetic compositions. In some preferred embodiments, the cosmetic compositions are selected from eye gels, eye shadows, high-melting point lipsticks, lipsticks, lip glosses, lip balms, mascaras, eyeliners, pressed powder formulations, and foundations. In some preferred embodiments, the makeup compositions comprise at least one pigment.

In some preferred embodiments, the makeup composition comprising at least one pigment is a mascara selected from non-waterproof mascaras, waterproof mascaras, volumizing mascaras, lengthening mascaras, curling mascaras, anhydrous waterproof mascaras, water-based mascaras, and eyelash or eyebrow treatments.

In yet additional embodiments, the makeup compositions are pressed powder formulations selected from loose powders, blushes, eye shadows, and bronzing powders. In still further embodiments, the makeup compositions are foundations selected from water-in-oil foundations, water-in-silicone foundations, oil-in-water foundations, anhydrous makeup sticks, and cream-to-powder foundations.

The present invention further provides personal care compositions having a scaffold, wherein the scaffold comprises the amino acid sequence set forth in SEQ ID NO:19. In additional embodiments, the scaffold further comprises the amino acid sequence(s) set forth in SEQ ID NOS:20 and/or 21. In alternative embodiments, the amino acid sequence(s) set forth in SEQ ID NOS: 20 and/or 21 is/are replaced by at least one peptide having an amino acid sequence selected from the group consisting of SEQ ID NOS:1-17. In alternative embodiments, any of the peptide sequences provided herein find use as a replacement of SEQ ID NOS:20 and/or 21. In alternative embodiments, any of the additional peptide sequences provided herein find use in the present invention. In further embodiments, additional sequences find use in the present invention, including but not limited to SEQ ID NOS: 20-25, 31, 32-34, 43, and 238. In yet further embodiments, the at least one peptide sequence is selected from the group consisting of YNLYGWT (SEQ ID NO:1), KYYLYWW (SEQ ID NO:239), WYTLYKW (SEQ ID NO:240), TYRLYWW (SEQ ID NO:241), RYSLYYW (SEQ ID NO:242), YYLYYWK (SEQ ID NO:243), NYQLYGW (SEQ ID NO:244), TLWKSYW (SEQ ID NO:245), TKWPSYW (SEQ ID NO:246), PLWPSYW (SEQ ID NO:247), RLWPSYW (SEQ ID NO:248), TLWPKYW (SEQ ID NO:249), KYDLYWW (SEQ ID NO:33), RYDLYWW (SEQ ID NO:250), DYRLYWW (SEQ ID NO:251), DYKLYWW (SEQ ID NO:34), EYKLYWW (SEQ ID NO:252), and RYPLYWW (SEQ ID NO:253). In some particularly preferred embodiments, the peptide sequence comprises the motif set forth in SEQ ID NO:31. In yet further embodiments, the scaffold comprises an amino acid sequence selected from the group consisting of SEQ ID NOS:22-25.

The present invention also provides methods for making the personal care compositions of the present invention, comprising combining an effective amount of the scaffold and at least one physiologically acceptable carrier or excipient.

The present invention further provides methods for modifying the skin tone of a subject, comprising the steps of: providing at least one composition comprising a personal care composition of the present invention; ii) providing a subject to be treated; and applying the composition to the subject in an area in which modifications to the subject's skin tone is desired. In some embodiments, the modification of skin tone comprises lightening the subject's skin tone. In some alternative embodiments, the modification of skin tone comprises reducing redness in the subject's skin tone. In yet additional embodiments, the methods comprise a personal care composition comprising the amino acid sequence set forth in SEQ ID NO:19. In alternative embodiments of the methods, the personal care composition comprises at least one of the amino acid sequences set forth in SEQ ID NOS:20 and 21. In yet further embodiments of the methods, at least one of the amino acid sequences set forth in SEQ ID NOS:20 and 21 is replaced by at least one peptide having an amino acid sequence selected from the group consisting of SEQ ID NOS:1-17. In alternative embodiments, any of the additional peptide sequences provided herein find use as a replacement of SEQ ID NOS:20 and/or 21. In further embodiments, additional sequences find use in the present invention, including but not limited to SEQ ID NOS:20-25, 31, 32-34, 43, and 238. In yet further embodiments, the at least one peptide sequence is selected from the group consisting of YNLYGWT (SEQ ID NO:1), KYYLYWW (SEQ ID NO:239), WYTLYKW (SEQ ID NO:240), TYRLYWW (SEQ ID NO:241), RYSLYYW (SEQ ID NO:242), YYLYYWK (SEQ ID NO:243), NYQLYGW (SEQ ID NO:244), TLWKSYW (SEQ ID NO:245), TKWPSYW (SEQ ID NO:246), PLWPSYW (SEQ ID NO:247), RLWPSYW (SEQ ID NO:248), TLWPKYW (SEQ ID NO:249), KYDLYWW (SEQ ID NO:33), RYDLYWW (SEQ ID NO:250), DYRLYWW (SEQ ID NO:251), DYKLYWW (SEQ ID NO:34), EYKLYWW (SEQ ID NO:252), and RYPLYWW (SEQ ID NO:253). In some particularly preferred embodiments, the peptide sequence comprises the motif set forth in SEQ ID NO:31. In yet further embodiments, the scaffold comprises an amino acid sequence selected from the group consisting of SEQ ID NOS:22-25.

The present invention also provides methods for modifying the hair growth of a subject, comprising the steps of: providing the personal care composition of the present invention; providing a subject to be treated; and applying the composition to the subject in an area in which modifications to the subject's hair growth is desired. In some embodiments, the modification of hair modification of hair growth comprises inhibiting the growth of the subject's hair, wherein the hair to be inhibited is selected from the group consisting of facial air, underarm hair, leg hair, torso hair, and arm hair, and head hair. In yet additional embodiments, the methods comprise a personal care composition comprising the amino acid sequence set forth in SEQ ID NO:19. In alternative embodiments of the methods, the personal care composition comprises at least one of the amino acid sequences set forth in SEQ ID NOS:20 and 21. In yet further embodiments of the methods, at least one of the amino acid sequences set forth in SEQ ID NOS:20 and 21 is replaced by at least one peptide having an amino acid sequence selected from the group consisting of SEQ ID NOS:1-17. In some alternative embodiments, any of the additional peptide sequences provided herein find use as a replacement of SEQ ID NOS:20 and/or 21. In further embodiments, additional sequences find use in the present invention, including but not limited to SEQ ID NOS:20-25, 31, 32-34, 43, and 238. In yet further embodiments, the at least one peptide sequence is selected from the group consisting of YNLYGWT (SEQ ID NO:1), KYYLYWW (SEQ ID NO:239), WYTLYKW (SEQ ID NO:240), TYRLYWW (SEQ ID NO:241), RYSLYYW (SEQ ID NO:242), YYLYYWK (SEQ ID NO:243), NYQLYGW (SEQ ID NO:244), TLWKSYW (SEQ ID NO:245), TKWPSYW (SEQ ID NO:246), PLWPSYW (SEQ ID NO:247), RLWPSYW (SEQ ID NO:248), TLWPKYW (SEQ ID NO:249), KYDLYWW (SEQ ID NO:33), RYDLYWW (SEQ ID NO:250), DYRLYWW (SEQ ID NO:251), DYKLYWW (SEQ ID NO:34), EYKLYWW (SEQ ID NO:252), and RYPLYWW (SEQ ID NO:253). In some particularly preferred embodiments, the peptide sequence comprises the motif set forth in SEQ ID NO:31. In yet further embodiments, the scaffold comprises an amino acid sequence selected from the group consisting of SEQ ID NOS:22-25.

In some embodiments, the present invention provides cosmetic and/or pharmaceutical compounds for improving the appearance of skin comprising at least one polypeptide or a peptide. In some preferred embodiments, the polypeptide or peptide binds to VEGF. In alternative embodiments, the binding of the polypeptide or peptide to VEGF blocks the downstream activity of VEGF. In some embodiments, the compounds comprise at least one peptide, while in other embodiments, the compounds comprise at least one polypeptide. In some preferred embodiments, the peptide has an amino acid sequence selected from the group consisting of SEQ ID NOS:1-17. In still further embodiments, the peptide has an amino acid sequence selected from the group consisting of KYDLYWW (SEQ ID NO:33) and DYKLYWW (SEQ ID NO:34). In additional preferred embodiments, the peptide has a conserved binding sequence, the sequence being XXL-WPXWC (SEQ ID NO:15). In some preferred embodiments, the sequence comprises SEQ ID NO:15. In further embodiments, the sequence comprises an amino acid sequence selected from the group consisting of SEQ ID NOS:1-17. In further embodiments, the sequence comprises an amino acid sequence selected from the group consisting of SEQ ID NOS: 22-25. In alternative preferred embodiments, the compounds have a sequence, the sequence being at least 70%, preferably 80%, more preferably 90%, and most preferably 95% homologous to the sequences set forth herein. In some preferred embodiments, the polypeptide has a molecular weight that is preferably between 500 Daltons and 30,000 Daltons, more preferably between 1000 Daltons and 10,000 Daltons, and most preferably from 1500 Daltons to 8,000 Daltons.

In some preferred embodiments, the compounds find use in the improvement of skin in an organism (i.e., subject) having a skin disorder. In some preferred embodiments, the skin disorder is an angiogenic skin disorder. In additional preferred embodiments, the skin disorder is at least one selected from the group consisting of psoriasis, venous ulcers, acne, rosacea, warts, eczema, hemangiomas and lymphangiogenesis, etc. In some particularly preferred embodiments, the skin disorder is rosacea.

In other preferred embodiments, the present invention provides cosmetic and/or pharmaceutical compounds for improving the appearance of skin. In these preferred embodiments, the compounds comprise at least one peptide or polypeptide and at least one scaffold, the peptide or polypeptide being expressed in the scaffold. In some particularly preferred embodiments, the at least one peptide or polypeptide is a loop. In other particularly preferred embodiments, the loop is closed by a disulfide bond. In some preferred embodiments, the polypeptide or peptide binds to VEGF. In alternative embodiments, the binding of the polypeptide or peptide to VEGF blocks the downstream activity of VEGF. In some particularly preferred embodiments, the peptide is expressed in a protease-resistant scaffold. In some especially preferred embodiments, the scaffold is a protease inhibitor (e.g., BBI, STI, or Eglin chymotrypsin inhibitor). In some most preferred embodiments, the protease inhibitor is BBI.

In some preferred embodiments, the compounds further comprise at least one peptide. Preferably, the peptide has an amino acid sequence selected from the group consisting of SEQ ID NOS: 1-17. Most preferably, the compounds comprise an amino acid sequence selected from the group consisting of SEQ ID NOS:22-25. In some preferred embodiments, the peptide has a conserved binding sequence, the sequence being XXLWPXWC (SEQ ID NO:15). In some preferred embodiments, the compounds have a sequence, the sequence being at least 70%, preferably 80%, more preferably 90%, and most preferably 95% identical to the sequences set forth herein. The peptide molecular weight is preferably between 500 Daltons and 45,000 Daltons, more preferably between 1000 Daltons and 12,000 Daltons, and most preferably from 1500 Daltons to 10,000 Daltons. In some preferred embodiments, the compounds comprise at least one polypeptide.

The present invention provides compositions comprising at least one peptide selected from the group consisting of SEQ ID NOS:1-17, wherein the peptide binds to a vascular endothelial growth factor. In some preferred embodiments, the peptide is expressed in a protease resistant scaffold. In alternative preferred embodiments, the scaffold comprises a protease inhibitor. In some more preferred embodiments, the protease inhibitor is selected from the group consisting of Bowman-Birk Inhibitor, soybean trypsin inhibitor, and Eglin chymotrypsin inhibitor. In some most preferred embodiments, the scaffold is Bowman-Birk inhibitor. In still further embodiments, the protease resistant scaffold and the peptide comprise a fusion protein. IN some particularly preferred embodiments, the composition comprises an amino acid sequence selected from the group consisting of SEQ ID NOS: 22-25. In additional embodiments, the scaffold comprises the amino acid sequence set forth in SEQ ID NO:19. In still further embodiments, the scaffold comprises at least one of the amino acid sequences set forth in SEQ ID NOS:20 and 21. In yet additional embodiments, at least one of the amino acid sequences set forth in SEQ ID NOS:20 and 21 is replaced by at least one peptide having an amino acid sequence selected from the group consisting of SEQ ID NOS:1-17.

The present invention also provides cosmetic and/or pharmaceutical compositions comprising the at least one peptide that binds to a vascular endothelial growth factor. In some embodiments, the composition is capable of modulating angiogenesis. In additional embodiments, the composition further comprises a scaffold comprising a protease inhibitor. In some preferred embodiments, the protease inhibitor is selected from the group consisting of Bowman-Birk Inhibitor, soybean trypsin inhibitor, and Eglin chymotrypsin inhibitor. In some preferred embodiments, the scaffold is Bowman-Birk inhibitor. In some particularly preferred embodiments, the scaffold comprises the amino acid sequence set forth in SEQ ID NO:19. In some alternative embodiments, the scaffold comprises at least one of the amino acid sequences set forth in SEQ ID NOS:20 and 21. In further preferred embodiments, at least one of the amino acid sequences set forth in SEQ ID NOS:20 and 21 is replaced by at least one peptide having an amino acid sequence selected from the group consisting of SEQ ID NOS:1-17.

The present invention also provides methods for modulating angiogenesis comprising: i) providing a composition comprising a peptide contained within a scaffold; ii) providing a subject to be treated; and iii) applying the composition to the subject in an area in which angiogenesis modulation is desired. In some embodiments, the peptide binds to a vascular endothelial growth factor (VEGF). In some preferred embodiments, the vascular endothelial growth factor (VEGF) is VEGF-A. In further preferred embodiments, the scaffold is selected from the group consisting of Bowman-Birk inhibitor, soybean trypsin inhibitor, and Eglin chymotrypsin inhibitor. In some particularly preferred embodiments, the scaffold is Bowman-Birk inhibitor. In some further embodiments, the scaffold comprises the amino acid sequence set forth in SEQ ID NO:19. In still further embodiments, the scaffold comprises at least one of the amino acid sequences set forth in SEQ ID NOS:20 and 21. In some particularly preferred embodiments, at least one of the amino acid sequences set forth in SEQ ID NOS:20 and 21 is replaced by at least one peptide having an amino acid sequence selected from the group consisting of SEQ ID NOS:1-17. In still further particularly preferred embodiments, the scaffold and the peptide are encoded by an amino acid sequence selected from the group consisting of SEQ ID NOS:22-25.

The present invention also provides methods for decreasing the activity of a vascular endothelial growth factor comprising the steps of: i) providing a subject; and ii) administering the composition comprising at least one peptide that binds to the vascular endothelial growth factor to the subject, under conditions such that the activity of the vascular endothelial growth factor is decreased. In some embodiments, the vascular endothelial growth factor (VEGF) is VEGF-A. In some particularly preferred embodiments, the composition comprises an amino acid sequence selected from the group consisting of SEQ ID NOS:22-25.

In some additional preferred embodiments, the compounds are used for the improvement of skin in an organism (i.e., a subject) having a skin disorder. In additional preferred embodiments, the skin disorder is at least one selected from the group consisting of psoriasis, venous ulcers, acne, rosacea, warts, eczema, hemangiomas and lymphangiogenesis, etc. In some particularly preferred embodiments, the skin disorder is rosacea.

In yet further embodiments, the present invention provides cosmetic and/or pharmaceutical compositions comprising at least one polypeptide or peptide, as set forth herein, and a physiologically acceptable carrier or excipient. Preferably, the compound is present in an amount of about 0.0001% to about 5% by weight based on the total weight of the composition. Also preferably, the compound is present in an amount of about 0.001% to about 0.5% by weight based on the total weight of the composition. The composition may be in the form of an emulsified vehicle, such as a nutrient cream or lotion, a stabilized gel or dispersion system, a treatment serum, a liposomal delivery system, a topical pack or mask, a surfactant-based cleansing system such as a shampoo or body wash, an aerosolized or sprayed dispersion or emulsion, a hair or skin conditioner, styling aid, or a pigmented product such as makeup, as well as other suitable make-up and cosmetic preparations. In some embodiments, the carrier is preferably at least one selected from the group consisting of water, propylene glycol, ethanol, propanol, glycerol, butylene glycol and polyethylene glycol.

In yet further embodiments, the present invention provides means for decreasing VEGF activity and/or levels. In some preferred embodiments, the VEGF activity and/or levels are decreased in the epidermis. In some embodiments, the method comprising applying an effective amount of at least one of the compounds described herein to an organism in need thereof.

In additional embodiments, the present invention provides applications for hair and/or skin treatment, as well as applications wound healing, treatment of proliferative diseases, etc. Thus, the present invention provides compositions and methods suitable for application in/on humans and other animals.

BRIEF DESCRIPTION OF THE DRAWINGS

FIG. 5 provides a summary of N-terminal fusion cloning strategy using Bbs1 cloning sites (SEQ ID NOS:227-237).

FIG. 9 provides the BBI gene and amino acid sequences (SEQ ID NOS:18 and 19, respectively) designed for efficient cloning. This sequence comprises the expression cassette used in E. coli. It codes for the pro-BBI protein with a C-terminal His tag and has extra sequences at the 5' and 3' ends for cloning into the E. coli expression vector. The protein signal sequence is italicized while the trypsin loop (CTKSNPPQC; SEQ ID NO:20) and chymotrypsin loop (CALSYPAQC; SEQ ID NO:21) are highlighted in bold and boxed.

FIG. 13 provides sequences of three BBI-VEGF fusions, BBI-VEGF1 (SEQ ID NO:22), BBI-VEGF2 (SEQ ID NO:23) and BBI-VEGF12 (SEQ ID NO:24). Fusions BBI-VEGF1 and BBI-VEGF2 have only one of the binding loops replaced; fusion BBI-VEGF12 has both of the binding loops replaced.

FIG. 14 provides the DNA and amino acid sequences of the aprE-BCE103-BBI-Histag expression cassette (EcoRI-HindIII) cloned into the pJM103 integration vector (SEQ ID NOS:35 and 36).

FIG. 16 provides the DNA and amino acid sequences of 12BBIck81 from the BCE103 fusion site (at the BamHI) to the end of the gene (SEQ ID NOS:37 and 38). The CK37281 peptide sequences (ACYNLYGWTC (SEQ ID NO:43)) are inserted into both the trypsin and chymotrypsin inhibitory loops.

FIG. 20 provides the sequence of the synthetic DNA fragment carrying the H. insolens PDI (hiPDI) that was inserted into the B. subtilis BBI expression vector, as well as the amino acid sequence (SEQ ID NOS:39 and 40)

FIG. 21 provides the DNA and amino acid sequences of the aprE-cutinase expression cassette that was ligated into the EcoRI-BamHI sites of p2JM103-lnk2-2BBIck81 (SEQ ID NOS:41 and 42).

DESCRIPTION OF THE INVENTION

Figure 1:
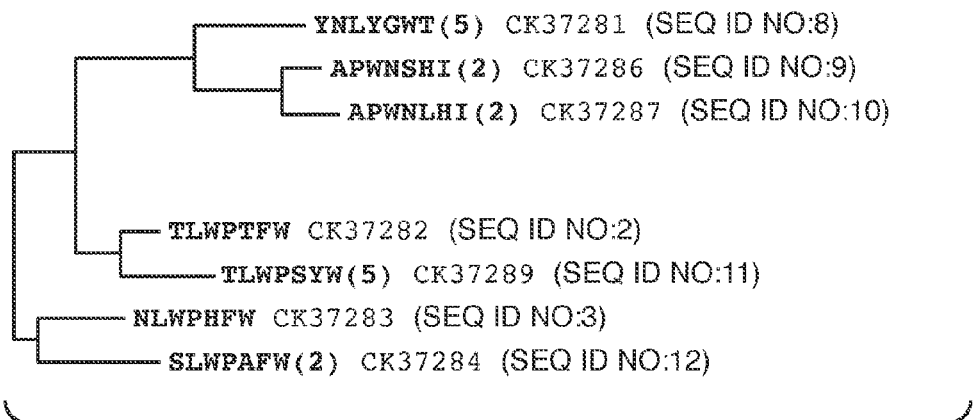
FIG. 1 provides a sequence summary of VEGF binding phage clones (SEQ ID NOS:1-12). Twenty-four phage clones were sequenced after 3 rounds of panning. The sequence alignment tree indicates a highly conserved sequence motif ACXLWPXXWC (SEQ ID NO:14). The number in parentheses represents the frequency of that sequence within the 24 clones sequenced after the third round of panning.

The present invention provides peptides and supported peptides for treating various diseases and conditions. In particularly preferred embodiments, the present invention provides compositions and methods for personal care. In some embodiments, the present invention provides compositions for use in skin and/or hair care, as well as cosmetic compositions. In alternative particularly preferred embodiments, the present invention provides peptides and supported peptides for treating diseases of the skin, such as rosacea. In some particularly preferred embodiments, the supported peptides of the present invention are anti-VEGF peptides. In alternative particularly preferred embodiments, the anti-VEGF peptides are expressed on a scaffold protein. In some most preferred embodiments, the scaffold protein comprises BBI.

As described in greater detail herein, the present invention provides compositions for use in numerous aspects of personal care, including but not limited to hair and skin care, as well as cosmetics (e.g., make-up). For example, the present invention provides compositions that find use in daily personal care, skin care, sun care (e.g., sunscreens, as well as tanners), hair care (e.g., shampoos, leave-on and/or rinse off conditioners, hair tonics, hair sprays, gels, foams, mousses, setting products, hair colorants, permanent formulations, other styling and cleaning products, etc.), after-sun care for skin, hair and lips, oral care (e.g., toothpastes and gels, mouthwashes, rinses, etc.), bathing (e.g., washes, shower soaps, bath soaps, salts, pearls, etc.), skin lighteners, cleansing treatments for skin conditions (e.g., pimples, acne, skin toners, etc.), depilatories, wet wipes, deodorants, anti-perspirants, facial masks, shaving (e.g., shaving creams, gels, etc.), after-shave, skin peeling (e.g., exfoliants), intimate care products (e.g., feminine hygiene products), personal fresheners, and foot care. The present invention also provides compositions that find use in cosmetics (e.g., foundations, mascara, eye shadows, eye liners, lipsticks, lip glosses, blushers, etc.). It is contemplated that the compositions of the present invention will find use various forms, including but not limited to solids, liquids, colloidal suspensions, emulsions, oils, gels, aerosols, foams, powders, pump sprays, etc., as well as being used in conjunction with items such as wet wipes, etc. Indeed, it is contemplated that the present invention will find use in any suitable form for the intended use(s).

Unless otherwise indicated, the practice of the present invention involves conventional techniques commonly used in molecular biology, microbiology, and recombinant DNA, which are within the skill of the art. Such techniques are known to those of skill in the art and are described in numerous texts and reference works (See e.g., Sambrook et al., "Molecular Cloning: A Laboratory Manual", Second Edition (Cold Spring Harbor), [1989]); and Ausubel et al., "Current Protocols in Molecular Biology" [1987]). All patents, patent applications, articles and publications mentioned herein, both supra and infra, are hereby expressly incorporated herein by reference.

Unless defined otherwise herein, all technical and scientific terms used herein have the same meaning as commonly understood by one of ordinary skill in the art to which this invention pertains. For example, Singleton and Sainsbury, *Dictionary of Microbiology and Molecular Biology*, 2d Ed., John Wiley and Sons, NY (1994); and Hale and Marham, *The Harper Collins Dictionary of Biology*, Harper Perennial, N.Y. (1991) provide those of skill in the art with a general dictionaries of many of the terms used in the invention. Although any methods and materials similar or equivalent to those described herein find use in the practice of the present invention, the preferred methods and materials are described herein. Accordingly, the terms defined immediately below are more fully described by reference to the Specification as a whole. Also, as used herein, the singular "a," "an," and "the" includes the plural reference unless the context clearly indicates otherwise. Numeric ranges are inclusive of the numbers defining the range. Unless otherwise indicated, nucleic acids are written left to right in 5' to 3' orientation; amino acid sequences are written left to right in amino to carboxy orientation, respectively. It is to be understood that this invention is not limited to the particular methodology, protocols, and reagents described, as these may vary, depending upon the context they are used by those of skill in the art.

Furthermore, the headings provided herein are not limitations of the various aspects or embodiments of the invention which can be had by reference to the specification as a whole. Accordingly, the terms defined immediately below are more fully defined by reference to the specification as a whole. Nonetheless, in order to facilitate understanding of the invention, a number of terms are defined below.

Definitions

As used herein, the term "scaffold" refers to a protease inhibitor having a heterologous and/or modified peptide sequence incorporated therein. In preferred embodiments, the term "scaffold" refers to a wild-type protein sequence into which a variant sequence is introduced. In some embodiments, the scaffold has portions (e.g., parts or all of one or both loops), that are replaced with heterologous sequence(s). For example, the BBI sequences having anti-VEGF (AV) sequences incorporated as provided herein, find use as scaffolds. Indeed, the present invention encompasses BBI-based sequences, but which have structural and functional differences from wild-type BBI.

As used herein, the term "vascular endothelial growth factor" (VEGF) refers to proteins with the ability to stimulate vascular growth, including those designated "VEGF-A" known to those of skill in the art.

As used herein, the term "anti-VEGF" ("aVEGF" and "AV") refers to peptides and other compositions that recognize (i.e., bind) to VEGF. In preferred embodiments, these peptides/compositions modulate VEGF activity.

The term "angiogenesis" refers to the biological processes which result in the development of blood vessels and/or increase in the vascularity of tissue in an organism. In particular embodiments herein, the term refers to the process through which tumors or other rapidly proliferating tissue derive a blood supply through the generation of microvessels.

The terms "angiogenic disease," "angiogenic disorder," and "angiogenic skin disorder," are used in reference to a disorder, generally a skin disorder or related disorder which occurs as a consequence of or which results in increased vascularization in tissue. Oftentimes, the etiology of the angiogenic disease is unknown. However, whether angiogenesis is an actual cause of a disease state or is simply a condition of the disease state is unimportant, but the inhibition of angiogenesis in treating or reversing the disease state or condition is an important aspect of the present invention. Thus, it is not intended that the present invention be limited to any particular mechanisms of action. Examples of angiogenic skin disorders which are suitable for treatment utilizing compounds of the present invention include, but are not limited to psoriasis, acne, rosacea, warts, eczema, hemangiomas and lymphangiogenesis, Sturge-Weber syndrome, neurofibromatosis, tuberous sclerosis, chronic inflammatory disease, and arthritis. Any skin disorder which has as a primary or secondary characterization, increased vascularization, is considered an angiogenic skin disorder herein. Thus, the compounds provided by the present invention find use in treatment of a wide variety of diseases and/or conditions.

The term "rosacea" is used to describe acne, rosacea, or erythematosa characterized by vascular and follicular dilation typically involving the nose and contiguous portions of the cheeks. Rosacea may vary from very mild but persistent erythema to extensive hyperplasia of the sebaceous glands with deep-seated papules and pustules and be accompanied by telangiectasia at the affected erythematous sites. This condition is also referred to as "hypertrophic rosacea" or "rhinophyma," depending upon the severity of the condition. It is intended that the term encompass all of the various forms of the condition.

The term "wart" is used to describe a small, usually hard growth on the skin. Also known as a "verruca," warts are flesh-colored growths of the skin which are characterized by circumscribed hypertrophy of the papillae of the corium, with thickening of the malpighian, granulation and keratin layers of the epidermis. Verucca vulgaris, a subset of warts or verruca, is characterized by infection of the keratinocytes with human papillomavirus.

The term "psoriasis" is used to describe a skin condition which is characterized by the eruption of circumscribed, discrete and confluent, reddish, silvery-scaled maculopapules. Although it is not intended that the present invention be limited to any particular body area, psoriatic lesions typically occur on the elbows, knees, scalp and trunk. Microscopically, these lesions demonstrate characteristic parakeratosis and elongation of rete ridges.

The term "acne" is used to describe a condition of the skin characterized by inflammatory follicular, papular and pustular eruptions involving the sebaceous apparatus. Although there are numerous forms of acne, the most common form is known as acne simplex or acne vulgaris which is characterized by eruptions of the face, upper back and chest and is primarily comprised of comedones, cysts, papules and pustules on an inflammatory base. The condition occurs primarily during puberty and adolescence due to an overactive sebaceous apparatus which is believed to be affected by hormonal activity.

The term "eczema" is a generic term used to describe acute or chronic inflammatory conditions of the skin, typically erythematous, edematous, papular, vesicular and/or crusting. These conditions are often followed by lichenification, scaling and occasionally, by duskiness of the erythema and, infrequently, hyperpigmentation. Eczema is often accompanied by the sensation of itching and burning. Eczema vesicles form due to intraepidermal spongiosis. Eczema is sometimes referred to colloquially as "tetter," "dry tetter," and "scaly tetter." There are numerous subcategories of eczema, all of which are treated by one or more of the compounds according to the present invention.

As used herein, "CK" followed by an integer refers to a specific peptide. Various peptide sequences that find use with the present invention are provided herein (See e.g., FIG. 1). As an example, CK37281 refers to the peptide sequence YNLYGWT (SEQ ID NO:1) which is also is included in various other sequences (e.g., "ACYNLYGWTCGGG" (SEQ ID NO:238).

As used herein, in some embodiments, the "compound" comprises the "complete" protein, (i.e., in its entire length as it occurs in nature (or as mutated)), while in other embodiments it comprises a truncated form of a protein. Thus, in some embodiments, the compounds of the present invention are either truncated or be "full-length." In addition, in some embodiments, the truncation is located at the N-terminal end, while in other embodiments the truncation is located at the C-terminal end of the protein. In further embodiments, the compound lacks one or more portions (e.g., sub-sequences, signal sequences, domains or moieties), whether active or not.

The term "organism" is used throughout the specification to describe an animal, preferably a human, to whom treatment, including prophylactic treatment, with the compounds according to the present invention is provided. For treatment of those infections, conditions or disease states which are specific for a specific animal such as a human patient, the term organism refers to that specific animal.

The "host cells" used in the present invention generally are prokaryotic or eukaryotic hosts which contain an expression vector and/or gene of interest. Host cells are transformed or transfected with vectors constructed using recombinant DNA techniques. Such transformed host cells are capable of either replicating vectors encoding the protein variants or expressing the desired protein variant. In the case of vectors which encode the pre- or prepro-form of the protein variant, such variants, when expressed, are typically secreted from the host cell into the host cell medium.

The term "effective amount" is used throughout the specification to describe concentrations or amounts of compounds according to the present invention which may be used to produce a favorable change in the disease or condition treated, whether that change is hair growth or prevention of hair growth.

As used herein, "active" (and "actives") refers to a composition that imparts a benefit to a subject being treated. For example, in preferred embodiments, the present invention provides personal care compositions comprising BBI-AV, a "primary active" which functions to provide benefit to the area to which it is applied. Thus, in some embodiments, BBI-AV is present in skin care formulations and serves to modify the skin tone of subjects to which is applied. It is not intended that the term be limited to BBI-AV, as there are additional constituents present in the personal care compositions of the present invention which impart benefits. In some preferred embodiments, these additional constituents are encompassed by the designation "secondary actives." Primary and secondary actives are collectively referred to as "actives" herein.

As used herein, "vitamin $B_3$ compound" means a compound having the formula:

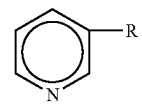

wherein R is —$CONH_2$ (i.e., niacinamide), —COOH (i.e., nicotinic acid) or —$CH_2OH$ (i.e., nicotinyl alcohol); derivatives thereof; and salts of any of the foregoing.

As used herein, "non-vasodilating" means that an ester does not commonly yield a visible flushing response after application to the skin in the subject compositions. It is contemplated that the majority of the general population would not experience a visible flushing response, although such compounds may cause vasodilation not visible to the naked eye.

As used herein, "retinoid" includes all natural and/or synthetic analogs of Vitamin A and/or retinol-like compounds which possess the biological activity of Vitamin A in/on the skin, as well as the geometric isomers and stereoisomers of these compounds. However, it is not intended that the term be limited to these compounds, as the term encompasses vitamin A alcohol (retinol) and its derivatives such as vitamin A aldehyde (retinal), vitamin A acid (retinoic acid) and vitamin A esters (e.g., retinyl acetate, retinyl propionate and retinyl palmitate), etc. It is further intended that the term encompass all-trans-retinoic acids and 13-cis-retinoic acids. It is also intended that the term encompass compositions that are encapsulated, as well as provided for use in various forms. The terms "retinol" and "retinal" preferably comprise the all-trans compounds. The retinoid preferably used for the formulation of the present invention is all-trans-retinol, generally referred to as "retinol" herein.

As used herein, "carotenoid" is used in reference to β-carotene, lycopene, lutein, astaxanthin, zeaxanthin, cryptoxanthin, citranaxanthin, canthaxanthin, bixin, β-apo-4-carotenal, β-apo-8-carotenal, β-apo-8-carotenoic esters, alone, as well as in combination. Carotenoids which are preferably used are β-carotene, lycopene, lutein, astaxanthin, zeaxanthin, citranaxanthin and canthaxanthin. In some embodiments, carotenoids are utilized in crystalline form, as well as in formulations, including but not limited to dry powders (See e.g., dry powders, as described in EP 0 065 193; hereby incorporated by reference).

In some embodiments, the preferred use in the case of lycopene, astaxanthin and canthaxanthin is of lycopene-, astaxanthin- and canthaxanthin-containing dry powders, for example LYCOVIT®, LUCANTIN® Pink and LUCANTIN® Red (10% dry powders respectively of lycopene, astaxanthin and canthaxanthin, commercially available from BASF AG, Ludwigshafen, Germany.

As used herein, the term "bioactivity" refers to a cause and effect relationship between a composition and a biological system. Thus, the term is used as by those skilled in the art of biotechnology and biological sciences as the phrase that describes a cause and effect relationship between a molecular composition and living biological matter (e.g., tissue, cells, etc.).

As used herein as a noun, the term "bioactive" refers a composition that exhibits bioactivity upon administration to living biological matter (e.g., tissue, cells, etc.). The term is used synonymously with "bioactive compound."

As used herein, "silicone gum" means high molecular weight silicones having an average molecular weight in excess of about 200,000 and preferably from about 200,000 to about 4,000,000. It is intended that the definition encompass non-volatile polyalkyl and polyaryl siloxane gums.

As used herein, the term "polypeptide" refers to a compound made up of a single chain of amino acid residues linked by peptide bonds. The term "protein" herein may be synonymous with the term "polypeptide" or may refer, in addition, to a complex of two or more polypeptides. The exact meaning is that known to those in the art.

As used herein, the terms "expression cassette" and "expression vector" refer to nucleic acid constructs generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. The term "expression cassette" may be used interchangeably herein with "DNA construct" and its grammatical equivalents.

As used herein, the terms "vector" and "cloning vector" refer to nucleic acid constructs designed to transfer nucleic acid sequences into cells.

As used herein, the term "expression vector" refers to a vector that has the ability to incorporate and express heterologous DNA fragments in a foreign cell. Many prokaryotic and eukaryotic expression vectors are commercially available. Selection of appropriate expression vectors is within the knowledge of those of skill in the art.

As used herein, the term "plasmid" refers to a circular double-stranded (ds) DNA construct used as a cloning vector, and which forms an extrachromosomal self-replicating genetic element in some eukaryotes or integrates into the host chromosomes.

As used herein, the term "expression" refers to the process by which a polypeptide is produced based on the nucleic acid sequence of the gene or the chemical synthetic peptide. The process includes both transcription and translation of the gene to produce polypeptide/protein.

As used herein, the term "gene" means the segment of DNA involved in producing a polypeptide chain that may or may not include regions preceding or following the coding region.

As used herein, the terms "nucleic acid molecule" and "nucleic acid sequence" include sequences of any form of nucleic acid, including, but not limited to RNA, DNA and cDNA molecules. It will be understood that, as a result of the degeneracy of the genetic code, a multitude of nucleotide sequences encoding a given protein may be produced, in addition to mutant proteins.

As used herein, "codon" refers to a sequence of three nucleotides in a DNA or mRNA molecule that represents the instruction for incorporation of a specific amino acid into a polypeptide chain.

As used herein, the term "disulfide bridge" or "disulfide bond" refers to the bond formed between the sulfur atoms of cysteine residues in a polypeptide or a protein. In this invention, a disulfide bridge or disulfide bond may be non-naturally occurring and introduced by way of point mutation.

As used herein, the term "salt bridge" refers to the bond formed between oppositely charged residues, amino acids in a polypeptide or protein. In this invention, a salt bridge may be non-naturally occurring and introduced by way of point mutation.

As used herein, an "enzyme" refers to a protein or polypeptide that catalyzes at least one chemical reaction.

As used herein, the term "activity" refers to any activity associated with a particular protein, such as enzymatic activity associated with a protease. In some embodiments, the activity is biological activity. In further embodiments, activity encompasses binding of proteins to receptors which results in measurable downstream effects (e.g., VEGF binding to its cognate receptor). "Biological activity" refers to any activity that would normally be attributed to that protein by one skilled in the art.

As used herein, the term "protease" refers to an enzyme that degrades peptide bonds.

As used herein, "peptide bond" refers to the chemical bond between the carbonyl group of one amino acid and the amino group of another amino acid.

As used herein, "wild-type" refers to a sequence or a protein that is native or naturally occurring.

As used herein, "point mutations" refers to a change in a single nucleotide of DNA, especially where that change results in a sequence change in a protein.

As used herein, "mutant" refers to a version of an organism or protein where the version is other than wild-type. The change may be effected by methods well known to one skilled in the art, for example, by point mutation in which the resulting protein may be referred to as a mutant.

As used herein, "mutagenesis" refers to the process of changing a composition (e.g., protein) from a wild-type composition (e.g., protein) into a mutant or variant composition (e.g., protein).

As used herein, "substituted" and "substitutions" refer to replacement(s) of an amino acid residue or nucleic acid base in a parent sequence. In some embodiments, the substitution involves the replacement of a naturally occurring residue or base.

As used herein, "modification" and "modify" refer to any change(s) in an amino acid or nucleic acid sequence, including, but not limited to deletions, insertions, interruptions, and substitutions. In some embodiments, the modification involves the replacement of a naturally occurring residue or base.

As used herein, "functional portion of a secreted polypeptide" and its grammatical equivalents refers to a truncated secreted polypeptide that retains its ability to fold into a normal, albeit truncated, configuration. In some embodiments, it is contemplated that sufficient residues of a domain of the naturally secreted polypeptide must be present to allow it to fold in its normal configuration independently of the desired polypeptide to which it is attached. However, in most cases, the portion of the secreted polypeptide are both correctly folded and result in increased secretion as compared to its absence. Similarly, in most cases, the truncation of the secreted polypeptide means that the functional portion retains a biological function. In a preferred embodiment, the catalytic domain of a secreted polypeptide is used, although other functional domains may be used, for example, the substrate binding domains. Additionally preferred embodiments utilize the catalytic domain and all or part of the linker region.

As used herein, "loop" refers to a sequence of amino acids, for example 3-20 amino acids, more preferably 5-15 amino acids, even more preferably 5-10 amino acids, and most preferably 7-9 amino acids, which connects structural elements of a protein. Such elements include, but are not limited to beta sheets and helical elements and the connecting loop of a beta-hairpin. In some embodiments, the loop is further stabilized through the use of covalent linkages. In some preferred embodiments, the covalent linkages comprise disulfide bonds, especially as provided herein. In alternative embodiments, the loops are stabilized by the use of other means, including but not limited to amides, hydrogen bonds, and/or salt bridges. In most embodiments, the loops are located on the surface of proteins and may be altered, as provided herein, to confer additional (e.g., desirable) properties to the requisite proteins.

As used herein, "oligonucleotide" refers to a short nucleotide sequence which may be used, for example, as a primer in a reaction used to create mutant proteins.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence which encodes a gene product. The coding region may be present in either a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein, the term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the term "polymerase chain reaction" ("PCR") refers to the method well-known in the art (See e.g., U.S. Pat. Nos. 4,683,195 4,683,202, and 4,965,188, hereby incorporated by reference), for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

As used herein, the terms "PCR product," "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

As used herein, the term "RT-PCR" refers to the replication and amplification of RNA sequences. In this method, reverse transcription is coupled to PCR, most often using a one enzyme procedure in which a thermostable polymerase is employed, as described in U.S. Pat. No. 5,322,770, herein incorporated by reference. In RT-PCR, the RNA template is converted to cDNA due to the reverse transcriptase activity of the polymerase, and then amplified using the polymerizing activity of the polymerase (i.e., as in other PCR methods).

As used herein, the term "hybridization" refers to the process by which a strand of nucleic acid joins with a complementary strand through base pairing, as known in the art.

As used herein, "maximum stringency" refers to the level of hybridization that typically occurs at about Tm−5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate or low stringency hybridization can be used to identify or detect polynucleotide sequence homologs.

The phrases "substantially similar and "substantially identical" in the context of two nucleic acids or polypeptides typically means that a polynucleotide or polypeptide comprises a sequence that has at least 75% sequence identity, preferably at least 80%, more preferably at least 90%, still more preferably 95%, most preferably 97%, sometimes as much as 98% and 99% sequence identity, compared to the reference (i.e., wild-type) sequence. Sequence identity may be determined using known programs such as BLAST, ALIGN, and CLUSTAL using standard parameters. (See e.g., Altschul, et al., J. Mol. Biol. 215:403-410 [1990]; Henikoff et al., Proc. Natl. Acad. Sci. USA 89:10915 [1989]; Karin et al., Proc. Natl Acad. Sci. USA 90:5873 [1993]; and Higgins et al., Gene 73:237-244 [1988]). Software for performing BLAST analyses is publicly available through the National Center for Biotechnology Information. Also, databases may be searched using FASTA (Pearson et al., Proc. Natl. Acad. Sci. USA 85:2444-2448 [1988]).

As used herein, "equivalent residues" refers to proteins that share particular amino acid residues. For example, equivalent resides may be identified by determining homology at the level of tertiary structure for a protein (e.g., VEGF) whose tertiary structure has been determined by x-ray crystallography. Equivalent residues are defined as those for which the atomic coordinates of two or more of the main chain atoms of a particular amino acid residue of the protein having putative equivalent residues and the protein of interest (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the proteins analyzed. The preferred model is the crystallographic model giving the lowest R factor for experimental diffraction data at the highest resolution available, determined using methods known to those skilled in the art of crystallography and protein characterization/analysis.

In some embodiments, modification is preferably made to the "precursor DNA sequence" which encodes the amino acid sequence of the precursor enzyme, but can be by the manipulation of the precursor protein. In the case of residues which are not conserved, the replacement of one or more amino acids is limited to substitutions which produce a variant which has an amino acid sequence that does not correspond to one found in nature. In the case of conserved residues, such replacements should not result in a naturally-occurring sequence. Derivatives provided by the present invention further include chemical modification(s) that change the characteristics of the protein.

In some preferred embodiments, the protein gene is ligated into an appropriate expression plasmid. The cloned protein gene is then used to transform or transfect a host cell in order to express the protein gene. In some embodiments, this plasmid replicates in the hosts, in the sense that it contains the well-known elements necessary for plasmid replication or the plasmid may be designed to integrate into the host chromosome. The necessary elements are provided for efficient gene expression (e.g., a promoter operably linked to the gene of interest). In some embodiments, these necessary elements are supplied as the gene's own homologous promoter if it is recognized, (i.e., transcribed, by the host), a transcription terminator (a polyadenylation region for eukaryotic host cells) which is exogenous or is supplied by the endogenous terminator region of the protein gene. In some embodiments, a selection gene such as an antibiotic resistance gene that enables continuous cultural maintenance of plasmid-infected host cells by growth in antimicrobial-containing media is also included.

As used herein, the terms "restriction endonucleases" and "restriction enzymes" refer to bacterial enzymes, each of which cut double-stranded DNA at or near a specific nucleotide sequence.

As used herein, the term "recombinant DNA molecule" as used herein refers to a DNA molecule which is comprised of segments of DNA joined together by means of molecular biological techniques.

The term "recombinant protein" or "recombinant polypeptide" as used herein refers to a protein molecule which is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

As used herein, the term "fusion protein" refers to a chimeric protein containing the protein of interest (i.e., VEGF and fragments thereof) joined to an exogenous protein fragment (the fusion partner which consists of a non-VEGF protein). In some embodiments, the fusion partner enhances solubility of the VEGF protein as expressed in a host cell, may provide an affinity tag to allow purification of the recombinant fusion protein from the host cell or culture supernatant, or both. If desired, the fusion protein may be removed from the protein of interest (i.e., VEGF and/or fragments thereof) by a variety of enzymatic or chemical means known to the art.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

As used herein the term "coding region" when used in reference to structural gene refers to the nucleotide sequences which encode the amino acids found in the nascent polypeptide as a result of translation of a mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

As used herein, the term "structural gene" refers to a DNA sequence coding for RNA or a protein. In contrast, "regulatory genes" are structural genes which encode products which control the expression of other genes (e.g., transcription factors).

As used herein, the term "purified" or "to purify" refers to the removal of contaminants from a sample. For example, recombinant VEGF or aVEGF polypeptides are expressed in host cells and the polypeptides are purified by the removal of host cell proteins; the percent of recombinant VEGF or aVEGF polypeptides is thereby increased in the sample.

As used herein, the term "substantially pure" when applied to the proteins or fragments thereof of the present invention means that the proteins are essentially free of other substances to an extent practical and appropriate for their intended use. In particular, the proteins are sufficiently pure and are sufficiently free from other biological constituents of the host cells so as to be useful in, for example, protein sequencing, and/or producing pharmaceutical preparations.

As used herein, the term "target protein" refers to protein (e.g., enzyme, hormone, etc.), whose action would be blocked by the binding of the variant inhibitors provided for herein.

As used herein, the terms "variant sequence" and "variant sequences" refer to the short polypeptide sequence(s) that replace the binding loops of the wild-type protease inhibitor. The variant sequence does not need to be of the same length as the binding loop sequence it is replacing in the wild-type protease inhibitor.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNA s which encode a multitude of proteins. However, isolated nucleic acid encoding a VEGF protein includes, by way of example, such nucleic acid in cells ordinarily expressing a VEGF protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may single-stranded), but may contain both the sense and anti-sense strands (i.e., the oligonucleotide or polynucleotide may be double-stranded).

As used herein, a "composition comprising a given polynucleotide sequence" refers broadly to any composition containing the given polynucleotide sequence. The composition may be in any form, particularly a form that is suitable for administration.

As used herein, a compound is said to be "in a form suitable for administration" when the compound may be administered to a human or other animal by any desired route (e.g., topical, oral, etc.).

As used herein, "safe and effective amount" refers to a sufficient amount of a material that significantly induces a positive modification to the area upon which the material is applied and also does not result in the production of serious side effects (at a reasonable risk/benefit ratio). The safe and effective amount of the material may vary with the particular skin or other body part being treated, the age of the subject being treated, the severity of the condition being treated, the duration of treatment, the nature of concurrent therapy, the specific material used, the particular carrier utilized, etc. Those of skill in the art are capable of adjusting the concentration of the personal care compositions provided herein for the desired application of the compositions.

As used herein, the term "personal care composition" refers to a product for application to the skin, hair, nails, oral cavity and related membranes for the purposes of improving, cleaning, beautifying, treating, and/or caring for these surfaces and membranes.

In some embodiments, the personal care composition is in the form of an emulsified vehicle, such as a nutrient cream or lotion, a stabilized gel or dispersioning system, such as skin softener, a nutrient emulsion, a nutrient cream, a massage cream, a treatment serum, a liposomal delivery system, a topical facial pack or mask, a surfactant-based cleansing system such as a shampoo or body wash, an aerosolized or sprayed dispersion or emulsion, a hair or skin conditioner, styling aid, or a pigmented product such as makeup in liquid, cream, solid, anhydrous or pencil form. However, it is not intended that the present invention be limited to any particular form, as various forms find use in the present invention.

Personal care products can be classified/described as cosmetic, over-the-counter ("OTC") compounds that find use in personal care applications (e.g., cosmetics, skin care, oral care, hair care, nail care). In some embodiments, the repeat sequence protein polymer is added to a personal care composition such as a hair care composition, a skin care composition, a nail care composition, a cosmetic composition, or any combinations thereof.

As used herein, "cosmetic composition" refers to compositions that find use in the cosmetics. The Food Drug and Cosmetic Act (FD&C Act) definition is used herein. Thus, cosmetics are defined by their intended use, as articles intended to be rubbed, poured, sprinkled, or sprayed on, introduced into, or otherwise applied to the human body for cleansing, beautifying, promoting attractiveness, or altering appearance. These compositions provide non-therapeutic benefits and are not regulated as pharmaceuticals. However, in some situations, cosmetic compositions are incorporated into pharmaceutical compositions to provide cosmetic benefits (e.g., products that treat skin or hair diseases, but also contain cosmetic compositions for their coloring or other benefits). Also, it is intended that the present invention encompass the use of cosmetics on animals other than humans.

As used herein, the terms "pharmaceutical compositions" and "therapeutic compositions" refer to compositions such as drugs that provide medical benefits, rather than solely cosmetic benefits. In the United States, pharmaceutical and therapeutic compositions are approved by the Food and Drug Administration for treatment and/or prevention of particular conditions.

As used herein, the term "drug" is defined as it is in the FD&C Act definition. Thus, drugs are defined as articles intended for use in the diagnosis, cure, mitigation, treatment or prevention of disease, and articles (other than food) intended to affect the structure or any function of the body of man or other animals.

As used herein, "leave-on" refers to a composition that is applied to a subject and not removed (e.g., cleansed by washing, rinsing, etc.) for a period of typically at least several hours (e.g., 4-12 hours) before the area exposed to the composition is cleansed.

As used herein, a "rinse-off" composition is a composition that is applied and cleansed (e.g., by washing, rinsing, etc.) soon after its application (generally within about 30 minutes of application). In some preferred embodiments, rinse-off compositions are formulated so as to deposit an effective amount of active(s) on the area treated.

As used herein, the term "cosmetic benefit" refers to a desired cosmetic change that results from the administration of a personal care composition. Cosmetic benefits include but are not limited to improvements in the condition of skin, hair, nails, and the oral cavity. In preferred embodiments, at least one cosmetic benefit is provided by the skin care, hair care, nail care, and makeup compositions of the present invention.

As used herein, "cosmetically acceptable" refers to materials that are suitable for use in contact with tissues of humans and/or other animals, without undue toxicity, incompatibility, instability, irritation, allergic responses, etc., commensurate with a reasonable benefit/risk ratio.

As used herein, "skin care composition" refers to compositions that are applied to skin in order to provide beneficial properties, including but not limited to wrinkle minimizing, wrinkle removal, decoloring, coloring, skin softening, skin smoothing, depilation, cleansing, etc. In some particularly preferred embodiments, the present invention provides skin care compositions that improve skin tone. In these embodiments, the improvement comprises lessening of wrinkles, smoothing skin texture, modifying skin coloration, and other desired cosmetic benefits. In further embodiments, the skin care composition is in a form selected from the group consisting of body washes, moisturizing body washes, deodorant body washes, antimicrobial cleansers, skin protecting treatments, body lotions, facial creams, moisturizing creams, facial cleansing emulsions, surfactant-based facial cleansers, facial exfoliating gels, facial toners, exfoliating creams, facial masks, after shave lotions, balms, and/or radioprotective compositions (e.g., sunscreens).

As used herein, "improving the visual appearance of skin" refers to any benefit achieved through use of the personal care compositions of the present invention. Examples of benefits include but are not limited to reducing the visual appearance of pores (e.g., by reducing pore size), reducing imperfections and/or blemishes in skin color, including lightening hyperpigmented regions of skin and/or evening skin pigmentation, relieving dryness, eliminating rough, dry spots, improving the skin's ability to retain moisture and/or protect itself from environmental stresses, reducing the appearance of fine lines and wrinkles, improving appearance and skin tone, increasing skin firmness and/or suppleness, decreasing sagging of skin, increasing skin glow and clarity, increasing the skin renewal process, and/or removing vellus hair. Improving the visual appearance of skin also encompasses regulating wrinkles, atrophy, skin lightening, skin darkening, skin smoothness, and/or reducing the visual appearance of pores.

As used herein, "modifying skin tone" refers to a change in skin color, either darkening or lightening the color of the skin. However, in other contexts, the term is also used in reference to modifications in the muscular and connective tissue health of the skin (i.e., it is not related to the color of the skin, but the firmness of the skin).

As used herein, "lightening skin tone" and "lightening skin" refer to a decrease in skin darkness visualized by eye and/or mechanical means. It is intended that the term encompass any range of observable lightening (i.e., "whitening") of the skin tone. In some embodiments, the term encompasses decreasing the concentration of melanin present in the skin, including skin areas with hyperpigmentation due to the presence of age spots, melasma, chloasma, freckles, post-inflammatory hyperpigmentation, and/or skin-induced hyperpigmentation.

As used herein, "hyperpigmented region" refers to a localize region of darker skin relative to the base skin tone of a particular individual. For example, in preferred embodiments, hyperpigmented regions are areas with localized increases in melanin.

As used herein, "preventing skin darkening," "preventing darkening of skin tone," "preventing skin tone darkening," "preventing skin color development," and other equivalent phrases refer to skin tone that is observed as less skin pigmentation or darkness compared to untreated skin after UV radiation and/or sun exposure. Thus, in some particularly preferred embodiments, the compositions of the present invention provide a benefit by preventing the skin darkening effects associated with exposure to sun and/or UV radiation. It is intended that the term encompass any range of observable difference between sun-exposed skin that is protected from darkening and sun-exposed skin that is not protected.

As used herein, "evening skin tone" refers to the evening of skin color in an application area. In preferred embodiments, the phrase refers to the use of compositions of the present invention to make the skin color the same or provide less of a contrast in the skin color in one or more skin region.

As used herein, "reducing redness in skin tone" refers to a lessening of red color in skin, as observed visually or by other means.

As used herein, "inhibiting hair growth" and "inhibition of hair growth" refer to an observed lessening of hair length and/or thickness. Thus, in some preferred embodiments, application of a personal care composition of the present invention provides a benefit in lessening hair length and/or thickness as compared to an area in which a personal care composition of the present invention has not been applied. In some embodiments, the observed reduction of hair growth and/or thickness is a range from less than 1% to more than 99%, as compared to untreated areas, while in other embodiments, the observed reduction is from about 100% to about 90%, from about 90% to about 80%, from about 80% to about 70%, from about 70% to about 60%, from about 60% to about 50%, from about 50% to about 40%, from about 40% to about 30%, from about 30% to about 20%, from about 20% to about 10%, from about 10% to about 1%. Indeed, it is not intended that the term be limited to any particular percentage reduction, as long as the reduction is observable by visual (i.e., by eye) or other means. It is also intended that the term encompass "preventing hair growth" to any degree, as described above. It is not intended that the term be limited to the complete prevention of hair growth (i.e., there is no observed growth of hair).

As used herein, "hair care composition" refers to compositions that are applied to hair to provide beneficial properties such as thickening, thinning, coloring, decoloring, cleansing, conditioning, softening, shaping, etc. In some embodiments, the hair care composition is in a form selected from the group consisting of shampoos, conditioners, anti-dandruff treatments, styling aids, styling conditioners, hair repair or treatment sera, lotions, creams, pomades, and chemical treatments. In other embodiments, the styling aids are selected from the group consisting of sprays, mousses, rinses, gels, foams, and combinations thereof. In further embodiments, the chemical treatments are selected from the group consisting of permanent waves, relaxers, and permanents, semi-permanents, temporary color treatments and combinations thereof.

As used herein, "makeup compositions" refer to cosmetic preparations that are used to beautify, caring for, maintaining, or augment the appearance of a human or other animal. "Makeup compositions" include, but are not limited to color cosmetics, such as mascaras, lipsticks, lip liners, eye shadows, eye-liners, rouges, face powders, foundations, blushes, and nail polish. In some embodiments, the cosmetic composition of the present invention is in a form selected from the group consisting of eye gels, eye shadows, high-melting point lipsticks, lipsticks, lip glosses, lip balms, mascara, brow liners, eyeliners, pressed powder formulations, foundations, protein coated pigments, and combinations thereof. In further embodiments, the cosmetic compositions comprise makeup compositions. In yet another embodiment, the nail care composition is in a form selected from the group consisting of nail enamel, cuticle treatment, nail polish, nail treatment, and polish remover.

As used herein, "oral care compositions" refer to personal care compositions suitable for use in the mouth, including but not limited to forms selected from the group consisting of toothpastes, tooth gels, mouth rinses, breath fresheners, whitening treatments, and inert carrier substrates.

As used herein, the term "dispersed phase" is used as by those of skill in the art of emulsion technology as the phase that exists as small particles or droplets suspended in and surrounded by a continuous phase. The dispersed phase is also known as the "internal" or "discontinuous" phase.

As used herein, "penetration enhancers" refer to compositions that facilitate penetration through the upper stratum corneum barrier to the deeper skin layers. Examples of penetration enhancers include, but are not limited to, propylene glycol, azone, ethoxydiglycol, dimethyl isosorbide, urea, ethanol, dimethyl sulfoxide, micoroemulsions, liposomes, and nanoemulsions.

As used herein, the terms "emulsifier" and "surfactant" refer to compounds that disperse and suspend the dispersed phase within the continuous phase of a material. Surfactants find particular use in products intended for skin and/or hair cleansing. In particular embodiments, the term "surfactant (s)" is used in reference to surface-active agents, whether used as emulsifiers or for other surfactant purposes such as skin cleansing.

In various embodiments, the present invention also includes "protectants" such as UV absorbers (e.g., octyl methoxycinnamate, benzophenone-3, titanium dioxide, and octyl salicylate); film-forming agents (e.g., VP/Eicosene copolymer); cosmeceutical agents (e.g., peptides and proteins, alpha hydroxy acids, and retinol and retinoic acid derivatives); antioxidants (e.g., tocopherol and derivatives thereof and ascorbic acid and derivatives thereof); vitamins (e.g., B, D, K and their derivatives); antiperspirant actives (e.g., aluminum hydroxide and zirconium hydroxide); depilating agents (e.g., thioglycolate salts); anti-acne agents (e.g., salicylic acid and benzoyl peroxide); abrasives and exfoliants (e.g., silicates, pumice, and polyethylene); and extracts of plant, fruit, vegetable and/or marine sources.

Thus, in some embodiments, the present invention provides compositions comprising any organic UV-A and UV-B filter, for example but not limited to the following:

| Nr. | Compound | CAS-Nr. (=Acid) |
|---|---|---|
| 1 | 4-Aminobenzoicacid | 150-13-0 |
| 2 | 3-(4'-Trimethylammonium)-benzylidenbornan-2-on-methylsulfate | 52793-97-2 |
| 3 | 3,3,5-Trimethyl-cyclohexyl-salicylate (Homosalatum) | 118-56-9 |
| 4 | 2-Hydroxy-4-methoxy-benzophenon (Oxybenzonum) | 131-57-7 |
| 5 | 2-Phenylbenzimidazol-5-sulfonic acid and their Calcium-, Sodium- and Triethanolaminosalts | 27503-81-7 |
| 6 | 3,3'-(1,4-Phenylendimethin)-bis(7,7-dimethyl-2-oxobicyclo[2.2.1]heptan-1-methansolfonicacid) and salts thereof | 90457-82-2 |
| 7 | 4-Bis(polyethoxy)amino-benzoesäurepolyethoxy-ethylester | 113010-52-9 |
| 8 | 4-Dimethylamino-benzoicacid-2-ethylhexylester | 21245-02-3 |
| 9 | Salicylicacid-2-ethylhexylester | 118-60-5 |
| 10 | 4-Methoxy-cinnamicacid-2-isoamylester | 71617-10-2 |
| 11 | 4-Methoxy-cinnamicacid-2-ethylhexylester | 5466-77-3 |
| 12 | 2-Hydroxy-4-methoxy-benzophenon-5-sulfonicacid- (Sulisobenzonum) and the sodiumsalt | 4065-45-6 |
| 13 | 3-(4'-Sulfobenzyliden)-bornan-2-on and salts thereof | 58030-58-6 |
| 14 | 3-Benzylidenbornan-2-on | 16087-24-8 |
| 15 | 1-(4'-Isopropylphenyl)-3-phenylpropan-1,3-dion | 63260-25-9 |
| 16 | 4-Isopropylbenzylsalicylat | 94134-93-7 |
| 17 | 3-Imidazol-4-yl-acrylicacid und ihr Ethylester | 104-98-3 |
| 18 | 2-Cyano-3,3-diphenylacrylicacidethylester | 5232-99-5 |
| 19 | 2-Cyano-3,3-diphenylacrylicacid-2'-ethylhexylester | 6197-30-4 |
| 20 | Menthyl-o-aminobenzoat oder: 5-Methyl-2-(1-methylethyl)-2-aminobenzoat | 134-09-8 |
| 21 | Glyceryl p-aminobenzoat oder: 4-Aminobenzoicacid-1-glyceryl-ester | 136-44-7 |
| 22 | 2,2'-Dihydroxy-4-methoxybenzophenon (Dioxybenzone) | 131-53-3 |
| 23 | 2-Hydroxy-4-methoxy-4-methylbenzophenon (Mexenon) | 1641-17-4 |

-continued

| Nr. | Compound | CAS-Nr. (=Acid) |
|---|---|---|
| 24 | Triethanolamin Salicylat | 2174-16-5 |
| 25 | Dimethoxyphenylglyoxalsäure oder: 3,4-dimethoxy-phenyl-glyoxal-saures Natrium | 4732-70-1 |
| 26 | 3-(4'Sulfobenzyliden)-bornan-2-on und seine Salze | 56039-58-8 |
| 27 | 4-tert.-Butyl-4'-methoxy-dibenzoylmethan | 70356-09-1 |
| 28 | 2,2',4,4'-Tetrahydroxybenzophenon | 131-55-5 |
| 29 | 2,2'-Methylen-bis-[6-(2H-benzotriazol-2-yl)-4-(1,1,3,3,-tetramethylbuty)phenol] | 103597-45-1 |
| 30 | 2,2'-(1,4-Phenylen)-bis-1H-benzimidazol-4,6-disulfonicacid, Sodiumsalt | 180898-37-7 |
| 31 | 2,4-bis-[4-(2-Ethylhexyloxy)-2-hydroxy]phenyl-6-(4-methoxyphenyl)-(1,3,5)-triazin | 187393-00-6 |
| 32 | 3-(4-Methylbenzyliden)-campher | 36861-47-9 |
| 33 | 4-Bis(polyethoxy)paraaminobenzoicacidpolyethoxyethylester | 113010-52-9 |
| 34 | 2,4-Dihydroxybenzophenon | 131-56-6 |
| 35 | 2,2'-Dihydroxy-4,4'-dimethoxybenzophenon-5,5'-disodiumsulfonat | 3121-60-6 |
| 36 | Benzoicacid,2-[4-(diethylamino)-2-hydroxybenzoyl]-,hexylester | 302776-68-7 |
| 37 | 2-(2H-Benzotriazol-2-yl)-4-methyl-6-[2-methyl-3-[1,3,3,3-tetramethyl-1-(trimethylsily)oxy]disiloxanyl]propyl]phenol | 155633-54-8 |
| 38 | 1,1-[(2,2'-Dimethylpropoxy)carbonyl]-4,4-diphenyl-1,3-butadien | 363602-15-7 |

In some embodiments, the present invention provides compositions comprising pigments, including, but not limited to inorganic pigments based on metaloxides and/or other in water slightly soluble or insoluble metal compounds such as zinc oxides (ZnO), titanium ($TiO_2$), iron (e.g., $Fe_2O_3$), zirconium ($ZrO_2$), silica ($SiO_2$), manganese (e.g., MnO), aluminium ($Al_2O_3$), cer (e.g., $Ce_2O_3$), and mixed compositions of these oxides, as well as blends thereof. In some preferred embodiments, the metaloxides are microfine, while in alternative preferred embodiments, the metaloxides are pigment grade. In yet additional embodiments, the pigments are "coated" such that they are surface treated. In some preferred embodiments, the coating comprises a thin, hydrophobic film layer, while in other embodiments, the coating comprises a thin, hydrophilic film layer.

As used herein, the terms "pigment," "color pigment," and "dye" used in reference to the compositions of the present invention encompasses any compound that provides a color to the composition and/or imparts a color to the surface (e.g., skin and/or hair) to which the composition is applied. In some embodiments, the dyes and pigments are chosen from the list of cosmetic colorants provided by the Cosmetics Directive or the EC. In most cases, these dyes and pigments are identical to the dyes approved for foods. Preferred pigments/dyes include for example, titanium dioxide, mica, iron oxides (e.g., $Fe_2O_3$, $Fe_3O_4$, FeO(OH)) and/or tin oxide. Advantageous pigments/dyes include for example, carmine, Berlin blue, chrome oxide green, ultramarine blue and/or manganese violet. In some preferred embodiments, the pigments/dyes include, but are not limited to those in the following table. The Colour Index Numbers (CIN) those known in the art (See, Society of Dyers and Colourists, *Rowe Colour Index*, 3rd Edition, Bradford, England, [1971]).

| CHEMICAL OR OTHER NAME | CIN | COLOR |
|---|---|---|
| Pigment Green | 10006 | green |
| Acid Green 1 | 10020 | green |
| 2,4-Dinitrohydroxynaphthalene-7-sulfonic acid | 10316 | yellow |
| Pigment Yellow 1 | 11680 | yellow |
| Pigment Yellow 3 | 11710 | yellow |
| Pigment Orange 1 | 11725 | orange |
| 2,4-Dihydroxyazobenzene | 11920 | orange |
| Solvent Red 3 | 12010 | red |
| 1-(2'-Chloro-4'-nitro-1'-phenylazo)-2-hydroxynaphthalene | 12085 | red |
| Pigment Red 3 | 12120 | red |
| Ceres red; Sudan red; Fat Red G | 12150 | red |
| Pigment Red 112 | 12370 | red |
| Pigment Red 7 | 12420 | red |
| Pigment Brown 1 | 12480 | brown |
| 4-(2'-Methoxy-5'-sulfodiethylamido-1'-phenylazo)-3-hydroxy-5"-chloro-2",4"-dimethoxy-2-naphthanilide | 12490 | red |
| Disperse Yellow 16 | 12700 | yellow |
| 1-(4-Sulfo-1-phenylazo)-4-aminobenzene-5-sulfonic acid | 13015 | yellow |
| 2,4-Dihydroxyazobenzene-4'-sulfonic acid | 14270 | orange |
| 2-(2,4-Dimethylphenylazo-5-sulfo)-1-hydroxynaphthalene-4-sulfonic acid | 14700 | red |
| 2-(4-Sulfo-1-naphthylazo)-1-naphthol-4-sulfonic acid | 14720 | red |
| 2-(6-Sulfo-2,4-xylylazo)-1-naphthol-5-sulfonic acid | 14815 | red |
| 1-(4'-Sulfophenylazo)-2-hydroxynaphthalene | 15510 | orange |
| 1-(2-Sulfo-4-chloro-5-carboxy-1-phenylazo)-2-hydroxynaphthalene | 15525 | red |
| 1-(3-Methylphenylazo-4-sulfo)-2-hydroxynaphthalene | 15580 | red |
| 1-(4',(8')-Sulfonaphthylazo)-2-hydroxynaphthalene | 15620 | red |
| 2-Hydroxy-1,2'-azonaphthalene-1'-sulfonic acid | 15630 | red |

-continued

| CHEMICAL OR OTHER NAME | CIN | COLOR |
|---|---|---|
| 3-Hydroxy-4-phenylazo-2-naphthylcarboxylic acid | 15800 | red |
| 1-(2-Sulfo-4-methyl-1-phenylazo)-2-naphthyl-carboxylic acid | 15850 | red |
| 1-(2-Sulfo-4-methyl-5-chloro-1-phenylazo)-2-hydroxynaphthalene-3-carboxylic acid | 15865 | red |
| 1-(2-Sulfo-1-naphthylazo)-2-hydroxynaphthalene-3-carboxylic acid | 15880 | red |
| 1-(3-Sulfo-1-phenylazo)-2-naphthol-6-sulfonic acid | 15980 | orange |
| 1-(4-Sulfo-1-phenylazo)-2-naphthol-6-sulfonic acid | 15985 | yellow |
| Allura Red | 16035 | red |
| 1-(4-Sulfo-1-naphthylazo)-2-naphthol-3,6-disulfonic acid | 16185 | red |
| Acid Orange 10 | 16230 | orange |
| 1-(4-Sulfo-1-naphthylazo)-2-naphthol-6,8-disulfonic acid | 16255 | red |
| 1-(4-Sulfo-1-naphthylazo)-2-naphthol-3,6,8-trisulfonic acid | 16290 | red |
| 8-Amino-2-phenylazo-1-naphthol-3,6-disulfonic acid | 17200 | red |
| Acid Red 1 | 18050 | red |
| Acid Red 155 | 18130 | red |
| Acid Yellow 121 | 18690 | yellow |
| Acid Red 180 | 18736 | red |
| Acid Yellow 11 | 18820 | yellow |
| Acid Yellow 17 | 18965 | yellow |
| 4-(4-Sulfo-1-phenylazo)-1-(4-sulfophenyl)-5-hydroxy-pyrazolone-3-carboxylic acid | 19140 | yellow |
| Pigment Yellow 16 | 20040 | yellow |
| 2,6-(4'-Sulfo-2'',4''-dimethyl)bisphenylazo)-1,3-dihydroxybenzene | 20170 | orange |
| Acid Black 1 | 20470 | black |
| Pigment Yellow 13 | 21100 | yellow |
| Pigment Yellow 83 | 21108 | yellow |
| Solvent Yellow | 21230 | yellow |
| Acid Red 163 | 24790 | red |
| Acid Red 73 | 27290 | red |
| 2-[4'-(4''-Sulfo-1''-phenylazo)-7'-sulfo-1'-naphthylazo]-1-hydroxy-7-aminonaphthalene-3,6-di-sulfonic acid | 27755 | black |
| 4'-[(4''-Sulfo-1''-phenylazo)-7'-sulfo-1'-naphthylazo]-1-hydroxy-8-acetylaminonaphthalene-3,5-disulfonic acid | 28440 | black |
| Direct Orange 34, 39, 44, 46, 60 | 40215 | orange |
| Food Yellow | 40800 | orange |
| trans-β-Apo-8'-carotinaldehyde (C$_{30}$) | 40820 | orange |
| trans-Apo-8'-carotinic acid (C$_{30}$)-ethyl ester | 40825 | orange |
| Canthaxanthin | 40850 | orange |
| Acid Blue 1 | 42045 | blue |
| 2,4-Disulfo-5-hydroxy-4'-4''-bis(diethylamino)triphenylcarbinol | 42051 | blue |
| 4-[(4-N-Ethyl-p-sulfobenzylamino)phenyol(4-hydroxy-2-sulfophenyl)(methylene)-1-(N-ethyl-N-p-sulfobenzyl)-2,5-cyclohexadienimine] | 42053 | green |
| Acid Blue 7 | 42080 | blue |
| (N-Ethyl-p-sulfobenzylamino)phenyl(2-sulfophenyl)methylene-(N-ethyl-N-p-sulfobenzyl)D$^{2,5}$-cyclohexadienimine | 42090 | blue |
| Acid Green 9 | 42100 | green |
| Diethyldisulfobenzyldi-4-amino-2-chloro-di-2-methyl-fuchsonimmonium | 42170 | green |
| Basic Violet 14 | 42510 | violet |
| Basic Violet 2 | 42520 | violet |
| 2'-Methy1-4'-(N-ethyl-N-m-sulfobenzyl)amino-4''-(N-diethyl)amino-2-methyl-N-ethyl-N-m-sulfobenzylfuchsonimmonium | 42735 | blue |
| 4'-(N-Dimethyl)amino-4''-(N-phenyl)aminonaphtho-N-dimethyl-fuchsonimmonium | 44045 | blue |
| 2-Hydroxy-3,6-disulfo-4,4'-bisdimethylaminonaphtho-fuchsonimmonium | 44090 | green |
| Acid Red 52 | 45100 | red |
| 3-(2'-Methylphenylamino)-6-(2'-methy1-4'-sulfophenylamino)-9-(2''-carboxyphenyl)xanthenium salt | 45190 | violet |
| Acid Red 50 | 45220 | red |
| Phenyl-2-oxyfluorone-2-carboxylic acid | 45350 | yellow |
| 4,5-Dibromofluorescein | 45370 | orange |
| 2,4,5,7-Tetrabromofluorescein | 45380 | red |
| Solvent Dye | 45396 | orange |
| Acid Red 98 | 45405 | red |
| 3',4',5',6'-Tetrachloro-2,4,5,7-tetrabromofluorescein | 45410 | red |
| 4,5-Diiodofluorescein | 45425 | red |
| 2,4,5,7-Tetraiodofluorescein | 45430 | red |
| Quinophthalone | 47000 | yellow |
| Quinophthalonedisulfonic acid | 47005 | yellow |
| Acid Violet 50 | 50325 | violet |
| Acid Black 2 | 50420 | black |
| Pigment Violet 23 | 51319 | violet |
| 1,2-Dioxyanthraquinone, calcium-aluminum complex | 58000 | red |
| 3-Oxypyrene-5,8,10-sulfonic acid | 59040 | green |
| 1-Hydroxy-4-N-phenylaminoanthraquinone | 60724 | violet |

-continued

| CHEMICAL OR OTHER NAME | CIN | COLOR |
|---|---|---|
| 1-Hydroxy-4-(4'-methylphenylamino)anthraquinone | 60725 | violet |
| Acid Violet 23 | 60730 | violet |
| 1,4-Di(4'-methylphenylamino)anthraquinone | 61565 | green |
| 1,4-Bis(o-sulfo-p-toluidino)anthraquinone | 61570 | green |
| Acid Blue 80 | 61585 | blue |
| Acid Blue 62 | 62045 | blue |
| N,N'-Dihydro-1,2,1',2'-anthraquinone azine | 69800 | blue |
| Vat Blue 6; Pigment Blue 64 | 69825 | blue |
| Vat Orange 7 | 71105 | orange |
| Indigo | 73000 | blue |
| Indigo-disulfonic acid | 73015 | blue |
| 4,4'-Dimethyl-6,6'-dichlorothioindigo | 73360 | red |
| 5,5'-Dichloro-7,7'-dimethylthioindigo | 73385 | violet |
| Quinacridone Violet 19 | 73900 | violet |
| Pigment Red 122 | 73915 | red |
| Pigment Blue 16 | 74100 | blue |
| Phthalocyanine | 74160 | blue |
| Direct Blue 86 | 74180 | blue |
| Chlorinated Phthalocyanines | 74260 | green |
| Natural Yellow 6,19; Natural Red 1 | 75100 | yellow |
| Bixin, Nor-Bixin | 75120 | orange |
| Lycopene | 75125 | yellow |
| trans-alpha-, beta- and gamma-carotene | 75130 | orange |
| Keto- and/or hydroxyl derivates of carotene | 75135 | yellow |
| Guanine or pearlizing agent | 75170 | white |
| 1,7-Bis(4-hydroxy-3-methoxyphenyl)-1,6-heptadiene-3,5-dione | 75300 | yellow |
| Complex salt (Na, Al, Ca) of carminic acid | 75470 | red |
| Chlorophyll a and b; copper compounds of chlorophylls and Chlorophyllins | 75810 | green |
| Aluminum | 77000 | white |
| Hydrated alumina | 77002 | white |
| Hydrous aluminum silicates | 77004 | white |
| Ultramarine | 77007 | blue |
| Pigment Red 101 and 102 | 77015 | red |
| Barium sulfate | 77120 | white |
| Bismuth oxychloride and its mixtures with mica | 77163 | white |
| Calcium carbonate | 77220 | white |
| Calcium sulfate | 77231 | white |
| Carbon | 77266 | black |
| Pigment Black 9 | 77267 | black |
| Carbo medicinalis vegetabilis | 77268 | black |
| Chromium oxide | 77288 | green |
| Chromium oxide, hydrous | 77289 | green |
| Pigment Blue 28, Pigment Green 14 | 77346 | green |
| Pigment Metal 2 | 77400 | brown |
| Gold | 77480 | brown |
| Iron oxides and hydroxides | 77489 | orange |
| Iron oxide | 77491 | red |
| Iron oxide, hydrated | 77492 | yellow |
| Iron oxide | 77499 | black |
| Mixtures of iron (II) and iron(III)hexacyano-ferrate | 77510 | blue |
| Pigment White 18 | 77713 | white |
| Manganese ammonium diphosphate | 77742 | violet |
| Manganese phosphate; $Mn_3(PO_4)_2 \cdot 7 H2O$ | 77745 | red |
| Silver | 77820 | white |
| Titanium dioxide and its mixtures with mica | 77891 | white |
| Zinc oxide | 77947 | white |
| 6,7-Dimethyl-9-(1'-D-ribityl)-isoalloxazine, lactoflavine | | yellow |
| Sugar coloring | | brown |
| Capsanthin, capsorubin | | orange |
| Betanin | | red |
| Benzopyrylium salts, Anthocyans | | red |
| Aluminum, zinc, magnesium and calcium stearate | | white |
| Bromothymol blue | | blue |
| Bromocresol green | | green |
| Acid Red 195 | | red |

In yet further embodiments, compositions of the present invention further comprise one or more substances from the following group: 2,4-dihydroxyazobenzene, 1-(2'-chloro-4'-nitro-1'-phenylazo)-2-hydroxynaphthalene, Ceres Red, 2-(4-sulfo-1-naphthylazo)-1-naphthol-4-sulfonic acid, calcium salt of 2-hydroxy-1,2'-azonaphthalene-1'-sulfonic acid, calcium and barium salts of 1-(2-sulfo-4-methyl-1-phenylazo)-2-naphthylcarboxylic acid, calcium salt of 1-(2-sulfo-1-naphthylazo)-2-hydroxynaphthalene-3-carboxylic acid, aluminum salt of 1-(4-sulfo-1-phenylazo)-2-naphthol-6-sulfonic acid, aluminum salt of 1-(4-sulfo-1-naphthylazo)-2-naphthol-3,6-disulfonic acid, 1-(4-sulfo-1-naphthylazo)-2-naphthol-6,8-disulfonic acid, aluminum salt of 4-(4-sulfo-1-phenylazo)-1-(4-sulfophenyl)-5-hydroxypyrazolone-3-carboxylic acid, aluminum and zirconium salts of 4,5-dibromofluorescein, aluminum and zirconium salts of 2,4,5, 7-tetrabromofluorescein, 3',4',5',6'-tetrachloro-2,4,5,7-tetrabromofluorescein and its aluminum salt, aluminum salt of 2,4,5,7-tetraiodofluorescein, aluminum salt of quinophthalone disulfonic acid, aluminum salt of indigo disulfonic acid, red and black iron oxide (CIN: 77 491 (red) and 77 499 (black)), iron oxide hydrate (CIN: 77 492), manganese ammonium diphosphate and titanium dioxide.

In yet further embodiments, oil-soluble natural dyes, such as, for example, paprika extracts, β-carotene or cochenille find use in the present invention.

In yet additional embodiments, gel cream compositions of the present invention comprise pearlescent pigments. In some preferred embodiments, various pearlescent pigments find use in the present invention, including but not limited to "natural pearlescent pigments" (e.g., "pearl essence" [guanine/hypoxanthine mixed crystals from fish scales], "mother of pearl" [ground mussel shells]), and "monocrystalline pearlescent pigments" (e.g., bismuth oxychloride [BiOCl]); and "layer substrate pigments" (e.g. mica/metal oxide).

Bases for pearlescent pigments include, but are not limited to pulverulent pigments, castor oil dispersions of bismuth oxychloride and/or titanium dioxide, bismuth oxychloride and/or titanium dioxide on mica. The luster pigment listed under CIN 77163, for example, is particularly advantageous.

An additional group of pearlescent pigments based on mica/metal oxide find particular use in the present invention is provided below.

| GROUP | COATING/LAYER THICKNESS | COLOR |
| --- | --- | --- |
| Silver-white pearlescent pigments | $TiO_2$: 40-60 nm | silver |
| Interference pigments | $TiO_2$: 60-80 nm | yellow |
|  | $TiO_2$: 80-100 nm | red |
|  | $TiO_2$: 100-140 nm | blue |
|  | $TiO_2$: 120-160 nm | green |
| Color luster pigments | $Fe_2O_3$ | bronze |
|  | $Fe_2O_3$ | copper |
|  | $Fe_2O_3$ | red |
|  | $Fe_2O_3$ | red-violet |
|  | $Fe_2O_3$ | red-green |
|  | $Fe_2O_3$ | black |
| Combination pigments | $TiO_2/Fe_2O_3$ | gold shades |
|  | $TiO_2/Cr_2O_3$ | green |
|  | $TiO_2$/Berlin blue | deep blue |
|  | $TiO_2$/carmine | red |

In some preferred embodiments, the pearlescent pigments available from Merck under the trade names Timiron, Colorona or Dichrona find use in the present invention. However, it is not intended that the present invention be limited to the specific pigments listed herein. Indeed, pearlescent pigments that find use in the present invention are obtainable from numerous sources. For example, other substrates apart from mica can be coated with further metal oxides, such as, for example, silica and the like. $SiO_2$ particles coated with, for example, $TiO_2$ and $Fe_2O_3$ ("ronaspheres"), which are sold by Merck and are particularly suitable for the optical reduction of fine lines find use in the present invention.

In alternative embodiments, the substrate (e.g., mica) is not included. In some preferred embodiments, particular preference is given to pearlescent pigments prepared using $SiO_2$. Such pigments, which may also additionally have goniochromatic effects, are available, for example, under the trade name Sicopearl Fantastico, available from BASF.

In additional embodiments, pigments obtained from Engelhard/Mearl based on calcium sodium borosilicate which have been coated with titanium dioxide also find use. These are available under the name Reflecks. In addition to the color, as a result of their particle size of from 40 nm to 180 mm, they have a glitter effect.

In yet further embodiments, effect pigments which are available under the trade name Metasomes Standard/Glitter in various colors (yellow, red, green, blue) from Flora Tech find use in the compositions of the present invention. The glitter particles are present here in the mixtures with various auxiliaries and dyes (such as, for example, the dyes with the Colour Index (CI) Numbers 19140, 77007, 77289, 77491).

In some embodiments, the dyes and pigments are present either individually or in a mixture. In alternative embodiments, they are mutually coated with one another, different coating thicknesses generally giving rise to different color effects. In some embodiments, the total amount of dyes and color-imparting pigments is chosen from a range of concentrations (e.g., from about 0.1% by weight to about 30% by weight; preferably from about 0.5 to about 15% by weight; and most preferably from about 1.0 to about 10% by weight, in each case based on the total weight of the preparations).

The yet further embodiments, the present invention provides methods for the preparation of the compositions of the present invention. In some embodiments, these methods include combining and heating the constituents of the oil phase and/or the water phase separately, and then combining them together with stirring. In some preferred embodiments, the phases are homogenized. In some particularly preferred embodiments, the compositions are stirred with moderate to high input of energy, advantageously using a gear rim dispersing machine at a rotary number up to at most 10000 rpm (preferably in the range from about 2500 to about 7700 rpm).

Cosmetic Formulations Comprising the Present Invention

It is contemplated that the present invention will find use in numerous personal care compositions. It is not intended that the present invention be limited to any particular format or type of composition. The following description provides exemplary, not limiting compositions comprising the following invention.

Emulsions comprises one group of customary, commonly-used cosmetics. The term "emulsion" is generally used in reference to a heterogeneous system of two liquids which are immiscible or miscible only to a limited extent with one another, which are usually referred to as "phases." One phase is typically in the form of droplets (i.e., the "dispersed," "discontinuous" or "internal" phase), while the other liquid forms a continuous (i.e., "coherent" or "external") phase. Less common forms of application include multiple emulsions (i.e. those in which the droplets of the dispersed [or discontinuous] phase, comprise for their part droplets of a further dispersed phase, such as water/oil/water [W/O/W] emulsions and oil/water/oil [O/W/O] emulsions).

If the oil phase is finely distributed in the water phase, then this is an oil-in-water emulsion (O/W emulsion; e.g. milk). The basic character of an O/W emulsion is determined by the water. These emulsions are generally less greasy on the skin, are rather matting, and absorb more rapidly into the skin than W/O (water-in-oil) emulsions.

Those of skill in the art are familiar with a large number of options of formulating stable W/O preparations for cosmetic and/or dermatological uses, including such formulations as creams and ointments, which are spreadable in the range from room temperature to skin temperature, as well as lotions and milks, which are more flowable in this temperature range.

The stability of emulsions is dependent on their viscosity, in particular on the viscosity of the external phase. An emulsion becomes unstable when the finely dispersed particles collect together to form relatively large aggregates, and the droplets which are in contact coalesce. This process is referred to as "coalescence." The more viscous the external phase of the emulsion, the slower the process of coalescence. Emulsions of "liquid" (=flowable) consistency are used in various cosmetics (e.g., skin care lotions, cleansing lotions, face lotions, hand lotions, etc.). These compositions generally have a viscosity of from about 2000 mPa·s to about 10,000 mPa·s. The stability of flowable emulsions is deserving of particular attention since the considerably greater mobility of the particles promotes more rapid coalescence.

It is known that liquid emulsions typically presently in use generally comprise thickeners and are not stable toward relatively high electrolyte concentrations. This is manifested in phase separation of the compositions. However, in some embodiments, it is desirable to use certain electrolytes (e.g., water-soluble UV filters), in order to be able to utilize the other physical, chemical or physiological properties thereof. Although in many cases appropriate choice of the emulsifier system can provide remedies to a certain extent, other disadvantages then arise just as often.

For example, some disadvantages result due to the fact that emulsifiers, like ultimately any chemical substance, may trigger allergic reactions or reactions based on oversensitivity (i.e., hypersensitivity) of the user. The use of customary cosmetic emulsifiers is generally entirely without risk, although for some individuals, "hypoallergenic" compositions are necessary and/or preferred. Indeed, in some particularly sensitive individuals, certain dermatoses are triggered by exposure to certain emulsifiers and simultaneous exposure to sunlight. Thus, as known to those in the art, in some compositions, particular emulsifiers are less preferred and/or are avoided.

It is possible to prepare emulsifier-free preparations. For example, some preparations have an oily phase which contains dispersed water droplets (i.e., it is similar to a W/O emulsion). Such systems are sometimes called "hydrodispersions" or "oleodispersions," depending upon which is the disperse phase and which is the continuous phase.

For cosmetic technology, it is, however, neither necessary nor possible to dispense with emulsifiers altogether, especially since there is a certain choice of particularly mild emulsifiers. However, the emulsifiers in current use lack a satisfactorily broad range of choices. Thus, the application spectrum of correspondingly mild cosmetic preparations which are tolerated by the skin is limited.

In addition to the deleterious effects of some emulsifiers, exposure to other factors is known to harm skin and hair. For example, the harmful effect of the ultraviolet portion of solar radiation on the skin is generally known. While rays having a wavelength of less than 290 nm (i.e., the UVC region) are absorbed by the ozone layer in the earth's atmosphere, rays in the range between 290 nm and 320 nm (i.e., the UVB region), cause erythema, simple sunburn or even burns of varying severity. The erythema activity maximum of sunlight is given as the relatively narrow region around 308 nm Numerous compounds are known to provide protection against harmful UVB radiation. Most commonly, these compounds are derivatives of 3-benzylidenecamphor, of 4-aminobenzoic acid, of cinnamic acid, of salicylic acid, of benzophenone, and of 2-phenyl-benzimidazole.

It is also important to have available filter substances for the range between about 320 nm and about 400 nm, the UVA region, since its rays can also cause damage. For a long time it was incorrectly assumed that the long-wave UV-A radiation having a wavelength of between 320 nm and 400 nm had only a negligible biological action and that, accordingly, the UV-B rays were responsible for most photodamage to the human skin. However, numerous recent studies have shown that UV-A radiation is much more harmful than UV-B radiation with regard to the triggering of photodynamic, specifically phototoxic, reactions and chronic changes in the skin. In addition, the harmful effects of UV-B radiation can be further intensified by exposure to UV-A radiation.

It has been shown that UV-A radiation by itself and under very normal everyday conditions, is sufficient to damage collagen and elastin fibers, which are of essential importance for the structure and strength of the skin, within a short period. This leads to chronic light-induced changes in the skin, such that the skin prematurely "ages." The clinical appearance of skin aged by light typically includes increased wrinkles and lines, and an irregular, furrowed relief. In addition, the skin areas affected by light-induced skin aging often show irregular pigmentation. In some cases, brown patches, keratoses, carcinomas, or malignant melanomas arise. Skin prematurely aged as a result of everyday UV exposure is also characterized has having lowered activity of the Langerhans cells and slight, chronic inflammation.

Approximately 90% of the ultraviolet radiation which reaches the Earth consists of UV-A rays. While amount of UV-B radiation reaching Earth varies widely depending on numerous factors (e.g., time of year and day and/or degree of latitude), the UV-A radiation levels that reach Earth remain relatively constant on a daily basis, irrespective of the time of year and day or geographical factors. Additionally, the majority of UV-A radiation penetrates the living epidermis, while about 70% of the UV-B rays are retained by the horny layer. Preventive protection against UV-A rays, for example by applying light protection filter substances in the form of a cosmetic or dermatological formulation to the skin, is therefore of fundamental importance.

In general, the light absorption behavior of light protection filter substances is very well known and documented, largely due to the fact that most industrialized countries have positive lists for the use of such substances, which impose very strict standards on the documentation that accompanies each product which incorporates these substances. For the concentration of the substances in the finished formulations, the absorbance values provide a guide, since interaction with substances within the skin or the surface of the skin itself often presents variables that may impact how well the compositions perform on each individual. However, it is usually difficult to estimate beforehand, how uniformly and thickly the filter substance is distributed in and on the horny layer of the skin.

To test UV-A protection performance, use is usually made of the IPD method (IPD 5 immediate pigment darkening) known to those in the art. This method is similar to the determination of the sun protection factor, and provides a method which indicates how much longer skin protected with the light protection composition can be irradiated with UV-A radiation before the pigmentation which occurs is the same as that produced for unprotected skin.

Another test method which has become established throughout Europe is the Australian standard AS/NZS 2604: 1997. In this method, the absorption of the preparation in the UV-A region is measured. In order to satisfy the standard, the preparation must absorb at least 90% of the UV-A radiation in the region 320-360 nm.

Of concern in the formulation of sunscreen compositions is that the use concentration of known light protection filter substances which also exhibit high filter action in the UV-A region are often limited by the very fact that they are combined with other substances which are in the form of solids. Thus, there are certain formulation difficulties associate with achieving relatively high sun protection factors and UV-A protection performance. However, those of skill in the art are generally aware of means to overcome and/or compensate for these difficulties.

As light protection filter substances are generally expensive and some light protection filter substances are additionally difficult to incorporate into cosmetic and/or dermatological preparations in relatively high concentrations, some embodiments of the present invention were designed to provide simple and cost-effective preparations which, despite having unusually low concentrations of conventional UV-A light protection filter substances, nevertheless achieve acceptable or even high UV-A protection performance.

However, as known in the art, UV radiation can also lead to photochemical reactions which produce products that interfere with the skin's metabolism. These photochemical reaction products are predominantly free-radical compounds (e.g., hydroxyl radicals). Undefined free-radical photoproducts which form in the skin itself can also exhibit uncontrolled secondary reactions as a result of their high reactivity. However, singlet oxygen, a non-free-radical excited state of the oxygen molecule, can also arise during UV irradiation, as can short-lived epoxides and many others. Singlet oxygen, for example, differs from normal triplet oxygen (free-radical ground state) by virtue of its increased reactivity. However, excited, reactive "free-radical" triplet states of the oxygen molecule also exist. Thus, in order to prevent these reactions, antioxidants and/or free-radical scavengers find use in cosmetic and/or dermatological formulations.

The compounds which are commonly used as light protection agents in cosmetic and/or dermatological light protection formulations are generally characterized as providing good light protection. However, they have the disadvantage that it is sometimes difficult to incorporate them into the desired formulations in a satisfactory manner.

As indicated above, the sun protection factor (SPF) indicates how much longer the skin protected with the light protection composition can be irradiated before the erythema reaction which occurs is the same as for unprotected skin (i.e., ten times as long compared with unprotected skin for an SPF=10). Consumers are very aware of the meaning of "SPF" and choose skin and/or hair care products based on the SPF values indicated on products. Consumers expect to receive reliable information from manufacturers regarding the sun protection factor, largely due to increased public awareness of the association between excess sun exposure and skin cancer, as well as premature aging. In addition, in some parts of the world, the degradation of the ozone layer is a major concern. Depending upon the skin type and the sun exposure expected, consumers choose products with a lower or a higher SPF. However, there appears to be a tendency for consumers to select relatively high SPF factors, particularly for products to be applied to children and those with fair skin. In some embodiments, the present invention provides compositions with relatively low concentrations of conventional light protection filter substances, yet with SPF values that are acceptable to consumers.

In some preferred embodiments, the basic constituents of the sunscreen preparations provided by the present invention include: water or aqueous solutions; aqueous ethanolic solutions; natural oils and/or chemically modified natural oils and/or synthetic oils; fats, waxes and other natural and synthetic fatty substances, preferably esters of fatty acids with alcohols of low carbon number (e.g., with isopropanol, propylene glycol or glycerol), or esters of fatty alcohols with alkanoic acids of low carbon number or with fatty acids; alcohols, diols or polyols of low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products. In alternatively preferred embodiments, mixtures of two or more of these constituents find use in the present invention.

The term "lipid" is often used as a generic term to refer to fats, oils, waxes and the like. In addition, the terms "oil phase" and "lipid phase" are also used synonymously. However, oils and fats differ from one another in their polarity, which is difficult to define. It has been proposed to adopt the interfacial tension toward water as a measure of the polarity index of an oil or of an oily phase. Thus, it is contemplated that the interfacial tension be regarded as a suitable measure of the polarity of a given oil component. The "interfacial tension" is the force which acts on an imaginary line one meter in length in the interface between two phases. In this measurement, the lower the interfacial tension between the oily phase and water, the greater the polarity of the oily phase being analyzed. The physical unit for this interfacial tension is conventionally calculated from the force/length relationship and is usually expressed in mN/m (millinewtons divided by meters). It has a positive sign if it endeavours to reduce the interface. In the converse case, it has a negative sign. As used herein, lipids are regarded as "polar," if their interfacial tension toward water is less than 30 mN/m.

"Polar oils" include those from the group of lecithins and of fatty acid triglycerides, namely the triglycerol esters of saturated and/or unsaturated, branched and/or unbranched alkane carboxylic acids having a chain length of from 8 to 24, in particular 12 to 18, carbon atoms. In some embodiments, the fatty acid triglycerides are chosen from the group consisting of synthetic, semi-synthetic and natural oils (e.g., olive oil, sunflower oil, soya oil, groundnut oil, rapeseed oil, almond oil, palm oil, coconut oil, castor oil, wheatgerm oil, grapeseed oil, thistle oil, evening primrose oil, macadamia nut oil and the like). However, is it not intended that the present invention be limited to compositions that contain particular polar oils. Additional examples of polar oils that find use in the present invention include the group of esters of saturated and/or unsaturated, branched and/or unbranched alkane carboxylic acids having a chain length of from 3 to 30 carbon atoms and saturated and/or unsaturated, branched and/or unbranched alcohols having a chain length of from 3 to 30 carbon atoms, and from the group of esters of aromatic carboxylic acids and saturated and/or unsaturated, branched and/or unbranched alcohols having a chain length of from 3 to 30 carbon atoms. In some embodiments, such ester oils are chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of such esters (e.g., jojoba oil).

In addition, in some embodiments, the oily phase is chosen from the group consisting of dialkyl ethers, as well as saturated or unsaturated, and branched or unbranched alcohols. In some particularly preferred embodiments, the oily phase of the compositions of the preferred embodiments also contains $C_{12-15}$-alkyl benzoate, while in alternative embodiments, the preferred embodiments contains only the latter. In yet additional embodiments, the oil phase is chosen from the group of Guerbet alcohols (i.e., the group of alcohols named after Marcel Guerbet who first described their preparation). These alcohols are formed according to the equation:

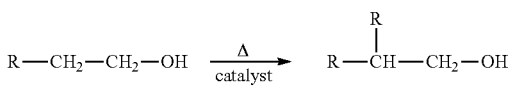

by oxidation of an alcohol to an aldehyde, by aldol condensation of the aldehyde, elimination of water from the aldol and hydrogenation of the allyl aldehyde. Guerbet alcohols are liquid even at low temperatures and result in virtually no skin irritations. Thus, they find use as fatting, superfatting and also refatting constituents in skincare and hair care compositions. Indeed, the use of Guerbet alcohols is known in the cosmetic art. In these applications, the species are generally characterized as having the following structure:

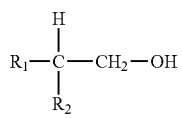

In this structure, $R_1$ and $R_2$ are usually unbranched alkyl radicals. In some preferred embodiments of the present invention the following Guerbet alcohols in which
$R_1$ is propyl, butyl, pentyl, hexyl, heptyl or octyl and/or $R_2$ is hexyl, heptyl, octyl, nonyl, decyl, undecyl, dodecyl, tridecyl or tetradecyl find use in the present invention. In additional embodiments, preferred Guerbet alcohols include 2-butyloctanol with the following chemical structure:

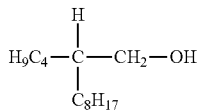

which is commercially available, for example, under the trade name ISOFOL® 12 (Condea Chemie GmbH), and 2-hexyldecanol with the following chemical structure:

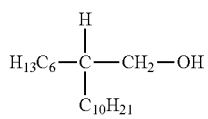

which is commercially available, for example, under the trade name ISOFOL® 16 (Condea Chemie GmbH).

In additional embodiments, mixtures of Guerbet alcohols find use in compositions of the present invention. For example, mixtures of 2-butyloctanol and 2-hexyldecanol find use in some embodiments. The total amount of Guerbet alcohols in the finished cosmetic or dermatological preparations is selected from the of range up to about 25.0% by weight, preferably about 0.5 to about 15.0% by weight, based on the total weight of the preparations. However, it is not intended that the present invention be limited to any particular concentration nor range of concentrations, as those of skill in the art know how to prepare compositions having suitable concentrations for the desired compositions and their use(s). In addition, it is contemplated that any mixtures of oil and/or wax components will find use in the present invention. For example, in some embodiments, waxes (e.g., cetyl palmitate) find use as the sole lipid component of the oil phase. In additional embodiments, nonpolar oils (e.g., those which are chosen from the group of branched and unbranched hydrocarbons and hydrocarbon waxes, in particular VASELINE® [i.e., petrolatum], paraffin oil, squalane and squalene, polyolefins and hydrogenated polyisobutenes find use in the present invention. In some embodiments containing polyolefins, polydecenes are the preferred substances.

Fatty and/or wax components which find use in embodiments of the present invention include but are not limited to vegetable waxes, animal waxes, mineral waxes and petrochemical waxes. Examples which particularly preferred waxes include candelilla wax, carnauba wax, japan wax, esparto grass wax, cork wax, guaruma wax, rice germ oil wax, sugar cane wax, berry wax, ouricury wax, montan wax, jojoba wax, shea butter, beeswax, shellac wax, spermaceti, lanolin (wool wax), uropygial grease, ceresin, ozokerite (earth wax), paraffin waxes and microcrystalline waxes.

Additional fatty and/or wax components that find use in the present invention include chemically modified waxes and/or synthetic waxes (e.g., those commercially available under the trade names SYNCROWAX® HRC [glyceryl tribehenate] and SYNSCROWAX® AW 1C [$C_{18}$-$C_{36}$ fatty acid], which are available from CRODA GmbH), and montan ester waxes, Sasol waxes, hydrogenated jojoba waxes, synthetic or modified beeswaxes (e.g., dimethicone copolyol beeswax and/or $C_{30-50}$ alkyl beeswax), polyalkylene waxes, polyethylene glycol waxes, as well as chemically modified fats (e.g., hydrogenated vegetable oils, such as hydrogenated castor oil and/or hydrogenated coconut fatty glycerides), triglycerides (e.g., trihydroxystearin, fatty acids, fatty acid esters, and glycol esters, such as, $C_{20}$-$C_{40}$-alkyl stearate, $C_{20}$-$C_{40}$-alkylhydroxystearoyl stearate and/or glycol montanate). In further embodiments, the present invention comprises certain organosilicone compounds, which have similar physical properties to the specified fatty and/or wax components (e.g., stearoxytrimethylsilane). In additional embodiments, the fatty and/or wax components are provided individually, while in still further embodiments, they are provided as a mixture. Indeed, it is intended that any desired mixture of such oil and/or wax components will find use in various embodiments of the present invention.

In some embodiments, the oily phase is selected from the group consisting of 2-ethylhexyl isostearate, octyldodecanol, isotridecyl isononanoate, isoeicosane, 2-ethylhexyl cocoate, $C_{12}$-$C_{15}$-alkyl benzoate, caprylic/capric triglyceride, and dicaprylyl ether. In alternative embodiments, mixtures of various oily phases are provided, including but not limited to mixtures comprising one or more of octyldodecanol, caprylic/capric triglyceride, dicaprylyl ether, $C_{12}$-$C_{15}$-alkyl benzoate, 2-ethylhexyl isostearate, isotridecyl isononanoate. The following table provides a list of lipids which find use alone or in combination with other lipids in various embodiments of the present invention. The corresponding interfacial tensions toward water are given in the last column. However, it is not intended that the present invention be limited to these specific components, as other components find use in various embodiments of the present invention, including mixtures of greater or lesser polar components and the like.

| | LIPIDS | |
|---|---|---|
| Trade name | INCI name | (m/Nm) |
| ISOFOL ® 14 T | Butyl Decanol + Hexyl Decanol + Hexyl Octanol + Butyl Octanol | 27.6 |
| ISOFOL ® 16 | Hexyl Decanol | 24.3 |

-continued

| LIPIDS | | |
|---|---|---|
| Trade name | INCI name | (m/Nm) |
| EUTANOL ® G | Octyldodecanol | 24.8 |
| CETIOL ® OE | Dicaprylyl Ether | 22.1 |
| MIGLYOL ® 812 | Caprylic/Capric Triglyceride | 21.3 |
| CEGESOFT ® C24 | Octyl Palmitate | 23.1 |
| Isopropyl stearate | Isopropyl Stearate | 21.9 |
| ESTOL ® 1540 EHC | Octyl Octanoate | 30.0 |
| FINSOLV ® TN | $C_{12}$-$C_{15}$ Alkyl Benzoate | 21.8 |
| CETIOL ® SN | Cetearyl Isonoanoate | 28.6 |
| DERMOFEEL ® BGC | Butylene Glycol Dicaprylate/Dicapate | 21.5 |
| TRIVENT ® OCG | Tricaprylin | 20.2 |
| MOD | Octyldodeceyl Myristate | 22.1 |
| COSMACOL ® ETI | Di-$C_{12}$-$C_{13}$ Alkyl Tartrate | 29.4 |
| MIGLYCOL ® 829 | Caprylic/Capric Diglyceryl Succinate | 29.5 |
| PRISORINE ® 2036 | Octyl Isostearate | 29.7 |
| TEGOSOFT ® SH | Stearyl Heptanoate | 28.7 |
| ABIL ® Wax 9840 | Cetyl Dimethicone | 25.1 |
| CETIOL ® LC | Coco-Caprylate/Caprate | 24.8 |
| IPP | Isopropyl Palmitate | 22.5 |
| LUVITOL ® EHO | Cetearyl Octanoate | 28.6 |
| CETIOL ® 868 | Octyl Stearate | 28.4 |

In some embodiments, some or all of the oil phase of the preparations are selected from the group consisting of cyclic and/or linear silicones which are also often referred to as "silicone oils." In some embodiments, these silicones or silicone oils are present as monomers which are generally characterized by structural elements as follows:

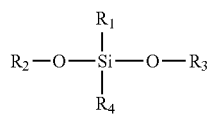

Silicones having two or more siloxyl units which find use in some embodiments of the present invention are generally characterized by structural elements as follows:

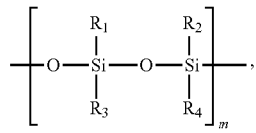

where the silicon atoms may be substituted by identical or different alkyl radicals and/or aryl radicals, which are represented in general terms by the radicals $R_1$ to $R_4$, where the number of different radicals is not necessarily limited to 4 and may assume values from 2 to 200,000.

Cyclic silicones to be used advantageously according to the invention are generally characterized by the structural elements as follows

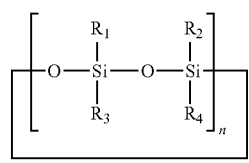

where the silicon atoms may be substituted by identical or different alkyl radicals and/or aryl radicals, which are represented here in general terms by the radicals $R_1$ to $R_4$, where the number of different radicals is not necessarily limited to 4. n can assume values of 3/2 to 20. Fractional values for "n" take into consideration that uneven numbers of siloxyl groups may be present in the cycle.

In some embodiments, phenyltrimethicone is selected as silicone oil. Other silicone oils suitable for use in various embodiments of the present invention include, but are not limited to dimethicone, phenyldimethicone, cyclomethicone (octamethylcyclotetrasiloxane), hexamethylcyclotrisiloxane, polydimethylsiloxane, poly(methylphenylsiloxane), cetyldimethicone, and behenoxydimethicone. In alternative embodiments, mixtures of these compounds find use in the present invention, including but not limited to mixtures of cyclomethicone and isotridecyl isononanoate, and mixtures of cyclomethicone and 2-ethylhexyl isostearate. It yet additional embodiments, silicone oils of similar constitution, such as the compounds referred to above whose organic side chains have been derivatized (e.g., polyethoxylated and/or polypropoxylated) find use in the present invention. These include, but are not limited to such compounds as polysiloxane-polyalkyl-polyether copolymers such as cetyldimethicone copolyol (i.e., cetyldimethicone copolyol (and) polyglyceryl-4 isostearate (and) hexyl laurate). Indeed, it is not intended that the present invention be limited to any specific silicone oil nor mixture of silicone oils, as various oils find use in various embodiments of the present invention.

In additional embodiments, water in oil (W/O) emulsions find use in the present invention. In some embodiments, W/O emulsifiers are used with or without additional co-emulsifiers. In still further embodiments, W/O emulsions of the present further comprise one or more emulsifiers, including, but not limited to one or more of the following compounds: lecithin, lanolin, microcrystalline wax (Cera microcristallina) in a mixture with paraffin oil (Paraffinum liquidum), ozokerite, hydrogenated castor oil, polyglyceryl-3 oleate, wool wax acid mixtures, wool wax alcohol mixtures, pentaerythrithyl isostearate, polyglyceryl-3 diisostearate, beeswax (Cera alba) and stearic acid, sodium dihydroxycetylphosphate in a mixture with isopropyl hydroxycetyl ether, methylglucose dioleate, methylglucose dioleate in a mixture with hydroxystearate and beeswax, mineral oil in a mixture with petrolatum and ozokerite and glyceryl oleate and lanolin alcohol, petrolatum in a mixture with ozokerite and hydrogenated castor oil and glyceryl isostearate and polyglyceyl-3 oleate, PEG-7 hydrogenated castor oil, ozokerite and hydrogenated castor oil, polyglyceryl-4 isostearate, polyglyceryl-4 isostearate in a mixture with cetyldimethicone copolyol and hexyl laurate, laurylmethicone copolyol, cetyldimethicone copolyol, acrylate/$C_{10}$-$C_{30}$-alkyl acrylate crosspolymer, Poloxamer 101, polyglyceryl-2 dipolyhydroxystearate, polyglyceryl-3 diisostearate, polyglyceryl-4 dipolyhydroxystearate, PEG-30 dipolyhydroxystearate, diisostearoyl polyglyceryl-3 diisostearate, polyglyceryl-2 dipolyhydroxystearate, polyglyceryl-3 dipolyhydroxystearate, polyglyceryl-4 dipolyhydroxystearate, polyglyceryl-3 dioleate.

In yet additional embodiments of the present invention, W/O emulsions of the present invention comprise one or more coemulsifiers, including, but not limited to the following:
glyceryl stearate in a mixture with ceteareth-20, ceteareth-25, ceteareth-6 in a mixture with stearyl alcohol, cetylstearyl alcohol in a mixture with PEG-40 castor oil and sodium cetylstearyl sulfate, triceteareth-4 phosphate, sodium cetylstearyl sulfate, lecithin trilaureth-4 phosphate, laureth-4 phosphate, stearic acid, propylene glycol stearate SE, PEG-25 hydrogenated castor oil, PEG-54 hydrogenated castor oil, PEG-6 caprylic/capric glycerides, glyceryl oleate in a mixture with propylene glycol, ceteth-2, ceteth-20, polysorbate 60, glyceryl stearate in a mixture with PEG-100 stearate, laureth-4, ceteareth-3, isostearyl glyceryl ether, cetylstearyl alcohol in a mixture with sodium cetylstearyl sulfate, laureth-23, steareth-2, glyceryl stearate in a mixture with PEG-30 stearate, PEG-40 stearate, glycol distearate, PEG-22 dodecyl glycol copolymer, polyglyceryl-2 PEG-4 stearate, ceteareth-20, methylglucose sesquistearate, steareth-10, PEG-20 stearate, steareth-2 in a mixture with PEG-8 distearate, steareth-21, steareth-20, isosteareth-20, PEG-45/dodecyl glycol copolymer, methoxy-PEG-22/dodecyl glycol copolymer, PEG-20 glyceryl stearate, PEG-8 beeswax, polyglyceryl-2 laurate, isostearyl diglyceryl succinate, stearamidopropyl PG dimonium chloride phosphate, glyceryl stearate SE, ceteth-20, triethyl citrate, PEG-20 methylglucose sesquistearate, ceteareth-12, glyceryl stearate citrate, cetyl phosphate, triceteareth-4 phosphate, trilaureth-4 phosphate, polyglyceryl methylglucose distearate, potassium cetyl phosphate, isosteareth-10, polyglyceryl-2 sesquiisostearate, ceteth-10, oleth-20, isoceteth-20, glyceryl stearate in a mixture with ceteareth-20, ceteareth-12, cetylstearyl alcohol and cetyl palmitate, cetylstearyl alcohol in a mixture with PEG-20 stearate, PEG-30 stearate, PEG-40 stearate, and PEG-100 stearate.

In yet additional embodiments in which the oil phase of the preparations consists at least partially of silicone oils, silicone emulsifiers find use. In some embodiments, the silicone emulsifiers are selected from the group of interface-active substances, alkylmethicone copolyols, and/or alkyl dimethicone copolyols, particularly from the group of compounds characterized by the following chemical structure:

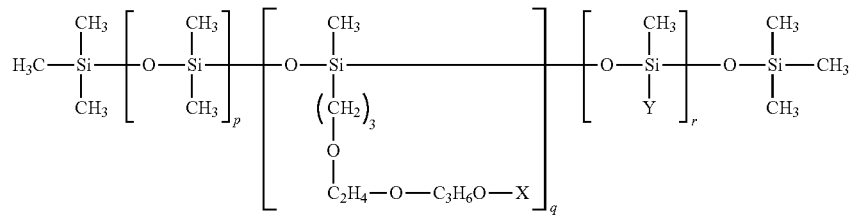

in which X and Y, independently of one another, are chosen from the group H and the branched and unbranched alkyl groups, acyl groups and alkoxy groups having 1 to 24 carbon atoms, p is a number from 0 to 200, q is a number from 1 to 40, and r is a number from 1 to 100. Some examples of silicone emulsifiers which find use in the present invention include, but are not limited to dimethicone copolyols (e.g., ABIL® B 8842, ABIL® B 8843, ABIL® B 8847, ABIL® B 8851, ABIL® B 8852, ABIL® B 8863, ABIL® B 8873, and ABIL® B 88183, all of which are commercially available from Th. Goldschmidt AG). An additional example of an interface-active substances which finds use in the present invention includes cetyldimethicone copolyol (ABIL® EM 90), as well as cyclomethiconedimethicone copolyol (ABTL® EM 97), both of which are commercially available from Th. Goldschmidt AG. An additional emulsifier which has proven useful in various compositions that finds use in embodiments of the present invention is laurylmethicone copolyol (Dow Corning® 5200 Formulation Aid), which is commercially available from Dow Corning Ltd.

In preferred embodiments of the present invention, the total amount of emulsifiers used in the personal care compositions (e.g., cosmetic or skin care preparations) are present in the range from about 0.1 to about 10.0% by weight, preferably about 0.5 to about 5.0% by weight, based on the total weight of the preparations. However, it is not intended that the present invention be limited to any specific concentration of emulsifier and/or co-emulsifier, as various embodiments of the present invention have different preferred concentrations and/or concentration ranges.

In some embodiments, the present invention provides emulsions in various forms, including skin protection creams, skin lotions, cosmetic milks, sunscreen creams, and sun protection milks. In some preferred embodiments, these compositions comprise fats, oils, waxes, and/or other fatty substances, as well as water, and one or more emulsifiers as are customarily used for such a type of formulation.

In addition to the liquid and somewhat more solid emulsions of the cosmetic cleansing lotions and/or cleansing creams of the present invention, the present invention also provides sprayable cleansing preparations ("cleansing sprays"), which are used, for example, for removing make-up or as mild washing lotion. In addition, these cleansing sprays find use in applications for treatment of blemished skin. These cleansing preparations also find use as "rinse-off preparations" (i.e., products which are rinsed off the skin following application).

In addition to the above constituents, various embodiments of the present invention include additional components, such as auxiliaries and additives, including but not limited to bodying agents, fillers, perfume, dyes, emulsifiers, additional active ingredients (e.g., vitamins and proteins), light protection agents, stabilizers, insect repellents, alcohol, self-tanning substances, water, salts, antimicrobials, proteases, and/or keratinase, etc. Indeed, it is not intended that the present invention be limited to any particular components, as long as the active component comprising a scaffold and a peptide is included. It is further contemplated that the present invention will find use in numerous and various medicinal preparations.

In some preferred embodiments, the present invention provides cosmetic and/or topical dermatological preparations suitable for use as skin protection creams, cleansing milks, sun screen lotions, nourishing creams, day creams, night creams etc. In some embodiments, the present invention finds use a components of drug (i.e., pharmaceutical) compositions. In additional embodiments, the present invention finds use in decorative cosmetics (e.g., make-up formulations).

In some particularly preferred embodiments, the present invention provides sunscreens useful in cosmetic and/or skin care preparations. In addition to the active ingredient used according to the embodiments of the present invention, in some embodiments, these preparations preferably additionally comprise at least one broadband filter and/or at least one UVA filter substance and/or at least one UVB filter substance and/or at least one inorganic pigment.

In yet further embodiments, the present invention provides personal care compositions which have UV protection components, but which are not primarily sunscreens. For example, in some embodiments, UV-A and/or UV-B filter substances are incorporated into day creams and/or hair care compositions.

In additional embodiments, the personal care compositions of the present invention comprise cosmetically active ingredients, auxiliaries and/or additives, as are customarily used in such preparations (e.g., antioxidants, preservatives, bacteriocides, perfumes, antifoams, dyes, pigments which have a coloring action, thickeners, surface-active substances, emulsifiers, emollients, moisturizers and/or humectants, fats, oils, waxes or other customary constituents of a cosmetic or dermatological formulation, such as alcohols, polyols, polymers, foam stabilizers, electrolytes, organic solvents or silicone derivatives). Indeed it is contemplated that various compounds will find use in the various embodiments of the present invention, as appropriate for the product and the user.

In still further embodiments, preservatives, such as those used in food and feed applications find use in various compositions of the present invention. The following table provides a list of such compounds, as well as the E number for each compound. However, it is not intended that the present invention be limited to these specific preservatives, as it is contemplated that additional preservatives will find use in various embodiments of the present invention.

| Examples of Food Grade Preservatives That Find Use in Embodiments of the Present Invention | |
|---|---|
| 200 | Sorbic acid |
| 201 | Sodium sorbate |
| 202 | Potassium sorbate |
| 203 | Calcium sorbate |
| 210 | Benzoic acid |
| 211 | Sodium benzoate |
| 212 | Potassium benzoate |
| 213 | Calcium benzoate |
| 214 | Ethyl p-hydroxybenzoate |
| 215 | p-hydroxybenzoic ethyl ester Na salt |
| 216 | n-propyl p-hydroxybenzoate |
| 217 | p-hydroxybenzoic-n-propyl ester Na salt |
| 218 | methyl p-hydroxybenzoate |
| 219 | p-hydroxybenzoic methyl ester Na salt |
| 220 | Sulfur dioxide |
| 221 | Sodium sulfite |
| 222 | Sodium hydrogensulfite |
| 223 | Sodium disulfite |
| 224 | Potassium disulfite |
| 226 | Calcium sulfite |
| 227 | Calcium hydrogen sulfite |
| 228 | Potassium hydrogen sulfite |
| 230 | Biphenyl (Diphenyl) |
| 231 | Orthophenylphenol |
| 232 | Sodium orthophenylphenoxide |
| 233 | Thiabendazole |
| 235 | Natamycin |
| 236 | Formic acid |
| 237 | Sodium formate |
| 238 | Calcium formate |
| 239 | Hexamethylenetetramine |
| 249 | Potassium nitrite |
| 250 | Sodium nitrite |
| 251 | Sodium nitrate |
| 252 | Potassium nitrate |
| 280 | Propionic acid |
| 281 | Sodium propionate |
| 282 | Calcium propionate |
| 283 | Potassium propionate |
| 290 | Carbon dioxide |

Additional preservatives that find use in various embodiments include but are not limited to dibromodicyanobutane (2-bromo-2-bromomethylglutarodinitrile), 3-iodo-2-propinylbutylcarbamate, 2-bromo-2-nitropropane-1,3-diol, imidazolidinylurea, 5-chloro-2-methyl-4-isothiazolin-3-one, 2-chloroacetamide, benzalkonium chloride, benzyl alcohol, and formaldehyde donors. Further preservatives that find use in various embodiments of the present invention include phenyl hydroxyalkyl ethers, in particular the compounds known as "phenoxyethanol," due to their bactericidal and fungicidal effects on a number of microorganisms.

Yet other antimicrobial agents are likewise suitable for use in various embodiments of the present invention, including but not limited to 2,4,4'-trichloro-2'-hydroxydiphenyl ether (i.e., IRGASAN®), 1,6-di(4-chlorophenylbiguanido)hexane (i.e., CHLORHEXIDIN), 3,4,4'-trichlorocarbanilide, quaternary ammonium compounds, oil of cloves, mint oil, thyme oil, triethyl citrate, FARNESOL® (3,7,11-trimethyl-2,6,10-dodecatrien-1-ol) and the active ingredients and/or active ingredient combinations described in DE-37 40 186, DE-39 38 140, DE-42 04 321, DE-42 29 707, DE-43 09 372, DE-44 11 664, DE-195 41 967, DE-195 43 695, DE-195 43 696, DE-195 47 160, DE-196 02 108, DE-196 02 110, DE-196 02 111, DE-196 31 003, DE-196 31 004, DE-196 34 019, DE-42 29 737, DE-42 37 081, DE-43 24 219, DE-44 29 467, DE-44 23 410, and DE-195 16 705, all of which are hereby incorporated by reference. In still further embodiments, sodium hydrogencarbonate is also included in some compositions of the present invention. However, it is not intended that the present invention be limited to any particular antimicrobial nor combination of anti-microbial, as various compounds having such effects will find use in various embodiments of the present invention.

In additional embodiments of the personal care compositions of the present invention, compounds such as anti-irritants and/or anti-inflammatory actives are included. In some embodiments, batyl alcohol (a-octadecyl glyceryl ether), selachyl alcohol (a-9-octadecenyl glyceryl ether), chimyl alcohol (a-hexadecyl glyceryl ether), bisabolol, and/or panthenol are included. However, it is not intended that the present invention be limited to the incorporation of any specific anti-irritant(s) and/or anti-inflammatory(ies), as various compounds suitable for such applications find use in the present invention.

In still further embodiments of the present invention, antioxidants are incorporated in the personal care compositions. It is contemplated that any suitable antioxidants will find use in the personal care compositions of the present invention. Suitable antioxidants include, but are not limited to amino acids (e.g., glycine, histidine, tyrosine, and tryptophan) and derivatives thereof, imidazoles (e.g. urocanic acid) and derivatives thereof, peptides (e.g., D,L-carnosine, D-carnosine, and L-carnosine) and derivatives thereof (e.g., anserine), carotenoids, carotenes (e.g., α-carotene, β-carotene, and γ-lycopene) and derivatives thereof, chlorogenic acid and derivatives thereof, aurothioglucose, propylthiouracil and other thiols (e.g., thioredoxin, glutathione, cysteine, cystine, cystamine and the glycosyl, N-acetyl, methyl, ethyl, propyl, amyl, butyl and lauryl, palmitoyl, oleyl, g-linoleyl, cholesteryl and glyceryl esters thereof) and salts thereof, dilauryl thiodipropionate, distearyl thiodipropionate, thiodipropionic acid and derivatives thereof (e.g., esters, ethers, peptides, lipids, nucleotides, nucleosides and salts), and sulfoximine compounds (e.g. buthionine sulfoximines, homocysteine sulfoximine, buthionine sulfones, penta-, hexa-, and heptathionine sulfoximine) in very small tolerated doses (e.g., typically pmol to mmol/kg), chelating agents (e.g., α-hydroxy fatty acids, palmitic acid, phytic acid, and lactoferrin), α-hydroxy acids (e.g. citric acid, lactic acid, and malic acid), humic acid, bile acid, bile extracts, bilirubin, biliverdin, EDTA, EGTA and derivatives thereof, unsaturated fatty acids and derivatives thereof (e.g., linolenic acids, linoleic acid, oleic acid), folic acid and derivatives thereof, furfurylidenesorbitol and derivatives thereof, ubiquinone and ubiquinol and derivatives thereof, vitamin C and derivatives thereof (e.g., sodium ascorbyl phosphate, ascorbyl palmitate, Mg ascorbyl phosphate, and ascorbyl acetate), tocopherols and derivatives (e.g., vitamin E acetate), coniferyl benzoate of benzoin resin, ferulic acid, furfurylideneglucitol, carnosine; butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and derivatives thereof (e.g., ZnO, ZnSO4), selenium and derivatives thereof (e.g., selenomethionine), stilbenes and derivatives thereof (e.g., stilbene oxide, trans-stilbene oxide) and the derivatives thereof (e.g., salts, esters, ethers, sugars, nucleotides, nucleosides, peptides and lipids) of said active ingredients which are suitable for the intended use of the particular embodiment(s) of the present invention.

In some embodiments, the concentration of one or more antioxidant in the compositions of the present invention is preferably from about 0.001 to about 30% by weight, particularly preferably from about 0.05 to about 20% by weight, and more preferably from about 1 to about 10% by weight, based on the total weight of the preparation. In additional embodiments, in which vitamin E and/or its derivatives are utilized as anti-oxidant(s), the preferred range is from about 0.001 to about 10% by weight, based on the total weight of the formulation. However, it is not intended that the present invention be limited to any specific antioxidant concentration(s), as various concentrations will find use in the various embodiments of the present invention.

In yet additional embodiments, the present invention provides preparations suitable for use as deodorants and/or anti-perspirants. It is contemplated that any of the active ingredients which commonly find use in such preparations will also find use in various embodiments of the present invention. Additional components that are commonly used in such preparations also find use in various embodiments of the present invention. Examples of such actives and inactive compounds include, but are not limited to odor maskers (e.g., perfumes), odor absorber (e.g., phyllosilicates described in DE-P 40 09 347); as well as montmorillonite, kaolinite, illite, beidellite, nontronite, saponite, hectorite, bentonite, smectite, and zinc salts of ricinoleic acid. In some embodiments of the present invention, the range of active ingredients (i.e., one or more compounds) in such preparations is preferably from about 0.001 to about 30% by weight; more preferably from about 0.05 to about 20% by weight; and most particularly in the range of from about 1 to about 10% by weight, based on the total weight of the preparation.

In some embodiments of the present invention, the water phase has a gel character which, in addition to an effective content of compounds and solvents (as appropriate) preferably comprises water, further organic and/or inorganic thickeners, and/or hydrocolloids.

In some embodiments, inorganic thickeners are selected from the group consisting of modified, unmodified, naturally occurring, and synthetic phyllosilicates. Although it is generally preferable to use pure components, in some embodiments, mixtures of different modified and/or unmodified phyllosilicates find use in various compositions of the present invention. As generally known in the art, phyllosilicates are silicates and alumosilicates in which the silicate or aluminate units are linked together via three Si—O— or Al—O— bonds and form a wavy sheet or layer structure. The fourth Si—O— or Al—O— valence is saturated by cations. Relatively weak electrostatic interactions (e.g. hydrogen bridge bonds), exist between the individual layers. The layer structure is largely defined by strong, covalent bonds. The stochiometry of the sheet silicates is $(Si_2O_5^{2-})$ for pure silicate structures and $(Al_mSi^{2-}_mO_5^{(2+m)-})$ for alumosilicates, wherein "m" is a number greater than zero and less than 2. In some embodiments in which alumosilicates are present in the absence of pure silicates, each $Si^{4+}$ group replaced by $Al^{3+}$ requires another singly charged cation to neutralize the charge. The charge balance is preferably evened out by $H^+$, alkali metal ions or alkaline earth metal ions. In alternative embodiments, aluminum is used as a counterion. In contrast to the alumosilicates, these compounds are referred to as "aluminum silicates." "Aluminum alumosilicates," in which aluminum is present both in the silicate network, and also as counterion, also find use in some embodiments of the present invention.

Phyllosilicates are well known in the art (See e.g., Hollemann et al., *Lehrbuch der Anorganischen Chemie* [Textbook of Inorganic Chemistry], 91st-100th Ed., Walter de Gruyter—Verlag [1985]; Remy, *Lehrbuch der Anorganischen Chemie*, $12^{th}$ Ed., Akademische Verlagsgesellschaft, Leipzig [1965]). The layer structure of montmorillonite is also known (See, Römpps Chemie-Lexikon, Franckh'sche Verlagshandlung, W. Keller & Co., Stuttgart, $8^{th}$ Ed., [1985], p. 2668 f). Examples of phyllosilicates include the following (montmorillonite is the main mineral comprising the naturally-occurring bentonites);

Montmorillonite $Na_{0.33}((Al_{1.67}Mg_{0.33})(OH)_2(S_{i4}O_{10}))$
often simplified: $Al_2O_3*4SiO_2*H_2O*nH_2O$ or
$Al_2[(OH)_2/Si_4O_{10}].n\ H_2O$
Kaolinite $Al_2(OH)_4(Si_2O_5)$
Illite $(K,H_3O)_y(Mg_3(OH)_2(Si_{4-y}Al_yO_{10})$ or
$(K,H_3O)_y(Al_2(OH)_2(Si_{4-y}Al_yO_{10}))$
where y=0.7-0.9
Beidellite $(Ca,Na)_{0.3}(Al_2(OH)_2(Al_{0.5}Si_{3.5}O_{10}))$
Nontronite $Na_{0.33}(Fe_2(OH)_2(Al_{0.33}S_{i3.67}O_{10}))$
Saponite $(Ca,Na)_{0.33}((Mg,Fe)_3(OH)_2(Al_{0.33}Si_{3.67}O_{10}))$
Hectorite $Na_{0.33}((Mg,Li)_3(OH,F)_2(Si_4O_{10}))$ In some preferred embodiments, inorganic gel formers including but not limited to aluminum silicates, such as the montmorillonites (bentonites, hectorites and derivatives thereof, such as quaternium-18 bentonite, quaternium-18 hectorites, stearalkonium bentonites and stearalkonium hectorites), and also magnesium-aluminum silicates (VEEGUM® grades), and sodium-magnesium silicates (LAPONITE® grades) find use in the present invention.

Montmorillonites represent clay minerals which are a type of dioctahedral smectites, and are masses which swell in water, but do not become plastic. The layer packets in the three-layer structure of the montmorillonites can swell as a result of reversible incorporation of water (in a 2- to 7-fold amount) and other substances, such as, for example, alcohols, glycols, pyridine, picoline, ammonium compounds, hydroxy-aluminosilicate ions etc. The chemical formula given above provides just an approximation of the formula, as montmorillonites have a large capacity for ion exchange. For example, Al can be replaced by Mg, $Fe^{2+}$, $Fe^{3+}$, Zn, Pb (e.g., from harmful substances in waste waters), Cr, Cu and other elements. The resulting negative charge of the octahedral layers is compensated for by the presence of cations, in particular $Na^+$ (i.e., sodium montmorillonite) and $Ca^{2+}$ (i.e., calcium montmorillonite, a compound that is only swellable to a very small extent) in interlayer positions.

In alternative embodiments, synthetic magnesium silicates and/or bentonites find use in the present invention, including but not limited to such commercially available compounds as OPTIGEL® (Süd-Chemie). As indicated above, in some embodiments, aluminum silicates such as the commercially available VEEGUM® (R.T. Vanderbilt Comp., Inc), find use in the present invention. Various VEEGUM® grades which find use in various embodiments of the present invention are provided below.

| VEEGUM ® Grades | | | | | |
|---|---|---|---|---|---|
|  | Regular Grade | HV | K | HS | S-728 |
| $SiO_2$ | 55.5 | 56.9 | 64.7 | 69.0 | 65.3 |
| MgO | 13.0 | 13.0 | 5.4 | 2.9 | 3.3 |
| $Al_2O_3$ | 8.9 | 10.3 | 14.8 | 14.7 | 17.0 |
| $Fe_2O_3$ | 1.0 | 0.8 | 1.5 | 1.8 | 0.7 |
| CaO | 2.0 | 2.0 | 1.1 | 1.3 | 1.3 |
| $Na_2O$ | 2.1 | 2.8 | 2.2 | 2.2 | 3.8 |
| $K_2O$ | 1.3 | 1.3 | 1.9 | 0.4 | 0.2 |
| Ashing loss | 11.1 | 12.6 | 7.6 | 5.5 | 7.5 |

The above products swell in water to form viscous gels, which have an alkaline reaction. The organophilization of montmorillonite or bentonites (exchange of the interlayer cations for quaternary alkylammonium ions) produces products (bentones) which are preferably used for dispersion in organic solvents and oils, fats, ointments, inks, surface coatings and in detergents.

BENTONE® is a trade name for various neutral and chemically inert gelling agents which are constructed from long-chain, organic ammonium salts and specific types of montmorillonite. BENTONE® gelling agents swell in organic media, which cause the media to also swell. The gels are resistant to diluted acids and alkalis, although they partially lose their gelling properties upon prolonged contact with strong acids and alkalis. Because of their organophilic character, BENTONE® gelling agents are only wettable by water with difficulty. There are various BENTONE® gelling agent grades commercially available, including those sold by Kronos Titan: BENTONE® 27, an organically modified montmorillonite; BENTONE® 34 (dimethyldioctylammonium bentonite; prepared in accordance with U.S. Pat. No. 2,531,427, incorporated herein by reference, which because of its lipophilic groups, swells more readily in lipophilic medium than in water); BENTONE® 38, an organically modified montmorillonite, available as a cream-colored to white powder; BENTONE® LT, a purified clay mineral; BENTONE® Gel MIO, an organically modified montmorillonite which is supplied as a very fine suspension in mineral oil (SUS-71) (10% bentonite, 86.7% mineral oil and 3.3% wetting agent); BENTONE® Gel IPM, an organically modified bentonite which is suspended in isopropyl myristate (10% bentonite, 86.7% isopropylmyristate, 3.3% wetting agent); BENTONE® Gel CAO, an organically modified montmorillonite which is taken up in castor oil (10% bentonite, 86.7% castor oil and 3.3% wetting agent); BENTONEϵ Gel Lantrol, an organically modified montmorillonite which, in paste form, is intended for the further processing, in particular for the preparation, of cosmetic compositions; 10% bentonite, 64.9 LANTROL® (wool wax oil), 22.0 isopropyl myristate, 3.0 wetting agent and 0.1 propyl p-hydroxybenzoate; BENTONE® Gel Lan I, a 10% strength BENTONE® 27 paste in a mixture of wool wax USP and isopropyl palmitate; BENTONE® Gel Lan II, a bentonite paste in pure liquid wool wax; BENTONE® Gel NV, a 15% strength BENTONE® 27 paste in dibutyl phthalate; BENTONE® Gel OMS, a bentonite paste in Shellsol T.; BENTONE® Gel OMS 25, a bentonite paste in isoparaffinic hydrocarbons (IDOPAR® H); and BENTONE® Gel IPP, a bentonite paste in isopropyl palmitate.

"Hydrocolloid" is the technological abbreviation for the more correct name "hydrophilic colloid." Hydrocolloids are macromolecules which have a largely linear structure and intermolecular forces of interaction which permit secondary and primary valence bonds between the individual molecules to form a recticular structure. Some hydrocolloids are water-soluble natural or synthetic polymers which, in aqueous systems, form gels or viscous solutions. These compounds increase the viscosity of water by either binding water molecules (hydration), or by absorbing and encapsulating the water into their interwoven macromolecules, while restricting the mobility of water. These water-soluble polymers represent a large group of natural and synthetic polymers that are chemically very different, but which share a common feature in their solubility in water or aqueous media. A prerequisite for this is that these polymers have a number of hydrophilic groups sufficient for solubility in water and are not too greatly crosslinked. These hydrophilic groups can be nonionic, anionic or cationic in nature, for example as follows:

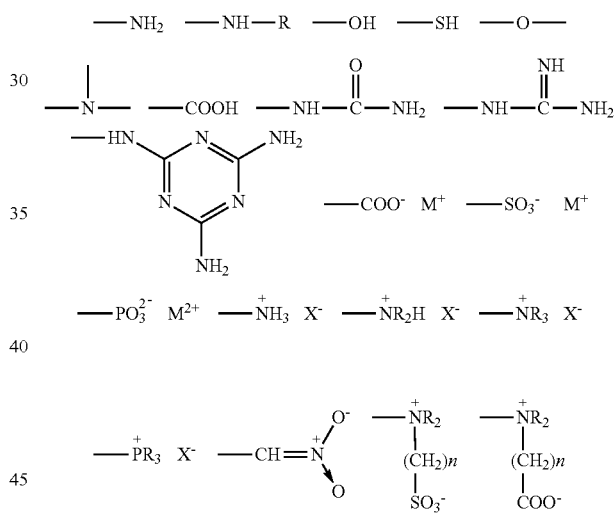

In some preferred embodiments, the group of the cosmetically and dermatologically relevant hydrocolloids are divided into the following groups: organic, natural compounds (e.g., agar agar, carrageen, tragacanth, gum arabic, alginates, pectins, polyoses, guar flour, carob bean flour, starch, dextrins, gelatins, and casein); organic, modified natural substances (e.g., carboxymethylcellulose and other cellulose ethers, hydroxyethylcellulose and hydroxypropylcellulose and microcristalline cellulose); organic, completely synthetic compounds (e.g., polyacrylic and polymethacrylic compounds, vinyl polymers, polycarboxylic acids, polyethers, polyimines, polyamides, and polyurethanes); and inorganic compounds (e.g., polysilicic acids, clay minerals, such as montmorillonites, zeolites, and silicas).

In alternative embodiments, ethylcelluloses find use in compositions of the present invention as stabilizers. Ethylcelluloses are characterized by the following structure. In this structure, the Rs are either ethyl groups or hydrogen atoms.

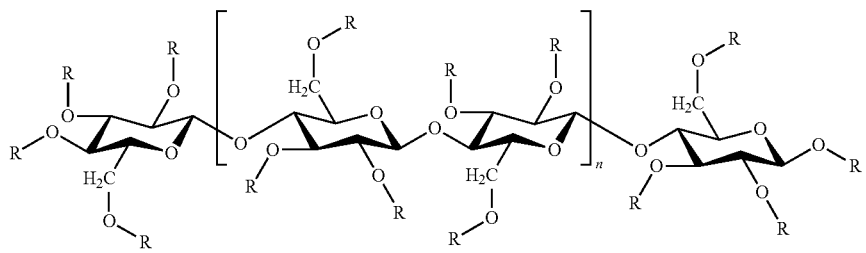

In some preferred embodiments, the degree of ethylation in the ethylcellulose is from about 2.0 to about 3.0, corresponding to about 40 to about 55%, and more preferably about 48.0 to about 49.5% ethylation. The average molecular mass is preferably chosen such that the viscosity of an approximately 5% strength solution in a mixture of 80 parts of toluene and 20 parts of ethanol at 25° C. is 3 to 110 mPas, and more preferably 9 to 11 mPas. In some particularly preferred embodiments, the average molar mass is from about 100,000 to about 400,000 g/mol. In some preferred embodiments, the ethylcellulose concentration in compositions of the present invention ranges from about 0.1 to about 10% by weight, based on the total weight of the preparations. Various ethylcelluloses find use in the present invention, including but not limited to those that are commercially available (e.g., ETHOCEL® Standard 10 Premium; Dow Chemicals).

In yet additional embodiments, microcristalline cellulose finds use as hydrocolloid in compositions of the present invention. Various microcrystalline cellulose preparations find use in the present invention, including but not limited to those that are commercially available (e.g., AVICEL®, such as AVICEL® RC-591, as well as AVICEL® RC/CL; AVICEL® CE-15; and AVICEL® 500; FMC Corporation Food and Pharmaceutical Products). In some particularly preferred embodiments, AVICEL® RC-591 (a modified microcristalline cellulose which is made up of 89% microcrystalline cellulose and 11% sodium carboxymethylcellulose) finds use in the present invention.

Additional hydrocolloids that find use in the present invention include methylcelluloses methylesters of cellulose). These compounds are characterized by the following structural formula

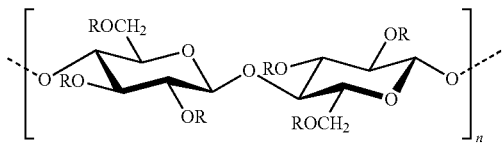

in which R can be a hydrogen or a methyl group.

Cellulose mixed ethers (generally referred to as methylcelluloses, which contain, in addition to a predominating content of methyl groups, also 2-hydroxyethyl, 2-hydroxypropyl or 2-hydroxybutyl groups) also find use in some embodiments of the present invention. In some preferred embodiments, hydroxypropyl)methyl-celluloses (e.g., METHOCEL® E4M; Dow Chemical Co.) find use in the present invention.

In yet further embodiments sodium carboxymethylcellulose (i.e., the sodium salt of the glycolic ether of cellulose, for which R in the above structural formula may be hydrogen and/or $CH_2$—COONa) finds use in the present invention. In some preferred embodiments, sodium carboxymethylcellulose, also sometimes referred to as "cellulose gum" (e.g., NATROSOL® Plus 330 CS; Aqualon) finds use in the present invention.

In additional embodiments, xanthan (CAS No. 11138-66-2), (i.e., xanthan gum), an anionic heteropolysaccharide generally formed by fermentation from maize sugar and isolated as potassium salt finds use in the present invention. It is produced by *Xanthomonas campestris* and some other species under aerobic conditions and has a molecular weight of from $2 \times 10^6$ to $24 \times 10^6$. Xanthan is formed from a chain having cellulose with side chains. The structure of the subgroups consists of glucose, mannose, glucuronic acid, acetate and pyruvate. The number of pyruvate units determines the viscosity of the xanthan.

In still further embodiments, carrageen is used as a gel former in compositions of the present invention. This compound is an extract from North Atlantic red algae (Florideae; *Chondrus crispus* and *Gigartina stellata*) that has a structure similar to that of agar. The term "carrageen" is frequently used in reference to a dried algae product and "carrageenan" is used in reference to the extract thereof. The carrageen precipitated from the hot-water extract of the algae is a colorless to sand-colored powder with a molecular weight range from about 100,000 to about 800,000 and a sulfate content of about 25%. Carrageen, which is very readily soluble in warm water, forms a thixotropic gel upon cooling, even if the water content is 95-98%. The rigidity of the gel is effected by the double helix structure of the carrageen.

In the case of carrageenan, three principle constituents are differentiated. The gel-forming "κ fraction" consists of D-galactose 4-sulfate and 3,6-anhydro-α-D-galactose, which has alternate glycoside bonds in the 1,3- and 1,4 position (in contrast, agar contains 3,6-anhydro-α-L-galactose). The non-gelling "λ fraction" is composed of 1,3-glycosidically linked D-galactose 2-sulfate and 1,4-bonded D-galactose-2,6-disulfate radicals, and is readily soluble in cold water. Finally, "ι-carrageenan," composed of D-galactose 4-sulfate in 1,3 bond and 3,6-anhydro-α-D-galactose 2-sulfate in 1,4 bond, is both water-soluble and also gel-forming. The nature of any cations which are present ($K^+$, $NH_4^+$, $Na^+$, $Mg^{2+}$, $Ca^{2+}$) also influences the solubility of the carrageens.

In yet additional embodiments, chitosan (i.e., partially deacylated chitin) finds use in various compositions of the present invention. Chitosan has film-forming properties and is characterized as having a silky feel on the skin. One disadvantage for some uses, is its severe stickiness on the skin which occurs in temporarily (usually) during application. Due to this stickiness, some preparations are not acceptable to consumers. However, chitosan finds use in some preparations, including hair care compositions, as it is better than chitin in thickening and/or stabilizing, as well as improving the adhesion and water resistance of polymeric films. The use of chitosan is well-known to those of skill in the personal care art (See e.g., Fiedler, *Lexikon der Hilfsstoffe für Pharmazie*,

*Kosmetik and angrenzende Gebiete*, [Lexikon of auxiliaries for pharmacy, cosmetics and related fields], 3rd edition, Editio Cantor, Aulendorf, [1989], p. 293). Chitosan is characterized by the following structural formula:

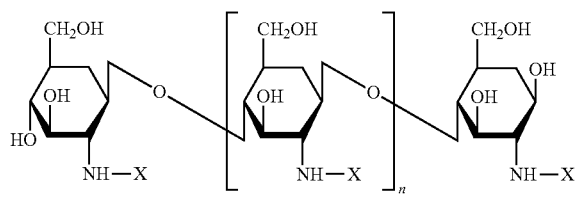

where n assumes values up to about 10 000, and X is either the acetyl radical or hydrogen. Chitosan forms by deacetylation and partial depolymerization (hydrolysis) of chitin, which is characterized by the structural formula

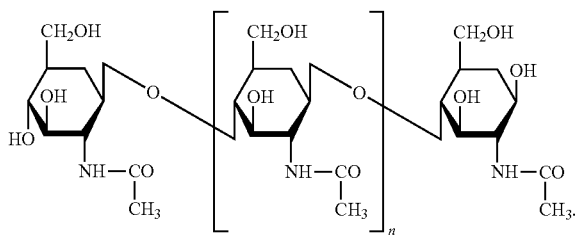

Chitin is an essential constituent of the arthropod (e.g. insects, crabs, and spiders) ectoskeleton, and is also found in the connective and/or supporting tissues of other organisms (e.g. mollusks, algae, and fungi). In the region of about pH<6, chitosan is positively charged and in that range is also soluble in aqueous systems. It is incompatible with anionic raw materials. For this reason, in order to prepare chitosan-containing oil-in-water emulsions, the use of nonionic emulsifiers is appropriate (See e.g., EP 776 657). In some preferred embodiments, the compositions of the present invention contain at least one chitosans with a degree of deacetylation of at least about >25%, and more preferably, a range of more than about 55 to about 99% (as determined by means of $^1$H-NMR). In some embodiments, chitosans of molecular weights between about 10,000 and about 1,000,000, in particular those with molecular weights between 100,000 and 1,000, 000 (determined by means of gel permeation chromatography) find use in the present invention.

In yet further embodiments, polyacrylates find use as gelling agents in some compositions of the present invention. Suitable polyacrylates include but are not limited to acrylate-alkyl acrylate copolymers, in particular those chosen from the group of carbomers or CARBOPOL® copolymers (B.F. Goodrich Co.). In particular, the acrylate-alkyl acrylate copolymers that find use in some embodiments of the present invention have the following structure:

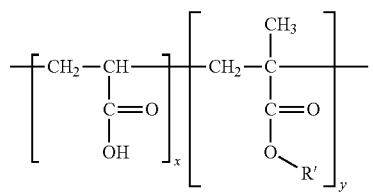

where R' is a long-chain alkyl radical, and x and y represent numbers which symbolize the respective stoichiometric proportion of each of the comonomers.

In some embodiments, acrylate copolymers and/or acrylate-alkyl acrylate copolymers, include but are not limited to those that are commercially available (e.g., CARBOPOL® 1382, CARBOPOL® 981, and CARBOPOL® 5984; B.F. Goodrich Co., and in particular, polyacrylates from the group of CARBOPOL grades 980, 981, 1382, 2984, 5984 and Carbomer 2001). In additional embodiments, copolymers of $C_{10-30}$-alkyl acrylates and one or more monomers of acrylic acid, of methacrylic acid or esters thereof which are crosslinked with an allyl ether of sucrose or an allyl ether of pentaerythrito find use in some embodiments of the present invention.

Compounds which carry the INCI name "Acrylates/$C_{10-30}$ Alkyl Acrylate Crosspolymer" also find use in some embodiments of the present invention. In some embodiments, commercially available polymers (e.g., PEMULEN® TR1 and PEMULEN® TR2; B.F. Goodrich Co.) find use in some embodiments of the present invention, although it is not intended that the present invention be limited to any specific acrylate-containing composition.

In yet additional embodiments, compounds which carry the INCI name "ammonium acryloyldimethyltaurates/vinylpyrrolidone copolymers" find use in the present invention. These ammonium acryloyldimethyl taurate/vinylpyrrolidone copolymers have the empirical formula $[C_7H_{16}N_2SO_4]_n$ $[C_6H_9NO]_m$, which corresponds to the following structure:

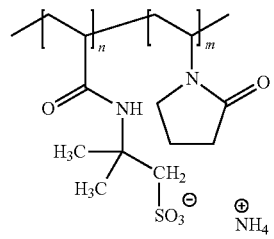

Preferred species of this compound are listed in Chemical Abstracts under the Registry numbers 58374-69-9, 13162-05-5 and 88-12-0, and are commercially available (e.g., ARISTOFLEX®; Clariant GmbH). However, it is not intended that the present invention be limited to any particular species. In yet additional embodiments of the present invention, copolymers/crosspolymers comprising acryloyldimethyl taurate (e.g., SIMUGEL® EG and SIMUGEL® EG; Seppic S.A.) find use in some compositions of the present invention.

Additional completely synthetic hydrocolloids that find use in the present invention include, but are not limited to anionic polyurethanes which are soluble or dispersible in water and which are advantageously obtainable from:
  Aa) at least one compound which contains two or more active hydrogen atoms per molecule,
  Ab) at least one diol containing acid or salt groups, and
  Ac) at least one diisocyanate.

In some preferred embodiments, the component Aa) is, in particular, a diol, aminoalcohol, diamine, polyesterol, polyetherol with a number-average molecular weight of in each case up to 3000, or mixtures thereof, where up to 3 mol % of said compounds may be replaced by triols or triamines. Preference is given to diols and polyesterdiols. In particular, the component Aa) comprises at least 50% by weight, based on the total weight of the component Aa), of a polyesterdiol.

Suitable polyesterdiols are all those which are customarily used for the preparation of polyurethanes, in particular the reaction products of phthalic acid and diethylene glycol, isophthalic acid and 1,4-butanediol, isophthalic acid/adipic acid and 1,6-hexanediol, and adipic acid and ethylene glycol or 5-NaSO$_3$-isophthalic acid, phthalic acid, adipic acid and 1,6-hexanediol.

Examples of diols which find use in some embodiments of the present invention include, but are not limited to ethylene glycol, propylene glycol, butylene glycol, neopentyl glycol, polyetherols (e.g., polyethylene glycols having molecular weights up to 3000), block copolymers of ethylene oxide and propylene oxide with number-average molecular weights of up to 3000, and block copolymers of ethylene oxide, propylene oxide and butylene oxide which contain the copolymerized alkylene oxide units in randomly distributed manner or in the form of blocks. Preference is given to ethylene glycol, neopentyl glycol, di-, tri-, tetra-, penta- or hexaethylene glycol. Other diols which find use include poly($\alpha$-hydroxycarboxylic acid)diols.

Suitable aminoalcohols that find use in some embodiments of the present invention include but are not limited to 2-aminoethanol, 2-(N-methylamino)ethanol, 3-aminopropanol, and 4-aminobutanol.

In some embodiments, diamines such as ethylenediamine, propylenediamine, 1,4-diaminobutan, 1,6-diaminohexane, and $\alpha,\omega$-diamines which can be prepared by amination of polyalkylene oxides with ammonia find use in some compositions of the present invention.

Component Ab) is, in particular, dimethylolpropanoic acid or a compound with the formula:

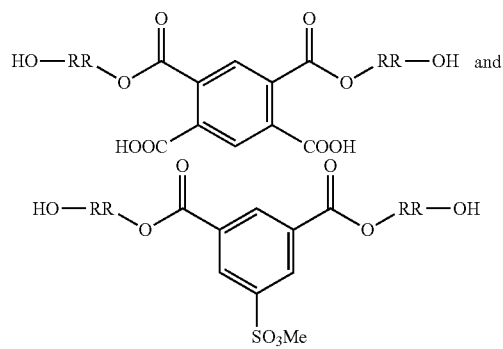

where RR is in each case a C$_2$-C$_{18}$-alkylene group and Me is Na or K.

Component Ac) is, in particular, hexamethylene diisocyanate, isophorone diisocyanate, methyldiphenyl isocyanate (MDI), and/or tolylene diisocyanate.

In some embodiments, the polyurethanes are obtained by reacting the compounds of groups Aa) and Ab) under an inert-gas atmosphere in an inert solvent at temperatures of from 70 to 130° C. with the compounds of group Ac). This reaction can be carried out, where appropriate, in the presence of chain extenders in order to prepare polyurethanes with relatively high molecular weights. As is customary in the preparation of polyurethanes, the components [(Aa)+(Ab)]: Ac are advantageously used in the molar ratio of from 0.8 to 1.1:1. The acid number of the polyurethanes is determined by the composition and the concentration of the compounds of component (Ab) in the mixture of components (Aa) and (Ab).

In some embodiments, the polyurethanes have K values according to H. Fikentscher (determined in 0.1% strength by weight solutions in N-methylpyrrolidone at 25° C. and pH 7) of from about 15 to about 100, and preferably about 25 to about 50. The K value (i.e., "intrinsic viscosity"), is a parameter which is easy to determine by means of viscosity measurements of polymer solutions and is therefore frequently used in the industrial sector for characterizing polymers. Polyurethanes containing acid groups that find use in some embodiments of the present invention include, but are not limited to polyurethanes that are water-soluble or dispersible without the aid of emulsifiers after partial or complete neutralization. The salts of the polyurethanes generally have better solubility or dispersibility in water than the unneutralized polyurethanes. Bases which find use for the neutralization of the polyurethanes include alkali metal bases (e.g., sodium hydroxide solution, potassium hydroxide solution, soda, sodium hydrogencarbonate, potassium carbonate or potassium hydrogen carbonate) and alkaline earth metal bases (e.g., calcium hydroxide, calcium oxide, magnesium hydroxide or magnesium carbonate, and ammonia and amines). In some embodiments, 2-amino-2-methylpropanol, diethylaminopropylamine and triisoproanolamine find particular use in the neutralization of the polyurethanes containing acid groups. In yet additional embodiments, the neutralization of the polyurethanes containing acid groups is carried out using mixtures of two or more bases (e.g. mixtures of sodium hydroxide solution and triisopropanolamine). Depending on the intended use, neutralization is partial (e.g. about 20 to about 40%) or complete (i.e., 100%). These polymers and their preparation are described in more detail in DE-A-42 25 045, incorporated herein by reference.

B. Water-soluble or -dispersible cationic polyurethanes and polyureas of:
  Ba) at least one diisocyanate, which may have already been reacted beforehand with one or more compounds which contain two or more active hydrogen atoms per molecule, and
  Bb) at least one diol, primary or secondary amino alcohol, primary or secondary diamine or primary or secondary triamine with one or more tertiary, quaternary or protonated tertiary amino nitrogen atoms.

Preferred diisocyanates are as given above under A). Compounds with two or more active hydrogen atoms are diols, aminoalcohols, diamines, polyesterols, polyamidediamines and polyetherols. Suitable compounds of this type are as given above under A).

The polyurethanes are prepared as described above under A). Charged cationic groups can be produced in the polyureas from the tertiary amino nitrogen atoms present either by protonation, (e.g., with carboxylic acids, such as lactic acid), or by quaternization (e.g. with alkylating agents, such as C$_1$ to C$_4$-alkyl halides) or sulfates. Examples of such alkylating agents include, but are not limited to ethyl chloride, ethyl bromide, methyl chloride, methyl bromide, dimethyl sulfate and diethyl sulfate. These polymers and their preparation are described in more detail in DE-A-42 41 118, which is incorporated herein by reference.

C. Linear polyurethanes with carboxylate groups of:
  Ca) a 2,2-hydroxymethyl-substituted carboxylic acid of the formula

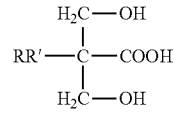

in which RR' is a hydrogen atom or a $C_1$-$C_{20}$-alkyl group, which is used in an amount which suffices for about 0.35 to about 2.25 milliequivalents of carboxyl groups to be present in the polyurethane per g of polyurethane, Cb) about 10 to about 90% by weight, based on the weight of the polyurethane, of one or more organic compounds with not more than two active hydrogen atoms and Cc) one or more organic diisocyanates.

In some preferred embodiments, the carboxyl groups present in the polyurethane are, finally, at least partially neutralized with a suitable base. These polymers and their preparation are described in EP-A-619 111, incorporated herein by reference.

D. Carboxyl-containing polycondensation products of anhydrides of tri- or tetracarboxylic acids and diols, diamines or aminoalcohols (polyesters, polyamides or polyester amides). These polymers and their preparation are described in more detail in DE-A-42 24 761, incorporated herein by reference.

E. Polyacrylates and polymethacrylates, as are described in more detail in DE-A-43 14 305, 36 27 970 and 29 17 504, all of which are incorporated herein by reference.

The polymers used in some embodiments of the present invention have a K value of from about 15 to about 100, and more preferably from about 25 to about 50. The polymers are generally present in the composition in an amount in the range from about 0.2 to about 20% by weight, based on the total weight of the compositions. The salt is used in an amount effective for improving the exchangeability of the polymers. The salt is generally used in an amount of from about 0.02 to about 10% by weight, and more preferably from about 0.05 to about 5% by weight, and in particular, from about 0.1 to about 3% by weight, based on the total weight of the composition.

The total amount of one or more hydrocolloids in some embodiments of the personal care compositions of the present invention is less than about 5% by weight, preferably between about 0.05 and about 3.0% by weight, and more preferably between about 0.1 and about 1.0% by weight, based on the total weight of the preparations.

In some additional embodiments, interface- and/or surface-active agents are included in some personal care compositions of the present invention, including but not limited to cationic emulsifiers (e.g., quaternary surfactants).

Quaternary surfactants that contain at least one N atom which is covalently bonded to 4 alkyl or aryl groups. This leads, irrespective of the pH, to a positive charge. Alkylbetain, alkylamidopropylbetain and alkylamidopropylhydroxysultaine are examples of quaternary surfactants that find use in some embodiments of the present invention.

The cationic surfactants provided in some embodiments of the present invention also include, but are not limited to quaternary ammonium compounds, in particular benzyltrialkylammonium chlorides or bromides (e.g., benzyldimethylstearylammonium chloride), alkyltrialkylammonium salts (e.g., cetyltrimethylammonium chloride or bromide), alkyldimethylhydroxyethylammonium chlorides or bromides, dialkyldimethylammonium chlorides or bromides, alkylamidoethyltrimethylammonium ether sulfates, alkylpyridinium salts (e.g., lauryl- or cetylpyrimidinium chloride), imidazoline derivatives, and compounds with a cationic character, such as amine oxides (e.g., alkyldimethylamine oxides or alkylaminoethyldimethylamine oxides). In some preferred embodiments, cetyltrimethylammonium salts find use in some personal care compositions of the present invention.

In yet additional embodiments, cationic polymers (e.g., JAGUAR® C 162 [hydroxypropyl guar hydroxypropyltrimonium chloride]), modified magnesium aluminum silicates (e.g., quaternium-18-hectorite, which is commercially available (e.g., BENTONE® 38; Rheox), and/or stearalkonium hectorite, which is commercially available (e.g., SOFTISAN® gel; Hills AG) find use in some personal care compositions of the present invention. However, it is not intended that the present invention be limited to any particular cationic polymer.

In some yet further embodiments, some compositions of the present invention comprise oil thickeners in order to improve the tactile properties of emulsions. Preferred oil thickeners include, but are not limited to other solids (e.g., hydrophobic silicon oxides of the AEROSIL® type, which are available from Degussa AG). Examples of advantageous AEROSIL® oxide grades include AEROSIL® OX50, AEROSIL® 130, AEROSIL® 150, AEROSIL® 200, AEROSIL® 300, AEROSIL® 380, AEROSIL® MOX 80, AEROSIL® MOX 170, AEROSIL® COK 84, AEROSIL® R 202, AEROSIL® R 805, AEROSIL® R 812, AEROSIL® R 972, AEROSIL® R 974 and AEROSIL® R976.

In some additional embodiments, some personal care compositions of the present invention comprise at least one "metal soap" (i.e., a salt of a higher fatty acid, with the exception of alkali metal salt), which are function as oil thickeners. Examples of such metal soaps include, but are not limited to aluminum stearate, zinc stearate and/or magnesium stearate.

In some further embodiments, some personal care compositions comprise at least one amphoteric and/or zwitterionic surfactant (e.g., cocamidopropylbetain) and/or moisturizer (e.g. betain). Examples of amphoteric surfactants that find use in such embodiments of the present invention include but are not limited to acyl/dialkylethylenediamine (e.g., sodium acylamphoacetate), disodium acylamphodipropionate, disodium alkylamphodiacetate, sodium acylamphohydroxypropylsulfonate, disodium acylamphodiacetate, sodium acylamphopropionate, N-alkylamino acids, for example aminopropylalkylglutamide, alkylaminopropionic acid, sodium alkylimidodipropionate, and lauroamphocarboxyglycinate.

In some embodiments, the amount of surface- or interface-active substances (one or more compounds) in the preparations is preferably between about 0.001 and about 30% by weight, and more preferably between about 0.05 and about 20% by weight, in most preferably between about 1 and about 10% by weight, based on the total weight of the preparation.

In some yet additional embodiments, the active ingredients (one or more compounds) comprise at least one lipophilic active ingredient. In some embodiments, these lipophilic active ingredients are selected from the group consisting of acetylsalicylic acid, atropine, azulene, hydrocortisone and derivatives thereof (e.g., hydrocortisone-17-valerate), B vitamins, D vitamins, vitamin $B_1$, vitamin $B_{12}$, vitamin $D_1$, retinoid, bisabolol, unsaturated fatty acids (e.g., the essential fatty acids often also referred to as "vitamin F"), γ-linolenic acid, oleic acid, eicosapentenoic acid, docosahexenoic acid and derivatives thereof, chloramphenicol, caffeine, prostaglandins, thymol, camphor, extracts or other products of a vegetable and animal origin (e.g. evening primrose oil, borrage oil or currant seed oil, fish oils, cod-liver oil), and ceramides and ceramide-like compounds, etc. In some embodiments, the active ingredient(s) are refatting substances (e.g., purcellin oil, EUCERIT® and/or NEROCERIT®).

In some yet further embodiments, the active ingredient(s) comprise NO synthesase inhibitors. These embodiments find particular use in treatment and/or prophylaxis of the signs and symptoms associated intrinsic and/or extrinsic skin aging, as well as for the treatment and/or prophylaxis associated with the harmful effects of ultraviolet radiation on the skin. In some preferred embodiments, the NO synthase inhibitor is nitroarginine.

In yet some additional embodiments, the active ingredient(s) is/are catechins, bile esters of catechins, and/or aqueous or organic extracts from plants or sections of plants which have a content of catechins or bile esters of catechins (e.g., the leaves of the Theaceae plant family, in particular of the species Camellia sinensis [green tea]). Their typical ingredients (e.g., polyphenols or catechins, caffeine, vitamins, sugars, minerals, aminoacids, lipids) find particular use in some embodiments of the present invention.

In some embodiments, catechins find use in the present invention. Catechins are a group of compounds which are regarded as hydrogenated flavones or anthocyanidines, and are derivatives of "catechin" (catechol, 3,3',4',5,7-flavanpentol, 2-(3,4-dihydroxyphenyl)chroman-3,5,7-triol). Epicatechin ((2R,3R)-3,3',4',5,7-flavanpentol) is also an active ingredient that finds use in some embodiments of the present invention.

In yet additional embodiments, plant extracts with a content of catechin, in particular extracts of green tea (e.g., extracts from leaves of the plants of the genus Camellia, in particular those used for tea, such as C. sinenis, C. assamica, C. taliensis. and C. irrawadiensis and hybrids of these species with other species, such as C. japonica) find use in some personal care compositions of the present invention.

In some further embodiments, preferred active ingredients include polyphenols and catechins from the group (−)-catechin, (+)-catechin, (−)-catechin gallate, (−)-gallocatechin gallate, (+)-epicatethin, (−)-epicatechin, (−)-epicatechin gallate, (−)-epigallocatechin, and (−)-epigallocatechin gallate.

In some additional embodiments of the compositions of the present invention flavone and its derivatives (also often collectively called "flavones") find used. These compounds have the following basic structure (substitution positions are shown):

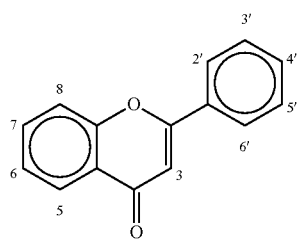

Some of the more important flavones which find use in some personal care compositions of the present invention are provided below. However, it is not intended that the present invention be limited to any particular flavone.

| FLAVONES | | | | | | | | |
|---|---|---|---|---|---|---|---|---|
| | OH Substitution Positions | | | | | | | |
| | 3 | 5 | 7 | 8 | 2' | 3' | 4' | 5' |
| Flavone | − | − | − | − | − | − | − | − |
| Flavonol | + | − | − | − | − | − | − | − |
| Chrysin | − | + | + | − | − | − | − | − |
| Galangin | + | + | + | − | − | − | − | − |
| Apigenin | − | + | + | − | − | − | + | − |
| Fisetin | + | − | + | − | − | + | + | − |
| Luteolin | − | + | + | − | − | + | + | − |

| FLAVONES | | | | | | | | |
|---|---|---|---|---|---|---|---|---|
| | OH Substitution Positions | | | | | | | |
| | 3 | 5 | 7 | 8 | 2' | 3' | 4' | 5' |
| Kaempferol | + | + | + | − | − | − | + | − |
| Quercetin | + | + | + | − | − | + | + | − |
| Morin | + | + | + | − | + | − | + | − |
| Robinetin | + | − | + | − | − | + | + | + |
| Gossypetin | + | + | + | + | − | + | + | − |
| Myricetin | + | + | + | − | − | + | + | + |

In nature, flavones are usually present in glycosylated form.

In some further embodiments, the personal care compositions of the present invention comprise at least one flavonoids having generic structural formula:

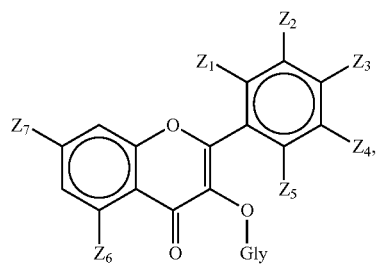

where $Z_1$ to $Z_7$, independently of one another, are chosen from the group consisting of H, OH, alkoxy and hydroxyalkoxy, where the alkoxy and hydroxyalkoxy groups can be branched or unbranched and have 1 to 18 carbon atoms, and where Gly is chosen from the group of mono- and oligoglycoside radicals.

In some alternative embodiments, the personal care compositions of the present invention comprise at least one flavonoids having the generic structural formula:

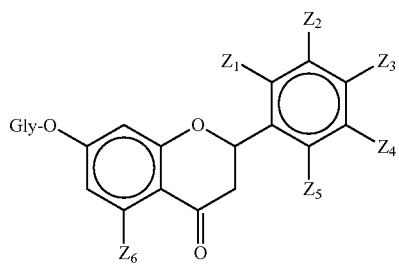

where $Z_1$ to $Z_6$, independently of one another, are chosen from the group consisting of H, OH, alkoxy and hydroxyalkoxy, where the alkoxy and hydroxyalkoxy groups may be branched or unbranched and have 1 to 18 carbon atoms, where Gly is chosen from the group mono and oligoglycoside radicals.

In some preferred embodiments, the composition has the generic structural formula

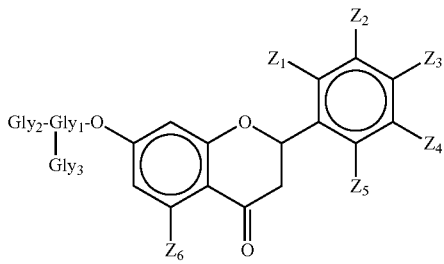

where $Gly_1$, $Gly_2$ and $Gly_3$, independently of one another, are monoglycoside radicals. $Gly_2$ and $Gly_3$ may also, individually or together, represent saturations by hydrogen atoms. In some preferred embodiments, $Gly_1$, $Gly_2$ and $Gly_3$, independently of one another, are selected from the group of hexosyl radicals, in particular the rhamnosyl radicals and glucosyl radicals. However, hexosyl radicals, for example allosyl, altrosyl, galactosyl, gulosyl, idosyl, mannosyl and talosyl, also find use in some embodiments of the present invention. In yet additional embodiments, pentosyl radicals find use in some personal care compositions of the present invention.

In some embodiments, $Z_1$ to $Z_5$ are, independently of one another, advantageously chosen from the group consisting of H, OH, methoxy, ethoxy and 2-hydroxyethoxy, and the flavone glycosides have the structure:

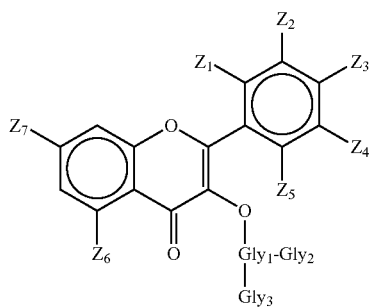

In some embodiments, the flavone glycosides provided in some of the personalcare compositions of the present invention have the following structure:

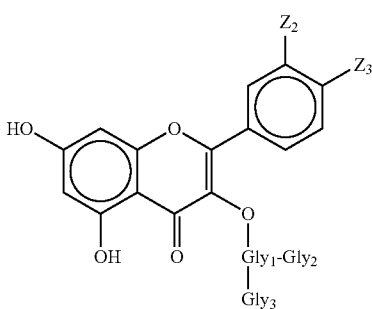

where $Gly_1$, $Gly_2$ and $Gly_3$, independently of one another, are monoglycoside radicals. $Gly_2$ and $Gly_3$ can also, individually or together, represent saturations by hydrogen atoms. In alternative embodiments, $Gly_1$, $Gly_2$ and $Gly_3$, independently of one another, are selected from the group of hexosyl radicals, in particular of rhamnosyl radicals and glucosyl radicals. However, other hexosyl radicals, for example allosyl, altrosyl, galactosyl, gulosyl, idosyl, mannosyl and talosyl, find use in some embodiments of the present invention. In addition, in some embodiments, pentosyl radicals find use in the present invention. In some preferred embodiments, the personal care compositions of the present invention comprise one or more flavone glucoside selected from the group consisting of a-glucosylrutin, a-glucosylmyricetin, a-glucosylisoquercitrin, a-glucosylisoquercetin and a-glucosylquercitrin. In some particularly preferred embodiments, the flavone glucoside is a-glucosylrutin.

In yet some additional embodiments, the personal care compositions of the present invention comprise at least one naringin (e.g., aurantin, naringenin-7-rhamno-glucoside), hesperidin 3',5,7-trihydroxy-4'-methoxyflavanone-7-rutinoside, hesperidoside, hesperetin-7-O-rutinoside), rutin (3,3',4', 5,7-pentahydroxyflavone-3-rutinoside, quercetin-3-rutinoside, sophorin, birutan, rutabion, taurutin, phytomelin, melin), troxerutin (3,5-dihydroxy-3',4',7-tris(2-hydroxyethoxy)flavone-3-(6-O-(6-deoxy-a-L-mannopyranosyl)-b-D-glucopyranoside)), monoxerutin (3,3',4',5-tetrahydroxy-7-(2-hydroxyethoxy)flavone-3-(6-O-(6-deoxy-a-L-mannopyranosyl)-b-D-glucopyranoside)), dihydrorobinetin (3,3',4',5',7-pentahydroxyflavanone), taxifolin (3,3',4',5,7-pentahydroxyflavanone), eriodictyol-7-glucoside (3',4',5,7-tetrahydroxyflavanone-7 glucoside), flavanomarein (3',4',7, 8-tetrahydroxyflavanone-7 glucoside), and/or isoquercetin (3,3',4',5,7-pentahydroxyflavanone-3-(b-D-glucopyranoside). In some yet further embodiments, the active ingredient is selected from the group consisting of ubiquinones and plastoquinones. Ubiquinones are characterized by the structural formula:

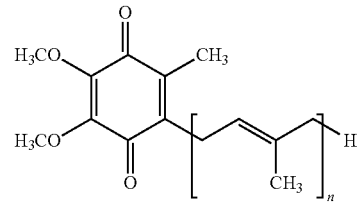

Ubiquinones are the most widespread and the most investigated bioquinones. Ubiquinones are referred to, depending on the number of isoprene units linked in the side chain, as Q-1, Q-2, Q-3 etc., or according to the number of carbon atoms, as U-5, U-10, U-15 etc. They preferably arise with certain chain lengths (e.g. in some microorganisms and yeasts where n=6). In most mammals, including humans, Q10 predominates. Coenzyme Q10 finds particular use in some embodiments of the present invention. Its structural formula is:

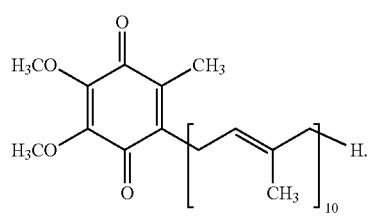

Plastoquinones have the general structural formula:

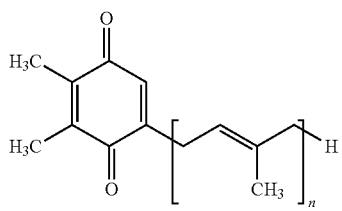

Plastoquinones differ in the number n of isoprene radicals and are referred to accordingly (e.g. PQ-9 [n=9]). In addition, other plastoquinones with varying substituents on the quinone ring exist in some embodiments.

In some still further embodiments, the present invention comprises at least one creatine and/or creatine derivative. Creatine has the following structure:

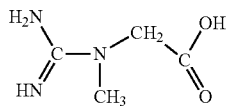

In some preferred embodiments of the personal care compositions of the present invention creatine phosphate, creatine sulfate, creatine acetate, creatine ascorbate, and/or derivatives esterified at the carboxyl group with mono- or polyfunctional alcohols find use.

In some additional embodiments, the personal care compositions of the present invention contain L-carnitine [3-hydroxy-4-(trimethylammonio)butyrobetaine]. Acylcarnitines have the following general structure:

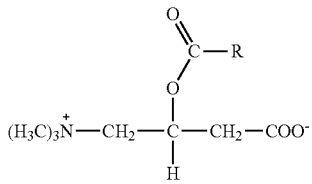

where R is chosen from the group of branched and unbranched alkyl radicals having up to 10 carbon atoms, and find use in some embodiments of the present invention. In some preferred embodiments, propionylcarnitine and/or acetylcarnitine find use. Both enantiomers (D and L form), as well as mixtures and racemates of the D- and L-forms find use in some personal care compositions of the present invention.

In some further embodiments, the active ingredients of the present invention include, but are not limited to sericoside, pyridoxol, vitamin K, biotin, and aroma substances. In addition, it is not intended that the active ingredients present in the personal care compositions of the present invention be limited to any particular constituent and/or mixture(s) of actives. Indeed, it is intended that various actives and mixtures of actives will find use in various embodiments of the present invention. It is also not intended that the concentration(s) of such actives be limited to any particular level. In some embodiments, the concentration is from about 0.001 to about 30% by weight, while in other embodiments it is from about 0.05 to about 20% by weight, and in still further embodiments, it is from about 0.1 to about 10% by weight, based on the total weight of the preparation. It is further contemplated that those of skill in the art will formulate personal care compositions of the present invention with active(s) concentrations that are suitable for the intended use of the compositions.

DETAILED DESCRIPTION OF THE INVENTION

The present invention provides peptides and supported peptides for treating various diseases and conditions. In particularly preferred embodiments, the present invention provides compositions and methods for personal care. In some embodiments, the present invention provides compositions for use in skin and/or hair care, as well as cosmetic compositions. In alternative particularly preferred embodiments, the present invention provides peptides and supported peptides for treating diseases of the skin, such as rosacea. In some particularly preferred embodiments, the supported peptides of the present invention are anti-VEGF peptides. In alternative particularly preferred embodiments, the anti-VEGF peptides are expressed on a scaffold protein. In some most preferred embodiments, the scaffold protein comprises BBI.

In some preferred embodiments, the present invention provides cosmetic and/or pharmaceutical compounds suitable for improving the appearance of skin. The present invention further provides peptides that block binding of a protein. In some preferred embodiments, the protein is VEGF. In some particularly preferred embodiments, the peptide is expressed in a protease-resistant scaffold. In some especially preferred embodiments, the scaffold is a protease inhibitor (e.g., BBI, STI, or Eglin chymotrypsin inhibitor). In some most preferred embodiments, the protease inhibitor is a BBI that has been functionally and/or structurally modified.

Figure 2:
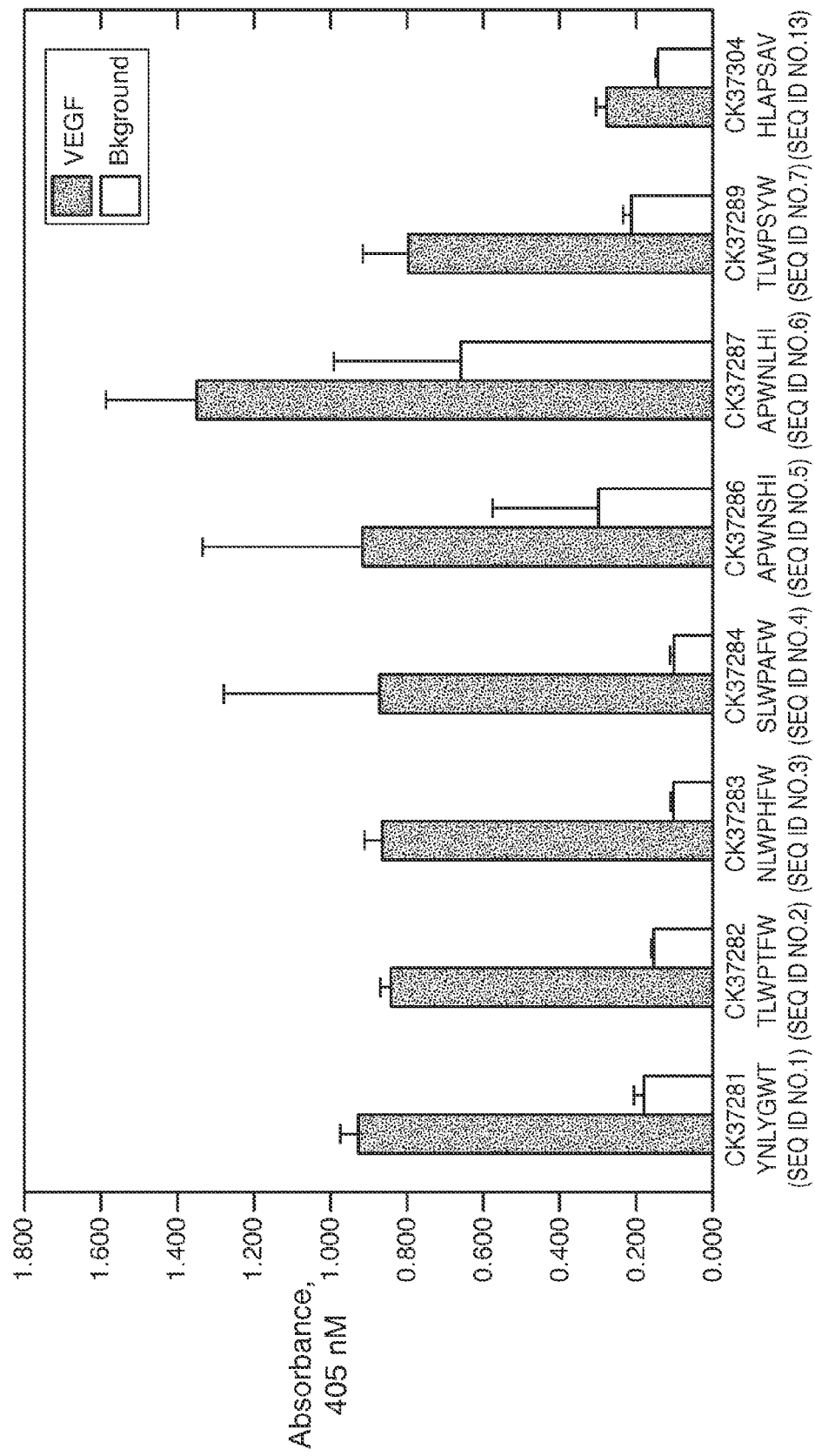
FIG. 2 provides results of a phage ELISA to demonstrate the binding of unique clones to VEGF and not to BSA. Equivalent amounts of phage were evaluated to determine their relative binding affinity to hVEGF$_{165}$. The clone number and randomized sequence (SEQ ID NOS:1-7, and 13) are indicated below each symbol. Target-bound phage were detected with anti-M13-HRP. The HRP was monitored with ABTS substrate at an A$_{405\ nm}$ after 30 minutes (n=3).

As indicated above, two protein protease inhibitors have been isolated from soybeans, the Kunitz-type trypsin inhibitor (soybean trypsin inhibitor, STI) and the Bowman-Birk protease inhibitor (BBI) (See e.g., Birk, Int. J. Pept. Protein Res., 25:113-131 [1985]; and Kennedy, Am. J. Clin. Neutr., 68:1406 S-1412S [1998]). These inhibitors serve as a beginning scaffold for the variant sequences provided herein to produce the protease inhibitor in combination with at least one peptide sequence that has been modified and/or substituted in the sequence (e.g., BBI-AV or STI-AV). In addition to alterations in the scaffold comprising the variant sequences, other desired proteins used herein include the addition of six histidine residues at the C-terminus (See, FIGS. 1 and 2).

Soybean Trypsin Inhibitor (STI)

STI inhibits the proteolytic activity of trypsin by the formation of a stable stoichiometric complex (See e.g., Liu, Chemistry and Nutritional Value of Soybean Components, In: *Soybeans, Chemistry, Technology and Utilization*, pp. 32-35, Aspen Publishers, Inc., Gaithersburg, Md., [1999]). STI consists of 181 amino acid residues with two disulfide bridges and is roughly spherically shaped (See e.g., Song et al., J. Mol. Biol., 275:347-63 [1998]). The trypsin inhibitory loop lies within the first disulfide bridge. The Kunitz-type soybean trypsin inhibitor (STI) has played a key role in the early study of proteinases, having been used as the main substrate in the biochemical and kinetic work that led to the definition of the standard mechanism of action of proteinase inhibitors.

Bowman-Birk Inhibitor (BBI)

Bowman-Birk inhibitor proteins are a kinetically and structurally well-characterized family of small proteins (60-90 residues) isolated from leguminous seeds, as well as other plants, including various grasses. They typically have a symmetrical structure of two tricyclic domains each containing an independent binding loop, although some have one domain and some have more than two domains. The major ~8 kDa Bowman-Birk inhibitor isolated from soybeans (BBI) has two separate reactive site loops, loop I inhibits proteases having trypsin-like specificity and loop II inhibits proteases with chymotrypsin-like specificity (See e.g., Chen et al., J. Biol. Chem., 267:1990-1994 [1992]; Werner and Wemmer, Biochem., 31:999-1010 [1992]; Lin et al., Eur. J. Biochem., 212:549-555 [1993]; Voss et al., Eur. J. Biochem., 242:122-131 [1996]; and Billings et al., Pro. Natl. Acad. Sci., 89:3120-3124 [1992]). These binding regions each contain a "canonical loop" structure, which is a motif found in a variety of serine proteinase inhibitors (Bode and Huber, Eur. J. Biochem., 204:433-451 [1992]). STI and BBI are found only in the soybean seed, and not in any other part of the plant (See e.g., Birk, Int. J. Pept. Protein Res., 25:113-131 [1985]).

Although numerous isoforms of BBI have been characterized, SEQ ID NO:47 shows the amino acid sequence of the BBI backbone used in some experiments described herein comprising approximately 71 amino acid residues (See Example 16).

In soybeans, BBI is produced as a pro-protein with an N-terminal pro-peptide that is 19 amino acids in length. Thus, in some embodiments, BBI is produced with all or at least a portion of the propeptide. In some embodiments, BBI is truncated, with as many as 10 amino acid residues being removed from either the N- or C-terminal. For example, upon seed desiccation, some BBI molecules have the C-terminal 9 or 10 amino acid residues removed. Thus, proteolysis is generally highly tolerated prior to the initial disulfide and just after the terminal disulfide bond, the consequences of which are usually not detrimental to the binding to target protein. However, it will be appreciated that any one of the isoforms or truncated forms find use in various embodiments of the present invention.

Protease Inhibitor Variants

As indicated above, the STI and BBI protease inhibitors have binding loops that inhibit proteases. The present invention provides protease inhibitor variants with alterations in one or more reactive sites (e.g., Loop I and/or Loop II of BBI). In some preferred embodiments, the loops are replaced with sequences that interact with a target protein.

For example, in some embodiments, the loops are replaced with sequences derived from VEGF binding proteins, inhibitors of the complement pathway such as C2, C3, C4 or C5 inhibitors, Compstatin, cytokines, other proteins of interest, etc. Indeed, it is not intended that the present invention be limited to any particular sequence substituted into either of these loops, as any suitable sequence finds use in the present invention.

In some embodiments, variant sequences are selected by various methods known in the art, including but not limited to phage display and other suitable screening methods. For example, a random peptide gene library is fused with phage PIII gene so the peptide library will be displayed on the surface of the phage. Subsequently, the phage display library is exposed to the target protein and washed with buffer to remove non-specific binding (this process is sometimes referred to as panning). Finally, the binding phage and PCR the DNA sequence for the peptide encoded are isolated.

In most embodiments, one of the loops is replaced with a variant sequence (i.e., peptides; often 3 to 14 amino acids in length, with 5 to 10 amino acids being preferred). Longer sequences find use in the present invention, as long as they provide the binding and/or inhibition desired. In addition, peptides suitable for use as replacements of the binding loop(s) preferably adopt a functional conformation when contained within a constrained loop (i.e., a loop formed by the presence of a disulfide bond between two cysteine residues). In some specific embodiments, the peptides are between 7 and 9 amino acids in length. These replacement sequences also provide protease inhibition or binding to the targeted proteins. In some embodiments, it is advantages to alter a single amino acid.

Fusion Proteins

In preferred embodiments, each protease inhibitor or variant thereof is expressed as a fusion protein by the host bacterial cell. Although cleavage of the fusion polypeptide to release the desired protein will often be useful, it is not necessary. Protease inhibitors and variants thereof expressed and secreted as fusion proteins surprisingly retain their function.

The above-defined DNA sequences encoding the corresponding amino acid sequences are combined to form a "fusion DNA sequence." Such fusion DNA sequences are assembled in proper reading frame from the 5' terminus to 3' terminus in the order of first, second, third and fourth DNA sequences. As so assembled, the DNA sequence encodes a "fusion polypeptide" encoding from its amino-terminus a signal peptide functional as a secretory sequence in a bacterial species, a secreted polypeptide or portion thereof normally secreted from a bacterial species, a cleavable linker peptide and a desired polypeptide (e.g., a protease inhibitor and variants thereof). Various methods are known to those in the art for the production of fusion proteins (See e.g., U.S. Pat. Nos. 5,411,873, 5,429,950, and 5,679,543, all of which are incorporated herein by reference). Thus, it is intended that any suitable method will find use in the present invention.

Expression of Recombinant Protease Inhibitors

To the extent that the present invention depends on the production of fusion proteins, it relies on routine techniques in the field of recombinant genetics. Basic texts disclosing the general methods of use in this invention include Sambrook et al., *Molecular Cloning, A Laboratory Manual* ((2nd ed.) [1989]); Kriegler, *Gene Transfer and Expression: A Laboratory Manual* (1990); and Ausubel et al., (eds.), *Current Protocols in Molecular Biology* (1994).

The present invention provides bacterial host cells which have been transduced, transformed or transfected with an expression vector comprising a protease inhibitor-encoding nucleic acid sequence. The culture conditions, such as temperature, pH and the like, are those previously used for the parental host cell prior to transduction, transformation or transfection are apparent to those skilled in the art.

Basically, a nucleotide sequence encoding a fusion protein is operably linked to a promoter sequence functional in the host cell. This promoter-gene unit is then typically cloned into intermediate vectors before transformation into the host cells for replication and/or expression. These intermediate vectors are typically prokaryotic vectors (e.g., plasmids, or shuttle vectors). However, it is not intended that the present invention be limited to the use of intermediate vectors, as this step is omitted in some preferred embodiments.

In one approach, a bacterial culture is transformed with an expression vector having a promoter or biologically active promoter fragment or one or more (e.g., a series) of enhancers which functions in the host cell, operably linked to a nucleic acid sequence encoding a protease inhibitor, such that the a protease is expressed in the cell. In some preferred embodiments, the DNA sequences encode a protease inhibitor or variant thereof. In another preferred embodiment, the promoter is a regulatable one.

Nucleic Acid Constructs/Expression Vectors.

Natural or synthetic polynucleotide fragments encoding a protease inhibitor (i.e., "PI-encoding nucleic acid sequences") may be incorporated into heterologous nucleic acid constructs or vectors, capable of introduction into, and replication in, a bacterial cell. The vectors and methods disclosed herein are suitable for use in various host cells for the expression of protease inhibitors and variants thereof. Any vector may be used as long as it is replicable and viable in the cells into which it is introduced. Large numbers of suitable vectors and promoters are known to those of skill in the art, and are commercially available. Appropriate cloning and expression vectors are also described in various references known to those in the art (See e.g., Sambrook et al., supra and Ausubel et al., supra, expressly incorporated by reference herein). The appropriate DNA sequence is inserted into a plasmid or vector (collectively referred to herein as "vectors") by any suitable method. In general, the DNA sequence is inserted into an appropriate restriction endonuclease site(s) by standard procedures known to those in the art.

Appropriate vectors are typically equipped with a selectable marker-encoding nucleic acid sequence, insertion sites, and suitable control elements, such as termination sequences. In some embodiments, the vectors comprise regulatory sequences, including, for example, control elements (i.e., promoter and terminator elements or 5' and/or 3' untranslated regions), effective for expression of the coding sequence in host cells (and/or in a vector or host cell environment in which a modified soluble protein coding sequence is not normally expressed), operably linked to the coding sequence. Large numbers of suitable vectors and promoters are known to those of skill in the art, many of which are commercially available and known to those in the art.

Exemplary promoters include both constitutive promoters and inducible promoters. Such promoters are well known to those of skill in the art. Those skilled in the art are also aware that a natural promoter can be modified by replacement, substitution, addition or elimination of one or more nucleotides without changing its function. The practice of the present invention encompasses and is not constrained by such alterations to the promoter. The choice of promoter used in the genetic construct is within the knowledge of one skilled in the art.

The choice of the proper selectable marker will depend on the host cell. Appropriate markers for different bacterial hosts are well known in the art. Typical selectable marker genes encode proteins that (a) confer resistance to antibiotics or other toxins (e.g., ampicillin, methotrexate, tetracycline, neomycin mycophenolic acid, puromycin, zeomycin, or hygromycin; or (b) complement an auxotrophic mutation or a naturally occurring nutritional deficiency in the host strain.

In some embodiments, a selected PI coding sequence is inserted into a suitable vector according to well-known recombinant techniques and used to transform a cell line capable of PI expression. Due to the inherent degeneracy of the genetic code, other nucleic acid sequences which encode substantially the same or a functionally equivalent amino acid sequence may be used to clone and express a specific protease inhibitor, as further detailed above. Therefore it is appreciated that such substitutions in the coding region fall within the sequence variants covered by the present invention. Any and all of these sequence variants can be utilized in the same way as described herein for a parent PI-encoding nucleic acid sequence. Those skilled in the art recognize that differing PIs will be encoded by differing nucleic acid sequences.

In some embodiments, once the desired form of a protease inhibitor nucleic acid sequence, homologue, variant or fragment thereof, is obtained, it is modified by any number of ways. Where the sequence involves non-coding flanking regions, the flanking regions may be subjected to resection, mutagenesis, etc. Thus, transitions, transversions, deletions, and insertions may be performed on the naturally occurring sequence.

In some preferred embodiments, heterologous nucleic acid constructs include the coding sequence for at least one protease inhibitor, or variant(s), fragment(s) or splice variant(s) thereof: (i) in isolation; (ii) in combination with additional coding sequences; such as fusion protein or signal peptide coding sequences, where the PI coding sequence is the dominant coding sequence; (iii) in combination with non-coding sequences, such as control elements, such as promoter and terminator elements or 5' and/or 3' untranslated regions, effective for expression of the coding sequence in a suitable host; and/or (iv) in a vector or host environment in which the PI coding sequence is a heterologous gene.

In some embodiments, heterologous nucleic acid containing the appropriate nucleic acid coding sequence, together with appropriate promoter and control sequences, is employed to introduced into bacterial host cells to permit the cells to express at least one protease inhibitor or variant thereof.

In some embodiments of the present invention, a heterologous nucleic acid construct is employed to transfer a PI-encoding nucleic acid sequence into a cell in vitro. In some preferred embodiments, the host cells stably integrate the nucleic acid sequences of the present invention. Thus, any suitable method for effectively generating stable transformants finds use in the present invention.

In additional embodiments of the present invention, the first and second expression cassettes are present on a single vector, while in other embodiments these cassettes are present on separate vectors.

In some preferred embodiments, in addition to a promoter sequence, the expression cassette also contains a transcription termination region downstream of the structural gene to provide for efficient termination. In some embodiments, the termination region is obtained from the same gene as the promoter sequence, while in other embodiments it is obtained from another gene. The selection of suitable transcription termination signals is well-known to those of skill in the art.

In addition, it is contemplated that any suitable expression vector will find use in the present invention. Indeed, it is contemplated that various conventional vectors used for expression in eukaryotic or prokaryotic cells will be suitable and find use with the present invention. Standard bacterial expression vectors include bacteriophages λ and M13, as well as plasmids such as pBR322 based plasmids, pSKF, pET23D, and fusion expression systems such as MBP, GST, and LacZ. In further embodiments, epitope tags are added to recombinant proteins, in order to provide convenient methods of isolation (e.g., c-myc).

Additional elements typically included in expression vectors are replicons, a gene encoding antibiotic resistance to permit selection of bacteria that harbor recombinant plasmids, and unique restriction sites in nonessential regions of the plasmid to allow insertion of heterologous sequences. The particular antibiotic resistance gene chosen is not critical, any of the many resistance genes known in the art are suitable.

Introduction of a Protease Inhibitor-Encoding Nucleic Acid Sequence into Host Cells.

In some preferred embodiments, the methods of the present invention provide host cells that contain a stably integrated sequence of interest (i.e., PI-encoding nucleic acid). However, in alternative embodiments, the methods of the present invention provide for maintenance of a self-replicating extra-chromosomal transformation vector.

The invention further provides cells and cell compositions which have been genetically modified to comprise an exogenously provided PI-encoding nucleic acid sequence. In some embodiments, a parental host cell is genetically modified by an expression vector. In some embodiments, the vector is a plasmid, while in other embodiments the vector is a viral particle, phage, naked DNA, etc. Thus, it is not intended that the form of the vector be limited to any particular type of vector, as various vectors will find use in the present invention.

Various methods may be employed for delivering an expression vector into cells in vitro. Methods of introducing nucleic acids into cells for expression of heterologous nucleic acid sequences are also known to the ordinarily skilled artisan, including, but not limited to electroporation; protoplast fusion with intact cells; transduction; high velocity bombardment with DNA-coated microprojectiles; infection with modified viral (e.g., phage) nucleic acids; chemically-mediated transformation, competence, etc. In addition, in some embodiments, heterologous nucleic acid constructs comprising a PI-encoding nucleic acid sequence are transcribed in vitro, and the resulting RNA introduced into the host cell by any of the suitable methods known in the art.

Following introduction of a heterologous nucleic acid construct comprising the coding sequence for a protease inhibitor, the genetically modified cells are cultured in conventional nutrient media modified as appropriate for activating promoters, selecting transformants, and/or amplifying expression of a PI-encoding nucleic acid sequence. The culture conditions, such as temperature, pH and the like, are those previously used for the host cell selected for expression, and are apparent to those skilled in the art.

The progeny of cells into which such heterologous nucleic acid constructs have been introduced are generally considered to comprise the PI-encoding nucleic acid sequence found in the heterologous nucleic acid construct.

Bacterial Hosts and Expression

Appropriate host cells include any suitable bacterial species. In some embodiments, the bacterial hosts serve both as the expression hosts and the source of the first and second nucleic acids. Using the present inventive methods and host cells, surprising levels of expression have been obtained. The system utilized herein has achieved levels of expression and secretion of greater than 0.5 g/l of protease inhibitor.

After the expression vector is introduced into the host cells, the transfected host cells are cultured under conditions favoring expression of gene encoding the desired protein. Large batches of transformed cells can be cultured as described above. Finally, product is recovered from the culture using techniques known in the art.

Accessory proteins such as thiol-disulfide oxidoreductases or chaperones find use in some embodiments, as they may be beneficial to help fold the secretory protein into its active conformation. Thiol-disulfide oxidoreductases and protein disulfide isomerases catalyze the formation of the correct disulfide bonds in the protein. Overexpression of the bdbDC operon in *B. subtilis* has been shown to be beneficial for the production of a protein with disulfide bonds (See e.g., Meima et al., J. Biol. Chem., 277:6994-7001, [2002]). Chaperones help the secretory protein to fold by binding to exposed hydrophobic regions in the unfolded states and preventing unfavorable interactions and prolyl-peptidyl cis-trans isomerases assist in formation of the proper conformation of the peptide chain adjacent to proline residues.

In some embodiments of the present invention, the host cells are transformed with an expression vector encoding at least one thiol-disulfide oxidoreductase or chaperone. It is not intended that the present invention be limited to any particular thiol-disulfide oxidoreductase or chaperone, as any suitable thiol-disulfide oxidoreductase or chaperone known to those skilled in the art will find use in the present invention.

In some embodiments of the present invention, the fraction of properly folded secretory protein is increased by the addition of chemicals to the growth medium that reduce/oxidize disulfide bonds, and/or alter the general redox potential, and/or chemicals that alter solvent properties thus affecting protein conformation and aggregation. In particularly preferred embodiments, a reagent that reduces disulfide bonds, such as 2-mercaptoethanol, is preferred to increase the fraction of correctly folded protein. However, in other embodiments and depending on the medium used, other disulfide reducing or oxidizing agents (e.g., DTT, TCEP, reduced and oxidized glutathione, cysteine, cystine, cysteamine, thioglycolate, $S_2O_3^{2-}$, $S_2O_4^{2-}$, $S_2O_5^{2-}$, $SO_3^{2-}$, $S_2O_7^{2-}$, Cu+, etc.), either used alone or in combination, find use in the present invention. It is contemplated that other adjuvants that alter solvent properties, (e.g., urea, DMSO, TWEEN®-80, etc.), either added to the growth medium alone or preferably in combination with disulfide reducing/oxidizing agents, such as βME, will also increase the fraction of correctly folded secretory protein and find use in various embodiments of the present invention. In some preferred embodiments, the βME is used at concentrations ranging from 0.5 to 4 mM, while in other embodiments, the concentrations range from 0.1 mM to 10 mM. Indeed, those of skill in the art know how to select the best growth medium and growth conditions to optimize the effects of the added thiol reducing/oxidizing agents and/or other adjuvants, as well as the concentration of thio reducing/oxidizing agents and/or other adjuvants to use. It is not intended that the present invention be limited to any particular disulfide reducing/oxidizing agent or adjuvant, as any suitable reagents known to those skilled in the art find use in the present invention.

Fermentation Parameters

The present invention relies on fermentation procedures for culturing bacterial species. Fermentation procedures for production of heterologous proteins by bacterial species are well known in the art. Culturing is accomplished in a growth medium comprising an aqueous mineral salts medium, organic growth factors, the carbon and energy source material, molecular oxygen (for aerobic and facultative bacteria), and, of course, a starting inoculum of one or more particular microorganism species to be employed.

In addition to the carbon and energy source, oxygen, assimilable nitrogen, and an inoculum of the microorganism, it is necessary to supply suitable amounts in proper proportions of mineral nutrients to assure proper microorganism growth, maximize the assimilation of the carbon and energy source by the cells in the microbial conversion process, and achieve maximum cellular yields with maximum cell density in the fermentation medium.

Various culture media find use in the present invention, as known to those of skill in the art. However, standard bacterial culture media find use in the present invention. In some preferred media formulations, the media include, in addition to nitrogen, suitable amounts of phosphorus, magnesium, calcium, potassium, sulfur, and sodium, in suitable soluble assimilable ionic and combined forms, and also present preferably should be certain trace elements such as copper, manganese, molybdenum, zinc, iron, boron, and iodine, and others, again in suitable soluble assimilable form, all as known in the art.

In some embodiments, the fermentation reaction involves an aerobic process in which the molecular oxygen needed is supplied by a molecular oxygen-containing gas such as air, oxygen-enriched air, or even substantially pure molecular oxygen, provided to maintain the contents of the fermentation vessel with a suitable oxygen partial pressure effective in assisting the microorganism species to grow in a thriving fashion. In effect, by using an oxygenated hydrocarbon substrate, the oxygen requirement for growth of the microorganism is reduced. Nevertheless, molecular oxygen must be supplied for growth of aerobic and to a lesser extent, facultative organisms.

Although the aeration rate can vary over a considerable range, aeration generally is conducted at a rate which is in the range of about 0.5 to 10, preferably about 0.5 to 7, volumes (at the pressure employed and at 25° C.) of oxygen-containing gas per liquid volume in the fermentor per minute. This amount is based on air of normal oxygen content being supplied to the reactor, and in terms of pure oxygen the respective ranges would be about 0.1 to 1.7, or preferably about 0.1 to 1.3, volumes (at the pressure employed and at 25° C.) of oxygen per liquid volume in the fermentor per minute.

The pressure employed for the microbial conversion process can range widely. Pressures generally are within the range of about 0 to 50 psig, presently preferably about 0 to 30 psig, more preferably at least slightly over atmospheric pressure, as a balance of equipment and operating cost versus oxygen solubility achieved. Greater than atmospheric pressures are advantageous in that such pressures do tend to increase a dissolved oxygen concentration in the aqueous ferment, which in turn can help increase cellular growth rates. At the same time, this is balanced by the fact that high atmospheric pressures do increase equipment and operating costs.

The fermentation temperature can vary somewhat, but for most bacterial species used in the present invention, the temperature generally will be within the range of about 20° C. to 40° C., generally preferably in the range of about 28° C. to 37° C., depending on the strain of microorganism chosen, as known to those skilled in the art.

The microorganisms also require a source of assimilable nitrogen. The source of assimilable nitrogen can be any nitrogen-containing compound or compounds capable of releasing nitrogen in a form suitable for metabolic utilization by the microorganism. While a variety of organic nitrogen source compounds, such as protein hydrolysates, can be employed, usually cheap nitrogen-containing compounds such as ammonia, ammonium hydroxide, urea, and various ammonium salts such as ammonium phosphate, ammonium sulfate, ammonium pyrophosphate, ammonium chloride, or various other ammonium compounds can be utilized. Ammonia gas itself is convenient for large scale operations, and can be employed by bubbling through the aqueous ferment (fermentation medium) in suitable amounts. At the same time, such ammonia can also be employed to assist in pH control.

The pH range in the aqueous microbial ferment (fermentation admixture) should be in the exemplary range of about 2.0 to 8.0. However, pH range optima for certain microorganisms are dependent on the media employed to some extent, as well as the particular microorganism, and thus change somewhat with change in media as known to those skilled in the art.

While the average retention time of the fermentation admixture in the fermentor can vary considerably, depending in part on the fermentation temperature and culture employed, as known in the art.

In some embodiments, the fermentation is preferably conducted in such a manner that the carbon-containing substrate can be controlled as a limiting factor, thereby providing good conversion of the carbon-containing substrate to cells and avoiding contamination of the cells with a substantial amount of unconverted substrate. The latter is not a problem with water-soluble substrates, since any remaining traces are readily removed. It may be a problem, however, in the case of non-water-soluble substrates, and require added product-treatment steps such as suitable washing steps. The time needed to reach this limiting substrate level is not critical and may vary with the particular microorganism and fermentation process being conducted. However, it is well known in the art how to determine the carbon source concentration in the fermentation medium and whether or not the desired level of carbon source has been achieved.

Although in some embodiments, the fermentation is conducted as a batch or continuous operation, fed batch operation is generally preferred for ease of control, production of uniform quantities of products, and most economical uses of all equipment.

If desired, part or all of the carbon and energy source material and/or part of the assimilable nitrogen source such as ammonia can be added to the aqueous mineral medium prior to feeding the aqueous mineral medium into the fermentor. Indeed, each of the streams introduced into the reactor preferably is controlled at a predetermined rate, or in response to a need determinable by monitoring such as concentration of the carbon and energy substrate, pH, dissolved oxygen, oxygen or carbon dioxide in the off-gases from the fermentor, cell density measurable by light transmittancy, or the like. The feed rates of the various materials can be varied so as to obtain as rapid a cell growth rate as possible, consistent with efficient utilization of the carbon and energy source, to obtain as high a yield of microorganism cells relative to substrate charge as possible, but more importantly to obtain the highest production of the desired protein per unit volume.

In either a batch, or the preferred fed batch operation, all equipment, reactor, or fermentation means, vessel or container, piping, attendant circulating or cooling devices, and the like, are initially sterilized, usually by employing steam such as at about 121° C. for at least about 15 minutes. The sterilized reactor then is inoculated with a culture of the selected microorganism in the presence of all the required nutrients, including oxygen, and the carbon-containing substrate. The type of fermentor employed is not critical, though in some embodiments, the 15 L Biolafitte (Saint-Germain-en-Laye, France) is preferred.

Protein Separations

In some particularly preferred embodiments, once the desired protein is expressed, the secreted protein is recovered. The present invention provides methods of separating a desired protein from its fusion analog. It is specifically contemplated that the methods described herein will find use in the separation of proteinase inhibitor and variants from the fusion analog.

The collection and purification of the desired protein from the fermentation broth can also be achieved using procedures known to those of skill in the art. The fermentation broth will generally contain cellular debris, including cells, various suspended solids and other biomass contaminants, as well as the desired protein product, which are preferably removed from the fermentation broth by means known in the art. Suitable processes for such removal include conventional solid-liquid separation techniques (e.g., centrifugation, filtration, dialysis, microfiltration, rotary vacuum filtration, or other known processes), to produce a cell-free filtrate. In some embodiments, it is preferable to further concentrate the fermentation broth or the cell-free filtrate prior to the purification and/or crystallization process using techniques such as ultrafiltration, evaporation and/or precipitation.

Precipitating the proteinaceous components of the supernatant or filtrate may be accomplished by means of a salt (e.g., ammonium sulfate) or low pH (typically less than 3), followed by purification by a variety of chromatographic procedures (e.g., ion exchange chromatography, affinity chromatography, hydrophobic interaction chromatography, hydrophobic charge induction chromatography etc.) or similar art recognized procedures. It is not intended that the present invention be limited to any particular separation method, as it is contemplated that any method will find use in the present invention.

In certain preferred embodiments, when the expressed desired polypeptide is secreted from the bacterial cells, the polypeptide is purified from the growth media. In preferred embodiments, the expression host cells are removed from the media before purification of the polypeptide (e.g. by centrifugation).

When the expressed recombinant desired polypeptide is not secreted from the host cell, the host cell is preferably disrupted and the polypeptide released into an aqueous "extract" which is the first stage of purification. Preferably, the expression host cells are collected from the media before the cell disruption (e.g. by centrifugation). The cell disruption may be performed by using any suitable means known in the art, such as by lysozyme or beta-glucanase digestion or by forcing the cells through high pressure (See e.g., Scobes, *Protein Purification*, Second edition, Springer-Verlag)

In some embodiments, the addition of six histidine residues (i.e., a "His Tag") to the C-terminus is used as an aid in the purification of the desired protein and its fusion analog. Use of the His tags as a purification aid is well known in the art (See e.g., Hengen, TIBS 20:285-286 [1995]). The 6×histagged proteins are easily purified using Immobilized Metal ion Affinity Chromatography (IMAC), as known to those skilled in the art.

Purity

For some applications, it is of great importance that the protease inhibitors produced using the present invention be very highly pure (e.g., having a purity of more than 99%). This is particularly true whenever the desired protein is to be used as a therapeutic, but is also necessary for other applications. The methods described herein provide a way of producing substantially pure desired proteins. The desired proteins described herein are useful in pharmaceutical and personal care compositions. However, it is contemplated that proteins of varying purity levels will be produced using the methods of the present invention and it is not intended that the proteins produced using the present invention be limited to any particular level of purity.

Activation of BBI During Purification

In some embodiments of the present invention, after growth during the purification process, the activity of the protein is increased by the addition of chemicals that reduce/oxidize disulfide bonds and/or alter the general redox potential, and/or chemicals that alter solvent properties thus affecting protein conformation and aggregation. In some particularly preferred embodiments, addition of a reagent that reduces disulfide bonds, such as 2-mercaptoethanol, is used to increase activity of the protein. However, as those skilled in the art appreciate, depending purity and buffer composition, other disulfide reducing or oxidizing agents (e.g., DTT, TCEP, reduced and oxidized glutathione, cysteine, cystine, cysteamine, thioglycolate, $S_2O_3^{2-}$, $S_2O_4^{2-}$, $S_2O_5^{2-}$, $SO_3^{2-}$, $S_2O_7^{2-}$, Cu+, protein disulfide isomerases, protein thiol-disulfide oxidoreductases, etc.), either used alone or in combination, find use in the present invention. Other adjuvants that alter solvent properties, (e.g. ethanolamine, DMSO, TWEEN®-80, arginine, urea, etc.), either added alone or preferably in combination with disulfide reducing/oxidizing agents, such as βME, during the purification process also find use in the present invention by increasing the activity of the protein. In certain preferred embodiments, partially purified protein is diluted in buffer (in some particularly preferred embodiments, a zwitterionic buffer with TWEEN®-80 at basic pH) and activated with bME and a disulfide oxidizing agent (in alternative preferred embodiments, oxidized glutathione or sodium sulfite).

In addition, it is contemplated that conditions will be screened in order to determine the optimal activation of the protein, if desired. For example, various βME concentrations (0.1-10 mM), oxidizing agent concentrations (0 to 1/20 to 20 times the βME concentration) pH (7.5-9.5), temperatures (15-40° C.), dilutions (1-20 fold), incubation times (12-72 h), aeration (incubations under inert gas to vigorous mixing under oxygen containing gases), buffer types (Tris, CHES, CAPS, Tricine, TAPS, other zwitterionic buffers, etc.), buffer concentrations (0.1-1 M), and the addition of various adjuvants known to alter solvent properties thereby affecting protein conformation and aggregation (e.g., ethanolamine, DMSO, TWEEN®-80, arginine, urea, etc.) are tested in order to determine the optimum conditions for the expression system used. It is not intended that the present invention be limited to any particular disulfide reducing/oxidizing agent, dilution, temperature, pH, buffer type or composition, or adjuvant, as any suitable reagents known to those skilled in the art find use in the present invention.

Personal Care Compositions

In particularly preferred embodiments, the present invention provides cosmetic and/or pharmaceutical compounds for improving the appearance of skin comprising at least one polypeptide or a peptide. In some preferred embodiments, the polypeptide or peptide binds to VEGF. In alternative embodiments, the binding of the polypeptide or peptide to VEGF blocks the downstream activity of VEGF. In some embodiments, the compounds comprise at least one peptide, while in other embodiments, the compounds comprise at least one polypeptide. In some preferred embodiments, the peptide comprises an amino acid sequence selected from the group consisting of SEQ ID NOS:1-7, 16, and 17. In additional preferred embodiments, the peptide has a conserved binding sequence, the sequence being XXLWPXWC (SEQ ID NO:15). In some preferred embodiments, the peptide comprises an amino acid sequence selected from the group consisting of SEQ ID NOS:22-24. In alternative preferred embodiments, the compounds have a sequence, the sequence being at least 70%, preferably 80%, more preferably 90%, and most preferably 95% homologous to the sequences set forth herein. In some preferred embodiments, the polypeptide has a molecular weight that is preferably between 500 Daltons and 30,000 Daltons, more preferably between 1000 Daltons and 10,000 Daltons, and most preferably from 1500 Daltons to 8,000 Daltons.

In some preferred embodiments, the compounds find use in the improvement of skin in an organism (i.e., subject) having a skin disorder. In some preferred embodiments, the skin disorder is an angiogenic skin disorder. In additional preferred embodiments, the skin disorder is at least one selected from the group consisting of psoriasis, venous ulcers, acne, rosacea, warts, eczema, hemangiomas and lymphangiogenesis, etc. In some particularly preferred embodiments, the skin disorder is rosacea.

It is not intended that the present invention be limited to any particular skin treatment or condition. For example, skin coloring has been of concern to human beings for many years. In particular, there is a desire to remove the hyperpigmentation associated with age spots, freckles, and other areas of darkening skin due to age or other factors. A uniformly colored complexion (i.e., without areas of redness, darkness or white) is preferred by many individuals. In addition, in some areas, whitening of the skin is a desired effect, while in others tanned skin is preferred. Various compounds have been used to achieve depigmentation, including kojic acid, hydroxyquinone, and retinoids. Much research has been devoted to the production of tanned skin without the use of radiation in order to avoid photodamage. Compounds that have found use in tanning skin without sun exposure include dihydroxyacetone and similar chemicals. However, the results obtained with these products are usually not optimal, as even and precise application is required in order to achieve the desired result. In addition, many of these compounds are skin irritants.

The chemical and enzymatic basis of melanogenesis is well known. Melanocytes migrate from the embryonal neural crest into the skin to produce the secretory granules known as melanosomes, which produce melanin via melanogenesis. The melanin produced by these cells is then distributed to keratinocytes via melanocyte dendrites. The key enzyme in melanogenesis is tyrosinase, which initiates a cascade of reactions which convert tyrosine to melanin, which is a polymer. Two tyrosinase-related proteins (TRP's) are known, which share about 40% homology with tyrosinase. These proteins (TRP-1 and TRP-2) have catalytic activities as well as regulatory roles in melanogenesis. TRP-1 is reported to be the most abundant glycoprotein in melanocytes.

Although the chemical and enzymatic basis of melanogenesis is well-documented, its regulation at the cellular level is only partially understood. Tyrosinase and the TRP's share structural and biological properties with the lysosomal-associated membrane protein (LAMP) gene family. Thus, it has been contemplated that their targeting to the melanosomal membrane might induce their activation. It is also contemplated that phosphorylation/dephosphorylation reaction occurring at the cytoplasmic tails of these proteins could be involved in the regulation of melanogenesis. The beta isoform of the Protein Kinase C (PKC) family has been shown to regulate human melanogenesis through tyrosinase activation. Gene expression of tyrosinase, TRP-1 and TRP-2 is coordinated. In addition, all three enzymes are expressed in human epidermis.

The Protease-activated receptor-2 (PAR-2) is a seven transmembrane G-protein-coupled receptor, that is related to, but distinct from the thrombin receptors (TR also named PAR-1, and PAR-3) in its sequence. Both receptors are activated proteolytically by an arginine-serine cleavage at the extracellular domain. The newly created N-termini then activate these receptors as tethered ligands. Both receptors may be activated by trypsin, but only the TRs are activated by thrombin. In addition, only PAR-2 is activated by mast cell tryptase. Both receptors may also be activated by the peptides that correspond to their new N-termini, independent of receptor cleavage. In addition, a peptide with the sequence SLIGRL (SEQ ID NO:32), known to be a mouse PAR-2 activating peptide, is equipotent in the activation of the human receptor. Although the TR functions are well documented, the biology of the PAR-2 system has not yet been fully identified. However, a role for PAR-2 activation in the inhibition of keratinocyte growth and differentiation has been recently described (Derian et al., Cell Growth Different., 8:743-749 [1997]).

In other preferred embodiments, the present invention provides cosmetic and/or pharmaceutical compounds for improving the appearance of skin. In these preferred embodiments, the compounds comprise at least one peptide or polypeptide within at least one scaffold, the peptide or polypeptide being expressed in the scaffold. In some particularly preferred embodiments, the at least one peptide or polypeptide is a loop. In other particularly preferred embodiments, the loop is closed by a disulfide bond. In some preferred embodiments, the polypeptide or peptide binds to VEGF. In alternative embodiments, the binding of the polypeptide or peptide to VEGF blocks the downstream activity of VEGF. In some particularly preferred embodiments, the peptide is expressed in a protease-resistant scaffold. In some especially preferred embodiments, the scaffold comprises a protease inhibitor (e.g., BBI, STI, or Eglin chymotrypsin inhibitor). In some most preferred embodiments, the protease inhibitor is BBI.

In some preferred embodiments, the compounds further comprise at least one peptide. Preferably, the peptide comprises an amino acid sequence selected from the group consisting of SEQ ID NOS: 1-7, 16, and 17. In some alternative embodiments the peptide comprises an amino acid sequence selected from the group consisting of SEQ ID NOS: 14). In some embodiments, the compounds comprise an amino acid sequence selected from the group consisting of SEQ ID NOS:22-24. Most preferably, the compounds comprise SEQ ID NO:22. In some preferred embodiments, the peptide has a conserved binding sequence, the sequence being XXLWPXWC (SEQ ID NO:15). In some preferred embodiments, the compounds have a sequence, the sequence being at least 70%, preferably 80%, more preferably 90%, and most preferably 95% identical to the sequences set forth herein. The peptide molecular weight is preferably between 500 Daltons and 45,000 Daltons, more preferably between 1000 Daltons and 12,000 Daltons, and most preferably from 1500 Daltons to 10,000 Daltons. In some preferred embodiments, the compounds comprise at least one polypeptide.

In some preferred embodiments, the compounds are used for the improvement of skin in an organism (i.e., a subject) having a skin disorder. In additional preferred embodiments, the skin disorder is at least one selected from the group consisting of psoriasis, venous ulcers, acne, rosacea, warts, eczema, hemangiomas and lymphangiogenesis, etc. In some particularly preferred embodiments, the skin disorder is rosacea.

In yet further embodiments, the present invention provides cosmetic and/or pharmaceutical compositions comprising at least one polypeptide or peptide, as set forth herein, and a physiologically acceptable carrier or excipient. Preferably, the compound is present in an amount of about 0.0001% to about 5% by weight based on the total weight of the composition. Also preferably, the compound is present in an amount of about 0.001% to about 0.5% by weight based on the total weight of the composition. The composition may be in the form of an emulsified vehicle, such as a nutrient cream or lotion, a stabilized gel or dispersion system, a treatment serum, a liposomal delivery system, a topical pack or mask, a surfactant-based cleansing system such as a shampoo or body wash, an aerosolized or sprayed dispersion or emulsion; a hair or skin conditioner, styling aid, or a pigmented product such as makeup, as well as other suitable make-up and cosmetic preparations. In some embodiments, the carrier is preferably at least one selected from the group consisting of water, propylene glycol, ethanol, propanol, glycerol, butylene glycol and polyethylene glycol.

In additional embodiments, the present invention provides cosmetic and/or pharmaceutical compounds comprising at least one polypeptide or a peptide suitable for modulating hair growth. In some preferred embodiments, the compounds comprise at least one polypeptide.

In some preferred embodiments, modulation comprises treatment of at least one disease or condition that involves loss of hair. In some embodiments, the disease or condition is at least one selected from the group consisting of inflammatory alopecias, pseudopelade, scleroderma, tick bites, lichen planus, psoriasis, lupus, seborrheic dermatitis, loose hair syndrome, hemochromatosis, androgenic alopecia, alopecia areata, cancer, conditions that affect defective hair fiber production, and environmental factors that affect hair production. In some preferred embodiments, the disease is androgenic alopecia or alopecia areata.

In some preferred embodiments, modulation comprises hair growth inhibition and/or hair removal for treatment of at least one disease or condition for which decreased hair growth is desirable. In some preferred embodiments, inhibition and/or removal comprises depilation.

In some preferred embodiments, the invention provides cosmetic and/or pharmaceutical compounds for modulating hair growth comprising at least one peptide or polypeptide and at least one scaffold, the peptide or polypeptide being contained within the scaffold, preferably the peptide or polypeptide being a loop, and most preferably, the loop being closed by a disulfide bond. In some preferred embodiments, the scaffold comprises STI, Eglin or BBI. In particularly preferred embodiments, the scaffold comprises BBI. In further preferred embodiments, the peptide or polypeptide comprises a polypeptide.

In yet further embodiments, the present invention provides means for decreasing VEGF activity and/or levels. In some preferred embodiments, the VEGF activity and/or levels are decreased in the epidermis. In some embodiments, the method comprising applying an effective amount of at least one of the compounds described herein to an organism in need thereof.

In additional embodiments, the present invention provides applications for hair and/or skin treatment, as well as applications wound healing, treatment of proliferative diseases, etc. Thus, the present invention provides compositions and methods suitable for application in/on humans and other animals.

In additional preferred embodiments, the present invention is directed to at least one protease-resistant scaffold comprising at least one peptide or polypeptide and at least one loop. Flexible native loops are found on the surface of most protein modules and exist as short stretches of amino acids that connect regions of defined secondary structure. Although crystallographic and NMR (nuclear magnetic resonance) studies show that native loops are usually less well defined than alpha-helices and beta-sheets, their conformational freedom is normally restricted substantially compared with free peptides. Consequently, the binding activities of native loops in proteins usually differ significantly from those of the corresponding linear amino acid sequence. However, it is not intended that the present invention be limited to any specific mechanism.

The loops provided by the present invention bind proteins such as VEGF (e.g., VEGF-A). Binding the loop to the protein prevents the protein from binding to its target. Thus, binding interactions are thought to be disrupted by binding the loop to the protein. As a result, bioactivity can be altered as desired. However, it is not intended that the present invention be limited to any particular mechanism.

The present invention further provides protease inhibitors to stabilize the loops. STI, BBI and Eglin C have native loops that bind to and inhibit proteases. In some embodiments, STI and BBI native loops are replaced with the polypeptides and/or peptides of the invention. In some embodiments, these sequences are replaced with inhibitors or enhancers of any VEFG, while in other embodiments, the sequences are replaced with inhibitors or enhancers of VEGF-A. In alternative embodiments, the sequences are replaced with inhibitors of FGF-5, TGFB-1 and TGFB-2, as well as inhibitors of the complement pathway such as C2, C3, C4 or C5 inhibitors and Compstatin, etc. In additional embodiments, STI and BBI native loops are replaced with sequences that have been isolated using various techniques known in the art (e.g., phage display), such as the VEGF binding proteins described herein.

In some embodiments, a native loop is replaced with a loop which is 3 to 20 amino acids in length, preferably 5 to 15 amino acids in length, and more preferably 5 to 10 amino acids in length. In alternative embodiments, longer sequences find use, as long as they provide binding and/or inhibition. In addition, peptides suitable for use as replacements of the native loop(s) can form constrained loops (i.e., a loop formed by the presence to a disulfide bond between two cysteine residues). In some particularly preferred embodiments, the peptides are between 7 and 9 amino acids in length.

There are several advantages to using scaffolds to stabilize peptide sequences. In some preferred embodiments, the biological activity of the peptide is higher and/or effectively modulates biological function as a result of limiting peptide flexibility and reducing the entropic cost of fixing the polypeptide sequence in the bioactive conformation. In addition, structural information obtained by x-ray crystallography finds use in guiding affinity maturation. Furthermore, in some embodiments, the sequence presented on a structural scaffold is more resistant to proteolytic degradation in different biological applications. In still further embodiments, the chimeric construction is obtained in large amount in low cost biological expression systems for industrial applications.

BBI represents a class of protein scaffolds whose binding to proteases is mediated by an exposed native loop that is fixed in a characteristic canonical conformation and which fits into the active site in a manner thought to be similar to that of a substrate (Laskowski and Kato, Ann. Rev. Biochem., 49:593-626 [1980]; and Bode & Huber, supra). The native loop is frequently constrained by the presence of disulfide bridges and/or extensive hydrogen-bonding networks that act to lock the structure into the correct canonical structure. The sequence of this loop determines the specificity of the inhibition, which mirrors the specificity of proteases for their substrates. For example, most trypsin inhibitors have Arg or Lys as their P1 residue. Inhibitors of the BBI family have a network of conserved disulfide bridges that help form a symmetrical structure of two tricyclic domains (Chen et al., supra; Werner and Wemmer, supra; and Liu et al., supra), each containing an independent serine protease binding site. The native binding loop is contained within a region joined by disulfide bridges formed between cysteine residues. The identity of the amino acid residue at the P1 site on each domain is the main determinant of the serine protease inhibited. Native domains possess lysine or arginine for trypsin, leucine or tyrosine for chymotrypsin and alanine for elastase (Tsunogae et al., J. Biochem. (Tokyo) 100:243-246 [1986]). In addition, serine is highly conserved at the P'1 position and proline at the P'3 position. The individual native loop regions of BBI are well suited for protein loop grafting of previously identified cysteine constrained peptides that bind to targets selectively, as described herein.

Numerous isoforms of BBI have been characterized. For example, the sequence DDESSKPCCDQCACTKSNP-PQCRCSDMRLNSCHSACKSCICALSY-PAQCFCVDITDFCYE PCKPSEDDKEN (SEQ ID NO:25) provides the amino acid sequence of a BBI backbone described herein. In addition, in some embodiments BBI is truncated with as many as 10 amino acid residues being removed from either the N- or C-terminal. Any of the isoforms described herein, as well as those additional ones known in the art, find use as scaffolds in the present invention.

The present invention provides several advantages over creation of, for example, chimeric proteins. Transfer of an entire protein can be difficult when, for example, a protein domain of interest carries more than one important biological activity. Maintaining one activity (e.g. functionally significant domain-domain interactions) while altering another (e.g. high affinity binding to a co-factor or receptor) can be problematic. The present invention, as indicated herein, overcomes that limitation, as in preferred embodiments the loops are transferred, instead of entire domains.

In addition, in some embodiments, the compounds of the present invention comprise at least one mutation in addition to those set out above. Other mutations, such as deletions, insertions, substitutions, transversions, transitions and inversions, at one or more other locations, also find use in the present invention.

In some embodiments, the compounds of the present invention also comprise a conservative substitution that may occur as a like-for-like substitution (e.g., basic for basic, acidic for acidic, polar for polar etc.). In additional embodiments, non-conservative substitutions are provided (i.e., from one class of residue to another or alternatively involving the inclusion of unnatural amino acids such as ornithine, diaminobutyric acid ornithine, norleucine ornithine, pyriylalanine, thienylalanine, naphthylalanine and phenylglycine).

In some embodiments, the sequences also have deletions, insertions and/or substitutions of amino acid residues that produce a silent change and result in a functionally equivalent substance.

In some embodiments, deliberate amino acid substitutions are made on the basis of similarity in amino acid properties (e.g., polarity, charge, solubility, hydrophobicity, hydrophilicity, and/or the amphipathic nature of the residues) and it is therefore useful to group amino acids together in functional groups Amino acids can be grouped together based on the properties of their side chain alone. However it is more useful to include mutation data as well. The sets of amino acids thus derived are likely to be conserved for structural reasons. These sets can be described in the form of a Venn diagram (See e.g., Livingstone and Barton, Comput. Appl. Biosci., 9:745-756 [1993]; and (Taylor, J. Theor. Biol., 119:205-218 [1986]). In some embodiments, conservative substitutions are made, for example according to the table below that describes a generally accepted Venn diagram grouping of amino acids.

| Set | | Sub-set | |
|---|---|---|---|
| Hydrophobic | F W Y H K M I L V A G C | Aromatic | F W Y H |
| | | Aliphatic | I L V |
| Polar | W Y H K R E D C S T N Q | Charged | H K R E D |
| | | Positively charged | H K R |
| | | Negatively charged | E D |
| Small | V C A G S P T N D | Tiny | A G S |

In some embodiments, variant amino acid sequences of the present invention also include suitable spacer groups inserted between any two amino acid residues of the sequence including alkyl groups such as methyl, ethyl or propyl groups in addition to amino acid spacers such as glycine or β-alanine residues. A further form of variation involves the presence of one or more amino acid residues in peptoid form.

In some embodiments, homology comparisons find use in identifying homologous sequences that find use in the present invention. Homology comparisons can be conducted by eye, or more usually, with the aid of readily available sequence comparison programs. Available computer programs can calculate the percent homology between two or more sequences. Additionally, percent homology may be calculated over contiguous sequences (i.e., one sequence is aligned with the other sequence and each amino acid in one sequence is directly compared with the corresponding amino acid in the other sequence one residue at a time). This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause following amino acid residues to be put out of alignment, thus potentially resulting in a large reduction in % homology when a global alignment is performed. Consequently, most sequence comparison methods are designed to produce optimal alignments that take into consideration possible insertions and deletions without penalizing unduly the overall homology score. This is achieved by inserting "gaps" in the sequence alignment to try to maximize local homology.

However, these more complex methods assign "gap penalties" to each gap that occurs in the alignment, so that for the same number of identical amino acids, a sequence alignment with as few gaps as possible (i.e., reflecting higher relatedness between the two compared sequences) will achieve a higher score than one with many gaps. "Affine gap costs" are typically used that charge a relatively high cost for the existence of a gap and a smaller penalty for each subsequent residue in the gap. This is one of the most commonly used gap scoring system. High gap penalties will of course produce optimized alignments with fewer gaps. Most alignment programs allow the gap penalties to be modified. However, it is preferred to use the default values when using such software for sequence comparisons. For example when using the GCG Wisconsin Bestfit package the default gap penalty for amino acid sequences is −12 for a gap and −4 for each extension.

Calculation of maximum % homology therefore firstly requires the production of an optimal alignment, taking into consideration gap penalties. A suitable computer program for carrying out such an alignment is the GCG Wisconsin Bestfit package (See e.g., Devereux et al., Nuc. Acids Res., 12:387 [1984]). Examples of other software packages than can perform sequence comparisons include, but are not limited to, the BLAST package FASTA, and the GENEWORKS suite of comparison tools, all of which are well-known to those in the art. Both BLAST and FASTA are available for offline and online searching. However, for some applications, it is preferred to use the GCG Bestfit program. The BLAST 2 Sequence package is also available for comparing protein and nucleotide sequences.

Although the final percent homology can be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied. For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (See e.g., Higgins and Sharp, Gene 73:237-244 [1988]).

Once the software has produced an optimal alignment, it is possible to calculate the percent of homology, and more preferably, the percent of sequence identity. The software typically does this as part of the sequence comparison and generates a numerical result.

In some embodiments, the present invention provides nucleic acids encoding any of the compounds described herein, as well as complements thereof. In additional preferred embodiments, the invention provides vectors comprising a compound, as disclosed herein, cells comprising the compound and methods of expressing the compound.

Those of skill in the art appreciate the relationship between nucleic acid sequences and polypeptide sequences, in particular as relate to the genetic code and the degeneracy of this code, and will be able to construct such nucleic acids without difficulty. For example, one skilled in the art is aware that for each amino acid substitution in a sequence there may be one or more codons that encode the substitute amino acid. Accordingly, it is evident that, depending on the degeneracy of the genetic code with respect to that particular amino acid residue, one or more nucleic acid sequences may be generated corresponding to that polypeptide sequence.

Mutations in amino acid sequence and nucleic acid sequence may be made by any of a number of techniques, as known in the art. In particularly preferred embodiments, the mutations are introduced into parent sequences by means of PCR (polymerase chain reaction) using appropriate primers. In some embodiments, the parent enzymes are modified at the amino acid level, while in other embodiments, the enzymes are modified at the nucleic acid level, in order to generate the sequences described herein. In some preferred embodiments, the present invention provides for the generation of compounds by introducing one or more corresponding codon changes in the nucleotide sequence encoding a compound. It will be appreciated that the above codon changes will find use in various nucleic acid sequences of the present invention. For example, in some embodiments, sequence changes are made to any of the homologous sequences described herein.

As indicated above, in some embodiments, the "compound" comprises the "complete" protein, (i.e., in its entire length as it occurs in nature (or as mutated)), while in other embodiments it comprises a truncated form of a protein. Thus, the compounds of the present invention are either truncated or be "full-length." In addition, in some embodiments, the truncation is located at the N-terminal end, while in other embodiments the truncation is located at the C-terminal end of the protein. In further embodiments, the compound lacks one or more portions (e.g., sub-sequences, signal sequences, domains or moieties), whether active or not.

In yet further alternative embodiments, the nucleotide sequences encoding the compounds are prepared synthetically by established standard methods (e.g. the phosphoroamidite method described by Beucage et al., Tetrahedr. Lett., 22:1859-1869 [1981]; or the method described by Matthes et al., EMBO J., 3:801-805 [1984]). In the phosphoroamidite method, oligonucleotides are synthesized (e.g., in an automatic DNA synthesizer), purified, annealed, ligated and cloned in appropriate vectors.

In some embodiments of the present invention, the nucleotide sequences are either of mixed genomic and synthetic origin, mixed synthetic and cDNA origin or mixed genomic and cDNA origin, prepared by ligating fragments of synthetic, genomic or cDNA origin, in accordance with standard techniques. Each ligated fragment corresponds to various parts of the entire nucleotide sequence. In some embodiments, the DNA sequence is prepared by polymerase chain reaction (PCR) using specific primers, as known in the art.

In some embodiments, the nucleotide sequences described here and suitable for use in the methods and compositions described here include within them synthetic or modified nucleotides. A number of different types of modification to oligonucleotides are known in the art. These include, but are not limited to methylphosphonate and phosphorothioate backbones and/or the addition of acridine or polylysine chains at the 3' and/or 5' ends of the molecule. However, it is not intended that the present invention be limited to any particular method, as any suitable method known to those in the art for modifying nucleotide sequences find use in the present invention. In some embodiments, these modifications are performed in order to enhance the in vivo activity and/or life span of nucleotide sequences.

In some preferred embodiments, the present invention provides nucleotide sequences and methods for using nucleotide sequences that are complementary to the sequences presented herein, as well as derivatives and/or fragments of these sequences.

In some embodiments, the polynucleotides of the present invention find use in the production of primers and/or probes. Thus, in some embodiments, the polynucleotide sequences are used to produce PCR primers, primers for other amplification methods as known in the art, labeled probes, and/or for cloning methods. In preferred embodiments, these primers, probes and other fragments are at least 15, preferably at least 20, and in some more preferable embodiments, at least 25, 30 or 40 nucleotides. In addition, these primers, probes and fragments are encompassed by the term "polynucleotide."

In some embodiments, polynucleotides such as DNA polynucleotides and probes are produced recombinantly, while in other embodiments they are produced synthetically. In additional embodiments, these sequences are cloned using standard methods. In general, primers are produced by synthetic means, involving a stepwise manufacture of the desired nucleic acid sequence one nucleotide at a time. Techniques for accomplishing this using automated techniques are readily available in the art. However, it is not intended that the present invention be limited to production of polynucleotides using any particular method, as any suitable method known to those in the art finds use in the present invention.

In some embodiments, longer polynucleotides are generally be produced using recombinant means, for example using PCR cloning techniques, as known in the art. In such embodiments, the primers are typically designed to contain suitable restriction enzyme recognition sites so that the amplified DNA can be readily cloned into a suitable cloning vector. Preferably, the variant sequences are at least as biologically active as the sequences presented herein.

In some preferred embodiments, sequences that are provided that are complementary to the compound or sequences that are capable of hybridizing to the nucleotide sequences of the compounds (including complementary sequences of those presented herein), as well as nucleotide sequences that are complementary to sequences that can hybridize to the nucleotide sequences of the compounds (including complementary sequences of those presented herein). In some preferred embodiments, polynucleotide sequences that are capable of hybridizing to the nucleotide sequences presented herein under conditions of intermediate to maximal stringency are provided.

In some preferred embodiments, nucleotide sequences that can hybridize to the nucleotide sequence of the compound nucleic acid, or the complement thereof, under stringent conditions (e.g., 50° C. and 0.2×SSC) are provided. More preferably, the nucleotide sequences can hybridize to the nucleotide sequence of the compound, or the complement thereof, under more highly stringent conditions (e.g. 65° C. and 0.1× SSC).

In some embodiments, it is desirable to mutate the sequence in order to prepare a compound. Accordingly, in some embodiments, mutants are prepared from the compounds provided herein. In some embodiments, mutations are introduced using synthetic oligonucleotides. These oligonucleotides contain nucleotide sequences flanking the desired mutation sites. Various methods known in the art find use in this embodiment (See e.g., Morinaga et al., Biotechnol., 2:646-649 [1984]; Nelson and Long, Anal. Biochem., 180:147-151 [1989]; and Sarkar and Sommer, Biotechn., 8:404-407 [1990]). However, additional methods find use in the present invention and it is not intended that the present invention be limited to any particular method.

In some preferred embodiments, the sequences used in the methods and compositions described herein is a recombinant sequence (i.e., a sequence that has been prepared using recombinant DNA techniques produced using any suitable method known in the art.

In additional embodiments, the present invention provides vectors comprising the compound, cells comprising the compound, and methods of expressing the compound. In some embodiments, the nucleotide sequences used in the methods and compositions described herein are incorporated into a recombinant replicable vector. In some embodiments, the vector is used to replicate and express the nucleotide sequence, in enzyme form, in and/or from a compatible host cell. In some embodiments, expression is controlled using control sequences (e.g., regulatory sequences). In some embodiments, proteins produced by a host cell by expression of the nucleotide sequence are secreted (i.e., into the growth medium), while in other embodiments, the proteins are contained intracellularly within the host cell. In some embodiments, the coding sequences are designed to include signal sequences which direct secretion of the substance coding sequences through a particular prokaryotic or eukaryotic cell membrane. In further embodiments, polynucleotides are incorporated into a recombinant replicable vector. In additional embodiments, the vector is used to replicate the nucleic acid in a compatible host cell. In preferred embodiments, the vector comprising the polynucleotide sequence is transformed into a suitable host cell. While any suitable host finds use in the present invention, in some preferred embodiments, the hosts are selected from the group consisting of bacterial, yeast, insect, fungal, and mammalian cells.

In some embodiments, compounds and their polynucleotides are expressed by introducing a polynucleotide into a replicable vector, introducing the vector into a compatible host cell, and growing the host cell under conditions which bring about replication of the vector. In some embodiments, the vector is recovered from the host cell.

In additional embodiments, the compound nucleic acid is operatively linked to transcriptional and translational regulatory elements active in the host cell. In some embodiments, the compound nucleic acid also encodes a fusion protein comprising at least one signal sequence (e.g., those derived from the glucoamylase gene from Schwanniomyces occidentalis, α-factor mating type gene from Saccharomyces cerevisiae and the TAKA-amylase from Aspergillus oryzae). In further alternative embodiments, the compound nucleic acid encodes a fusion protein comprising a membrane binding domain.

In some preferred embodiments, the compound is expressed at the desired levels in a host organism using an expression vector. It is contemplated that any expression vector comprising a compound nucleic acid that is capable of expressing the gene encoding the compound nucleic acid in the selected host organism will find use in the present invention. The choice of vector depends upon the host cell into which it is to be introduced. Thus, in some embodiments, the vector is an autonomously replicating vector (i.e., a vector that exists as an episomal entity, the replication of which is independent of chromosomal replication, such as, for example, a plasmid, a bacteriophage or an episomal element, a minichromosome or an artificial chromosome). Alternatively, in some embodiments, the vector integrates into the host cell genome and replicates together with the chromosome.

In some preferred embodiments, the expression vector includes the components of a cloning vector, including but not limited to such components as an element that permits autonomous replication of the vector in the selected host organism and one or more phenotypically detectable markers for selection purposes. In preferred embodiments, the expression vector further comprises control nucleotide sequences encoding a promoter, operator, ribosome binding site, translation initiation signal, and optionally, a repressor gene or one or more activator genes. Additionally, in some embodiments, the expression vector comprises a sequence coding for an amino acid sequence capable of targeting the compound to a host cell organelle such as a peroxisome or to a particular host cell compartment. Such a targeting sequence includes but is not limited to the sequence SKL. For expression under the direction of control sequences, the nucleic acid sequence encoding the compound is operably linked to the control sequences in proper manner with respect to expression.

In some preferred embodiments, the polynucleotide in a vector is operably linked to a control sequence that is capable of providing for the expression of the coding sequence by the host cell (i.e., the vector is an expression vector). In some embodiments, the control sequences are modified (e.g., by the addition of further transcriptional regulatory elements) in order to make the level of transcription directed by the control sequences more responsive to transcriptional modulators. In some preferred embodiments, the control sequences comprise promoters.

In some preferred embodiments of the vectors, the nucleic acid sequence encoding for the compound is operably combined with a suitable promoter sequence. The promoter can be any DNA sequence having transcription activity in the host organism of choice and can be derived from genes that are homologous or heterologous to the host organism. Examples of suitable promoters for directing the transcription of the modified nucleotide sequence, such as compound nucleic acids, in a bacterial host include, but are not limited to the promoter of the lac operon of E. coli, the Streptomyces coelicolor agarase gene dagA promoters, the promoters of the Bacillus licheniformis α-amylase gene (amyL), the aprE promoter of Bacillus subtilis, the promoters of the Bacillus stearothermophilus maltogenic amylase gene (amyM), the promoters of the Bacillus amyloliquefaciens α-amylase gene (amyQ), the promoters of the Bacillus subtilis xylA and xylB genes and a promoter derived from a Lactococcus sp.-derived promoter including the P170 promoter. When the gene encoding the compound is expressed in a bacterial species such as E. coli, a suitable promoter can be selected, for example, from a bacteriophage promoter including a T7 promoter and a phage lambda promoter. For transcription in a fungal species, examples of useful promoters are those derived from the genes encoding the Aspergillus oryzae TAIGA amylase, Rhizomucor miehei aspartic proteinase, A. niger neutral α-amylase, *A. niger* acid stable α-amylase, *A. niger* glucoamylase, *Rhizomucor miehei* lipase, *A. oryzae* alkaline protease, *A. oryzae* triose phosphate isomerase, and *A. nidulans* acetamidase. Examples of suitable promoters for the expression in a yeast species include but are not limited to the Gal 1 and Gal 10 promoters of *Saccharomyces cerevisiae* and the *Pichia pastoris* AOX1 or AOX2 promoters.

Examples of suitable bacterial host organisms are Gram positive species, including, but not limited to members of the Bacillaceae, (e.g., *B. subtilis, B. licheniformis, B. lentus, B. brevis, B. stearothermophilus, B. alkalophilus, B. amyloliquefaciens, B. coagulans, B. lautus, B. megaterium* and *B. thuringiensis*), *Streptomyces* species (e.g., *S. murinus* and *S. lividans*) lactic acid bacteria (e.g., *Lactococcus* spp. such as *Lactococcus lactis; Lactobacillus* spp. including *Lactobacillus reuteri; Leuconostoc* spp.; *Pediococcus* spp.; and *Streptococcus* spp. Alternatively, strains of Gram-negative species belonging to *Enterobacteriaceae* (e.g., *E. coli*) or members of the *Pseudomonadaceae* find use in the present invention.

In some embodiments, a suitable yeast host organism is selected from various biotechnologically useful yeasts species, including but not limited to *Pichia* sp., *Hansenula* sp or *Kluyveromyces, Yarrowinia, Saccharomyces* (e.g., *Saccharomyces cerevisiae*), *Schizosaccharomyce* (e.g., *S. pombe*). In some embodiments, strains of the methylotrophic yeast species *Pichia pastoris* are used as the host organism, while in other embodiments, the host organism is a *Hansenula* species. Suitable host organisms among filamentous fungi include species of *Aspergillus* (e.g., *A. niger, A. oryzae, A. tubigensis, A. awamori* and *Aspergillus nidulans*). Alternatively, strains of *Fusarium* species (e.g. *F. oxysporum*) and *Rhizomucor* (e.g., *Rhizomucor miehei*) find used as the host organism. Additional suitable strains include, but are not limited to *Thermomyces* and *Mucor* species.

In some preferred embodiments, host cells comprising polynucleotides are used to express polypeptides, such as the compounds disclosed herein, fragments, homologues, variants or derivatives thereof. Host cells are cultured under suitable conditions which allow expression of the proteins. In some embodiments, expression of the polypeptides is constitutive (i.e., the peptides are continually produced), while in other embodiments, expression is inducible. In the case of inducible expression, protein production is initiated when required by addition of an inducer substance to the culture medium (e.g., dexamethasone or IPTG). Polypeptides can be extracted from host cells by a variety of techniques known in the art, including enzymatic, chemical, and/or osmotic lysis and physical disruption. Indeed, it is not intended that the present invention be limited to any particular means of harvesting expressed polypeptides.

In alternative embodiments, polypeptides are produced recombinantly in any suitable (including commercially available) in vitro cell-free system, such as the TnT™ (Promega) rabbit reticulocyte system.

In additional preferred embodiments, the present invention provides cosmetic and/or pharmaceutical compositions comprising at least one polypeptide or peptide, as set forth herein, and a physiologically acceptable carrier or excipient. Preferably, the compound is present in an amount of about 0.0001% to about 5% by weight, based on the total weight of the composition. Also preferably, the compound is present in an amount of about 0.001% to about 0.5% by weight based on the total weight of the composition. The composition may be in the form of an emulsified vehicle, such as a nutrient cream or lotion, a stabilized gel or dispersion system, a treatment serum, a liposomal delivery system, a topical pack or mask, a surfactant-based cleansing system such as a shampoo or body wash, an aerosolized or sprayed dispersion or emulsion, a hair or skin conditioner, styling aid, or a pigmented product such as makeup. Preferably, the carrier is at least compound selected from the group consisting of water, propylene glycol, ethanol, propanol, glycerol, butylene glycol and polyethylene glycol.

In some liposomal embodiments, the liposomes comprise water and one or more ingredients capable of forming lipid bilayer vesicles that can hold one or more functional or active ingredient(s). Non-limiting examples of ingredients capable of forming lipid bilayer vesicles include: phospholipids, hydrogenated phosphatidylcholine, lecithin, cholesterol and sphingolipids. Preferred liposomes include, without limitation: a) lipoid liposome 0003 (composed of water and lecithin and glycerin); b) lipoid liposome 0300 (composed of water and phosphatidylcholine); c) lipoid liposome 0111 (composed of water, *Ginkgo biloba* leaf extract, denatured alcohol, hydrogenated lecithin and cholesterol); d) anti-irritant liposomes (composed of water, cola acuminata seed extract, bisabolol and phospholipids); e) vitamin C and E liposomes (composed of water, phospholipids, tocopheryl acetate and ascorbyl palmitate); f) firming liposomes (composed of water, butylene glycol, pyrus malus (Apple) fruit extract, phospholipids, tocopheryl acetate and carbomer); and g) moisturizing liposomes (composed of water, sodium PCA, tocopheryl acetate, xanthan gum, arginine, lysine, glycine and proline).

In other embodiments, the personal care composition of the present invention further comprise at least one active ingredient in addition to the scaffolds provide herein. There are numerous active ingredients known to those of skill in the art that find use in the personal care compositions of the present invention. Indeed, it is contemplated that any suitable active ingredient or combination of suitable active ingredients will find use in the present invention (See e.g., McCutcheon's *Functional Materials*, North American and International Editions, published by MC Publishing Co. [2003]). For example, in some embodiments, the personal care compositions herein comprise a skin care active ingredient at a level from about 0.0001% to about 20%, by weight of the composition. In another embodiment, the personal care compositions comprise a skin care active ingredient from about 0.001% to about 5%, by weight of the composition. In yet another embodiment, the personal care compositions comprise a skin care active ingredient from about 0.01% to about 2%, by weight of the composition.

Non-limiting examples of functional or active ingredients that can be delivered via liposomes include: vitamins and their derivatives, antioxidants, proteins and peptides, keratolytic agents, bioflavinoids, terpenoids, phytochemicals, and extracts of plant, marine or fermented origin. In a preferred embodiment, the composition further comprises a skin care or hair care active. Active ingredients can include any of a wide variety of ingredients such as are known in the art. (See e.g., *McCutcheon's Functional Materials*, North American and International Editions, (2003), published by MC Publishing Co.). Preferably, such actives include but are not limited to antioxidants, such as tocopheryl and ascorbyl derivatives, bioflavinoids, terpenoids, synthetics and the like, vitamins and vitamin derivatives, hydroxyl- and polyhydroxy acids and their derivatives, such as AHAs and BHAs and their reaction products, peptides and polypeptides and their derivatives, such as glycopeptides and lipophilized peptides, heat shock proteins and cytokines, enzymes and enzymes inhibitors and their derivatives, such as proteases, MMP inhibitors, catalases, glucose oxydase and superoxide dismutase, amino acids and their derivatives, bacterial, fungal and yeast fermentation products and their derivatives, including mushrooms, algae and seaweed and their derivatives, phytosterols and plant and plant part extracts and their derivatives and phospholipids and their derivatives, anti-dandruff agents such as zinc pyrithione and delivery systems containing them, as provided herein and/or known in the art.

In some preferred embodiments, the skin care active is selected from the group consisting of a Vitamin B3 component, panthenol, Vitamin E, Vitamin E acetate, retinol, retinyl propionate, retinyl palmitate, retinoic acid, Vitamin C, theobromine, alpha-hydroxyacid, farnesol, phytrantriol, salicylic acid, palmityl peptapeptide-3 and mixtures thereof. In some preferred embodiments, the Vitamin B3 component is niacinamide. In some embodiments, the compositions provided herein comprise a skin care active at a level from about 0.0001% to about 20%, preferably from about 0.001% to about 5%, more preferably from about 0.01% to about 2%, by, weight.

Exemplary derivatives of the foregoing vitamin $B_3$ compounds include nicotinic acid esters, including non-vasodilating esters of nicotinic acid, nicotinyl amino acids, nicotinyl alcohol esters of carboxylic acids, nicotinic acid N-oxide and niacinamide N-oxide. Suitable esters of nicotinic acid include nicotinic acid esters of $C_1$-$C_{22}$, preferably $C_1$-$C_{16}$, more preferably $C_1$-$C_6$ alcohols. In these embodiments, the alcohols are suitably straight-chain or branched chain, cyclic or acyclic, saturated or unsaturated (including aromatic), and substituted or unsubstituted. The esters are preferably non-vasodilating.

Non-vasodilating esters of nicotinic acid include tocopherol nicotinate and inositol hexanicotinate; tocopherol nicotinate are preferred. A more complete description of vitamin $B_3$ compounds is provided in WO 98/22085. Preferred vitamin $B_3$ compounds include niacinamide and tocopherol nicotinate.

In additional embodiments, the skin care active comprises at least one retinoid. The retinoid is preferably retinol, retinol esters (e.g., $C_2$-$C_{22}$ alkyl esters of retinol, including retinyl palmitate, retinyl acetate, retinyl proprionate), retinal, and/or retinoic acid (including all-trans retinoic acid and/or 13-cis-retinoic acid), more preferably retinoids other than retinoic acid. These compounds are well known in the art and are commercially available from a number of sources (e.g., Sigma and Boehringer Mannheim). Preferred retinoids include retinol, retinyl palmitate, retinyl acetate, retinyl proprionate, retinal, retinoic acid and combinations thereof. More preferred are retinol, retinoic propionate, retinoic acid and retinyl palmitate. In some embodiments, the retinoid is included as a substantially pure material, while in other embodiments, it is provided as an extract obtained by suitable physical and/or chemical isolation from natural (e.g., plant) sources. When a retinoid is included in the compositions herein, it preferably comprises from about 0.005% to about 2%, preferably from about 0.01% to about 1% retinoid. Retinol is preferably used in an amount of from about 0.01% to about 0.15%; retinol esters are preferably used in an amount of from about 0.01% to about 2% (e.g., about 1%).

In some embodiments, the compositions of the present invention comprise safe and effective amounts of a dermatologically acceptable carrier that is suitable for topical application to the skin or hair within which the essential materials and optional other materials are incorporated to enable the essential materials and optional components to be delivered to the skin or hair at an appropriate concentration. Thus, in some embodiments, the carrier acts as a diluent, dispersant, solvent or the like for the essential components, ensuring that these components can be applied and distributed evenly over the selected target at an appropriate concentration.

In further embodiments, an effective amount of one or more compounds described herein is also be included in compositions to be applied to keratinous materials such as nails and hair, including but not limited to those useful as hair spray compositions, hair styling compositions, hair shampooing and/or conditioning compositions, compositions applied for the purpose of hair growth regulation and compositions applied to the hair and scalp for the purpose of treating seborrhoea, dermatitis and/or dandruff.

In yet additional embodiments, an effective amount of one or more compounds described herein is included in compositions suitable for topical application to the skin or hair. These compositions are provided in any suitable form, including but not limited to creams, lotions, gels, suspensions dispersions, microemulsions, nanodispersions, microspheres, hydrogels, emulsions (e.g., oil-in-water and water-in-oil, as well as multiple emulsions), and multilaminar gels and the like (See e.g., Schlossman et al., *The Chemistry and Manufacture of Cosmetics,* [1998], incorporated by reference, herein). In some embodiments, the compositions are formulated as aqueous or silicone compositions, while in other embodiments they are formulated as emulsions of one or more oil phases in an aqueous continuous phase (or an aqueous phase in an oil phase).

The type of carrier utilized in the present invention depends on the type of product form desired for the composition. The carrier can be solid, semi-solid or liquid. Suitable carriers include liquids, semi-solids (e.g., creams, lotions, gels, sticks, ointments, and pastes), sprays and mousses. Preferably the carrier is in the form of a lotion, cream or a gel, more preferably one which has a sufficient thickness or yield point to prevent the particles from sedimenting. In some embodiments, the carrier is inert, while in other embodiments it provides dermatological benefits. In some embodiments, the carrier is applied directly to the skin and/or hair, while in other embodiments, it is applied via a woven or non-woven wipe or cloth. In yet other embodiments, it is in the form of a patch, mask or wrap. In still further embodiments, it is aerosolized or otherwise sprayed or pumped onto the skin and/or hair. The carrier chosen is physically and chemically compatible with the essential components described herein, and should not unduly impair stability, efficacy or other use benefits associated with the compositions of the present invention.

Preferred carriers contain a dermatologically acceptable, hydrophilic diluent. Suitable hydrophilic diluents include water, organic hydrophilic diluents such as $C_2$-$C_{10}$, preferably $C_2$-$C_6$, preferably, $C_3$-$C_6$ monohydric alcohols and low molecular weight glycols and polyols, including propylene glycol, polyethylene glycol polypropylene glycol, glycerol, butylene glycol, 1,2,4-butanetriol, sorbitol esters, 1,2,6-hexametriol, pentylene glycol, hexylene glycol, sorbitol esters, ethoxylated ethers, propoxylated ethers, and combinations thereof. The diluent is preferably liquid. Water is a preferred diluent. The composition preferably comprises at least about 20% of the hydrophilic diluent.

In some embodiments, suitable carriers also comprise an emulsion comprising a hydrophilic phase, especially an aqueous phase, and a hydrophobic phase (e.g., a lipid, oil or oily material). As well known to those skilled in the art, the hydrophilic phase is dispersed in the hydrophobic phase, or vice versa, to form respectively hydrophilic or hydrophobic dispersed and continuous phases, depending on the composition of ingredients. The term "dispersed phase" is a term well-known to one skilled in the art of emulsion technology, used in reference to the phase which exists as small particles or droplets that are suspended in and surrounded by a continuous phase. The dispersed phase is also known as the internal or discontinuous phase. The emulsion may be or comprise (e.g., in a triple or other multi-phase emulsion) an oil-in-water emulsion or a water-in-oil emulsion such as a water-in-silicone emulsion. Oil-in-water emulsions typically comprise from about 1% to about 60% (preferably about 1% to about 30%) of the dispersed hydrophobic phase and from about 1% to about 99% (preferably from about 10% to about 90%) of the continuous hydrophilic phase, while water-in-oil emulsions typically comprise from about 1% to about 98% (preferably from about 40% to about 90%) of the dispersed hydrophilic phase and from about 1% to about 50% (preferably about 1% to about 30%) of the continuous hydrophobic phase.

In further embodiments, the carrier also includes one or more components that facilitate penetration through the upper stratum corneum barrier to the lower levels of the skin. Examples of penetration enhancers include, but are not limited to, propylene glycol, azone, ethoxydiglycol, dimethyl isosorbide, urea, ethanol and dimethyl sulfoxide, as well as microemulsions, liposomes and nanoemulsions.

In some additional embodiments, the compositions of the present invention comprise humectants which are preferably present at a level of from about 0.01% to about 20%, preferably from about 0.1% to about 15% and preferably from about 0.5% to about 10%. Preferred humectants include, but are not limited to, compounds selected from polyhydric alcohols, sorbitol, glycerol, urea, betaine, D-panthenol, DL-panthenol, calcium pantothenate, royal jelly, panthetine, pantotheine, panthenyl ethyl ether, pangamic acid, pyridoxin, pantoyl lactose Vitamin B complex, sodium pyrrolidone carboxylic acid, hexane-1,2,6,-triol, guanidine or its derivatives, and mixtures thereof.

Suitable polyhydric alcohols for use herein include, but are not limited to polyalkylene glycols and preferably alkylene polyols and their derivatives, including propylene glycol, dipropylene glycol, polypropylene glycol, polyethylene glycol and derivatives thereof, sorbitol, hydroxypropyl sorbitol, erythritol, threitol, pentaerythritol, xylitol, glucitol, mannitol, pentylene glycol, hexylene glycol, butylene glycol (e.g., 1,3-butylene glycol), hexane triol (e.g., 1,2,6-hexanetriol), trimethylol propane, neopentyl glycol, glycerine, ethoxylated glycerine, propane-1,3 diol, propoxylated glycerine and mixtures thereof. The alkoxylated derivatives of any of the above polyhydric alcohols are also suitable for use herein. Preferred polyhydric alcohols of the present invention are selected from glycerine, butylene glycol, propylene glycol, pentylene glycol, hexylene glycol, dipropylene glycol, polyethylene glycol, hexane triol, ethoxylated glycerine and propoxylated glycerine and mixtures thereof.

Suitable humectants useful herein are sodium 2-pyrrolidone-5-carboxylate (NaPCA), guanidine; glycolic acid and glycolate salts (e.g., ammonium and quaternary alkyl ammonium); lactic acid and lactate salts (e.g., ammonium and quaternary alkyl ammonium); aloe vera in any of its variety of forms (e.g., aloe vera gel); hyaluronic acid and derivatives thereof (e.g., salt derivatives such as sodium hyaluronate); lactamide monoethanolamine; acetamide monoethanolamine; urea; betaine, panthenol and derivatives thereof; and mixtures thereof.

In some embodiments, at least part (up to about 5% by weight of composition) of a humectant is incorporated into the compositions of the present invention in the form of an admixture with a particulate cross-linked hydrophobic acrylate or methacrylate copolymer, itself preferably present in an amount of from about 0.1% to about 10%, which can be added either to the aqueous or disperse phase. This copolymer is particularly valuable for reducing shine and controlling oil while helping to provide effective moisturization benefits and is described in further detail in WO96/03964, incorporated herein by reference.

In some embodiments, the oil-in-water and water-in-oil compositions of the present invention comprise from about 0.05% to about 20%, preferably from about 1% to about 15%, preferably from about 2% to about 10%, preferably from about 2% to about 5% of a dermatologically acceptable emollient. Emollients tend to lubricate the skin, increase the smoothness and suppleness of the skin, prevent or relieve dryness of the skin and/or protect the skin. Emollients are typically water-immiscible, oily or waxy materials and emollients can confer aesthetic properties to a topical composition. A wide variety of suitable emollients are known (See e.g., Sagarin, *Cosmetics, Science and Technology*, 2nd Edition, Vol. 1, pp. 32-43 [1972]; and WO 00/24372), and find use herein, contains numerous examples of materials suitable as emollients. Additional emollients include, but are not limited to the following:

i) Straight and branched chain hydrocarbons having from about 7 to about 40 carbon atoms, such as mineral oils, dodecane, squalane, cholesterol, hydrogenated polyisobutylene, isohexadecane, isoeicosane, isooctahexacontane, isohexapentacontahectane, and the $C_7$-$C_{40}$ isoparaffins, which are $C_7$-$C_{40}$ branched hydrocarbons. Suitable branched chain hydrocarbons for use herein are selected from isopentacontaoctactane, petrolatum and mixtures thereof;

ii) $C_1$-$C_{30}$ fatty acid esters of $C_1$-$C_{30}$ carboxylic acids, $C_{12-15}$ alkyl benzoates and of $C_2$-$C_{30}$ dicarboxylic acids, e.g. isononyl isononanoate, isostearyl neopentanoate, isodecyl octanoate, isodecyl isononanoate, tridecyl isononanoate, myristyl octanoate, octyl pelargonate, octyl isononanoate, myristyl myristate, myristyl neopentanoate, myristyl octanoate, isopropyl myristate, myristyl propionate, isopropyl stearate, isopropyl isostearate, methyl isostearate, behenyl behenate, dioctyl maleate, diisopropyl adipate, and diisopropyl dilinoleate and mixtures thereof also find use in the present invention;

iii) $C_1$-$C_{30}$ mono- and poly-esters of sugars and related materials. These esters are derived from a sugar or polyol moiety and one or more carboxylic acid moieties. Depending on the constituent acid and sugar, these esters can be in either liquid or solid form at room temperature. Examples include: glucose tetraoleate, the galactose tetraesters of oleic acid, the sorbitol tetraoleate, sucrose tetraoleate, sucrose pentaoleate, sucrose hexaoleate, sucrose heptaoleate, sucrose octaoleate, sorbitol hexaester. Other materials include cottonseed oil or soybean oil fatty acid esters of sucrose. Other examples of such materials are described in WO 96/16636, incorporated by reference herein;

iv) Vegetable oils and hydrogenated vegetable oils. Examples of vegetable oils and hydro-genated vegetable oils include safflower oil, grapeseed oil, coconut oil, cottonseed oil, menhaden oil, palm kernel oil, palm oil, peanut oil, soybean oil, rapeseed oil, linseed oil, rice bran oil, pine oil, nut oil, sesame oil, sunflower seed oil, partially and fully hydrogenated oils from the foregoing sources and mixtures thereof;

v) Soluble or colloidally-soluble moisturizing agents. Examples include hyaluronic acid and chondroitin sulfate.

In some embodiments, the compositions of the present invention contain an emulsifier and/or surfactant, generally to help disperse and suspend the disperse phase within the continuous aqueous phase. A surfactant may also be useful if the product is intended for skin or hair cleansing. For convenience hereinafter, "emulsifiers" are encompassed by the term "surfactants." Thus, as used herein, the term "surfactant(s)" refers to surface active agents, whether used as emulsifiers or for other surfactant purposes such as skin cleansing. Known, including conventional surfactants find use in the present invention, provided that the selected agent is chemically and physically compatible with essential components of the composition and provides the desired characteristics (See e.g., WO 00/24372). Suitable surfactants include non-silicone derived materials, silicone-derived materials, and mixtures thereof.

In further embodiments, the compositions of the present invention comprise preferably from about 0.05% to about 30%, more preferably from about 0.5% to 15%, and most preferably from about 1% to 10% of a surfactant or mixture of surfactants. The exact surfactant or surfactant mixture chosen depends upon the pH of the composition, the other components present and the desired final product aesthetics.

Among the nonionic surfactants that are useful herein are those that can be broadly defined as condensation products of long chain alcohols (e.g., $C_{8-30}$ alcohols), with sugar or starch polymers (e.g., glycosides). Other useful nonionic surfactants include the condensation products of alkylene oxides with fatty acids (i.e., alkylene oxide esters of fatty acids). These materials have the general formula $RCO(X)_nOH$ wherein R is a $C_{10-30}$ alkyl group, X is —$OCH_2CH_2$— (i.e., derived from ethylene glycol or oxide) or —$OCH_2CHCH_3$— (i.e., derived from propylene glycol or oxide) and n is an integer from about 6 to about 200. Other nonionic surfactants are the condensation products of alkylene oxides with 2 moles of fatty acids (i.e., alkylene oxide diesters of fatty acids). These materials have the general formula $RCO(X)_nOOCR$ wherein R is a $C_{10-30}$ alkyl group, X is —$OCH_2CH_2$— (i.e., derived from ethylene glycol or oxide) or —$OCH_2CHCH_3$— (i.e., derived from propylene glycol or oxide) and n is an integer from about 6 to about 100. In some embodiments, an emulsifier for use herein is preferably a fatty acid ester blend based on a mixture of sorbitan fatty acid ester and sucrose fatty acid ester, especially a blend of sorbitan stearate and sucrose cocoate. Further suitable examples include a mixture of cetearyl alcohols and cetearyl glucosides. However, it is not intended that the present invention be limited to any particular emulsifier, as various suitable emulsifiers are known in the art.

In additional embodiments, the hydrophilic surfactants useful herein alternatively or additionally include any of a wide variety of cationic, anionic, zwitterionic, and amphoteric surfactants such as are known in the art (See, e.g., *McCutcheon's, Emulsifiers and Detergents*, North American and International Editions, MC Publishing Co. [2003]; U.S. Pat. No. 5,011,681 U.S. Pat. No. 4,421,769; and U.S. Pat. No. 3,755,560).

A variety of anionic surfactants are also useful herein (See e.g., U.S. Pat. No. 3,929,678). Exemplary anionic surfactants include, but are not limited to alkoyl isethionates (e.g., $C_{12}$-$C_{30}$), alkyl and alkyl ether sulfates and salts thereof, alkyl and alkyl ether phosphates and salts thereof, alkyl methyl taurates (e.g., $C_{12}$-$C_{30}$), and soaps (e.g., substituted alkylamine and alkali metal salts, e.g., sodium or potassium salts) of fatty acids.

Amphoteric and zwitterionic surfactants are also useful herein. Examples of preferred amphoteric and zwitterionic surfactants which find use in the compositions of the present invention are those which are broadly described as derivatives of aliphatic secondary and tertiary amines in which the aliphatic radical can be straight or branched chain and wherein one of the aliphatic substituents contains from about 8 to about 22 carbon atoms (preferably $C_8$-$C_{18}$) and one contains an anionic water solubilizing group (e.g., carboxy, sulfonate, sulfate, phosphate, or phosphonate). Examples, include but are not limited to alkyl imino acetates and iminodialkanoates and aminoalkanoates, imidazolinium and ammonium derivatives. Other suitable amphoteric and zwitterionic surfactants are those selected from the group consisting of betaines, sultaines, hydroxysultaines, and branched and unbranched alkanoyl sarcosinates, and mixtures thereof.

In further embodiments, some emulsions of the present invention include a silicone containing emulsifier or surfactant. A wide variety of silicone emulsifiers find use herein. These silicone emulsifiers are typically organically modified organopolysiloxanes, also known to those skilled in the art as silicone surfactants. Useful silicone emulsifiers include, but are not limited to dimethicone copolyols. These materials are polydimethyl siloxanes which have been modified to include polyether side chains such as polyethylene oxide chains, polypropylene oxide chains, mixtures of these chains and polyether chains containing moieties derived from both ethylene oxide and propylene oxide. Other examples include alkyl-modified dimethicone copolyols (i.e., compounds which contain $C_2$-$C_{30}$ pendant side chains). Still other useful dimethicone copolyols include materials having various cationic, anionic, amphoteric, and zwitterionic pendant moieties.

In some embodiments, the compositions of the present invention comprise at least one polymeric thickening agent. The polymeric thickening agents useful herein preferably have a number average molecular weight of greater than about 20,000, more preferably greater than about 50,000, and most preferably greater than about 100,000. In some embodiments, the compositions of the present invention comprise from about 0.01% to about 10%, preferably from about 0.1% to about 8% and more preferably from about 0.2% to about 5% by weight of the composition of the polymeric thickening agent or mixtures thereof.

Preferred polymer thickening agents for use herein include, but are not limited to non-ionic thickening agents and anionic thickening agents or mixtures thereof. Suitable non-ionic thickening agents include, but are not limited to polyacrylamide polymers, crosslinked poly(N-vinylpyrrolidones), polysaccharides, natural or synthetic gums, polyvinylpyrrolidone and polyvinylalcohol. Suitable anionic thickening agents include, but are not limited to acrylic acid/ ethyl acrylate copolymers, carboxyvinyl polymers and crosslinked copolymers of alkyl vinyl ethers and maleic anhydride. Commercially available thickeners (e.g., Carbopol; Noveon) find use in some embodiments of the present invention. Suitable Carbopol resins may be hydrophobically modified, and other suitable resins are described in WO98/ 22085, or mixtures thereof.

In some embodiments, the present compositions comprise at least one silicone oil phase. Silicone oil phase(s) generally comprises from about 0.1% to about 20%, preferably from about 0.5% to about 10%, and more preferably from about 0.5% to about 5%, of the composition. The silicone oil phase preferably comprises one or more silicone components.

In some embodiments, silicone components are fluids, including straight chain, branched and cyclic silicones. Suitable silicone fluids useful herein include silicones inclusive of polyalkyl siloxane fluids, polyaryl siloxane fluids, cyclic and linear polyalkylsiloxanes, polyalkoxylated silicones, amino and quaternary ammonium modified silicones, polyalkylaryl siloxanes or a polyether siloxane copolymer and mixtures thereof. Volatile, as well as non-volatile silicone fluids find use herein. Silicone fluids generally have an average molecular weight of less than about 200,000. In preferred embodiments, suitable silicone fluids have a molecular weight of about 100,000 or less, preferably about 50,000 or less, and more preferably about 10,000 or less. Preferably the silicone fluid is selected from silicone fluids having a weight average molecular weight in the range from about 100 to about 50,000 and preferably from about 200 to about 40,000. Typically, silicone fluids have a viscosity ranging from about 0.65 to about 600,000 mm$^2$s$^{-1}$, preferably from about 0.65 to about 10,000 mm$^2$.s$^{-1}$ at 25° C. The viscosity can be measured by means of a glass capillary viscometer as set forth in Dow Corning Corporate Test Method CTM0004, Jul. 29, 1970. Suitable polydimethyl siloxanes that can be used herein include commercially available compounds (e.g., from the General Electric Company and Dow Corning). Also useful are essentially non-volatile polyalkylarylsiloxanes, for example, polymethylphenylsiloxanes, having viscosities of about 0.65 to 30,000 mm$^2$ s$^{-1}$ at 25° C. (General Electric Company or from Dow Corning). Cyclic polydimethylsiloxanes suitable for use herein are those having a ring structure incorporating from about 3 to about 7 $(CH_3)_2SiO$ moieties, preferably about 5 or more.

In additional embodiments, silicone gums find use herein. In some preferred embodiments, a silicone oil phase comprises a silicone gum or a mixture of silicones including the silicone gum. Typically, silicone gums have a viscosity at 25° C. in excess of about 1,000,000 mm$^2$ s$^{-1}$. The silicone gums include dimethicones as known in the art (See e.g., U.S. Pat. No. 4,152,416; and Noll, *Chemistry and Technology of Silicones*, Academic Press, New York [1968]). Silicone gums such as those described in General Electric Silicone Rubber Product Data Sheets SE 30, SE 33, SE 54 and SE 76, also find use in the present invention. Specific examples of silicone gums include polydimethylsiloxane, (polydimethylsiloxane) (methylvinylsiloxane) copolymer, poly(dimethylsiloxane) (diphenyl)(methylvinylsiloxane) copolymer and mixtures thereof. Preferred silicone gums for use herein are silicone gums having a molecular weight of from about 200,000 to about 4,000,000 selected from dimethiconol, dimethicone copolyol, dimethicone and mixtures thereof.

In some embodiments, a silicone phase herein preferably comprises a silicone gum incorporated into the composition as part of a silicone gum-fluid blend. When the silicone gum is incorporated as part of a silicone gum-fluid blend, the silicone gum preferably constitutes from about 5% to about 40%, especially from about 10% to 20% by weight of the silicone gum-fluid blend. Suitable silicone gum-fluid blends herein are mixtures consisting essentially of:

(i) a silicone having a molecular weight of from about 200,000 to about 4,000,000 selected from dimethiconol, fluorosilicone and dimethicone and mixtures thereof; and (ii) a carrier which is a silicone fluid, the carrier having a viscosity from about 0.65 mm$^2$ s$^{-1}$ to about 100 mm$^2$ s$^{-1}$, wherein the ratio of i) to ii) is from about 10:90 to about 20:80 and wherein said silicone gum-based component has a final viscosity of from about 100 mm$^2$ s$^{-1}$ to about 100,000 mm$^2$ s$^{-1}$, preferably from 500 mm$^2$ s$^{-1}$ to about 10,000 mm$^2$ s$^{-1}$.

Further silicone components suitable for use in a silicone oil phase herein include crosslinked polyorganosiloxane polymers, optionally dispersed in a fluid carrier. In general, when present the crosslinked polyorganosiloxane polymers, together with its carrier (if present) comprises from about 0.1% to about 20%, preferably from about 0.5% to about 10%, and more preferably from about 0.5% to about 5% of the composition. Such polymers comprise polyorganosiloxane polymers crosslinked by a crosslinking agent (See e.g., WO98/22085). Examples of suitable polyorganosiloxane polymers for use herein include, but are not limited to methyl vinyl dimethicone, methyl vinyl diphenyl dimethicone and methyl vinyl phenyl methyl diphenyl dimethicone.

Another class of silicone components suitable for use in a silicone oil phase herein includes polydiorganosiloxane-polyoxyalkylene copolymers containing at least one polydiorganosiloxane segment and at least one polyoxyalkylene segment (See e.g., WO98/22085). Suitable polydiorganosiloxane-polyalkylene copolymers are available commercially under the tradenames BELSIL® from Wacker-Chemie GmbH. A particularly preferred copolymer fluid blend for use herein includes Dow Corning DC3225C which has the CTFA designation Dimethicone/Dimethicone copolyol.

In further embodiments, compositions of the present invention comprise an organic sunscreen. In some embodiments, suitable sunscreens have UVA absorbing properties, while others have UVB absorbing properties, and still others comprise a mixture thereof. The exact amount of the sunscreen active varies, depending upon the desired Sun Protection Factor (i.e., the "SPF") of the composition, as well as the desired level of UV protection. SPF is a commonly used measure of photoprotection of a sunscreen against erythema. The SPF is defined as a ratio of the ultraviolet energy required to produce minimal erythema on protected skin to that required to produce the same minimal erythema on unprotected skin in the same individual. Amounts of the sunscreen used are preferably from about 2% to about 20%, and more preferably from about 4% to about 14%. Suitable sunscreens include, but are not limited to those approved for use in the United States, Japan, Europe and Australia. The compositions of the present invention preferably comprise an SPF of about 2 to about 30, preferably about 4 about 30, and more preferably about 4 to about 15.

In some embodiments, the compositions of the present invention comprise one or more UVA absorbing sunscreen actives that absorb UV radiation having a wavelength of from about 320 nm to about 400 nm. Suitable UVA absorbing sunscreen actives include, but are not limited to dibenzoylmethane (See e.g., Lowe and Shaath (eds.), *Sunscreens: Development, Evaluation, and Regulatory Aspects*, Marcel Dekker, Inc.) derivatives, anthranilate derivatives such as methylanthranilate and homomethyl, 1-N-acetylanthranilate, and mixtures thereof. The UVA absorbing sunscreen active is preferably present in an amount sufficient to provide broad spectrum UVA protection either independently, or in combination with, other UV protective actives which may be present in the composition.

Suitable UVA sunscreen actives include dibenzoylmethane sunscreen actives and their derivatives. They include, but are not limited to, those selected from 2-methyldibenzoylmethane, 4-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'-diisopropylbenzoylmethane, 4-(1,1-dimethylethyl)-4'-methoxydibenzoylmethane, 2-methyl-5-isopropyl-4'-methoxydibenzoylmethane, 2-methyl-5-tert-butyl-4'-methoxy-dibenzoylmethane, 2,4-dimethyl-4'-methoxydibenzoylmethane, 2,6-dimethyl-4'-tert-butyl-4'-methoxydibenzoylmethane, and mixtures thereof. Preferred dibenzoyl sunscreen actives include those selected from 4-(1,1-dimethylethyl)-4'-methoxydibenzoylmethane, 4-isopropyldibenzoylmethane, and mixtures thereof. A preferred sunscreen active is 4-(1,1-dimethylethyl)-4'-methoxydibenzoylmethane.

The sunscreen active 4-(1,1-dimethylethyl)-4'-methoxydibenzoylmethane, which is also known as butyl methoxydibenzoylmethane or "avobenzone," is commercially available under the names of Parsol® 1789 from Givaudan Roure (International) S. A., and Eusolex® 9020 from Merck & Co., Inc. The sunscreen 4-isoproplydibenzoylmethane, which is also known as isopropyldibenzoylmethane, is commercially available from Merck under the name of Eusolex® 8020.

In some embodiments, the compositions of the present invention further include one or more UVB sunscreen actives that absorb(s) UV radiation having a wavelength of about 290 nm to about 320 nm. The compositions comprise an amount of the UVB sunscreen active that is safe and effective in providing UVB protection either independently, or in combination with, other UV protective actives which may be present in the compositions. The compositions comprise from about 0.1% to about 20%, preferably from about 0.1% to about 12%, and more preferably from about 0.5% to about 8% by weight, of each UVB absorbing organic sunscreen, or as mandated by the relevant regulatory authority(s).

A variety of UVB sunscreen actives are suitable for use herein (See e.g., U.S. Pat. Nos. 5,087,372; 5,073,371; 5,073,372; 4,937,370; and 4,999,186). Preferred UVB sunscreen actives are selected from 2-ethylhexyl-2-cyano-3,2-ethylhexyl N,N-dimethyl-p-aminobenzoate, p-aminobenzoic acid, oxybenzone, homomethyl salicylate, octyl salicylate, 4,4'-methoxy-t-butyldibenzoylmethane, 4-isopropyl dibenzoylmethane, 3-benzylidene camphor, 3-(4-methylbenzylidene) camphor, 3-diphenylacrylate, 2-phenyl-benzimidazole-5-sulphonic acid (PBSA), cinnamate esters and their derivatives such as 2-ethylhexyl-p-methoxycinnamate, salicylate esters and their derivatives such as triethanolamine salicylate, ethylhexyl salicylate, octyldimethyl para-aminobenzoic acid, camphor derivatives and their derivatives, and mixtures thereof. Preferred organic sunscreen actives include 2-ethylhexyl-2-cyano-3,3-diphenylacrylate, 2-phenyl-benzimidazole-5-sulphonic acid (PBSA), octyl-p-methoxycinnamate, and mixtures thereof. Salt and acid neutralized forms of the acidic sunscreens are also useful herein.

In some embodiments, at least one agent is added to any of the compositions useful in the present invention to stabilize the UVA sunscreen to prevent it from photo-degrading on exposure to UV radiation and thereby maintaining its UVA protection efficacy. A wide range of compounds are reported to have these stabilizing properties and should be chosen to complement both the UVA sunscreen and the composition as a whole (See e.g., U.S. Pat. Nos. 5,972,316; 5,968,485; 5,935,556; 5,827,508; and WO 00/06110). Preferred examples of stabilizing agents for use in the present invention include 2-ethylhexyl-2-cyano-3,3-diphenylacrylate, ethyl-2-cyano-3,3-diphenylacrylate, 2-ethylhexyl-3,3-diphenylacrylate, ethyl-3,3-bis(4-methoxyphenyl)acrylate, diethylhexyl 2,6 napthalate and mixtures thereof (Symrise Chemical Company).

In some embodiments, at least one agent is added to any of the compositions useful in the present invention to improve the skin substantivity of those compositions, particularly to enhance their resistance to being washed off by water or rubbed off. Examples include, but are not limited to, acrylates/$C_{12-22}$ alkylmethacrylate copolymer, acrylate/acrylate copolymer, dimethicone, dimethiconol, graft-copoly (dimethylsiloxane/i-butyl methacrylate), lauryl dimethicone, PVP/Hexadecane copolymer, PVP/Eicosene copolymer, tricontanyl PVP and trimethoxysiloxysilicate.

In addition to organic sunscreens, in some embodiments, the compositions of the present invention additionally comprise inorganic physical sunblocks (See e.g., TFA International Cosmetic Ingredient Dictionary, 6$^{th}$ Edition, pp. 1026-28 and 1103 [1995]; Sayre et al., J. Soc. Cosmet. Chem., 41:103-109 [1990]; and Lowe et al., supra). Preferred inorganic physical sunblocks include zinc oxide and titanium dioxide and mixtures thereof.

When used in preferred embodiments, the physical sunblocks are present in an amount such that the present compositions are transparent on the skin (i.e., non-whitening), preferably from about 0.5% to about 20%, preferably from about 0.5% to about 10%, and more preferably from about 0.5% to 5% by weight. When titanium dioxide is used, it can have an anatase, rutile or amorphous structure. Manufacturers of micronized grade titanium dioxide and zinc oxide for sunscreen use include, but are not limited to Tayca Corporation, Uniqema, Shinetsu Chemical Corporation, Kerr-McGee, Nanophase, Nanosource, Sachtleben, Elementis, and BASF Corporation, as well as their distribution agents and those companies that further process the material for sunscreen use. Physical sunblock particles (e.g., titanium dioxide and zinc oxide) can be uncoated or coated with a variety of materials including but not limited to amino acids, aluminum compounds such as alumina, aluminum stearate, aluminum laurate, and the like; carboxylic acids and their salts (e.g., stearic acid and its salts); phospholipids, such as lecithin; organic silicone compounds; inorganic silicone compounds such as silica and silicates and mixtures thereof. In some preferred embodiments, the compositions of the present invention comprise from about 0.1% to about 15%, preferably from about 0.1% to about 7%, and more preferably from about 0.5% to about 5%, by weight, of inorganic sunscreen.

In some preferred embodiments, the composition of the present invention also includes preservatives. Such preservatives include, but are not limited to pentylene glycol, ethylene diamine tetra acetate (EDTA) and their salts, chlorhexidine (and its diacetate, dihydrochloride, digluconate derivatives), 1,1,1-trichloro-2-methyl-2-propanol, parachloro metaxylenol, polyhexamethylenebiguanide hydrochloride, dehydroacetic acid, diazolidinyl urea, 2,4-dichlorobenzyl alcohol, 4,4-dimethyl-1,3-oxazolidine, formaldehyde (e.g., 37% aqueous solution, with 10-15% methanol to avoid polymerization), glutaraldehyde, dimethylidantoin, imidazolidinyl urea, 5-Chloro-2-methyl-4-isothiazolin-3-one, ortho-phenylphenol, 4-hydroxybenzoic acid esters (e.g., "paraben") and its methyl-, ethyl-, propyl-, isopropyl-, butyl-, and isobutyl-esters, trichlosan, 2-phenoxyethanol, phenyl mercuric acetate, borate, nitrate, quaternium-15, salicylate, salicylic acid and its salts, calcium, calcium sorbate, sorbic acid and its salts, iodopropanyl butylcarbamate zinc pyrithione, benzyl alcohol, 5-bromo-5-nitro-1,3-dioxane, 2-bromo-2-nitropropane-1,3-diol, benzoic acid and its salts, sulfites, bisulfites, phenyoxyethanol, chloroxylenol, diazolidinyl urea, methylparabens, propylparabens, isoproplyparabens, isobutylparabens, butylparabens, ethylparaben, phenoxyethanol PG, and benzalkonium chloride.

A variety of optional ingredients such as neutralizing agents, perfumes and perfume solubilizing agents, and coloring agents, also find use in some of the compositions herein. It is preferred that any additional ingredients enhance the skin softness/smoothness benefits of the product. In addition it is preferred that any such ingredients do not negatively impact the aesthetic properties of the product.

Other optional materials include keratolytic agents, as well as water-soluble and/or solubilizable preservatives preferably at a level of from about 0.1% to about 5% (e.g., Germall 115, methyl, ethyl, propyl and butyl esters of hydroxybenzoic acid, benzyl alcohol, DMDM hydantoin iodopropanyl butylcarbamate available under the trade name Glydant Plus from Lonza; EDTA, EUXYL® K400, Bromopol (2-bromo-2-nitropropane-1,3-diol) and phenoxypropanol); anti-bacterials (e.g., IRGASAN®) and phenoxyethanol (preferably at levels of from about 0.1% to about 5%); as well as soluble or colloidally-soluble moisturizing agents such as hyaluronic acid, chondroitin sulfate, and starch-grafted sodium polyacrylates (e.g., SANWET® IM-1000, IM-1500 and IM-2500, available from Celanese Superabsorbent Materials, Portsmith, Va., See e.g., U.S. Pat. No. 4,076,663; vitamins such as vitamin A, vitamin C, vitamin E and derivatives thereof and building blocks thereof such as phytantriol, and vitamin K and components thereof such as the fatty alcohol dodecatrienol; alpha and beta hydroxyacids; aloe vera; sphingosines and phytosphingosines, cholesterol; skin whitening agents; N-acetyl cysteine; colouring agents; antibacterial agents such as TCC/TCS, also known as triclosan and trichlorocarbon; perfumes and perfume solubilizers. Examples of alpha hydroxy acids include glycolic acid, lactic acid, malic acid, citric acid, glycolic acid in conjunction with ammonium glycolate, alpha-hydroxy ethanoic acid, alpha-hydroxyoctanoic acid, alpha-hydroxycaprylic acid, hydroxycaprylic acid, mixed fruit acid, tri-alpha hydroxy fruit acids, triple fruit acid, sugar cane extract, alpha hydroxy and botanicals, 1-alpha hydroxy acid and glycomer in crosslinked fatty acids (e.g., alpha nutrium). Preferred examples of alpha hydroxy acids are glycolic acid and lactic acid. It is preferred that alpha hydroxy acids are used in levels of up to about 10%. It is not intended that the present invention be limited to any particular compound derived from any particular source, as any suitable additive compound, whether obtained from natural sources or through synthesis in the laboratory find use in the present invention.

Other optional materials include water-soluble or solubilizable preservatives preferably at a level of from about 0.1% to about 5% each, such as Germall 115, methyl, ethyl, propyl and butyl esters of hydroxybenzoic acid, benzyl alcohol, DMDM hydantoin iodopropanyl butylcarbanate available under the trade name Glydant Plus from Lonza, EDTA, Euxyl® K400, Bromopol (2-bromo-2-nitropropane-1,3-diol), pentylene glycol and phenoxypropanol; anti-bacterials such as Irgasan® and phenoxyethanol (preferably at levels of from 0.1% to about 5%). Antibacterial agents such as TCC/TCS, also known as triclosan and trichlorocarbon are also useful in compositions of the present invention.

Neutralizing agents suitable for use in neutralizing acidic group containing hydrophilic gelling agents herein include sodium hydroxide, potassium hydroxide, ammonium hydroxide, monoethanolamine, diethanolamine, amino methyl propanol, tris-buffer and triethanolamine.

Other optional materials that find use in the present invention include any of the numerous functional and/or active ingredients known to those skilled in the art (See e.g., *McCutcheon's Functional Materials*, North American and International Editions, MC Publishing Co. [2003]) As indicated above, non-limiting examples include keratolytic agents; soluble or colloidally-soluble moisturizing agents such as hyaluronic acid and chondroitin sulfate; vitamins such as vitamin A, vitamin C, vitamin E, vitamin K and derivatives thereof and building blocks thereof; phytantriol; fatty alcohols such as dodecatrienol; alpha and beta hydroxyacids; aloe vera; sphingosines and phytosphingosines, cholesterol; skin whitening agents; N-acetyl cysteine; coloring agents; Examples of alpha hydroxy acids include glycolic acid, lactic acid, malic acid, and citric acid (whether derived synthetically or from natural sources and whether used alone or in combination) and their esters or relevant buffered combinations. Other examples of alpha-hydroxy acids include: alpha-hydroxy ethanoic acid, alpha-hydroxyoctanoic acid, alpha-hydroxycaprylic acid, and hydroxycaprylic acid. Preferred examples of alpha hydroxy acids include glycolic acid and lactic acid. It is preferred that alpha hydroxy acids are used in levels of up to about 10%.

Optional materials include pigments that, where water-insoluble, contribute to and are included in the total level of oil phase ingredients. Pigments suitable for use in the compositions of the present invention can be organic and/or inorganic. Also included within the term "pigment" are materials having a low color or luster, such as matte finishing agents, light scattering agents, and formulation aids such as micas, seracites, and carbonate salts. Further examples of suitable pigments include titanium dioxide, iron oxides, glutamate iron oxides, zinc oxide, bismuth oxychloride, ultramarine blue (all of which may be either pre-dispersed and/or pre-coated or not) D&C dyes and lakes, FD&C colors, natural color additives such as carmine, and mixtures thereof. Depending upon the type of composition, a mixture of pigments is usually used in preferred embodiments of the present invention. Preferred pigments for use herein from the viewpoint of moisturization, skin feel, skin appearance and emulsion compatibility are treated pigments. In some embodiments, the pigments are treated with compounds, including but not limited to amino acids, silicones, lecithin and ester oils.

In preferred embodiments, the pH of the compositions herein is in the range from about 3.5 to about 10, preferably from about 4 to about 8, and more preferably from about 5 to about 7, wherein the pH of the final composition is adjusted by addition of acidic, basic or buffer salts as necessary, depending upon the composition of the forms and the pH-requirements of the compounds.

The compositions of the present invention are prepared by standard techniques well known to those skilled in the art. In general the aqueous phase and/or the oil phase are prepared separately, with materials of similar phase partitioning being added in any order. If the final product is an emulsion, the two phases are then combined with vigorous stirring and/or homogenization as necessary, to reduce the size of the internal phase droplets. Any ingredients in the formulation with high volatility, or which are susceptible to hydrolysis or decomposition at high temperatures, are added with gentle stirring towards the end of the process, post emulsification if applicable. Dosage frequency and amount will depend upon the desired performance criteria.

In some embodiments of the present invention, method of decreasing VEGF activity are provided. In these embodiments, the methods comprise applying to an organism in need thereof an effective amount of any one of the compounds set forth herein. In additional preferred embodiments, the present invention provides compounds for treatment of an organism in need thereof, including humans and other animals.

EXPERIMENTAL

The following Examples serve to illustrate certain preferred embodiments and aspects of the present invention and are not to be construed as limiting the scope thereof.

In the experimental disclosure which follows, the following abbreviations apply: PI (proteinase inhibitor), BBI (Bowman-Birk inhibitor), STI (Soybean Trypsin inhibitor); ppm (parts per million); VEGF and VegF (vascular endothelial growth factor); M (molar); mM (millimolar); μM (micromolar); nM (nanomolar); mol (moles); mmol (millimoles); μmol (micromoles); nmol (nanomoles); gm (grams); mg (milligrams); mg (micrograms); pg (picograms); L (liters); ml and mL (milliliters); μl and μL (microliters); cm (centimeters); mm (millimeters); μm (micrometers); nm (nanometers); U (units); V (volts); MW (molecular weight); sec (seconds); min(s) (minute/minutes); hr(s) (hour/hours); ° C. (degrees Centigrade); QS (quantity sufficient); ND (not done); SA (see able); NA (not applicable); rpm (revolutions per minute); H₂O (water); dH₂O (deionized water); (HCl (hydrochloric acid); aa (amino acid); by (base pair); kb (kilobase pair); kD (kilodaltons); cDNA (copy or complimentary DNA); DNA (deoxyribonucleic acid); ssDNA (single stranded DNA); dsDNA (double stranded DNA); dNTP (deoxyribonucleotide triphosphate); RNA (ribonucleic acid); $MgCl_2$ (magnesium chloride); NaCl (sodium chloride); w/v (weight to volume); v/v (volume to volume); g (gravity); OD (optical density); $A_{405}$ (absorbance at 405 nm); Vmax (the maximum initial velocity of an enzyme catalyzed reaction); FGFrI(IIIc) (FGF-5 receptor); Dulbecco's phosphate buffered solution (DPBS); SOC (2% Bacto-Tryptone, 0.5% Bacto Yeast Extract, 10 mM NaCl, 2.5 mM KCl); Terrific Broth (TB; 12 g/l Bacto Tryptone, 24 g/l glycerol, 2.31 g/l $KH_2PO_4$, and 12.54 g/l $K_2HPO_4$); $OD_{280}$ (optical density at 280 nm); $OD_{600}$ (optical density at 600 nm); PAGE (polyacrylamide gel electrophoresis); PBS (phosphate buffered saline [150 mM NaCl, 10 mM sodium phosphate buffer, pH 7.2]); PBST (PBS+0.25% Tween® 20); PEG (polyethylene glycol); PCR (polymerase chain reaction); RT-PCR (reverse transcription PCR); SDS (sodium dodecyl sulfate); bME, BME and βME (beta-mercaptoethanol or 2-mercaptoethanol); Tris-HCl (tris [Hydroxymethyl]aminomethane-hydrochloride); Tricine (N-[tris-(hydroxymethyl)-methyl]-glycine); CHES (2-(N-cyclo-hexylamino) ethane-sulfonic acid); TAPS (3-{[tris-(hydroxymethyl)-methyl]-amino}-propanesulfonic acid); CAPS (3-(cyclo-hexylamino)-propane-sulfonic acid; DMSO (dimethyl sulfoxide); DTT (1,4-dithio-DL-threitol); Glut and GSH (reduced glutathione); GSSG (oxidized glutathione); TCEP (Tris[2-carboxyethyl] phosphine); Tris (tris(hydroxymethyl)aminomethane); HEPES (N-[2-Hydroxyethyl] piperazine-N-[2-ethanesulfonic acid]); HBS (HEPES buffered saline); SDS (sodium dodecylsulfate); Tris-HCl (tris [Hydroxymethyl]aminomethane-hydrochloride); Ci (Curies) mCi (milliCuries); μCi (microCuries); TLC (thin layer achromatography); O/W (oil in water emulsion); W/O (water in oil emulsion); W/S (water in silicon emulsion); pickering emulsion (emulsion stabilized with a solid compound); hydrodispersion (emulsifier-free formulations); PIT (phase inversion temperature technology used to manufacture special emulsions); sticks (any product that is provided in a stick format, including but not limited to lipsticks, anti-perspirants, deodorants); Ts (tosyl); Bn (benzyl); Ph (phenyl); Ms (mesyl); Et (ethyl), Me (methyl); Klenow (DNA polymerase I large (Klenow) fragment); rpm (revolutions per minute); EGTA (ethylene glycol-bis(β-aminoethyl ether) N,N,N',N'-tetraacetic acid); EDTA (ethylenediaminetetracetic acid); bla (β-lactamase or ampicillin-resistance gene); PDS (plasma-derived bovine serum that has been dialyzed to remove growth factors; dialysis of defibrinated bovine plasma is performed against DMEM for about 6 hours at 4° C., with stirring, the media is changed and dialysis is continued overnight; the dialyzed PDS is collected after 24 hours, and sterile filtered twice through a 0.2 μm filter); FCS and FBS (fetal calf serum); GE Healthcare (GE Healthcare, Chalfont St. Giles, United Kingdom); DNA2.0 (DNA2.0, Menlo Park, Calif.); OXOID (Oxoid, Basingstoke, Hampshire, UK); Megazyme (Megazyme International Ireland Ltd., Bray Business Park, Bray, Co., Wicklow, Ireland); Corning (Corning Life Sciences, Corning, N.Y.); (NEN (NEN Life Science Products, Boston, Mass.); Pharma AS (Pharma AS, Oslo, Norway); Dynal (Dynal, Oslo, Norway); Bio-Synthesis (Bio-Synthesis, Lewisville, Tex.); ATCC (American Type Culture Collection, Rockville, Md.); Gibco/BRL (Gibco/BRL, Grand Island, N.Y.); Sigma (Sigma Chemical Co., St. Louis, Mo.); Pharmacia (Pharmacia Biotech, Pisacataway, N.J.); NCBI (National Center for Biotechnology Information); Applied Biosystems (Applied Biosystems, Foster City, Calif.); Clontech (CLONTECH Laboratories, Palo Alto, Calif.); Difco (Difco Laboratories, Detroit, Mich.); Oxoid (Oxoid Inc., Ogdensburg, N.Y.); GIBCO BRL or Gibco BRL (Life Technologies, Inc., Gaithersburg, Md.); Millipore (Millipore, Billerica, Mass.); Bio-Rad (Bio-Rad, Hercules, Calif.); Invitrogen (Invitrogen Corp., San. Diego, Calif.); NEB (New England Biolabs, Beverly, Mass.); Cambrex (Cambrex Bioproducts, East Rutherford, N.J.); Sigma (Sigma Chemical Co., St. Louis, Mo.); Pierce (Pierce Biotechnology, Rockford, Takara (Takara Bio Inc. Otsu, Japan); Roche (Hoffmann-La Roche, Basel, Switzerland); EM Science (EM Science, Gibbstown, N.J.); Qiagen (Qiagen, Inc., Valencia, Calif.); Biodesign (Biodesign Intl., Saco, Maine); Biosource (Biosource, Intl., Camarillo, Calif.); Aptagen (Aptagen, Inc., Herndon, Va.); Molecular Devices (Molecular Devices, Corp., Sunnyvale, Calif.); R&D Systems (R&D Systems, Minneapolis, Minn.); Stratagene (Stratagene Cloning Systems, La Jolla, Calif.); Marsh (Marsh Biosciences, Rochester, N.Y.); Bio-Tek (Bio-Tek Instruments, Winooski, Vt.); (Biacore (Biacore, Inc., Piscataway, N.J.); PeproTech (PeproTech, Rocky Hill, N.J.); SynPep (SynPep, Dublin, Calif.); Chemicon (CHEMICON, Temecula, Calif.); Clinical Research Laboratories, (Clinical Research Laboratories, Inc., Piscataway, N.J.); and Microsoft (Microsoft, Inc., Redmond, Wash.).

Example 1

Personal Care Compositions

In this Example, various personal care compositions comprising any of the compounds of the present invention are provided as follows. In these formulations, the amounts are given as percentages of the total composition, unless otherwise indicated. Also, unless otherwise indicated in the following formulations, the concentration of BBI-AV (referred to as "Compound" below) ranges from about 0.01% to about 1.0%. In some formulations, the preferred concentration is in the range of about 0.1% to about 0.2%, while in other formulations, the preferred concentration is in the range of about 0.05% to about 0.1% (e.g., for some hair growth inhibition embodiments); from about 0.02 to 0.1% (e.g., for some skin lightening embodiments); from about 0.5% to about 1.0% (e.g., for some skin lightening embodiments); or at concentrations greater than about 0.1% (e.g., for some rosacea treating embodiments). Those of skill in the art know how to determine the suitable (i.e., optimum) concentration of BBI-AV for each product. In some

| MOISTURIZING BODYWASH (pH 7) | |
|---|---|
| RAW MATERIAL (INCI Designation) | Amount |
| Deionized Water | QS |
| Glycerin | 4.0 |
| PEG-6 Caprylic/Capric Glycerides | 4.0 |
| Palm Kernel Fatty acids | 3.0 |
| Sodium Laureth-3 Sulphate | 45.0 |
| Cocamide MEA | 3.0 |
| Sodium Lauroamphoacetate | 25.0 |
| Soybean Oil | 10.0 |
| Polyquaternium-10 | 0.70 |
| Preservative, fragrance, color | QS |
| Compound | 1000 ppm |

BODY WASH

| RAW MATERIAL (INCI Designation) | pH 8 Amount | pH 6.5 Amount | pH 7 Amount |
|---|---|---|---|
| Deionized water | QS | QS | QS |
| Sodium Laureth Sulphate | 12 | 15 | 8 |
| Cocamidopropyl Betaine | 8 | 10 | 15 |
| Decyl Glucoside | 0 | 2 | 1 |
| Polyquaternium-10 | 0.25 | 0 | 0 |
| Polyquaternium-7 | 0 | 0 | 0.7 |
| Preservative, fragrance, color | QS | QS | QS |
| Compound | 250 ppm | 500 ppm | 1000 ppm |

BODY LOTION

| RAW MATERIAL (INCI Designation) | pH 7 Amount | pH 7 Amount | pH 7.5 Amount | pH 7 Amount |
|---|---|---|---|---|
| Deionized Water | QS | QS | QS | QS |
| Glycerine | 8 | 8 | 0 | 12 |
| Isohexadecane | 3 | 3 | 3 | 6 |
| Niacinamide | 0 | 3 | 5 | 6 |
| Isopropyl Isostearate | 3 | 3 | 3 | 3 |
| Polyacrylamide (and) Isoparaffin (and) Laureth-7 | 3 | 3 | 3 | 3 |
| Petrolatum | 4 | 4 | 4 | 2 |
| Nylon 12 | 2 | 2 | 2.5 | 2.5 |
| Dimethicone | 2 | 2 | 2.5 | 2.5 |
| Sucrose Polycottonseed Oil | 1.5 | 1.5 | 1.5 | 1.5 |
| Stearyl Alcohol 97% | 1 | 1 | 1 | 1 |
| D Panthenol | 1 | 1 | 1 | 1 |
| DL-alphaTocopherol Acetate | 1 | 1 | 1 | 1 |
| Cetyl Alcohol 95% | 0.5 | 0.5 | 0.5 | 1 |
| Behenyl Alcohol | 1 | 1 | 1 | 0.5 |
| Cetearyl Alcohol (and) Cetearyl Glucoside | 0.4 | 0.4 | 0.5 | 0.5 |
| Stearic Acid | 0.15 | 0.15 | 0.15 | 0.15 |
| PEG-100-Stearate | 0.15 | 0.15 | 0.15 | 0.15 |
| Preservative, fragrance, color | QS | QS | QS | QS |
| Compounds | 250 ppm | 500 ppm | 750 ppm | 1000 ppm |

ULTRA-HIGH MOISTURIZING EMULSION

| RAW MATERIAL (INCI Designation) | pH 7 Amount | pH 7 Amount |
|---|---|---|
| Deionized water | QS | QS |
| Glycerin | 12 | 5 |
| PEG 400 | 0 | 10 |
| Niacinamide | 5 | 7 |
| Isohexadecane | 5 | 5 |
| Dimethicone | 3 | 2 |
| Polyacrylamide (and) Isoparaffin (and) Laureth-7 | 3 | 3 |
| Isopropyl Isostearate | 2 | 2 |
| Polymethylsilsesquioxane | 2 | 2 |
| Cetyl Alcohol 95% | 1 | 1 |
| Sucrose polycottonseed oil | 1 | 1 |
| D-Panthenol | 1 | 1 |
| Tocopherol Acetate | 1 | 1 |
| Stearyl Alcohol 95% | 0.5 | 0.5 |
| Cetearyl Glucoside | 0.5 | 0.5 |
| Titanium dioxide | 0.3 | 0.3 |
| Stearic Acid | 0.15 | 0.15 |
| PEG-100-Stearate | 0.15 | 0.15 |
| Preservative, fragrance, color | QS | QS |
| Compound | 250 ppm | 100 ppm |

MOISTURIZING CREAM

| RAW MATERIAL (INCI Designation) | pH 7 Amount | pH 7 Amount | pH 7.5 Amount |
|---|---|---|---|
| Deionized water | QS | QS | QS |
| Glycerine | 3 | 5 | 10 |
| Petrolatum | 3 | 3 | 0 |
| Cetyl Alcohol 95% | 1.5 | 1.5 | 1 |
| Dimethicone Copolyol | 2 | 2 | 2 |
| Isopropyl Palmitate | 1 | 1 | 0.5 |
| Carbopol 954 (Noveon) | 0.7 | 0.7 | 0.7 |
| Dimethicone (350cs) | 1 | 1 | 1 |
| Stearyl Alcohol 97% | 0.5 | 0.5 | 1 |
| Stearic acid | 0.1 | 0.1 | 0.1 |
| Peg-100-stearate | 0.1 | 0.1 | 0.1 |
| Titanium Dioxide | 0.3 | 0.3 | 0.3 |
| Preservative, color, fragrance | QS | QS | QS |
| Compound | 50 ppm | 250 ppm | 1000 ppm |

FACIAL CLEANSING EMULSION

| RAW MATERIAL (INCI Designation) | Amount |
|---|---|
| Water | 69.05 |
| Disodium EDTA | 0.1 |
| Glyceryl polymethacrylate (and) Propylene glycol | 1.0 |
| Glycerin | 2.0 |
| Xanthan gum | 0.5 |
| Hydroxyethyl cellulose | 0.5 |
| Tridecyl neopentanoate | 4.0 |
| Isocetyl stearate | 6.0 |
| Octyl palmitate | 8.0 |
| Glyceryl dilaurate | 4.0 |
| PEG-20 stearate | 2.0 |
| Glyceryl stearate (and) Laureth-23 | 2.0 |
| Lauryl pyrrolidone | 0.5 |
| Chamomile extract | 0.2 |
| Aloe vera (200x) | 0.05 |
| Fragrance, preservative | QS |
| Compound | SA |

SURFACTANT-BASED FACIAL CLEANSER

| RAW MATERIAL (INCI Designation) | Amount |
|---|---|
| Water | 62.55 |
| Acrylates/Steareth-20 methacrylate copolymer | 3.3 |
| Disodium EDTA | 0.05 |
| Glycerin | 2.0 |
| Glyceryl polymethacrylate (and) Propylene glycol (and) PVM/MA copolymer | 0.5 |
| Sodium laureth sulfate (30%) | 17.5 |
| Cetearyl alcohol | 1.0 |
| Shea butter | 1.0 |
| Disodium oleamido PEG-2 sulfosuccinate | 5.0 |
| Cocoamidopropyl Betaine | 3.0 |
| Sodium lauroyl sarcosinate | 1.0 |
| PEG-7 glyceryl cocoate | 1.0 |
| Isodecyl oleate | 1.5 |
| Peppermint extract | 0.25 |
| Eucalyptus extract | 0.25 |
| Fragrance, preservative, color, pH adjust | QS |
| Compound | SA |

FACIAL EXFOLIATING GEL

| RAW MATERIAL (INCI Designation) | Amount |
| --- | --- |
| Water | 64.39 |
| Disodium EDTA | 0.05 |
| Aloe vera (200x) | 0.01 |
| Benzophenone-4 | 0.25 |
| Propylene glycol | 1.0 |
| Acrylates/C10-30 alkyl acrylate crosspolymer (2%) | 20.0 |
| Glyceryl polymethacrylate (and) Propylene glycol | 10.0 |
| Glyceryl polymethacrylate (and) Propylene glycol (and) PVM/MA copolymer | 1.0 |
| Hydrogenated jojoba oil | 1.5 |
| Fragrance, preservative, color, pH adjust | QS |
| Compound | SA |

FACIAL TONER

| RAW MATERIAL (INCI Designation) | Amount |
| --- | --- |
| Water | 93.99 |
| Disodium EDTA | 0.1 |
| Butylene glycol | 2.0 |
| Aloe vera (200x) | 0.1 |
| Allantoin | 0.1 |
| Benzophenone-4 | 0.5 |
| Witch hazel extract | 0.3 |
| Propylene glycol (and) Euphrasia extract (and) Golden seal root extract (and) Green tea extract | 0.01 |
| PEG-40 hydrogenated castor oil | 0.5 |
| Quaternium-22 | 0.5 |
| Sandlewood oil | 0.02 |
| Fragrance, preservative, color, pH adjust | QS |
| Compound | SA |

EXFOLIATING CREAM

| RAW MATERIAL (INCI Designation) | Amount |
| --- | --- |
| Water | 68.80 |
| Disodium EDTA | 0.1 |
| PVM/MA decadiene crosspolymer | 1.0 |
| Butylene glycol | 3.0 |
| PEG-20 stearate | 1.0 |
| Glyceryl stearate (and) Laureth-23 | 2.0 |
| Diisopropyl adipate | 2.0 |
| Isodecyl oleate | 2.0 |
| Isocetyl stearoyl stearate | 5.0 |
| Myristyl myristate | 1.0 |
| Glyceryl dilaurate | 2.0 |
| Sodium hydroxide, 10% | 2.6 |
| Glyceryl polymethacrylate (and) Propylene glycol | 5.0 |
| Glyceryl polymethacrylate (and) Propylene glycol (and) PVM/MA copolymer | 0.5 |
| Hydrogenated jojoba oil | 3.0 |
| Fragrance, preservative, color, pH adjust | QS |
| Compound | SA |

FACIAL MASK

| RAW MATERIAL (INCI Designation) | Amount |
| --- | --- |
| Water | 76.4 |
| Disodium EDTA | 0.1 |
| Bentonite | 12.5 |
| Potassium C12-13 Alkyl Phosphate | 5.0 |

FACIAL MASK (continued)

| RAW MATERIAL (INCI Designation) | Amount |
| --- | --- |
| Propylene glycol | 4.0 |
| Sodium Coco PG-Dimonium Chloride Phosphate | 1.0 |
| Fragrance, preservative, color, pH adjust | QS |
| Compound | SA |

AFTER-SHAVE BALM

| RAW MATERIAL (INCI Designation) | Amount |
| --- | --- |
| Water | 82.12 |
| Disodium EDTA | 0.1 |
| Acrylate copolymer | 2.0 |
| Acrylate/Stareth-20 methacrylate copolymer | 1.0 |
| Propylene glycol | 3.0 |
| Sodium hydroxide (10%) | 1.28 |
| Glyceryl stearate (and) Cetyl alcohol (and) Stearyl alcohol (and) Behenyl alcohol (and) Palmitic acid (and) Stearic acid (and) Hydroxyethyl cetearamidopropyldimonium chloride | 3.5 |
| Isocetyl stearate | 1.0 |
| C12-15 alkyl lactate | 1.5 |
| Octyldodecyl stearate | 3.0 |
| Glyceryl polymethacrylate (and) Propylene glycol (and) PVM/MA copolymer | 1.0 |
| Poly quaternium-11 | 0.5 |
| Fragrance, preservative, color, pH adjust | QS |
| Compound | SA |

EYE GEL

| RAW MATERIAL (INCI Designation) | Amount |
| --- | --- |
| Water | 89.14 |
| VP/Acrylates/Lauryl methacrylate copolymer | 0.5 |
| Glycerin | 5.0 |
| Aminomethyl propanol | 0.3 |
| Aloe vera (200x) | 0.05 |
| Benzophenone-4 | 0.1 |
| Glyceryl polymethacrylate (and) Propylene glycol (and) PVM/MA copolymer | 0.2 |
| Butylene glycol (and) Water (and) Witch hazel extract | 0.5 |
| Butylene glycol (and) Water (and) Cucumber extract | 0.3 |
| PEG-40 hydrogenated castor oil | 0.01 |
| Acrylates/Beheneth-25 methacrylate copolymer | 2.4 |
| Fragrance, preservative, color, pH adjust | QS |
| Compound | SA |

HIGH MELTING POINT LIPSTICK

| RAW MATERIAL (INCI Designation) | Amount |
| --- | --- |
| Ozokerite wax | 5.0 |
| Candelilla wax | 11.0 |
| Octyl dodecanol | 26.0 |
| C30-45 alkyl methicone | 5.0 |
| Cyclomethicone | 4.8 |
| Petrolatum | 3.0 |
| Lanolin oil | 9.0 |
| Avocado oil | 2.0 |

HIGH MELTING POINT LIPSTICK

| RAW MATERIAL (INCI Designation) | Amount |
| --- | --- |
| Oleyl alcohol | 8.0 |
| Pigment/cyclomethicone | 25.0 |
| Fragrance, preservative | QS |
| Compound | SA |

LIPSTICK

| RAW MATERIAL (INCI Designation) | Amount |
| --- | --- |
| Candelilla wax | 9.1 |
| Isopropyl myristate | 9.6 |
| Lanolin | 5.0 |
| Beeswax | 4.0 |
| Paraffin (130/135) | 2.0 |
| Ozokerite wax | 2.5 |
| Castor oil | 53.7 |
| Carnauba wax | 1.5 |
| Pigments | 7.5 |
| Mineral oil | 4.0 |
| Fragrance, preservative | QS |
| Compound | SA |

LIP GLOSS

| RAW MATERIAL (INCI Designation) | Amount |
| --- | --- |
| Bis-diglyceryl polyacyladipate-1 | 43.5 |
| Bis-diglyceryl polyacyladipate-2 | 10 |
| Glycerol ricinoleate | 10 |
| Polyisobutene 1000 | 13 |
| Lanolin wax | 10 |
| Candelilla wax | 2.5 |
| Mica (and) titanium dioxide | 3 |
| d-Panthenol | 5 |
| Fragrance, preservative, color | QS |
| Compound | SA |

LIP GLOSS WITH SUNSCREEN

| RAW MATERIAL (INCI Designation) | Amount |
| --- | --- |
| Triisostearyl Citrate | 58.4 |
| Candelilla wax | 8.0 |
| Myristyl lactate | 7.5 |
| Microcrystalline wax | 5.0 |
| Carnauba wax | 2.0 |
| Diisopropyl dimmer dilinoleate | 10.0 |
| Mica (and) Bismuth oxychloride (and) Carmine | 6.0 |
| Zinc oxide (microfine) | 2.0 |
| Fragrance, preservative | QS |
| Compound | SA |

LIP BALM

| RAW MATERIAL (INCI Designation) | Amount |
| --- | --- |
| Petrolatum | 47.3 |
| Isopropyl lanolate | 6.0 |
| Ozokerite wax | 16.5 |
| Candelilla wax | 4.5 |
| Diisopropyl dilinoleate | 25.0 |
| Retinyl palmitate | 0.5 |
| Tocopherol acetate | 0.2 |
| Fragrance, preservative | QS |
| Compound | SA |

WATERPROOF MASCARA

| RAW MATERIAL (INCI Designation) | Amount |
| --- | --- |
| Water | 49.45 |
| Propylene glycol | 3.0 |
| Triethanolamine (99%) | 3.1 |
| Acrylates/Octylacrylamine Copolymer | 5.0 |
| Diisostearoyl trimethylolpropane siloxy silicate | 5.0 |
| Candelilla wax | 4.5 |
| Beeswax | 5.5 |
| Ozokerite wax | 2.0 |
| Carnauba wax | 1.0 |
| Cetyl alcohol | 3.0 |
| Stearic acid | 5.0 |
| Iron oxides | 11.0 |
| Fragrance, preservative | QS |
| Compound | SA |

ANHYDROUS WATERPROOF MASCARA

| RAW MATERIAL (INCI Designation) | Amount |
| --- | --- |
| C9-11 Isoparaffin | 30.95 |
| Polyethylene | 11.0 |
| Candelilla wax | 4.5 |
| Hydroxylated lanolin | 0.25 |
| Pentaerythrityl rosinate | 2.0 |
| Zinc stearate | 1.0 |
| Silica silylate | 1.0 |
| Petroleum distillates (and) Quaternium-18 hectorite (and) Propylene Carbonate | 35.0 |
| Iron oxides | 12.0 |
| Fragrance, preservative | QS |
| Compound | SA |

WATER-BASED MASCARA

| RAW MATERIAL (INCI Designation) | Amount |
| --- | --- |
| Water | 43.32 |
| Polyvinyl pyrrolidone (K30) | 2.0 |
| Hydroxyethyl cellulose | 1.0 |
| Triethanolamine (99%) | 2.0 |
| Disodium EDTA | 0.1 |
| Iron Oxides | 10.0 |
| Stearic acid | 4.5 |
| Glyceryl monostearate | 2.0 |
| Beeswax | 7.0 |
| Carnauba wax | 4.5 |
| Hydroxylated lanolin | 1.0 |
| Acrylates copolymer | 20.0 |

WATER-BASED MASCARA -continued

| RAW MATERIAL (INCI Designation) | Amount |
|---|---|
| Fragrance, preservative | QS |
| Compound | SA |

LIQUID EYELINER

| RAW MATERIAL (INCI Designation) | Amount |
|---|---|
| Water | 50-70 |
| Gellant | 0.5-1.5 |
| Wetting agent(s) | 1-3 |
| Polyol | 4-8 |
| Colorants | 10-20 |
| Alcohol | 5-10 |
| Film former | 3-8 |
| Fragrance, preservative | QS |
| Compound | SA |

NAIL ENAMEL

| RAW MATERIAL (INCI Designation) | Amount |
|---|---|
| Solvent(s) | 40-70 |
| Resin(s) | 10-20 |
| Plasticizer | 3-12 |
| Gellant | 0-2 |
| Colorants | 0-3 |
| Fragrance, preservative | QS |
| Compound | SA |

CUTICLE TREATMENT

| RAW MATERIAL (INCI Designation) | Amount |
|---|---|
| Petrolatum | 34.8 |
| Beeswax | 7.2 |
| Ozokerite wax | 4.3 |
| Candelilla wax | 4.0 |
| Cocoa butter | 1.0 |
| Shea butter | 1.0 |
| Glyceryl dilaurate | 8.0 |
| Ethylhexyl palmitate | 20.0 |
| C12-15 alkyl lactate | 6.0 |
| PVP/Eicosene copolymer | 3.5 |
| Diisopropyl adipate | 2.0 |
| Octinoxate | 7.5 |
| Retinyl palmitate | 0.1 |
| Tocopherol acetate | 0.1 |
| Fragrance, preservative, color, pH adjust | QS |
| Compound | SA |

PRESSED POWDER FORMULATIONS

| | Loose Powder | Pressed Powder | Foundation | Blush | Eye Shadow |
|---|---|---|---|---|---|
| Fillers (e.g., talc, mica, seracite) | 70-95 | 40-90 | 40-80 | 40-80 | 40-80 |
| Compression aids (e.g., metallic soaps, waxes) | 0-2.5 | 3-5 | 2-5 | 2-7 | 2-10 |
| Texture enhancers | 10-40 | 5-40 | 10-40 | 10-40 | 0-30 |
| Colorants (e.g., iron oxides, organic colors) | 2-10 | 2-10 | 5-20 | 2-10 | 1-40 |
| Pearls (e.g. titanated mica, bismuth oxychloride) | 0-20 | 0-10 | 0-5 | 0-20 | 0-60 |
| Wet binder (e.g., Octyldodecyl stearoyl stearate, di-PPG3 myristyl ether adipate, isocetyl stearate, cetyl dimethicone) | 0-3 | 2-5 | 2-5 | 3-10 | 3-15 |
| Dry binder (e.g., calcium silicate, kaolin) | 0-2 | 2-5 | 2-5 | 3-8 | 3-8 |
| Fragrance, preservative | QS | QS | QS | QS | QS |
| Compound | SA | SA | SA | SA | SA |

WATER-IN-OIL FOUNDATION

| RAW MATERIAL (INCI Designation) | Amount |
|---|---|
| Cyclomethicone | 12.0 |
| Dimethicone | 5.0 |
| Cyclomethicone (and) Dimethicone copolyol | 20.0 |
| Laureth-7 | 0.5 |
| Colorants (hydrophobically treated) | 2.2 |
| Titanium dioxide (and) methicone | 8.5 |
| Talc (and) methicone | 3.3 |
| Water | 37.2 |
| Sodium chloride | 2.0 |
| Propylene glycol | 8.0 |
| Fragrance, preservative | QS |
| Compound | SA |

ANHYDROUS MAKEUP STICK

| RAW MATERIAL (INCI Designation) | Amount |
|---|---|
| Ozokerite wax | 5.6 |
| Polyethylene | 5.3 |
| Glyceryl dilaurate | 5.5 |
| Isostearyl neopentanoate | 13.0 |
| Octyldodecyl stearoyl stearate | 12.0 |
| Myristyl myristate | 11.0 |
| Ethylhexyl methoxycinnamate | 7.5 |
| PVP/Eicosene copolymer | 0.5 |
| Tocopherol acetate | 0.1 |
| Dimethicone (and) Trimethylsiloxysilicate | 8.0 |
| Cyclopentasiloxane | 9.0 |
| Mica | 10.0 |
| Talc | 1.7 |
| Titanium dioxide (and) Isopropyl titanium triisostearate | 8.86 |
| Iron oxides (and) Isopropyl titanium triisostearate | 1.94 |
| Fragrance, preservative | QS |
| Compound | SA |

WATER-IN-SILICONE FOUNDATION

| RAW MATERIAL (INCI Designation) | Amount |
|---|---|
| Cetyl dimethicone copolyol | 0.45 |
| Polyglycerol-4 isostearate (and) Cetyl dimethicone copolyol (and) Hexyl laurate | 1.75 |
| Polyalkylene polysiloxane copolymer | 0.9 |
| Cetyl dimethicone | 0.9 |
| Beeswax | 0.7 |
| Castor wax (and) hydrogenated castor oil | 0.35 |
| Octyl palmitate | 7.0 |
| Cyclomethicone | 7.95 |
| Phenyl trimethicone | 2.2 |
| Titanium dioxide (and) Caprylyl silane | 7.5 |
| Iron oxides (and) Caprylyl silane | 1.1 |
| Talc (and) Caprylyl silane | 3.8 |
| Cyclomethicone | 7.95 |
| Dimethicone | 1.3 |
| Water | 49.55 |
| Sodium chloride | 0.5 |
| Propylene glycol | 5.3 |
| Fragrance, preservative | QS |
| Compound | SA |

OIL-IN-WATER FOUNDATION

| RAW MATERIAL (INCI Designation) | Amount |
|---|---|
| Water | 59.85 |
| Polyvinylpyrrolidone | 5.0 |
| Magnesium aluminum silicate | 2.0 |
| Xanthan gum | 0.4 |
| Trisodium EDTA | 0.05 |
| Glyceryl polymethacrylate (and) Propylene glycol (and) PVM/MA copolymer | 1.0 |
| Polysorbate 20 | 1.0 |
| Kaolin | 0.8 |
| Butylene glycol | 4.0 |
| Titanium dioxide | 6.05 |
| Iron oxides | 1.15 |
| Dimethicone | 6.0 |
| Ethylhexyl palmitate | 2.0 |
| PEG/PPG-25/25 Dimethicone | 1.0 |
| Tocopherol acetate | 0.1 |
| Retinyl palmitate | 0.1 |
| Silica | 3.0 |
| Cyclopentasiloxane | 5.0 |
| Fragrance, preservative | QS |
| Compound | SA |

SUNSCREEN FORMULAE

| RAW MATERIAL (INCI Designation) | SPF~25 | SPF~15 |
|---|---|---|
| Water | 52.65 | 71.10 |
| PVM/MA decadiene crosspolymer | 0.5 | 0.5 |
| Butylene glycol | 3.0 | 3.0 |
| Disodium EDTA | 0.1 | 0.1 |
| PEG-20 stearate | 1.5 | 1.5 |
| Glyceryl stearate (and) Laureth-23 | 2.0 | 2.0 |
| Isostearyl neopentanoate | 1.0 | 1.0 |
| Ethylhexyl palmitate | 2.0 | 2.0 |
| Glyceryl dilaurate | 0.5 | 0.5 |
| Octinoxate | 7.5 | 7.5 |
| Oxybenzone | 2.0 | 2.0 |
| Ethylhexyl salicylate | 3.0 | 3.0 |
| Sodium hydroxide (10%) | 1.3 | 1.3 |
| Glyceryl polymethacrylate (and) Propylene glycol | 3.0 | 3.0 |
| Glyceryl polymethacrylate (and) Propylene glycol (and) PVM/MA copolymer | 0.5 | 0.5 |
| Styrene/Acrylates copolymer (27% solids) | 18.45 | — |
| Fragrance, preservative | QS | QS |
| Compound | SA | SA |

VERY WATER-RESISTANT SUNSCREEN FORMULAE

| RAW MATERIAL (INCI Designation) | SPF~12 | SPF~22 |
|---|---|---|
| Water | 65.16 | 46.53 |
| Acrylates copolymer | 3.0 | 3.0 |
| Disodium EDTA | 0.1 | 0.1 |
| Butylene glycol | 2.0 | 2.0 |
| Gylceryl polymethacrylate (and) Propylene glycol (and) PVM/MA copolymer | 1.0 | 1.0 |
| Butylated PVP | 0.05 | 0.05 |
| Glyceryl stearate (and) Behenyl alcohol (and) Palmitic acid (and) Stearic acid (and) Lecithin (and) Lauryl alcohol | 4.5 | 4.5 |
| Tricontanyl PVP | 1.0 | 1.0 |
| Octyl palmitate | 2.0 | 2.0 |
| Octinoxate | 7.5 | 7.5 |
| Oxybenzone | 2.0 | 2.0 |
| Ethylhexyl salicylate | 3.0 | 3.0 |
| Tridecyl neopentanoate | 3.0 | 3.0 |
| Glyceryl dilaurate | 0.5 | 0.5 |
| Sodium hydroxide (10%) | 1.89 | 1.89 |
| Cyclopentasiloxane | 2.0 | 2.0 |
| Butylene glycol | 1.0 | 1.0 |
| Styrene/Acrylates copolymer (27% solids) | 18.45 | — |
| Fragrance, preservative | QS | QS |
| Compound | SA | SA |

WATER-IN-SILICONE SUNSCREEN

| RAW MATERIAL (INCI Designation) | Amount |
|---|---|
| Cetyl PEG/PPG-15/15 butyl ether dimethicone | 2.0 |
| Mineral oil | 3.0 |
| Ethylhexyl palmitate | 1.0 |
| Ethylhexyl salicylate | 5.0 |
| Hydrogenated castor oil | 0.5 |
| Beeswax | 0.5 |
| Octinoxate | 7.5 |
| Polyethylene | 1.0 |
| PEG-30 dipolyhydroxystearate | 2.0 |
| Cyclopentasiloxane | 5.0 |
| Dimethicone | 5.0 |
| Sodium chloride | 0.6 |
| Acrylates/C12-22 alkylmethacrylate copolymer | 0.5 |
| Water | 66.4 |
| Fragrance, preservative | QS |
| Compound | SA |

LEAVE-ON HAIR CONDITIONER

| RAW MATERIAL (INCI Designation) | Amount |
|---|---|
| Deionized Water | QS |
| Isostearamidopropyl Morpholine Lactate | 6.0 |

LEAVE-ON HAIR CONDITIONER

| RAW MATERIAL (INCI Designation) | Amount |
|---|---|
| Hydroxyethylcellulose | 1.0 |
| Preservative, fragrance, color | QS |
| Compound | 1000 ppm |

CREAM RINSE (pH 4)

| RAW MATERIAL (INCI Designation) | Amount |
|---|---|
| Deionized Water | QS |
| Behentrimonium Chloride | 2.0 |
| Trilaureth-4 Phosphate | 1.5 |
| Cetyl alcohol | 2.0 |
| Citric acid | QS |
| Preservative, fragrance, color | QS |
| Compound | 1000 ppm |

NOURISHING HAIR CONDITIONER/TREATMENT (pH 6)

| RAW MATERIAL (INCI Designation) | Amount |
|---|---|
| Deionized Water | QS |
| Behentrimonium Methosulfate (and) Cetyl Alcohol | 4.0 |
| Wheat germ oil | 1.0 |
| Cetyl alcohol | 0.5 |
| Propylene glycol | 5.0 |
| PEG-60 Lanolin | 1.0 |
| Panthenol | 2.0 |
| Lupin amino acids | 1.0 |
| Cocodimonium Hydroxypropyl Hydrolyzed Wheat Protein | 1.0 |
| Fragrance, preservative, color | QS |
| Compound | 1000 ppm |

CONDITIONING SHAMPOO

| RAW MATERIAL (INCI Designation) | Amount |
|---|---|
| Deionized Water | QS |
| Sodium Laureth Sulfate 30% | 27.0 |
| Cocamidopropyl Betaine | 3.7 |
| Coco-Glucoside (and) Glyceryl Oleate | 5.0 |
| Coco-Glucoside (and) Glycol Distearate (and) Glycerine | 3.0 |
| Guar Hydroxypropyl Trimonium Chloride | 0.1 |
| Laureth-2 | 1.55 |
| Fragrance, preservative, color | QS |
| Compound | 1000 ppm |

ANTI-DANDRUFF SHAMPOO

| RAW MATERIAL (INCI Designation) | Amount |
|---|---|
| Deionized Water | QS |
| Magnesium Aluminum Silicate | 1.0 |
| Hydroxypropyl Methylcellulose | 0.8 |
| Sodium Olefin Sulfate 40% | 35.0 |
| Lauramide DEA | 4.0 |
| Soyamide DEA | 1.0 |
| Quaternium-70 Hydrolyzed Collagen | 2.0 |

ANTI-DANDRUFF SHAMPOO

| RAW MATERIAL (INCI Designation) | Amount |
|---|---|
| Zinc Pyrithione 40% | 4.0 |
| Fragrance, preservative, color | QS |
| Compound | 1000 ppm |

CLEAR SHAMPOO

| RAW MATERIAL (INCI Designation) | Formulations (Amounts) | | | | |
|---|---|---|---|---|---|
| | 1 | 2 | 3 | 4 | 5 |
| Texapon N 70 | 13.00 | 15.00 | 10.50 | 12.50 | 10.00 |
| Dehyton PK 45 | 7.50 | 7.00 | 5.00 | 5.50 | 10.00 |
| Cetiol HE | 2.00 | 2.50 | 3.50 | 5.00 | 2.30 |
| Fragrance | 0.10 | 0.10 | 0.10 | 0.10 | 0.10 |
| Compound | SA | SA | SA | SA | SA |
| D-Panthenol USP | 1.00 | 1.50 | 1.80 | 1.70 | 1.40 |
| Preservative | 0.10 | 0.10 | 0.10 | 0.10 | 0.10 |
| Citric Acid | 0.10 | 0.10 | 0.10 | 0.10 | 0.10 |
| Luviquat Ultra Care | 1.50 | 1.00 | 1.50 | 1.20 | 1.10 |
| Sodium Chloride | 1.50 | 1.40 | 1.40 | 1.30 | 1.50 |
| Water | QS (100) | QS (100) | QS (100) | QS (100) | QS (100) |

SHAMPOO

| RAW MATERIAL (INCI Designation) | Formulations (Amounts) | | | | |
|---|---|---|---|---|---|
| | 1 | 2 | 3 | 4 | 5 |
| Texapon NSO | 35.00 | 40.00 | 30.00 | 45.00 | 27.00 |
| Plantacare 2000 | 5.00 | 5.50 | 4.90 | 3.50 | 7.00 |
| Tego Betain L7 | 10.00 | 5.00 | 12.50 | 7.50 | 15.00 |
| Fragrance | 0.10 | 0.10 | 0.10 | 0.10 | 0.10 |
| Compound | SA | SA | SA | SA | SA |
| D-Panthenol USP | 0.50 | 1.00 | 0.80 | 1.50 | 0.50 |
| Preservative | 0.10 | 0.10 | 0.10 | 0.10 | 0.10 |
| Citric Acid | 0.10 | 0.10 | 0.10 | 0.10 | 0.10 |
| Rewopal LA 3 | 0.50 | 2.00 | 0.50 | 0.50 | 2.00 |
| Sodium Chloride | 1.50 | 1.50 | 1.50 | 1.50 | 1.50 |
| Water | QS (100) | QS (100) | QS (100) | QS (100) | QS (100) |

CLEAR CONDITIONING SHAMPOO

| RAW MATERIAL (INCI Designation) | Formulations (Amounts) | | | | |
|---|---|---|---|---|---|
| | 1 | 2 | 3 | 4 | 5 |
| Amphotensid GB 2009 | 10.00 | 15.00 | 20.00 | 12.00 | 17.00 |
| Plantacare 2000 | 5.00 | 6.00 | 7.00 | 8.00 | 4.00 |
| Tego Betain L7 | 15.00 | 12.00 | 10.00 | 18.00 | 20.00 |
| Luviquat FC 550 | 0.30 | 0.20 | 0.20 | 0.20 | 0.30 |
| Fragrance | 0.10 | 0.10 | 0.10 | 0.10 | 0.10 |
| Compound | SA | SA | SA | SA | SA |
| Cremophor PS 20 | 5.00 | 1.00 | 1.00 | 7.00 | 5.00 |
| Preservative | 0.10 | 0.10 | 0.10 | 0.10 | 0.10 |
| Rewopal LA 3 | 2.00 | 1.00 | 0.50 | 2.00 | 2.00 |
| Citric Acid | 0.20 | 0.20 | 0.20 | 0.20 | 0.20 |
| Stepan PEG 600 DS | 3.00 | 2.00 | 2.00 | 3.00 | 2.50 |
| Water | QS (100) | QS (100) | QS (100) | QS (100) | QS (100) |

| FOAM O/W-EMULSION RAW MATERIAL | Formulations (Amounts) | |
|---|---|---|
| (INCI Designation) | 1 | 2 |
| Stearic acid | 5.00 | 1.00 |
| Cetyl alcohol | 5.50 | |
| Cetylstearyl alcohol | | 2.00 |
| PEG-40 Stearate | 8.50 | |
| PEG-20 Stearate | | 1.00 |
| Caprylsäure/Caprinsäure triglyceride | 4.00 | 2.00 |
| C12-15 Alkylbenzoate | 10.00 | 15.00 |
| Cyclomethicone | 4.00 | |
| Dimethicone | | 0.50 |
| Compound | SA | SA |
| Octylisostearate | | 5.00 |
| Myristyl Myristate | | 2.00 |
| Ceresin | 1.50 | |
| Glycerine | | 3.00 |
| Filter | | |
| Hydroxypropyl distärke phosphate | 1.00 | 3.50 |
| BHT | | 0.02 |
| Disodium EDTA | 0.50 | 0.10 |
| Parfüm, Konservierungsmittel | QS | QS |
| Colorant | QS | QS |
| Potassium hydroxide | QS | QS |
| Water dem. | QS (100) | QS (100) |
| | pH adjusted to 65-7.5 | pH adjusted to 5.0-6.0 |
| Emulsion 1 | | |
| Emulsion 2 | | |
| Gas (Stickstoff) | | |
| Gas (Helium) | | |

| CONDITIONER SHAMPOO WITH PEARLESCENT RAW MATERIAL | Formulations (Amounts) | | |
|---|---|---|---|
| (INCI Designation) | 1 | 2 | 3 |
| Polyquarternium-10 | 0.50 | 0.50 | 0.40 |
| Sodiumlaurethsulfat | 9.00 | 8.50 | 8.90 |
| Cocoamidopropylbetain | 2.50 | 2.60 | 3.00 |
| Benzophenon-4 | 1.50 | 0.50 | 1.00 |
| Compound | SA | SA | SA |
| Pearlescent compound | 2.00 | 2.50 | |
| Disodium EDTA | 0.10 | 0.15 | 0.05 |
| Preservative, Perfume, thickener | QS | QS | QS |
| Water dem. | QS (100) | QS (100) | QS (100) | pH adjusted to 6.0

| CLEAR CONDITIONING SHAMPOO | Formulations (Amounts) | | |
|---|---|---|---|
| RAW MATERIAL | | | |
| (INCI Designation) | 1 | 2 | 3 |
| Polyquarternium-10 | 0.50 | 0.50 | 0.50 |
| Sodiumlaurethsulfat | 9.00 | 8.50 | 9.50 |
| Compound | SA | SA | SA |
| Benzophenon-3 | 1.00 | 1.50 | 0.50 |
| Imidosuccinicacid, Na | 0.20 | 0.20 | 0.80 |
| Preservative, Perfume, thickener | QS | QS | QS |
| Water dem. | QS (100) | QS (100) | QS (100) | pH adjusted to 6.0

| CLEAR CONDITIONING SHAMPOO WITH VOLUME EFFECT | Formulations (Amounts) | | |
|---|---|---|---|
| RAW MATERIAL | | | |
| (INCI Designation) | 1 | 2 | 3 |
| Natriumlaurethsulfat | 10.00 | 10.50 | 11.00 |
| Ethylhexyl Methoxycinnamat | 2.00 | 1.50 | 2.30 |
| Compound | SA | SA | SA |
| Cocoamidopropylbetain | 2.50 | 2.60 | 2.20 |
| Disodium EDTA | 0.01 | 0.10 | 0.01 |
| Preservative, Perfume, thickener | QS | QS | QS |
| Water dem. | QS (100) | QS (100) | QS (100) | pH adjusted to 6.0

| CONDITIONING SHAMPOO WITH PEARLESCENT | Formulations (Amounts) | | |
|---|---|---|---|
| RAW MATERIAL | | | |
| (INCI Designation) | 1 | 2 | 3 |
| Polyquarternium-10 | 0.50 | 0.50 | 0.40 |
| Sodiumlaurethsulfat | 9.00 | 8.50 | 8.90 |
| Cocoamidopropylbetain | 2.50 | 2.60 | 3.00 |
| Benzophenon-4 | 1.50 | 0.50 | 1.00 |
| Compound | SA | SA | SA |
| Pearlescent compound | 2.00 | 2.50 | |
| Disodium EDTA | 0.10 | 0.15 | 0.05 |
| Preservative, Perfume, thickener | QS | QS | QS |
| Water dem. | QS (100) | QS (100) | QS (100) | pH adjusted to 6.0

| CLEAR CONDITIONING SHAMPOO | Formulations (Amounts) | | |
|---|---|---|---|
| RAW MATERIAL | | | |
| (INCI Designation) | 1 | 2 | 3 |
| Polyquarternium-10 | 0.50 | 0.50 | 0.50 |
| Sodiumlaurethsulfat | 9.00 | 8.50 | 9.50 |
| Compound | SA | SA | SA |
| Benzophenon-3 | 1.00 | 1.50 | 0.50 |
| Imidosuccinicacid, Na | 0.20 | 0.20 | 0.80 |
| Preservative, Perfume, thickener | QS | QS | QS |
| Water dem. | QS (100) | QS (100) | QS (100) | pH adjusted to 6.0

| CLEAR CONDITIONING SHAMPOO WITH VOLUME EFFECT | Formulations (Amounts) | | |
|---|---|---|---|
| RAW MATERIAL | | | |
| (INCI Designation) | 1 | 2 | 3 |
| Natriumlaurethsulfate | 10.00 | 10.50 | 11.00 |
| Ethylhexyl Methoxycinnamat | 2.00 | 1.50 | 2.30 |
| Compound | SA | SA | SA |
| Cocoamidopropylbetain | 2.50 | 2.60 | 2.20 |
| Disodium EDTA | 0.01 | 0.10 | 0.01 |
| Preservative, Perfume, thickener | QS | QS | QS |
| Water dem. | QS (100) | QS (100) | QS (100) | pH adjusted to 6.0

GEL CREME

| RAW MATERIAL (INCI Designation) | Formulations (Amounts) | | | |
|---|---|---|---|---|
| | 1 | 2 | 3 | 4 |
| Acrylat/C10-30 Alkylacrylat Crosspolymer | 0.40 | 0.35 | 0.40 | 0.35 |
| Polyacrylicacid | 0.20 | 0.22 | 0.20 | 0.22 |
| Xanthan Gummi | 0.10 | 0.13 | 0.10 | 0.13 |
| Cetearylalkohol | 3.00 | 2.50 | 3.00 | 2.50 |
| C12-15 Alkylbenzoat | 4.00 | 4.50 | 4.00 | 4.50 |
| Caprylic/Capric Triglycerid | 3.00 | 3.50 | 3.00 | 3.50 |
| Aminobenzophenon (e.g., UVINUL A PLUS ™) | 2.00 | 1.50 | 0.75 | 1.00 |
| UVASorb K2A | | 3.00 | | |
| Ethylhexyl Methoxycinnamat | 3.00 | | 1.00 | |
| Bis-Ethylhexyloxyphenol methoxyphenyl Triazin | | 1.50 | | 2.00 |
| Butyl Methoxydibenzoylmethan | | | 2.00 | |
| Disodium Phenyl Dibenzimidazol Tetrasulfonat | 2.50 | | 0.50 | 2.00 |
| Ethyhexyl Triazon | 4.00 | | 3.00 | 4.00 |
| Octocrylen | | 4.00 | | |
| Diethylhexyl Butamido Triazon | 1.00 | | | 2.00 |
| Phenylbenzimidazol Sulfonsäure | 0.50 | | 3.00 | |
| Methylen Bis-Benzotriazolyl Tetramethylbutylphenol | 2.00 | | 0.50 | 1.50 |
| Ethylhexysalicylate | | | 3.00 | |
| Drometrizol Trisiloxan | | | 0.50 | |
| Terephthaliden Dicamphor Sulfonsäure | | 1.50 | | 1.00 |
| Diethylhexyl-2,6-naphthalate | 3.50 | 4.00 | 7.00 | 9.00 |
| Titanium dioxide- microfine | 1.00 | | 3.00 | |
| Zincoxide- microfine | | | | 0.25 |
| Compound | SA | SA | SA | SA |
| Cyclisches Dimethylpolysiloxane | 5.00 | 5.50 | 5.00 | 5.50 |
| Dimethicon Polydimethylsiloxane | 1.00 | 0.60 | 1.00 | 0.60 |
| Glycerine | 1.00 | 1.20 | 1.00 | 1.20 |
| Sodium hydoxide | QS. | QS | QS | QS |
| Preservative | 0.30 | 0.23 | 0.30 | 0.23 |
| Perfume | 0.20 | | 0.20 | |
| Water | QS (100) | QS (100) | QS (100) | QS (100) | pH adjusted to 6.0

GELCREME

| RAW MATERIAL (INCI Designation) | Formulations (Amounts) | | | |
|---|---|---|---|---|
| | 1 | 2 | 3 | 4 |
| Acrylat/C10-30 Alkylacrylat Crosspolymer | 0.40 | 0.35 | 0.40 | 0.35 |
| Polyacrylicacid | 0.20 | 0.22 | 0.20 | 0.22 |
| Xanthan Gummi | 0.10 | 0.13 | 0.10 | 0.13 |
| Cetearylalkohol | 3.00 | 2.50 | 3.00 | 2.50 |
| C12-15 Alkylbenzoat | 4.00 | 4.50 | 4.00 | 4.50 |
| Caprylic/Capric Triglycerid | 3.00 | 3.50 | 3.00 | 3.50 |
| Aminobenzophenon (e.g., UVINUL A PLUS ™) | 2.00 | 1.50 | 0.75 | 1.00 |
| UVASorb K2A | | 3.00 | | |
| Ethylhexyl Methoxycinnamat | 3.00 | | 1.00 | |
| Bis-Ethylhexyloxyphenol methoxyphenyl Triazin | | 1.50 | | 2.00 |
| Butyl Methoxydibenzoylmethan | | | 2.00 | |
| Disodium Phenyl Dibenzimidazol Tetrasulfonat | 2.50 | | 0.50 | 2.00 |
| Ethyhexyl Triazon | 4.00 | | 3.00 | 4.00 |
| Octocrylen | | 4.00 | | |
| Diethylhexyl Butamido Triazon | 1.00 | | | 2.00 |
| Phenylbenzimidazol Sulfonsäure | 0.50 | | 3.00 | |
| Methylen Bis-Benzotriazolyl Tetramethylbutylphenol | 2.00 | | 0.50 | 1.50 |
| Ethylhexysalicylat | | | 3.00 | |
| Drometrizol Trisiloxan | | | 0.50 | |
| Terephthaliden Dicamphor Sulfonsäure | | 1.50 | | 1.00 |
| Diethylhexyl-2,6-naphthalat | 3.50 | 4.00 | 7.00 | 9.00 |
| Titaniumdioxide- microfine | 1.00 | | 3.00 | |
| Zincoxide- microfine | | | | 0.25 |
| Compound | SA | SA | SA | SA |
| Cyclisches Dimethylpolysiloxan | 5.00 | 5.50 | 5.00 | 5.50 |
| Dimethicon Polydimethylsiloxan | 1.00 | 0.60 | 1.00 | 0.60 |
| Glycerin | 1.00 | 1.20 | 1.00 | 1.20 |
| Sodiumhydoxid | QS | QS | QS | QS |

GELCREME

| RAW MATERIAL | Formulations (Amounts) | | | |
|---|---|---|---|---|
| (INCI Designation) | 1 | 2 | 3 | 4 |
| Preservative | 0.30 | 0.23 | 0.30 | 0.23 |
| Perfume | 0.20 | | 0.20 | |
| Water | QS (100) | QS (100) | QS (100) | QS (100) | pH adjusted to 6.0

O/W SUNSCREEN FORMULATION

| RAW MATERIAL | Formulation (Amounts) | | | | | | |
|---|---|---|---|---|---|---|---|
| (INCI Designations) | 1 | 2 | 3 | 4 | 5 | 6 | 7 |
| Glycerin monostearate SE | 0.50 | 1.00 | 3.00 | | | 1.50 | |
| Glycerl Stearate Citrate | 2.00 | | 1.00 | 2.00 | 4.00 | | |
| Stearic acid | | 3.00 | | 2.00 | | | |
| PEG-40 Stearate | 0.50 | | | | | 2.00 | |
| Cetyl Phosphate | | | | | | 1.00 | |
| Cetearyl Sulfate | | | | | | | 0.75 |
| Stearyl Alcohol | | | 3.00 | | | 2.00 | 0.60 |
| Cetyl Alcohol | 2.50 | 1.10 | | 1.50 | 0.60 | | 2.00 |
| Compound | SA | SA | SA | SA | SA | SA | SA |
| Aminobenzophenon (e.g., UVINUL A PLUS ™) | 2.00 | 1.50 | 0.75 | 1.00 | 2.10 | 4.50 | 5.00 |
| UVASorb K2A | | | | | | | |
| Ethylhexyl Methoxycinnamate | | | | 5.00 | 6.00 | 8.00 | |
| Bis-Ethylhexyl-oxyphenol methoxyphenyl Triazin | | 1.50 | | 2.00 | 2.50 | | 2.50 |
| Butyl Methoxy-dibenzoylmethane | | | 2.00 | | 2.00 | 1.50 | |
| Dinatrium Phenyl Dibenzimidazol Tetrasulfonate | 2.50 | | 0.50 | 2.00 | | 0.30 | |
| Ethyhexyl Triazone | 4.00 | | 3.00 | 4.00 | | 2.00 | |
| Octocrylen | | 4.00 | | | | | 7.50 |
| Diethylhexyl Butamido Triazon | 1.00 | | | 2.00 | 1.00 | | 1.00 |
| Phenylbenzimidazol Sulfonsäure | 0.50 | | 3.00 | | | | |
| Methylen Bis-Benzotriazolyl Tetramethylbutyl-phenol | 2.00 | | 0.50 | 1.50 | 2.50 | | |
| Ethylhexysalicylat | | | 3.00 | | | 5.00 | |
| Drometrizol Trisiloxan | | | 0.50 | | 1.00 | | |
| Terephthaliden Dicamphor Sulfonic Acid | | 1.50 | | 1.00 | 1.00 | | 0.50 |
| Diethylhexyl-2,6-naphthalat | 3.50 | | 7.00 | | 6.00 | 9.00 | |
| Titandioxid-microfine | 1.00 | | 3.00 | | 3.50 | | 1.50 |
| Zinkoxid-microfine | | | | 0.25 | | 2.00 | |
| C12-15 Alkyl Benzoate | | 0.25 | | | 4.00 | 7.00 | |
| Dicapryl Ether | | | 3.50 | | 2.00 | | |
| Butylenglycol | 5.00 | | 6.00 | | | | |
| Dicaprylat/Dicaprat Cocoglyceride | | | 6.00 | | 2.00 | | |
| Dimethicon | 0.50 | | 1.00 | | 2.00 | | |
| Cyclomethicone | 2.00 | | 0.50 | | 0.50 | | |
| Shea Butter | | 2.00 | | | | | |
| PVP Hexadecen Copolymer | 0.20 | | | 0.50 | | 1.00 | |
| Glycerin | 3.00 | 7.50 | | 7.50 | 5.00 | | 2.50 |
| Xanthan Gum | 0.15 | | 0.05 | | | 0.30 | |
| Sodium Carbomer | | 0.20 | | 0.15 | 0.25 | | |
| Vitamin E Acetat | 0.60 | | 0.23 | | 0.70 | 1.00 | |
| Fucogel 1000 | | | 3.00 | 10.00 | | | |
| Glycin Soja | | | | | 0.50 | 1.50 | 1.00 |
| Ethylhexyloxyglycin | 0.30 | | | | | | |
| DMDM Hydantoin | | 0.60 | 0.40 | 0.20 | | | |
| Glyacil-L | | | | | 0.18 | 0.20 | |
| Methylparaben | 0.15 | | 0.25 | | 0.50 | | |
| Phenoxyethanol | 1.00 | 0.40 | | | 0.40 | 0.50 | 0.40 |
| Trinatrium EDTA | 0.02 | | 0.05 | | | | |
| Iminosuccinicacid | | | | 0.25 | 1.00 | | |
| Ethanol | 2.00 | 1.50 | | 3.00 | | 1.20 | 5.00 |
| Perfume | 0.10 | 0.25 | 0.30 | | 0.40 | 0.20 | |
| Water | QS (100) | QS (100) | QS (100) | QS (100) | QS (100) | QS (100) | QS (100) |

HYDRODISPERSION

| RAW MATERIAL | Formulations (Amounts) | | | | |
|---|---|---|---|---|---|
| (INCI Designation) | 1 | 2 | 3 | 4 | 5 |
| Ceteaereth-20 | 1.00 | | | 0.50 | |
| Cetyl Alkohol | | | 1.00 | | |
| Sodium Carbomer | | 0.20 | | 0.30 | |
| Acrylat/C10-30 Alkyl Acrylat Crosspolymer | 0.50 | | 0.40 | 0.10 | 0.50 |
| Xanthan Gummi | | 0.30 | 0.15 | | |
| Compound | SA | SA | SA | SA | SA |
| Aminobenzophenon (e.g., UVINUL A PLUS ™) | 2.00 | 1.50 | 0.75 | 1.00 | 2.10 |
| UVASorb K2A | | 3.50 | | | |
| Ethylhexyl Methoxycinnamat | | | | | 5.00 |
| Bis-Ethylhexyloxyphenol methoxyphenyl Triazin | | 1.50 | | 2.00 | 2.50 |
| Butyl Methoxydibenzoylmethan | | | 2.00 | | 2.00 |
| Dinatrium Phenyl Dibenzimidazol Tetrasulfonat | 2.50 | | 0.50 | 2.00 | |
| Ethylhexyl Triazon | | 4.00 | | 3.00 | 4.00 |

HYDRODISPERSION

| RAW MATERIAL (INCI Designation) | Formulations (Amounts) | | | | |
|---|---|---|---|---|---|
| | 1 | 2 | 3 | 4 | 5 |
| Octocrylen | | 4.00 | | | |
| Diethylhexyl Butamido Triazon | 1.00 | | | 2.00 | 1.00 |
| Phenylbenzimidazol Sulfonsäure | 0.50 | | 3.00 | | |
| Methylen Bis-Benzotriazolyl Tetramethylbutylphenol | 2.00 | | 0.50 | 1.50 | 2.50 |
| Ethylhexysalicylat | | | 3.00 | | |
| Drometrizol Trisiloxan | | | 0.50 | | |
| Terephthaliden Dicamphor Sulfonsäure | | 1.50 | | 1.00 | 1.00 |
| Diethylhexyl-2,6-naphthalat | | | 7.00 | | 9.00 |
| Titaniumdioxide- microfine | 1.00 | | 3.00 | | 3.50 |
| Zincoxide- microfine | | | | 0.25 | |
| C12-15 Alkyl Benzoat | 2.00 | 2.50 | | | |
| Dicapryl Ether | | 4.00 | | | |
| Butylenglycol Dicaprylat/Dicaprat | 4.00 | | 2.00 | 6.00 | |
| Dicapryl Carbonat | | 2.00 | 6.00 | | |
| Dimethicon | | 0.50 | 1.00 | | |
| Phenyltrimethicon | 2.00 | | 0.50 | | |
| Shea Butter | | 2.00 | | 5.00 | |
| PVP Hexadecen Copolymer | 0.50 | | | 0.50 | 1.00 |
| Tricontanyl PVP | 0.50 | | 1.00 | | |
| Ethylhexylglycerin | | | 1.00 | | 0.80 |
| Glycerin | 3.00 | 7.50 | | 7.50 | 8.50 |
| *Gylcin Soja* | | | 1.50 | | 1.00 |
| Vitamin E Acetat | 0.50 | | 0.25 | | 1.00 |
| Alpha-Glucosilrutin | 0.60 | | | 0.25 | |
| Fucogel 1000 | | 2.50 | 0.50 | | 2.00 |
| DMDM Hydantoin | | 0.60 | 0.45 | 0.25 | |
| Glyacil-S | 0.20 | | | | |
| Methylparaben | 0.50 | | 0.25 | 0.15 | |
| Phenoxyethanol | 0.50 | 0.40 | | 1.00 | |
| Trinatrium EDTA | | 0.01 | 0.05 | | 0.10 |
| Ethanol | 3.00 | 2.00 | | 1.50 | 7.00 |
| Perfume | 0.20 | | 0.05 | 0.40 | |
| Water | QS (100) | QS (100) | QS (100) | QS (100) | QS (100) |

W/O SUNSCREEN EMULSION

| RAW MATERIAL (INCI Designation) | Formulations (Amounts) | | | | |
|---|---|---|---|---|---|
| | 1 | 2 | 3 | 4 | 5 |
| Cetyldimethicon Copolyol | | 2.50 | | 4.00 | |
| Polyglyceryl-2-dipolyhydroxystearat | 5.00 | | | | 4.50 |
| PEG-30-dipolyhydroxystearat | | | 5.00 | | |
| Compound | SA | SA | SA | SA | SA |
| Aminobenzophenon (e.g., UVINUL A PLUS ™) | 2.00 | 1.50 | 0.75 | 1.00 | 2.10 |
| UVASorb K2A | | 2.00 | | | |
| Ethylhexyl Methoxycinnamat | | | | | 5.00 |
| Bis-Ethylhexyloxyphenol methoxyphenyl Triazin | | 1.50 | | 2.00 | 2.50 |
| Butyl Methoxydibenzoylmethan | | | 2.00 | | 2.00 |
| Dinatrium Phenyl Dibenzimidazol Tetrasulfonat | 2.50 | | 0.50 | 2.00 | |
| Ethyhexyl Triazon | 4.00 | | 3.00 | 4.00 | |
| Octocrylen | | 4.00 | | | |
| Diethylhexyl Butamido Triazon | 1.00 | | | 2.00 | 1.00 |
| Phenylbenzimidazol Sulfonsäure | 0.50 | | 3.00 | | |
| Methylen Bis-Benzotriazolyl Tetramethylbutylphenol | 2.00 | | 0.50 | 1.50 | 2.50 |
| Ethylhexysalicylat | | | 3.00 | | |
| Drometrizol Trisiloxan | | | 0.50 | | |
| Terephthaliden Dicamphor Sulfonsäure | | 1.50 | | 1.00 | 1.00 |
| Diethylhexyl-2,6-naphthalat | | | 7.00 | | 4.00 |
| Titaniumdioxide- microfine | 1.00 | | 3.00 | | 3.50 |
| Zincoxide- microfine | | | | 0.25 | |
| Mineraloil | | 12.00 | 10.00 | | 8.00 |
| C12-15 Alkyl Benzoat | | | | 9.00 | |
| Dicaprylyl Ether | 10.00 | | | | 7.00 |
| Butylenglycol Dicaprylat/Dicaprat | | | 2.00 | 8.00 | 4.00 |
| Dicaprylyl Carbonat | 5.00 | | 6.00 | | |
| Dimethicon | | 4.00 | 1.00 | | 5.00 |
| Cyclomethicon | 2.00 | 2.50 | | | 2.00 |
| Shea Butter | | | 3.00 | | |
| Vaseline | | 4.50 | | | |
| PVP Hexadecen Copolymer | 0.50 | | | 0.50 | 1.00 |
| Ethylhexylglycerin | | 0.30 | 1.00 | | 0.50 |
| Glycerin | 3.00 | 7.50 | | 7.50 | 8.50 |
| *Glycin Soja* | | | 1.00 | 1.50 | 1.00 |
| MgSO4 | 1.00 | 0.50 | | 0.50 | |
| MgCl2 | | | 1.00 | | 0.70 |
| Vitamin E Acetat | 0.50 | | 0.25 | | 1.00 |
| Ascorbyl Palmitat | 0.50 | | | 2.00 | |
| Fucogel 1000 | | | | 3.50 | 1.00 |
| DMDM Hydantoin | | 0.60 | 0.40 | 0.20 | |
| Methylparaben | 0.50 | | 0.25 | 0.15 | |
| Phenoxyethanol | 0.50 | 0.40 | | 1.00 | |

W/O SUNSCREEN EMULSION

| RAW MATERIAL (INCI Designation) | Formulations (Amounts) | | | | |
|---|---|---|---|---|---|
| | 1 | 2 | 3 | 4 | 5 |
| Trisodium EDTA | 0.12 | 0.05 | | 0.30 | |
| Ethanol | 3.00 | | 1.50 | | 5.00 |
| Perfume | 0.20 | | 0.40 | 0.35 | |
| Water | QS (100) | QS (100) | QS (100) | QS (100) | QS (100) |

STICKS

| RAW MATERIAL (INCI Designation) | Formulations (Amounts) | | | |
|---|---|---|---|---|
| | 1 | 2 | 3 | 4 |
| Caprylic/Capric Triglycerid | 12.00 | 10.00 | 6.00 | |
| Octyldodecanol | 7.00 | 14.00 | 8.00 | 3.00 |
| Butylene Glycol Dicaprylat/Dicaprat | | | | 12.00 |
| Pentaerythrityl Tetraisostearat | 10.00 | 6.00 | 8.00 | 7.00 |
| Polyglyceryl-3 Diisostearat | 2.50 | | | |
| Bis-Diglyceryl Polyacyladipate-2 | 9.00 | 8.00 | 10.00 | 8.00 |
| Cetearyl Alcohol | 8.00 | 11.00 | 9.00 | 7.00 |
| Myristyl Myristate | 3.50 | 3.00 | 4.00 | 3.00 |
| Beeswax | 5.00 | 5.00 | 6.00 | 6.00 |
| Cera Carnauba | 1.50 | 2.00 | 2.00 | 1.50 |
| Cera Alba | 0.50 | 0.50 | 0.50 | 0.40 |
| C16-40 Alkyl Stearat | | 1.50 | 1.50 | 1.50 |
| Compound | SA | SA | SA | SA |
| Aminobenzophenon (e.g., UVINUL A PLUS ™) | 2.00 | 1.50 | 0.75 | 9.00 |
| UVASorb K2A | | 2.00 | | 4.00 |
| Ethylhexyl Methoxycinnamat | | 3.00 | | |
| Bis-Ethylhexyloxyphenol methoxyphenyl Triazin | | 1.50 | | 2.00 |
| Butyl Methoxydibenzoylmethan | | | 2.00 | |
| Dinatrium Phenyl Dibenzimidazol Tetrasulfonat | 2.50 | | 0.50 | 2.00 |
| Ethyhexyl Triazon | 4.00 | | 3.00 | 4.00 |
| Octocrylen | | 4.00 | | |
| Diethylhexyl Butamido Triazon | 1.00 | | | 2.00 |
| Phenylbenzimidazol Sulfonsäure | 0.50 | | 3.00 | |
| Methylen Bis-Benzotriazolyl Tetramethylbutylphenol | 2.00 | | 0.50 | 1.50 |
| Ethylhexysalicylat | | | 3.00 | |
| Drometrizol Trisiloxan | | | 0.50 | |
| Terephthaliden Dicamphor Sulfonsäure | | 1.50 | | 1.00 |
| Diethylhexyl-2,6-naphthalat | | | 7.00 | |
| Titaniumdioxide- microfine | 1.00 | | 3.00 | |
| Zincoxide- microfine | | | | 0.25 |
| Vitamin E Acetat | 0.50 | 1.00 | | |
| Ascorbyl Palmitat | 0.05 | | 0.05 | |
| *Buxux Chinensis* | 2.00 | 1.00 | | 1.00 |
| Perfume, BHT | 0.10 | 0.25 | | 0.35 |
| *Ricinus Communis* | QS (100) | QS (100) | QS (100) | QS (100) |

PIT-EMULSION

| RAW MATERIAL (INCI Designation) | Formulations (Amounts) | | | | | | | |
|---|---|---|---|---|---|---|---|---|
| | 1 | 2 | 3 | 4 | 5 | 6 | 7 | 8 |
| Glycerinmonostearat SE | 0.50 | 2.00 | 3.00 | 5.00 | | 0.50 | 4.00 | |
| Glyceryl Isostearat | | | | | 3.50 | 4.00 | 2.00 | |
| Isoceteth-20 | | 0.50 | | 2.00 | | | | |
| Ceteareth-12 | | 5.00 | | 1.00 | | | 3.50 | 5.00 |
| Ceteareth-20 | | 5.00 | | 1.00 | | | | 3.50 |
| PEG-100 Stearat | | | | 2.80 | | 2.30 | 3.30 | |
| Cetyl Alkohol | 5.20 | | 1.20 | 1.00 | 1.30 | | 0.50 | 0.30 |
| Cetyl Palmitat | 2.50 | 1.20 | | 1.50 | | 0.50 | | 1.50 |

PIT-EMULSION

| RAW MATERIAL (INCI Designation) | Formulations (Amounts) | | | | | | | |
|---|---|---|---|---|---|---|---|---|
| | 1 | 2 | 3 | 4 | 5 | 6 | 7 | 8 |
| Cetyl Dimethicon Copolyol | | | | 0.50 | | 1.00 | | |
| Polyglyceryl-2 | | | | 0.75 | 0.30 | | | |
| Compound | SA | SA | SA | SA | SA | SA | SA | SA |
| Aminobenzophenon (e.g., UVINUL A PLUS ™) | 2.00 | 1.50 | 0.75 | 1.00 | 2.10 | 4.50 | 5.00 | 2.10 |
| UVASorb K2A | | | 4.00 | | | | 1.50 | |
| Ethylhexyl Methoxycinnamat | | | | | 5.00 | 6.00 | 8.00 | 5.00 |
| Bis-Ethylhexyloxyphenol methoxyphenyl Triazin | | 1.50 | | 2.00 | 2.50 | | 2.50 | 2.50 |
| Butyl Methoxydibenzoylmethan | | | 2.00 | | 2.00 | 1.50 | | 2.00 |
| Dinatrium Phenyl Dibenzimidazol Tetrasulfonat | 2.50 | | 0.50 | 2.00 | | 0.30 | | |
| Ethyhexyl Triazon | 4.00 | | 3.00 | 4.00 | | 2.00 | | |
| Octocrylen | | 4.00 | | | | | 7.50 | |
| Diethylhexyl Butamido Triazon | 1.00 | | | 2.00 | 1.00 | | 1.00 | 1.00 |
| Phenylbenzimidazol Sulfonsäure | 0.50 | | 3.00 | | | | | |
| Methylen Bis-Benzotriazolyl Tetramethylbutylphenol | 2.00 | | 0.50 | 1.50 | 2.50 | | | 2.50 |
| Ethylhexysalicylat | | | 3.00 | | | | 5.00 | |
| Drometrizol Trisiloxan | | | 0.50 | | | 1.00 | | |
| Terephthaliden Dicamphor Sulfonsäure | | 1.50 | | 1.00 | 1.00 | | 0.50 | 1.00 |
| Diethylhexyl-2,6-naphthalat | | | 7.00 | | 10.00 | 7.50 | | 8.00 |
| Titandioxid-microfine | 1.00 | | 3.00 | | 3.50 | | 1.50 | 3.50 |
| Zinkoxid-microfine | | | | 0.25 | | 2.00 | | |
| C12-15 Alkyl Benzoat | 3.50 | | | 6.35 | | | | 0.10 |
| Cocoglyceride | | 3.00 | | 3.00 | | | | 1.00 |
| Dicapryl Ether | 4.50 | | | | | | | |
| Dicaprylyl Carbonat | | 4.30 | | 3.00 | | | | 7.00 |
| Dibutyl Adipate | | | | 0.50 | | | | 0.30 |
| Phenyltrimethicone | 2.00 | | | 3.50 | | 2.00 | | |
| Cyclomethicon | | 3.00 | | | | | | |
| Ethyl Galaktomannan | | 0.50 | | | 2.00 | | | |
| Hydrierte Coco-Glyceride | | | | | 3.00 | 4.00 | | |
| Abil Wax 2440 | | | | | 1.50 | 2.00 | | |
| PVP Hexadecen Copolymer | | | | 1.00 | 1.20 | | | |
| Glycerin | 4.00 | 6.00 | 5.00 | | 8.00 | 10.00 | | |
| Vitamin E Acetat | 0.20 | 0.30 | 0.40 | | 0.30 | | | |
| Shea Butter | | 2.00 | | 3.60 | | 2.00 | | |
| Iodopropyl Butylcarbamat | 0.12 | | | | 0.20 | | | |
| Fucogel 1000 | | | | 0.10 | | | | |
| DMDM Hydantoin | 0.10 | | | | 0.12 | | 0.13 | |
| Methylparaben | | 0.50 | 0.30 | | 0.35 | | | |
| Phenoxyethanol | 0.50 | 0.40 | | 1.00 | | | | |
| Octoxyglycerin | | 0.30 | | | 1.00 | | 0.35 | |
| Ethanol | 2.00 | | 2.00 | | | 5.00 | | |
| Trinatrium EDTA | 0.40 | | 0.15 | | | 0.20 | | |
| Perfume | 0.20 | | 0.20 | | 0.24 | 0.16 | 0.10 | 0.10 |
| Water | QS (100) | QS (100) | QS (100) | QS (100) | QS (100) | QS (100) | QS (100) | QS (100) |

GEL CREME

| RAW MATERIAL (INCI Designation) | Formulations (Amounts) | | | |
|---|---|---|---|---|
| | 1 | 2 | 3 | 4 |
| Acrylat/C10-30 alkylacrylat crosspolymer | 0.40 | 0.35 | 0.40 | 0.35 |
| Polyacrylic acid | 0.20 | 0.22 | 0.20 | 0.22 |
| Luvigel EM | 1.50 | 2.50 | 2.80 | 3.50 |
| Xanthan gum | 0.10 | 0.13 | 0.10 | 0.13 |
| Cetearylalkohol | 3.00 | 2.50 | 3.00 | 2.50 |
| C12-15 Alkylbenzoate | 4.00 | 4.50 | 4.00 | 4.50 |
| Caprylic/Capric Triglyceride | 3.00 | 3.50 | 3.00 | 3.50 |
| Titan dioxide- microfine | 1.00 | | 1.50 | |
| Zinc oxide- microfine | | 2.00 | | 0.25 |
| Compound | SA | SA | SA | SA |
| Dihydroxyacetone | | | 3.00 | 5.00 |
| Cyclisches Dimethylpolysiloxan | 5.00 | 5.50 | 5.00 | 5.50 |
| Dimethicon Polydimethylsiloxan | 1.00 | 0.60 | 1.00 | 0.60 |
| Glycerine | 1.00 | 1.20 | 1.00 | 1.20 |
| Natrium hydroxide | QS | QS | QS | QS |
| Preservatives | 0.30 | 0.23 | 0.30 | 0.23 |
| Perfume | 0.20 | | 0.20 | |
| Water | QS (100) | QS (100) | QS (100) | QS (100) | pH adjusted to 6.0

O/W SELF TANNER FORMULATIONS

| RAW MATERIAL (INCI Designation) | Formulations (Amounts) | | | | | | |
|---|---|---|---|---|---|---|---|
| | 1 | 2 | 3 | 4 | 5 | 6 | 7 |
| Glycerin monostearate SE | 0.50 | 1.00 | 3.00 | | | 1.50 | |
| Glycerlstearate citrate | 2.00 | | 1.00 | 2.00 | 4.00 | | |
| Stearic acid | | 3.00 | | 2.00 | | | |
| PEG-40 stearate | 0.50 | | | | | 2.00 | |
| Cetyl phosphate | | | | | | 1.00 | |
| Cetearyl sulfate | | | | | | | 0.75 |
| Stearyl alcohol | | | 3.00 | | | 2.00 | 0.60 |
| Cetyl alcohol | 2.50 | 1.10 | | 1.50 | 0.60 | | 2.00 |
| Compound | SA | SA | SA | SA | SA | SA | SA |
| Dihydroxy acetone | | | 3.00 | 5.00 | | 4 | |
| Titanium dioxide-microfine | 1.00 | | | | 1.50 | | 1.50 |
| Zinc oxide-microfine | | | | 0.25 | | 2.00 | |
| C12-15 Alkyl benzoate | | 0.25 | | | 4.00 | 7.00 | |
| Dicapryl ether | | | 3.50 | | 2.00 | | |
| Butylenglycol | 5.00 | | 6.00 | | | | |
| Dicaprylaet/Dicaprat | | | | | | | |
| Cocoglyceride | | | 6.00 | | 2.00 | | |
| Dimethicon | 0.50 | | 1.00 | | 2.00 | | |
| Cyclomethicon | 2.00 | | 0.50 | | 0.50 | | |
| Shea butter | | 2.00 | | | | | |
| PVP hexadecen copolymer | 0.20 | | | 0.50 | | 1.00 | |
| Glycerin | 3.00 | 7.50 | | 7.50 | 5.00 | | 2.50 |
| Xanthan gum | 0.15 | | 0.05 | | | 0.30 | |
| Sodium carbomer | | 0.20 | | 0.15 | 0.25 | | |
| Vitamin E acetate | 0.60 | | 0.23 | | 0.70 | 1.00 | |
| Fucogel 1000 | | 3.00 | 10.00 | | | | |
| Glycin Soja | | | | 0.50 | | 1.50 | 1.00 |
| Ethylhexyloxy glycin | 0.30 | | | | | | |
| DMDM hydantoin | | 0.60 | 0.40 | 0.20 | | | |
| Glyacil-L | | | | 0.18 | 0.20 | | |
| Methylparaben | 0.15 | | 0.25 | | 0.50 | | |
| Phenoxyethanol | 1.00 | 0.40 | | | 0.40 | 0.50 | 0.40 |
| Trinatrium EDTA | 0.02 | | 0.05 | | | | |
| Iminobernsteinsäure | | | | 0.25 | 1.00 | | |
| Ethanol | 2.00 | 1.50 | | 3.00 | | 1.20 | 5.00 |
| Perfume | 0.10 | 0.25 | 0.30 | | 0.40 | 0.20 | |
| Water | QS (100) | QS (100) | QS (100) | QS (100) | QS (100) | QS (100) | QS (100) |

O/W MAKE UP

| RAW MATERIAL (INCI Desigation) | Formulations (Amounts) | | | | | | |
|---|---|---|---|---|---|---|---|
| | 1 | 2 | 3 | 4 | 5 | 6 | 7 |
| Glycerinmonostearat SE | 0.50 | 1.00 | 3.00 | | | 1.50 | |
| Glycerl Stearat Citrat | 2.00 | | 1.00 | 2.00 | 4.00 | | |
| Stearicacid | | 3.00 | | 2.00 | | | |
| PEG-40 Stearat | 0.50 | | | | | 2.00 | |
| Cetyl Phosphat | | | | | | 1.00 | |
| Cetearyl Sulfat | | | | | | | 0.75 |
| Stearyl Alkohol | | | 3.00 | | | 2.00 | 0.60 |
| Cetyl Alkohol | 2.50 | 1.10 | | 1.50 | 0.60 | | 2.00 |
| Compound | SA | SA | SA | SA | SA | SA | SA |
| Titaniumoxide | 10.00 | 12.00 | 9.00 | 8.50 | 11.00 | 9.50 | 10.00 |
| Ironoxide | 2.00 | 4.00 | 3.00 | 5.00 | 3.40 | 6.00 | 4.40 |
| Zincoxide | | 4.00 | | 2.00 | | 3.00 | |
| C12-15 Alkyl Benzoat | | 0.25 | | | 4.00 | 7.00 | |
| Dicapryl Ether | | | 3.50 | | 2.00 | | |
| Butylenglycol | 5.00 | | 6.00 | | | | |
| Dicaprylat/Dicaprat | | | | | | | |
| Cocoglyceride | | | 6.00 | | 2.00 | | |
| Dimethicon | 0.50 | | 1.00 | | 2.00 | | |
| Cyclomethicon | 2.00 | | 0.50 | | 0.50 | | |
| Shea Butter | | 2.00 | | | | | |
| PVP Hexadecen Copolymer | 0.20 | | | 0.50 | | 1.00 | |
| Glycerin | 3.00 | 7.50 | | 7.50 | 5.00 | | 2.50 |
| Xanthan Gummi | 0.15 | | 0.05 | | | 0.30 | |
| Sodium Carbomer | | 0.20 | | 0.15 | 0.25 | | |
| Vitamin E Acetat | 0.60 | | 0.23 | | 0.70 | 1.00 | |
| Glycin Soja | | | | 0.50 | | 1.50 | 1.00 |
| Ethylhexyloxyglycin | 0.30 | | | | | | |
| DMDM Hydantoin | | 0.60 | 0.40 | 0.20 | | | |
| Glyacil-L | | | | 0.18 | 0.20 | | |
| Methylparaben | 0.15 | | 0.25 | | 0.50 | | |
| Phenoxyethanol | 1.00 | 0.40 | | | 0.40 | 0.50 | 0.40 |
| Trinatrium EDTA | 0.02 | | 0.05 | | | | |
| Iminosuccinicacid | | | | 0.25 | 1.00 | | |
| Ethanol | 2.00 | 1.50 | | 3.00 | | 1.20 | 5.00 |
| Perfume | 0.10 | 0.25 | 0.30 | | 0.40 | 0.20 | |
| Water | QS (100) | QS (100) | QS (100) | QS (100) | QS (100) | QS (100) | QS (100) |

SELF TANNER HYDRODISPERSION

| RAW MATERIAL (INCI Designation) | Formulations (Amounts) | | | | |
|---|---|---|---|---|---|
| | 1 | 2 | 3 | 4 | 5 |
| Ceteaereth-20 | 1.00 | | | 0.50 | |
| Cetyl Alkohol | | | 1.00 | | |
| Luvigel EM | | 2.00 | | 2.50 | 2.00 |
| Acrylat/C10-30 Alkyl Acrylat Crosspolymer | 0.50 | | 0.40 | 0.10 | 0.50 |
| Xanthan Gummi | | 0.30 | 0.15 | | |
| Compound | SA | SA | SA | SA | SA |
| Dihydroxyaceton | | | 3.00 | 5.00 | |
| Aminobenzophenon (e.g., UVINUL A PLUS ™) | 2.00 | 1.50 | 0.75 | 1.00 | 2.10 |
| Titandioxid- microfine | 1.00 | | 1.00 | | 1.00 |
| Zinkoxid- microfine | | 1.90 | | 0.25 | |
| C12-15 Alkyl Benzoat | 2.00 | 2.50 | | | |
| Dicapryl Ether | | 4.00 | | | |
| Butylenglycol Dicaprylat/Dicaprat | 4.00 | | 2.00 | | 6.00 |
| Dicapryl Carbonat | | 2.00 | 6.00 | | |
| Dimethicon | | 0.50 | 1.00 | | |
| Phenyltrimethicon | 2.00 | | 0.50 | | |
| Shea Butter | | 2.00 | | 5.00 | |
| PVP Hexadecen Copolymer | 0.50 | | | 0.50 | 1.00 |
| Tricontanyl PVP | 0.50 | | 1.00 | | |
| Ethylhexylglycerin | | | 1.00 | | 0.80 |
| Glycerin | 3.00 | 7.50 | | 7.50 | 8.50 |
| Gylcin Soja | | | 1.50 | | 1.00 |
| Vitamin E Acetat | 0.50 | | 0.25 | | 1.00 |
| Alpha-Glucosilrutin | 0.60 | | | 0.25 | |
| DMDM Hydantoin | | 0.60 | 0.45 | 0.25 | |
| Glyacil-S | 0.20 | | | | |
| Methylparaben | 0.50 | | 0.25 | 0.15 | |
| Phenoxyethanol | 0.50 | 0.40 | | 1.00 | |
| Trinatrium EDTA | | 0.01 | 0.05 | | 0.10 |
| Ethanol | 3.00 | 2.00 | 1.50 | | 7.00 |
| Parfüm | 0.20 | | 0.05 | 0.40 | |
| Water | QS (100) | QS (100) | QS (100) | QS (100) | QS (100) |

AFTER SUN HYDRODISPERSION

| | Formulations (Amounts) | | | | |
|---|---|---|---|---|---|
| | 1 | 2 | 3 | 4 | 5 |
| Ceteaereth-20 | 1.00 | | | 0.50 | |
| Cetyl Alkohol | | | 1.00 | | |
| Luvigel EM | | 2.00 | | 2.50 | 2.00 |
| Acrylat/C10-30 Alkyl Acrylat Crosspolymer | 0.50 | 0.30 | 0.40 | 0.10 | 0.50 |
| Xanthan Gummi | | | 0.30 | 0.15 | |
| Compound | SA | SA | SA | SA | SA |
| C12-15 Alkyl Benzoat | 2.00 | 2.50 | | | |
| Dicapryl Ether | | 4.00 | | | |
| Butylenglycol Dicaprylat/Dicaprat | 4.00 | | 2.00 | 6.00 | |
| Dicapryl Carbonat | | | 2.00 | 6.00 | |
| Dimethicon | | | 0.50 | 1.00 | |
| Phenyltrimethicon | 2.00 | | 0.50 | | |
| Tricontanyl PVP | 0.50 | | 1.00 | | |
| Ethylhexylglycerin | | | 1.00 | | 0.80 |
| Glycerin | 3.00 | 7.50 | | 7.50 | 8.50 |
| *Gylcin Soja* | | | 1.50 | | 1.00 |
| Vitamin E Acetat | 0.50 | | 0.25 | | 1.00 |
| Alpha-Glucosilrutin | 0.60 | | | 0.25 | |
| Trinatrium EDTA | | 0.01 | 0.05 | | 0.10 |
| Ethanol | 1.00 | 10.00 | 8.00 | 12.00 | 9.00 |
| Perfume | 0.20 | | 0.05 | 0.40 | |
| Water | QS (100) | QS (100) | QS (100) | QS (100) | QS (100) |

WO-EMULSIONS

| RAW MATERIAL (INCI Designation) | Formulations (Amounts) | | | | |
|---|---|---|---|---|---|
| | 1 | 2 | 3 | 4 | 5 |
| Cetyldimethicon Copolyol | | 2.50 | | 4.00 | |
| Polyglyceryl-2-dipolyhydroxystearat | 5.00 | | | | 4.50 |
| PEG-30-dipolyhydroxystearat | | | 5.00 | | |
| Compound | SA | SA | SA | SA | SA |
| Aminobenzophenon (e.g., UVINUL A PLUS ™) | 2.00 | 1.50 | 0.75 | 1.00 | 2.10 |
| Titaniumdioxide- microfine | 1.00 | | 3.00 | | 3.50 |
| Zincoxide- microfine | | 0.90 | | 0.25 | |
| Mineralöl | | 12.00 | 10.00 | | 8.00 |
| C12-15 Alkyl Benzoat | | | | 9.00 | |
| Dicaprylyl Ether | 10.00 | | | | 7.00 |
| Butylenglycol Dicaprylat/Dicaprat | | | 2.00 | 8.00 | 4.00 |
| Dicaprylyl Carbonat | 5.00 | | 6.00 | | |
| Dimethicon | | 4.00 | 1.00 | 5.00 | |
| Cyclomethicon | 2.00 | 25.00 | | | 2.00 |
| Shea Butter | | | 3.00 | | |
| Vaseline | | 4.50 | | | |
| PVP Hexadecen Copolymer | 0.50 | | | 0.50 | 1.00 |
| Ethylhexylglycerin | | 0.30 | 1.00 | | 0.50 |
| Glycerin | 3.00 | 7.50 | | 7.50 | 8.50 |
| *Glycin Soja* | | | 1.00 | 1.50 | 1.00 |
| MgSO4 | 1.00 | 0.50 | | 0.50 | |
| MgCl2 | | | 1.00 | | 0.70 |
| Vitamin E Acetat | 0.50 | | 0.25 | | 1.00 |
| Ascorbyl Palmitat | 0.50 | | | 2.00 | |
| Fucogel 1000 | | | | 3.50 | 7.00 |
| DMDM Hydantoin | | 0.60 | 0.40 | 0.20 | |
| Methylparaben | 0.50 | | 0.25 | 0.15 | |
| Phenoxyethanol | 0.50 | 0.40 | | 1.00 | |
| Trinatrium EDTA | 0.12 | 0.05 | | 0.30 | |
| Ethanol | 3.00 | | 1.50 | | 5.00 |
| Perfume | 0.20 | | 0.40 | 0.35 | |
| Water | QS (100) | QS (100) | QS (100) | QS (100) | QS (100) |

SOLID STABILIZED EMULSIONS (PICKERING EMULSIONS)

| RAW MATERIAL (INCI Designation) | Formulations (Amounts) | | | | |
|---|---|---|---|---|---|
| | 1 | 2 | 3 | 4 | 5 |
| Mineral oil | | | 16.00 | 16.00 | |
| Octyldodecanol | 9.00 | 9.00 | 5.00 | | |
| Caprylic/Capric Triglycerid | 9.00 | 9.00 | 6.00 | | |

SOLID STABILIZED EMULSIONS (PICKERING EMULSIONS)

| RAW MATERIAL (INCI Designation) | Formulations (Amounts) | | | | |
|---|---|---|---|---|---|
| | 1 | 2 | 3 | 4 | 5 |
| C12-15 Alkyl Benzoat | | | | 5.00 | 8.00 |
| Butylen Glycol Dicaprylat/Dicaprat | | | | | 8.00 |
| Dicaprylyl Ether | 9.00 | | | 4.00 | |
| Dicaprylyl Carbonat | | 9.00 | | | |
| Hydroxyoctacosanyl Hydroxystearat | 2.00 | 2.00 | 2.20 | 2.50 | 1.50 |
| Disteardimonium Hectorit | 1.00 | 0.75 | | 0.50 | 0.25 |
| Cera Microcristallina + Paraffinum Liquidum | | 0.35 | | | 5.00 |
| Hydroxypropyl Methylcellulose | | | 0.10 | | 0.05 |
| Dimethicon | | | | | 3.00 |
| Compound | SA | SA | SA | SA | SA |
| Titaniumdioxide + Alumina + Simethicon + Aqua | | 3.00 | | | |
| Titaniumdioxide + Trimethoxycaprylylsilan | | 2.00 | 4.00 | 2.00 | 4.00 |
| Silica Dimethyl Silylat | 2.50 | | | 6.00 | 2.50 |
| Bornitrid | | | 1.00 | | |
| Stärke/-Natriummetaphosphat-Polymer | 2.00 | | | | |
| Tapioca Stärke | | 0.50 | | | |
| Sodium Chlorid | 5.00 | 7.00 | 8.50 | 3.00 | 4.50 |
| Glycerin | | | | 1.00 | |
| Trinatrium EDTA | 1.00 | 1.00 | 1.00 | 1.00 | 1.00 |
| Vitamin E Acetat | 5.00 | 10.00 | 3.00 | 6.00 | 10.00 |
| Ascorbyl Palmitat | 1.00 | 1.00 | | 1.00 | |
| Methylparaben | | 0.60 | | | 0.20 |
| Propylparaben | | | | | 0.20 |
| Phenoxyethanol | | | 0.20 | | |
| Hexamidin Diisethionat | | | 0.40 | 0.50 | 0.40 |
| Diazolidinyl Harnstoff | | | | | 0.08 |
| Ethanol | | | 0.23 | 0.20 | |
| Perfume | 5.00 | | 3.00 | 4.00 | |
| Water | 0.20 | | 0.30 | 0.10 | |
| | QS (100) | QS (100) | QS (100) | QS (100) | QS (100) |

STICKS

| RAW MATERIAL (INCI Designation) | Formulations (Amounts) | | | |
|---|---|---|---|---|
| | 1 | 2 | 3 | 4 |
| Caprylic/Capric Triglycerid | 12.00 | 10.00 | 6.00 | |
| Octyldodecanol | 7.00 | 14.00 | 8.00 | 3.00 |
| Butylene Glycol Dicaprylat/Dicaprat | | | | 12.00 |
| Pentaerythrityl Tetraisostearat | 10.00 | 6.00 | 8.00 | 7.00 |
| Polyglyceryl-3 Diisostearat | 2.50 | | | |
| Bis-Diglyceryl Polyacyladipate-2 | 9.00 | 8.00 | 10.00 | 8.00 |
| Cetearyl Alcohol | 8.00 | 11.00 | 9.00 | 7.00 |
| Myristyl Myristate | 3.50 | 3.00 | 4.00 | 3.00 |
| Beeswax | 5.00 | 5.00 | 6.00 | 6.00 |
| Cera Carnauba | 1.50 | 2.00 | 2.00 | 1.50 |
| Cera Alba | 0.50 | 0.50 | 0.50 | 0.40 |
| C16-40 Alkyl Stearat | | 1.50 | 1.50 | 1.50 |
| Compound | SA | SA | SA | SA |
| Aminobenzophenon (e.g., UVINUL A PLUS ™) | 2.00 | 1.50 | 0.75 | 9.00 |
| Titaniumdioxide- microfine | 1.00 | | 3.00 | |
| Zincoxide- microfine | | 1.00 | | 0.25 |
| Vitamin E Acetat | 0.50 | 1.00 | | |
| Ascorbyl Palmitat | 0.05 | | 0.05 | |
| Buxux Chinensis | 2.00 | 1.00 | | 1.00 |
| Perfume, BHT | 0.10 | 0.25 | | 0.35 |
| Ricinus Communis | QS (100) | QS (100) | QS (100) | QS (100) |

| SELF TANNER PIT-EMULSION | | | | | | | | |
|---|---|---|---|---|---|---|---|---|
| | Formulations (Amounts) | | | | | | | |
| | 1 | 2 | 3 | 4 | 5 | 6 | 7 | 8 |
| Glycerinmonostearat SE | 0.50 | 2.00 | 3.00 | 5.00 | | 0.50 | 4.00 | |
| Glyceryl Isostearat | | | | | 3.50 | 4.00 | 2.00 | |
| Isoceteth-20 | | | 0.50 | | 2.00 | | | |
| Ceteareth-12 | | | 5.00 | 1.00 | | | 3.50 | 5.00 |
| Ceteareth-20 | | | 5.00 | 1.00 | | | | 3.50 |
| PEG-100 Stearat | | | | 2.80 | | 2.30 | 3.30 | |
| Cetyl Alkohol | 5.20 | | 1.20 | 1.00 | 1.30 | | 0.50 | 0.30 |
| Cetyl Palmitat | 2.50 | 1.20 | | 1.50 | | 0.50 | | 1.50 |
| Cetyl Dimethicon Copolyol | | | | 0.50 | | 1.00 | | |
| Polyglyceryl-2 | | | | 0.75 | 0.30 | | | |
| Compound | SA | SA | SA | SA | SA | SA | SA | SA |
| Dihydroxyaceton | | | 3.00 | 5.00 | | | 4.00 | |
| Aminobenzophenon (e.g., UVINUL A PLUS ™) | 2.00 | 1.50 | 0.75 | 1.00 | 2.10 | 4.50 | 5.00 | 2.10 |
| Titandioxide-microfine | 1.00 | | 1.50 | | 3.50 | | 1.50 | 1.00 |
| Zinkoxide-microfine | | 1.00 | | 0.25 | | 2.00 | | 1.50 |
| C12-15 Alkyl Benzoat | 3.50 | | | 6.35 | | | | 0.10 |

| SELF TANNER PIT-EMULSION | | | | | | | | |
|---|---|---|---|---|---|---|---|---|
| | Formulations (Amounts) | | | | | | | |
| | 1 | 2 | 3 | 4 | 5 | 6 | 7 | 8 |
| Cocoglyceride | | 3.00 | | 3.00 | | | | 1.00 |
| Dicapryl Ether | 4.50 | | | | | | | |
| Dicaprylyl Carbonat | | 4.30 | | 3.00 | | | | 7.00 |
| Dibutyl Adipate | | | | 0.50 | | | | 0.30 |
| Phenyltrimethicone | 2.00 | | | 3.50 | | 2.00 | | |
| Cyclomethicon | | 3.00 | | | | | | |
| Ethyl Galaktomannan | | 0.50 | | | 2.00 | | | |
| Hydrogenated Coco-Glyceride | | | | | 3.00 | 4.00 | | |
| Abil Wax 2440 | | | | | | 1.50 | 2.00 | |
| PVP Hexadecen Copolymer | | | | 1.00 | 1.20 | | | |
| Glycerin | 4.00 | 6.00 | 5.00 | | 8.00 | 10.00 | | |
| Vitamin E Acetat | 0.20 | 0.30 | 0.40 | | 0.30 | | | |
| Shea Butter | | 2.00 | | 3.60 | | 2.00 | | |
| Iodopropyl Butylcarbamat | 0.12 | | | | 0.20 | | | |
| DMDM Hydantoin | 0.10 | | | | 0.12 | | 0.13 | |
| Methylparaben | | 0.50 | 0.30 | | 0.35 | | | |
| Phenoxyethanol | 0.50 | 0.40 | | 1.00 | | | | |
| Octoxyglycerin | | 0.30 | | | 1.00 | | 0.35 | |
| Ethanol | 2.00 | | 2.00 | | | 5.00 | | |
| Trinatrium EDTA | 0.40 | | 0.15 | | | 0.20 | | |
| Perfume | 0.20 | | 0.20 | | 0.24 | 0.16 | 0.10 | 0.10 |
| Water | QS (100) | QS (100) | QS (100) | QS (100) | QS (100) | QS (100) | QS (100) | QS (100) |

| OILGELS | | | | |
|---|---|---|---|---|
| RAW MATERIAL (INCI Designation) | Formulations (Amounts) | | | |
| | 1 | 2 | 3 | 4 |
| Caprylic/Capric Triglycerid | 12.00 | 10.00 | 6.00 | |
| Octyldodecanol | 7.00 | 14.00 | 8.00 | 3.00 |
| Butylene Glycol | | | | 12.00 |
| Dicaprylat/Dicaprat | | | | |
| Pentaerythrityl Tetraisostearat | 10.00 | 6.00 | 8.00 | 7.00 |
| Polyglyceryl-3 Diisostearat | 2.50 | | | |
| Bis-Diglyceryl Polyacyladipate-2 | 9.00 | 8.00 | 10.00 | 8.00 |
| Myristyl Myristate | 3.50 | 3.00 | 4.00 | 3.00 |
| Bentone -34 | 5.00 | 5.00 | 6.00 | 6.00 |
| Propylencarbonat | 15.00 | 20.00 | 18.00 | 19.50 |
| Compound | SA | SA | SA | SA |
| Vitamin E Acetat | 0.50 | 1.00 | | |
| Ascorbyl Palmitat | 0.05 | | 0.05 | |
| *Buxux Chinensis* | 2.00 | 1.00 | | 1.00 |
| Perfume, BHT | 0.10 | 0.25 | | 0.35 |
| *Ricinus Communis* | QS (100) | QS (100) | QS (100) | QS (100) |

In still further embodiments, the present invention comprises at least one inorganic pigment. In some preferred embodiments, these inorganic pigments are based on metaloxides and/or other water slightly soluble or insoluble metal compounds, including but not limited to compounds such as zinc oxides (ZnO), titanium ($TiO_2$), iron (e.g., $Fe_2O_3$), zirconium ($ZrO_2$), silica ($SiO_2$), manganese (e.g., MnO), aluminium ($Al_2O_3$), cer (e.g., $Ce_2O_3$), and mixed oxides of these oxides, as well as blends thereof. In some embodiments, the metaloxides are microfine grade, while in other embodiments, the metaloxides are pigment grade. In further embodiments, the metaloxides are a mixture of microfine and pigment grades.

In additional embodiments, the inorganic pigments are coated (i.e., they are treated on the surface). In some particularly preferred embodiments, the surface is coated with a thin, hydrophobic film. In some other particularly preferred embodiments, the surface is coated with a thin, hydrophilic film. In yet additional embodiments, the present invention provides compositions comprising various make ups and make up constituents. For example, in some embodiments, the present invention provides various dyes and/or pigments. In some embodiments, useful pigments include, but are not limited to titanium dioxide, mica, iron oxides (e.g. $Fe_2O_3$, $Fe_3O_4$, FeO(OH), etc.) and/or stannous oxide. The present invention further provides colorants, including but not limited to carmine, blue, chromooxide, ultramarine and/or purple manganese. The colorants and pigments of some most preferred embodiments are known to those in the art and provided previously (See e.g., Colour Index Nummern (CIN), Rowe Colour Index, $3^{rd}$ ed., Society of Dyers and Colourists, Bradford, England [1971]).

In additional embodiments, pearlescent pigments based on mica/metaloxide find use, as described above. However, it is not intended that the present invention be limited to these particular pigments, as additional pearlescent pigments find use in various embodiments of the present invention.

The following formulations provide additional examples of the use of the present invention.

| RAW MATERIAL | Formulation (Amounts) | | | | |
|---|---|---|---|---|---|
| (INCI Designation | 1 | 2 | 3 | 4 | 5 |
| Sodium Carbomer | | 0.2 | | | |
| Acrylates/$C_{10}$-$C_{30}$ Alkyl Acrylate Crosspolymer | 0.3 | 0.2 | 0.6 | | |
| Hydroxypropyl Cellulose | | | | 1.0 | 1.50 |
| Xanthan Gummi | | 0.6 | 0.2 | 1.0 | 1.0 |
| Compound | 0.5 | 0.1 | 0.01 | 0.01 | 1.0 |
| Dioctyl Butamidotriazon | 2.0 | 2.0 | 1.0 | | |
| Ethylhexyl Triazon | 4.0 | 4.0 | 5.0 | | |
| Aniso Triazin | 1.0 | 0.5 | | 2.0 | 2.5 |
| Bisoctyltriazol | | | | 6.0 | |
| Drometrizole Trisiloxane | | | | | |
| PhenylbenzmidazSulfonicacid | 2.0 | | | 1.0 | |

| RAW MATERIAL | Formulation (Amounts) | | | | |
|---|---|---|---|---|---|
| (INCI Designation | 1 | 2 | 3 | 4 | 5 |
| Bisimidazylate | | | | 1.0 | |
| Terephthalylidene Dicamphor Sulfonic Acid | | | | 0.2 | |
| Ethylhexyl Methoxycinnamat | 7.5 | 10.0 | | 5.0 | |
| Octocrylen | | | | | 5.0 |
| Dimethicone-diethylbenzalmalonate | | | | 4.0 | |
| Ethylhexyl Salicylate | | | | | |
| Homosalate | | | | | |
| Butyl Methoxydibenzoylmethan | 1.0 | 1.0 | 4.0 | | |
| Titan dioxide | 1.0 | 4.0 | | | |
| Zinc oxide | | | | 4.0 | |
| Caprylic/Capric Triglycerid | | | 2.0 | | |
| Hydrogenated Coco-Glyceride | | | 3.0 | | |
| C12-15 Alkyl Benzoat | 2.0 | 2.5 | 3.0 | | |
| Dicaprylyl Ether | | 4.0 | | | |
| Butylenglycol Di-caprylat/Dicaprat | 4.0 | | 2.0 | 6.0 | |
| Dicaprylyl Carbonat | | 2.0 | | | |
| Cetyl Dimethicon | 2.0 | 0.5 | 1.0 | | |
| Shea Butter | | 2.0 | | | |
| PVP Hexadecen Copolymer | 0.5 | | 0.05 | 0.5 | |
| Glycerin | 3.0 | 7.5 | | 7.5 | 2.5 |
| Tocopherol | | 0.5 | 0.75 | | 0.2 |
| Trisodium EDTA | 1.0 | 0.5 | 0.5 | 1.0 | 1.5 |
| Natriumcitrat | | 0.2 | | | |
| Zitronensäure | | 0.1 | | 0.1 | 0.1 |
| DMDM Hydantoin | | 0.6 | | 0.2 | |
| Methylparaben | 0.5 | | 0.3 | 0.15 | |
| Phenoxyethanol | 0.5 | 0.4 | 0.4 | 1.0 | 0.60 |
| Ethanol | 3.0 | 2.0 | 3.0 | | 1.0 |
| Perfume | 0.2 | | | 0.2 | 0.2 |
| Water | QS (100) | QS (100) | QS (100) | QS (100) | QS (100) |

| RAW MATERIAL (INCI Designation) | Formulations (Amounts) | | | | |
|---|---|---|---|---|---|
| | 1 | 2 | 3 | 4 | 5 |
| Sodium Carbomer | 0.5 | | | 1.5 | |
| Acrylates/C$_{10}$-C$_{30}$ Alkyl Acrylate Crosspolymer | | 0.4 | 0.1 | | 0.75 |
| Hydroxypropyl Cellulose | | | 0.5 | | 0.25 |
| Xanthan Gummi | 0.2 | 0.4 | | | |
| Compound | 0.5 | 0.1 | 0.01 | 0.01 | 1.0 |
| Dioctyl Butamidotriazon | 1.0 | | 2.0 | | |

| RAW MATERIAL (INCI Designation) | Formulations (Amounts) | | | | |
|---|---|---|---|---|---|
| | 1 | 2 | 3 | 4 | 5 |
| Ethylhexyl Triazon | | 2.0 | | 2.0 | |
| Aniso Triazin | 1.0 | 0.2 | 3.0 | 1.0 | |
| Bisoctyltriazol | | | | | 8.0 |
| Drometrizole Trisiloxane | | | | | 4.0 |
| Phenylbenzmidazole Sulfonicacid | | 1.5 | | | |
| Bisimidazylate | | | 1.5 | | |
| Terephthalylidene Dicamphor Sulfonic Acid | | | | | 0.5 |
| Ethylhexyl Methoxycinnamat | | 7.5 | 5.0 | 10.0 | |
| Octocrylen | 10.0 | | 5.0 | | 5.0 |
| Dimethicone-diethylbenzalmalonate | | | | | 2.5 |
| Ethylhexyl Salicylate | | | 3.5 | 5.0 | |
| Homosalate | | | 4.0 | | |
| Butyl Methoxydibenzoylmethan | 0.5 | | | | |
| Titandioxide | 1.5 | 2.0 | 1.0 | | 2.5 |
| Zincoxide | | | 1.0 | | 0.5 |
| Caprylic/Capric Triglycerid | | | | | |
| Hydrogenierte Coco-Glyceride | | | | | |
| C12-15 Alkyl Benzoat | | | | | 5.0 |
| Dicaprylyl Ether | | | | | 7.5 |
| Butylenglycol Dicaprylat/Dicaprat | | | | | |
| Dicaprylyl Carbonat | | 7.5 | | | |
| Cetyl Dimethicon | | | | | |
| Shea Butter | | | | | 3.0 |
| PVP Hexadecen Copolymer | 0.5 | | 0.75 | | 1.0 |
| Glycerin | 5.0 | | 10.0 | | |
| Tocopherol | 0.3 | | 1.5 | | 1.0 |
| Trisodium EDTA | 0.5 | | 0.1 | 0.5 | |
| Natriumcitrat | | | 0.3 | | |
| Zitronensäure | | | 0.15 | | |
| DMDM Hydantoin | | | | 0.3 | 0.15 |
| Methylparaben | | 0.4 | | | |
| Phenoxyethanol | | 1.0 | | | |
| Ethanol | 7.5 | | 5.0 | | 7.0 |
| Perfume | | 0.25 | | 0.2 | |
| Water | QS (100) | QS (100) | QS (100) | QS (100) | QS (100) |

| RAW MATERIAL (INCI Designation) | Formulations (Amounts) | | | | | |
|---|---|---|---|---|---|---|
| | 1 | 2 | 3 | 4 | 5 | 6 |
| Sodium Carbomer | 0.5 | 1.5 | 1.0 | | | 0.5 |
| Acrylates/C$_{10}$-C$_{30}$ Alkyl Acrylate Crosspolymer | 1.0 | | | 0.75 | 1.0 | |
| Hydroxypropyl Cellulose | | | 0.4 | 1.0 | | 1.0 |
| Xanthan Gummi | | 0.6 | 0.2 | 1.0 | 1.0 | |
| BBI | 4.0 | 0.5 | 3.0 | 2.0 | 4.0 | 1.5 |
| Dioctyl Butamidotriazon | 2.0 | 2.0 | | 2.0 | | 1.0 |
| Ethylhexyl Triazon | | 4.0 | 5.0 | 4.0 | | |
| Aniso Triazin | 1.0 | | | 1.0 | 2.5 | 1.0 |
| Bisoctyltriazol | | | 4.0 | | | |
| Drometrizole Trisiloxane | | 3.0 | | | | |
| Phenylbenzmidazole Sulfonicacid | 2.0 | | | 1.0 | | |
| Bisimidazylate | | | 1.5 | | | 3.5 |
| Terephthalylidene Dicamphor Sulfonic Acid | | | | 0.2 | | 1.0 |
| Ethylhexyl Methoxycinnamat | | 10.0 | | 5.0 | | |
| Octocrylen | 10.0 | | | | 5.0 | |
| Dimethicone-diethylbenzalmalonate | | | | 4.0 | | |
| Ethylhexyl Salicylate | | | | | | 5.0 |
| Homosalate | | | | 5.0 | | |
| Butyl Methoxydibenzoylmethan | 1.0 | 1.0 | 4.0 | | | 0.5 |
| Titandioxide | 1.0 | 4.0 | | | | 1.5 |
| Zincoxide | | | | | 4.0 | |

-continued

| RAW MATERIAL (INCI Designation) | Formulations (Amounts) | | | | | |
|---|---|---|---|---|---|---|
| | 1 | 2 | 3 | 4 | 5 | 6 |
| Caprylic/Capric Triglycerid | | | 2.0 | | | |
| Paraffinöl | | | | 1.0 | | |
| C$_{12}$-C$_{15}$ Alkyl Benzoat | 2.0 | 2.5 | 3.0 | | | |
| Dicaprylyl Ether | | 4.0 | | | | |
| Isohexadecen | 4.0 | | | 2.0 | 6.0 | |
| Dicaprylyl Carbonat | | 2.0 | | | | |
| Dibutyl Adipat | 2.0 | 0.5 | 1.0 | | | |
| Cylomethicon | | | | 3.0 | | |
| Jojobaöl | | 2.0 | | | | |
| PVP Hexadecen Copolymer | 0.5 | | 0.05 | 0.5 | | 0.5 |
| Butylen Glycol | 3.0 | 7.5 | | 7.5 | 2.5 | 5.0 |
| Ascorbyl-Palmitate | | 0.5 | 0.75 | | 0.2 | 0.3 |

| RAW MATERIAL (INCI Designation) | Formulations (Amounts) | | | | | |
|---|---|---|---|---|---|---|
| | 1 | 2 | 3 | 4 | 5 | 6 |
| Octoxyglycerin | | 1.0 | | 0.5 | | 1.0 |
| Glycin Soja | | | 2.0 | | | 1.5 |
| Trisodium EDTA | 1.0 | 0.5 | 0.5 | | 1.5 | 0.5 |
| Caustic acid | 1.0 | 0.2 | 0.25 | | | |
| Iodopropyl Butylcarbamat | | | 0.6 | | 0.2 | |
| Phenoxyethanol | | | 0.4 | 1.0 | | |
| Ethanol | 5.0 | 2.0 | 7.0 | | | |
| Perfume | 0.2 | | | 0.2 | 0.2 | |
| Water | QS (100) | QS (100) | QS (100) | QS (100) | QS (100) | QS (100) |

The following formula provides an example of an after-shave product comprising the BBI-AV of the present invention.

| AFTER SHAVE LOTION | | | |
|---|---|---|---|
| | % | Ingredient | INCI |
| A | 10.0 | Luvitol EHO | Cetearyl Ethylhexanoate |
| | 5.0 | Vitamin E Acetate | Tocopheryl Acetate |
| | 1.0 | Bisabolol rac. | Bisabolol |
| | 0.1 | Perfume | |
| | 0.3 | Carbopol Ultrez 21 | Acrylates/C10-30 Alkyl Acrylate Crosspolymer |
| B | 15.0 | Ethanol | Alcohol |
| | 1.0 | D-Panthenol USP | Panthenol |
| | 3.0 | Glyerin 87% | Glycerin |
| | 0.1 | Triethanolamine Care | Triethanolamine |
| | SA | Compound | |
| | QS | Water dem. | Aqua dem. |

Production: Weigh out the components of Phase A and mix them. Dissolve Phase B, stir it into Phase A and homogenize well.

Measure Values:
 Viscosity: 18 500 mPa s Brookfield RVD II+
 pH value: 5.8

The following formula provides an example of an after-shave product comprising the BBI-AV of the present invention.

| PRE SHAVE | | | |
|---|---|---|---|
| | % | Ingredient | INCI |
| A | 80 | Ethanol | Alcohol |
| | 3.0 | Vitamin E Acetate | Tocopheryl Acetate |
| | 1.0 | Bisabolol rac. | Bisabolol |
| | 0.2 | Perfume | |
| | 0.1 | Menthol | Menthol |
| | 4.0 | Luvitol EHO | Cetearyl Ethylhexanoate |
| | 2.0 | Eutanol G | Octyldodecanol |
| | 2.0 | Miglyol 812 | Caprylic/Capric Triglyceride |
| | 2.0 | D-Panthenol USP | Panthenol |
| | 2.0 | Whitch Hazel Distillate | *Hamamelis Virginiana* (Whitch Hazel) Distillate |
| | 2.0 | Jojoba Oil | *Simmondsia Chinensis* (Jojoba) Seed Oil |
| | SA | Compound | |

Production: Weigh out the components of Phase A and dissolve them clearly.

The after-shave and pre-shave formula provided above contain sufficient BBI-AV (Compound) to provide the desired effect(s). In some embodiments, the concentration of BBI-AV is in the range of about 1,000 ppm to about 10,000 ppm. In the following formulations, typical concentrations of BBI-AV used range from about 100 ppm to about 1,000 ppm or from about 1,000 ppm to about 10,000 ppm. However, it is not intended that the present invention be limited to this specific concentration range, as other concentrations find use in other embodiments of the present invention.

The following formula provides an example of an after-sun product comprising the BBI-AV of the present invention.

| AFTER SUN LOTION | | | |
|---|---|---|---|
| | % | Ingredient | INCI |
| A | 0.4 | Carbopol 1342 | Acrylates/C10-30 Alkyl Acrylate Crosspolymer |
| | 15.0 | Luvitol EHO | Cetearyl Ethylhexanoate |
| | 0.2 | Bisabolol rac. | Bisabolol |
| | 1.0 | Vitamin E Acetate | Tocopheryl Acetate |
| | q.s. | Perfume | |
| B | 1.0 | D-Panthenol USP | Panthenol |
| | 15.0 | Ethanol 96% | Alcohol |
| | 3.0 | Glycerin 87% | Glycerin |
| | SA | Compound | |
| | 64.2 | Water dem. | Aqua dem. |
| C | 0.2 | Triethanolamine Care | Triethanolamine |

Production: Mix the components of Phase A. Dissolve Phase B and stir it into Phase A whilst homogenizing. Neutralize with Phase C and homogenize again.

Measure Values:
 Viscosity: 7 500 mPa s Haake Viscotester VT-02
 pH value: 6.0

The following formula provides an example of a facial cleanser product comprising the BBI-AV of the present invention.

| FACIAL CLEANSER | | | |
|---|---|---|---|
| | % | Ingredient | INCI |
| A | 10.0 | Luvitol EHO | Cetearyl Ethylhexanoate |
| | 10.0 | Miglyol 812 | Caprylic/Capric Triglyceride |
| | 1.5 | Dow Corning 345 Fluid | Cyclopentasiloxane, Cyclohexasiloxane |
| | 2.0 | Cremophor CO 40 | PEG-40 Hydrogenated Castor Oil |

-continued

FACIAL CLEANSER

| | % | Ingredient | INCI |
|---|---|---|---|
| B | 3.5 | Luvigel EM | Caprylic/Capric Triglyceride, Sodium Acrylates Copolymer |
| C | 1.0 | Vitamin E Acetate | Tocopheryl Acetate |
| | 0.2 | Bisabolol rac. | Bisabolol |
| | QS | Preservative | |
| | QS | Perfume | |
| D | 3.0 | Luviquat Care | Polyquaternium-44 |
| | 0.5 | Luviquat Mono LS | Cocotrimonium Methosulfate |
| | 0.5 | Cremophor A 25 | Ceteareth-25 |
| | 0.2 | D-Panthenol 50 P | Panthenol, Propylene Glycol |
| | 4.0 | 1,2 Propylene Glycol Care | Propylene Glycol |
| | 0.1 | Edeta BD | Disodium EDTA |
| | SA | Compound | |
| | QS | Water dem. | Aqua dem. |

Production: Dissolve Phase A, then stir in Phase B. Fold in Phase C. Dissolve Phase D, stir it into the combined Phases A+B+C, homogenize and stir again for 15 min.
Measure Values:
Viscosity: 7 200 mPa s Brookfield RVT
pH value: 5.8

The following formula provides an example of a daily care body spray product with SPF 8 comprising the BBI-AV of the present invention.

DAILY CARE BODY SPRAY - SPF 8

| | % | Ingredient | INCI |
|---|---|---|---|
| A | 3.0 | Uvinul MC 80 | Ethylhexyl Methoxycinnamate |
| | 2.0 | Uvinul A Plus ™ | Diethylamino Hydroxybenzoyl Hexyl Benzoate |
| | 1.0 | Luviquat UltraCare | Polyquaternium-44 |
| | 3.0 | 1,2 Propylenglycol Care | Propylene Glycol |
| | 2.0 | D-Panthenol 50 P | Panthenol, Propylene Glycol |
| | 1.0 | Dow Corning 345 Fluid | Cyclopentasiloxane, Cyclohexasiloxane |
| | 10.0 | Eutanol G | Octyldodecanol |
| | 0.5 | Luviskol K 30 | PVP |
| | 10.0 | Miglyol 812 | Caprylic/Capric Triglyceride |
| | 3.0 | Finsolv TN | C12-15 Alkyl Benzoate |
| | 3.0 | Glycerin 87% | Glycerin |
| | 1.0 | Vitamin E Acetate | Tocopheryl Acetate |
| | 0.3 | Bisabolol rac. Compound | Bisabolol |
| | QS | Ethanol | Alcohol |

Production: Weigh out the components of Phase A and dissolve them clearly.
Measure Values:
SPF: 8 Colipa Task Force "Sun Protection Measurement"

The following formula provides an example of a daily care sun care lotion product with SPF 27 comprising the BBI-AV of the present invention.

SUN CARE LOTION - SPF 27

| | % | Ingredient | INCI |
|---|---|---|---|
| A | 4.5 | Uvinul MC 80 | Ethylhexyl Methoxycinnamate |
| | 2.0 | Uvinul A Plus ™ | Diethylamino Hydroxybenzoyl Hexyl Benzoate |
| | 3.0 | Uvinul N 539 T | Octocrylene |
| | 2.5 | Cosmacol EMI | Di-C12-13 Alkyl Malate |

SUN CARE LOTION - SPF 27

| | % | Ingredient | INCI |
|---|---|---|---|
| | 0.5 | Vitamin E Acetate | Tocopheryl Acetate |
| | 4.0 | Tego Care 450 | Polyglyceryl-3 Methyl Glucose Distearate |
| B | 3.5 | Cetiol SN Deo | Cetearyl Isononanoate |
| | 1.0 | Ganex V-220 | VP/Eicosene Copolymer |
| | 5.0 | Isohexadecane | Isohexadecane |
| | 2.5 | Cosmacol EMI | Di-C12-13 Alkyl Malate |
| | 3.0 | Uvinul TiO2 | Titanium Dioxide, Trimethoxycaprylylsilane |
| C | 5.0 | Glycerin 87% | Glycerin |
| | 1.0 | Lanette E | Sodium Cetearyl Sulfate |
| | 0.5 | Keltrol | Xanthan Gum |
| | 60.7 | Water dem. | Aqua dem. |
| D | SA | Compound | |
| | 1.0 | Phenonip | Phenoxyethanol, Methylparaben, Ethylparaben, |
| | 0.3 | Bisabolol rac. | Bisabolol |

Production: Heat Phases A and B separately to about 80° C. Stir Phase B into Phase A whilst homogenizing. Heat Phase C to about 80° C. and stir it into the combined Phases A+B whilst homogenizing. Cool to about 40° C. add Phase D and homogenize again.
Measure Values:
Viscosity: 3 200 mPa s Brookfield RVD II+
pH value: 6.0
SPF: 27 Colipa Task Force "Sun Protection Measurement"

SUN CARE LOTION - SPF 24

| | % | Ingredient | INCI |
|---|---|---|---|
| A | 2.0 | Cremophor A 6 | Ceteareth-6, Stearyl Alcohol |
| | 2.0 | Cremophor A 25 | Ceteareth-25 |
| | 3.0 | Syncrowax HRC | Tribehenin |
| | 2.0 | Lanette O | Cetearyl Alcohol |
| | 2.0 | Luvitol EHO | Cetearyl Ethylhexanoate |
| | 5.0 | Uvinul MC 80 | Ethylhexyl Methoxycinnamate |
| | 1.0 | Uvinul T 150 | Ethylhexyl Triazone |
| | 1.0 | Ganex V-220 | VP/Eicosene Copolymer |
| | 7.0 | Isopropyl Myristate | Isopropyl Myristate |
| B | 5.0 | Z-Cote HP-1 | Zinc Oxide, Triethoxycaprylylsilane |
| C | 0.2 | Keltrol | Hydroxyethyl Acrylate/Sodium Acryloyldimethyl Taurate Copolymer, Squalane, Polysorbate 60 |
| | 0.2 | Edeta BD | Disodium EDTA |
| | 5.0 | 1,2 Propylene Glycol Care | Propylene Glycol |
| | 0.5 | D-Panthenol USP | Panthenol |
| | 61.9 | Water dem. | Aqua dem. |
| D | SA | Compound | |
| | 0.5 | Euxyl K 300 | Phenoxyethanol, Methylparaben, Butylparaben, Ethylparaben, Propylparaben, Isobutylparaben |
| | 1.0 | Vitamin E Acetate | Tocopheryl Acetate |
| | 0.2 | Bisabolol rac. | Bisabolol |

Production: Heat Phase A to 80° C., add Phase B and homogenize for 3 min. Heat Phase C to about 80° C., and stir it into the combined Phases A+B whilst homogenizing. Cool to about 40° C., add Phase D, and homogenize.
Measure Values:
Viscosity: 5 000 mPa s Brookfield RVD II+
pH value: 7.5
SPF: 24 Colipa Task Force "Sun Protection Measurement"

The following formula provides an example of a sun screen emulsion product with SPF 28 comprising the BBI-AV of the present invention.

| SUN SCREEN EMULSION - SPF 28 | | | |
|---|---|---|---|
| | % | Ingredient | INCI |
| A | 3.5 | Cremophor A 6 | Ceteareth-6, Stearyl Alcohol |
| | 1.5 | Cremophor A 25 | Ceteareth-25 |
| | 7.5 | Uvinul MC 80 | Ethylhexyl Methoxycinnamate |
| | 2.0 | Uvinul A Plus ™ | Diethylamino Hydroxybenzoyl Hexyl Benzoate |
| | 2.0 | Dow Corning 345 Fluid | Cyclopentasiloxane, Cyclohexasiloxane |
| | 0.5 | Bees Wax 3044 PH | Bees Wax |
| | 3.0 | Lanette O | Cetearyl Alcohol |
| | 10.0 | Miglyol 812 | Caprylic/Capric Triglyceride |
| B | 5.0 | T-Lite SF-S | Titanium Dioxide, Silica, Methicone, Alumina |
| C | 3.0 | Glycerin 87% | Glycerin |
| | 0.2 | Edeta BD | Disodium EDTA |
| | 0.3 | Keltrol T | Xanthan Gum |
| | 1.0 | Plantacare 2000 | Decyl Glucoside |
| | 2.0 | D-Panthenol 50 P | Panthenol, Propylene Glycol |
| | 57.3 | Water dem. | Aqua dem. |
| D | SA | Compound | |
| | 1.0 | Vitamin E Acetate | Tocopheryl Acetate |
| | 0.2 | Bisabolol rac. | Bisabolol |
| | QS | Perfume | |
| | QS | Preservative | |

Production: Heat Phase A to 80° C., add Phase B and homogenize for 3 min. Heat Phase C to about 80° C., and stir it into the combined Phases A+B whilst homogenizing. Cool to about 40° C., add Phase D and homogenize.

Measure Values:

Viscosity: 7 500 mPa s Brookfield RVD II+ pH value: 6.6

SPF: 28 Colipa Task Force "Sun Protection Measurement"

The following formula provides an example of a foot balm product comprising the BBI-AV of the present invention.

| FOOT BALM | | | |
|---|---|---|---|
| | % | Ingredient | INCI |
| A | 2.0 | Cremophor A 6 | Ceteareth-6, Stearyl Alcohol |
| | 2.0 | Cremophor A 25 | Ceteareth-25 |
| | 5.0 | Luvitol EHO | Cetearyl Ethylhexanoate |
| | 4.0 | Lanette 16 | Cetyl Alcohol |
| | 4.0 | Cutina Gms | Glyceryl Stearate |
| | 5.0 | Paraffin Oil | Mineral Oil |
| | 0.2 | Menthol | Menthol |
| | 0.5 | Camphor | Camphor |
| B | 70.3 | Water dem. | Aqua dem. |
| | QS | Preservative | |
| C | SA | Compound | |
| | 1.0 | Bisabolol rac. | Bisabolol |
| | 1.0 | Vitamin E Acetate | Tocopheryl Acetate |
| D | 5.0 | Witch Hazel Extract | Witch Hazel Extract |

Production: Heat Phases A and B to about 80° C. separately. Stir Phase B into Phase A whilst homogenizing. Cool to about 40° C., add Phases C and D and homogenize again. Cool to room temperature.

Measure Values:

Viscosity: 20 500 mPa s Brookfield RVD II+ pH value: 6.0

The following formula provides an example of a refreshing foot gel product comprising the BBI-AV of the present invention.

| REFRESHING FOOT GEL | | | |
|---|---|---|---|
| | % | Ingredient | INCI |
| A | 0.6 | Carbopol Ultrez 21 | Acrylates/C10-30 Alkyl Acrylate Crosspolymer |
| | 45.9 | Water dem. | Aqua dem. |
| B | 1.0 | Bisabolol rac. | Bisabolol |
| | 0.5 | Farnesol | Farnesol |
| | q.s. | Perfume | |
| | 4.5 | Cremophor CO 40 | PEG-40 Hydrogenated Castor Oil |
| | 1.0 | Neutrol TE | Tetrahydroxypropyl Ethylenediamine |
| | 1.5 | Menthol | Menthol |
| | SA | Compound | |
| | 45.0 | Ethanol 96% | Alcohol |
| | QS | FD&C Blue No. 1 | C.I. 42 090, FD&C Blue No. 1 |

Production: Phase A: Intersperse the Carbopol and let it settle on the bottom of the beaker. Dissolve Phase B and stir it into Phase A.

Measure Values:

Viscosity: 14 500 mPa s Brookfield RVD II+ pH value: 7.5

The following formula provides an example of a skin conditioning gel product comprising the BBI-AV of the present invention.

| Skin Conditioning Gel | | | |
|---|---|---|---|
| | % | Ingredient | INCI |
| A | 3.6 | Cremophor CO 40 | PEG-40 Hydrogenated Castor Oil |
| | 15.0 | Ethanol | Alcohol |
| | 0.1 | Bisabolol rac. | Bisabolol |
| | 0.5 | Vitamin E Acetate | Tocopheryl Acetate |
| | QS | Perfume | |
| B | 3.0 | D-Panthenol USP | Panthenol |
| | 0.6 | Carbopol 940 | Carbomer |
| | SA | Compound | |
| | 76.4 | Water dem. | Aqua dem. |
| C | 0.8 | Triethanolamine Care | Triethanolamine |

Production: Dissolve Phase A clearly. Allow Phase B to swell and neutralize with Phase C. Stir Phase A into the neutralized Phase B and homogenize.

Measure Values:

Viscosity: 57 600 mPa s Brookfield RVD II+ pH value: 7.7

The following formula provides an example of a W/O emulsion comprising the BBI-AV of the present invention.

| W/O EMULSION | | | |
|---|---|---|---|
| | % | Ingredient | INCI |
| A | 6.0 | Cremophor WO 7 | PEG-7 Hydrogenated Castor Oil |
| | 8.0 | Luvitol EHO | Cetearyl Ethylhexanoate |
| | 5.0 | Isopropyl Myristate | Isopropyl Myristate |
| | 15.0 | Paraffin Oil | Mineral Oil |
| | 0.3 | Magnesium Stearate | Magnesium Stearate |
| | 0.3 | Aluminum Stearate | Aluminum Stearate |
| | 2.0 | Elfacos ST9 | PEG-45/Dodecyl Glycol Copolymer |
| B | 5.0 | Glycerin 87% | Glycerin |
| | 0.7 | Magnesium Sulfate-7-hydrate | Magnesium Sulfate |
| | 56.6 | Water dem. | Aqua dem. |
| C | SA | Compound | |
| | 0.5 | Vitamin E Acetate | Tocopheryl Acetate |
| | 0.6 | Bisabolol rac. | Bisabolol |

Production: Heat Phases A and B separately to about 85° C. Stir Phase B into Phase A and homogenize. Cool to about 40° C. whilst stirring, add Phase C and homogenize again. Cool to room temperature.

Measure Values:
Viscosity: 37 500 mPa s Brookfield RVD II+

The following formula provides an example of a O/W emulsion product comprising the BBI-AV of the present invention.

O/W EMULSION

| | % | Ingredient | INCI |
|---|---|---|---|
| A | 1.7 | Cremophor A 6 | Ceteareth-6, Stearyl Alcohol |
|   | 0.7 | Cremophor A 25 | Ceteareth-25 |
|   | 2.0 | Uvinul A Plus ™ | Diethylamino Hydroxybenzoyl Hexyl Benzoate |
|   | 2.0 | Abil B 8843 | PEG-14 Dimethicone |
|   | 3.6 | Lanette O | Cetearyl Alcohol |
|   | 6.0 | Uvinul MC 80 | Ethylhexyl Methoxycinnamate |
|   | 2.0 | Cetiol B | Dibutyl Adipate |
| B | 5.0 | Glycerin 87% | Glycerin |
|   | 0.2 | Edeta BD | Disodium EDTA |
|   | 1.0 | D-Panthenol 75 W | Panthenol |
|   | q.s. | Preservative | |
|   | 68.8 | Water dem. | Aqua dem. |
| C | 4.0 | Luvigel EM | Caprylic/Capric Triglyceride, Sodium Acrylates Copolymer |
| D | 0.2 | Sodium Ascorbyl Phosphate | Sodium Ascorbyl Phosphate |
|   | 1.0 | Vitamin E Acetate | Tocopheryl Acetate |
|   | 0.2 | Bisabolol rac. | Bisabolol |
| E | q.s. | Sodium Hydroxide 10% aq. w/w | Sodium Hydroxide |
| F | 1.0 | RetiSTAR | Caprylic/Capric Triglyceride, Sodium Ascorbate, Tocopherol, Retinol |
|   | SA | Compound | |

Production: Heat Phase A and B separately to about 80° C. Stir Phase B into Phase A and homogenize. Stir Phase C into the combined Phases A+B and homogenize. Cool to about 40° C., add Phase D, then adjust the pH value with Phase E to 6.5. Add Phase F and homogenize. Cool to room temperature.

Measure Values:
Viscosity: 37 500 mPa s Brookfield RVD II+
pH value: 6.3

The following formula provides an example of a protective day cream product comprising the BBI-AV of the present invention.

PROTECTIVE DAY CREAM

| | % | Ingredient | INCI |
|---|---|---|---|
| A | 1.7 | Cremophor A 6 | Ceteareth-6, Stearyl Alcohol |
|   | 0.7 | Cremophor A 25 | Ceteareth-25 |
|   | 2.0 | Uvinul A Plus ™ | Diethylamino Hydroxybenzoyl Hexyl Benzoate |
|   | 2.0 | Abil B 8843 | PEG-14 Dimethicone |
|   | 3.6 | Lanette O | Cetearyl Alcohol |
|   | 6.0 | Uvinul MC 80 | Ethylhexyl Methoxycinnamate |
|   | 2.0 | Cetiol B | Dibutyl Adipate |
| B | 5.0 | Glycerin 87% | Glycerin |
|   | 0.2 | Edeta BD | Disodium EDTA |
|   | 1.0 | D-Panthenol 75 W | Panthenol |
|   | QS | Preservative | |
|   | 69.6 | Water dem. | Aqua dem. |
| C | 4.0 | Luvigel EM | Caprylic/Capric Triglyceride, Sodium Acrylates Copolymer |
| D | 1.0 | Sodium Ascorbyl Phosphate | Sodium Ascorbyl Phosphate |
|   | 1.0 | Vitamin E Acetate | Tocopheryl Acetate |
|   | SA | Compound | |
|   | 0.2 | Bisabolol rac. | Bisabolol |
| E | QS | Sodium Hydroxide 10% aq. w/w | Sodium Hydroxide |

Production: Heat Phase A and B separately to about 80° C. Stir Phase B into Phase A and homogenize. Stir Phase C into the combined Phases A+B and homogenize. Cool to about 40° C., add Phase D, then adjust the pH value with Phase E to 6.5 and homogenize. Cool to room temperature.

Measure Values:
Viscosity: 24 000 mPa s Brookfield RVD II+
pH value: 6.4

The following formulae provide examples of hair care products comprising the BBI-AV of the present invention.

HAIR CONDITIONERS

| | % | Ingredients (INCI) |
|---|---|---|
| A | 10.0 | PVP/VA Copolymer |
|   | 0.2 | Hydroxyethyl Cetyldimonium Phosphate |
|   | 0.2 | Ceteareth-25 |
|   | 0.5 | Dimethicone Copolyol |
|   | QS | Perfume |
|   | 10.0 | Alcohol |
|   | SA | Compound |
|   | 68.1 | Aqua dem. |
| B | 10.0 | Propane/Butane |
| A | 10.0 | PVP/VA Copolymer |
|   | 0.2 | Hydroxyethyl Cetyldimonium Phosphate |
|   | 0.2 | Ceteareth-25 |
|   | 0.5 | Dimethicone Copolyol |
|   | QS | Perfume |
|   | 10.0 | Alcohol |
|   | SA | Compound |
|   | 64.1 | Aqua dem. |
| B | 10.0 | Propane/Butane |

Production: Add all compounds to Phase A and stir to homogenize. Fill into appropriate container and charge with Phase B.

FOAM CONDITIONERS

| | % | Ingredients (INCI) |
|---|---|---|
| A | 1.0 | Polyquaternium-4 |
|   | 0.5 | Hydroxyethyl Cetyldimonium Phosphate Compound |
|   | QS | Perfume |
|   | QS | Preservative |
|   | 91.5 | Aqua dem. |
| B | 6.0 | Propane/Butane |
| A | 1.0 | Polyquaternium-4 |
|   | 0.5 | Hydroxyethyl Cetyldimonium Phosphate Compound |
|   | QS | Perfume |
|   | QS | Preservative |
|   | 87.5 | Aqua dem. |
| B | 6.0 | Propane/Butane |

Production: Add all compounds to Phase A and stir to homogenize. Fill into appropriate container and charge with Phase B.

FOAM CONDITIONERS

| | % | Ingredients (INCI) |
|---|---|---|
| A | 1.0 | Polyquaternium-11 |
| | 0.5 | Hydroxyethyl Cetyldimonium Phosphate Compound |
| | QS | Perfume |
| | QS | Preservative |
| | 91.5 | Aqua dem. |
| B | 6.0 | Propane/Butane |
| A | 1.0 | Polyquaternium-11 |
| | 0.5 | Hydroxyethyl Cetyldimonium Phosphate |
| | SA | Compound |
| | QS | Perfume |
| | QS | Preservative |
| | 87.5 | Aqua dem. |
| B | 6.0 | Propane/Butane |

Production: Add all compounds to Phase A and stir to homogenize. Fill into appropriate container and charge with Phase B.

STYLING FOAMS

| | % | Ingredients (INCI) |
|---|---|---|
| A | 0.5 | Laureth-4 |
| | QS | Perfume |
| B | 77.3 | Aqua dem. |
| | 10.0 | Polyquaternium-28 Compound |
| | 0.5 | Dimethicone Copolyol |
| | 0.2 | Ceteareth-25 |
| | 0.2 | Panthenol |
| | 0.1 | PEG-25 PABA |
| | 0.2 | Hydroxyethylcellulose |
| C | 10.0 | HFC 152 A |
| A | 0.5 | Laureth-4 |
| | QS | Perfume |
| B | 73.3 | Aqua dem. |
| | 10.0 | Polyquaternium-28 |
| | SA | Compound |
| | 0.5 | Dimethicone Copolyol |
| | 0.2 | Ceteareth-25 |
| | 0.2 | Panthenol |
| | 0.1 | PEG-25 PABA |
| | 0.2 | Hydroxyethylcellulose |
| C | 10.0 | HFC 152 A |

Production: Weight out the compounds of Phase A and mix them. Dissolve Phase B, stir into Phase A and homogenize. Fill into appropriate container and charge with Phase C.

| | % | Ingredients (INCI) |
|---|---|---|
| A | 2.0 | Cocotrimonium Methosulfate |
| | QS | Perfume |
| B | 78.5 | Aqua dem. |
| | 6.7 | Acrylates Copolymer |
| | 0.6 | AMP |
| | SA | Compound |
| | 0.5 | Dimethicone Copolyol |
| | 0.2 | Ceteareth-25 |
| | 0.2 | Panthenol |
| | 0.1 | PEG-25 PABA |
| | 0.2 | Hydroxyethylcellulose |
| C | 10.0 | HFC 152 A |
| A | 2.0 | Cocotrimonium Methosulfate |
| | QS | Perfume |
| B | 74.5 | Aqua dem. |
| | 6.7 | Acrylates Copolymer |
| | 0.6 | AMP |
| | SA | Compound |
| | 0.5 | Dimethicone Copolyol |
| | 0.2 | Ceteareth-25 |
| | 0.2 | Panthenol |
| | 0.1 | PEG-25 PABA |
| | 0.2 | Hydroxyethylcellulose |
| C | 10.0 | HFC 152 A |

Production: Weight out the compounds of Phase A and mix them. Dissolve Phase B, stir into Phase A and homogenize. Fill into appropriate container and charge with Phase C.

STYLING FOAM

| | % | Ingredients (INCI) |
|---|---|---|
| A | 2.0 | Cocotrimonium Methosulfate |
| | QS | Perfume |
| B | 7.70 | Polyquaternium-44 |
| | SA | Compound |
| | QS | Preservative |
| | 79.3 | Aqua dem. |
| C | 10.0 | Propane/Butane |

Production: Weight out the compounds of Phase A and mix them. Dissolve Phase B, stir into Phase A and homogenize. Adjust pH to 6-7. Fill into appropriate container and charge with Phase C.

STYLING FOAM

| | % | Ingredients (INCI) |
|---|---|---|
| A | 2.00 | Cocotrimonium Methosulfate |
| | QS | Perfume |
| B | 72.32 | Aqua dem. |
| | 2.00 | VP/Acrylates/Lauryl Methacrylate Copolymer |
| | 0.53 | AMP |
| | SA | Compound |
| | 0.20 | Ceteareth-25 |
| | 0.50 | Panthenol |
| | 0.05 | Benzophenone-4 |
| | 0.20 | Amodimethicone, Cetrimonium Chloride, Trideceth-12 |
| | 15.00 | Alcohol |
| C | 0.20 | Hydroxyethylcellulose |
| D | 6.00 | Propane/Butane |
| A | 2.00 | Cocotrimonium Methosulfate |
| | QS | Perfume |
| B | 68.32 | Aqua dem. |
| | 2.00 | VP/Acrylates/Lauryl Methacrylate Copolymer |
| | 0.53 | AMP |
| | SA | Compound |
| | 0.20 | Ceteareth-25 |
| | 0.50 | Panthenol |
| | 0.05 | Benzophenone-4 |
| | 0.20 | Amodimethicone, Cetrimonium Chloride, Trideceth-12 |
| | 15.00 | Alcohol |
| C | 0.20 | Hydroxyethylcellulose |
| D | 6.00 | Propane/Butane |

Production: Weight out the compounds of Phase A and mix them. Dissolve Phase B, stir into Phase A and homogenize. Add Phase C and homogenize again. Adjust pH to 6-7. Fill into appropriate container and charge with Phase D.

STYLING FOAMS

| | % | Ingredients (INCI) |
|---|---|---|
| A | 2.00 | Cetrimonium Chloride |
| | QS | Perfume |
| B | 67.85 | Aqua dem. |
| | 7.00 | Polyquaternium-46 |
| | SA | Compound |
| | 0.20 | Ceteareth-25 |
| | 0.50 | Panthenol |
| | 0.05 | Benzophenone-4 |
| | 0.20 | Amodimethicone, Cetrimonium Chloride, Trideceth-12 |
| | 15.00 | Alcohol |
| C | 0.20 | Hydroxyethylcellulose |
| D | 6.00 | Propane/Butane |
| A | 2.00 | Cetrimonium Chloride |
| | QS | Perfume |
| B | 63.85 | Aqua dem. |
| | 7.00 | Polyquaternium-46 |
| | SA | Compound |
| | 0.20 | Ceteareth-25 |
| | 0.50 | Panthenol |
| | 0.05 | Benzophenone-4 |
| | 0.20 | Amodimethicone, Cetrimonium Chloride, Trideceth-12 |
| | 15.00 | Alcohol |
| C | 0.20 | Hydroxyethylcellulose |
| D | 6.00 | Propane/Butane |

Production: Weight out the compounds of Phase A and mix them. Dissolve Phase B, stir into Phase A and homogenize. Add Phase C and homogenize again. Adjust pH to 6-7. Fill into appropriate container and charge with Phase D.

STYLING FOAMS

| | % | Ingredients (INCI) |
|---|---|---|
| A | QS | PEG-40 Hydrogenated Castor Oil |
| | QS | Perfume |
| | 85.5 | Aqua dem. |
| B | 7.0 | Sodium Polystyrene Sulfonate |
| | SA | Compound |
| | 0.5 | Cetrimonium Bromide |
| | QS | Preservative |
| C | 6.0 | Propane/Butane |
| A | QS | PEG-40 Hydrogenated Castor Oil |
| | QS | Perfume |
| | 81.5 | Aqua dem. |
| B | 7.0 | Sodium Polystyrene Sulfonate |
| | SA | Compound |
| | 0.5 | Cetrimonium Bromide |
| | QS | Preservative |
| C | 6.0 | Propane/Butane |

Production: Weight out the compounds of Phase A and mix them. Dissolve Phase B, stir into Phase A and homogenize. Adjust pH to 6-7. Fill into appropriate container and charge with Phase C.

STYLING FOAMS

| | % | Ingredients (INCI) |
|---|---|---|
| A | QS | PEG-40 Hydrogenated Castor Oil |
| | QS | Perfume |
| | 92.0 | Aqua dem. |
| B | 0.5 | Polyquaternium-10 |
| | 1.0 | Compound |
| | 0.5 | Cetrimonium Bromide |
| | QS | Preservative |
| C | 6.0 | Propane/Butane |

STYLING FOAMS

| | % | Ingredients (INCI) |
|---|---|---|
| A | QS | PEG-40 Hydrogenated Castor Oil |
| | QS | Perfume |
| | 88.0 | Aqua dem. |
| B | 0.5 | Polyquaternium-10 |
| | 5.0 | Compound |
| | 0.5 | Cetrimonium Bromide |
| | QS | Preservative |
| C | 6.0 | Propane/Butane |

Production: Weight out the compounds of Phase A and mix them. Dissolve Phase B, stir into Phase A and homogenize. Adjust pH to 6-7. Fill into appropriate container and charge with Phase C.

| | % | Ingredients (INCI) |
|---|---|---|
| A | QS | PEG-40 Hydrogenated Castor Oil |
| | QS | Perfume |
| | 82.5 | Aqua dem. |
| B | 10.0 | Polyquaternium-16 |
| | SA | Compound |
| | 0.5 | Hydroxyethyl Cetyldimonium Phosphate |
| | QS | Preservative |
| C | 6.0 | Propane/Butane |
| A | QS | PEG-40 Hydrogenated Castor Oil |
| | QS | Perfume |
| | 78.5 | Aqua dem. |
| B | 100 | Polyquaternium-16 |
| | SA | Compound |
| | 0.5 | Hydroxyethyl Cetyldimonium Phosphate |
| | QS | Preservative |
| C | 6.0 | Propane/Butane |

Production: Weight out the compounds of Phase A and mix them. Dissolve Phase B, stir into Phase A and homogenize. Adjust pH to 6-7. Fill into appropriate container and charge with Phase C.

STYLING FOAMS

| | % | Ingredients (INCI) |
|---|---|---|
| A | 2.0 | Cocotrimonium Methosulfate |
| | QS | Perfume |
| B | 84.0 | Aqua dem. |
| | 2.0 | Chitosan |
| | SA | Compound |
| | 0.5 | Dimethicone Copolyol |
| | 0.2 | Ceteareth-25 |
| | 0.2 | Panthenol |
| | 0.1 | PEG-25 PABA |
| C | 10.0 | HFC 152 A |
| A | 2.0 | Cocotrimonium Methosulfate |
| | QS | Perfume |
| B | 80.0 | Aqua dem. |
| | 2.0 | Chitosan |
| | SA | Compound |
| | 0.5 | Dimethicone Copolyol |
| | 0.2 | Ceteareth-25 |
| | 0.2 | Panthenol |
| | 0.1 | PEG-25 PABA |
| C | 10.0 | HFC 152 A |

Production: Weight out the compounds of Phase A and mix them. Dissolve Phase B, stir into Phase A and homogenize. Adjust pH to 6-7. Fill into appropriate container and charge with Phase C.

SHAMPOOS

| | % | Ingredients (INCI) |
|---|---|---|
| A | 30.0 | Sodium Laureth Sulfate |
| | 6.0 | Sodium Cocoamphoacetate |
| | 6.0 | Cocamidopropyl Betaine |
| | 3.0 | Sodium Laureth Sulfate, Glycol Distearate, Cocamide MEA, Laureth-10 |
| | SA | Compound |
| | 7.7 | Polyquaternium-44 |
| | 2.0 | Amodimethicone |
| | QS | Perfume |
| | QS | Preservative |
| | 1.0 | Sodium Chloride |
| | 43.3 | Aqua dem. |
| B | QS | Citric Acid |
| A | 30.0 | Sodium Laureth Sulfate |
| | 6.0 | Sodium Cocoamphoacetate |
| | 6.0 | Cocamidopropyl Betaine |
| | 3.0 | Sodium Laureth Sulfate, Glycol Distearate, Cocamide MEA, Laureth-10 Compound |
| | 7.7 | Polyquaternium-44 |
| | 2.0 | Amodimethicone |
| | QS | Perfume |
| | QS | Preservative |
| | 1.0 | Sodium Chloride |
| | 39.3 | Aqua dem. |
| B | QS | Citric Acid |

Production: Weight out the compounds of Phase A and mix them. Adjust pH to 6-7 with citric acid.

SHOWER GELS

| | % | Ingredients (INCI) |
|---|---|---|
| A | 40.0 | Sodium Laureth Sulfate |
| | 5.0 | Decyl Glucoside |
| | 5.0 | Cocamidopropyl Betaine |
| | SA | Compound |
| | 1.0 | Panthenol |
| | QS | Perfume |
| | QS | Preservative |
| | 2.0 | Sodium Chloride |
| | 46.0 | Aqua dem. |
| B | QS | Citric Acid |
| A | 40.0 | Sodium Laureth Sulfate |
| | 5.0 | Decyl Glucoside |
| | 5.0 | Cocamidopropyl Betaine |
| | SA | Compound |
| | 1.0 | Panthenol |
| | QS | Perfume |
| | QS | Preservative |
| | 2.0 | Sodium Chloride |
| | 42.0 | Aqua dem. |
| B | QS | Citric Acid |

Production: Weight out the compounds of Phase A and mix them. Adjust pH to 6-7 with citric acid.

SHAMPOOS

| | % | Ingredients (INCI) |
|---|---|---|
| A | 40.0 | Sodium Laureth Sulfate |
| | 5.0 | Sodium C12-15 Pareth-15 Sulfonate |
| | 5.0 | Decyl Glucoside |
| | QS | Perfume |
| | 0.1 | Phytantriol |
| | 44.6 | Aqua dem. |
| | SA | Compound |
| | 0.3 | Polyquaternium-10 |
| | 1.0 | Panthenol |
| | QS | Preservative |
| | 1.0 | Laureth-3 |
| | 2.0 | Sodium Chloride |
| A | 40.0 | Sodium Laureth Sulfate |
| | 5.0 | Sodium C12-15 Pareth-15 Sulfonate |
| | 5.0 | Decyl Glucoside |
| | QS | Perfume |
| | 0.1 | Phytantriol |
| | 40.6 | Aqua dem. |
| | SA | Compound |
| | 0.3 | Polyquaternium-10 |
| | 1.0 | Panthenol |
| | QS | Preservative |
| | 1.0 | Laureth-3 |
| | 2.0 | Sodium Chloride |

Production: Weight out the compounds of Phase A and mix them. Adjust pH to 6-7 with citric acid.

SHAMPOOS

| | % | Ingredients (INCI) |
|---|---|---|
| A | 15.00 | Cocamidopropyl Betaine |
| | 10.00 | Disodium Cocoamphodiacetate |
| | 5.00 | Polysorbate 20 |
| | 5.00 | Decyl Glucoside |
| | QS | Perfume |
| | QS | Preservative |
| | SA | Compound |
| | 0.15 | Guar Hydroxypropyltrimonium Chloride |
| | 2.00 | Laureth-3 |
| | 58.00 | Aqua dem. |
| | QS | Citric Acid |
| B | 3.00 | PEG-150 Distearate |
| A | 15.00 | Cocamidopropyl Betaine |
| | 10.00 | Disodium Cocoamphodiacetate |
| | 5.00 | Polysorbate 20 |
| | 5.00 | Decyl Glucoside |
| | QS | Perfume |
| | QS | Preservative |
| | | Compound |
| | 0.15 | Guar Hydroxypropyltrimonium Chloride |
| | 2.00 | Laureth-3 |
| | 54.00 | Aqua dem. |
| | QS | Citric Acid |
| B | 3.00 | PEG-150 Distearate |

Production: Weight out the compounds of Phase A and mix them. Adjust pH to 6-7. Add Phase B and heat to max. 40° C.

BODY LOTIONS

| | % | Ingredients (INCI) |
|---|---|---|
| A | 2.0 | Ceteareth-25 |
| | 2.0 | Ceteareth-6, Stearyl Alcohol |
| | 3.0 | Cetearyl Ethylhexanoate |
| | 1.0 | Dimethicone |
| | 4.0 | Cetearyl Alcohol |
| | 3.0 | Glyceryl Stearate SE |
| | 5.0 | Mineral Oil |
| | 4.0 | *Simmondsia Chinensis* (Jojoba) Seed Oil |
| | 3.0 | Mineral Oil, Lanolin Alcohol |
| B | 5.0 | Propylene Glycol |
| | SA | Compound |
| | 1.0 | Panthenol |
| | 0.5 | Magnesium Aluminum Silicate |
| | QS | Preservative |
| | 65.5 | Aqua dem. |

BODY LOTIONS

| | % | Ingredients (INCI) |
|---|---|---|
| C | QS | Perfume |
| D | QS | Citric Acid |
| A | 2.0 | Ceteareth-25 |
| | 2.0 | Ceteareth-6, Stearyl Alcohol |
| | 3.0 | Cetearyl Ethylhexanoate |
| | 1.0 | Dimethicone |
| | 4.0 | Cetearyl Alcohol |
| | 3.0 | Glyceryl Stearate SE |
| | 5.0 | Mineral Oil |
| | 4.0 | *Simmondsia Chinensis* (Jojoba) Seed Oil |
| | 3.0 | Mineral Oil, Lanolin Alcohol |
| B | 5.0 | Propylene Glycol |
| | SA | Compound |
| | 1.0 | Panthenol |
| | 0.5 | Magnesium Aluminum Silicate |
| | QS | Preservative |
| | 61.5 | Aqua dem. |
| C | QS | Perfume |
| D | QS | Citric Acid |

Production: Heat Phases A and B separately to approx. 40° C. Add Phase B to Phase A and homogenize by stirring. Add Phase C to the combined Phase A and B and homogenize again. Adjust pH with Phase D to 6-7. Homogenize by stirring and cool to room temperature.

BODY LOTIONS

| | % | Ingredients (INCI) |
|---|---|---|
| A | 6.0 | PEG-7 Hydrogenated Castor Oil |
| | 10.0 | Cetearyl Ethylhexanoate |
| | 5.0 | Isopropyl Myristate |
| | 7.0 | Mineral Oil |
| | 0.5 | Shea Butter (*Butyrospermum Parkii*) |
| | 0.5 | Aluminum Stearate |
| | 0.5 | Magnesium Stearate |
| | 0.2 | Bisabolol |
| | 0.7 | Quaternium-18-Hectorite |
| B | 5.0 | Dipropylene Glycol |
| | 0.7 | Magnesium Sulfate |
| | QS | Preservative |
| | 62.9 | Aqua dem. |
| C | QS | Perfume |
| | SA | Compound |
| A | 6.0 | PEG-7 Hydrogenated Castor Oil |
| | 10.0 | Cetearyl Ethylhexanoate |
| | 5.0 | Isopropyl Myristate |
| | 7.0 | Mineral Oil |
| | 0.5 | Shea Butter (*Butyrospermum Parkii*) |
| | 0.5 | Aluminum Stearate |
| | 0.5 | Magnesium Stearate |
| | 0.2 | Bisabolol |
| | 0.7 | Quaternium-18-Hectorite |
| B | 5.0 | Dipropylene Glycol |
| | 0.7 | Magnesium Sulfate |
| | QS | Preservative |
| | 58.9 | Aqua dem. |
| C | QS | Perfume |
| | SA | Compound |

Production: Heat Phases A and B separately to approx. 80° C. Add Phase B to Phase A and homogenize by stirring. Cool to 40° C. and add Phase C. Homogenize again and cool to room temperature.

HAIR CONDITIONERS

| | % | Ingredients (INCI) |
|---|---|---|
| A | 10.0 | PVP/VA Copolymer |
| | 0.2 | Hydroxyethyl Cetyldimonium Phosphate |
| | 0.2 | Ceteareth-25 |
| | 0.5 | Dimethicone Copolyol |
| | QS | Perfume |
| | 10.0 | Alcohol |
| | SA | Compound |
| | 68.1 | Aqua dem. |
| B | 10.0 | Propane/Butane |
| A | 10.0 | PVP/VA Copolymer |
| | 0.2 | Hydroxyethyl Cetyldimonium Phosphate |
| | 0.2 | Ceteareth-25 |
| | 0.5 | Dimethicone Copolyol |
| | QS | Perfume |
| | 10.0 | Alcohol |
| | SA | Compound |
| | 64.1 | Aqua dem. |
| B | 10.0 | Propane/Butane |

Production: Add all compounds to Phase A and stir to homogenize. Fill into appropriate container and charge with Phase B.

FOAM CONDITIONERS

| | % | Ingredients (INCI) |
|---|---|---|
| A | 1.0 | Polyquaternium-4 |
| | 0.5 | Hydroxyethyl Cetyldimonium Phosphate |
| | SA | Compound |
| | QS | Perfume |
| | QS | Preservative |
| | 91.5 | Aqua dem. |
| B | 6.0 | Propane/Butane |
| A | 1.0 | Polyquaternium-4 |
| | 0.5 | Hydroxyethyl Cetyldimonium Phosphate |
| | SA | Compound |
| | QS | Perfume |
| | QS | Preservative |
| | 87.5 | Aqua dem. |
| B | 6.0 | Propane/Butane |

Production: Add all compounds to Phase A and stir to homogenize. Fill into appropriate container and charge with Phase B.

FOAM CONDITIONERS

| | % | Ingredients (INCI) |
|---|---|---|
| A | 1.0 | Polyquaternium-11 |
| | 0.5 | Hydroxyethyl Cetyldimonium Phosphate |
| | SA | Compound |
| | QS | Perfume |
| | QS | Preservative |
| | 91.5 | Aqua dem. |
| B | 6.0 | Propane/Butane |
| A | 1.0 | Polyquaternium-11 |
| | 0.5 | Hydroxyethyl Cetyldimonium Phosphate |
| | SA | Compound |
| | QS | Perfume |
| | QS | Preservative |
| | 87.5 | Aqua dem. |
| B | 6.0 | Propane/Butane |

Production: Add all compounds to Phase A and stir to homogenize. Fill into appropriate container and charge with Phase B.

STYLING FOAMS

| | % | Ingredients (INCI) |
|---|---|---|
| A | 0.5 | Laureth-4 |
| | QS | Perfume |
| B | 77.3 | Aqua dem. |
| | 10.0 | Polyquaternium-28 |
| | SA | Compound |
| | 0.5 | Dimethicone Copolyol |
| | 0.2 | Ceteareth-25 |
| | 0.2 | Panthenol |
| | 0.1 | PEG-25 PABA |
| | 0.2 | Hydroxyethylcellulose |
| C | 10.0 | HFC 152 A |
| A | 0.5 | Laureth-4 |
| | QS | Perfume |
| B | 73.3 | Aqua dem. |
| | 10.0 | Polyquaternium-28 |
| | SA | Compound |
| | 0.5 | Dimethicone Copolyol |
| | 0.2 | Ceteareth-25 |
| | 0.2 | Panthenol |
| | 0.1 | PEG-25 PABA |
| | 0.2 | Hydroxyethylcellulose |
| C | 10.0 | HFC 152 A |

Production: Weight out the compounds of Phase A and mix them. Dissolve Phase B, stir into Phase A and homogenize. Fill into appropriate container and charge with Phase C.

STYLING FOAMS

| | % | Ingredients (INCI) |
|---|---|---|
| A | 2.0 | Cocotrimonium Methosulfate |
| | QS | Perfume |
| B | 78.5 | Aqua dem. |
| | 6.7 | Acrylates Copolymer |
| | 0.6 | AMP |
| | SA | Compound |
| | 0.5 | Dimethicone Copolyol |
| | 0.2 | Ceteareth-25 |
| | 0.2 | Panthenol |
| | 0.1 | PEG-25 PABA |
| | 0.2 | Hydroxyethylcellulose |
| C | 10.0 | HFC 152 A |
| A | 2.0 | Cocotrimonium Methosulfate |
| | QS | Perfume |
| B | 74.5 | Aqua dem. |
| | 6.7 | Acrylates Copolymer |
| | 0.6 | AMP |
| | SA | Compound |
| | 0.5 | Dimethicone Copolyol |
| | 0.2 | Ceteareth-25 |
| | 0.2 | Panthenol |
| | 0.1 | PEG-25 PABA |
| | 0.2 | Hydroxyethylcellulose |
| C | 10.0 | HFC 152 A |

Production: Weight out the compounds of Phase A and mix them. Dissolve Phase B, stir into Phase A and homogenize. Fill into appropriate container and charge with Phase C.

STYLING FOAMS

| | % | Ingredients (INCI) |
|---|---|---|
| A | 2.0 | Cocotrimonium Methosulfate |
| | QS | Perfume |
| B | 7.70 | Polyquaternium-44 |
| | SA | Compound |
| | QS | Preservative |
| | 79.3 | Aqua dem. |
| C | 10.0 | Propane/Butane |
| A | 2.0 | Cocotrimonium Methosulfate |
| | QS | Perfume |
| B | 7.70 | Polyquaternium-44 |
| | SA | Compound |
| | QS | Preservative |
| | 75.3 | Aqua dem. |
| C | 10.0 | Propane/Butane |

Production: Weight out the compounds of Phase A and mix them. Dissolve Phase B, stir into Phase A and homogenize. Adjust pH to 6-7. Fill into appropriate container and charge with Phase C.

STYLING FOAMS

| | % | Ingredients (INCI) |
|---|---|---|
| A | 2.00 | Cocotrimonium Methosulfate |
| | QS | Perfume |
| B | 72.32 | Aqua dem. |
| | 2.00 | VP/Acrylates/Lauryl Methacrylate Copolymer |
| | 0.53 | AMP |
| | SA | Compound |
| | 0.20 | Ceteareth-25 |
| | 0.50 | Panthenol |
| | 0.05 | Benzophenone-4 |
| | 0.20 | Amodimethicone, Cetrimonium Chloride, Trideceth-12 |
| | 15.00 | Alcohol |
| C | 0.20 | Hydroxyethylcellulose |
| D | 6.00 | Propane/Butane |
| A | 2.00 | Cocotrimonium Methosulfate |
| | QS | Perfume |
| B | 68.32 | Aqua dem. |
| | 2.00 | VP/Acrylates/Lauryl Methacrylate Copolymer |
| | 0.53 | AMP |
| | SA | Compound |
| | 0.20 | Ceteareth-25 |
| | 0.50 | Panthenol |
| | 0.05 | Benzophenone-4 |
| | 0.20 | Amodimethicone, Cetrimonium Chloride, Trideceth-12 |
| | 15.00 | Alcohol |
| C | 0.20 | Hydroxyethylcellulose |
| D | 6.00 | Propane/Butane |

Production: Weight out the compounds of Phase A and mix them. Dissolve Phase B, stir into Phase A and homogenize. Add Phase C and homogenize again. Adjust pH to 6-7. Fill into appropriate container and charge with Phase D.

STYLING FOAMS

| | % | Ingredients (INCI) |
|---|---|---|
| A | 2.00 | Cetrimonium Chloride |
| | QS | Perfume |
| B | 67.85 | Aqua dem. |
| | 7.00 | Polyquaternium-46 |
| | SA | Compound |
| | 0.20 | Ceteareth-25 |
| | 0.50 | Panthenol |
| | 0.05 | Benzophenone-4 |
| | 0.20 | Amodimethicone, Cetrimonium Chloride, Trideceth-12 |
| | 15.00 | Alcohol |

-continued

| | STYLING FOAMS | |
|---|---|---|
| | % | Ingredients (INCI) |
| C | 0.20 | Hydroxyethylcellulose |
| D | 6.00 | Propane/Butane |
| A | 2.00 | Cetrimonium Chloride |
| | QS | Perfume |
| B | 63.85 | Aqua dem. |
| | 7.00 | Polyquaternium-46 |
| | SA | Compound |
| | 0.20 | Ceteareth-25 |
| | 0.50 | Panthenol |
| | 0.05 | Benzophenone-4 |
| | 0.20 | Amodimethicone, Cetrimonium Chloride, Trideceth-12 |
| | 15.00 | Alcohol |
| C | 0.20 | Hydroxyethylcellulose |
| D | 6.00 | Propane/Butane |

Production: Weight out the compounds of Phase A and mix them. Dissolve Phase B, stir into Phase A and homogenize. Add Phase C and homogenize again. Adjust pH to 6-7. Fill into appropriate container and charge with Phase D.

| | STYLING FOAMS | |
|---|---|---|
| | % | Ingredients (INCI) |
| A | QS | PEG-40 Hydrogenated Castor Oil |
| | QS | Perfume |
| | 85.5 | Aqua dem. |
| B | 7.0 | Sodium Polystyrene Sulfonate |
| | SA | Compound |
| | 0.5 | Cetrimonium Bromide |
| | QS | Preservative |
| C | 6.0 | Propane/Butane |
| A | QS | PEG-40 Hydrogenated Castor Oil |
| | QS | Perfume |
| | 81.5 | Aqua dem. |
| B | 7.0 | Sodium Polystyrene Sulfonate |
| | SA | Compound |
| | 0.5 | Cetrimonium Bromide |
| | QS | Preservative |
| C | 6.0 | Propane/Butane |

Production: Weight out the compounds of Phase A and mix them. Dissolve Phase B, stir into Phase A and homogenize. Adjust pH to 6-7. Fill into appropriate container and charge with Phase C.

| | STYLING FOAMS | |
|---|---|---|
| | % | Ingredients (INCI) |
| A | QS | PEG-40 Hydrogenated Castor Oil |
| | QS | Perfume |
| | 92.0 | Aqua dem. |
| B | 0.5 | Polyquaternium-10 |
| | 1.0 | Compound |
| | 0.5 | Cetrimonium Bromide |
| | QS | Preservative |
| C | 6.0 | Propane/Butane |
| A | QS | PEG-40 Hydrogenated Castor Oil |
| | QS | Perfume |
| | 88.0 | Aqua dem. |
| B | 0.5 | Polyquaternium-10 |
| | 5.0 | Compound |
| | 0.5 | Cetrimonium Bromide |
| | QS | Preservative |
| C | 6.0 | Propane/Butane |

Production: Weigh out the compounds of Phase A and mix them. Dissolve Phase B, stir into Phase A and homogenize. Adjust pH to 6-7. Fill into appropriate container and charge with Phase C.

| | STYLING FOAMS | |
|---|---|---|
| | % | Ingredients (INCI) |
| A | QS | PEG-40 Hydrogenated Castor Oil |
| | QS | Perfume |
| | 82.5 | Aqua dem. |
| B | 10.0 | Polyquaternium-16 |
| | SA | Compound |
| | 0.5 | Hydroxyethyl Cetyldimonium Phosphate |
| | QS. | Preservative |
| C | 6.0 | Propane/Butane |
| A | QS | PEG-40 Hydrogenated Castor Oil |
| | QS | Perfume |
| | 78.5 | Aqua dem. |
| B | 10.0 | Polyquaternium-16 |
| | SA | Compound |
| | 0.5 | Hydroxyethyl Cetyldimonium Phosphate |
| | QS | Preservative |
| C | 6.0 | Propane/Butane |

Production: Weigh out the compounds of Phase A and mix them. Dissolve Phase B, stir into Phase A and homogenize. Adjust pH to 6-7. Fill into appropriate container and charge with Phase C.

| | STYLING FOAMS | |
|---|---|---|
| | % | Ingredients (INCI) |
| A | 2.0 | Cocotrimonium Methosulfate |
| | QS | Perfume |
| B | 84.0 | Aqua dem. |
| | 2.0 | Chitosan |
| | SA | Compound |
| | 0.5 | Dimethicone Copolyol |
| | 0.2 | Ceteareth-25 |
| | 0.2 | Panthenol |
| | 0.1 | PEG-25 PABA |
| C | 10.0 | HFC 152 A |
| A | 2.0 | Cocotrimonium Methosulfate |
| | QS | Perfume |
| B | 80.0 | Aqua dem. |
| | 2.0 | Chitosan |
| | SA | Compound |
| | 0.5 | Dimethicone Copolyol |
| | 0.2 | Ceteareth-25 |
| | 0.2 | Panthenol |
| | 0.1 | PEG-25 PABA |
| C | 10.0 | HFC 152 A |

Production: Weigh out the compounds of Phase A and mix them. Dissolve Phase B, stir into Phase A and homogenize. Adjust pH to 6-7. Fill into appropriate container and charge with Phase C.

| | SHAMPOOS | |
|---|---|---|
| | % | Ingredients (INCI) |
| A | 30.0 | Sodium Laureth Sulfate |
| | 6.0 | Sodium Cocoamphoacetate |
| | 6.0 | Cocamidopropyl Betaine |
| | 3.0 | Sodium Laureth Sulfate, Glycol Distearate, Cocamide MEA, Laureth-10 |
| | SA | Compound |
| | 7.7 | Polyquaternium-44 |
| | 2.0 | Amodimethicone |

SHAMPOOS

| | % | Ingredients (INCI) |
|---|---|---|
| | QS | Perfume |
| | QS | Preservative |
| | 1.0 | Sodium Chloride |
| | 43.3 | Aqua dem. |
| B | QS | Citric Acid |
| A | 30.0 | Sodium Laureth Sulfate |
| | 6.0 | Sodium Cocoamphoacetate |
| | 6.0 | Cocamidopropyl Betaine |
| | 3.0 | Sodium Laureth Sulfate, Glycol Distearate, Cocamide MEA, Laureth-10 |
| | SA | Compound |
| | 7.7 | Polyquaternium-44 |
| | 2.0 | Amodimethicone |
| | SA | Perfume |
| | SA. | Preservative |
| | 1.0 | Sodium Chloride |
| | 39.3 | Aqua dem. |
| B | QS | Citric Acid |

Production: Weight out the compounds of Phase A and mix them. Adjust pH to 6-7 with citric acid.

SHOWER GELS

| | % | Ingredients (INCI) |
|---|---|---|
| A | 40.0 | Sodium Laureth Sulfate |
| | 5.0 | Decyl Glucoside |
| | 5.0 | Cocamidopropyl Betaine |
| | SA | Compound |
| | 1.0 | Panthenol |
| | QS | Perfume |
| | QS | Preservative |
| | 2.0 | Sodium Chloride |
| | 46.0 | Aqua dem. |
| B | QS | Citric Acid |
| A | 40.0 | Sodium Laureth Sulfate |
| | 5.0 | Decyl Glucoside |
| | 5.0 | Cocamidopropyl Betaine |
| | SA | Compound |
| | 1.0 | Panthenol |
| | QS | Perfume |
| | QS | Preservative |
| | 2.0 | Sodium Chloride |
| | 42.0 | Aqua dem. |
| B | QS | Citric Acid |

Production: Weight out the compounds of Phase A and mix them. Adjust pH to 6-7 with citric acid.

SHAMPOOS

| | % | Ingredients (INCI) |
|---|---|---|
| A | 40.0 | Sodium Laureth Sulfate |
| | 5.0 | Sodium C12-15 Pareth-15 Sulfonate |
| | 5.0 | Decyl Glucoside |
| | QS | Perfume |
| | 0.1 | Phytantriol |
| | 44.6 | Aqua dem. |
| | SA | Compound |
| | 0.3 | Polyquaternium-10 |
| | 1.0 | Panthenol |
| | QS | Preservative |
| | 1.0 | Laureth-3 |
| | 2.0 | Sodium Chloride |
| A | 40.0 | Sodium Laureth Sulfate |
| | 5.0 | Sodium C12-15 Pareth-15 Sulfonate |
| | 5.0 | Decyl Glucoside |
| | QS | Perfume |
| | 0.1 | Phytantriol |
| | 40.6 | Aqua dem. |
| | SA | Compound |
| | 0.3 | Polyquaternium-10 |
| | 1.0 | Panthenol |
| | QS | Preservative |
| | 1.0 | Laureth-3 |
| | 2.0 | Sodium Chloride |

Production: Weight out the compounds of Phase A and mix them. Adjust pH to 6-7 with citric acid.

SHAMPOOS

| | % | Ingredients (INCI) |
|---|---|---|
| A | 15.00 | Cocamidopropyl Betaine |
| | 10.00 | Disodium Cocoamphodiacetate |
| | 5.00 | Polysorbate 20 |
| | 5.00 | Decyl Glucoside |
| | QS | Perfume |
| | QS | Preservative |
| | SA | Compound |
| | 0.15 | Guar Hydroxypropyltrimonium Chloride |
| | 2.00 | Laureth-3 |
| | 58.00 | Aqua dem. |
| | QS | Citric Acid |
| B | 3.00 | PEG-150 Distearate |
| A | 15.00 | Cocamidopropyl Betaine |
| | 10.00 | Disodium Cocoamphodiacetate |
| | 5.00 | Polysorbate 20 |
| | 5.00 | Decyl Glucoside |
| | QS | Perfume |
| | QS | Preservative |
| | SA | Compound |
| | 0.15 | Guar Hydroxypropyltrimonium Chloride |
| | 2.00 | Laureth-3 |
| | 54.00 | Aqua dem. |
| | QS | Citric Acid |
| B | 3.00 | PEG-150 Distearate |

Production: Weight out the compounds of Phase A and mix them. Adjust pH to 6-7. Add Phase B and heat to max. 40° C.

BODY LOTIONS

| | % | Ingredients (INCI) |
|---|---|---|
| A | 2.0 | Ceteareth-25 |
| | 2.0 | Ceteareth-6, Stearyl Alcohol |
| | 3.0 | Cetearyl Ethylhexanoate |
| | 1.0 | Dimethicone |
| | 4.0 | Cetearyl Alcohol |
| | 3.0 | Glyceryl Stearate SE |
| | 5.0 | Mineral Oil |
| | 4.0 | *Simmondsia Chinensis* (Jojoba) Seed Oil |
| | 3.0 | Mineral Oil, Lanolin Alcohol |
| B | 5.0 | Propylene Glycol |
| | SA | Compound |
| | 1.0 | Panthenol |
| | 0.5 | Magnesium Aluminum Silicate |
| | QS | Preservative |
| | 65.5 | Aqua dem. |
| C | QS | Perfume |
| D | QS | Citric Acid |
| A | 2.0 | Ceteareth-25 |
| | 2.0 | Ceteareth-6, Stearyl Alcohol |
| | 3.0 | Cetearyl Ethylhexanoate |
| | 1.0 | Dimethicone |
| | 4.0 | Cetearyl Alcohol |

BODY LOTIONS

| | % | Ingredients (INCI) |
|---|---|---|
| | 3.0 | Glyceryl Stearate SE |
| | 5.0 | Mineral Oil |
| | 4.0 | *Simmondsia Chinensis* (Jojoba) Seed Oil |
| | 3.0 | Mineral Oil, Lanolin Alcohol |
| B | 5.0 | Propylene Glycol |
| | SA | Compound |
| | 1.0 | Panthenol |
| | 0.5 | Magnesium Aluminum Silicate |
| | QS | Preservative |
| | 61.5 | Aqua dem. |
| C | QS | Perfume |
| D | QS | Citric Acid |

Production: Heat Phases A and B separately to approx. 40° C. Add Phase B to Phase A and homogenize by stirring. Add Phase C to the combined Phase A and B and homogenize again. Adjust pH with Phase D to 6-7. Homogenize by stirring and cool to room temperature.

BODY LOTIONS

| | % | Ingredients (INCI) |
|---|---|---|
| A | 6.0 | PEG-7 Hydrogenated Castor Oil |
| | 10.0 | Cetearyl Ethylhexanoate |
| | 5.0 | Isopropyl Myristate |
| | 7.0 | Mineral Oil |
| | 0.5 | Shea Butter (*Butyrospermum Parkii*) |
| | 0.5 | Aluminum Stearate |
| | 0.5 | Magnesium Stearate |
| | 0.2 | Bisabolol |
| | 0.7 | Quaternium-18-Hectorite |
| B | 5.0 | Dipropylene Glycol |
| | 0.7 | Magnesium Sulfate |
| | QS | Preservative |
| | 62.9 | Aqua dem. |
| C | QS. | Perfume |
| | SA | Compound |
| A | 6.0 | PEG-7 Hydrogenated Castor Oil |
| | 10.0 | Cetearyl Ethylhexanoate |
| | 5.0 | Isopropyl Myristate |
| | 7.0 | Mineral Oil |
| | 0.5 | Shea Butter (*Butyrospermum Parkii*) |
| | 0.5 | Aluminum Stearate |
| | 0.5 | Magnesium Stearate |
| | 0.2 | Bisabolol |
| | 0.7 | Quaternium-18-Hectorite |
| B | 5.0 | Dipropylene Glycol |
| | 0.7 | Magnesium Sulfate |
| | QS | Preservative |
| | 58.9 | Aqua dem. |
| C | QS | Perfume |
| | SA | Compound |

Production: Heat Phases A and B separately to approx. 80° C. Add Phase B to Phase A and homogenize by stirring. Cool to 40° C. and add Phase C. Homogenize again and cool to room temperature.

DAILY SKIN CARE O/W

| | % | Ingredients (INCI) |
|---|---|---|
| A | 1.7 | Ceteareth-6, Stearyl Alcohol |
| | 0.7 | Ceteareth-25 |
| | 2.0 | Diethylamino Hydroxybenzoyl Hexyl Benzoate |
| | 2.0 | PEG-14 Dimethicone |
| | 3.6 | Cetearyl Alcohol |
| | 6.0 | Ethylhexyl Methoxycinnamate |
| | 2.0 | Dibutyl Adipate |
| B | 5.0 | Glycerin |
| | 0.2 | Disodium EDTA |
| | 1.0 | Panthenol |
| | QS | Preservative |
| | 67.8 | Aqua dem. |
| C | 4.0 | Caprylic/Capric Triglyceride, Sodium Acrylates Copolymer |
| D | 0.2 | Sodium Ascorbyl Phosphate |
| | 1.0 | Tocopheryl Acetate |
| | 0.2 | Bisabolol |
| | 1.0 | Caprylic/Capric Triglyceride, Sodium Ascorbate, Tocopherol, Retinol |
| | SA | Compound |
| E | QS | Sodium Hydroxide |
| A | 1.7 | Ceteareth-6, Stearyl Alcohol |
| | 0.7 | Ceteareth-25 |
| | 2.0 | Diethylamino Hydroxybenzoyl Hexyl Benzoate |
| | 2.0 | PEG-14 Dimethicone |
| | 3.6 | Cetearyl Alcohol |
| | 6.0 | Ethylhexyl Methoxycinnamate |
| | 2.0 | Dibutyl Adipate |
| B | 5.0 | Glycerin |
| | 0.2 | Disodium EDTA |
| | 1.0 | Panthenol |
| | QS | Preservative |
| | 63.8 | Aqua dem. |
| C | 4.0 | Caprylic/Capric Triglyceride, Sodium Acrylates Copolymer |
| D | 0.2 | Sodium Ascorbyl Phosphate |
| | 1.0 | Tocopheryl Acetate |
| | 0.2 | Bisabolol |
| | 1.0 | Caprylic/Capric Triglyceride, Sodium Ascorbate, Tocopherol, Retinol |
| | SA | Compound |
| E | QS | Sodium Hydroxide |

Production: Heat Phase A and B separately to approx. 80° C. Add Phase B to Phase A and homogenize by stirring. Add Phase C to the combined Phase A and B and homogenize again. Cool to approx. 40° C. and add Phase D. Adjust pH with Phase E to approx. 6.5. Homogenize by stirring and cool to room temperature.

PROTECTIVE DAY SKIN CREME O/W

| | % | Ingredients (INCI) |
|---|---|---|
| A | 1.7 | Ceteareth-6, Stearyl Alcohol |
| | 0.7 | Ceteareth-25 |
| | 2.0 | Diethylamino Hydroxybenzoyl Hexyl Benzoate |
| | 2.0 | PEG-14 Dimethicone |
| | 3.6 | Cetearyl Alcohol |
| | 6.0 | Ethylhexyl Methoxycinnamate |
| | 2.0 | Dibutyl Adipate |
| B | 5.0 | Glycerin |
| | 0.2 | Disodium EDTA |
| | 1.0 | Panthenol |
| | QS | Preservative |
| | 68.6 | Aqua dem. |
| C | 4.0 | Caprylic/Capric Triglyceride, Sodium Acrylates Copolymer |
| D | 1.0 | Sodium Ascorbyl Phosphate |
| | 1.0 | Tocopheryl Acetate |
| | 0.2 | Bisabolol |
| | SA | Compound |
| E | QS | Sodium Hydroxide |
| A | 1.7 | Ceteareth-6, Stearyl Alcohol |
| | 0.7 | Ceteareth-25 |
| | 2.0 | Diethylamino Hydroxybenzoyl Hexyl Benzoate |
| | 2.0 | PEG-14 Dimethicone |
| | 3.6 | Cetearyl Alcohol |

PROTECTIVE DAY SKIN CREME O/W

| | % | Ingredients (INCI) |
|---|---|---|
| | 6.0 | Ethylhexyl Methoxycinnamate |
| | 2.0 | Dibutyl Adipate |
| B | 5.0 | Glycerin |
| | 0.2 | Disodium EDTA |
| | 1.0 | Panthenol |
| | QS | Preservative |
| | 64.6 | Aqua dem. |
| C | 4.0 | Caprylic/Capric Triglyceride, Sodium Acrylates Copolymer |
| D | 1.0 | Sodium Ascorbyl Phosphate |
| | 1.0 | Tocopheryl Acetate |
| | 0.2 | Bisabolol |
| | | Compound |
| E | QS | Sodium Hydroxide |

Production: Heat Phase A and B separately to approx. 80° C. Add Phase B to Phase A and homogenize by stirring. Add Phase C to the combined Phase A and B and homogenize again. Cool to approx. 40° C. and add Phase D. Adjust pH with Phase E to approx. 6.5. Homogenize by stirring and cool to room temperature.

FACIAL CLEANSER O/W

| | % | Ingredients (INCI) |
|---|---|---|
| A | 10.0 | Cetearyl Ethylhexanoate |
| | 10.0 | Caprylic/Capric Triglyceride |
| | 1.5 | Cyclopentasiloxane, Cyclohexasilosane |
| | 2.0 | PEG-40 Hydrogenated Castor Oil |
| B | 3.5 | Caprylic/Capric Triglyceride, Sodium Acrylates Copolymer |
| C | 1.0 | Tocopheryl Acetate |
| | 0.2 | Bisabolol |
| | QS | Preservative |
| | QS | Perfume |
| D | 3.0 | Polyquaternium-44 |
| | 0.5 | Cocotrimonium Methosulfate |
| | 0.5 | Ceteareth-25 |
| | 2.0 | Panthenol, Propylene Glycol |
| | 4.0 | Propylene Glycol |
| | 0.1 | Disodium EDTA |
| | SA | Compound |
| | 60.7 | Aqua dem. |
| A | 10.0 | Cetearyl Ethylhexanoate |
| | 10.0 | Caprylic/Capric Triglyceride |
| | 1.5 | Cyclopentasiloxane, Cyclohexasilosane |
| | 2.0 | PEG-40 Hydrogenated Castor Oil |
| B | 3.5 | Caprylic/Capric Triglyceride, Sodium Acrylates Copolymer |
| C | 1.0 | Tocopheryl Acetate |
| | 0.2 | Bisabolol |
| | QS | Preservative |
| | QS | Perfume |
| D | 3.0 | Polyquaternium-44 |
| | 0.5 | Cocotrimonium Methosulfate |
| | 0.5 | Ceteareth-25 |
| | 2.0 | Panthenol, Propylene Glycol |
| | 4.0 | Propylene Glycol |
| | 0.1 | Disodium EDTA |
| | SA | Compound |
| | 56.7 | Aqua dem. |

Production: Dissolve Phase A and add Phase B to Phase A and homogenize by stirring. Add. Phase C to the combined Phase A and B and homogenize again. Add. Phase D to the combined Phase A, B and C and homogenize again. Dissolve Phase D and add to Phase A, B, and C and homogenize again. Stir for 15 minutes.

DAILY CARE BODY SPRAY

| | % | Ingredients (INCI) |
|---|---|---|
| A | 3.0 | Ethylhexyl Methoxycinnamate |
| | 2.0 | Diethylamino Hydroxybenzoyl Hexyl Benzoate |
| | 1.0 | Polyquaternium-44 |
| | 3.0 | Propylene Glycol |
| | 2.0 | Panthenol, Propylene Glycol |
| | 1.0 | Cyclopentasiloxane, Cyclohexasiloxane |
| | 10.0 | Octyldodecanol |
| | 0.5 | PVP |
| | 10.0 | Caprylic/Capric Triglyceride |
| | 3.0 | C12-15 Alkyl Benzoate |
| | 3.0 | Glycerin |
| | 1.0 | Tocopheryl Acetate |
| | 0.3 | Bisabolol |
| | SA | Compound |
| | 59.2 | Alcohol |
| A | 3.0 | Ethylhexyl Methoxycinnamate |
| | 2.0 | Diethylamino Hydroxybenzoyl Hexyl Benzoate |
| | 1.0 | Polyquaternium-44 |
| | 3.0 | Propylene Glycol |
| | 2.0 | Panthenol, Propylene Glycol |
| | 1.0 | Cyclopentasiloxane, Cyclohexasiloxane |
| | 10.0 | Octyldodecanol |
| | 0.5 | PVP |
| | 10.0 | Caprylic/Capric Triglyceride |
| | 3.0 | C12-15 Alkyl Benzoate |
| | 3.0 | Glycerin |
| | 1.0 | Tocopheryl Acetate |
| | 0.3 | Bisabolol |
| | SA | Compound |
| | 55.2 | Alcohol |

Production: Weight all ingredients of Phase A and dissolve completely by stirring.

SKIN CARE GEL

| | % | Ingredients (INCI) |
|---|---|---|
| A | 3.6 | PEG-40 Hydrogenated Castor Oil |
| | 15.0 | Alcohol |
| | 0.1 | Bisabolol |
| | 0.5 | Tocopheryl Acetate |
| | QS | Perfume |
| B | 3.0 | Panthenol |
| | 0.6 | Carbomer |
| | SA | Compound |
| | 75.4 | Aqua dem, |
| C | 0.8 | Triethanolamine |
| A | 3.6 | PEG-40 Hydrogenated Castor Oil |
| | 15.0 | Alcohol |
| | 0.1 | Bisabolol |
| | 0.5 | Tocopheryl Acetate |
| | QS | Perfume |
| B | 3.0 | Panthenol |
| | 0.6 | Carbomer |
| | SA | Compound |
| | 71.4 | Aqua dem, |
| C | 0.8 | Triethanolamine |

Production: Dissolve Phase A. Swell Phase B and neutralize with Phase C. Add Phase A to Phase B and C and homogenize by stirring.

AFTER SHAVE LOTIONS

| | % | Ingredients (INCI) |
|---|---|---|
| A | 10.0 | Cetearyl Ethylhexanoate |
| | 5.0 | Tocopheryl Acetate |
| | 1.0 | Bisabolol |
| | 0.1 | Perfume |
| | 0.3 | Acrylates/C10-30 Alkyl Acrylate Crosspolymer |
| B | 15.0 | Alcohol |
| | 1.0 | Panthenol |
| | 3.0 | Glycerin |
| | SA | Compound |
| | 1.0 | Triethanolamine |
| | 63.5 | Aqua dem. |
| A | 10.0 | Cetearyl Ethylhexanoate |
| | 5.0 | Tocopheryl Acetate |
| | 1.0 | Bisabolol |
| | 0.1 | Perfume |
| | 0.3 | Acrylates/C10-30 Alkyl Acrylate Crosspolymer |
| B | 15.0 | Alcohol |
| | 1.0 | Panthenol |
| | 3.0 | Glycerin |
| | SA | Compound |
| | 0.1 | Triethanolamine |
| | 59.5 | Aqua dem. |

Production: Dissolve Phase A. Dissolve Phase B and add to Phase A. Homogenize by stirring.

AFTER SUN LOTIONS

| | % | Ingredients (INCI) |
|---|---|---|
| A | 0.4 | Acrylates/C10-30 Alkyl Acrylate Crosspolymer |
| | 15.0 | Cetearyl Ethylhexanoate |
| | 0.2 | Bisabolol |
| | 1.0 | Tocopheryl Acetate |
| | QS. | Perfume |
| B | 1.0 | Panthenol |
| | 15.0 | Alcohol |
| | 3.0 | Glycerin |
| | SA | Compound |
| | 63.2 | Aqua dem, |
| C | 0.2 | Triethanolamine |
| A | 0.4 | Acrylates/C10-30 Alkyl Acrylate Crosspolymer |
| | 15.0 | Cetearyl Ethylhexanoate |
| | 0.2 | Bisabolol |
| | 1.0 | Tocopheryl Acetate |
| | QS | Perfume |
| B | 1.0 | Panthenol |
| | 15.0 | Alcohol |
| | 3.0 | Glycerin |
| | SA | Compound |
| | 59.2 | Aqua dem, |
| C | 0.2 | Triethanolamine |

Production: Dissolve Phase A. Dissolve Phase B and add to Phase A. Homogenize by stirring. Neutralize Phase A and B by adding Phase C and homogenize again.

SUNSCREEN LOTIONS

| | % | Ingredients (INCI) |
|---|---|---|
| A | 4.5 | Ethylhexyl Methoxycinnamate |
| | 2.0 | Diethylamino Hydroxybenzoyl Hexyl Benzoate |
| | 3.0 | Octocrylene |
| | 2.5 | Di-C12-13 Alkyl Malate |
| | 0.5 | Tocopheryl Acetate |
| | 4.0 | Polyglyceryl-3 Methyl Glucose Distearate |
| B | 3.5 | Cetearyl Isononanoate |
| | 1.0 | VP/Eicosene Copolymer |
| | 5.0 | Isohexadecane |
| | 2.5 | Di-C12-13 Alkyl Malate |
| | 3.0 | Titanium Dioxide, Trimethoxycaprylylsilane |
| C | 5.0 | Glycerin |
| | 1.0 | Sodium Cetearyl Sulfate |
| | 0.5 | Xanthan Gum |
| | 59.7 | Aqua dem. |
| D | SA | Compound |
| | 1.0 | Phenoxyethanol, Methylparaben, Ethylparaben, Butylparaben, Propylparaben, Isobutylparaben |
| | 0.3 | Bisabolol |
| A | 4.5 | Ethylhexyl Methoxycinnamate |
| | 2.0 | Diethylamino Hydroxybenzoyl Hexyl Benzoate |
| | 3.0 | Octocrylene |
| | 2.5 | Di-C12-13 Alkyl Malate |
| | 0.5 | Tocopheryl Acetate |
| | 4.0 | Polyglyceryl-3 Methyl Glucose Distearate |
| B | 3.5 | Cetearyl Isononanoate |
| | 1.0 | VP/Eicosene Copolymer |
| | 5.0 | Isohexadecane |
| | 2.5 | Di-C12-13 Alkyl Malate |
| | 3.0 | Titanium Dioxide, Trimethoxycaprylylsilane |
| C | 5.0 | Glycerin |
| | 1.0 | Sodium Cetearyl Sulfate |
| | 0.5 | Xanthan Gum |
| | 55.7 | Aqua dem. |
| D | SA | Compound |
| | 1.0 | Phenoxyethanol, Methylparaben, Ethylparaben, Butylparaben, Propylparaben, Isobutylparaben |
| | 0.3 | Bisabolol |

Production: Heat Phase A and B separately to approx. 80° C. Add Phase B to Phase A and homogenize by stirring. Heat Phase C to 80° C. and add to the combined Phase A and B and homogenize again. Cool to approx. 40° C. and add Phase D. Homogenize again.

SUNSCREEN LOTIONS O/W

| | % | Ingredients (INCI) |
|---|---|---|
| A | 2.0 | Ceteareth-6, Stearyl Alcohol |
| | 2.0 | Ceteareth-25 |
| | 3.0 | Tribehenin |
| | 2.0 | Cetearyl Alcohol |
| | 2.0 | Cetearyl Ethylhexanoate |
| | 5.0 | Ethylhexyl Methoxycinnamate |
| | 1.0 | Ethylhexyl Triazone |
| | 1.0 | VP/Eicosene Copolymer |
| | 7.0 | Isopropyl Myristate |
| B | 5.0 | Zinc Oxide, Triethoxycaprylylsilane |
| C | 0.2 | Xanthan Gum |
| | 0.5 | Hydroxyethyl Acrylate/Sodium Acryloyldimethyl Taurate Copolymer, Squalane, Polysorbate 60 |
| | 0.2 | Disodium EDTA |
| | 5.0 | Propylene Glycol |
| | 0.5 | Panthenol |
| | 60.9 | Aqua dem. |
| D | SA | Compound |
| | 0.5 | Phenoxyethanol, Methylparaben, Butylparaben, Ethylparaben, Propylparaben, Isopropylparaben |
| | 1.0 | Tocopheryl Acetate |
| | 0.2 | Bisabolol |
| A | 2.0 | Ceteareth-6, Stearyl Alcohol |
| | 2.0 | Ceteareth-25 |
| | 3.0 | Tribehenin |
| | 2.0 | Cetearyl Alcohol |
| | 2.0 | Cetearyl Ethylhexanoate |
| | 5.0 | Ethylhexyl Methoxycinnamate |
| | 1.0 | Ethylhexyl Triazone |

SUNSCREEN LOTIONS O/W

| | % | Ingredients (INCI) |
|---|---|---|
| | 1.0 | VP/Eicosene Copolymer |
| | 7.0 | Isopropyl Myristate |
| B | 5.0 | Zinc Oxide, Triethoxycaprylylsilane |
| C | 0.2 | Xanthan Gum |
| | 0.5 | Hydroxyethyl Acrylate/Sodium Acryloyldimethyl Taurate Copolymer, Squalane, Polysorbate 60 |
| | 0.2 | Disodium EDTA |
| | 5.0 | Propylene Glycol |
| | 0.5 | Panthenol |
| | 56.9 | Aqua dem. |
| D | SA | Compound |
| | 0.5 | Phenoxyethanol, Methylparaben, Butylparaben, Ethylparaben, Propylparaben, Isopropylparaben |
| | 1.0 | Tocopheryl Acetate |
| | 0.2 | Bisabolol |

Production: Heat Phase A and B separately to approx. 80° C. Add Phase B to Phase A and homogenize by stirring. Heat Phase C to 80° C. and add to the combined Phase A and B and homogenize again. Cool to approx. 40° C. and add Phase D. Homogenize again.

SUNSCREEN LOTIONS O/W

| | % | Ingredients (INCI) |
|---|---|---|
| A | 3.5 | Ceteareth-6, Stearyl Alcohol |
| | 1.5 | Ceteareth-25 |
| | 7.5 | Ethylhexyl Methoxycinnamate |
| | 2.0 | Diethylamino Hydroxybenzoyl Hexyl Benzoate |
| | 2.0 | Cyclopentasiloxane, Cyclohexasiloxane |
| | 0.5 | Bees Wax |
| | 3.0 | Cetearyl Alcohol |
| | 10.0 | Caprylic/Capric Triglyceride |
| B | 5.0 | Titanium Dioxide, Silica, Methicone, Alumina |
| C | 3.0 | Glycerin |
| | 0.2 | Disodium EDTA |
| | 0.3 | Xanthan Gum |
| | 1.0 | Decyl Glucoside |
| | 2.0 | Panthenol, Propylene Glycol |
| | 56.3 | Aqua dem. |
| D | SA | Compound |
| | 1.0 | Tocopheryl Acetate |
| | 0.2 | Bisabolol |
| | QS | Parfümöl |
| | QS | Preservative |
| A | 3.5 | Ceteareth-6, Stearyl Alcohol |
| | 1.5 | Ceteareth-25 |
| | 7.5 | Ethylhexyl Methoxycinnamate |
| | 2.0 | Diethylamino Hydroxybenzoyl Hexyl Benzoate |
| | 2.0 | Cyclopentasiloxane, Cyclohexasiloxane |
| | 0.5 | Bees Wax |
| | 3.0 | Cetearyl Alcohol |
| | 10.0 | Caprylic/Capric Triglyceride |
| B | 5.0 | Titanium Dioxide, Silica, Methicone, Alumina |
| C | 3.0 | Glycerin |
| | 0.2 | Disodium EDTA |
| | 0.3 | Xanthan Gum |
| | 1.0 | Decyl Glucoside |
| | 2.0 | Panthenol, Propylene Glycol |
| | 52.3 | Aqua dem. |
| D | SA | Compound |
| | 1.0 | Tocopheryl Acetate |
| | 0.2 | Bisabolol |
| | QS | Perfume |
| | QS | Preservative |

Production: Heat Phase A and B separately to approx. 80° C. Add Phase B to Phase A and homogenize by stirring. Heat Phase C to 80° C. and add to the combined Phase A and B and homogenize again. Cool to approx. 40° C. and add Phase D. Homogenize again.

FOOT BALM

| | % | Ingredients (INCI) |
|---|---|---|
| A | 2.0 | Ceteareth-6, Stearyl Alcohol |
| | 2.0 | Ceteareth-25 |
| | 5.0 | Cetearyl Ethylhexanoate |
| | 4.0 | Cetyl Alcohol |
| | 4.0 | Glyceryl Stearate |
| | 5.0 | Mineral Oil |
| | 0.2 | Menthol |
| | 0.5 | Camphor |
| B | 69.3 | Aqua dem. |
| | QS | Preservative |
| C | 1.0 | Bisabolol |
| | 1.0 | Tocopheryl Acetate |
| D | SA | Compound |
| | 5.0 | Witch Hazel Extract |
| A | 2.0 | Ceteareth-6, Stearyl Alcohol |
| | 2.0 | Ceteareth-25 |
| | 5.0 | Cetearyl Ethylhexanoate |
| | 4.0 | Cetyl Alcohol |
| | 4.0 | Glyceryl Stearate |
| | 5.0 | Mineral Oil |
| | 0.2 | Menthol |
| | 0.5 | Camphor |
| B | 65.3 | Aqua dem. |
| | QS | Preservative |
| C | 1.0 | Bisabolol |
| | 1.0 | Tocopheryl Acetate |
| D | SA | Compound |
| | 5.0 | Witch Hazel Extract |

Production: Heat Phase A and B separately to approx. 80° C. Add Phase B to Phase A and homogenize by stirring. Cool to approx. 40° C. and add Phase C and D. Homogenize by stirring and cool to room temperature

W/O

| | % | Ingredients (INCI) |
|---|---|---|
| A | 6.0 | PEG-7 Hydrogenated Castor Oil |
| | 8.0 | Cetearyl Ethylhexanoate |
| | 5.0 | Isopropyl Myristate |
| | 15.0 | Mineral Oil |
| | 0.3 | Magnesium Stearate |
| | 0.3 | Aluminum Stearate |
| | 2.0 | PEG-45/Dodecyl Glycol Copolymer |
| B | 5.0 | Glycerin |
| | 0.7 | Magnesium Sulfate |
| | 55.6 | Aqua dem. |
| C | 1.0 | Compound |
| | 0.5 | Tocopheryl Acetate |
| | 0.6 | Bisabolol |
| A | 6.0 | PEG-7 Hydrogenated Castor Oil |
| | 8.0 | Cetearyl Ethylhexanoate |
| | 5.0 | Isopropyl Myristate |
| | 15.0 | Mineral Oil |
| | 0.3 | Magnesium Stearate |
| | 0.3 | Aluminum Stearate |
| | 2.0 | PEG-45/Dodecyl Glycol Copolymer |
| B | 5.0 | Glycerin |
| | 0.7 | Magnesium Sulfate |
| | 51.6 | Aqua dem. |
| C | 5.0 | Compound |
| | 0.5 | Tocopheryl Acetate |

Production: Heat Phase A and B separately to approx. 85° C. Add Phase B to Phase A and homogenize by stirring. Cool to approx. 40° C. and add Phase C. Homogenize by stirring and cool to room temperature.

LIQUID MAKE-UP - TYPE O/W

| | % | Ingredients (INCI) |
|---|---|---|
| A | 2.0 | Ceteareth-6, Stearyl Alcohol |
| | 2.0 | Ceteareth-25 |
| | 6.0 | Glyceryl Stearate |
| | 1.0 | Cetyl Alcohol |
| | 8.0 | Mineral Oil |
| | 7.0 | Cetearyl Ethylhexanoate |
| | 0.2 | Dimethicone |
| B | 3.0 | Propylene Glycol |
| | 1.0 | Panthenol |
| | QS | Preservative |
| | 61.9 | Aqua dem. |
| C | 0.1 | Bisabolol |
| | SA | Compound |
| | QS | Perfume |
| D | 5.7 | C.I. 77 891, Titanium Dioxide |
| | 1.1 | Iron Oxides |
| A | 2.0 | Ceteareth-6, Stearyl Alcohol |
| | 2.0 | Ceteareth-25 |
| | 6.0 | Glyceryl Stearate |
| | 1.0 | Cetyl Alcohol |
| | 8.0 | Mineral Oil |
| | 7.0 | Cetearyl Ethylhexanoate |
| | 0.2 | Dimethicone |
| B | 3.0 | Propylene Glycol |
| | 1.0 | Panthenol |
| | QS | Preservative |
| | 57.9 | Aqua dem. |
| C | 0.1 | Bisabolol |
| | SA | Compound |
| | QS | Perfume |
| D | 5.7 | C.I. 77 891, Titanium Dioxide |
| | 1.1 | Iron Oxides |

Production: Heat Phase A and B separately to approx. 80° C. Add Phase B to Phase A and homogenize by stirring. Cool to 40° C. and add Phase C and D. Homogenize again and cool to room temperature.

FOUNDATION

| Ingredient | INCI Name | % |
|---|---|---|
| Water Phase | | |
| Dow Corning 9011 | Cyclopentasiloxane, PEG-12 Dimethicone | |
| Elastomer Blend | Copolymer | 15.00 |
| Dow Corning 245 Fluid | Cyclopentasiloxane | 5.00 |
| Silcare 31 M50 SV | Caprylyl Trimethicone | 6.35 |
| Propylparaben | | 0.05 |
| AS 5811 | Titanium Dioxide, Triethoxycaprylylsilane | 7.50 |
| AS 5131 | Iron Oxides, Triethoxycaprylylsilane | 0.70 |
| AS 5146 | Iron Oxides, Triethoxycaprylylsilane | 0.05 |
| AS 5126 | Iron Oxides, Triethoxycaprylylsilane | 0.35 |
| AS 50230 | Talc, Triethoxycaprylylsilane | 3.50 |
| Oil Phase | | |
| Deionized Water | | 53.30 |
| 1.80Butylene Glycol | | 6.00 |
| Methylparaben | | 0.20 |
| Benzoic Acid | | 0.20 |
| Compound | | SA |

The pigments (AS 5811, 5131, 5146, 5126, and 50230; Color Techniques) and propylparaben are dispersed in Silcare 31 M50 SV (Clariant), stirring until wet: The mixture is then passed over a three roll mill at tight setting until particle size is <10 μm. Then, DC 9011 Elastomer Blend (Dow Corning) and DC 245 Fluid are combined in finishing vessel, stirring until homogenous. The color grind is added with slow homogenizer agitation. The water is weighed into a separate vessel and Compound is gradually added with propeller agitation. stirring until dissolved. Methylparaben and benzoic acid are added to butylene glycol. The mixture is warmed slightly, and stirred until dissolved. The mixture is cooled to 30° C. and added to the Compound-containing solution. The water phase is added slowly to the oil phase with rapid agitation. When addition is complete, the preparation is homogenized for five minutes. This preparation is useful as a makeup foundation for application to skin.

Mascara Formulation

The ingredients of both a control preparation and a mascara containing 2% are as follows:

| | | | % | |
|---|---|---|---|---|
| | | | Control | 2% Compound |
| | Trade Name | INCI Name | 1 | 2 |
| Phase # Water Phase | | | | |
| 1 | Deionized Water | | 42.96 | 42.96 |
| 2 | Butylene Glycol | | 5.00 | 5.00 |
| 2 | Methylparaben | | 0.30 | 0.30 |
| 3 | 33-5198 | (Black) Iron Oxides (Sun) | 10.00 | 10.00 |
| 4 | Natrosol 250 MR | Hydroxyethylcellulose (Aqualon) | 0.20 | 0.20 |

-continued

| Trade Name | INCI Name | Control 1 % | 2% Compound 2 % |
|---|---|---|---|
| 5 10% KOH | Potassium Hydroxide | 0.01 | 0.01 |
| 6 Arlacel 165 | Glyceryl Stearate, PEG-100 Stearate (Uniqema) | 3.00 | 3.00 |
| 7 10% Citric Acid | | 0.27 | 0.27 |
| Phase # Wax Phase | | | |
| 8 Arlacel 165 | | 1.00 | 1.00 |
| 8 Cerasynt SD | Glyceryl Stearate (ISP) | 3.50 | 3.50 |
| 8 Beeswax, White SP 424 | Beeswax (S&P) | 7.50 | 7.50 |
| 8 Carnauba #1 | *Copernica Cerifera* (Carnauba) Wax (S&P) | 4.80 | 4.80 |
| 8 Propylparaben | | 0.10 | 0.10 |
| 9 Deionized Water | | 20.00 | — |
| 9 10% Compound/Water | | — | 20.00 |
| 10 Deionized Water | | 1.00 | 1.00 |
| 10 Glydant | DMDM Hydantoin (Lonza) | 0.36 | 0.36 |
| | | 100.00 | 100.00 |

To produce the mascara formulation, the wax phase 8 is combined and heated to 85-90° C. with propeller mixing. The 10% Compound solution is prepared by adding Compound to water while propeller mixing. Phase 1 water is added to a tared stainless steel beaker (approximately 50 g excess is added to compensate for loss). Phase 2 methylparaben is added to butylene glycol and stirred while warming on top of a steam bath until dissolved, then added to the water with slow homomixer agitation. Then, the phase 4 black iron oxide is added, while maintaining agitation. Then, Natrosol is sprinkled in, while maintaining agitation. The 10% KOH is added, and heating is begun to 85° C., with the beaker covered as tightly as possible. When the Natrosol is dissolved, the 10% citric acid is added dropwise, maintaining temperature and agitation. Then, the Arlacel 165 is added slowly and mixed for at least 5 minutes to insure dissolution. At 85-90° C., the wax phase is slowly added to the water phase while homomixing. The temperature and agitation are maintained for 10 minutes. The batch is removed from the steam bath and allowed to cool while homomixing with occasional hand scraping of the beaker walls. At 55° C., the batch is weighed to check for water loss. Mixing is resumed and water is added back, if necessary. At 45° C., phases 9 and 10 are added. Cooling is continued using cold water to 30° C. At this point, continuous hand scraping of beaker walls is necessary.

In this preparation, the small amount of KOH (in Phase 5) is used to raise the pH to disperse the Natrosol which is coated with glyoxal to retard wetting, and prevent agglomeration. In phase 7, the citric acid is added slowly to adjust pH to ~5.5, below the isoelectric point of the iron oxides. In phases 7 and 8, the Arlacel 165 is split between the oil and water phases, as the emulsification is easier to accomplish with surfactant in both phases. In phase 9, the deionized water is added in the control batch instead of Compound. The Compound solution is prepared while the emulsion is being processed, so it is absolutely fresh. This preparation provides a formulation suitable for use as a mascara.

Example 2

Skin Lightening Studies

In this Example, experiments conducted to assess the skin lightening capabilities of BBI-AV are described. Thirteen subjects, ages 18-65, with Fitzpatrick skin types III or IV participated in this 22-day study. The Fitzpatrick skin classification is based on the skin's unprotected response to the first 30 to 45 minutes of sun exposure following a winter season without sun exposure. The categories of skin types are:

l Always burns easily; never tans
ll Always burns easily; tans minimally
lll Burns moderately; tans gradually
IV Burns minimally; always tans well
V Rarely burns; tans profusely
Vl Never burns; deeply pigmented Five test sites of uniform color were marked on the lower back of each subject. The clinical grader assessed the degree of tan at each site using a 0-10 scale (0=very slight tan and 10=very deep tanning.). Each subject was pre-treated with one concentration of Molecule A, two concentrations of Molecule B, vehicle control buffer, and an untreated site for 11 consecutive days. Approximately 150 uL of test materials (0.1% and 0.9% of BBI-AV) and vehicle control were dosed onto the lower back using occlusive patches. Occlusive patches consisted of a Webril® (non-woven cotton) pad held to the skin with a porous, hypoallergenic tape (e.g., SCANPORE® or MICROPORE®). A strip of BLENDERM® tape equal in width of the cotton pad covered the outside of the tape to provide the occlusive patch. Patches remained in place until a clinician removed them the next day. This patching procedure was repeated for 11 days.

On day 12, the clinician removed the patches that were applied the previous day and the site was gently wiped to remove residual test material. The clinical grader assessed the degree of tan at each site using a 0-11 scale (0=no tan and 11=very deep tanning). The results are provided in the Table below. As indicated, there was a greater change in the tanning grade observed with the BBI-AV than the vehicle control.

| Test Material | Average Day 1 Tanning Grade | Average Day 11 Tanning Grade | Change in Average Tanning Grade |
|---|---|---|---|
| Vehicle Control | 4.92 | 4.82 | −0.1 |
| 0.9% BBI-AV | 4.96 | 4.69 | −0.27 |

Example 3

Reduction in Skin Pigmentation

In this Example, experiments conducted to test the ability of BBI-AV to reduce skin pigmentation induced by UVA exposure are described. This study was conducted with 13 individuals of skin type III and IV based on The Fitzpatrick skin classification.

On day one, each subject's minimal persistent pigment darkening dose (MPPD) was determined on the lower back of each individual, in an area that is equal in color to the area that received test material application. Subjects received five to seven exposures of UVA, with each exposure representing about a 25% increase over the previous exposure. Subjects returned to the clinic 34 hours after the MPPD exposures were complete. The test sites were scored for pigment darkening using the following scale:

- no visible pigment darkening

? questionable response; unclear

+ slight darkening over essentially the whole irradiation field

++ definite darkening over the whole irradiation field

The site treated with the lowest dose of UVA producing a score of '+' represented that subject's MPPD.

On day two, sites of uniform color were marked on the lower back. The clinical grader assessed the degree of tan at each site using a 0-10 scale (0=very slight tan and 10=very deep tanning.) Then the Test material (0.1% and 0.9% of BBI-AV) and the vehicle control applied under occlusion. A volume of 150 µl was dosed onto each patch. The occlusive patches used hte these experiments were the same as described in Example 2. As described in Example 2, the patches remained in place until the next day, when a clinician removed them. This patching procedure was repeated for 11 days. On the days 12-14, the clinician removed the patches that were applied the previous day and the site was gently wiped to remove residual test material. The clinical grader assessed the degree of tan at each site using a 0-10 scale (0=no tan and 10=very deep tanning.) After grading was complete, each site was exposed to 1.0 MPPD of UVA as described for Day 1. New patches were applied after exposures were completed. On day 15, patches were removed and the degree of tan at each site was assessed using a 0-10 scale (0=no tan and 10=very deep tanning). The results are provided below.

| Treatment | Day 12 Avg. Tanning Grade | Day 13 Avg. Tanning Grade | Day 14 Avg. Tanning Grade | Day 15 Avg. Tanning Grade |
|---|---|---|---|---|
| Buffer | 4.82 | 5.29 | 5.59 | 5.98 |
| 0.1% BBI-AV | 4.76 | 5.08 | 5.13 | 5.5 |
| 0.9% BBI-AV | 4.69 | 4.92 | 5.04 | 5.5 |

The results showed that UVA induced pigmentation is decreased in case of BBI-AV exposed sites. This is further evident when the increase in tanning grade is tabulated in Table below. In this table, the tanning grade results are shown as the results obtained for day 12 subtracted from grades of days 13, 14 and 15.

| Treatment | Change on Day 13 | Change on Day 14 | Change on Day 15 |
|---|---|---|---|
| Buffer | 0.41 | 0.77 | 1.16 |
| 0.1% BBI-AV | 0.32 | 0.37 | 0.74 |
| 0.9% BBI-AV | 0.23 | 0.35 | 0.81 |

Example 4

Hair Growth Inhibition

In this Example, experiments to determine the ability of the compositions of the present invention to inhibit the growth of hair are described. In particular, these experiments are conducted in order to assess the ability of the compositions of the present invetnion to decrease hair growth after depilation by shaving or use of depilatory creams or waxing.

Facial Hair Experiments

In these experiments, a group (e.g., 5) male subjects with Fitzpatrick Skin Classification II are tested. Individuals are requested to use no topical facial treatment prior to beginning the experiments. On day 1, facial hair growth is visually evaluated and photographed. Following this evaluation and photography, the composition(s) to be tested, as well as a vehicle control are applied at the desired concentration(s). Beginning on day 2, the individuals apply the composition(s) immediately after shaving. No other pre- or post-shave treatment is used for the duration of the experiments. In most cases, the experiment continues for a time period of 30 to 45 days. Facial hair growth is visually evaluated and photographed every third day during the experiments. The number of hairs, as well as the hair shaft length and width are measured using computerized image analysis. In preferred embodiments, there is a decrease in the number of hairs, hair thickness and/or hair length due to the application of the test compound(s).

Leg Hair Experiments

In these experiments, a group (e.g., 5) female subjects with Fitzpatrick Skin Classification II are tested. Individuals are requested to use no topical leg treatment prior to beginning the experiments. On day 1, areas on both legs of each individual are marked and the hair growth is visually evaluated and photographed. Following this evaluation and photography, the composition(s) to be tested are applied at the desired concentration(s). Following this evaluation and photography, the composition(s) to be tested (i.e., test compounds containing a desired concentration of BBI-AV), as well as a vehicle control, are applied at the desired concentration(s). In some methods, each individual is provided with two tubes, one of which contains the BBI-AV and the other containing the vehicle control. These tubes are marked "left" and "right." Each day during the experiments, the subject applies the compositions in the two tubes the respective legs. After 7 days of application, the individuals are visually evaluated and photographs are taken. Both legs are then shaved or exposed to a depilatory and the test individuals continue to apply the compositions as before. Hair growth is then evaluated visually and by photographing appropriate areas on the legs every 2 days. After 10 days, the legs are again shaved and the test subjects continue to apply the compositions as before. In some methods, the experiments are conducted for 3 cycles and the hair growth is visually evalated and photographs were taken. The experiments are then continued for an additional 8 days. In preferred embodiments, there is a decrease in the number of hairs, hair thickness and/or hair length due to the application of the test compound(s) in the marked area(s).

Beginning on day 2, the individuals apply the composition(s) immediately after shaving. No other pre- or post-shave treatment is used for the duration of the experiments. In most cases, the experiment continues for a time period of 30 to 45 days. Facial hair growth is visually evaluated and photographed every third day during the experiments. The number of hairs, as well as the hair shaft length and width are measured using computerized image analysis. In preferred embodiments, there is a decrease in the number of hairs, hair thickness and/or hair length due to the application of the test compound(s).

Example 5

Panning of a Phage Displayed Peptide Library

In this Example, experiments conducted to pan a phage displayed library are described. A commercially available phage peptide library PhD C7C (NEB) was panned against hVEGF$_{165}$ (R&D systems) for 3 rounds according to the manufacturer's instructions. This procedure yielded the sequence profiles summarized in FIG. 1. Individual clones were confirmed using phage ELISA according to the manufacturer's instructions (See, FIG. 2).

Example 6

BIAcore™ Binding Analysis of VEGF-Binding Peptides

In this Example, experiments conducted to assess the affinities of the peptides for VEGF are described. Affinities of the peptides for VEGF were measured using a BIAcore™-3000 surface plasmon resonance system (Biacore). A CM5 sensor chip was conditioned with 50 mM NaOH, 0.1% HCl, 0.1% SDS, and 0.08% H$_3$PO$_4$, and activated for covalent coupling of VEGF using N-ethyl-N'-(3-dimethylaminopropyl)-carbodiimide hydrochloride (EDC) and N-hydroxysuccinimide (NHS) according to the supplier's instructions (Biacore). Human VEGF$_{165}$ (Biosource) was diluted to 5 µg/ml in 20 mM sodium acetate, pH 4.8 and injected at a flow rate of 2 µl/min to achieve approximately 1000 to 6000 response units (RU) of coupled protein. TNF-alpha (human TNF-alpha, Biosource, Int., Camarillo, Calif.) was similarly coupled to the CM5 sensor chip to approximately 850 to 3500 RU in the reference lane. A solution of 1 M ethanolamine was injected as a blocking agent. In some experiments, an additional solution of EDC and NHS were injected to improve baseline stability and a solution of 1 M ethanolamine injected as a blocking agent. The reference lane was activated with EDC and NHS and blocked with ethanolamine.

Figure 3A:
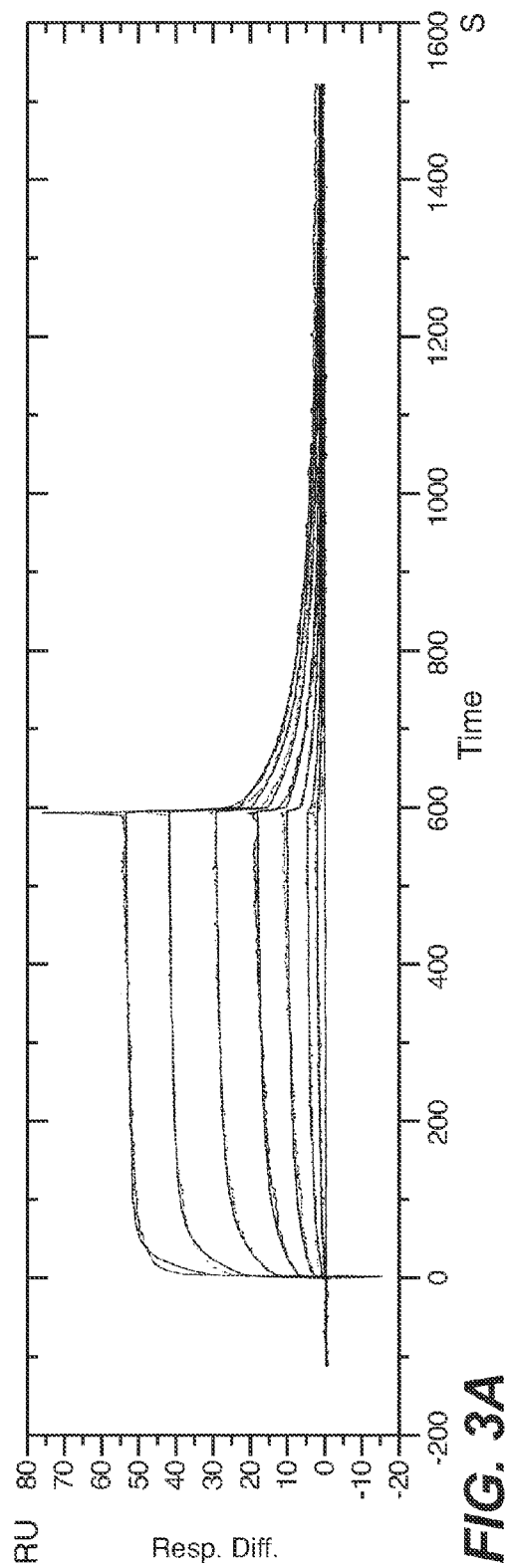
FIG. 3 provides results of a BIACORE binding analysis of VEGF binding peptides. Binding curves were obtained as described in the Examples. Data were fit to a two state reaction model with conformation change: Analyte (A) binds to ligand (B) to form complex AB. Complex AB changes to AB* which cannot dissociate directly to A+B. Panel A provides results for biotinylated peptide CK37281. ka1=2.84 e$^3$ M$^{-1}$ s$^{-1}$, kd1=0.0122 s$^{-1}$, ka2=1.5 e-3 s$^{-1}$ kd2=3.36 e$^{-3}$ s$^{-1}$K$_D$=1.92 e$^{-6}$ M. Panel B provides results for CK37283 (6000 RU VEGF, 3500 RU TNFα no buffer only subtraction); ka1=1.24 e$^4$ M$^{-1}$ s$^{-1}$, kd1=0.318 s$^{-1}$, ka2=6.34 e-3 s$^{-1}$, kd2=1.23 e$^{-3}$ s$^{-1}$ K$_D$=4.90 e$^{-6}$ M. Panel C provides results for v114 control peptide (1000 RU VEGF, 850 RU TNFα. Data were fit to a 1:1 Langmuir binding ka1=7.51 e$^5$ M$^{-1}$ s$^{-1}$ kd1=0.167 s$^{-1}$K$_D$=2.23 e$^{-7}$ M.
Figure 3B:
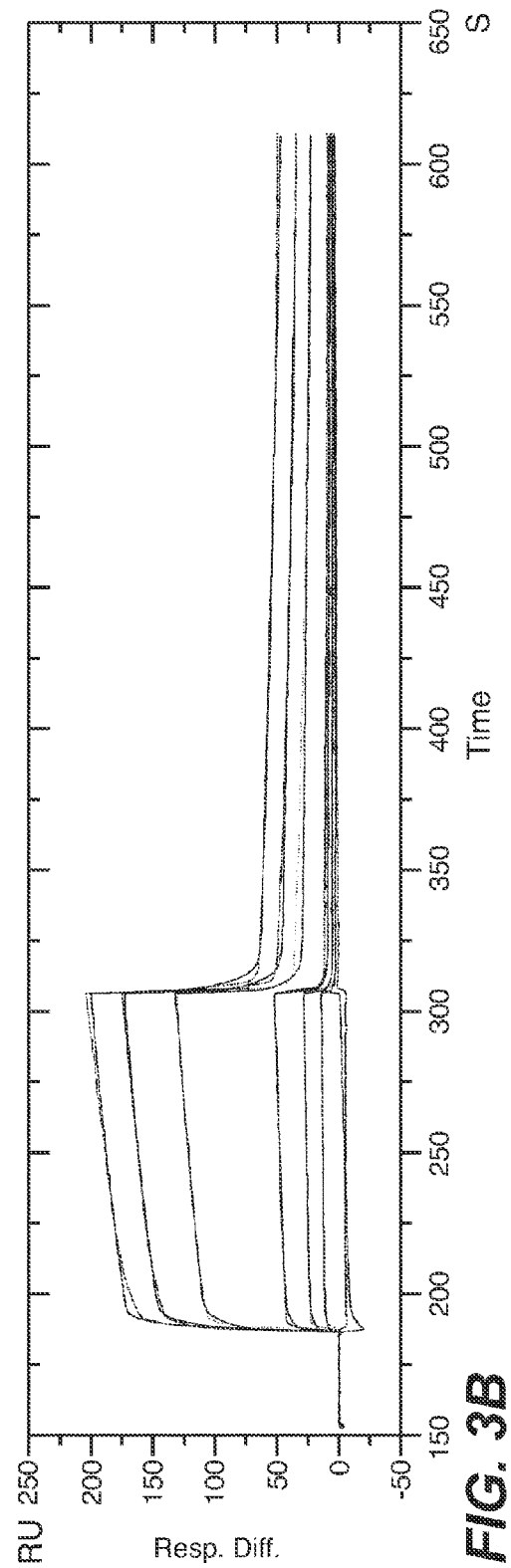
Figure 3C:
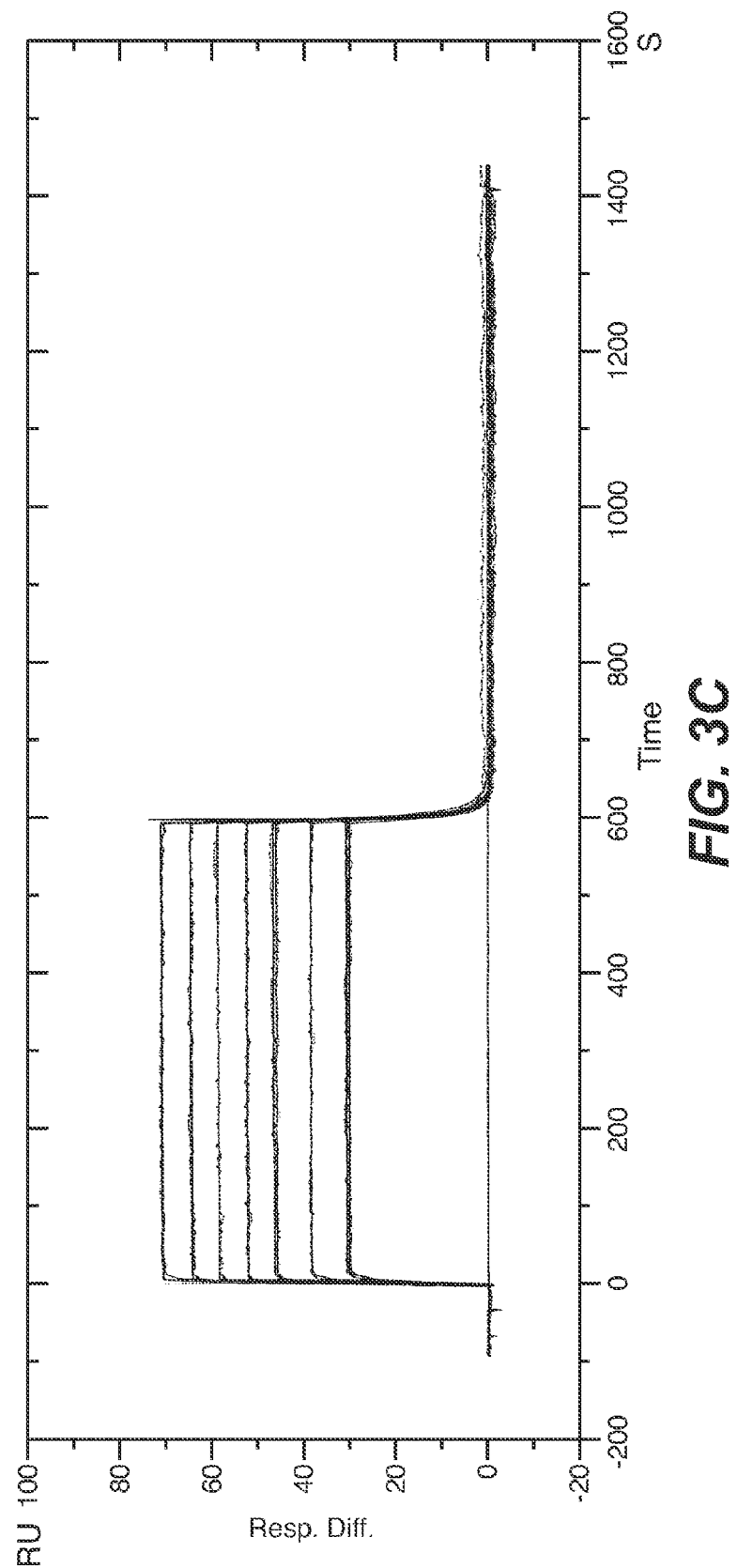

Peptides were synthesized using standard FMOC chemistry, purified by reverse phase HPLC to >95% purity (SynPep), and stored at 10 mg/mL in DMSO. For kinetic measurements, twofold serial diluted peptides in HBS-EP buffer, 0.01 M HEPES pH 7.4, 0.15 M NaCl, 3 mM EDTA, 0.005% Surfactant P20 (Biacore), were injected at 25° C. at a flow rate of 20 µL/min. Two-fold serial diluted DMSO samples and buffer samples were also injected for background subtraction. Kinetic parameters were calculated using BIAevaluation 3.1 software. Results from these experiments are provided in FIG. 3.

Example 7

Construction of Peptide-BLA Scaffolds

Figure 4A:
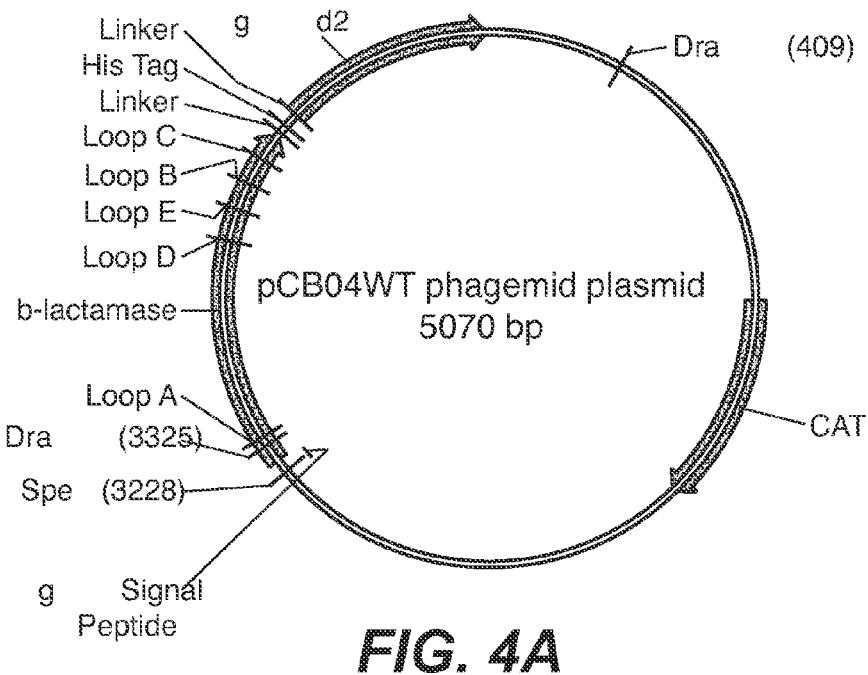
FIG. 4 provides plasmid maps used in the Examples. Panel A provides the map for pCB04WT expression phagemid for expression of C-terminal His6× tagged beta-lactamase. Panel B provides the map for pME22 N-terminal stuffer phagemid for cloning using Bbs1 restriction sites. Panel C provides the map for pCM01 N-terminal aVEGF-BLA fusion expression phagemid.
Figure 4B:
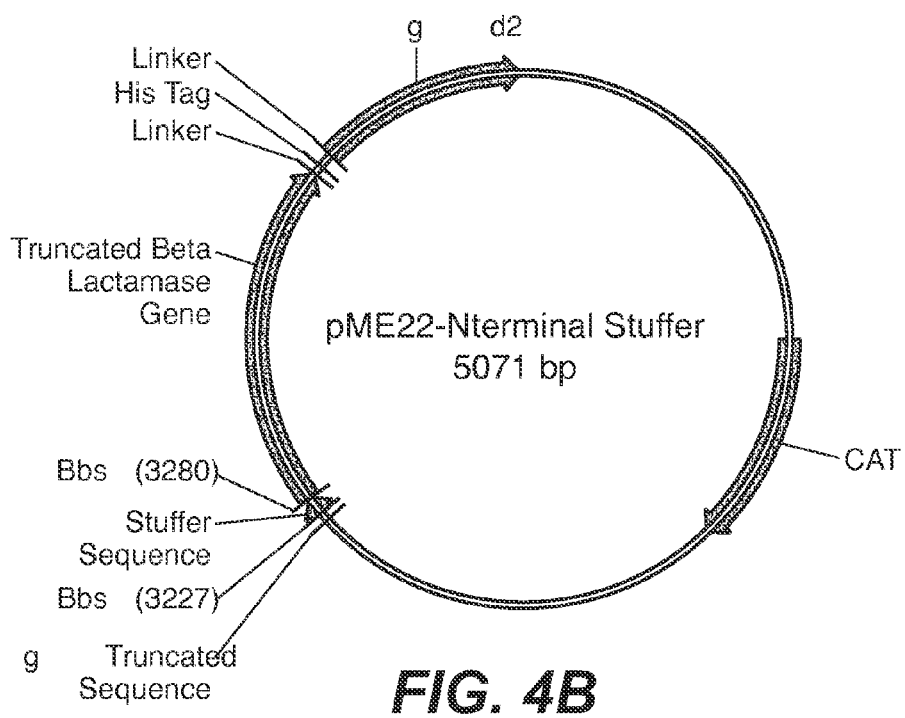
Figure 4C:
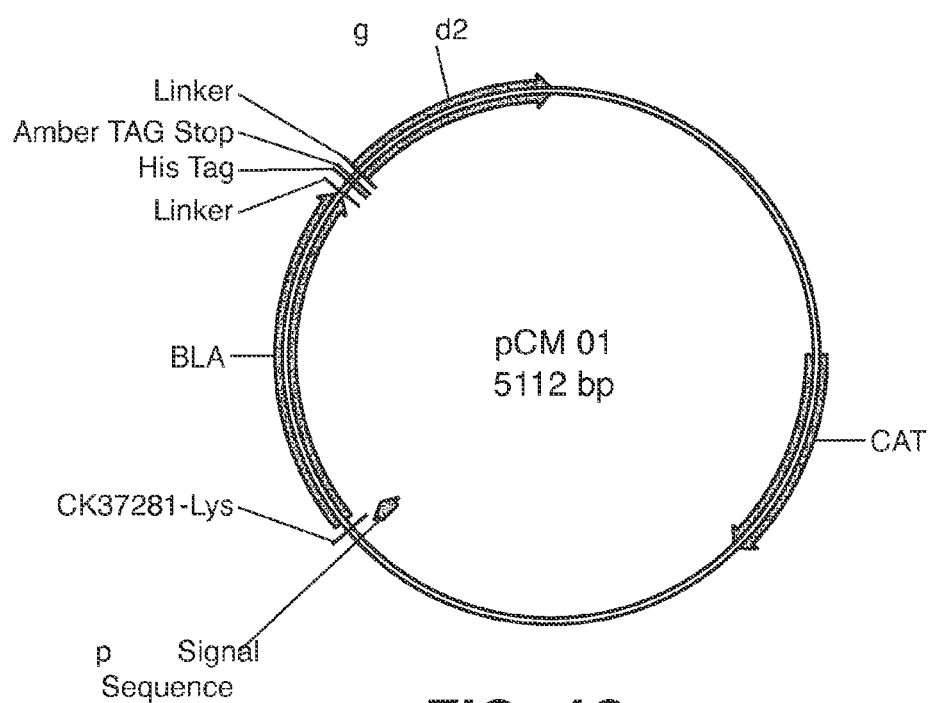

In this Example, methods used in the construction of anti-VEGF-BBI constructs are described. Plasmid pCM01 (5.1 kb) encodes a 15-amino acid peptide sequence CK37281 fused to the N-terminus of *Enterobacter cloaceae* β-lactamase (BLA) with a pIII signal sequence and C-terminal 6×His tag, (See, FIG. 4). The plasmid also carries a chloramphenicol resistance gene (CAT) as a selectable marker and expression is driven by a lac promoter (Plac). Plasmid pCM01 was constructed using a Bbs1 vector, pME30 constructed from pCB04. pCB04 was digested with DraIII and Spe I (NEB), resulting in 2.8 kb and 2.1 kb fragments. To make the inserts, the oligo pairs NtermStf2-F and NtermStf2-R (5 µM) were combined in 50 µl total volume in water, the mixture was heated at 95 C in heat block for 5 minutes, and the block was allowed to cool to room temperature.

Oligos: NtermStf2-F and NtermStf2-R for stuffer vector insert:

```
NtermStf2-F
5'[Phos]
                                                      (SEQ ID NO: 26)
CTAGTGTCTTCGATCAAGTCGACAACAGCCTGTCTGCAGATCCTGAAGACTGGCGGAGGTGGTC

GCGAATACGATTACCCCGCTGATGAAAGCACAGA 3'

NtermStf2-R
5'[Phos]
                                                      (SEQ ID NO: 27)
GTGCTTTCATCAGCGGGGTAATCGTATTCGCGACCACCTCCGCCAGTCTTCAGGATCTGCAGAC

AGGCTGTTGTCGACTTGATCGAAGACA 3'
```

The 2.8 kb fragment, 2.1 kb fragment, and stuffer insert (100 bp) were ligated overnight at 16° C. in a 1:1:5 molar ratio respectively using 10 µl of the DNA mix and 10 µl of Takara solution I ligase. Ligations were purified using Zymo Research DNA clean kit and eluted in 2×8 µl of water. Then, 5 µl of ligation mix was transformed into 50 µl Top 10 electrocompetent cells (Invitrogen), 250 µl SOC was added and the cells grown for 1 hr at 37° C. The transformation mix was diluted 1/10 and plated on both LA+5 ppm CMP and LA+5 ppm CMP+0.1 ppm CTX plates, followed by incubation overnight at 37° C. 12 colonies were picked from CMP plates, grown in LB+5 ppm CMP, DNA was isolated and digested with BbsI enzyme (2 sites in stuffer plasmid). pCB04 (WT) was also digested as control. One clone had the correct sequence and was designated pME22.

The VEGF peptide-BLA expression plasmid pCM01 was constructed from pME22 using the following primers for the BBs1 insert (See, FIG. 5); Oligos VegF-F, VegF-5R, VegF-3RP for peptide insert.

VegF-F
(SEQ ID NO: 28)
5'ACTAGTCGTTCCTTTCTATTCTCACTCTGCTTGTACCCTGTGGCCGACCTTCTGGTGCGGTGGA

GGTTCGACGCCAGTGTCAGAAAAACAGCTG 3'

VegF-5R
(SEQ ID NO: 29)
5'AGCAGAGTGAGAATAGAAAGGAACGAC 3'

VegF-3RP
(SEQ ID NO: 30)
5' [Phos]CCGCCAGCTGTTTTTCTGACACTGG 3'

Figure 6:
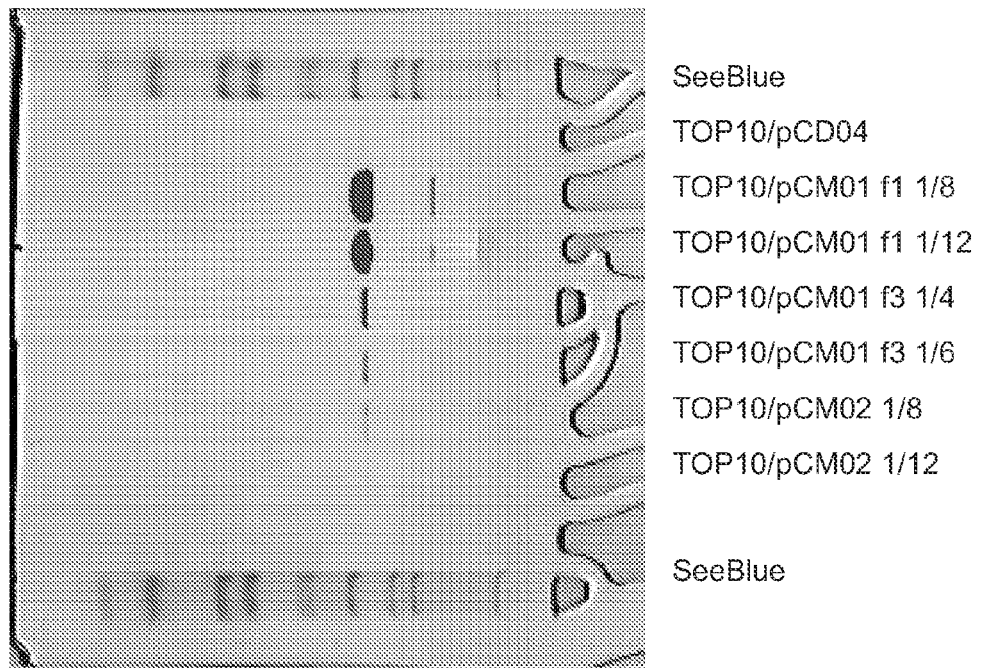
FIG. 6 provides an SDS-PAGE gel of His-tag purified beta-lactamase fusions with peptides. IMAC purified BLA versions and different peptides were concentrated and loaded onto an SDS PAGE gel (4-12%). Lanes 1 & 10: MW markers. Lane 2: pCB04 (WT with 6×his tag); Lanes 3,4,5,6: pCM01 aVEGF-BLA N-terminal fusion protein scaffold; and Lanes 7,8: pCM02 achymotrypsin-BLA N-terminal fusion protein.

BLA-peptide fusion proteins pCM01 and pCB04 (WT) and a biased library pCM04 were expressed in E. coli (TOP10; Invitrogen) in 1-L shake flasks in the presence of 5 ppm CMP and 0.1 ppm cefotoxime antibiotic at 25° C. for 40 hrs. Cell pastes were harvested from the 200 ml cell cultures by centrifugation at 3,000×g for 10 min. The pastes were then treated with 25 ml of B-PER reagent (Pierce) for 40 min with slow mixing. The extract was separated by centrifugation at 20,000×g for 20 min. BLA activity of all liquid fractions was assayed using nitrocefin and the concentration of fusion proteins in each fraction was calculated assuming the same specific activity as the WT enzyme. Fusion proteins were purified by IMAC chromatography. The imidazole-eluted BLA-active fractions were pooled and the purity was found better than 95% as checked by SDS-PAGE (See, FIG. 6).

Example 8

Screening a Peptide-BLA Scaffold Library

Figure 7:
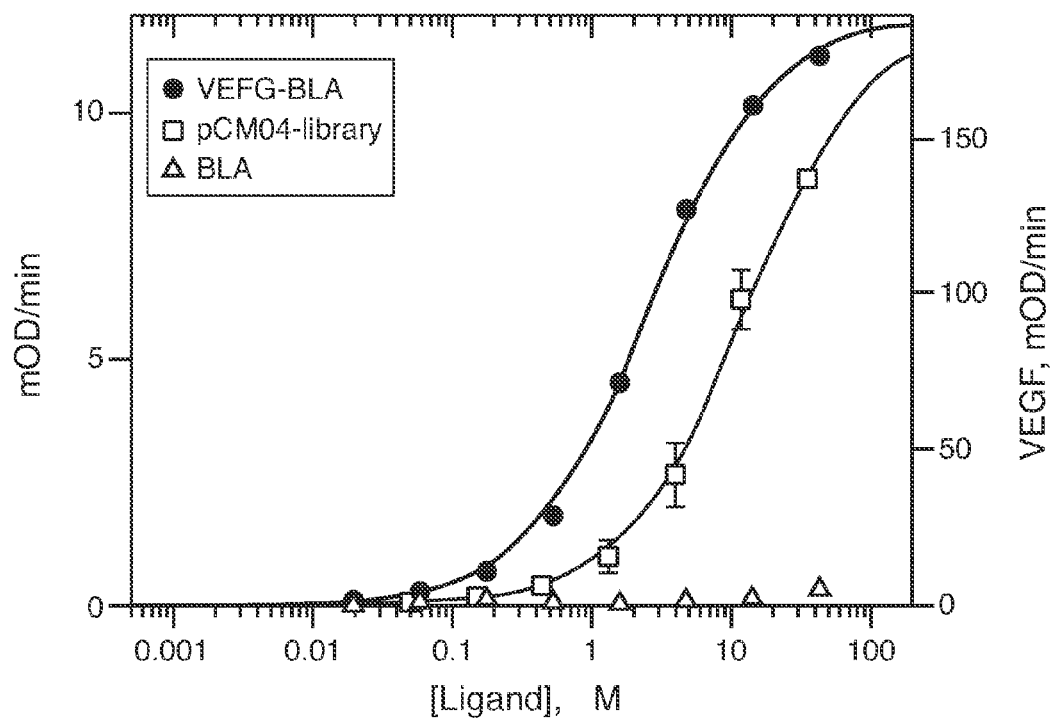
FIG. 7 provides a graph showing that aVEGF peptide-BLA fusion binds specifically to VEGF. Increasing concentrations of pCM01 (aVEGF peptide-BLA fusion) and pCB04 (WT) were added to VEGF coated wells of a microtiter plate. Residual bound nitrocefin activity was measured after washing 5× with nitrocefin assay buffer (0.125% n-octyl-beta-D-glucopyranoside in PBS).

In this Example, experiments to screen a peptide-BLA scaffold library are described. COSTAR plates (96-well) were coated with 0.5 µg (100 µL of 5 µg/mL) hVEGF$_{165}$ (Preprotech) with gentle rocking at 4° C. overnight, followed by blocking with Superblock blocking buffer (Pierce) for several hours at room temperature. His-tag purified samples of pCM01 and pCM04 were diluted serially into BLA assay buffer and 100 µl portions were transferred to VEGF coated wells. After one hour, plates were washed six times with PBS, 0.05% TWEEN®-20 and 200 µL of nitrocefin assay buffer containing 0.1 mg/ml nitrocefin (Oxoid) was added to measure residual bound beta-lactamase activity at Abs$_{490}$/min. Control wells contained pCB04 beta-lactamase as a control (See, FIG. 7).

Example 9

Inhibition of HUVE Cell Proliferation by aVEGF Peptides

Figure 8:
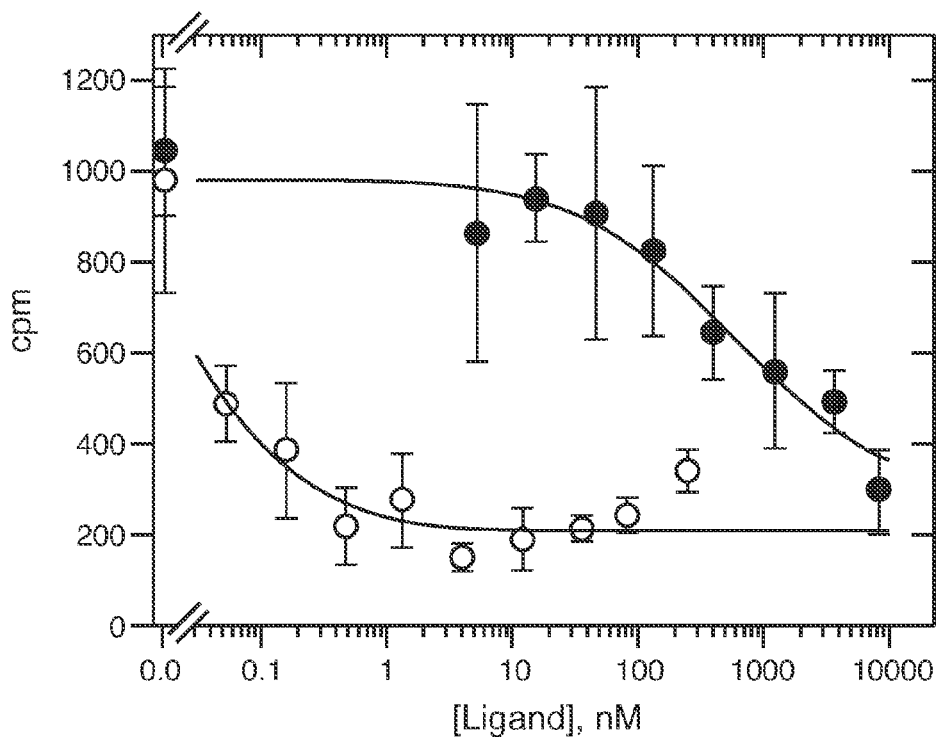
FIG. 8 provides a graph showing inhibition of VEGF-induced HUVEC proliferation by anti-VEGF peptide (filled circles). Proliferation was monitored by radioactive incorporation of $^3$H thymidine (n=3). Anti-VEGF antibody (open circles) was used as a positive control, as described in the Examples.

In this Example, experiments conducted to determine the effects of aVEGF peptides on HUVE cells are described. HUVE cells (human umbilical vein cells; Cambrex) were passaged 1-5 times and maintained according to manufacturer's instructions. HUVE cell growth was stimulated by 0.03 to 20 ng/ml VEGF with the highest proliferation at 10 ng/ml VEGF$_{165}$. This concentration was also used in subsequent experiments. A series of a VEGF peptides from 0.5 nM to 25 µM (and an anti-VEGF monoclonal antibody control (R&D Systems)) were mixed with 10 ng/mL VEGF prior to addition to HUVE cells seeded in triplicate in 96-well plates. Cell proliferation was measured by $^3$H-thymidine incorporation (See, FIG. 8). Significant inhibition was observed down to 0.4 µM anti-VEGF.

Example 10

Inhibition of Blood Vessel Tube Formation by VEGF Peptide Conjugates

In this Example, experiments conducted to assess blood vessel tube formation are described. This in vitro angiogenesis assay was obtained as a kit from Chemicon and used according to the manufacturer's instructions.

This assay provides a simple model of angiogenesis in which the induction or inhibition of tube formation by exogenous signals can be monitored. An endothelial cell suspension of low passage HUVE cells was mixed with different concentrations of the inhibitor in the presence of 10 ng/mL VEGF, before adding the cells to "ECMatrix" (i.e., a solution that is polymerized in situ and provides a solid gel of basement proteins prepared so that endothelial cells align and form hollow tube-like structures). Tube formation is a multi-step process involving cell adhesion, migration, differentiation and growth. The resulting tube formation was measured under an inverted light microscope at 20×-100× magnification. Significant inhibition of tubule formation was observed at concentrations above 1 µM peptide.

Example 11

Construction of Phage-Displayed VEGF-Biased Peptide Libraries

In this Example, experiments conducted to constructed phage-display libraries are described. The affinity maturation libraries used for panning VEGF were constructed using the C7C gene III phage-display system known in the art (See, Noren and Noren [2001]). Oligonucleotides were synthesized and phosphorylated as known in the art. The oligonucleotides used to construct the libraries employ NNK (where N=G, A, T, C and K=G or T) codons. The NNK cloning scheme eliminates the potential for two stop codons and still encodes all twenty amino acids. The random peptide library displayed 9 random amino acids with two cysteines fixed at positions 2 and 9 (XC(X)$_7$CGGGS; SEQ ID NO:31; X represents any amino acid). Seven CK37282 biased peptide libraries were created using the same methods as for the random library.

Example 12

Construction of aVEGF Bowman Birk Inhibitor (BBI$^{vEGF}$)

In this Example, construction of an anti-VEGF BBI (BBI-AV) construct is described. A synthetic gene coding for Bowman Birk Inhibitor (See, FIG. 9) with appropriate restriction sites for introducing small peptide coding sequences into the trypsin loop (SacI-EcoRI) and/or chymotrypsin loop (EcoRI-SalI) was cloned into pET-22b (Novagen) using NdeI/XhoI cloning sites according to standard procedures known in the art. The resulting vector, pET BBI, was used as a template to insert the sequences CK37281, CK37282 into BBI loops as double-stranded oligonucleotide cassettes (Operon). Constructs were transformed into BL-21(DE3) *E. coli*, and plated on medium containing 50 μg/mL ampicillin. Plasmid DNA from individual clones was isolated using methods known in the art (Qiagen) and the correct inserts confirmed by DNA sequencing. Additional peptides of interest include PS-AV1 (1KSAIC-KYYLYWW-CF1V; SEQ ID NO:16) and PS-AV2 (1KSAIC-TLWKSYW-CF1V; SEQ ID NO:17).

Figure 10:
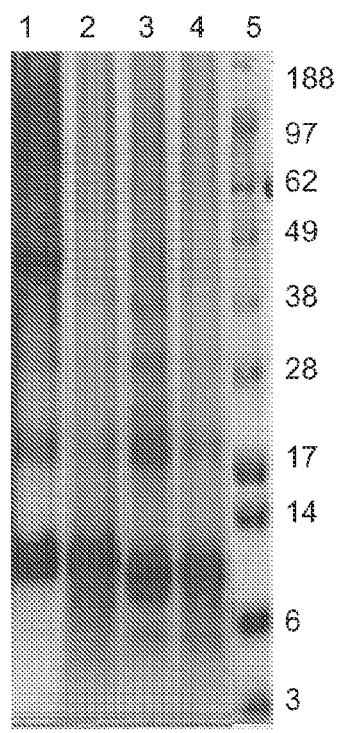
FIG. 10 provides an SDS PAGE gel showing the results of refolding anti-VEGF BBI. Anti-VEGF BBI was refolded in the presence or absence of subtilisin BPN' Y217L. The lanes are as follows: Lane 1: Hampton Foldit 11, refolding buffer, −subtilisin; Lane 2: Hampton Foldit 11 refolding buffer, +subtilisin; Lane 3: Hampton Foldit 13 refolding buffer, −subtilisin; Lane 4, Hampton Foldit 13 refolding buffer, +subtilisin; and Lane 5, molecular weight markers.

Fusion proteins and wild-type BBI were expressed in 14-L fermentors. Cell pastes were harvested and protein isolated from inclusion bodies using a modification of the FoldIt screening procedure (Hampton) (See, FIG. 10).

Example 13

BIAcore™ Binding Analysis of BBI-VEGF

Figure 11:
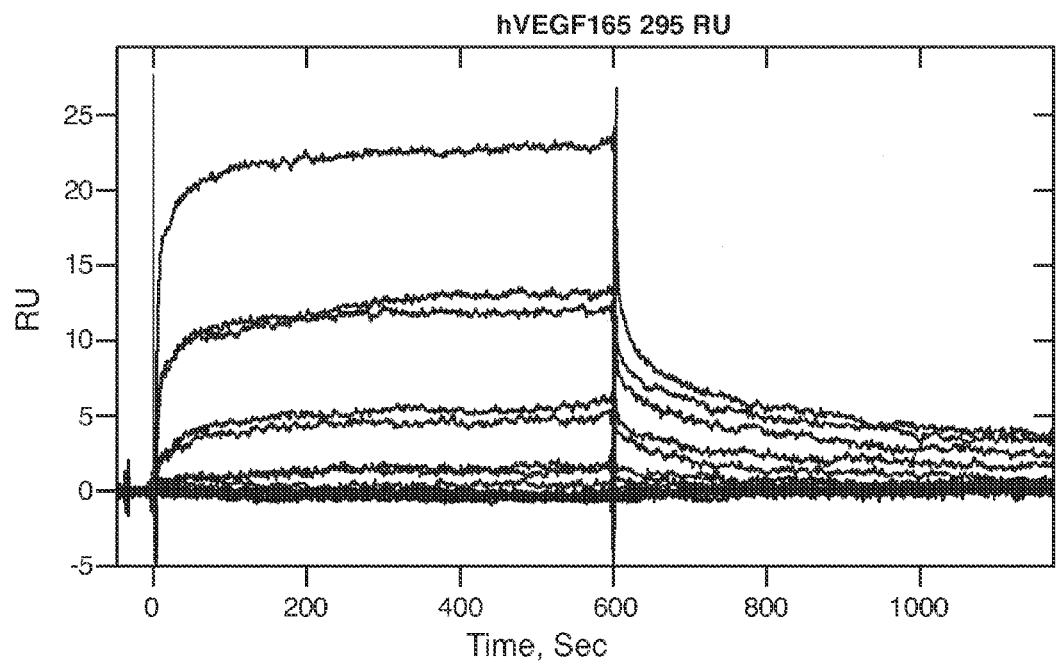
FIG. 11 provides a graph showing that BBI-VEGF1 (SEQ ID NO:22) binds specifically to VEGF.
Figure 12:
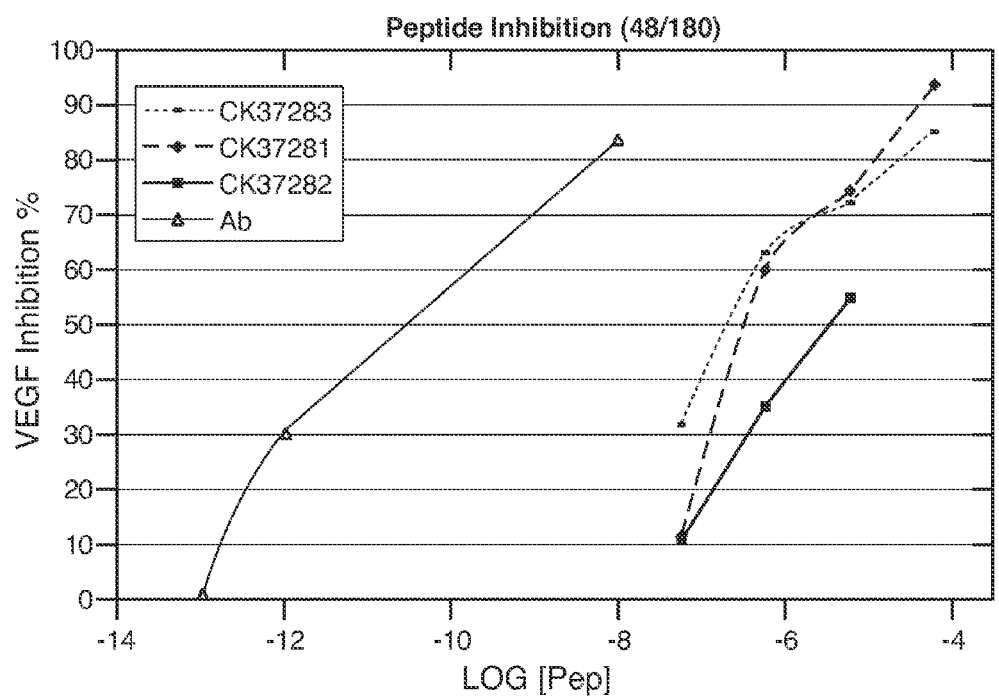
FIG. 12 provides a graph showing HUVEC results for designated peptides.

In this Example, experiments conducted to determine the binding affinity of constructs produced as indicated in Example 9 are described. Affinities of BBI-VEGF constructs for VEGF were measured using BIAcore-3000 surface plasmon resonance (Biacore). A CM5 sensor chip was conditioned with 50 mM NaOH and activated for covalent coupling of VEGF using N-ethyl-N'-(3-dimethylaminopropyl)-carbodiimide hydrochloride (EDC) and N-hydroxysuccinimide (NHS) according to the supplier's instructions (Biacore). VEGF (human VEGF$_{165}$, Biosource) was diluted to 5 μg/mL in 20 mM sodium acetate, pH 4.8, and injected at a flow rate of 2 μL/min to achieve approximately 1000 to 6000 response units (RU) of coupled protein. Trypsin and chymotrypsin were similarly coupled to the CM5 sensor chip to approximately 850 to 3500 RU in remaining lanes. A solution of 1M ethanolamine was injected as a blocking agent. Selective binding affinity to VEGF of refolded BBI-VEGF is shown in FIG. 11.

Example 14

In Vitro Cell Proliferation Assay to Test the Activity of hVEGF Inhibitory Peptides In this Example, experiments conducted to determine the anti-proliferative activity of anti-VEG peptides are described. The antiproliferative activity of VEGF inhibitory peptides was determined using human umbilical vein endothelial cells (HUVEC) as follows. An early passage (less than six) of HUVEC was seeded in 96-well plates at 5000 cells per well and starved for 18 hrs in 200 μl EBM medium (Cambrex) without growth factors and supplemented with 0.5% FBS, at 37° C. with 5% $CO_2$. The medium was replaced with 180 μl of growth medium containing EBM medium with 5% fetal bovine serum and 1% DMSO. Then, 20 μl of VEGF preincubated for one hour with varying peptide concentrations (the final DMSO concentration of all the wells was 1%) were added to the wells for a final VEGF concentration of 10 ng/ml. Human VEGF antibody (R & D Systems) was used as a positive control. Cells with 0.31 to 20 ng/ml concentrations of VEGF alone in the growth medium were used to construct a standard growth curve. The cells were further incubated for 48 hrs, and the cell proliferation was measured using an MTS assay (CellTiter 96 Aqueous One Solution Cell Proliferation Assay Kit; Promega). Then, 40 μl of the MTS tetrazolium solution was added to each well and after 3 and 4 hours incubation, the plates were read at 490 nM. The absorption of media alone was subtracted from all data points. The results indicated that the VEGF inhibitory peptides CK37281 and CK37283 have IC50 in the micromolar range.

Example 15

Repeat Insult Patch Testing (RIPT) of an Anti-VEGF Peptide on Human Skin

In this Example, experiments conducted to determine the patch test result for anti-VEGF peptides are described. Samples of the aVEGF peptide CK37281 dosed at 0.5% (w/v) were formulated in a base formulation containing deionized water/butylene glycol. Approximately 0.2 mL of the formulation was applied to 200 human volunteers in a repeated insult patch test according to procedures designed by Clinical Research Laboratories, Inc. (Piscataway, N.J.). The results indicated that there was no dermal irritation or sensitization on the skin of these volunteers.

Having described the preferred embodiments of the present invention, it will appear to those ordinarily skilled in the art that various modifications may be made to the disclosed embodiments, and that such modifications are intended to be within the scope of the present invention.

Example 16

Production of BCE103-BBI Fusion Proteins in *B. subtilis*

In this Example, experiments conducted to produce BCE103-BBI fusion proteins in *B. subtilis* are described. The DNA sequence of the synthetic gene (Operon Technologies) coding for the pro-BBI protein with a C-terminal hexa-histidine tag used in these experiments is:

(SEQ ID NO: 44)
AACCTGCGTCTGTCTAAGCTTGGCCTGCTTATGAAATCAGACCATCAGCACAGCAATGACGATG

AGAGCTCTAAACCCTGTTGCGATCAATGCGCATGTACGAAATCAAATCCTCCACAGTGTCGGTG

TTCCGATATGCGTCTGAATAGCTGTCATAGTGCATGCAAAAGCTGTATCTGCGCCCTGAGTTAT

CCAGCTCAATGTTTTTGCGTCGACATCACGGACTTCTGCTATGAGCCATGTAAACCAAGCGAGG

ACGATAAAGAGAACCATCATCACCATCACCAT

The protein sequence of pro-BBI with a C-terminal hexa-histidine tagged coded for by the above synthetic gene is:

(SEQ ID NO: 45)
NLRLSKLGLLMKSDHQHSNDDESSKPCCDQCACTKSNPPQCRCSDMRLNSCHSACKSCICALSYPA

QCFCVDITDFCYEPCKPSEDDKENHHHHHH

The portion of the DNA sequence of the synthetic gene that codes for the major mature form of BBI is:

(SEQ ID NO: 46)
GACGATGAGAGCTCTAAACCCTGTTGCGATCAATGCGCATGTACGAAATCAAATCCTCCACAGT

GTCGGTGTTCCGATATGCGTCTGAATAGCTGTCATAGTGCATGCAAAAGCTGTATCTGCGCCCT

GAGTTATCCAGCTCAATGTTTTTGCGTCGACATCACGGACTTCTGCTATGAGCCATGTAAACCA

AGCGAGGACGATAAAGAGAAC

The protein sequence of the major mature form of BBI coded by the above synthetic gene is:

(SEQ ID NO: 47)
DDESSKPCCDQCACTKSNPPQCRCSDMRLNSCHSACKSCICALSYPAQCFCVDITDFCYEPCKPSED
DKEN

The PCR primers used to amplify the BBI gene for fusion to the BCE103 cellulase expression cassette in the pJ103 vector were:

```
BBIfusion_FW:
                                       (SEQ ID NO: 48)
5' CAGCACGGATCCAGACGATGAGAGCTCTAAACCC 3'

BBIHindIII_RV:
                                       (SEQ ID NO: 49)
5' CTGCAGAAGCTTAAAAATAAAAAAACGGATTTCCTTCAGGAAATC

CGTCCTCTGTTAACTTTTAGTTCTCTTTATCGTCCTCGC 3'

BBIHIS-HindIII_RV:
                                       (SEQ ID NO: 50)
5' CTGCAGAAGCTTAAAAATAAAAAAACGGATTTCCTTCAGGAAATC

CGTCCTCTGTTAACTTTTAATGGTGATGGTGATGATGGTTCTC 3'
```

Figure 15:
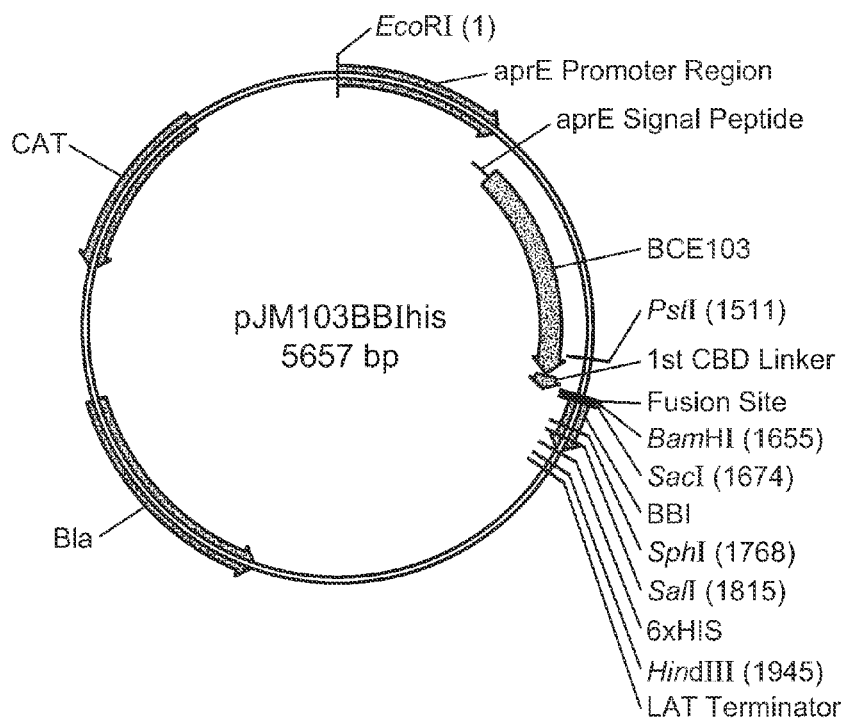
FIG. 15 provides a schematic map of the pJM103BBIhis expression vector.

The sequence of the aprE-BCE103-BBI-HisTag expression cassette (EcoRI-HindIII) that was cloned into the pJM103 integration vector is provided in FIG. 14. A schematic plasmid map of the pJM103BBIHis expression vector is provided in FIG. 15.

The alkaline cellulase (BCE103) gene (See, van Soligen, U.S. Pat. No. 6,063,611, hereby incorporated by reference) fused to the *B. subtilis* aprE promoter and signal sequence, was cloned from pUCAPR103 (Shaw et al., J. Mol. Biol., 320:303-309 [2002]) as an EcoRI-BamHI fragment (i.e., a fragment that carries the coding sequence of the BCE103 catalytic domain and first cellulose binding domain linker only) into pJM103 (Perego, "Integrational vectors for genetic manipulation in *Bacillus subtilis*" In, *Bacillus subtilis and Other Gram-positive Bacteria: Biochemistry, Physiology, and Molecular Genetics*, Sonenshein, Hoch, and Losick (eds), American Society for Microbiology, Washington D.C., pp. 615-624 [1993]). A gene encoding the soybean Bowman-Birk protease inhibitor (BBI) (Swiss-Prot Accession # P01055; See, Odani and Ikenaka, J. Biochem., 71: 839-848 [1972]) with a C-terminal hexa-histidine tag (His-Tag) was synthesized by Operon Technologies (See, DNA sequence above). The BBI gene was amplified by PCR with primers (all primers were synthesized by MWG Biotech, Oligos Etc., or Operon Technologies) that generated a 5' BamHI site in the correct reading frame with the BCE103 gene, and at the 3' end introduced a strong transcriptional terminator (LAT, from the *Bacillus licheniformis* α-amylase gene) after the end of the BBI gene with a 3' HindIII site for cloning into the pJM103 vector.

PCR fragments with or without a C-terminal His-Tag were generated with the primers BBIfusion_FW (SEQ ID NO:48) and BBIHISHindIII_RV (SEQ ID NO:50), or BBIfusion_FW (SEQ ID NO:48) and BBI-HindIII_RV (SEQ ID NO:49), respectively, using the synthetic BBI gene as a template. Unless indicated otherwise, PCR reactions were typically performed on a thermocycler for 30 cycles with High Fidelity Platinum Taq polymerase (Invitrogen) according to the instructions of the supplier (with an annealing temperature of 55° C.). The PCR fragments were cloned as BamHI-HindIII fragments into pJM103 carrying the aprE-BCE103 expression cassette. The correct gene sequence was verified by DNA sequencing.

Thus, as shown in FIG. 14, the N-terminus of the mature coding region of the BBI gene (with or without the His-Tag) was fused in frame to the C-terminal coding region of the first CBD (cellulose binding domain) linker sequence coded by the BCE103 cellulase gene. Thereby, the two CBD's of BCE103 (Shaw et al., supra) are replaced by BBI in the final expression vectors, pJM103BBI or pJM103BBIhis (See, FIG. 15). The aprE promoter controls the expression of the BCE103-BBI gene fusions (See, Ferrari et al., J. Bact., 170: 289-295 [1988]; and Henner et al., J. Bact., 170: 296-300 [1988]).

Competent *Bacillus subtilis* cells, BG3934comK, were transformed with the expression plasmids, pJM103BBI or pJM103BBIhis. The bacteria were made competent by the induction of the comK gene under control of a xylose inducible promoter (Hahn et al., Mol. Microbiol., 21:763-775 [1996]). The transformants were selected on Luria Broth agar (LA) plates containing 5 µg/ml chloramphenicol. To increase the expression by gene amplification, colonies were streaked and grown several times on LA plates with 25 µg/ml chloramphenicol until the growth rate with the antibiotic was similar to growth rate in the absence of chloramphenicol. The BCE103-BBI fusion protein was produced by growth in shake flasks at 37° C. in TSB medium (Tryptone Soya Broth from OXOID, 30 g/L) or in MBD medium, a MOPS based defined medium. MBD medium was made essentially as described (Neidhardt et al., J. Bacteriol., 119: 736-747 [1974]), except $NH_4Cl_2$, $FeSO_4$, and $CaCl_2$ were left out of the base medium, 3 mM $K_2HPO_4$ was used, and the base medium was supplemented with 60 mM urea, 75 g/L glucose, and 1% soytone. Also, the micronutrients were made up as a 100× stock containing in one liter, 400 mg $FeSO_4.7H_2O$, 100 mg $MnSO_4.H_2O$, 100 mg $ZnSO_4.7H_2O$, 50 mg $CuCl_2.2H_2O$, 100 mg $CoCl_2.6H_2O$, 100 mg $NaMoO_4.2H_2O$, 100 mg $Na_2B_4O_7.10H_2O$, 10 ml of 1M $CaCl_2$, and 10 ml of 0.5 M sodium citrate.

BCE103-BBI fusion protein could be easily visualized in samples from cell free supernatants (after 24 h of growth in TSB medium or 48 h in MBD medium) as the major protein band on SDS-PAGE gels (10% NuPAGE in MES buffer, run as described by the manufacturer, Invitrogen) running at ~44 kDa by using standard protein stains (e.g. GelCode Blue Stain Reagent; Pierce). The identity of the BCE103-BBI fusion protein was verified by immunoblots of SDS-PAGE gels using the protocols supplied by the manufacturer (BM Chromogenic Western Blotting Kit; Roche Applied Science using an anti-H isTag antibody or an anti-BCE103 cellulase polyclonal antibody for detection).

To determine the BCE103 activity, cellulase degradation was assessed qualitatively on LA cellulase indicator plates (with 1% carboxymethylcellulose stained with 0.2% Congo Red, or with 0.5% azo-CM-cellulose, Megazyme), or quantitatively by a direct assay in Assay Buffer (100 mM Tris pH 8.6, 0.005% Tween-80) on the culture broth using a the synthetic substrate, 4-nitrophenyl β-D-cellobioside (Sigma), using methods known in the art (See e.g., van Tilbeurgh et al., Meth. Enzymol., 160:45-59 [1988]).

Trypsin inhibitory assays were performed in Assay Buffer to determine the BBI activity. Specifically, a standard curve was generated by making eleven 1:1 serial dilutions (100 μL BBI+100 μL Assay Buffer) of a 2 μg/mL standard BBI solution. The BBI standard was purified from a 1 mg/ml Trypsin-Chymotrypsin Inhibitor (Sigma Cat. #T-9777) solution in 20 mM MES pH 6.0 using a hydrophobic interaction column (POROS HP2, Phenyl column, Applied Biosystems). The column was equilibrated with 20 mM MES pH 6.0, loaded with 5 mg of the inhibitor, washed with the equilibration buffer, and then the BBI was eluted with water. Unknown BBI samples to be tested in the inhibitory assay were diluted as necessary, so that two or more data points would fall within the standard curve (usually 1:10, 1:100, 1:200, 1:1000, 1:2000 sample dilutions were tested and then the dilutions fine tuned if necessary). Each diluted BBI standard or sample, 20 μL, was added to 80 μL of 50 ng/ml bovine pancreatic trypsin (Worthington) (made by diluting a stock 1 mg/mL trypsin solution into Assay Buffer). For convenience, the standards and samples were arrayed in 96 well microtiter plates. The reactions were mixed and incubated 15 min at 25° C. After the incubation, 100 μL of the 0.5 mg/ml trypsin substrate (diluted in Assay Buffer from a 100 mg/ml solution in DMSO), Suc-AAPR-pNA (succinyl-Ala-Ala-Pro-Arg-para-nitroanilide, Bachem), was added, mixed and the OD ($A_{405}$) was monitored for 15 min, with 1 time point recorded every 12 sec using a Spectra Max 250 (Molecular Devices). The data points were used to determine the Vmax for each reaction. The standard curve was generated by plotting Vmax versus BBI concentration and was fitted to a four-parameter curve. All data fitting was done using software supplied by the manufacturer (Molecular Devices). The BBI concentration of the unknown samples was calculated from the standard curve.

Alternatively, the BBI activity was measured using the same protocol but by determining bovine pancreatic chymotrypsin (Worthington) inhibition (chymotrypsin was used at the same concentration as trypsin and chymotrypsin activity was measured by adding 100 μL of a 0.4 mg/ml chymotrypsin substrate, succinyl-Ala-Ala-Pro-Phe-para-nitroanilide, Bachem).

Titers from shake flask runs (500 ml MBD medium in 2.8 L Fernbach 6 baffled flasks, 37° C., 225 rpm, harvested 60 h after of growth) typically ranged from 0.4-0.9 mg/ml BCE activity and 40-150 μg/ml BBI trypsin inhibitory activity. However, it is contemplated that titers likely could be improved further by optimizing the bacterial strain, culture medium and growth conditions (aeration, temperature, time of harvest, etc.).

In addition to the BCE103 fusion to wild-type BBI, fusion proteins to BBI variants and fusion proteins with various linkers between BCE103 and BBI were produced using the methods outlined above, as described in the following Examples. In addition, fusion proteins were also produced when the BBI was fused to the $2^{nd}$ CBD linker (BCE-cbdD-BBI; See, Example 19) making it possible to use the $1^{st}$ CBD to aid in the purification process.

Example 17

Production of Peptides Substituted into the BBI Reactive Site Loops as BCE103-BBI Fusion Proteins In this Example, experiments conducted to produce peptides substituted into the BBI reactive site loops as BCE103-BBI fusion proteins are described. The primers, as well as other sequences used in the various steps of these experiments are provided below. The sequence of 12BBIck81 from the BCE103 fusion site (at the BamHI site) to the end of the gene is provided in FIG. 16. Peptides containing the CK37281 sequence (ACYNLYGWTC (SEQ ID NO:43) were inserted into both the trypsin and chymotrypsin inhibitory loops.

The primers used to introduce an EcoRI site in the BBI gene using QuikChange® site-directed mutagenesis (Stratagene) were:

```
BowBeco-F
5'-GATATGCGTCTGAATTCCTGTCATAGTGCAT (SEQ ID NO: 51)

BowBeco-R
5'-ATGCACTATGACAGGAATTCAGACGCATATC (SEQ ID NO: 52)
```

The sequences of the DNA oligonucleotides that were annealed and cloned in the BBI gene (Sad-EcoRI) to replace the trypsin inhibitory loop with the VegF binding peptide CK37281 were:

```
1BBck81+
                                          (SEQ ID NO: 53)
5'-CTAAACCCTGTTGCGATCAATGCGCATGTTATAATTTGTATGGGT

GGACTTGTCGCTGCAGCGATATGCGTCTG

1BBck81-
                                          (SEQ ID NO: 54)
5'-AATTCAGACGCATATCGCTGCAGCGACAAGTCCACCCATACAAAT

TATAACATGCGCATTGATCGCAACAGGGTTTAGAGCT
```

The sequences of the DNA oligonucleotides that were annealed and cloned in the BBI gene (EcoRI-SalI) to replace the chymotrypsin inhibitory loop with the VegF binding peptide CK37281 were:

2BBck81+

(SEQ ID NO: 55)

5'-AATTCCTGTCATAGTGCCTGCAAAAGCTGCGCATGTTATAACCTG

TACGGGTGGACCTGTTTTTGCG

-continued

2BBck81-

(SEQ ID NO: 56)

5'-TCGACGCAAAAACAGGTCCACCCGTACAGGTTATAACATGCGCAG

CTTTTGCAGGCACTATGACAGG

The DNA sequences of the oligonucleotide pairs used to make cassettes to introduce peptides into the trypsin (SacI and EcoRI restriction sites) or chymotypsin (EcoRI and SalI restriction sites) reactive site loops of the synthetic BBI gene are provided below. These peptide coding sequences were then moved into the p2JM103BBI expression vector as Sad-SalI fragments.

Comstatin (1$^{st}$ loop)

(SEQ ID NO: 57)

CTAAACCCTGTTGCGATCAATGCGCATGTGTTGTTCAGGACTGGGGTCACCACCGTTGTCGCTG

CAGCGATATGCGTCTG and (SEQ ID NO: 58)

AATTCAGACGCATATCGCTGCAGCGACAACGGTGGTGACCCCAGTCCTGAACAACACATGCGCA

TTGATCGCAACAGGGTTTAGAGCT

Comstatin (2$^{nd}$ loop)

(SEQ ID NO: 59)

CAAAAGCTGTATCTGCGTTGTTCAGGACTGGGGTCACCACCGTTGTTTTTGCG and (SEQ ID NO: 60)

TCGACGCAAAAACAACGGTGGTGACCCCAGTCCTGAACAACGCAGATACAGCTTTTGCATG

C2c (1$^{s}$t loop)

(SEQ ID NO: 61)

CTAAACCCTGTTGCGATCAATGCAGCTGTGGTCGTAAAATCCCGATCCAGTGTCGCTGCAGCGA

TATGCGTCTG and (SEQ ID NO: 62)

AATTCAGACGCATATCGCTGCAGCGACACTGGATCGGGATTTTACGACCACAGCTGCATTGATC

GCAACAGGGTTTAGAGCT

C3c (1$^{st}$ loop)

(SEQ ID NO: 63)

CTAAACCCTGTTGCGATCAATGCGGTTGTGCTCGTTCTAACCTGGACGAATGTCGCTGCAGCGA

TATGCGTCTG and (SEQ ID NO: 64)

AATTCAGACGCATATCGCTGCAGCGACATTCGTCCAGGTTAGAACGAGCACAACCGCATTGATC

GCAACAGGGTTTAGAGCT

C4c (1$^{st}$ loop)

(SEQ ID NO: 65)

CTAAACCCTGTTGCGATCAATGCGGTTGTCAGCGTGCTCTGCCGATCCTGTGTCGCTGCAGCGA

TATGCGTCTG and (SEQ ID NO: 66)

AATTCAGACGCATATCGCTGCAGCGACACAGGATCGGCAGAGCACGCTGACAACCGCATTGATC

GCAACAGGGTTTAGAGCT

C5c (1$^{st}$ loop)

(SEQ ID NO: 67)

CTAAACCCTGTTGCGATCAATGCCAGTGTGGTCGTCTGCACATGAAAACCTGTCGCTGCAGCGA

TATGCGTCTG and

```
                                                  (SEQ ID NO: 68)
AATTCAGACGCATATCGCTGCAGCGACAGGTTTTCATGTGCAGACGACCACACTGGCATTGATC

GCAACAGGGTTTAGAGCT

Xa1 (2nd loop)
                                                  (SEQ ID NO: 69)
AATTCCTGTCATAGTGCCTGCAAAAGCTGTATCTGCGCCCGTAGTTTGCCAGCTCAATGTTTTT GCG
and
                                                  (SEQ ID NO: 70)
TCGACGCAAAAACATTGAGCTGGCAAACTACGGGCGCAGATACAGCTTTTGCAGGCACTATGAC

AGG hSCC1 (1st loop)
                                                  (SEQ ID NO: 71)
CTAAACCCTGTTGCGATCAATGCAACTGTACGTACTCAACCCCTCCACAGTGTCGCTGCAGCGA TATGCGTCTG
and
                                                  (SEQ ID NO: 72)
AATTCAGACGCATATCGCTGCAGCGACACTGTGGAGGGGTTGAGTACGTACAGTTGCATTGATC

GCAACAGGGTTTAGAGCT
```

The DNA sequences of oligonucleotide primer pairs used to introduce peptide sequences into the trypsin or chymotrypsin reactive site loops using a QuikChange® II XL site-directed mutagenesis kit (Stratagene) are provided below. The reactions were performed as outlined by the manufacturer and described in this Example. Twenty cycles were performed with extensions of 6 minutes at 68° C., denaturations of 50 s at 95° C., and annealings at 55° C. for 50 s. After the cycles, a final extension was performed at 68° C. for 20 minutes.

```
1A (2nd loop)
                                                  (SEQ ID NO: 73)
CTGTATCTGCAAACGCTCAAAATCTCGTGGCTGTTTTTGCGTCGACATC AC
and
                                                  (SEQ ID NO: 74)
CGCAAAAACAGCCACGAGATTTTGAGCGTTTGCAGATACAGCTTTTGCA

TG 2B (2nd loop)
                                                  (SEQ ID NO: 75)
CTGTATCTGCTGGTATAATCAAATGACAACATGTTTTTGCGTCGACATC AC
and
                                                  (SEQ ID NO: 76)
CGCAAAAACATGTTGTCATTTGATTATACCAGCAGATACAGCTTTTGCA

TG 4A (2nd loop)
                                                  (SEQ ID NO: 77)
CTGTATCTGCCATCAACTTGGCCCGAATTCATGTTTTTGCGTCGACATC AC
and
                                                  (SEQ ID NO: 78)
CGCAAAAACATGAATTCGGGCCAAGTTGATGGCAGATACAGCTTTTGCA

TG 5A (2nd loop)
                                                  (SEQ ID NO: 79)
CTGTATCTGCCATCCGTGGGCACCGTATTCTTGTTTTTGCGTCGACATC AC
and
                                                  (SEQ ID NO: 80)
CGCAAAAACAAGAATACGGTGCCCACGGATGGCAGATACAGCTTTTGCA

TG 6-1A (2nd loop)
                                                  (SEQ ID NO: 81)
CTGTATCTGCAATCTTCATTATCTTCAACAGTGTTTTTGCGTCGACATC AC
and
                                                  (SEQ ID NO: 82)
CGCAAAAACACTGTTGAAGATAATGAAGATTGCAGATACAGCTTTTGCA

TG 7A (2nd loop)
                                                  (SEQ ID NO: 83)
CTGTATCTGCACACCGTCTCTTTATCGCCCGTGTTTTTGCGTCGACATC AC
and
                                                  (SEQ ID NO: 84)
CGCAAAAACACGGGCGATAAAGAGACGGTGTGCAGATACAGCTTTTGCA

TG 8B (2nd loop)
                                                  (SEQ ID NO: 85)
CTGTATCTGCCTTACAGATCAATCTAAACCGTGTTTTTGCGTCGACATC AC
and
                                                  (SEQ ID NO: 86)
CGCAAAAACACGGTTTAGATTGATCTGTAAGGCAGATACAGCTTTTGCA

TG
```

9A (2<sup>nd</sup> loop)

(SEQ ID NO: 87)
CTGTATCTGCGTTACAACATCAATGGGCATGTGTTTTGCGTCGACATC
AC and (SEQ ID NO: 88)
CGCAAAAACACATGCCCATTGATGTTGTAACGCAGATACAGCTTTTGCA
TG

10B (2<sup>nd</sup> loop)

(SEQ ID NO: 89)
CTGTATCTGCCGCGCATCACCGTATGATTGGTGTTTTTGCGTCGACATC
AC and (SEQ ID NO: 90)
CGCAAAAACACCAATCATACGGTGATGCGCGGCAGATACAGCTTTTGCA
TG

11-1A (2<sup>nd</sup> loop)

(SEQ ID NO: 91)
CTGTATCTGCTCAACACAAAAAATTCCGCAATGTTTTTGCGTCGACATC
AC and (SEQ ID NO: 92)
CGCAAAAACATTGCGGAATTTTTTGTGTTGAGCAGATACAGCTTTTGCA
TG

12B (2<sup>nd</sup> loop)

(SEQ ID NO: 93)
CTGTATCTGCACACAATTTCGCTCTGCAACATGTTTTTGCGTCGACATC
AC and (SEQ ID NO: 94)
CGCAAAAACATGTTGCAGAGCGAAATTGTGTGCAGATACAGCTTTTGCA
TG

13A (2<sup>nd</sup> loop)

(SEQ ID NO: 95)
CTGTATCTGCCCGGATCATGTTCCGCATCTTTGTTTTGCGTCGACATC
AC and (SEQ ID NO: 96)
CGCAAAAACAAAGATGCGGAACATGATCCGGGCAGATACAGCTTTTGCA
TG

15-1A (2<sup>nd</sup> loop)

(SEQ ID NO: 97)
CTGTATCTGCTCAGGCTTTCCGCTTTCTACATGTTTTTGCGTCGACATC
AC and (SEQ ID NO: 98)
CGCAAAAACATGTAGAAAGCGGAAAGCCTGAGCAGATACAGCTTTTGCA
TG

1A6 (1<sup>st</sup> loop)

(SEQ ID NO: 99)
TCAATGCGCATGTGAAGAGATCTGGACTATGCTTTGCCGGTGTTCCGAT
GATCGTC and (SEQ ID NO: 100)
CGGAACACCGGCAAAGCATAGTCCAGATCTCTTCACATGCGCATTGATC
GCAACAGG

1A6 (2<sup>nd</sup> loop)

(SEQ ID NO: 101)
CAAAAGCTGTGCTTGTGAAGAGATCTGGACTATGCTTTGCTTTTGCGTC
CGAATCACGG and (SEQ ID NO: 102)
ACGCAAAAGCAAAGCATAGTCCAGATCTCTTCACAAGCACAGCTTTTGC
ATGCACTATG

1C2 (1<sup>st</sup> loop)

(SEQ ID NO: 103)
TCAATGCGCATGTTGGGCCCTTACTGTCAAAACATGCCGGTGTTCCGAT
ATGCGTC and (SEQ ID NO: 104)
CGGAACACCGGCATGTTTTGACAGTAAGGGCCCAACATGCGCATTGATC
GCAACAGG

1C2 (2<sup>nd</sup> loop)

(SEQ ID NO: 105)
CAAAAGCTGTGCTTGTTGGGCCCTTACTGTCAAAACATGCTTTTGCGTC
GACATCACGG and (SEQ ID NO: 106)
ACGCAAAAGCATGTTTTGACAGTAAGGGCCCAACAAGCACAGCTTTTGC
ATGCACTATG

2E2 (1<sup>st</sup> loop)

(SEQ ID NO: 107)
TCAATGCGCATGTCTTACAGTACTGTGGACTACATGCCGGTGTTCCGAT
ATGCGTC and (SEQ ID NO: 108)
CGGAACACCGGCATGTAGTCCACAGTACTGTAAGACATGCGCATTGATC
GCAACAGG

2E2 (2<sup>nd</sup> loop)

(SEQ ID NO: 109)
CAAAAGCTGTGCTTGTCTTACAGTACTGTGGACTACATGCTTTTGCGTC
GACATCACGG and (SEQ ID NO: 110)
ACGCAAAAGCATGTAGTCCACAGTACTGTAAGACAAGCACAGCTTTTGC
ATGCACTATG

2E5 (1<sup>st</sup> loop)

(SEQ ID NO: 111)
TCAATGCGCATGTACTCTTTGGAACAGATCTCCTTGCCGGTGTTCCGAT
ATGCGTC and (SEQ ID NO: 112)
CGGAACACCGGCAAGGAGATCTGTTCCAAAGAGTACATGCGCATTGATC
GCAACAGG 2E5 (2nd loop)

(SEQ ID NO: 113)
CAAAAGCTGTGCTTGTACTCTTTGGAATCGATCTCCTTGCTTTTGCGTC
GACATCACGG
and (SEQ ID NO: 114)
ACGCAAAAGCAAGGAGATCGATTCCAAAGAGTACAAGCACAGCTTTTGC
ATGCACTATG FGFns (1st loop)

(SEQ ID NO: 115)
TCAATGCGCATGTACAAACATCGATTCTACTCCTTGCCGGTGTTCCGAT
ATGCGTC
and (SEQ ID NO: 116)
CGGAACACCGGCAAGGAGTAGAATCGATGTTTGTACATGCGCATTGATC
GCAACAGG FGFns (2nd loop)

(SEQ ID NO: 117)
CAAAAGCTGTGCTTGCACAAACATCGATTCTACTCCTTGTTTTGCGTC
GACATCACGG
and (SEQ ID NO: 118)
ACGCAAAACAAGGAGTAGAATCGATGTTTGTGCAAGCACAGCTTTTGC
ATGCACTATG FGFkr (1st loop)

(SEQ ID NO: 119)
TCAATGCGCATGTACAAAAATCGATCGTACTCCTTGCCGGTGTTCCGAT
ATGCGTC
and (SEQ ID NO: 120)
GCCGGAACACCGGCAAGGAGTACGATCGATTTTTGTACATGCGCATTGA
TCAACAGG FGFkr (2nd loop)

(SEQ ID NO: 121)
CAAAAGCTGTGCTTGCACAAAAATCGATCGTACTCCTTGTTTTGCGTC
GACATCACGG
and (SEQ ID NO: 122)
ACGCAAAACAAGGAGTACGATCGATTTTTGTGCAAGCACAGCTTTTGC
ATGCACTATG FGFhl (1st loop)

(SEQ ID NO: 123)
TCAATGCGCATGTCACCTGCAGACAACTGAAACATGCCGGTGTTCCGAT
ATGCGTC
and (SEQ ID NO: 124)
CGGAACACCGGCATGTTTCAGTTGTCTGCAGGTGACATGCGCATTGATC
GCAACAGG FGFhl (2nd loop)

(SEQ ID NO: 125)
CAAAAGCTGTGCTTGCCACCTGCAGACAACTGAAACATGTTTTGCGTC
GACATCACGG
and (SEQ ID NO: 126)
ACGCAAAACATGTTTCAGTTGTCTGCAGGTGGCAAGCACAGCTTTTGC
ATGCACTATG FGFgy (1st loop)

(SEQ ID NO: 127)
TCAATGCGCATGTGGCTACTTCATCCCATCGATTTGCCGGTGTTCCGAT
ATGCGTC
and (SEQ ID NO: 128)
CGGAACACCGGCAAATCGATGGGATGAAGTAGCCACATGCGCATTGATC
GCAACAGG FGFgy (2nd loop)

(SEQ ID NO: 129)
CAAAAGCTGTGCTTGCGGCTACTTCATCCCATCGATTTGTTTTTGCGTC
GACATCACGG
and (SEQ ID NO: 130)
ACGCAAAAACAAATCGATGGGATGAAGTAGCCGCAAGCACAGCTTTTGC
ATGCACTATG MM005 (1st loop)

(SEQ ID NO: 131)
TCAATGCGCATGTTTACGTATCCTTGCTAACAAATGCCGGTGTTCCGAT
ATGCGTC
and (SEQ ID NO: 132)
CGGAACACCGGCATTTGTTAGCAAGGATACGTAAACATGCGCATTGATC
GCAACAGG MM005 (2nd loop)

(SEQ ID NO: 133)
CAAAAGCTGTGCTTGCTTACGTATCCTTGCTAACAAATGTTTTGCGTC
GACATCACGG
and (SEQ ID NO: 134)
ACGCAAAAACATTTGTTAGCAAGGATACGTAAGCAAGCACAGCTTTTGC
ATGCACTATG MM007 (1st loop)

(SEQ ID NO: 135)
GCGATCAATGCGCCTGCAGAACTCAACCATATCCTTTATGTCGGTGTTC
CGATATGCGTC
and (SEQ ID NO: 136)
GGAACACCGACATAAAGGATATGGTTGAGTTCTGCAGGCGCATTGATCG
CAACAGGGTTT MM007 (2nd loop)

(SEQ ID NO: 137)
CAAAAGCTGTGCCTGCAGAACACAACCTTACCCACTTTGTTTTGCGTC
GACATCACGG
and (SEQ ID NO: 138)
ACGCAAAAACAAAGTGGGTAAGGTTGTGTTCTGCAGGCACAGCTTTTGC
ATGCACTATG MM009 (2nd loop)
(SEQ ID NO: 139)
CAAAAGCTGTGCCTGCCTGTTAACACCTACTCTTAACTGTTTTTGCGTCGACATCACGG
and (SEQ ID NO: 140)
ACGCAAAAACAGTTAAGAGTAGGTGTTAACAGGCAGGCACAGCTTTTGCATGCACTATG MM010 (1st loop)
(SEQ ID NO: 141)
TCAATGCGCATGCGCTCTTCCAACTCATTCTAACTGTCGGTGTTCCGATATGCGTCT
and (SEQ ID NO: 142)
CGGAACACCGACAGTTAGAATGAGTTGGAAGAGCGCATGCGCATTGATCGCAACAGG MM010 (2nd loop)
(SEQ ID NO: 143)
CAAAAGCTGTGCCTGCGCGCTTCCTACACACTCTAACTGTTTTTGCGTCGACATCACGG
and (SEQ ID NO: 144)
ACGCAAAAACAGTTAGAGTGTGTAGGAAGCGCGCAGGCACAGCTTTTGCATGCACTATG MM017 (2nd loop)
(SEQ ID NO: 145)
CAAAAGCTGTGCCTGCCCTTTAGGCCTTTGCCCACCTTGTTTTTGCGTCGACATCACGG
and (SEQ ID NO: 146)
ACGCAAAAACAAGGTGGGCAAAGGCCTAAAGGGCAGGCACAGCTTTTGCATGCACTATG FGFps1 (2nd loop)
(SEQ ID NO: 147)
AAGCTGTATCTGCTGGAACATCGATTCTACACCTTGTTTTTGCGTCGACATCACGG
and (SEQ ID NO: 148)
ACGCAAAAACAAGGTGTAGAATCGATGTTCCAGCAGATACAGCTTTTGCATGCACT FGFps2 (1st loop)
(SEQ ID NO: 149)
GCGATCAATGCATCTGTACTTGGATTGACAGTACTCCTTGTCGGTGTTCGATATGCGTC
and (SEQ ID NO: 150)
GGAACACCGACAAGGAGTACTGTCAATCCAAGTACAGATGCATTGATCGCAACAGGGTTT FGFps2 (2nd loop)
(SEQ ID NO: 151)
AAGCTGTATCTGCACATGGATCGATAGTACTCCTTGTTTTTGCGTCGACATCACGG
and (SEQ ID NO: 152)
ACGCAAAAACAAGGTGTAGAATCGATCCATGTGCAGATACAGCTTTTGCATGCACT FGFpsB (2nd loop)
(SEQ ID NO: 153)
AAGCTGTATCTGTACATGGATCGATTGGACACCTTGTTTTTGCGTCGACATCACGG
and (SEQ ID NO: 154)
ACGCAAAAACAAGGTGTCCAATCGATCCATGTACAGATACAGCTTTTGCATGCACT 1A8 (2nd loop)
(SEQ ID NO: 155)
CAAAAGCTGCGCATGTGTTACTACAGATTGGATCGAATGTTTTTGCGTCGACATCACGG
and (SEQ ID NO: 156)
ACGCAAAAACATTCGATCCAATCTGTAGTAACACATGCGCAGCTTTTGCATGCACTATG 1A12 (2nd loop)
(SEQ ID NO: 157)
CAAAAGCTGTGCCTGCCCAACACTTTGGACTCATATGTGTTTTTGCGTCGACATCACGGAC
and (SEQ ID NO: 158)
ACGCAAAAACACATATGAGTCCAAAGTGTTGGGCAGGCACAGCTTTTGCATGCACTATGAC 1E11 (2nd loop)
(SEQ ID NO: 159)
CAAAAGCTGCGCATGTTACTACTCTCAATTCCACCAATGTTTTTGCGTCGACATCACGG
and (SEQ ID NO: 160)
ACGCAAAAACATTGGTGGAATTGAGAGTAGTAACATGCGCAGCTTTTGCATGCACTATG TGFps1 (2nd loop)
(SEQ ID NO: 161)
CAAAAGCTGTCTTTGTCCGGAAAACGATAACGTTTCTCCTTGTAATTGCGTCGACATCACGGACTTCTG
and (SEQ ID NO: 162)
TGTCGACGCAATTACAAGGAGAAACGTTATCGTTTTCCGGACAAAGACAGCTTTTGCATGCACTATGAC The DNA sequences of the oligonucleotide pairs used to make cassettes to introduce peptide sequences into the chymotrypsin reactive site loops of the p2JM103-lnk2-BBI expression vector are provided below. The cassettes were ligated into the SphI and SalI restriction sites in the vector.

MM021 (2nd loop)
(SEQ ID NO: 163)
CAAAAGCTGTGCTTGTAAACACAACGTACGTCTTTTATGTTTTTGCG
and -continued (SEQ ID NO: 164)
TCGACGCAAAAACATAAAAGACGTACGTTGTGTTTACAAGCACAGCTT

TTGCATG

VegT (2$^{nd}$ loop)
(SEQ ID NO: 165)
CAAATCTTGCGCGTGCACACTTTGGAAATCTTACTGGTGTTTTGCG
and (SEQ ID NO: 166)
TCGACGCAAAAACACCAGTAAGATTTCCAAAGTGTGCACGCGCAAGA

TTTGCATG

VegK (2$^{nd}$ loop)
(SEQ ID NO: 167)
CAAATCTTGCGCATGTAAATATTACCTTTACTGGTGGTGTTTTGCG
and (SEQ ID NO: 168)
TCGACGCAAAAACACCACCAGTAAAGGTAATATTTACATGCGCAAGA

TTTGCATG

VegKD (2$^{nd}$ loop)
(SEQ ID NO: 169)
CAAATCTTGCATCTGTAAATATGATCTTTACTGGTGGTGTTTTGCG
and (SEQ ID NO: 170)
TCGACGCAAAAACACCACCAGTAAAGATCATATTTACAGATGCAAGAT

TTGCATG

VegDK (2$^{nd}$ loop)
(SEQ ID NO: 171)
CAAATCTTGCATCTGTGATTATAAACTTTACTGGTGGTGTTTTGCG
and (SEQ ID NO: 172)
TCGACGCAAAAACACCACCAGTAAAGTTTATAATCACAGATGCAAGA

TTTGCATG

Libraries made of cysteine constrained peptides are popular reagents (e.g. the commercially available PhD-C7C Phage Display Peptide Library Kit; NEB) for selecting peptides that bind to substrates of interest. BBI has two cysteine constrained reactive site loops that are structurally similar to the peptide loops displayed in various methods used to select peptide binders. So, once a cysteine constrained binding peptide has been selected, BBI is suitable for use as a scaffold to present the peptide in a binding reaction.

The VegF binding peptide CK37281 (See e.g., co-pending U.S. patent application Ser. No. 10/984,270, filed Nov. 8, 2004, incorporated herein by reference) was grafted into BBI by replacing the trypsin, chymotrypsin, or both reactive site loops, with the peptide sequence (ACYNLYGWTC) (SEQ ID NO:43) by using DNA oligonucleotide cassettes. To facilitate the construction, an EcoRI site was introduced in the coding region of the BBI gene (custom synthesized by Operon Technologies; See, Example 16) between the trypsin and chymotrypsin reactive site loops by QuikChange® site-directed mutagenesis, using methods described by the manufacturer (Stratagene) using the primers BowBeco-F and BowBeco-R, shown above (0.5 pmol of each primer was used in the QuikChange® reaction; after an initial denaturation step of 97° C. for 3 minutes, 18 PCR cycles of 68° C. for 12 minutes, 95° C. for 30 seconds and 55° C. for one minute, followed by a final extension reaction for 15 minutes at 68° C.).

To replace the trypsin inhibitory peptide loop, two DNA oligonucleotides (1BBCK81+ and 1BBCk81−) were annealed and ligated into the SacI and EcoRI restriction sites. Likewise, to replace the chymotrypsin inhibitory peptide loop, EcoRI and SalI sites were used for insertion of a DNA cassette made by annealing the oligonucleotides (2BBck81+ an 2BBck81−). The (ACYNLYGWTC)(SEQ ID NO:43) peptide was grafted into both loops by inserting the peptide in the chymotrypsin loop (using the oligonucleotides (2BBck81+an 2BBck81−) after the trypsin loop was first replaced by the peptide. BBI with the grafted peptide in the trypsin loop (1BBIck81) was moved into the pJM103BBI expression vector as a SacI-SphI fragment. BBI with the grafted peptide in the chymotrypsin loop (2BBIck81), or both loops (12BBIck81), was moved into pJM103BBI as Sad-SalI fragments. The correct sequences were verified by DNA sequencing (the sequence of 12BBIck81 gene is shown in FIG. 16). The resulting vectors, pJM103-1BBIck81, pJM103-2BBIck81, or pJM103-12BBIck81, were used to transform *B. subtilis* BG3934comK, and the production of the BCE fusion proteins was determined as in Example 16, above.

The fusion protein running at ~44 kDa was detected by SDS-PAGE to be the major protein present in the cell free broth. Although in some cases, there was significant degradation (up to 50%) of the BBI moiety (especially after >48 h of growth in MBD medium), as observed by the presence of a prominent protein band running at ~34 kDa corresponding to the BCE103 catalytic core. In these cases, the titers of the BCE103 cellulase were similar to that measured with fusions to the wild-type BBI (Example 16), but the activity of the BBI (trypsin inhibition with 2BBIck81, or chymotrypsin inhibition with 1BBIck81) was generally about two fold less.

To reduce the proteolytic degradation of BBI variants during growth (i.e. decrease the amount of BCE103 cellulase core present on SDS-PAGE gels in comparison to the fusion protein), a *Bacillus subtilis* strain with nine protease genes deleted, BG6006 (degU$^{Hy}$32, oppA, ΔspoIIE3501, ΔaprE, ΔnprE, Δepr, ΔispA, Δbpr, Δvpr ΔwprA, Δmpr-ybjF, ΔnprB, amyE::xylRPxylAcomK-ermC), was used as an expression host, and the growth temperature (35° C.) and aeration (200 rpm) were reduced. With these changes, a major fusion protein band (~44 kDa) was observed on SDS-PAGE gels with an insignificant band present at the molecular weight expected for the BCE catalytic core protein (~34 kDa).

In addition to the above peptide, a number of other cysteine constrained peptides were produced when substituted into the trypsin and/or chymotrypsin reactive site loops of BBI fused to the C-terminus of the BCE103 cellulase. Specific examples included:

(1) Peptides designed or selected as complement antagonists, compstatin introduced into the 1$^{st}$ or 2$^{nd}$ reactive site loops (See, Sahu et al., J. Immunol., 157: 884-891, [1996]), C2c (1$^{st}$ loop), C3c (1$^{st}$ loop), C4c (1$^{st}$ loop) and C5c (1$^{st}$ loop); or peptides selected in a Factor B binding reaction 1B, 2B, 4A, 5A, 6-1A,7A, 8B, 9A, 10B, 11-1A, 12B, 13A, and 15-1A (all in 2$^{nd}$ loop);

(2) Peptides designed to bind to the proteases Factor Xa or stratum corenum chymotrypsin, Xal (2$^{nd}$ loop) or hSCC1 (1$^{st}$ loop), respectively;

(3) Peptides selected in FGF5 binding reactions 1A6 (1$^{st}$ or 2nd loop), 1C2 (1$^{st}$ or 2nd loop), 2E2 (1$^{st}$ or 2nd loop), 2E5 (1$^{st}$, 2$^{nd}$ or both loops), FGFns (1$^{st}$ or 2$^{nd}$ loop), FGFkr (1$^{st}$ or 2$^{nd}$ loop), FGFh1 (1$^{st}$ or 2$^{nd}$ loop), FGFgy (1$^{st}$ or 2$^{nd}$ loop), MM005 (1$^{st}$ or 2$^{nd}$ loop), MM007 (1$^{st}$, 2$^{nd}$ or both loops), MM009 (2$^{nd}$ loop), MM010 (1$^{st}$, 2$^{nd}$ or both loops), MM017 (2$^{nd}$ loop), FGFps1 (2$^{nd}$ loop), FGFps2 (1$^{st}$, 2$^{nd}$ or both loops), and FGFpsB (2$^{nd}$ loop); and (4) Peptides selected in TGFβ-1 binding reactions 1A8 (2nd loop), 1A12 (2nd loop), 1E11 (2nd loop), TGFps1 (2nd loop), and MM021 (2nd loop)
(5) Peptides selected in VEGF binding reactions VegK (2nd loop), VegT (2nd loop), VegKD (2nd loop), and VegDK (2nd loop), The oligonucleotides used to introduce these peptides into either the trypsin (1st loop) or chymotrypsin (2nd loop) reactive site loops, and methods used to graft these peptides into BBI, are provided above. In all cases, fusion proteins were produced as determined by SDS-PAGE gels. However, with some substituted peptides, the amount of intact fusion protein was increased by reducing the proteolytic degradation as described above for the grafted (ACYNLYGWTC) (SEQ ID NO:43) peptide.

Example 18

Activation of BBI By Thiol Reducing/Oxidizing Agents

After growth, the activity of the BBI (by trysin or chymotrypsin inhibition) is typically some 5-20 times lower than what would be expected from the activity of the BCE103 cellulase measured in the cell free supernatants (the two molecules should be present at a 1:1 molar ratio in the fusion protein). An increase in the activity of BBI (measured by either trypsin or chymotrypsin inhibition) in the BCE103-BBI fusion protein can be routinely obtained by adding bME, typically concentrations of 1-4 mM added to the MBD growth medium about 14 h after inoculation. The trypsin or chymotrypsin inhibitory activity of BBI in the fusion protein is also lower than expected when binding peptides (e.g. VegF binding peptide CK37281) replaced the chymotrypsin or trypsin reactive site loop, respectively. As with the wild-type BBI, the inhibitory activity can be increased by treatment with bME. Unexpectedly, other thiol reducing agents (e.g., cysteine, reduced glutathione, DL-dithiothreitol and Tris[2-carboxyethyl] phosphine) had small or negligible effects on the activation of BBI during growth in these experiments. Also, additions of antioxidants (e.g., ascorbic acid or DL-α-tocopherol acetate) or other adjuvants to the growth medium (e.g., isoleucine, soybean oil, Tween-80), or growth at 30° C. did not significantly improve the BCE103:BBI activity ratio.

Figure 17:
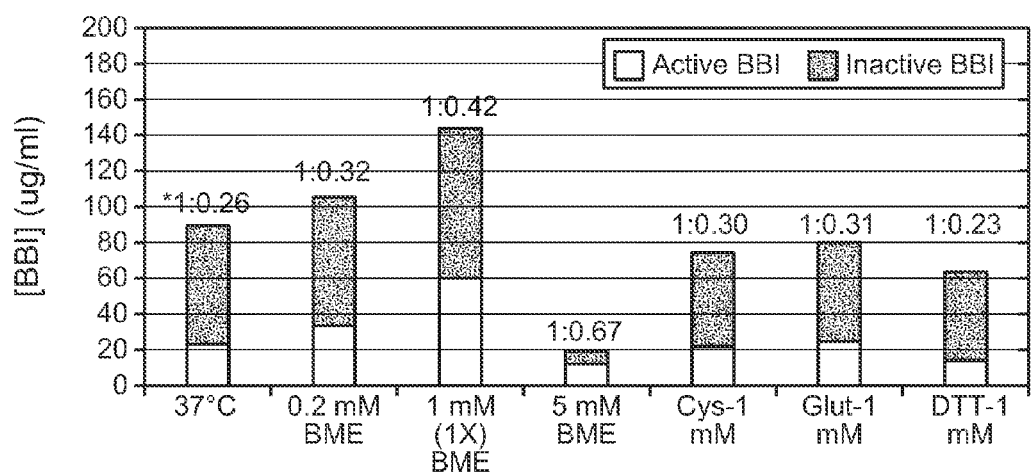
FIG. 17 provides a graph showing titers of active versus inactive 2BBIck81 (by trypsin inhibition) and the ratio of the activities of BCE103 cellulase to 2BBck81 with various thiol reducing agents added during the growth of the culture. In this Figure, BME=2-mercaptoethanol, Cyt=cysteine, Glut=reduced glutathione, DTT=dithiothreitol).

Specifically, to determine the BBI activation during growth, cultures of *B. subtilis* BG6006 transformed with p2JM103-E3-2BBIck81 (See, Example 19, below) were grown in 40 ml MBD medium in 250 ml shake flasks at 37° C. for 13 h. Then, the thiol reducing agents indicated on the graph in FIG. 17 were added and cell supernatants harvested after 62 h of growth. The reagents 2-mercaptoethanol (BME), cysteine (Cys), reduced glutathione (Glut), and DL-dithiothreitol (DTT) were added to the growth medium to the final concentrations indicated on the graph provided in FIG. 17. Concentrations of 5 mM βME can result in better BCE103:BBI activity ratios but typically result in an overall decrease in both BCE103 and BBI titers (See, FIG. 17), at least partially due to the reduction in bacterial growth caused by the added reagent. Titers of BCE103 and 2BBIck81 were determined using the assays described in Example 16.

BBI activation was also achieved after partial purification of the fusion proteins (e.g. BCE-lnk2-2BBIck81; See, Example 19, below) by Q-Sepharose ion exchange chromatography.

The fusion protein was purified from cell free broth obtained from shake flasks or fermentor runs. The broth was filtered, diluted five to ten fold in water and the pH adjusted to pH 7.5-8.0. The diluted sample was loaded onto a column packed with Q-Sepharose resin (GE Healthcare). The column was washed with 50 mM Tris pH 7.5 and then washed again in the same buffer containing 300 mM NaCl. The fusion protein was eluted in the same buffer with 700 mM NaCl.

To activate the BBI, the pooled fusion protein fractions were diluted ten fold in Assay Buffer then treated with 2 mM βME and 0.2 mM oxidized glutathione (GSSG) with constant mixing on a stir plate or rocker platform for about 24 h at room temperature. The BBI could generally be activated to about 70-100% of the expected trypsin inhibitory activity based on the measured concentration of the BCE103 cellulase. Although the activation method outlined above generally yielded the best results, in some cases, in order to maximize the activation of a given sample, screens were performed in 96-well plates to determine the optimal conditions. Initially, the typical conditions screened were the dilution in Assay Buffer (e.g., a 2-50 fold dilution series), PME concentration (e.g., series between 0.5-5 mM) and oxidized glutathione concentration (e.g. 0 mM then a series of ½0 to ½ the βME concentration).

Figure 18:
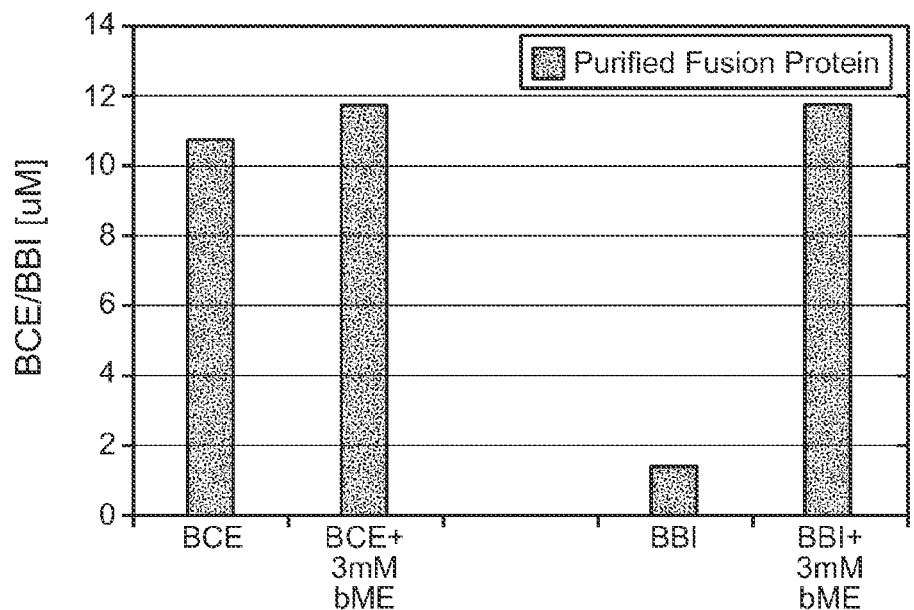
FIG. 18 provides a graph showing activation of BCE-lnk2-2BBIck81 with 2-mercaptoethanol (bME) after partial purification by ion exchange chromatography.

The activation of the fusion protein BCE-lnk2-2BBIck81 is shown in FIG. 18. In this specific example, the fusion protein from a Q-Sepharose purification was diluted 1:10 in Dulbecco's PBS (Mediatech) with 0.005% TWEEN®-80. Beta-mercaptoethanol was added to a final concentration of 3 mM and incubated overnight at room temperature on a rocker. The sample was further incubated at room temperature for about 60 h with vigorous stirring on a magnetic stir plate. The titers of the BCE103 and 2BBIck81 (before and after βME treatment) were determined by cellulase assays and trypsin inhibitory assays, respectively.

In some embodiments, such as for activating BBI or it variants in cell free broth from large volume fermentations, it is desirable to reduce the dilution and βME concentration in the activation reaction. This can be accomplished by using higher concentrations of buffer (500 mM Tris pH 8.6), or changing to zwitterionic buffers such as CHES (also CAPS, Tricine, TAPS, and other suitable zwitterionic buffers). For example, cell free broth (or fusion protein fractions purified by ion exchange chromatography) was diluted 1:1 in 375 mM CHES pH 8.6 with 0.005% TWEEN®-80 then activated with 1 mM βME and 10 mM $Na_2SO_3$ and incubated with stirring at room temperature for about 24 h. BBI or its variants, as BCE103 cellulase fusion proteins, were routinely activated by this method to 70-100% of the expected value (based on BCE103 cellulase activities).

In some other embodiments, it is desirable to activate BBI or its variants in whole fermentation broth with the cells present. For example, in some experiments, whole broth was diluted 1:1 in 250 mM glycine pH 9.0 with 0.05% TWEEN®-80, and then activated with 2 mM βME and 10 mM $Na_2SO_3$ (or with 10 mM $Na_2S_2O_4$ alone) and incubated with stirring, at room temperature for about 24 h. BBI or its variants, as BCE103 cellulase fusion proteins, were routinely activated by this method to 30-100% of the expected value (based on BCE103 cellulase activities).

Example 19

Release of Free BBI/Variants by Cleavage of the BCE103-BBI Fusion Proteins

This Example describes experiments developed to release free BBI or its variants by cleavage of the BCE103-BBI fusion proteins.

The sequences of the DNA oligonucleotide pairs that were annealed and ligated into the BamHI and SacI sites of pJM103-BBI to generate potential cleavage sites during culture growth between the BCE103 catalytic domain and BBI are provided below.

```
BCEsubBBI (a subtilisin-type
sensitive peptide sequence)
                                    (SEQ ID NO: 173)
GATCCAGGTGGAGCTGCTTTAGTTGACGATGAGAGCT
and
                                    (SEQ ID NO: 174)
CTCATCGTCAACTAAAGCAGCTCCACCTG BCEcbdLBBI (a portion of the 1st CBD)
                                    (SEQ ID NO: 175)
GATCCAGGTGAACCTGACCCAACTCCTCCATCTGATCCTGGAGAATACC CAGCTTGGGACGATGAGAGCT
and
                                    (SEQ ID NO: 176)
CTCATCGTCCCAAGCTGGGTATTCTCCAGGATCAGATGGAGGAGTTGGG

TCAGGTTCACCTG

BCEproBBI (the entire pro peptide of BBI)
                                    (SEQ ID NO: 177)
GATCCGGCGAACCTGCGTCTGTCTAAGCTTGGCCTGCTTATGAAATCAG ACCATCAGCACAGCAATGACGATGAGAGCT
and
                                    (SEQ ID NO: 178)
CTCATCGTCATTGCTGTGCTGATGGTCTGATTTCATAAGCAGGCCAAGC

TTAGACAGACGCAGGTTCGCCG

BCEshortproBBl (a C-terminal portion
of the pro peptide of BBI)
                                    (SEQ ID NO: 179)
GATCCAAAATCAGACCATCAGCACAGCAATGACGATGAGAGCT
and
                                    (SEQ ID NO: 180)
CTCATCGTCATTGCTGTGCTGATGGTCTGATTTTG
```

The sequences of the DNA oligonucleotide pair that was annealed and ligated into the BamHI and SacI sites of p2JM103-BBI to fuse BBI to the $2^{nd}$ CBD linker of BCE103 cellulase are provided below.

```
BCEcbdDBBI
                                    (SEQ ID NO: 181)
GATCCAGGAGAACCGGACCCAACGCCCCCAAGTGATCCAGGAGAGTATC

CAGCATGGGATTCA AATCAAATTTACACAAATGAAATTGTGTATCATA

ACGGTCAGTTATGGCAAGCGAAATGGTGGACACAAAATCAAGAGCCAGG

TGACCCATACGGTCCGTGGGAACCACTCAAATCTGACCCAGATTCAGAC

GATGAGAGCT
and
                                    (SEQ ID NO: 182)
CTCATCGTCTGAATCTGGGTCAGATTTGAGTGGTTCCCACGGACCGTAT

GGGTCACCTGGCTCTTGATTTTGTGTCCACCATTTCGCTTGCCATAACT

GACCGTTATGATACACAATTTCATTTGTGTAAATTTGATTTGAATCCCA

TGCTGGATACTCTCCTGGATCACTTGGGGGCGTTGGGTCCGGTTCTCCT

G
```

The peptide sequences susceptible to acid cleavage between aspartic acid and proline residues are provided below.

Linker 1—WGDPHY (SEQ ID NO:183)(Lidell et al., J. Biol. Chem. 278:13944-51 [2003])

Linker 2 —DNNDPI (SEQ ID NO:184)(Segalas et al., FEBS Lett., 371:171-175 [1995])

Linker 3 —VVADPN (SEQ ID NO:185)(Kemperman et al., Appl. Env. Microbiol., 69:1589-1597 [2003])

Oligonucleotide primers used to introduce a BssHII site into pJM103BBI by QuikChange® site-directed mutagenesis are provided below.

```
BCEbss-F
                                    (SEQ ID NO: 186)
5'-TGGCGTTCAGCAACATGAGCGCGCAGGCTGATGATTA BCEbss-R
                                    (SEQ ID NO: 187)
5'-TAATCATCAGCCTGCGCGCTCATGTTGCTGAACGCCA
```

Sequences of the DNA oligonucleotides that were annealed as a cassette (SalI-HindIII) to introduce HindIII and XhoI sites after the stop codon of BBI, to introduce a Pad site after the LAT, and remove the original HindIII site are provided below.

```
BCEterm+
                                    (SEQ ID NO: 188)
5'-GACATCACGGACTTCTGCTATGAGCCATGTAAACCAAGCGAGGACG

ATAAAGAGAACTAAAAGCTTAACTCGAGGTTAACAGAGGACGGATTTCC

TGAAGGAAATCCGTTTTTTTATTTTTAATTAAG

BCEterm-
                                    (SEQ ID NO: 189)
5'-AGCTCTTAATTAAAAATAAAAAAACGGATTTCCTTCAGGAAATCCG

TCCTCTGTTAACCTCGAGTTAAGCTTTTAGTTCTCTTTATCGTCCTCGC

TTGGTTTACATGGCTCATAGCAGAAGTCCGTGATG
```

PCR primers used to generate the acid labile linkers provided above (i.e., Linker 1, Linker 2, and Linker 3) inserted between the BCE103 catalytic domain and BBI are provided below.

```
BCE103coreBssHII_FW
                                    (SEQ ID NO: 190)
5'-CAGCAACATGAGCGCGCAGGCTG linkerWGDPHY_RV
                                    (SEQ ID NO: 191)
5'-ATCGTCTGGATCCGGATAGTGGGGGTCTCCCCAAGATGCTGATTC

TCTTATTTTTTCCC linkerDNNDPI_RV
                                    (SEQ ID NO: 192)
5'-ATCGTCTGGATCCGGTATGGGATCATTGTTGTCAGATGCTGATTCT

CTTATTTTTTCCC linkerVVADPN_RV
                                    (SEQ ID NO: 193)
5'-ATCGTCTGGATCCGGGTTGGGATCTGCAACTACAGATGCTGATTC

TCTTATTTTTTCCC
```

PCR primers used to generate the acid labile linkers provided above (i.e., Linker 1, Linker 2, and Linker 3) inserted into the $1^{st}$ CBD linker.

```
BCE103corePstI_FW
                                      (SEQ ID NO: 194)
GCATAAGGAT GAGTCATCTG CAGCG LplusWGDPHY_RV
                                      (SEQ ID NO: 195)
5'-ATCGTCTGGATCCGGATAGTGGGGGTCTCCCCACGGTTCTCCTGG

ATCAGATGGCGG

LplusDNNDPI_RV
                                      (SEQ ID NO: 196)
5'-ATCGTCTGGATCCGGTATGGGATCATTGTTGTCCGGTTCTCCTGG

ATCAGATGGCGG

LplusVVADPN_RV
                                      (SEQ ID NO: 197)
5'-ATCGTCTGGATCCGGGTTGGGATCTGCAACTACCGGTTCTCCTGG

ATCAGATGGCGG
```

Protein sequence of the acid labile linkers inserted between the BCE103 catalytic domain and BBI are provided below. The acid labile linkers are shown in bold type and the sequences from the first CBD domain are underlined.

```
    Linker 1
                                      (SEQ ID NO: 198)
    BCE-WGDPHY-PDP-BBI Linker 2
                                      (SEQ ID NO: 199)
    BCE-DNNDPI-PDP-BBI Linker 3
                                      (SEQ ID NO: 200)
    BCE-VVADPN-PDP-BBI LinkerPlus 1
                                      (SEQ ID NO: 201)
    BCE-IPPSDPTPPSDPGEP-WGDPHY-PDP-BBI LinkerPlus 2
                                      (SEQ ID NO: 202)
    BCE-IPPSDPTPPSDPGEP-DNNDPI-PDP-BBI LinkerPlus 3
                                      (SEQ ID NO: 203)
    BCE-IPPSDPTPPSDPGEP-VVADPN-PDP-BBI
```

The sequences of the DNA oligonucleotide pairs that were annealed and ligated into the BamHI and SacI sites of pJM103-BBI to generate potential cleavage sites between the BCE103 catalytic domain and BBI during the purification process are provided below.

```
    BCEentBBI (Enteropeptidase cleaveage site)
                                      (SEQ ID NO: 204)
    GATCCAGGTGGAGACGACGATGACAAAGACGATGAGAGCT
    and
                                      (SEQ ID NO: 205)
    CTCATCGTCTTTGTCATCGTCGTCTCCACCTG BCEgenen1BBI (Genenase I cleavage site)
                                      (SEQ ID NO: 206)
    GATCCAGGTGCTGCTCATTACGACGATGAGAGCT
    and
                                      (SEQ ID NO: 207)
    CTCATCGTCGTAATGAGCAGCACCTG
```

The sequences of the DNA oligonucleotide pairs that were annealed and ligated into the BamHI and SacI sites of pJM103-lnk2-1BBIck81 to generate potential cleavage sites between the BCE103 catalytic domain and BBI during the purification process are provided below.

```
    BCEfurinBBI (Furin/Blisterase cleavage site)
                                      (SEQ ID NO: 208)
    GATCCACGTGCTAAAAGAGACGATGAGAGCT
    and
                                      (SEQ ID NO: 209)
    CTCATCGTCTCTTTTAGCACGTG BCEgenen2BBI (Genenase I cleavage site)
                                      (SEQ ID NO: 210)
    GATCCAGGCGCTGCACACTACAACGACGATGAGAGCT
    and
                                      (SEQ ID NO: 211)
    CTCATCGTCGTTGTAGTGTGCAGCGCCTG BCEfleBBI (Mpr cleavage site)
                                      (SEQ ID NO: 212)
    GATCCATTCCTTGAAGACGATGAGAGCT
    and
                                      (SEQ ID NO: 213)
    CTCATCGTCTTCAAGGAATG
```

Sequences of the oligonucleotide primer pairs used to introduce the E and E3 linkers in Linker 2 by QuikChange site-directed mutagenensis (Stratagene) are provided below.

```
    BCE-Elnk-BBI (Mpr cleavage site)
                                      (SEQ ID NO: 214)
    CCCATACCGGAGCCAGACGATGAGAGCTC
    and
                                      (SEQ ID NO: 215)
    CATCGTCTGGCTCCGGTATGGGATCATTGTTG
```

The protein sequence of the E3 linker between the BCE103 catalytic domain and BBI was DNNDPIPEPDDESFNMPIPEP (SEQ ID NO:216). In this sequence, the E Linker is underlined and the sequence generated by faulty recombination in *E. coli* is shown in bold type. Cleavage by Mpr (or V8 protease) can occur after any of the three glutamic acids present in the E3 Linker. Thus, the structure was BCE-(SEQ ID NO:216)-BBI The sequences of the DNA oligonucleotide pairs that were annealed and ligated into the BamHI and SacI sites of p2JM103-lnk2-2BBIck81 to generate potential Genenase I cleavage sites between the BCE103 catalytic domain and BBI are provided below.

```
BCEgenen3BBI
                                      (SEQ ID NO: 217)
GATCCAGGCGCTGCACACTACAAATCAGACCATCAGCACAGCAATGA
CGATGAGAGCT
and
                                      (SEQ ID NO: 218)
CTCATCGTCATTGCTGTGCTGATGGTCTGATTTGTAGTGTGCAGCGCCTG BCEgenen4BBI
                                      (SEQ ID NO: 219)
GATCCAGGCGCTGCACACTACGTAGAATTTCAAGACGATGAGAGCT
and
                                      (SEQ ID NO: 220)
CTCATCGTCTTGAAATTCTACGTAGTGTGCAGCGCCTG
```

The protein sequence of a Genenase I sensitive cleavage site (also acid and Mpr sensitive) inserted between the BCE103 catalytic domain and BBI was DNNDPIPDPGAAHYVEFQ (SEQ ID NO:221). The Genenase I site (Gen4 Linker) is in bold type (cleavage occurs between the tyrosine and valine) (NEB) and Linker 2 is underlined. Cleavage by Mpr can also occur after the glutamic acid that follows the valine in the Gen4 linker. The sequence used herein was BCE-SEQ ID NO:221)-BBI Cleavage sites in the BCE103-lnk2-2BBIck81 fusion protein are indicated below. The C-terminal seven amino acids of the BCE103 catalytic domain (underlined), linker 2 sequence (bold type), and 2BBIck81 sequences are shown. The acid/heat labile Asp-Pro bonds are indicated with solid headed arrows and the Mpr sensitive bonds after glutamic acids are indicated with line headed arrows.

(SEQ ID NO: 222)

. . . KIRESASDNNDPIPDPDDESSKPCCDQCACTKSNPPQCRCSDMR

LNSCHSACKSCACYNLYGWTCFCVDITDFCYEPCKPSEDDKEN

In order to isolate free BBI or its variants, the BBI moiety needs to be cleaved from the BCE103-BBI fusion protein. In some embodiments, this is accomplished during growth, by proteases intrinsically produced by *B. subtilis*. In some alternative embodiments, this cleavage occurs after growth, during the purification process (e.g. by acid/heat or proteolytic cleavage). Linkers potentially susceptible to cleavage during growth were designed (See, above, sub, cbdL, pro, shortpro, and cbdD) and cloned into the pJM103BBI or p2JM103BBI expression vectors as BamHI-SacI cassettes. The production of fusion protein versus BCE103 catalytic domain was analyzed on SDS-PAGE gels as described in Example 16.

Little cleavage of the fusion protein was observed for all these linkers except with the pro linker, which was nearly completely cleaved so that very little intact fusion protein was observed on gels, although there was a large band corresponding to the BCE103 catalytic core. Unfortunately, this cleavage during growth resulted in negligible BBI activity measured in cell free supernatants and no BBI band could be identified on SDS-PAGE gels. Although it is not intended that the present invention be limited to any particular mechanism or theory, it is possible that the BBI is particularly sensitive to proteolytic degradation in its inactive form. Thus, cleavage during the purification process after activation is generally preferred.

In some embodiments, the bonds between aspartic acid and proline residues are cleaved by heat treatment at acidic pH as known in the art (See e.g., Landon, Meth. Enzymol., 47:145-149 [1977]). The 1$^{st}$ CBD linker in the BCE103 cellulase has three Asp-Pro dipeptide sequences (See, FIG. 14) with the potential to be cleaved by acid/heat treatment. However, cleavage by acid/heat treatment at these sites was found to be inefficient. Protein sequences that are especially labile to acid/heat have been described in the literature, three of such sequences are WGDPHY (SEQ ID NO:183), DNNDPI (SEQ ID NO:184), and VVADPN (SEQ ID NO:185)(i.e., Linkers 1, 2 and 3).

Before these acid labile linkers were introduced into the BCE103-BBI expression vector, pJM103BBI, a BssHII site was introduced by QuikChange® XL (Stratagene) mutagenesis (using the manufacturer's methods; and described in Example 17 above, except 8 minute extension and 1 minute denaturation steps were used) in the aprE signal sequence coding region using the oligonucleotide primers BCEbss-F and BCEbss-R (provided above). Then, HindIII and XhoI sites were inserted in front of the LAT terminator (after the BBI stop codon) and a PacI site was added after the terminator (the original HindIII site after the LAT terminator was removed) by inserting an oligonucleotide cassette (BCEterm+ and BCEterm−; provided above) into the SalI and the original HindIII sites. This new vector was called "p2JM103BBI."

The acid labile linker fragments were generated by PCR, using forward primer BCE103coreBssHII_FW with each of the reverse primers, linker WGDPHY_RV (SEQ ID NO:191), linker DNNDPI_RV (SEQ ID NO:192), or linkerVVADPN_RV (SEQ ID NO:193) and p2JM103BBI as the template (See, Example 16, for the PCR protocol). The PCR fragments of 970 by were digested with BamHI and PstI, the 154 by fragments encoding the acid linker fragments were isolated from an agarose gel after electrophoresis, and ligated into the p2JM103 vector digested with BamHI and PstI that had also been purified from a gel. The linker sequences in the final expression vectors, p2JM103lnk1-BBI, p2JM103lnk2-BBI and p2JM103lnk3-BBI, were verified by DNA sequencing.

Competent *B. subtilis* strain BG3934comK or BG6006 were transformed with the plasmids, colonies selected on 5 µg/ml chloramphenicol LA plates and amplified to 25 µg/ml chloramphenicol as described in Example 16.

Similarly, the acid labile linkers were inserted into the first CBD linker. Specifically, PCR fragments were generated using the forward primer BCE103corePstI_FW (SEQ ID NO:194) with the reverse primers LplusWGDPHY_RV (SEQ ID NO:195), LplusDNNDPI_RV (SEQ ID NO:196), or LplusVVADPN_RV (SEQ ID NO:197) with p2JM103BBI as a template. The PCR fragments of about 150 bp were digested with BamHI and PstI, purified and ligated to the p2JM103BBI vector digested with BamHI and PstI. The correct sequences were verified by DNA sequencing and the plasmids p2JM103pllnk1-BBI, p2JM103pllnk2-BBI and p2JM103pllnk3-BBI were used to transform *B. subtilis* strains as described above.

After growth in MBD medium, the fusion proteins were purified by ion exchange chromatography essentially as described above (See, Example 17). The fusion protein was cleaved by treatment at 55° C. for 16 h in 10% formic acid. The BCE103 catalytic domain precipitated during the acid treatment and was removed by centrifugation. The free BBI in the supernatant was dried overnight on a SpeedVac. The sample was suspended in 50 mM Tris pH 8 before loading on the SDS-PAGE gel. By analysis of the protein stained SDS-PAGE gels, it was observed that acid cleavage was much more efficient in the fusion proteins where Linker 2 was inserted between the BCE103 catalytic domain and BBI (BCE-DNNDPI-PDP-BBI; SEQ ID NO:199). This linker was found to be cleaved in a couple of hours at 75° C. in 20 mM glycine pH 2.

In alternative embodiments, the fusion protein was cleaved by treatment with a protease during the purification process. Linkers were designed with cleavage sites for glutamic acid specific proteases (e.g., Mpr or V8 protease), furin/blisterase, genenase I, and enteropeptidase (enterokinase). These linkers were introduced as oligonucleotide cassettes (See above, for the sequences) between the BCE103 catalytic core and BBI in the expression vector using the BamHI and SacI sites (See, FIG. 14). In the coding region of the original expression vector (pJM103BBI), there is a glutamic acid residue in the 1s$^r$ CBD domain and at the third residue in BBI (See, FIG. 14), which is contemplated to be susceptible to cleavage by glutamic acid specific proteases such as *B. subtilis* Mpr (BsMpr) or V8 protease. However, neither BsMpr nor V8 protease were found to cleave the BCE-BBI fusion protein very efficiently at these sites. Thus, it was necessary to design other linkers that were susceptible to cleavage by these proteases.

The six acid labile linkers described above were tested for cleavage by BsMpr. These fusion proteins were cleaved by treatment for 16 h with 16 µg of BsMpr at room temperature. After cleavage, the BCE103 catalytic domain was precipitated by the addition of 10% formic acid and removed by centrifugation. The free BBI in the supernatant was dried overnight on a SpeedVac. The sample was suspended in 50 mM Tris pH 8, before loading on the SDS-PAGE. Similar to the acid cleavage, the BCE-DNNDPI-PDP-BBI (Linker 2; SEQ ID NO:199) fusion protein was much more efficiently cleaved by BsMpr than any of the other linkers. Therefore, BBI and its variants were found to be effectively released from the BCE-DNNDPI-PDP-BBI (SEQ ID NO:199) fusion protein either by acid/heat treatment or proteolytic digestion with a glutamic acid specific protease such as BsMpr. Several other linkers designed for cleaved by Mpr (e.g., E, E3 linker, and fle, provided above) were tested but none of them had any advantages over Linker 2 (the E3 linker was generated by faulty recombination in E. coli after transformation with the QuikChange® site-directed mutagensis reaction designed to construct the E linker). As shown above, there are two acid/heat labile cleavage sites in Linker 2 and three sites sensitive to cleavage by Mpr.

Linkers designed for cleavage by furin or blisterase (NEB) (BCEfurinBBI), or enteropeptidase (enterokinase, NEB) (BCEentBBI) were tested, but none of these sequences were cleaved efficiently by the appropriate protease. Four linkers were also designed (BCEgenen1BBI, BCEgenen2BBI, BCEgenen3BBI, and BCEgenen4BBI) and tested for cleavage by genenase I (NEB). Efficient cleavage of the fusion protein was observed only with the Gen4 Linker (BCEgenen4BBI). BsMpr was also found to efficiently cleave the Gen4 linker.

After activation of the purified BCE-lnk2-2BBIck81 fusion protein, cleavage by BsMpr does not go to completion as judged by SDS-PAGE gels. However, it was discovered that complete cleavage after activation of BCE-BBI fusion proteins with Linker 2 (or the Gen4 linker) can be accomplished by using the Mpr protease isolated from Bacillus licheniformis (BlMpr). While it is not intended that the present invention be limited to any particular mechanism, cleavage after the third amino acid in mature BBI appeared to be more sensitive to BlMpr while cleavage after the sixth amino acid from the C-terminus of BBI is more sensitive to BsMpr cleavage.

In some embodiments, after cleavage, the BBI is purified away from the BCE103 catalytic domain by selective acid precipitation (pH 3 or lower) of the BCE103 catalytic domain as described above, ion exchange chromatography (See, Example 20), or by selective binding of BBI on an anhydrotrypsin-agarose (Sigma) column loaded in 50 mM Tris pH 8.0, washed with 50 mM Tris pH 8.0 with 150 mM NaCl, then eluting bound BBI with 50 mM glycine pH 2.2 with 300 mM NaCl).

Example 20

Binding of BBIck81 to VegF

In this Example, experiments conducted to assess the binding of BBIck81 to VegF are described. The BCE103-lnk2-2BBIck81 fusion protein was produced in B. subtilis as described in Example 17. The fusion protein was purified, and the BBI trypsin inhibitory activity was increased by treatment with βME and oxidized glutathione as described in Example 18. The fusion protein was cleaved by BsMpr protease (See, Example 19) and the free 2BBIck81 was purified from the BCE103 catalytic domain by ion exchange chromatography using a Q-Sepharose column.

Briefly, after cleavage, the pH of the cleaved sample was adjusted to 5.5, the sample was then loaded onto the column (equilibrated with 25 mM MES pH 5.5). The free 2BBIck81 was washed through the column using 25 mM sodium acetate pH 5.0 while the BCE103 catalytic core remained bound to the resin. The 2BBIck81 fraction was concentrated by ultrafiltration and analyzed using an electrochemiluminescence (ECL) based binding assay (BioVeris). The Anti-VegF antibody (Santa Cruz) and VegF (PeproTech) were labeled with the electrochemiluminescent dye and biotin, respectively, as described by the manufacturer (BioVeris). All materials were in Dulbecco's PBS (Mediatech) supplemented with 0.1% TWEEN®-80. An initial dilution series of Anti-VegF antibody (125, 250 and 500 ng/ml) and VegF (100, 150, 200 and 250 ng/ml) were tested in the binding assay to determine the concentrations of each that would give a robust ECL signal.

Figure 19:
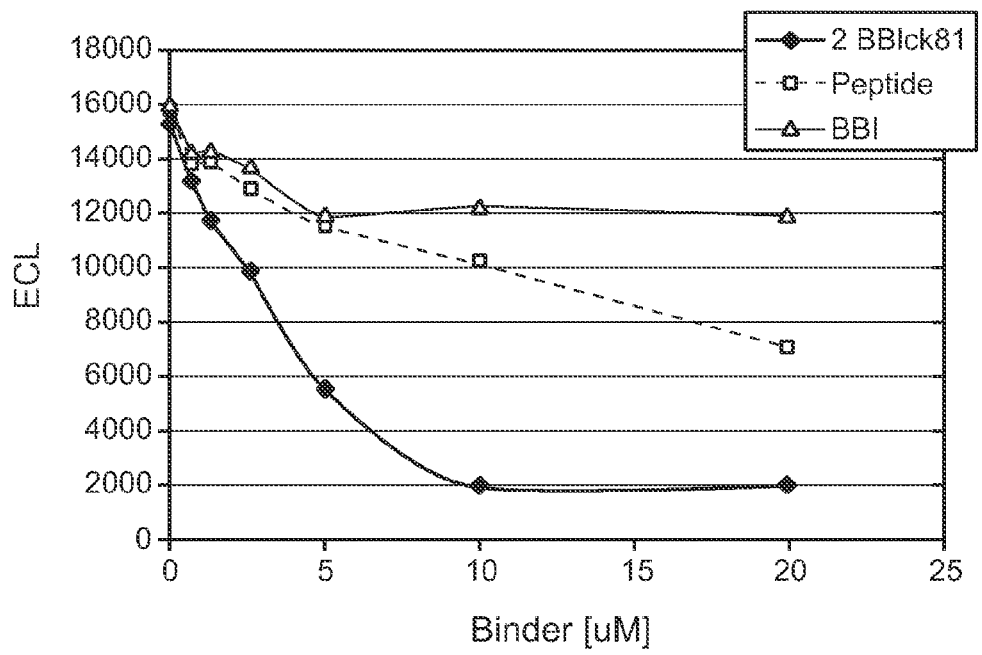
FIG. 19 provides a graph showing results from a competition analysis of 2BBIck81 versus anti-VegF antibody binding to VegF.

For testing 2BBIck81 binding, 50 µL of 500 ng/ml ECL labeled Anti-VegF antibody, 50 µL of 250 ng/ml biotinylated VegF and 100 µL 2BBIck81 (series of 12.5, 15, 31.25, 62.5, 125, 250 or 500 ng/ml) were incubated at room temperature for 2 h with shaking. Then, 50 µL of 0.2 mg/ml streptavidin coated beads were added and the reaction was incubated at room temperature for 30 minutes. The ECL signal was measured using a BioVeris M8/384 Analyzer as described by the manufacturer (BioVeris). As shown in FIG. 19, the ECL signal decreased as increasing concentrations of 2BBIck81 displaced more of the labeled Anti-VegF antibody bound to VegF attached to the magnetic beads.

Thus, the CK37281 peptide when grafted onto the chymotrypsin inhibitory loop of BBI (2BBIck81) competed with the Anti-VegF antibody for binding to VegF at micromolar concentrations. In fact, 2BBIck81 competed for VegF binding better than the synthesized CK37281 peptide itself (See, FIG. 19). The CK37281 peptide inserted into the trypsin inhibitory loop, 1BBIck81, also competed with the Anti-VegF antibody in the BioVeris assay. Thus, BBI was found to be useful as part of a scaffold to present active binding peptides selected by various screening methods.

Example 21

Use of Alternative Fusion Partners for the Production of 2BBIck81

In this Example, experiments conducted to evaluate alternative fusion partners are described. The DNA sequence of the oligonucleotide primers used to amplify the dsbC gene (E. coli) from pET-40b(+) are provided below. These primers generate a BssHII site at the 5' end and a BamHI at the 3' end for cloning into p2JM103-Gen4-2BBIck81.

```
DsbCBBI-F
                                          (SEQ ID NO: 223)
AACATGAGCGCGCAGGCTGATGACGCGGCAATTCAACAAACGTTAG

DsbCBBI-R
                                          (SEQ ID NO: 224)
TCGTCTGGATCCGGTATGGGATCATTGTTGTCACCAGAACCACTAGTTG

ATCCTTTACCGCTGGTCATTTTTTGGTG
```

The DNA sequences of the oligonucleotides that were annealed together to make a cassette (Alw44I-BamHI) for fusing the P. mendocina cutinase gene to BBI with Linker 2, are provided below.

```
CutinaseBBI+
                                              (SEQ ID NO: 225)
TGCACTTCTCTGCTTTGGTCTGTTGAACGCAGAGGTCTTGACAACAATG
ATCCTATTCCG CutinaseBBI-
                                              (SEQ ID NO: 226)
GATCCGGAATAGGATCATTGTTGTCAAGACCTCTGCGTTCAACAGACCA
AAGCAGAGAAG
```

Because the BBI moiety has seven disulfide bonds, it is contemplated that higher titers of active BBI will be obtained using fusion proteins other than the BCE103 cellulase catalytic domain. For example, in some embodiments, compositions such as thiol-disulfide oxidoreductases and/or protein disulfide isomerases find use as fusion proteins to help produce correctly folded BBI moieties. In this embodiment, no additional activation step is needed under most circumstances. In additional embodiments, other proteins produced at high titers in *B. subtilis* also find use as fusion partners. For example, the thermostable protein disulfide isomerase from the fungus *Humicola insolens* (hiPDI) has been used as a fusion partner to produce the light chain of immunoglobulin G (2 disulfides) in *Bacillus brevis* (See, Kajino et al., Appl. Env. Microbiol., 66:638-642 [2000]).

To determine whether hiPDI could be a better fusion partner than BCE103 for the production of BBI, this hiPDI gene was synthesized (DNA2.0) and cloned into the expression vector, p2JM103-lnk2-2BBIck81 (See, Example 19) as a BssHII-SacI fragment. In designing the synthetic gene, codons occurring with high frequency in highly expressed *B. subtilis* genes were selected except in cases where restriction sites were introduced or deleted. In the final construction, the N-terminus of the mature hiPDI gene was fused to the AprE signal sequence and the C-terminus was fused to a linker with an Enteropeptidase cleaveage site (Kajino et al., Appl. Env. Microbiol., 66:638-642 [2000]), which in turn was fused to 2BBIck81 (See, FIG. 20). This expression vector, p2JM-PDI-EK-2BBIck81, was used to transform *B. subtilis* BG6006 and the production of the fusion protein was determined in MBD medium (as described in Example 16) with or without 2 mM βME added 14 h after inoculation.

As determined by SDS-PAGE gels, the production of the PDI-2BBIck81 fusion protein was typically somewhat less than the BCE-2BBck81 grown under identical conditions. The BBI titers (trypsin inhibition) measured from the PDI-2BBIck81 cell free supernatants were also typically less than the BCE-2BBIck81 fusion. As with fusions to BCE103, the measured activities of BBI when fused to PDI were higher when grown in 2 mM βME and the BBI activity was increased by the addition of βME to the cell free supernatants after growth when grown in βME-free medium (as described in Example 18). Thus, the thiol-disulfide oxidoreductase activity of PDI does not seem to significantly improve the titers of active 2BBIck81 in the fusion protein or obviate the need for activation of the BBI molecule.

In order to increase the reduction potential of the fusion protein, which was contemplated to improve the BBI titers during growth, DsbC from *Escherichia coli* was used as a fusion partner for 2BBIck81. The dsbC gene was amplified by PCR using Herculase Enhanced DNA polymerase as described by the manufacturer (Stratagene) using Dsb-CBBI-F and DsbCBBI-R as primers (sequences shown above) and pET-40b(+) (Novagen) as a template. The isolated PCR fragment was cloned into the vector p2JM103-Gen4-2BBIck81 (See, Example 19) as a BssHII-BamHI fragment.

The correct sequence of the fusion gene was verified by DNA sequencing. In this case, the titers of the DsbC-2BBIck81 fusion protein were significantly lower than the BCE-2BBIck81 fusion protein as judged on SDS-PAGE gels and the titers of the active 2BBIck81 measured by trypsin inhibition were much lower as well.

Other proteins that are produced at high titers in *B. subtilis* find use as fusion partners for the production of BBI. One such protein is the cutinase from *Pseudomonas mendocina*, which has been expressed at high titers utilizing the aprE promoter from *B. subtilis* (See e.g., U.S. Pat. No. 5,429,950, herein incorporated by reference). The aprE-cutinase gene fusion as an EcoRI-Alw44I fragment (from pAK-15) was ligated with an Alw44I-BamHI linker oligonucleotide cassette (See, sequence above) into the p2JM103-lnk2-2BBIck81 (See, Example 19) that had been cut with EcoRI and BamHI. This cutinase-linker2-2BBIck81 expression vector (See, FIG. 21 for the EcoRI-BamHI aprE-cutinase-linker2 sequence) was used to transform *B. subtilis* BG6006 cells and the fusion protein was produced in MBD medium as described previously for the other fusion proteins (See, Example 16). In this case, the cutinase-linker2-2BBIck81 fusion protein was not the major band observed on SDS-PAGE gels and the measured lipase titers (as measured using the methods provided in U.S. Pat. No. 5,429,950) and BBI titers were much less (ca. 20 fold) than found with the BCE-2BBIck81 fusion protein. Also, the BBI titers in the cutinase fusion protein were not improved significantly when 3 mM βME was added to the growth medium. Thus, the highest titers of active 2BBIck81 was consistently obtained by activation of the BCE-2BBIck81 fusion protein. Nonetheless, it is contemplated that various fusion partners will find use in the present invention.

Those of skill in the art readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined herein.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

The invention claimed is:

1. A personal care composition comprising a scaffold, wherein said scaffold comprises a protease inhibitor and at least one peptide selected from the group consisting of SEQ ID NOS:1-17.

2. The personal care composition of claim 1, wherein said protease inhibitor is selected from the group consisting of Bowman-Birk inhibitor, soybean trypsin inhibitor, and Elgin chymotrypsin inhibitor.

3. The personal care composition of claim 2, wherein said Bowman-Birk inhibitor is a modified Bowman-Birk inhibitor.

4. The personal care composition of claim 1, wherein said scaffold comprises from about 0.001 weight percent to about 5 weight percent of said personal care composition.

5. The personal care composition of claim 4, wherein said scaffold comprises from about 0.01 weight percent to about 2.0 weight percent of said personal care composition.

6. The personal care composition of claim 5, wherein said scaffold comprises from about 0.01 weight percent to about 1 weight percent of said personal care composition.

7. The composition of claim 1, wherein said personal care composition is a skin care composition selected from the group consisting of skin creams, lotions, sprays, emulsions, colloidal suspensions, foams, aerosols, liquids, gels, sera, and solids.

8. The composition of claim 7, wherein said skin care composition comprising topically applied over-the-counter compositions, anti-fungal treatments, anti-acne treatments, skin protectants, sunscreens, deodorants, and antiperspirants.

9. The composition of claim 7, wherein said composition is:
   i) capable of lightening the skin tone;
   ii) capable of reducing redness in skin tone;
   iii) capable of preventing skin tone darkening;
   iv) capable of preventing skin color development; and/or
   v) radioprotective.

10. The composition of claim 1, wherein said personal care composition is capable of preventing hair growth.

11. The composition of claim 1, wherein said personal care composition is a hair care composition.

12. A personal care composition comprising a scaffold, wherein said scaffold comprises a protease inhibitor and at least one peptide selected from the group consisting of SEQ ID NOS:1-17 and is a cosmetic composition.

13. The composition of claim 12, wherein said cosmetic composition is a makeup composition selected from eye gels, eye shadows, high-melting point lipsticks, lipsticks, lip glosses, lip balms, mascaras, eyeliners, pressed powder formulations, and foundations.

14. The composition of claim 13, wherein said makeup composition comprises at least one pigment.

15. The personal care composition of claim 1, wherein said scaffold comprises the amino acid sequence set forth in SEQ ID NO:19.

16. The personal care composition of claim 1, wherein said scaffold further comprises at least one amino acid sequence set forth in SEQ ID NOS:20 and 21.

17. The personal care composition of claim 16, wherein at least one of said amino acid sequences set forth in SEQ ID NOS: 20 and 21 is replaced by at least one peptide having an amino acid sequence selected from the group consisting of SEQ ID NOS:1-17.

18. The personal care composition of claim 1, wherein said scaffold comprises an amino acid sequence selected from the group consisting of SEQ ID NOS:22-25.

19. A method for making the personal care composition of claim 1, comprising combining an effective amount of said scaffold and at least one physiologically acceptable carrier or excipient.

20. A method for modifying the skin tone of a subject, comprising the steps of:
   i) providing a composition comprising the personal care composition of claim 1;
   ii) providing a subject to be treated; and
   iii) applying said composition to said subject in an area in which modifications to said subject's skin tone is desired.

21. The method of claim 20, wherein said personal care composition comprises the amino acid sequence set forth in SEQ ID NO:19.

22. The method of claim 20, wherein said personal care composition comprises at least one amino acid sequence set forth in SEQ ID NOS:20 and 21.

23. The method of claim 20, wherein at least one of said amino acid sequences set forth in SEQ ID NOS:20 and 21 is replaced by at least one peptide having an amino acid sequence selected from the group consisting of SEQ ID NOS: 1-17.

24. The method of claim 20, wherein said personal care composition is encoded by an amino acid sequence selected from the group consisting of SEQ ID NOS:22-25.

25. A method for modifying the hair growth of a subject, comprising the steps of:
   i) providing the personal care composition of claim 1;
   ii) providing a subject to be treated; and
   iii) applying said composition to said subject in an area in which modifications to said subject's hair growth is desired.

26. The method of claim 25, wherein said modification of hair growth comprises inhibiting the growth of said subject's hair.

27. The method of claim 25, wherein said modification of hair growth comprises inhibiting the growth of said subject's hair, wherein said hair to be inhibited is selected from the group consisting of facial air, underarm hair, leg hair, torso hair, and arm hair, and head hair.

28. The method of claim 25, wherein said personal care composition comprises the amino acid sequence set forth in SEQ ID NO:19.

29. The method of claim 25, wherein said personal care composition comprises at least one amino acid sequence set forth in SEQ ID NOS:20 and 21.

30. The method of claim 29, wherein at least one of said amino acid sequences set forth in SEQ ID NOS:20 and 21 is replaced by at least one peptide having an amino acid sequence selected from the group consisting of SEQ ID NOS: 1-17.

31. The method of claim 22, wherein said personal care composition is encoded by an amino acid sequence selected from the group consisting of SEQ ID NOS:22-25.

* * * * *